United States Patent
Karpusas et al.

(10) Patent No.: US 9,644,030 B2
(45) Date of Patent: May 9, 2017

(54) ANTIBODIES TO VLA-1

(71) Applicant: BIOGEN MA INC., Cambridge, MA (US)

(72) Inventors: Michael Karpusas, Upper Darby, PA (US); Paul D. Lyne, Arlington, MA (US); Ellen A. Garber Stark, Cambridge, MA (US); Jose William Saldanha, Enfield (GB)

(73) Assignee: BIOGEN MA INC., Cambridge, MA (US)

( * ) Notice: Subject to any disclaimer, the term of this patent is extended or adjusted under 35 U.S.C. 154(b) by 206 days.

(21) Appl. No.: 14/597,262

(22) Filed: Jan. 15, 2015

(65) Prior Publication Data

US 2015/0299323 A1     Oct. 22, 2015

Related U.S. Application Data

(60) Division of application No. 13/297,124, filed on Nov. 15, 2011, now abandoned, which is a continuation of application No. 13/017,919, filed on Jan. 31, 2011, now Pat. No. 8,084,028, which is a continuation of application No. 12/727,965, filed on Mar. 19, 2010, now Pat. No. 7,910,099, which is a division of application No. 12/015,213, filed on Jan. 16, 2008, now Pat. No. 7,723,073, which is a division of application No. 10/474,832, filed as application No. PCT/US02/11521 on Apr. 12, 2002, now Pat. No. 7,358,054.

(60) Provisional application No. 60/303,689, filed on Jul. 6, 2001, provisional application No. 60/283,794, filed on Apr. 13, 2001.

(51) Int. Cl.
*A61K 39/395* (2006.01)
*C07K 16/28* (2006.01)
*A61K 39/00* (2006.01)

(52) U.S. Cl.
CPC .... *C07K 16/2842* (2013.01); *A61K 2039/505* (2013.01); *C07K 2299/00* (2013.01); *C07K 2317/24* (2013.01); *C07K 2317/34* (2013.01); *C07K 2317/51* (2013.01); *C07K 2317/515* (2013.01); *C07K 2317/56* (2013.01); *C07K 2317/565* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 5,391,481 A | 2/1995 | Chess et al. |
| 5,530,101 A | 6/1996 | Queen et al. |
| 5,565,332 A | 10/1996 | Hoogenboom et al. |
| 5,585,089 A | 12/1996 | Queen et al. |
| 5,648,260 A | 7/1997 | Winter et al. |
| 5,693,761 A | 12/1997 | Queen et al. |
| 5,693,762 A | 12/1997 | Queen et al. |
| 5,733,743 A | 3/1998 | Johnson et al. |
| 5,773,743 A | 6/1998 | Ogawa et al. |
| 5,788,966 A | 8/1998 | Chess et al. |
| 5,789,650 A | 8/1998 | Lonberg et al. |
| 5,798,230 A | 8/1998 | Bornkamm et al. |
| 5,827,690 A | 10/1998 | Meade et al. |
| 5,849,992 A | 12/1998 | Meade et al. |
| 5,855,888 A | 1/1999 | Nishida et al. |
| 5,859,205 A | 1/1999 | Adair et al. |
| 6,001,961 A | 12/1999 | Jonczyk et al. |
| 6,016,159 A | 1/2000 | Faris |
| 6,075,181 A | 6/2000 | Kucherlapati et al. |
| 6,127,524 A | 10/2000 | Casipit et al. |
| 6,150,584 A | 11/2000 | Kucherlapati et al. |
| 6,162,963 A | 12/2000 | Kucherlapati et al. |
| 6,180,370 B1 | 1/2001 | Queen et al. |
| 6,291,650 B1 | 9/2001 | Winter et al. |
| 6,300,064 B1 | 10/2001 | Knappik et al. |
| 6,303,313 B1 | 10/2001 | Wigler et al. |
| 6,307,026 B1 | 10/2001 | King et al. |
| 6,326,403 B1 | 12/2001 | Holzemann et al. |
| 6,407,213 B1 | 6/2002 | Carter et al. |
| 6,602,503 B1 | 8/2003 | Lobb et al. |
| 6,632,927 B2 | 10/2003 | Adair et al. |
| 6,652,856 B2 | 11/2003 | Gotwals et al. |
| 6,955,810 B2 | 10/2005 | Gotwals et al. |
| 7,358,054 B2 | 4/2008 | Lyne et al. |
| 7,462,353 B2 | 12/2008 | Gotwals et al. |
| 7,612,181 B2 | 11/2009 | Wu et al. |

(Continued)

FOREIGN PATENT DOCUMENTS

| | | |
|---|---|---|
| EP | 239400 A2 | 9/1987 |
| EP | 0843691 A1 | 5/1998 |
| EP | 843961 A1 | 5/1998 |
| JP | 08131185 A | 5/1996 |
| JP | 2005-507639 A | 3/2005 |

(Continued)

OTHER PUBLICATIONS

Seiffge, "Protective Effects of Monoclonal Antibody to VLA-4 on Leukocyte Adhesion and Course of Disease in Adjuvant Arthritis in Rats" J. Rheumatol. 23:2086-2091 (1996).

(Continued)

*Primary Examiner* — Maher Haddad
(74) *Attorney, Agent, or Firm* — McCarter & English, LLP; Jonathan M. Sparks; Marcie B. Clarke

(57) ABSTRACT

Antibodies that specifically bind to VLA-1 integrin and methods of using these antibodies to treat immunological disorders in a subject. Also included are crystal structures of complexes formed by VLA-1 antibodies and their ligands, and VLA-1 antagonists and agonists identified by using the structure coordinates of these structures.

21 Claims, 133 Drawing Sheets

(56) References Cited

U.S. PATENT DOCUMENTS

| | | | |
|---|---|---|---|
| 7,723,073 | B2 | 5/2010 | Karpusas et al. |
| 7,745,396 | B2 | 6/2010 | Lucas |
| 7,910,099 | B2 | 3/2011 | Karpusas et al. |
| 8,084,028 | B2 | 12/2011 | Karpusas et al. |
| 8,084,029 | B2 | 12/2011 | Hansen et al. |
| 8,084,031 | B2 | 12/2011 | Gotwals et al. |
| 8,557,240 | B2 | 10/2013 | Gotwals et al. |
| 2003/0070185 | A1 | 4/2003 | Jakobovits et al. |
| 2003/0232333 | A1 | 12/2003 | Ladner et al. |
| 2004/0081651 | A1 | 4/2004 | Karpusas et al. |
| 2004/0208870 | A1 | 10/2004 | Allan |
| 2005/0226877 | A1 | 10/2005 | Gotwals et al. |
| 2006/0286112 | A1 | 12/2006 | Kellermann et al. |
| 2007/0071675 | A1 | 3/2007 | Wu et al. |
| 2008/0118496 | A1 | 5/2008 | Medich et al. |
| 2009/0238762 | A1 | 9/2009 | Totoritis et al. |
| 2010/0027216 | A1 | 2/2010 | Matsushima et al. |
| 2010/0233159 | A1 | 9/2010 | Relton et al. |
| 2010/0272716 | A1 | 10/2010 | Karpusas et al. |
| 2012/0087925 | A1 | 4/2012 | Gotwals et al. |
| 2012/0177638 | A1 | 7/2012 | Karpusas et al. |
| 2013/0216556 | A1 | 8/2013 | Fowler et al. |
| 2014/0017261 | A1 | 1/2014 | Totoritis |
| 2014/0110827 | A1 | 4/2014 | Tsukahara et al. |
| 2014/0154259 | A1 | 6/2014 | De Fougerolles et al. |

FOREIGN PATENT DOCUMENTS

| | | |
|---|---|---|
| WO | 9007861 A1 | 7/1990 |
| WO | 9313798 A1 | 7/1993 |
| WO | 9417828 A2 | 8/1994 |
| WO | 9519790 A1 | 7/1995 |
| WO | 9634096 A1 | 10/1996 |
| WO | 9711718 A1 | 4/1997 |
| WO | 9718838 A1 | 5/1997 |
| WO | 9856418 A1 | 12/1998 |
| WO | 99/61040 A2 | 12/1999 |
| WO | 00/20459 A1 | 4/2000 |
| WO | 00/72881 A1 | 12/2000 |
| WO | 0078221 A1 | 12/2000 |
| WO | 01/73444 A2 | 10/2001 |
| WO | 01/96365 A1 | 12/2001 |
| WO | 02072030 A2 | 9/2002 |
| WO | 02/083854 A2 | 10/2002 |
| WO | 03/068262 A1 | 8/2003 |
| WO | 2005/016883 A2 | 2/2005 |
| WO | 2005/019177 A1 | 3/2005 |
| WO | 2005/019200 A2 | 3/2005 |
| WO | 2006/124269 A2 | 11/2006 |
| WO | 2006133286 A2 | 12/2006 |
| WO | 2007124090 A2 | 11/2007 |
| WO | 2007/140249 A1 | 12/2007 |
| WO | 2010102241 A1 | 9/2010 |
| WO | 2011084750 A1 | 7/2011 |
| WO | 2012106497 A2 | 8/2012 |
| WO | 2013123114 A2 | 8/2013 |

OTHER PUBLICATIONS

Senger, D.R., et al., "The alpha1beta1 and alpha2beta1 Integrins Provide Critical Support for Vascular Endothelial Growth Factor Signaling, Endothelial Cell Migration, and Tumor Angiogenesis," American Journal of Pathology, 160 (1):195 (2002).

Shakin-Eshleman et al., "The Amino Acid at the X Position of an Asn-X-Ser Sequon Is an Important Determinant of N-Linked Core-glycosylation Efficiency", J. Biol. Chem. (1996), 271(11), 6363-6366.

Shaw et al., "Molecular Cloning of the Human Mucosal Lymphocyte Integrin alphaE Subunit" J. Biol. Chem. 269:6016-6025 (1994).

Shimaoka, "Computational design of an integrin I domain stabilized in the open high affinity conformation." Nature Structural Biol. 7(8):674-678 (2000).

Snyder et al. "The binding conformation of Taxol in beta-tubulin: A model based on electron crystallographic density" PNAS, 2001; 98(9) 5312-5316.

Solenski et al., "Transient Ischemic Attacks: Part II. Treatment" American Family Physician, 69(7):1681-1688 (2004).

Sonnenberg et al., "A Complex of Platelet Glycoproteins Ic and IIa Identified by a Rat Monoclonal Antibody" J. Biol. Chem. 262:10376-10383 (1987).

Springer et al., "Adhesion receptors of the immune system" Nature 346:425-434 (1990).

Stacker et al., "Leukocyte integrin P150,95 (CD11c/CD18) functions as an adhesion molecule binding to a counter-receptor on stimulated endothelium" J. Immunol., 146:648-655 (1991).

Supplemental European Search Report and Opinion for EP 07 78 4108 dated Nov. 18, 2010.

Suzuki, K. et al., "Semaphorin 7A initiates T-cell-mediated inflammatory responses through alpha 1 beta 1 integrin", Nature, 446:680-684, 2007.

Takada et al., "The primary structure of the VLA-2/Collagen receptor alpha 2 subunit (platelet GPIa): homology to other integrins and the presence of a possible collagen-binding domain" J. Cell Biol. 109:397-407 (1989).

Takeuchi, et al. Upregulated Expression and Function of Integrin Adhesive Receptors in Systemic Lupus Erythematosus Patients with Vasculitis. J. Clin. Invest. 92:3008-3016, 1993.

Tawil, et al., "Alpha 1 beta 1 integrin heterodimer functions as a dual laminin/collagen receptor in neural cells." Biochemistry. Jul. 10, 1990;29(27):6540-4.

Taylor et al., "Transfer of Type II Collagen-Induced Arthritis From DBAII to Severe Combined Immunodeficiency Mice Can Be Prevented by Blockage of Mac-I" Immunology 88: 315-321 (1996).

Tedder et al., "L-Selectin-deficient Mice Have Impaired Leukocyte Recruitment into Inflammatory Sites" J. Exp. Med. 181:2259-2264 (1995).

Tempest et al. "Reshaping a human monoclonal antibody to inhibit human respiratory syncytial virus infection in vivo" (1991) Bio-technology 9:266-271.

Tempest et al., "Reshaping a Human Monoclonal Antibody to Inhibit Human Respiratory Syncytical Virus Infection in Vivo" Bio. Tech. 9:266-271 (1991).

Terashita et al., "Enhancement of Delayed-Type Hypersensitivity to Sheep Red Blood Cells in Miche by Granulocyte Colony-Stimulating Factor Administration at the Elicitation Phase" J. Immunol. 156:4638-4643 (1996).

Terato et al., "Collagen-Induced Arthritis in Mice: Synergistic Effect of *E. coli* Lipopolysaccharide Bypasses Epitope Specificity in the Induction of Arthritis with Monoclonal Antibodies to Type II Collagen" Autoimmunity 22: 137-147 (1995).

Terato et al., "Induction of Arthritis with Monoclonal Antibodies to Collagen" J. Immunol. 148:2103-2108 (1992).

Tomizuka et al., "Functional Expression of Germline Transmission of a Human Chromosome Fragment in Chimaeric Mice" Nature Genetics 16:133-143 (1997).

Tsunoda, I. et al., "Modulation of Experimental Autoimmune Encephalomyelitis by VLA-2 Blockade", Brain Pathol., 17:45-55, 2007.

Van der Vieren et al., A Novel Leukointegrin alpha d beta 2, Binds Preferentially to ICAM-3 Immunity 3:683-690 (1995).

Verhoeyen et al., "Reshaping Human Antibodies: Grafting an Antilysozyme Activity" Science 239:1534:1536 (1987).

Wang et al., "Differential regulation of airway epithelial integrins by growth factors" Am. J. Respir.Cell Mol. Biol. 15:664-672 (1996).

Ward et al., "Binding activities of a repertoire of single immunoglobulin variable domains secreted from *Escherichia coli*" Nature 341 :544-546 (1989).

Watts, G.M., et al., "Manifestations of Inflammatory Arthritis Are Critically Dependent on LFA-1", J. Immunology, 174:3668-3675, 2005.

Wayner et al., "The function of multiple extracellular matrix receptors in mediating cell adhesion to extracellular matrix: preparation of monoclonal antibodies to the fibronectin receptor that specifically inhibit cell adhesion to fibronectin and react with platelet glycoproteins Ic-IIa" J. Cell Biol. 107:1881-1891 (1988).

(56) References Cited

OTHER PUBLICATIONS

Weinacker et al., "Role of the Integrin alpha v beta 6 in Cell Attachment to Fibronectin" J. Biol.Chem. 269:6940-6948 (1993).
Weitz-Schmidt et al. "Statins selectively inhibit leukocyte function antigen-1 by binding to a novel regulatory integrin site." (2001) Nat. Med. 7:687-692.
Welschof et al., "Amino Acid Sequence based PCR Primers for Amplification of Rearranged Human Heavy and Light Chain Immunoglobulin Variable Region Genes" J. Immuno. Meth. 179:203-214 (1995).
Woessner et al., "The determination of hydroxyproline in tissue and protein samples containing small proportions of this imino acid" Arch. Biochem. Biophys. 93:440-447 (1961).
Wright, A. and Morrison, S.L., Effect of Altered CH2-associated Carbohydrate Structure on the Functional Properties and In Vivo Fate of Chimeric Mouse-Human Immunoglobulin G1, J. Exp. Med. (1994), 180:1087-1096.
Written Opinion European Patent Office for European application No. 04018151.3 dated Mar. 22, 2012.
Written Opinion for European Application No. 00942654.5 dated Mar. 9, 2001.
Yao et al., "Laminins promote the locomotion of skeletal myoblasts via the alpha 7 integrin receptor" J. Cell Science 109:3139-3150 (1996).
Yednock, T.A. et al., "Prevention of experimental autoimmune encephalomyelitis by antibodies against alpha4 betal integrin", Nature, 356:63-66, 1992.
Li et al., "Three-Dimensional Structures of the Free and Antigen-Bound Fab from Monoclonal Antilysozyme Antibody HyHEL-63" Biochemistry 39:6296-6309 (2000).
Lin et al., "Very late antigen 4 (VLA4) antagonists as anti-inflammatory agents", Current Opinion in Chem. Biology, 2, 453-457, 1998.
Little, et al., "Of mice and Men: hybridoma and recombant antibodies", Review Immunology Today, vol. 21, No. 8, pp. 364-370, 2000.
Lobb et al., "The Pathophysiologic Role of alpha4 Integrins in Vivo", J. Clin. Invest., 94, 1722-1728, 1994.
Lobb et al., "The role of alpha 4 Integrins in lung pathophysiology", European Resp. Journ. Supp., 9(22), 1996.
Lowry et al., "Protein Measurement with the folin phenol reagent" Dept. of Pharma., Washington Univ. School of Med. 265-275 (1951).
Luque et al., "Functional regulation of the human integrin VLA-1 (CD49a/CD29) by divalent cations and stimulatory beta 1 antibodies", FEBS Letters 346 (1994) 278-284.
Mackay et al., "Lymphotoxin Receptor Triggering Induces Activation of the Nuclear Factor B Transcription Factor in Some Cell Types" J. Biol. Chem. 271:24934-24938 (1996).
Mendez et al., "Functional Transplant of Megabase Human Immunoglobulin Loci Recapitulates Human Antibody Response in Mice" Nature Genetics 15:146-156 (1997).
Mendrick et al., "Glomerular Epithelial and Mesangial Cells Differentially Modulate the Binding Specificities ofVLA-I and VLA-2" Laboratory Investigation 72:367-375 (1995).
Mendrick et al., "Temporal Expression of VLA-2 and Modulation of its ligand Specificity by Rat Glomerular Epithelial Cells in vitro" Lab. Invest. 69:690-702 (1993).
Michishita et al., "A Novel Divalent Cation-Binding Site in the A Domain of the Beta2 Integrin CR3 (CD11b/CD18) Is Essential for Ligand Binding" Cell Press 72:857-867 (1993).
Miyake et al., "Evidence for a Role of the Integrin VLA-4 in Lympho-hemapoiesis" J. Exp. Med. 173:599-607 (1991).
Miyake et al., "Integrin-mediated interaction with Extracellular Matrix Proteins Regulates Cytokine Gene Expression in Synovial Fluid Cells of Rheumatoid Arthritis Patients" J. Exp. Med. 177:863-868 (1993).
Mombaerts et al., "RAG-I-Deficient Mice Have No Mature Band T Lymphocytes" Cell 68:869-877 -1992.

Mori et al., "Attenuation of Collagen-Induced Arthritis in 55-kDa TNF Receptor Type 1 (TNFRI)- IgGI-Treated and TNFRI-Deficient Mice" J. Immunol. 157:3178-3182 (1996).
Muller et al., "VEGF and the Fab Fragment of a Humanized Neutralizing Antibody: Crystal Structure of the Complex at 2.4 A Resolution and Mutational Analysis of the Interface" Structure 6:1153-1167 (1998).
Nagler et al., "Reduction in Pulmonary Fibrosis In Vivo by Halofuginone" A.m. J. Respir. Crit.Care Med. 154:-1082-1086 (1996).
Nishimura et al., "Integrin alpha v beta 8" J. Biol. Chem. 269:28708-28715 (1994).
Nolte et al., "Crystal Structure of the Integrin I-Domain: Insights into Integrin I-Domain Function" FEBS Lett. 452:379-385 (1999).
Noto et al., "Identification and Functional Characterization of Mouse CD29 with a mAB" Int. Immunol. 7:835-842 (1995).
Odum, N. et al., "Prevalence of late stage T cell activation antigen (VLA-1) in active juvenile chronic arthritis", Ann. Rheumatic Diseases, 46:846-852, 1987.
Orlandi, "Cloning immunoglobulin variable domains for expression by the polymerase chain reaction" Proc. Natl., Acad. Sci. USA 86:3833-3837 (1989).
Padlan, E.A., "Anatomy of the antibody molecule", Mol Immunol. (1994), 31(3):169-217.
Panka et al., "Variable region framework differences result in decreased or increased affinity of variant anti-digoxin antibodies" Proc. Natl. Acad. Sci. USA 85(9):3080-3084 (1988).
Papadopoulos et al., "Expression of Integrins in Alveolar Epithelia of Fetal and Adult Lung Tissue and in Interstitial Lung Diseases", Verh. Dtsch. Ges. Path., 77, 292-295 (1993). Abstract Only.
Partial European Search Report for EP 02 72 8745 dated Feb. 16, 2005.
Partial European Search Report for EP 02 72 8745 dated Dec. 13, 2004.
Persson et al., "Generation of diverse high-affinity human monoclonal antibodies by repertoire cloning" Proc. Natl. Acad. Sci. USA 88:2432-2436 (1991).
Pfaff et al. "Binding of purified collagen receptors (alpha 1 beta 1, alpha 2 beta 1) and RGD-dependent integrins to laminins and laminin fragments." (1994) Eur. J. Biochem. 225:975-84.
Pischel et al., "Use of the monoclonal antibody 12F1 to Characterize the Differentiation Antigen VLA-21" J. Immunol. 138:226-233 (1987).
Plows et al., "Mice Lacking Mature T and B Lymphocytes Develop Arthritic Lesions After Immunization with Type II Collagen" J. Immunol. 162:1018-1023 (1999).
Portolano et al., "Lack of promiscuity in autoantigen-specific H and L chain combinations as revealed by human H and L chain Roulette", J. Immunol. (1993), 150(3):880-887.
Powers et al. "Expression of single-chain Fv-Fc fusions in *Pichia pastoris*." (2001) J. Immunol. Methods 251:123-35.
Pozzi et al., "Integrin alpha 1 beta 1 Mediates a Unique Collagen-Dependent Proliferation Pathway In Vivo", Journal of Cell Biology, 142(2), 587-594, 1998.
Qu et al., "The role of the divalent cation in the structure of the I domain from the CDIIA/CD18 integrin" Structure 4:931-942 (1996).
Qu et al., Crystal structure of the I-domain form the CDIIa1CDI8 (LFA-I, aLbeta2) integrin Proc. Natl. Acad. Sci. USA 92:10277-10281 (1995).
Queen et al., "A humanized antibody that binds to the interleukin 2 receptor" Proc. Natl. Acad. Sci.USA 86:10029-10033 (1989).
Rich et al., "Trench-shaped Binding Sites Promote Multiple Classes of Interactions between Collagen and the Adherence Receptors, alpha beta1 Integrin and *Staphylococcus aureus* Cna MSCRAMM" J. Biol. Chem. 274:24906-24913 (1999).
Riechmann et al., "Reshaping human antibodies for therapy" Nature 332:323-327 (1988).
Riikonen et al., "Antibody against human alpha 1 beta 1 integrin inhibits HeLa cell adhesion to laminin and to type I, IV, and V collagens" Biochem. Biophys. Res. Commun. 209:205-212 (1995).

(56) References Cited

OTHER PUBLICATIONS

Riikonen et al., "Transforming growth factor-beta regulates collagen gel contraction by increasing alpha 2 beta 1 integrin expression in osteogenic cells" J. Biol. Chem. 270:376-382 (1994).
Roy-Chaudhury et al., "Adhesion molecule interactions in human glomerulonephritis: Importance of the tubulointerstitium", Kidney International, 49, 127-134, 1996.
Sampson et al., "Global Gene Expression Analysis Reveals a Role for the Integrin in Renal Pathogenesis" J. Biol. Chem. 276:34182-34188 (2001).
Sanchez-Madrid et al., "Three distinct antigens associated with human T-lymphocyte-mediated cytolysis: LFA-1, LFA-2, and LFA-3." Immunol. 79:7489-7493 (1982).
Santarus: "Santarus Initiates Phase I Clinical Study with SAN-300," http://ir.santarus.com/releasedetail.cfm?releaseid+555930, XP002696720, Mar. 11, 2011 [retrieved on May 8, 2012].
Schapira, K., et al., "Genetic Deletion or Antibody Blockade of alpha1beta1 Integrin Induces a Stable Plaque Phenotype in ApoE-/-Mice," Arteriosclerosis, Thrombosis, and Vascular Biology, 25:1917-1924 (2005).
Scheynius et al., "Reduced Contact Sensitivity Reactions in Mice Treated with Monoclonal Antibodies to Leukocyte Function-Associated Molecule-I and intercellular Adhesion Molecule-I" J. Immunol. 150:655-663 (1993).
Schiro et al., "Integrin alpha 2 beta 1 (VLA-2) Mediates Reorganization and Contraction of Collagen Matrices by Human Cells" Cell 67:403-410 (1991).
Schwartz, B.R. et al., "Identification of Surface Proteins Mediating Adherence of CD11/CD18-deficient Lymphoblastoid Cells to Cultured Human Endothelium", J. Clin. Invest, 85:2019-2022, 1990.
Abraham, W.M., et al. "A Monoclonal Antibody to alpha1beta1 Blocks Antigen-Induced Airway Responses in Sheep," American Journal of Respiratory and Critical Care Medicine, 169:97-104 (2004).
Adams et al., "Coronary Risk Evaluation in Patients with Transient Ischemic Attack and Ischemic Stroke" Circulation, 108(9):1278-1290 (2003).
Alcocer-Varela, J., et al., "Interleukin-1 and Interleukin-6 Activities are Increased in the Cerebrospinal Fluid of Patients with CNS Lupus Erythematosus and Correlate with Local Late T-Cell Acitvation Markers," Lupus, 1:111-117 (1992).
Baker, et al., "Developmental and injury-induced expression of alpha1beta1 and alpha6beta1 integrins in the rat spinal cord", Brain Res. Jan. 26, 2007; 1130(1): 54-66.
Baldwin et al., "Cation binding to the integrin CDII b I domain and activation model assessment" Structure 6:923-935 (1998).
Bank et al. Lymphocytes Expressing alpha1beta1 integrin (Very Late Antigen-1) in peripheral blood of patients with arthritis are a subset of CD45RO(+) T-cells primed for rapid adhesion to collagen IV. Clin Immunol. Dec. 2002;105(3):247-58.
Bank, I. et al., Analysis of recombinant human alpha1 integrin I-domain with a function-blocking monoclonal antibody, 1B3.1, IMAJ, vol. 2, Supplement 2, pp. 19-20, Dec. 2000.
Bank, I. et al., "Expression and Functions of Very Late Antigen 1 in Inflammatory Joint Diseases", J. Clin. Immunol. 11(1):29-38, 1991.
Bennett et al., "Inhibition of fibrinogen binding to stimulated human platelets by a monoclonal antibody" Proc. Natl. Acad. Sci.USA 80:2417-2421 (1983).
Boerner et al., "Production of Antigen-Specific Human Monoclonal Antibodies From In Vitro-Primed Human Splenocytes" J. Immunol. 147:86-95 (1991).
Border et al., "Transforming Growth Factor Beta in Tissue Fibrosis" New England J. Medicine 331:1286-1292 (1994).
Bossy et al., "Characterization of the Integrin Alpha8 subunit: A new integrin beta1-associated subunit, which is prominently expressed on axons and on cells in contact with basal laminae in chick embryos" EMBO J. 10:2375-2385 (1991).
Brezinsky et al., "A Simple Method of Enriching Populations of Transfected CHO Cells for Cells of Higher Specific Productivity" J. Immunol. Methods 277:141-155 (2003).
Bridges et al., "Variable Region cDNA Sequences and Characterization of Murine Anti-Human Interferon gamma Receptor Monoclonal Antibodies that Inhibit Receptor Binding by Interferon gamma" Mol. Immunol. 32:1329-2989 (1995).
Briesewitz, et al., "Expression of Native and Truncated Forms of the Human Integrin alpha 1 Subunit," Journal of Biological Chemistry, 268(4):2989-2996 (1993).
Camper et al., "Isolation, Cloning, and Sequence Analysis of the Integrin Subunit alpha 10, a beta 1-associated Collagen Binding integrin Expressed on Chondrocytes*" J. Biol. Chem. 273:20383-20389 (1998).
Carter et al., "Humanization of an Anti-p185 HER2 Antibody for Human Cancer Therapy" Proc. Natl. Acad. Sci. USA 89:4285-4289 (1992).
Cerf-Bensussan et al., "The human intraepithelial lymphocyte marker HML-1 is an integrin consisting of a Beta7 subunit associated with a distinctive alpha chain" Eur. J. Immunol. 22:273-277 (1992).
Chapman, et al., "Leukocyte adhesion molecules", British Medical Bulletin, 51(2):296-311, 1995.
Chothia et al., "Conformations of Immunoglobulin Hypervariable Regions" Nature 342:877-883 (1989).
Clackson et al., "Making antibody fragments using phage display libraries" Proc. Natl. Acad. Sci.USA 352:624-628 (1991).
Co et al., "Humanized antibodies for antiviral therapy" Proc. Natl. Acad. Sci. USA 88:2869-2873 (1991).
Colbert et al., "The effect of fluorescein labels on the affinity of antisera to small haptens" J. Imunol. Methods 140:227-233 (1991).
Colognato et al. "The Laminin alpha 2-Chain Short Arm Mediates Cell Adhesion through Both the alpha 1 beta 1 and alpha 2 beta 1 Integrins" (1997) J. Biol. Chem. 272:29330-29336.
Colognato-Pyke et al. "Mapping of network-forming, heparin-binding, and alpha 1 beta 1 integrin-recognition sites within the alpha-chain short arm of laminin-1" (1995) J. Biol. Chem. 270:9398-9406.
Cook et al., "Treatment with an Antibody to VLA-1 Integrin Reduces Glomerular and Tubulointerstitial Scarring in a Rat Model of Crescentic Glomerulonaphritis" Am. J. Pathol. 161:1265-1272 (2002).
Corbi et al., "cDNA cloning and complete primary structure for the alpha subunit of a leukocyte adhesion glycoprotein, p150,95" EMBO Journal, vol. 6, No. 13, p. 4023-4028, 1987.
Corbi et al., The Human Leukocyte Adhesion Glycoprotein Mac-I (Complement Receptor Type 3, CDIIb) alpha Subunit' J. Biol. Chem. 263:12403-12411, 1988.
Cosgrove et al., "Integrin and Transforming Growth Factor-I Play Distinct Roles in Alport Glomerular Pathogenesis and Serve as Dual Targets for Metabolic Therapy" Am. J. Path. 157:16498-1659 (2000).
Davies et al., "Interactions of Protein Antigens with Antibodies" Proc. Natl. Acad. Sci. USA 93:7-12 (1996).
Davies, "The osteoclast Functional Antigen, Implicated in the Regulation of Bone Resorption, Is Biochemically Related to the Vitronectin Receptor" J. Cell Biology 109:1817-1826 (1989).
de Fougerolles et al., "Global Expression Analysis of Extracellular Matrix-Integrin interactions in Monocytes" Immunity 13:749-758 (2000).
de Fougerolles et al., "Regulation of Inflammation by Collagen-Binding Integrins and integrins alpha 1 beta 1 and alpha 2 beta 1 in Models of Hypersensitivity and Arthritis" J. Clin. Invest 105:721-729 (2000).
Diamond et al., "The I Domain Is a Major Recognition Site on the Luekocyte Integrin Mac-1 (CD-11b/CD18) for Four distinct Adhesion Ligands", J. Cell Biology 120:1031-1043 (1993).
Edwards et al., "Identification of Amino Acids in the CDIIa I-domain Important for Binding of the DA Leukocyte Function-associated Antigen-I (LFA-I) to Intercellular Adhesion Molecules-I (ICAM-1)*"J. Biol. Chem. 270:12635-12640 (1995).
Eigenbrot et al., "X-ray Structures of the Antigen-binding Domains from Three Variants of Humanized anti-p185 HER2 Antibody 4D5 and Comparison with Molecular Modeling" J. Mol. Biol. 229:969-995 (1993).

(56) References Cited

OTHER PUBLICATIONS

Elices, M.J. et al., "VCAM-1 on Activated Endothelium Interacts with the Leukocyte Integrin VLA-4 at a Site Distinct from the VLA-4/Fibronectin Binding Site", Cell, 60:577-584, 1990.
Emsley et al., "Crystal Structure of the I Domain from Integrin " J. Biol. Chem. 272:28512-28517 (1997).
Emsley et al., "Structural Basis of Collagen Recognition by Integrin " Cell 100:47-56 (2000).
European Search Report & Opinion for EP 10 185 467.7 dated Mar. 2, 2011.
European Search Report for European Application Serial No. 04 01 8151.3 dated Feb. 28, 2011.
Extended European Search Report for EP 14178388.6 dated Jan. 27, 2015.
Fabbri et al., "A functional monoclonal antibody recognizing the human alpha1-integrin I-domain" Tissue Antigens 48:47-51 (1996).
Fiorucci et al., "Importance of Innate Immunity and Collagen Binding Integrin alpha 1 beta 1 in TNBS-Induced Colitis", Immunity, 17, 769-780, 2002.
Fischmann et al., "Crystallographic Refinement of the Three-Dimensional Structure of the FabD1.3-Lysozyme Complex at 2.5-ÅResolution" J. Biol. Chem. 266:12915-12920 (1991).
Foote et al., "Antibody Framework Residues Affecting the Conformation of the Hypervariable Loops" J. Mol. Biol. 224:487-499 (1992).
Gardner et al., "Absence of integrin alpha 1 beta 1 in the mouse causes loss of feedback regulation of collagen synthesis in normal and wounded dermis", J. Cell Science, 112, 263-272, 1999.
Gardner et al., "Deletion of Integrin alpha 1 by Homologous Recombination Permits Normal Murine Development but Gives Rise to a Specific Deficit in Cell Adhesion", Developmental Biology, 175, 301-313, 1996.
Gaspari et al., "Contact Hypersensitivity" Current Protocols in Immunology J.E. Coligan et al., Editors, John Wiley & Sons, New York, Section 4.2.1-4.2.5 (1991).
Go et al: "Antithrombotic Therapy for Stroke Prevention in Atrial Fibrillation", Progress in Cardiovascular Diseases, Saunders, Philadelphia, PA, US, vol. 48, No. 2, Sep. 1, 2005, pp. 108-124, XP005127137, ISSN: 0033-0620, DOI: D01:10.1016/J.PCAD. 2005.06.007.
Diffuse Connective Tissue Disease: Rheumatoid Arthritis, The Merk Manual, 17th Edition, 1999, pp. 416-423.
Extended European Search Report for EP 12742734.2 dated Apr. 20, 2015.
Morand et al.: "Continuation of long term treatment with hydroxychloroquine in systemic lupus erythematosus and rheumatoid arthritis", Annals of the Rheumatic Diseases, 1992, 51: 1318-1321.
Patient Information on Etanercept, Australian Rheumatology Association, Revised May 2009—next review May 2010, pp. 1-3.
Rubbert-Roth et al.: "Treatment options in patients with rheumatoid arthritis failing intial TNF inhibitor therapy: a critical review", Arthritis Research & Therapy, 2009, 11 (Suppl 1): S1, pp. 1-12.
Bank I et al., "A novel monoclonal antibody, 1B3.1, binds to a new epitope of the VLA-1 molecule", Cellular Immunology, 122:416-423 (1989).
Edmundson et al. "Binding of peptides to proteins: an exercise in molecular design." Ciba Found Symp. 158: 213-25, (1991), Abstract.
International Preliminary Report on Patentability for International Application No. PCT/US2013/026034 dated Aug. 19, 2014.
Nienaber VL et al., "Discovering novel ligands for macromolecules using X-ray crytallographic screening", Nature Biotechnology, 18; 1105-1108, (2000).
Van Regenmortel, Mapping Epitope Structure and Activity: From One-Dimensional Prediction to Four-Dimensional Description of Antigenic Specificity, Methods: A Comparaion to Methods in Enzymology, 9, 465-472 (1996).
Weinachter et al., "Group Report 8: Models of Hypoxia and Cerebral Ischemia", Pharmacopsychiat, 23, 94-98, (1990).

Gotwals et al., "Divalent Cations Stabilize the alpha 1 beta 1 Integrin I Domain" Biochemistry 38:8280-8288 (1999).
Gotwals et al., "The alpha 1 beta 1 Integrin is expressed during Neointima Formation in Rat Arteries and Mediates Collagen Matrix Reorganization" J. Clin. Invets. 97:2469-2477 (1996).
Grayson et al., "alpha d beta 2 Integrin Is Expressed on Human Eosinophils and Functions as an Alternative Ligand for Vascular Cell Adhesion Molecule 1 (VCAM-I)" J. Exp. Med. 188:2187-2191 (1984).
Green et al., "Antigen-specific Human Monoclonal Antibodies From Mice Engineered with Human Heavy and Light Chain YACs" Nature Genetics 7:13-21 (1994).
Hemler et al. "Characterization of the Cell Surface Heterodimer VLA-4 and Related Peptides" J.Immunol. 262:11478-11485 (1987).
Hemler et al., "Glycoproteins of 210,000 and 130,000 M.W. on Activated T Cells: Cell Distribution and Antigenic Relation to Components on Resting Cells and T Cell Lines" J. Imunnol. 132:3011-3018 (1984).
Hemler et al., "Very Late Activation Antigens on Rheumatoid Synovial Fluid T Lymphocytes: Association with Stages of T Cell Activation" J. Clin. Invest 78:696-702 (1986).
Hemler et al., "VLA-I:A T Cell Surface Antigen which Defines a Novel Late Stage of Human T Cell Activation" Eur. J. Immunol. 15:502-508 (1985).
Hessle et al., "Basement membrane diversity detected by monoclonal antibodies" Differentiation 26:49-54 (1984).
Hokibara et al., "Effects of monoclonal antibodies to adhesion molecules on eosinophilic myocarditis in Toxocara canis-infected CBA/J mice", Clin. Exp. Immunol. 114, 236-244, 1998.
Holmes et al., "Conformational Correction Mechanisms Aiding Antigen Recognition by a Humanized Antibody" J. Exp. Med. 187:479-485 (1998).
Holt et al., "Domain antibodies: proteins for therapy", Trends Biotechnol. 2003; 21(11):484-490. (Abstract Only).
Hoogenboom et al. "Antibody phage display technology and its applications" (1998) Immunotechnology 4:1-20.
Hoogenboom et al. "Natural and designer binding sites made by phage display technology" (2000) Immunol Today 2:371-8.
Huang and Stollar "Construction of representative immunoglobulin variable region cDNA libraries from human peripheral blood lymphocytes without in vitro stimulation." (1991) J. Immunol. Methods 141:227-236.
Huang et al., "A Majority of Ig H Chain cDNA of Normal Human Adult Blood Lymphocytes Resembles cDNA for Fetal Ig and Natural Autoantibodies" J. Immunol. 151:5290-5300 (1993).
Hurtrel et al., "Different Time Course Patterns of Local Expression of Delayed—Typed Hypersensitivity to Sheep Red Blood Cells in Mice" Cell. Immunol. 142:252-263 (1992).
Huth et al., "NMR and Mutagenesis Evidence for an I Domain Allosteric Site that Regulates Lymphocyte Function-Associated Antigen 1 Ligand Binding" Proc. Natl. Acad. Sci. USA 97:5231-5236 (2000).
Ianaro et al., "Anti-Very Late Antigen-1 Monoclonal Antibody Modulates the Development of Secondary Lesion and T-Cell Response in Experimental Arthritis" Lab. Invest. 80:73-80 (2000).
Ignatius et al., "Molecular Cloning of the Rat Integrin alphal Subunit: A Receptor for Laminin and Collagen" J.Cell Biology 111:709-720 (1990).
International Preliminary Examination Report for PCT/US01/15004 dated Jul. 7, 2001.
International Preliminary Examination Report for PCT/US02/11521 dated Apr. 28, 2004.
International Preliminary Report on Patentability & Written Opinion for PCT/US2007/069654 dated Oct. 10, 2007.
International Preliminary Report on Patentability and Written Opinion for PCT/US12/23590 issued Aug. 8, 2013.
International Search Report and Written Opinion, International Application No. PCT/US2013/026034, dated Oct. 21, 2013.
International Search Report dated Feb. 24, 2004 from International Application No. PCT/US02/11521.
International Search Report dated Nov. 13, 2000 from International Application No. PCT/US00/15004.
International Search Report for PCT/07/69654 Dated Oct. 23, 2007.

(56) References Cited

OTHER PUBLICATIONS

International Search Report for PCT/US12/023590 dated Jul. 23, 2012.
Jones et al., "Principles of Protein-Protein Interactions" Proc. Natl. Acad. Sci. USA 93: 13-20 (1996).
Jones et al., "Replacing the Complementarity-Determining Regions in a Human Antibody with Those from a Mouse" Nature 321:522-525 (1986).
Jordi, "Integrin-collagen complex: a metal glutamate handshake" Structure 8(6):RI21-RI26 -2000.
Kakimoto et al., "The Effect of Anti-adhesion Molecule Antibody on the Development of Collagen- Induced Arthritis" Cell Immunol. 142:326-337 (1992).
Kamata et al., "Critical Threonine and Aspartic Acid Residues within the I Domains of beta 2 Integrins for Interactions with Intercellular Adhesion Molecule 1 (ICAM-1) and C3bi" J. Biological Chem. 270:12531-12535 (1995).
Karpusas et al., "Crystal Structure of the alpha 1 beta 1 Integrin I Domain in Complex with an Antibody Fab Fragment" J. Mol. Biol. 327:1031-1041 (2003).
Keely et al., "Alteration of collagen-dependent adhesion, motility, and morphogenesis by the expression of antisense alpha2 integrin mRNA in mammary cells" J. Cell Science 108:595-607 1995.
Kern et al., "The Role of the I Domain in Ligand Binding of the Human Integrin alpha 1 beta 1" J. Biol. Chem. 269:22811-55816 (1994).
Kim et al. "A novel binding site in collagen type III for integrins alpha1beta1 and alpha2beta1." (2005) J. Biol. Chem. 280:32512-32520.
Kinashi et al., "Adhesion Molecules in Hematopoietic Cells" Blood Cells 20:25-44 (1994).
King et al., "Echovirus 1 Interaction with the Human Very Late Antigen-2 (Integrin) Domain" J. Biol. Chem. 272:28518-28522 (1997).
Knight et al., "The Collagen-binding A-domains of Integrins and Recognize the Same Specific Amino Acid Sequence, GFOGER, in Native (Triple-helical) Collagens" J. Biol. Chem. 275:35-40 2000.
Kolbinger et al., "Humanization of a Mouse Anti-human IgE Antibody: A Potential Therapeutic for IgE-mediated Allergies" Protein Eng. 6:971-980 (1993).
Krieglstein, C.F., et al., "Collagen-Binding Integrin alpha1beta1 Regulates Intestinal Inflammation in Experimental Colitis," J. Clin. Invest., 110:1173-1782 (2002).
Laffon et al., Very Late Activation Antigen of Synovial Fluid T cells from Patients with Rheumatoid Arthritis and other Rheumatic Diseases Arthritis and Rheumatism 32:386-392 (1989).
Langholz et al., "Collagen and Collagenase Gene Expression in Three-dimensional Collagen Lattices Are Differentially Regulated by alpha 1 beta 1 and alpha 2 beta 1 Integrins" J. Cell Biol. 131:1903-1915 (1995).
Larson et al., "Primary Structure of the Leukocyte Function-associated Molecule-1 alpha Subunit: an Integrin with an Embedded Domain Defining a Protein Superfamily" J. Cell Biol. 108:703-712 (1989).
Lee et al., "Crystal Structure of the A Domain from the Subunit of Integrin CR3 (CD11b/CD18)" Cell 80:631-638 (1995).
Lee et al., "Two conformations of the integrin A-domain (I-domain): a pathway for activation" Structure 3:1333-1340 (1995).
Lees et al. "NXY-059 for acute ischemic stroke." (2006) N. Engl. J. Med. 354:588-600.
Leibiger et al., "Variable domain-linked oligosaccharides of a human monoclonal IgG: structure and influence on antigen binding", Biochem. J. (1999) 338:529-538.
U.S. Appl. No. 14/379,095, filed Feb. 14, 2013.

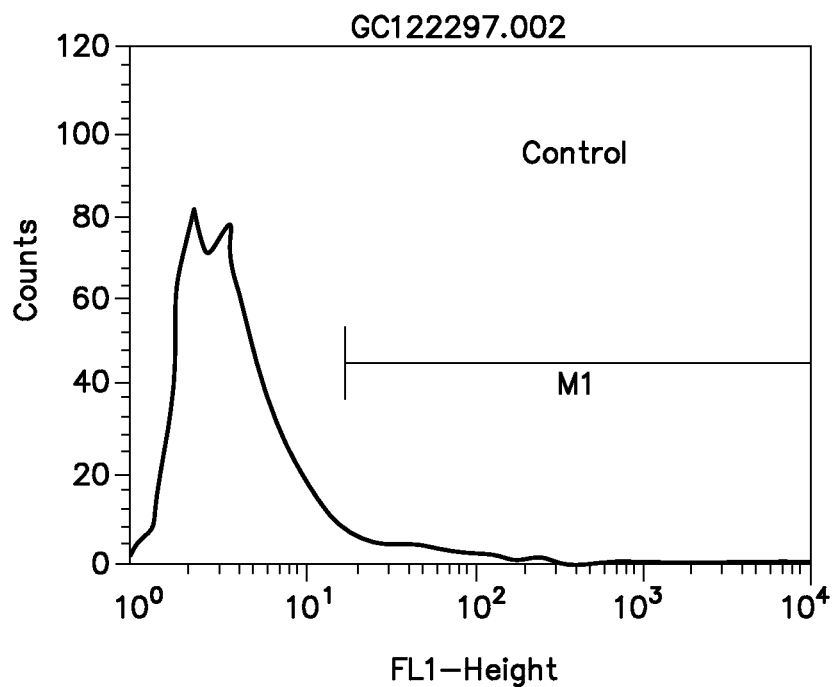
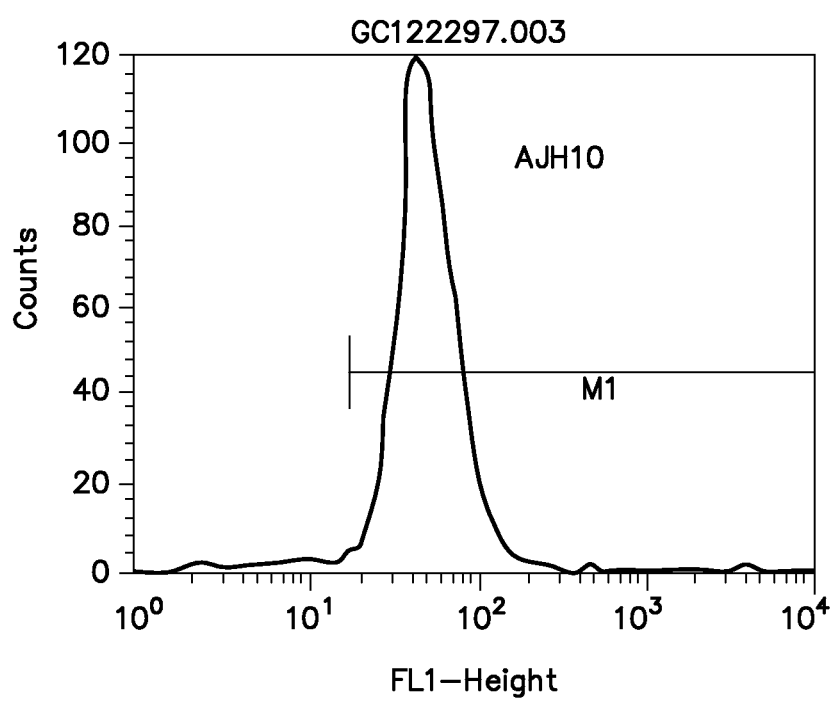
FIG. 14

FIG.19A-1

| | | | | | | | | | | | |
|---|---|---|---|---|---|---|---|---|---|---|---|
| ATOM | 1 | CB | THR | 145 | 131.250 | 52.244 | -9.297 | 1.00 | 82.68 | A | C |
| ATOM | 2 | OG1 | THR | 145 | 131.373 | 51.127 | -10.191 | 1.00 | 82.68 | A | O |
| ATOM | 3 | CG2 | THR | 145 | 132.601 | 52.936 | -9.145 | 1.00 | 82.68 | A | C |
| ATOM | 4 | C | THR | 145 | 129.280 | 51.301 | -8.080 | 1.00 | 146.54 | A | C |
| ATOM | 5 | O | THR | 145 | 128.489 | 51.352 | -7.134 | 1.00 | 146.94 | A | O |
| ATOM | 6 | N | THR | 145 | 131.576 | 50.663 | -7.360 | 1.00 | 144.92 | A | N |
| ATOM | 7 | CA | THR | 145 | 130.726 | 51.757 | -7.915 | 1.00 | 144.52 | A | C |
| ATOM | 8 | N | GLN | 146 | 128.941 | 50.856 | -9.288 | 1.00 | 36.14 | A | N |
| ATOM | 9 | CA | GLN | 146 | 127.592 | 50.397 | -9.569 | 1.00 | 34.29 | A | C |
| ATOM | 10 | CB | GLN | 146 | 127.046 | 51.086 | -10.823 | 1.00 | 99.89 | A | C |
| ATOM | 11 | CG | GLN | 146 | 127.887 | 50.902 | -12.065 | 1.00 | 99.89 | A | C |
| ATOM | 12 | CD | GLN | 146 | 127.274 | 51.575 | -13.279 | 1.00 | 99.89 | A | C |
| ATOM | 13 | OE1 | GLN | 146 | 127.787 | 51.454 | -14.392 | 1.00 | 99.89 | A | O |
| ATOM | 14 | NE2 | GLN | 146 | 126.170 | 52.290 | -13.070 | 1.00 | 99.89 | A | N |
| ATOM | 15 | C | GLN | 146 | 127.535 | 48.883 | -9.721 | 1.00 | 34.71 | A | C |
| ATOM | 16 | O | GLN | 146 | 128.084 | 48.314 | -10.667 | 1.00 | 36.57 | A | O |
| ATOM | 17 | N | LEU | 147 | 126.876 | 48.240 | -8.762 | 1.00 | 33.54 | A | N |
| ATOM | 18 | CA | LEU | 147 | 126.718 | 46.794 | -8.767 | 1.00 | 32.67 | A | C |
| ATOM | 19 | CB | LEU | 147 | 127.491 | 46.143 | -7.609 | 1.00 | 35.25 | A | C |
| ATOM | 20 | CG | LEU | 147 | 128.963 | 46.398 | -7.301 | 1.00 | 35.44 | A | C |
| ATOM | 21 | CD1 | LEU | 147 | 129.205 | 47.877 | -7.087 | 1.00 | 30.65 | A | C |
| ATOM | 22 | CD2 | LEU | 147 | 129.325 | 45.637 | -6.037 | 1.00 | 35.29 | A | C |
| ATOM | 23 | C | LEU | 147 | 125.247 | 46.451 | -8.575 | 1.00 | 31.65 | A | C |
| ATOM | 24 | O | LEU | 147 | 124.506 | 47.194 | -7.939 | 1.00 | 32.95 | A | O |
| ATOM | 25 | N | ASP | 148 | 124.832 | 45.325 | -9.142 | 1.00 | 25.19 | A | N |
| ATOM | 26 | CA | ASP | 148 | 123.477 | 44.817 | -8.976 | 1.00 | 22.65 | A | C |
| ATOM | 27 | CB | ASP | 148 | 122.907 | 44.329 | -10.302 | 1.00 | 27.55 | A | C |
| ATOM | 28 | CG | ASP | 148 | 122.330 | 45.446 | -11.125 | 1.00 | 27.17 | A | C |
| ATOM | 29 | OD1 | ASP | 148 | 121.787 | 45.158 | -12.208 | 1.00 | 26.28 | A | O |
| ATOM | 30 | OD2 | ASP | 148 | 122.413 | 46.612 | -10.686 | 1.00 | 25.35 | A | O |
| ATOM | 31 | C | ASP | 148 | 123.664 | 43.638 | -8.025 | 1.00 | 19.03 | A | C |
| ATOM | 32 | O | ASP | 148 | 124.119 | 42.567 | -8.422 | 1.00 | 18.33 | A | O |
| ATOM | 33 | N | ILE | 149 | 123.341 | 43.848 | -6.760 | 1.00 | 16.75 | A | N |
| ATOM | 34 | CA | ILE | 149 | 123.502 | 42.809 | -5.761 | 1.00 | 15.69 | A | C |
| ATOM | 35 | CB | ILE | 149 | 124.041 | 43.391 | -4.442 | 1.00 | 18.53 | A | C |
| ATOM | 36 | CG2 | ILE | 149 | 124.401 | 42.269 | -3.485 | 1.00 | 13.54 | A | C |
| ATOM | 37 | CG1 | ILE | 149 | 125.271 | 44.251 | -4.718 | 1.00 | 14.25 | A | C |
| ATOM | 38 | CD1 | ILE | 149 | 125.819 | 44.932 | -3.497 | 1.00 | 17.00 | A | C |
| ATOM | 39 | C | ILE | 149 | 122.185 | 42.129 | -5.456 | 1.00 | 17.34 | A | C |
| ATOM | 40 | O | ILE | 149 | 121.191 | 42.794 | -5.181 | 1.00 | 17.74 | A | O |
| ATOM | 41 | N | VAL | 150 | 122.175 | 40.805 | -5.526 | 1.00 | 11.00 | A | N |
| ATOM | 42 | CA | VAL | 150 | 120.987 | 40.036 | -5.193 | 1.00 | 12.56 | A | C |
| ATOM | 43 | CB | VAL | 150 | 120.571 | 39.089 | -6.336 | 1.00 | 16.85 | A | C |
| ATOM | 44 | CG1 | VAL | 150 | 119.409 | 38.210 | -5.885 | 1.00 | 19.04 | A | C |
| ATOM | 45 | CG2 | VAL | 150 | 120.164 | 39.894 | -7.555 | 1.00 | 18.66 | A | C |
| ATOM | 46 | C | VAL | 150 | 121.367 | 39.212 | -3.970 | 1.00 | 10.12 | A | C |
| ATOM | 47 | O | VAL | 150 | 122.387 | 38.526 | -3.973 | 1.00 | 8.27 | A | O |
| ATOM | 48 | N | ILE | 151 | 120.573 | 39.303 | -2.912 | 1.00 | 20.50 | A | N |
| ATOM | 49 | CA | ILE | 151 | 120.856 | 38.537 | -1.699 | 1.00 | 19.30 | A | C |
| ATOM | 50 | CB | ILE | 151 | 120.653 | 39.392 | -0.439 | 1.00 | 14.22 | A | C |
| ATOM | 51 | CG2 | ILE | 151 | 121.039 | 38.601 | 0.785 | 1.00 | 10.58 | A | C |
| ATOM | 52 | CG1 | ILE | 151 | 121.515 | 40.659 | -0.532 | 1.00 | 12.64 | A | C |
| ATOM | 53 | CD1 | ILE | 151 | 121.283 | 41.660 | 0.593 | 1.00 | 14.62 | A | C |
| ATOM | 54 | C | ILE | 151 | 119.931 | 37.329 | -1.646 | 1.00 | 17.42 | A | C |
| ATOM | 55 | O | ILE | 151 | 118.715 | 37.459 | -1.777 | 1.00 | 17.66 | A | O |
| ATOM | 56 | N | VAL | 152 | 120.511 | 36.150 | -1.470 | 1.00 | 17.56 | A | N |
| ATOM | 57 | CA | VAL | 152 | 119.741 | 34.915 | -1.428 | 1.00 | 18.41 | A | C |
| ATOM | 58 | CB | VAL | 152 | 120.395 | 33.849 | -2.309 | 1.00 | 11.45 | A | C |
| ATOM | 59 | CG1 | VAL | 152 | 119.470 | 32.664 | -2.460 | 1.00 | 10.58 | A | C |
| ATOM | 60 | CG2 | VAL | 152 | 120.758 | 34.458 | -3.667 | 1.00 | 7.89 | A | C |
| ATOM | 61 | C | VAL | 152 | 119.675 | 34.404 | -0.003 | 1.00 | 16.31 | A | C |
| ATOM | 62 | O | VAL | 152 | 120.602 | 33.755 | 0.469 | 1.00 | 9.91 | A | O |
| ATOM | 63 | N | LEU | 153 | 118.568 | 34.692 | 0.672 | 1.00 | 19.79 | A | N |
| ATOM | 64 | CA | LEU | 153 | 118.367 | 34.297 | 2.061 | 1.00 | 19.90 | A | C |
| ATOM | 65 | CB | LEU | 153 | 117.530 | 35.361 | 2.766 | 1.00 | 21.44 | A | C |
| ATOM | 66 | CG | LEU | 153 | 118.250 | 36.403 | 3.623 | 1.00 | 23.22 | A | C |
| ATOM | 67 | CD1 | LEU | 153 | 119.699 | 36.561 | 3.185 | 1.00 | 23.73 | A | C |
| ATOM | 68 | CD2 | LEU | 153 | 117.494 | 37.721 | 3.530 | 1.00 | 25.76 | A | C |
| ATOM | 69 | C | LEU | 153 | 117.732 | 32.929 | 2.300 | 1.00 | 20.96 | A | C |
| ATOM | 70 | O | LEU | 153 | 116.724 | 32.574 | 1.690 | 1.00 | 19.96 | A | O |
| ATOM | 71 | N | ASP | 154 | 118.336 | 32.165 | 3.200 | 1.00 | 19.89 | A | N |
| ATOM | 72 | CA | ASP | 154 | 117.820 | 30.854 | 3.554 | 1.00 | 19.37 | A | C |
| ATOM | 73 | CB | ASP | 154 | 118.952 | 29.983 | 4.129 | 1.00 | 22.72 | A | C |

FIG. 19A-2

| ATOM | 74 | CG | ASP | 154 | 118.486 | 28.601 | 4.546 | 1.00 | 21.92 | A | C |
|---|---|---|---|---|---|---|---|---|---|---|---|
| ATOM | 75 | OD1 | ASP | 154 | 117.266 | 28.363 | 4.537 | 1.00 | 25.43 | A | O |
| ATOM | 76 | OD2 | ASP | 154 | 119.340 | 27.754 | 4.893 | 1.00 | 18.24 | A | O |
| ATOM | 77 | C | ASP | 154 | 116.770 | 31.153 | 4.623 | 1.00 | 22.71 | A | C |
| ATOM | 78 | O | ASP | 154 | 117.062 | 31.802 | 5.630 | 1.00 | 19.03 | A | O |
| ATOM | 79 | N | GLY | 155 | 115.540 | 30.718 | 4.393 | 1.00 | 3.06 | A | N |
| ATOM | 80 | CA | GLY | 155 | 114.491 | 30.948 | 5.370 | 1.00 | 5.13 | A | C |
| ATOM | 81 | C | GLY | 155 | 113.840 | 29.638 | 5.788 | 1.00 | 6.39 | A | C |
| ATOM | 82 | O | GLY | 155 | 112.751 | 29.633 | 6.368 | 1.00 | 8.88 | A | O |
| ATOM | 83 | N | SER | 156 | 114.512 | 28.521 | 5.494 | 1.00 | 19.70 | A | N |
| ATOM | 84 | CA | SER | 156 | 114.011 | 27.191 | 5.832 | 1.00 | 24.28 | A | C |
| ATOM | 85 | CB | SER | 156 | 114.994 | 26.111 | 5.353 | 1.00 | 33.45 | A | C |
| ATOM | 86 | OG | SER | 156 | 116.261 | 26.252 | 5.967 | 1.00 | 36.37 | A | O |
| ATOM | 87 | C | SER | 156 | 113.773 | 27.054 | 7.330 | 1.00 | 21.27 | A | C |
| ATOM | 88 | O | SER | 156 | 114.270 | 27.843 | 8.128 | 1.00 | 24.45 | A | O |
| ATOM | 89 | N | ASN | 157 | 113.008 | 26.037 | 7.700 | 1.00 | 21.98 | A | N |
| ATOM | 90 | CA | ASN | 157 | 112.686 | 25.802 | 9.091 | 1.00 | 19.06 | A | C |
| ATOM | 91 | CB | ASN | 157 | 112.027 | 24.435 | 9.247 | 1.00 | 21.82 | A | C |
| ATOM | 92 | CG | ASN | 157 | 110.586 | 24.434 | 8.785 | 1.00 | 23.31 | A | C |
| ATOM | 93 | OD1 | ASN | 157 | 109.944 | 23.385 | 8.706 | 1.00 | 20.38 | A | O |
| ATOM | 94 | ND2 | ASN | 157 | 110.066 | 25.612 | 8.479 | 1.00 | 20.59 | A | N |
| ATOM | 95 | C | ASN | 157 | 113.859 | 25.913 | 10.048 | 1.00 | 17.03 | A | C |
| ATOM | 96 | O | ASN | 157 | 113.720 | 26.498 | 11.132 | 1.00 | 15.01 | A | O |
| ATOM | 97 | N | SER | 158 | 115.006 | 25.367 | 9.653 | 1.00 | 15.99 | A | N |
| ATOM | 98 | CA | SER | 158 | 116.179 | 25.378 | 10.510 | 1.00 | 14.20 | A | C |
| ATOM | 99 | CB | SER | 158 | 117.327 | 24.603 | 9.864 | 1.00 | 26.18 | A | C |
| ATOM | 100 | OG | SER | 158 | 117.597 | 25.067 | 8.562 | 1.00 | 28.89 | A | O |
| ATOM | 101 | C | SER | 158 | 116.656 | 26.753 | 10.941 | 1.00 | 14.97 | A | C |
| ATOM | 102 | O | SER | 158 | 117.053 | 26.930 | 12.097 | 1.00 | 12.14 | A | O |
| ATOM | 103 | N | ILE | 159 | 116.623 | 27.730 | 10.039 | 1.00 | 8.33 | A | N |
| ATOM | 104 | CA | ILE | 159 | 117.050 | 29.083 | 10.379 | 1.00 | 12.93 | A | C |
| ATOM | 105 | CB | ILE | 159 | 116.801 | 30.035 | 9.193 | 1.00 | 9.66 | A | C |
| ATOM | 106 | CG2 | ILE | 159 | 117.138 | 31.479 | 9.592 | 1.00 | 9.57 | A | C |
| ATOM | 107 | CG1 | ILE | 159 | 117.650 | 29.609 | 8.000 | 1.00 | 14.44 | A | C |
| ATOM | 108 | CD1 | ILE | 159 | 119.134 | 29.804 | 8.204 | 1.00 | 19.60 | A | C |
| ATOM | 109 | C | ILE | 159 | 116.292 | 29.604 | 11.616 | 1.00 | 17.24 | A | C |
| ATOM | 110 | O | ILE | 159 | 115.059 | 29.575 | 11.659 | 1.00 | 16.65 | A | O |
| ATOM | 111 | N | TYR | 160 | 117.032 | 30.084 | 12.611 | 1.00 | 29.54 | A | N |
| ATOM | 112 | CA | TYR | 160 | 116.438 | 30.600 | 13.849 | 1.00 | 31.67 | A | C |
| ATOM | 113 | CB | TYR | 160 | 115.775 | 29.455 | 14.639 | 1.00 | 16.89 | A | C |
| ATOM | 114 | CG | TYR | 160 | 115.094 | 29.869 | 15.941 | 1.00 | 13.65 | A | C |
| ATOM | 115 | CD1 | TYR | 160 | 113.717 | 30.089 | 15.993 | 1.00 | 16.07 | A | C |
| ATOM | 116 | CE1 | TYR | 160 | 113.088 | 30.466 | 17.186 | 1.00 | 13.67 | A | C |
| ATOM | 117 | CD2 | TYR | 160 | 115.828 | 30.038 | 17.116 | 1.00 | 11.30 | A | C |
| ATOM | 118 | CE2 | TYR | 160 | 115.211 | 30.416 | 18.304 | 1.00 | 15.01 | A | C |
| ATOM | 119 | CZ | TYR | 160 | 113.841 | 30.627 | 18.338 | 1.00 | 14.36 | A | C |
| ATOM | 120 | OH | TYR | 160 | 113.227 | 30.987 | 19.522 | 1.00 | 19.36 | A | O |
| ATOM | 121 | C | TYR | 160 | 117.498 | 31.264 | 14.734 | 1.00 | 33.39 | A | C |
| ATOM | 122 | O | TYR | 160 | 118.567 | 30.703 | 14.970 | 1.00 | 39.31 | A | O |
| ATOM | 123 | N | PRO | 161 | 117.206 | 32.467 | 15.248 | 1.00 | 31.87 | A | N |
| ATOM | 124 | CD | PRO | 161 | 117.988 | 33.002 | 16.380 | 1.00 | 14.17 | A | C |
| ATOM | 125 | CA | PRO | 161 | 115.969 | 33.234 | 15.055 | 1.00 | 30.15 | A | C |
| ATOM | 126 | CB | PRO | 161 | 115.831 | 33.976 | 16.379 | 1.00 | 18.55 | A | C |
| ATOM | 127 | CG | PRO | 161 | 117.278 | 34.291 | 16.703 | 1.00 | 21.71 | A | C |
| ATOM | 128 | C | PRO | 161 | 116.038 | 34.183 | 13.852 | 1.00 | 28.81 | A | C |
| ATOM | 129 | O | PRO | 161 | 117.074 | 34.792 | 13.580 | 1.00 | 28.13 | A | O |
| ATOM | 130 | N | TRP | 162 | 114.919 | 34.320 | 13.149 | 1.00 | 29.23 | A | N |
| ATOM | 131 | CA | TRP | 162 | 114.839 | 35.170 | 11.967 | 1.00 | 30.30 | A | C |
| ATOM | 132 | CB | TRP | 162 | 113.388 | 35.250 | 11.493 | 1.00 | 29.17 | A | C |
| ATOM | 133 | CG | TRP | 162 | 113.214 | 35.826 | 10.120 | 1.00 | 29.69 | A | C |
| ATOM | 134 | CD2 | TRP | 162 | 113.838 | 35.375 | 8.912 | 1.00 | 24.53 | A | C |
| ATOM | 135 | CE2 | TRP | 162 | 113.338 | 36.175 | 7.859 | 1.00 | 28.08 | A | C |
| ATOM | 136 | CE3 | TRP | 162 | 114.768 | 34.373 | 8.615 | 1.00 | 23.94 | A | C |
| ATOM | 137 | CD1 | TRP | 162 | 112.387 | 36.854 | 9.758 | 1.00 | 28.88 | A | C |
| ATOM | 138 | NE1 | TRP | 162 | 112.455 | 37.071 | 8.403 | 1.00 | 30.75 | A | N |
| ATOM | 139 | CZ2 | TRP | 162 | 113.741 | 36.000 | 6.532 | 1.00 | 26.62 | A | C |
| ATOM | 140 | CZ3 | TRP | 162 | 115.167 | 34.202 | 7.288 | 1.00 | 22.27 | A | C |
| ATOM | 141 | CH2 | TRP | 162 | 114.652 | 35.012 | 6.268 | 1.00 | 27.18 | A | C |
| ATOM | 142 | C | TRP | 162 | 115.381 | 36.579 | 12.210 | 1.00 | 32.08 | A | C |
| ATOM | 143 | O | TRP | 162 | 116.074 | 37.133 | 11.352 | 1.00 | 31.23 | A | O |
| ATOM | 144 | N | GLU | 163 | 115.077 | 37.147 | 13.381 | 1.00 | 25.22 | A | N |
| ATOM | 145 | CA | GLU | 163 | 115.510 | 38.504 | 13.734 | 1.00 | 27.00 | A | C |
| ATOM | 146 | CB | GLU | 163 | 115.108 | 38.857 | 15.172 | 1.00 | 105.95 | A | C |

FIG. 19A-3

| | | | | | | | | | | | |
|---|---|---|---|---|---|---|---|---|---|---|---|
| ATOM | 147 | CG | GLU | 163 | 115.906 | 38.145 | 16.248 | 1.00 | 112.26 | A | C |
| ATOM | 148 | CD | GLU | 163 | 115.816 | 38.833 | 17.603 | 1.00 | 114.40 | A | C |
| ATOM | 149 | OE1 | GLU | 163 | 116.310 | 39.975 | 17.732 | 1.00 | 116.11 | A | O |
| ATOM | 150 | OE2 | GLU | 163 | 115.253 | 38.232 | 18.541 | 1.00 | 113.36 | A | O |
| ATOM | 151 | C | GLU | 163 | 117.008 | 38.723 | 13.557 | 1.00 | 26.66 | A | C |
| ATOM | 152 | O | GLU | 163 | 117.448 | 39.799 | 13.136 | 1.00 | 22.83 | A | O |
| ATOM | 153 | N | SER | 164 | 117.800 | 37.709 | 13.865 | 1.00 | 20.71 | A | N |
| ATOM | 154 | CA | SER | 164 | 119.241 | 37.850 | 13.715 | 1.00 | 17.90 | A | C |
| ATOM | 155 | CB | SER | 164 | 119.955 | 36.647 | 14.335 | 1.00 | 27.61 | A | C |
| ATOM | 156 | OG | SER | 164 | 119.716 | 36.582 | 15.731 | 1.00 | 33.50 | A | O |
| ATOM | 157 | C | SER | 164 | 119.601 | 37.988 | 12.235 | 1.00 | 18.66 | A | C |
| ATOM | 158 | O | SER | 164 | 120.436 | 38.813 | 11.863 | 1.00 | 21.86 | A | O |
| ATOM | 159 | N | VAL | 165 | 118.956 | 37.179 | 11.398 | 1.00 | 9.03 | A | N |
| ATOM | 160 | CA | VAL | 165 | 119.189 | 37.213 | 9.961 | 1.00 | 8.42 | A | C |
| ATOM | 161 | CB | VAL | 165 | 118.303 | 36.166 | 9.226 | 1.00 | 21.53 | A | C |
| ATOM | 162 | CG1 | VAL | 165 | 118.296 | 36.430 | 7.721 | 1.00 | 22.92 | A | C |
| ATOM | 163 | CG2 | VAL | 165 | 118.826 | 34.760 | 9.505 | 1.00 | 24.53 | A | C |
| ATOM | 164 | C | VAL | 165 | 118.873 | 38.595 | 9.411 | 1.00 | 9.58 | A | C |
| ATOM | 165 | O | VAL | 165 | 119.610 | 39.131 | 8.574 | 1.00 | 11.40 | A | O |
| ATOM | 166 | N | ILE | 166 | 117.772 | 39.169 | 9.887 | 1.00 | 17.73 | A | N |
| ATOM | 167 | CA | ILE | 166 | 117.351 | 40.482 | 9.427 | 1.00 | 17.05 | A | C |
| ATOM | 168 | CB | ILE | 166 | 115.903 | 40.763 | 9.840 | 1.00 | 21.02 | A | C |
| ATOM | 169 | CG2 | ILE | 166 | 115.489 | 42.162 | 9.413 | 1.00 | 20.23 | A | C |
| ATOM | 170 | CG1 | ILE | 166 | 114.997 | 39.737 | 9.164 | 1.00 | 20.88 | A | C |
| ATOM | 171 | CD1 | ILE | 166 | 113.538 | 39.919 | 9.499 | 1.00 | 17.28 | A | C |
| ATOM | 172 | C | ILE | 166 | 118.281 | 41.564 | 9.929 | 1.00 | 16.50 | A | C |
| ATOM | 173 | O | ILE | 166 | 118.560 | 42.520 | 9.206 | 1.00 | 18.25 | A | O |
| ATOM | 174 | N | ALA | 167 | 118.774 | 41.413 | 11.157 | 1.00 | 25.46 | A | N |
| ATOM | 175 | CA | ALA | 167 | 119.711 | 42.391 | 11.710 | 1.00 | 26.06 | A | C |
| ATOM | 176 | CB | ALA | 167 | 120.095 | 42.021 | 13.100 | 1.00 | 7.73 | A | C |
| ATOM | 177 | C | ALA | 167 | 120.941 | 42.371 | 10.823 | 1.00 | 27.27 | A | C |
| ATOM | 178 | O | ALA | 167 | 121.546 | 43.414 | 10.544 | 1.00 | 23.87 | A | O |
| ATOM | 179 | N | PHE | 168 | 121.303 | 41.167 | 10.383 | 1.00 | 18.13 | A | N |
| ATOM | 180 | CA | PHE | 168 | 122.442 | 40.989 | 9.498 | 1.00 | 16.65 | A | C |
| ATOM | 181 | CB | PHE | 168 | 122.626 | 39.513 | 9.158 | 1.00 | 32.51 | A | C |
| ATOM | 182 | CG | PHE | 168 | 123.514 | 39.273 | 7.970 | 1.00 | 31.01 | A | C |
| ATOM | 183 | CD1 | PHE | 168 | 122.968 | 39.066 | 6.701 | 1.00 | 32.61 | A | C |
| ATOM | 184 | CD2 | PHE | 168 | 124.894 | 39.290 | 8.106 | 1.00 | 29.32 | A | C |
| ATOM | 185 | CE1 | PHE | 168 | 123.792 | 38.882 | 5.585 | 1.00 | 31.09 | A | C |
| ATOM | 186 | CE2 | PHE | 168 | 125.724 | 39.109 | 7.000 | 1.00 | 31.14 | A | C |
| ATOM | 187 | CZ | PHE | 168 | 125.173 | 38.906 | 5.738 | 1.00 | 33.63 | A | C |
| ATOM | 188 | C | PHE | 168 | 122.222 | 41.796 | 8.227 | 1.00 | 17.51 | A | C |
| ATOM | 189 | O | PHE | 168 | 123.139 | 42.475 | 7.750 | 1.00 | 13.95 | A | O |
| ATOM | 190 | N | LEU | 169 | 121.007 | 41.719 | 7.680 | 1.00 | 16.88 | A | N |
| ATOM | 191 | CA | LEU | 169 | 120.677 | 42.467 | 6.471 | 1.00 | 19.47 | A | C |
| ATOM | 192 | CB | LEU | 169 | 119.262 | 42.140 | 6.000 | 1.00 | 14.12 | A | C |
| ATOM | 193 | CG | LEU | 169 | 119.041 | 40.860 | 5.213 | 1.00 | 13.28 | A | C |
| ATOM | 194 | CD1 | LEU | 169 | 117.662 | 40.952 | 4.603 | 1.00 | 9.74 | A | C |
| ATOM | 195 | CD2 | LEU | 169 | 120.100 | 40.694 | 4.127 | 1.00 | 10.14 | A | C |
| ATOM | 196 | C | LEU | 169 | 120.777 | 43.966 | 6.731 | 1.00 | 21.77 | A | C |
| ATOM | 197 | O | LEU | 169 | 121.409 | 44.694 | 5.968 | 1.00 | 23.20 | A | O |
| ATOM | 198 | N | ASN | 170 | 120.150 | 44.419 | 7.815 | 1.00 | 20.45 | A | N |
| ATOM | 199 | CA | ASN | 170 | 120.159 | 45.832 | 8.175 | 1.00 | 17.58 | A | C |
| ATOM | 200 | CB | ASN | 170 | 119.534 | 46.018 | 9.562 | 1.00 | 31.53 | A | C |
| ATOM | 201 | CG | ASN | 170 | 119.017 | 47.426 | 9.791 | 1.00 | 34.95 | A | C |
| ATOM | 202 | OD1 | ASN | 170 | 119.740 | 48.282 | 10.284 | 1.00 | 30.48 | A | O |
| ATOM | 203 | ND2 | ASN | 170 | 117.762 | 47.671 | 9.421 | 1.00 | 32.86 | A | N |
| ATOM | 204 | C | ASN | 170 | 121.587 | 46.341 | 8.151 | 1.00 | 17.59 | A | C |
| ATOM | 205 | O | ASN | 170 | 121.941 | 47.174 | 7.321 | 1.00 | 17.80 | A | O |
| ATOM | 206 | N | ASP | 171 | 122.412 | 45.812 | 9.040 | 1.00 | 11.82 | A | N |
| ATOM | 207 | CA | ASP | 171 | 123.816 | 46.218 | 9.120 | 1.00 | 13.94 | A | C |
| ATOM | 208 | CB | ASP | 171 | 124.588 | 45.282 | 10.048 | 1.00 | 56.27 | A | C |
| ATOM | 209 | CG | ASP | 171 | 124.405 | 45.627 | 11.508 | 1.00 | 63.92 | A | C |
| ATOM | 210 | OD1 | ASP | 171 | 123.248 | 45.689 | 11.971 | 1.00 | 66.14 | A | O |
| ATOM | 211 | OD2 | ASP | 171 | 125.427 | 45.834 | 12.196 | 1.00 | 65.78 | A | O |
| ATOM | 212 | C | ASP | 171 | 124.509 | 46.244 | 7.760 | 1.00 | 15.43 | A | C |
| ATOM | 213 | O | ASP | 171 | 125.223 | 47.194 | 7.435 | 1.00 | 14.15 | A | O |
| ATOM | 214 | N | LEU | 172 | 124.289 | 45.200 | 6.966 | 1.00 | 15.45 | A | N |
| ATOM | 215 | CA | LEU | 172 | 124.910 | 45.099 | 5.650 | 1.00 | 16.13 | A | C |
| ATOM | 216 | CB | LEU | 172 | 124.633 | 43.717 | 5.047 | 1.00 | 10.67 | A | C |
| ATOM | 217 | CG | LEU | 172 | 125.667 | 43.058 | 4.123 | 1.00 | 10.16 | A | C |
| ATOM | 218 | CD1 | LEU | 172 | 124.905 | 42.379 | 2.979 | 1.00 | 7.76 | A | C |
| ATOM | 219 | CD2 | LEU | 172 | 126.672 | 44.070 | 3.594 | 1.00 | 8.33 | A | C |

FIG. 19A-4

| | | | | | | | | | | | |
|---|---|---|---|---|---|---|---|---|---|---|---|
| ATOM | 220 | C   | LEU | 172 | 124.401 | 46.178 |  4.699 | 1.00 |  16.47 | A | C |
| ATOM | 221 | O   | LEU | 172 | 125.182 | 46.951 |  4.156 | 1.00 |  16.46 | A | O |
| ATOM | 222 | N   | LEU | 173 | 123.088 | 46.226 |  4.509 | 1.00 |  30.03 | A | N |
| ATOM | 223 | CA  | LEU | 173 | 122.475 | 47.193 |  3.609 | 1.00 |  32.78 | A | C |
| ATOM | 224 | CB  | LEU | 173 | 120.967 | 46.932 |  3.474 | 1.00 |  23.11 | A | C |
| ATOM | 225 | CG  | LEU | 173 | 120.357 | 45.803 |  2.627 | 1.00 |  24.46 | A | C |
| ATOM | 226 | CD1 | LEU | 173 | 121.069 | 45.702 |  1.292 | 1.00 |  27.98 | A | C |
| ATOM | 227 | CD2 | LEU | 173 | 120.456 | 44.501 |  3.353 | 1.00 |  25.01 | A | C |
| ATOM | 228 | C   | LEU | 173 | 122.675 | 48.663 |  3.984 | 1.00 |  34.21 | A | C |
| ATOM | 229 | O   | LEU | 173 | 122.937 | 49.495 |  3.105 | 1.00 |  30.93 | A | O |
| ATOM | 230 | N   | LYS | 174 | 122.558 | 48.989 |  5.271 | 1.00 |  33.34 | A | N |
| ATOM | 231 | CA  | LYS | 174 | 122.684 | 50.379 |  5.693 | 1.00 |  33.56 | A | C |
| ATOM | 232 | CB  | LYS | 174 | 122.428 | 50.508 |  7.193 | 1.00 |  32.34 | A | C |
| ATOM | 233 | CG  | LYS | 174 | 123.590 | 50.195 |  8.102 | 1.00 |  32.67 | A | C |
| ATOM | 234 | CD  | LYS | 174 | 123.170 | 50.471 |  9.551 | 1.00 |  31.92 | A | C |
| ATOM | 235 | CE  | LYS | 174 | 124.365 | 50.601 | 10.504 | 1.00 |  27.17 | A | C |
| ATOM | 236 | NZ  | LYS | 174 | 125.178 | 49.351 | 10.664 | 1.00 |  23.64 | A | N |
| ATOM | 237 | C   | LYS | 174 | 124.004 | 51.046 |  5.317 | 1.00 |  31.92 | A | C |
| ATOM | 238 | O   | LYS | 174 | 124.060 | 52.256 |  5.142 | 1.00 |  32.79 | A | O |
| ATOM | 239 | N   | ARG | 175 | 125.059 | 50.255 |  5.176 | 1.00 |  34.34 | A | N |
| ATOM | 240 | CA  | ARG | 175 | 126.385 | 50.759 |  4.797 | 1.00 |  36.57 | A | C |
| ATOM | 241 | CB  | ARG | 175 | 127.468 | 49.712 |  5.125 | 1.00 |  50.56 | A | C |
| ATOM | 242 | CG  | ARG | 175 | 127.708 | 49.400 |  6.606 | 1.00 |  57.49 | A | C |
| ATOM | 243 | CD  | ARG | 175 | 128.550 | 48.120 |  6.760 | 1.00 |  61.77 | A | C |
| ATOM | 244 | NE  | ARG | 175 | 129.398 | 48.107 |  7.957 | 1.00 |  66.67 | A | N |
| ATOM | 245 | CZ  | ARG | 175 | 128.954 | 48.049 |  9.211 | 1.00 |  70.25 | A | C |
| ATOM | 246 | NH1 | ARG | 175 | 127.653 | 47.997 |  9.461 | 1.00 |  70.45 | A | N |
| ATOM | 247 | NH2 | ARG | 175 | 129.819 | 48.039 | 10.219 | 1.00 |  71.15 | A | N |
| ATOM | 248 | C   | ARG | 175 | 126.461 | 51.051 |  3.288 | 1.00 |  34.10 | A | C |
| ATOM | 249 | O   | ARG | 175 | 127.487 | 51.522 |  2.796 | 1.00 |  33.94 | A | O |
| ATOM | 250 | N   | MET | 176 | 125.384 | 50.766 |  2.557 | 1.00 |  18.81 | A | N |
| ATOM | 251 | CA  | MET | 176 | 125.371 | 50.959 |  1.104 | 1.00 |  15.29 | A | C |
| ATOM | 252 | CB  | MET | 176 | 124.758 | 49.728 |  0.431 | 1.00 |  45.67 | A | C |
| ATOM | 253 | CG  | MET | 176 | 125.646 | 48.505 |  0.474 | 1.00 |  42.57 | A | C |
| ATOM | 254 | SD  | MET | 176 | 124.887 | 47.063 | -0.292 | 1.00 |  46.71 | A | S |
| ATOM | 255 | CE  | MET | 176 | 124.633 | 46.046 |  1.139 | 1.00 |  40.22 | A | C |
| ATOM | 256 | C   | MET | 176 | 124.679 | 52.199 |  0.546 | 1.00 |  18.80 | A | C |
| ATOM | 257 | O   | MET | 176 | 123.797 | 52.768 |  1.176 | 1.00 |  18.87 | A | O |
| ATOM | 258 | N   | ASP | 177 | 125.098 | 52.605 | -0.652 | 1.00 |  31.75 | A | N |
| ATOM | 259 | CA  | ASP | 177 | 124.504 | 53.744 | -1.344 | 1.00 |  34.24 | A | C |
| ATOM | 260 | CB  | ASP | 177 | 125.584 | 54.671 | -1.903 | 1.00 | 129.70 | A | C |
| ATOM | 261 | CG  | ASP | 177 | 126.196 | 55.556 | -0.838 | 1.00 | 132.65 | A | C |
| ATOM | 262 | OD1 | ASP | 177 | 127.004 | 56.437 | -1.194 | 1.00 | 132.32 | A | O |
| ATOM | 263 | OD2 | ASP | 177 | 125.869 | 55.372 |  0.354 | 1.00 | 134.30 | A | O |
| ATOM | 264 | C   | ASP | 177 | 123.638 | 53.207 | -2.480 | 1.00 |  34.16 | A | C |
| ATOM | 265 | O   | ASP | 177 | 124.085 | 53.107 | -3.617 | 1.00 |  33.88 | A | O |
| ATOM | 266 | N   | ILE | 178 | 122.402 | 52.848 | -2.153 | 1.00 |  22.62 | A | N |
| ATOM | 267 | CA  | ILE | 178 | 121.464 | 52.307 | -3.122 | 1.00 |  22.76 | A | C |
| ATOM | 268 | CB  | ILE | 178 | 120.326 | 51.524 | -2.407 | 1.00 |  26.30 | A | C |
| ATOM | 269 | CG2 | ILE | 178 | 119.208 | 51.207 | -3.390 | 1.00 |  24.58 | A | C |
| ATOM | 270 | CG1 | ILE | 178 | 120.866 | 50.222 | -1.803 | 1.00 |  27.36 | A | C |
| ATOM | 271 | CD1 | ILE | 178 | 121.188 | 50.292 | -0.325 | 1.00 |  29.20 | A | C |
| ATOM | 272 | C   | ILE | 178 | 120.848 | 53.398 | -4.009 | 1.00 |  21.90 | A | C |
| ATOM | 273 | O   | ILE | 178 | 120.532 | 54.501 | -3.539 | 1.00 |  23.89 | A | O |
| ATOM | 274 | N   | GLY | 179 | 120.669 | 53.077 | -5.292 | 1.00 |  18.17 | A | N |
| ATOM | 275 | CA  | GLY | 179 | 120.091 | 54.029 | -6.226 | 1.00 |  17.89 | A | C |
| ATOM | 276 | C   | GLY | 179 | 120.123 | 53.536 | -7.658 | 1.00 |  18.65 | A | C |
| ATOM | 277 | O   | GLY | 179 | 121.019 | 52.786 | -8.023 | 1.00 |  16.80 | A | O |
| ATOM | 278 | N   | PRO | 180 | 119.150 | 53.937 | -8.498 | 1.00 |  18.34 | A | N |
| ATOM | 279 | CD  | PRO | 180 | 117.980 | 54.770 | -8.159 | 1.00 |  16.60 | A | C |
| ATOM | 280 | CA  | PRO | 180 | 119.094 | 53.512 | -9.901 | 1.00 |  19.40 | A | C |
| ATOM | 281 | CB  | PRO | 180 | 118.044 | 54.442 |-10.498 | 1.00 |  15.44 | A | C |
| ATOM | 282 | CG  | PRO | 180 | 117.074 | 54.573 | -9.365 | 1.00 |  17.83 | A | C |
| ATOM | 283 | C   | PRO | 180 | 120.432 | 53.622 |-10.597 | 1.00 |  21.18 | A | C |
| ATOM | 284 | O   | PRO | 180 | 120.706 | 52.877 |-11.529 | 1.00 |  21.82 | A | O |
| ATOM | 285 | N   | LYS | 181 | 121.262 | 54.553 |-10.139 | 1.00 |  25.85 | A | N |
| ATOM | 286 | CA  | LYS | 181 | 122.581 | 54.751 |-10.732 | 1.00 |  26.27 | A | C |
| ATOM | 287 | CB  | LYS | 181 | 122.737 | 56.187 |-11.253 | 1.00 |  26.21 | A | C |
| ATOM | 288 | CG  | LYS | 181 | 121.801 | 56.557 |-12.403 | 1.00 |  26.81 | A | C |
| ATOM | 289 | CD  | LYS | 181 | 122.014 | 55.683 |-13.627 | 1.00 |  25.67 | A | C |
| ATOM | 290 | CE  | LYS | 181 | 121.014 | 56.031 |-14.719 | 1.00 |  28.19 | A | C |
| ATOM | 291 | NZ  | LYS | 181 | 121.097 | 55.146 |-15.923 | 1.00 |  27.76 | A | N |
| ATOM | 292 | C   | LYS | 181 | 123.684 | 54.451 | -9.729 | 1.00 |  25.62 | A | C |

FIG. 19A-5

```
ATOM    293  O    LYS  181     124.854  54.742   -9.975  1.00  23.94  A  O
ATOM    294  N    GLN  182     123.300  53.870   -8.599  1.00  34.95  A  N
ATOM    295  CA   GLN  182     124.246  53.513   -7.548  1.00  33.61  A  C
ATOM    296  CB   GLN  182     123.797  54.096   -6.207  1.00  89.66  A  C
ATOM    297  CG   GLN  182     123.331  55.528   -6.251  1.00  90.94  A  C
ATOM    298  CD   GLN  182     124.443  56.478   -6.597  1.00  92.56  A  C
ATOM    299  OE1  GLN  182     125.007  56.418   -7.686  1.00  93.40  A  O
ATOM    300  NE2  GLN  182     124.772  57.364   -5.667  1.00  93.92  A  N
ATOM    301  C    GLN  182     124.258  51.991   -7.439  1.00  32.52  A  C
ATOM    302  O    GLN  182     124.398  51.278   -8.429  1.00  36.85  A  O
ATOM    303  N    THR  183     124.096  51.507   -6.216  1.00  26.87  A  N
ATOM    304  CA   THR  183     124.052  50.083   -5.953  1.00  23.79  A  C
ATOM    305  CB   THR  183     124.642  49.767   -4.584  1.00  30.55  A  C
ATOM    306  OG1  THR  183     125.983  50.262   -4.526  1.00  27.00  A  O
ATOM    307  CG2  THR  183     124.629  48.274   -4.331  1.00  28.23  A  C
ATOM    308  C    THR  183     122.590  49.687   -5.944  1.00  23.45  A  C
ATOM    309  O    THR  183     121.752  50.380   -5.368  1.00  21.98  A  O
ATOM    310  N    GLN  184     122.269  48.592   -6.608  1.00  25.73  A  N
ATOM    311  CA   GLN  184     120.897  48.127   -6.612  1.00  21.38  A  C
ATOM    312  CB   GLN  184     120.399  47.898   -8.042  1.00  35.06  A  C
ATOM    313  CG   GLN  184     120.016  49.181   -8.770  1.00  34.81  A  C
ATOM    314  CD   GLN  184     118.982  48.942   -9.856  1.00  34.28  A  C
ATOM    315  OE1  GLN  184     119.215  48.164  -10.781  1.00  29.98  A  O
ATOM    316  NE2  GLN  184     117.834  49.604   -9.748  1.00  32.58  A  N
ATOM    317  C    GLN  184     120.862  46.839   -5.800  1.00  21.76  A  C
ATOM    318  O    GLN  184     121.832  46.087   -5.780  1.00  19.15  A  O
ATOM    319  N    VAL  185     119.753  46.599   -5.112  1.00  33.23  A  N
ATOM    320  CA   VAL  185     119.634  45.408   -4.298  1.00  31.60  A  C
ATOM    321  CB   VAL  185     119.868  45.742   -2.810  1.00  20.42  A  C
ATOM    322  CG1  VAL  185     119.572  44.535   -1.938  1.00  20.41  A  C
ATOM    323  CG2  VAL  185     121.294  46.148   -2.614  1.00   6.28  A  C
ATOM    324  C    VAL  185     118.297  44.701   -4.445  1.00  32.19  A  C
ATOM    325  O    VAL  185     117.237  45.322   -4.469  1.00  29.34  A  O
ATOM    326  N    GLY  186     118.369  43.382   -4.554  1.00  17.76  A  N
ATOM    327  CA   GLY  186     117.177  42.573   -4.672  1.00  19.39  A  C
ATOM    328  C    GLY  186     117.355  41.424   -3.711  1.00  17.37  A  C
ATOM    329  O    GLY  186     118.470  40.929   -3.543  1.00  22.73  A  O
ATOM    330  N    ILE  187     116.278  40.995   -3.073  1.00  15.41  A  N
ATOM    331  CA   ILE  187     116.395  39.906   -2.133  1.00  14.00  A  C
ATOM    332  CB   ILE  187     116.117  40.403   -0.675  1.00  10.12  A  C
ATOM    333  CG2  ILE  187     116.053  39.225    0.299  1.00   7.45  A  C
ATOM    334  CG1  ILE  187     117.232  41.364   -0.253  1.00  10.64  A  C
ATOM    335  CD1  ILE  187     117.156  41.817    1.176  1.00  11.69  A  C
ATOM    336  C    ILE  187     115.496  38.731   -2.485  1.00  13.29  A  C
ATOM    337  O    ILE  187     114.301  38.896   -2.768  1.00  12.19  A  O
ATOM    338  N    VAL  188     116.097  37.546   -2.473  1.00  16.67  A  N
ATOM    339  CA   VAL  188     115.403  36.303   -2.769  1.00  16.34  A  C
ATOM    340  CB   VAL  188     116.082  35.567   -3.951  1.00  11.96  A  C
ATOM    341  CG1  VAL  188     115.642  34.122   -3.993  1.00   7.23  A  C
ATOM    342  CG2  VAL  188     115.742  36.251   -5.248  1.00  12.38  A  C
ATOM    343  C    VAL  188     115.464  35.404   -1.536  1.00  14.88  A  C
ATOM    344  O    VAL  188     116.509  35.286   -0.895  1.00  14.29  A  O
ATOM    345  N    GLN  189     114.348  34.774   -1.194  1.00  30.23  A  N
ATOM    346  CA   GLN  189     114.335  33.873   -0.049  1.00  29.91  A  C
ATOM    347  CB   GLN  189     113.374  34.363    1.039  1.00  26.02  A  C
ATOM    348  CG   GLN  189     113.277  33.399    2.210  1.00  23.53  A  C
ATOM    349  CD   GLN  189     112.257  33.807    3.267  1.00  24.24  A  C
ATOM    350  OE1  GLN  189     111.891  32.998    4.125  1.00  25.46  A  O
ATOM    351  NE2  GLN  189     111.800  35.058    3.219  1.00  25.28  A  N
ATOM    352  C    GLN  189     113.911  32.490   -0.520  1.00  26.90  A  C
ATOM    353  O    GLN  189     113.056  32.366   -1.401  1.00  25.26  A  O
ATOM    354  N    TYR  190     114.516  31.455    0.063  1.00  12.87  A  N
ATOM    355  CA   TYR  190     114.196  30.084   -0.310  1.00  16.39  A  C
ATOM    356  CB   TYR  190     115.267  29.539   -1.257  1.00  17.86  A  C
ATOM    357  CG   TYR  190     116.599  29.241   -0.590  1.00  13.63  A  C
ATOM    358  CD1  TYR  190     116.887  27.963   -0.092  1.00  13.63  A  C
ATOM    359  CE1  TYR  190     118.104  27.687    0.517  1.00  13.63  A  C
ATOM    360  CD2  TYR  190     117.569  30.233   -0.453  1.00  13.63  A  C
ATOM    361  CE2  TYR  190     118.787  29.968    0.159  1.00  13.63  A  C
ATOM    362  CZ   TYR  190     119.053  28.698    0.640  1.00  13.63  A  C
ATOM    363  OH   TYR  190     120.278  28.442    1.228  1.00  13.63  A  O
ATOM    364  C    TYR  190     114.035  29.135    0.878  1.00  18.24  A  C
ATOM    365  O    TYR  190     114.456  29.424    2.003  1.00  18.32  A  O
```

FIG. 19A-6

```
ATOM    366  N    GLY   191     113.417  27.994   0.588  1.00  15.40   A  N
ATOM    367  CA   GLY   191     113.171  26.954   1.572  1.00  13.15   A  C
ATOM    368  C    GLY   191     112.683  25.776   0.764  1.00  14.59   A  C
ATOM    369  O    GLY   191     113.482  25.084   0.139  1.00  17.97   A  O
ATOM    370  N    GLU   192     111.371  25.552   0.769  1.00  27.03   A  N
ATOM    371  CA   GLU   192     110.764  24.475  -0.020  1.00  29.04   A  C
ATOM    372  CB   GLU   192     109.400  24.089   0.537  1.00  28.96   A  C
ATOM    373  CG   GLU   192     109.412  23.507   1.929  1.00  29.34   A  C
ATOM    374  CD   GLU   192     108.020  23.089   2.390  1.00  29.53   A  C
ATOM    375  OE1  GLU   192     107.890  22.532   3.505  1.00  32.42   A  O
ATOM    376  OE2  GLU   192     107.051  23.322   1.633  1.00  27.40   A  O
ATOM    377  C    GLU   192     110.562  25.062  -1.410  1.00  28.85   A  C
ATOM    378  O    GLU   192     110.692  24.380  -2.422  1.00  30.22   A  O
ATOM    379  N    ASN   193     110.236  26.350  -1.433  1.00  34.68   A  N
ATOM    380  CA   ASN   193     110.019  27.088  -2.668  1.00  35.89   A  C
ATOM    381  CB   ASN   193     108.566  27.527  -2.769  1.00  60.91   A  C
ATOM    382  CG   ASN   193     107.606  26.388  -2.564  1.00  64.08   A  C
ATOM    383  OD1  ASN   193     107.545  25.804  -1.488  1.00  68.19   A  O
ATOM    384  ND2  ASN   193     106.849  26.058  -3.601  1.00  66.19   A  N
ATOM    385  C    ASN   193     110.910  28.315  -2.640  1.00  34.07   A  C
ATOM    386  O    ASN   193     111.759  28.459  -1.760  1.00  35.07   A  O
ATOM    387  N    VAL   194     110.712  29.206  -3.598  1.00  31.94   A  N
ATOM    388  CA   VAL   194     111.511  30.423  -3.660  1.00  34.28   A  C
ATOM    389  CB   VAL   194     112.524  30.365  -4.803  1.00  32.89   A  C
ATOM    390  CG1  VAL   194     113.514  31.495  -4.671  1.00  33.92   A  C
ATOM    391  CG2  VAL   194     113.227  29.036  -4.799  1.00  30.16   A  C
ATOM    392  C    VAL   194     110.601  31.608  -3.914  1.00  32.05   A  C
ATOM    393  O    VAL   194     109.651  31.507  -4.688  1.00  30.17   A  O
ATOM    394  N    THR   195     110.877  32.730  -3.261  1.00  26.46   A  N
ATOM    395  CA   THR   195     110.058  33.915  -3.474  1.00  27.64   A  C
ATOM    396  CB   THR   195     109.050  34.135  -2.307  1.00  36.45   A  C
ATOM    397  OG1  THR   195     109.728  34.654  -1.163  1.00  40.46   A  O
ATOM    398  CG2  THR   195     108.396  32.820  -1.918  1.00  38.08   A  C
ATOM    399  C    THR   195     110.927  35.161  -3.656  1.00  28.48   A  C
ATOM    400  O    THR   195     111.977  35.309  -3.032  1.00  31.07   A  O
ATOM    401  N    HIS   196     110.492  36.040  -4.545  1.00  36.83   A  N
ATOM    402  CA   HIS   196     111.196  37.281  -4.819  1.00  36.93   A  C
ATOM    403  CB   HIS   196     110.843  37.772  -6.225  1.00  33.18   A  C
ATOM    404  CG   HIS   196     111.434  36.951  -7.326  1.00  29.68   A  C
ATOM    405  CD2  HIS   196     110.933  35.910  -8.032  1.00  30.31   A  C
ATOM    406  ND1  HIS   196     112.707  37.169  -7.813  1.00  28.33   A  N
ATOM    407  CE1  HIS   196     112.965  36.296  -8.772  1.00  25.05   A  C
ATOM    408  NE2  HIS   196     111.905  35.521  -8.924  1.00  23.26   A  N
ATOM    409  C    HIS   196     110.730  38.315  -3.802  1.00  36.79   A  C
ATOM    410  O    HIS   196     109.687  38.933  -3.997  1.00  35.45   A  O
ATOM    411  N    GLU   197     111.480  38.508  -2.721  1.00  21.51   A  N
ATOM    412  CA   GLU   197     111.069  39.488  -1.732  1.00  18.84   A  C
ATOM    413  CB   GLU   197     112.091  39.588  -0.604  1.00  43.52   A  C
ATOM    414  CG   GLU   197     112.094  38.384   0.339  1.00  43.86   A  C
ATOM    415  CD   GLU   197     110.717  38.043   0.882  1.00  42.93   A  C
ATOM    416  OE1  GLU   197     109.909  38.967   1.100  1.00  41.51   A  O
ATOM    417  OE2  GLU   197     110.444  36.847   1.111  1.00  44.59   A  O
ATOM    418  C    GLU   197     110.882  40.832  -2.442  1.00  16.31   A  C
ATOM    419  O    GLU   197     109.802  41.419  -2.403  1.00  21.51   A  O
ATOM    420  N    PHE   198     111.921  41.325  -3.098  1.00  11.53   A  N
ATOM    421  CA   PHE   198     111.786  42.562  -3.845  1.00  13.33   A  C
ATOM    422  CB   PHE   198     111.803  43.785  -2.901  1.00  15.90   A  C
ATOM    423  CG   PHE   198     113.092  44.003  -2.153  1.00  14.15   A  C
ATOM    424  CD1  PHE   198     114.262  44.390  -2.823  1.00  20.29   A  C
ATOM    425  CD2  PHE   198     113.115  43.912  -0.756  1.00  10.34   A  C
ATOM    426  CE1  PHE   198     115.427  44.685  -2.113  1.00  16.32   A  C
ATOM    427  CE2  PHE   198     114.274  44.208  -0.039  1.00  14.80   A  C
ATOM    428  CZ   PHE   198     115.431  44.594  -0.719  1.00  18.60   A  C
ATOM    429  C    PHE   198     112.829  42.652  -4.956  1.00  16.01   A  C
ATOM    430  O    PHE   198     113.974  42.239  -4.771  1.00  17.30   A  O
ATOM    431  N    ASN   199     112.418  43.152  -6.123  1.00  19.42   A  N
ATOM    432  CA   ASN   199     113.321  43.265  -7.276  1.00  19.71   A  C
ATOM    433  CB   ASN   199     112.540  43.562  -8.548  1.00  30.06   A  C
ATOM    434  CG   ASN   199     111.465  42.548  -8.824  1.00  31.32   A  C
ATOM    435  OD1  ASN   199     111.726  41.350  -8.934  1.00  32.85   A  O
ATOM    436  ND2  ASN   199     110.236  43.029  -8.948  1.00  30.20   A  N
ATOM    437  C    ASN   199     114.458  44.288  -7.173  1.00  22.17   A  C
ATOM    438  O    ASN   199     114.430  45.215  -6.351  1.00  19.98   A  O
```

FIG. 19A-7

```
ATOM    439  N    LEU  200     115.445  44.107   -8.044  1.00   18.99  A  N
ATOM    440  CA   LEU  200     116.619  44.958   -8.078  1.00   20.95  A  C
ATOM    441  CB   LEU  200     117.556  44.524   -9.212  1.00   24.87  A  C
ATOM    442  CG   LEU  200     118.631  43.490   -8.869  1.00   22.72  A  C
ATOM    443  CD1  LEU  200     119.348  43.048  -10.130  1.00   27.84  A  C
ATOM    444  CD2  LEU  200     119.617  44.089   -7.869  1.00   23.89  A  C
ATOM    445  C    LEU  200     116.282  46.415   -8.246  1.00   21.35  A  C
ATOM    446  O    LEU  200     116.960  47.274   -7.688  1.00   22.37  A  O
ATOM    447  N    ASN  201     115.231  46.691   -9.011  1.00   18.94  A  N
ATOM    448  CA   ASN  201     114.816  48.061   -9.284  1.00   20.79  A  C
ATOM    449  CB   ASN  201     114.546  48.208  -10.773  1.00   21.69  A  C
ATOM    450  CG   ASN  201     113.401  47.336  -11.236  1.00   23.97  A  C
ATOM    451  OD1  ASN  201     113.119  47.246  -12.424  1.00   24.11  A  O
ATOM    452  ND2  ASN  201     112.727  46.684  -10.292  1.00   21.81  A  N
ATOM    453  C    ASN  201     113.572  48.510   -8.509  1.00   20.84  A  C
ATOM    454  O    ASN  201     112.969  49.522   -8.851  1.00   16.74  A  O
ATOM    455  N    LYS  202     113.182  47.770   -7.477  1.00   23.30  A  N
ATOM    456  CA   LYS  202     111.998  48.137   -6.710  1.00   23.42  A  C
ATOM    457  CB   LYS  202     111.621  47.022   -5.741  1.00   34.18  A  C
ATOM    458  CG   LYS  202     110.337  47.265   -4.944  1.00   35.72  A  C
ATOM    459  CD   LYS  202     109.099  47.092   -5.803  1.00   37.63  A  C
ATOM    460  CE   LYS  202     109.162  45.813   -6.678  1.00   43.38  A  C
ATOM    461  NZ   LYS  202     109.316  44.491   -5.962  1.00   42.40  A  N
ATOM    462  C    LYS  202     112.188  49.428   -5.930  1.00   22.29  A  C
ATOM    463  O    LYS  202     111.338  50.313   -5.984  1.00   19.57  A  O
ATOM    464  N    TYR  203     113.292  49.538   -5.203  1.00   24.72  A  N
ATOM    465  CA   TYR  203     113.538  50.731   -4.407  1.00   24.40  A  C
ATOM    466  CB   TYR  203     113.769  50.348   -2.942  1.00   32.57  A  C
ATOM    467  CG   TYR  203     112.679  49.461   -2.396  1.00   31.24  A  C
ATOM    468  CD1  TYR  203     112.869  48.086   -2.282  1.00   31.85  A  C
ATOM    469  CE1  TYR  203     111.842  47.251   -1.844  1.00   28.32  A  C
ATOM    470  CD2  TYR  203     111.427  49.986   -2.050  1.00   34.13  A  C
ATOM    471  CE2  TYR  203     110.393  49.161   -1.611  1.00   36.88  A  C
ATOM    472  CZ   TYR  203     110.607  47.794   -1.512  1.00   36.50  A  C
ATOM    473  OH   TYR  203     109.590  46.962   -1.095  1.00   41.50  A  O
ATOM    474  C    TYR  203     114.713  51.541   -4.938  1.00   25.04  A  C
ATOM    475  O    TYR  203     115.755  50.986   -5.280  1.00   23.21  A  O
ATOM    476  N    SER  204     114.536  52.861   -4.998  1.00   28.94  A  N
ATOM    477  CA   SER  204     115.557  53.764   -5.513  1.00   30.79  A  C
ATOM    478  CB   SER  204     114.892  54.863   -6.338  1.00   29.83  A  C
ATOM    479  OG   SER  204     113.945  55.577   -5.558  1.00   31.66  A  O
ATOM    480  C    SER  204     116.372  54.402   -4.412  1.00   33.37  A  C
ATOM    481  O    SER  204     117.247  55.214   -4.680  1.00   33.88  A  O
ATOM    482  N    SER  205     116.089  54.027   -3.173  1.00   27.33  A  N
ATOM    483  CA   SER  205     116.787  54.615   -2.048  1.00   26.99  A  C
ATOM    484  CB   SER  205     115.874  55.628   -1.378  1.00   50.70  A  C
ATOM    485  OG   SER  205     116.409  56.032   -0.137  1.00   56.19  A  O
ATOM    486  C    SER  205     117.251  53.608   -1.016  1.00   25.12  A  C
ATOM    487  O    SER  205     116.650  52.551   -0.857  1.00   21.38  A  O
ATOM    488  N    THR  206     118.318  53.949   -0.301  1.00   23.44  A  N
ATOM    489  CA   THR  206     118.854  53.075    0.735  1.00   24.79  A  C
ATOM    490  CB   THR  206     120.176  53.614    1.286  1.00   12.85  A  C
ATOM    491  OG1  THR  206     121.137  53.683    0.227  1.00   11.66  A  O
ATOM    492  CG2  THR  206     120.696  52.712    2.392  1.00   11.22  A  C
ATOM    493  C    THR  206     117.889  52.879    1.900  1.00   25.38  A  C
ATOM    494  O    THR  206     117.798  51.785    2.447  1.00   28.17  A  O
ATOM    495  N    GLU  207     117.173  53.926    2.299  1.00   23.18  A  N
ATOM    496  CA   GLU  207     116.238  53.746    3.394  1.00   22.34  A  C
ATOM    497  CB   GLU  207     115.800  55.083    3.986  1.00  114.79  A  C
ATOM    498  CG   GLU  207     115.317  56.095    2.992  1.00  115.51  A  C
ATOM    499  CD   GLU  207     114.757  57.325    3.675  1.00  116.92  A  C
ATOM    500  OE1  GLU  207     115.428  57.857    4.587  1.00  116.15  A  O
ATOM    501  OE2  GLU  207     113.648  57.761    3.302  1.00  115.82  A  O
ATOM    502  C    GLU  207     115.038  52.937    2.908  1.00   22.84  A  C
ATOM    503  O    GLU  207     114.515  52.094    3.640  1.00   22.79  A  O
ATOM    504  N    GLU  208     114.614  53.163    1.668  1.00   31.71  A  N
ATOM    505  CA   GLU  208     113.485  52.412    1.126  1.00   33.44  A  C
ATOM    506  CB   GLU  208     113.168  52.841   -0.308  1.00   38.62  A  C
ATOM    507  CG   GLU  208     112.661  54.265   -0.441  1.00   36.09  A  C
ATOM    508  CD   GLU  208     112.288  54.633   -1.875  1.00   35.61  A  C
ATOM    509  OE1  GLU  208     111.943  55.811   -2.111  1.00   41.38  A  O
ATOM    510  OE2  GLU  208     112.338  53.757   -2.767  1.00   34.33  A  O
ATOM    511  C    GLU  208     113.808  50.920    1.148  1.00   34.14  A  C
```

FIG. 19A-8

| | | | | | | | | | | | |
|---|---|---|---|---|---|---|---|---|---|---|---|
| ATOM | 512 | O | GLU | 208 | 112.942 | 50.093 | 1.426 | 1.00 | 35.14 | A | O |
| ATOM | 513 | N | VAL | 209 | 115.057 | 50.575 | 0.855 | 1.00 | 17.60 | A | N |
| ATOM | 514 | CA | VAL | 209 | 115.472 | 49.180 | 0.853 | 1.00 | 16.52 | A | C |
| ATOM | 515 | CB | VAL | 209 | 116.790 | 48.982 | 0.077 | 1.00 | 10.63 | A | C |
| ATOM | 516 | CG1 | VAL | 209 | 117.501 | 47.719 | 0.538 | 1.00 | 10.96 | A | C |
| ATOM | 517 | CG2 | VAL | 209 | 116.491 | 48.889 | -1.398 | 1.00 | 11.65 | A | C |
| ATOM | 518 | C | VAL | 209 | 115.656 | 48.691 | 2.276 | 1.00 | 14.54 | A | C |
| ATOM | 519 | O | VAL | 209 | 115.278 | 47.558 | 2.596 | 1.00 | 13.50 | A | O |
| ATOM | 520 | N | LEU | 210 | 116.230 | 49.548 | 3.123 | 1.00 | 19.45 | A | N |
| ATOM | 521 | CA | LEU | 210 | 116.459 | 49.205 | 4.521 | 1.00 | 19.78 | A | C |
| ATOM | 522 | CB | LEU | 210 | 117.148 | 50.354 | 5.242 | 1.00 | 21.61 | A | C |
| ATOM | 523 | CG | LEU | 210 | 118.589 | 50.100 | 5.683 | 1.00 | 21.85 | A | C |
| ATOM | 524 | CD1 | LEU | 210 | 119.093 | 51.347 | 6.358 | 1.00 | 18.40 | A | C |
| ATOM | 525 | CD2 | LEU | 210 | 118.687 | 48.916 | 6.632 | 1.00 | 15.30 | A | C |
| ATOM | 526 | C | LEU | 210 | 115.148 | 48.894 | 5.223 | 1.00 | 18.04 | A | C |
| ATOM | 527 | O | LEU | 210 | 115.078 | 48.022 | 6.093 | 1.00 | 18.81 | A | O |
| ATOM | 528 | N | VAL | 211 | 114.107 | 49.618 | 4.839 | 1.00 | 25.49 | A | N |
| ATOM | 529 | CA | VAL | 211 | 112.798 | 49.443 | 5.432 | 1.00 | 25.25 | A | C |
| ATOM | 530 | CB | VAL | 211 | 111.916 | 50.685 | 5.175 | 1.00 | 19.83 | A | C |
| ATOM | 531 | CG1 | VAL | 211 | 110.457 | 50.391 | 5.537 | 1.00 | 22.01 | A | C |
| ATOM | 532 | CG2 | VAL | 211 | 112.446 | 51.859 | 5.989 | 1.00 | 20.44 | A | C |
| ATOM | 533 | C | VAL | 211 | 112.107 | 48.214 | 4.871 | 1.00 | 24.50 | A | C |
| ATOM | 534 | O | VAL | 211 | 111.437 | 47.483 | 5.593 | 1.00 | 25.18 | A | O |
| ATOM | 535 | N | ALA | 212 | 112.262 | 47.986 | 3.577 | 1.00 | 29.23 | A | N |
| ATOM | 536 | CA | ALA | 212 | 111.624 | 46.839 | 2.964 | 1.00 | 28.21 | A | C |
| ATOM | 537 | CB | ALA | 212 | 111.725 | 46.935 | 1.439 | 1.00 | 1.87 | A | C |
| ATOM | 538 | C | ALA | 212 | 112.275 | 45.559 | 3.465 | 1.00 | 26.02 | A | C |
| ATOM | 539 | O | ALA | 212 | 111.603 | 44.543 | 3.657 | 1.00 | 25.96 | A | O |
| ATOM | 540 | N | ALA | 213 | 113.587 | 45.618 | 3.680 | 1.00 | 33.07 | A | N |
| ATOM | 541 | CA | ALA | 213 | 114.339 | 44.464 | 4.147 | 1.00 | 34.24 | A | C |
| ATOM | 542 | CB | ALA | 213 | 115.803 | 44.787 | 4.176 | 1.00 | 20.72 | A | C |
| ATOM | 543 | C | ALA | 213 | 113.875 | 44.011 | 5.522 | 1.00 | 33.04 | A | C |
| ATOM | 544 | O | ALA | 213 | 113.659 | 42.824 | 5.746 | 1.00 | 30.67 | A | O |
| ATOM | 545 | N | ASN | 214 | 113.723 | 44.952 | 6.446 | 1.00 | 10.19 | A | N |
| ATOM | 546 | CA | ASN | 214 | 113.268 | 44.608 | 7.788 | 1.00 | 14.06 | A | C |
| ATOM | 547 | CB | ASN | 214 | 113.357 | 45.817 | 8.713 | 1.00 | 18.34 | A | C |
| ATOM | 548 | CG | ASN | 214 | 114.763 | 46.094 | 9.158 | 1.00 | 20.07 | A | C |
| ATOM | 549 | OD1 | ASN | 214 | 115.597 | 46.563 | 8.377 | 1.00 | 22.00 | A | O |
| ATOM | 550 | ND2 | ASN | 214 | 115.045 | 45.794 | 10.425 | 1.00 | 20.49 | A | N |
| ATOM | 551 | C | ASN | 214 | 111.847 | 44.081 | 7.828 | 1.00 | 16.45 | A | C |
| ATOM | 552 | O | ASN | 214 | 111.448 | 43.500 | 8.825 | 1.00 | 17.17 | A | O |
| ATOM | 553 | N | LYS | 215 | 111.080 | 44.289 | 6.764 | 1.00 | 16.88 | A | N |
| ATOM | 554 | CA | LYS | 215 | 109.705 | 43.817 | 6.744 | 1.00 | 17.32 | A | C |
| ATOM | 555 | CB | LYS | 215 | 108.804 | 44.772 | 5.926 | 1.00 | 20.45 | A | C |
| ATOM | 556 | CG | LYS | 215 | 108.670 | 46.176 | 6.531 | 1.00 | 28.03 | A | C |
| ATOM | 557 | CD | LYS | 215 | 107.387 | 46.902 | 6.115 | 1.00 | 31.57 | A | C |
| ATOM | 558 | CE | LYS | 215 | 107.304 | 47.155 | 4.607 | 1.00 | 35.03 | A | C |
| ATOM | 559 | NZ | LYS | 215 | 106.135 | 48.007 | 4.237 | 1.00 | 36.02 | A | N |
| ATOM | 560 | C | LYS | 215 | 109.617 | 42.399 | 6.193 | 1.00 | 15.45 | A | C |
| ATOM | 561 | O | LYS | 215 | 108.529 | 41.825 | 6.124 | 1.00 | 16.67 | A | O |
| ATOM | 562 | N | ILE | 216 | 110.757 | 41.824 | 5.812 | 1.00 | 28.84 | A | N |
| ATOM | 563 | CA | ILE | 216 | 110.754 | 40.475 | 5.262 | 1.00 | 25.66 | A | C |
| ATOM | 564 | CB | ILE | 216 | 112.088 | 40.123 | 4.594 | 1.00 | 13.08 | A | C |
| ATOM | 565 | CG2 | ILE | 216 | 112.088 | 38.681 | 4.163 | 1.00 | 9.86 | A | C |
| ATOM | 566 | CG1 | ILE | 216 | 112.298 | 41.002 | 3.362 | 1.00 | 9.76 | A | C |
| ATOM | 567 | CD1 | ILE | 216 | 113.597 | 40.713 | 2.626 | 1.00 | 6.72 | A | C |
| ATOM | 568 | C | ILE | 216 | 110.459 | 39.445 | 6.333 | 1.00 | 24.10 | A | C |
| ATOM | 569 | O | ILE | 216 | 111.076 | 39.441 | 7.404 | 1.00 | 24.80 | A | O |
| ATOM | 570 | N | VAL | 217 | 109.503 | 38.574 | 6.017 | 1.00 | 14.68 | A | N |
| ATOM | 571 | CA | VAL | 217 | 109.065 | 37.511 | 6.904 | 1.00 | 16.45 | A | C |
| ATOM | 572 | CB | VAL | 217 | 107.535 | 37.425 | 6.901 | 1.00 | 9.81 | A | C |
| ATOM | 573 | CG1 | VAL | 217 | 107.065 | 36.144 | 7.569 | 1.00 | 9.81 | A | C |
| ATOM | 574 | CG2 | VAL | 217 | 106.967 | 38.647 | 7.626 | 1.00 | 9.81 | A | C |
| ATOM | 575 | C | VAL | 217 | 109.641 | 36.173 | 6.483 | 1.00 | 17.61 | A | C |
| ATOM | 576 | O | VAL | 217 | 109.794 | 35.895 | 5.298 | 1.00 | 17.07 | A | O |
| ATOM | 577 | N | GLN | 218 | 109.959 | 35.348 | 7.474 | 1.00 | 15.74 | A | N |
| ATOM | 578 | CA | GLN | 218 | 110.512 | 34.024 | 7.234 | 1.00 | 16.40 | A | C |
| ATOM | 579 | CB | GLN | 218 | 111.064 | 33.446 | 8.531 | 1.00 | 14.26 | A | C |
| ATOM | 580 | CG | GLN | 218 | 111.752 | 32.109 | 8.372 | 1.00 | 14.26 | A | C |
| ATOM | 581 | CD | GLN | 218 | 112.331 | 31.589 | 9.675 | 1.00 | 14.26 | A | C |
| ATOM | 582 | OE1 | GLN | 218 | 113.166 | 30.685 | 9.668 | 1.00 | 14.26 | A | O |
| ATOM | 583 | NE2 | GLN | 218 | 111.887 | 32.156 | 10.802 | 1.00 | 14.26 | A | N |
| ATOM | 584 | C | GLN | 218 | 109.392 | 33.151 | 6.719 | 1.00 | 15.85 | A | C |

FIG. 19A-9

| | | | | | | | | | | |
|---|---|---|---|---|---|---|---|---|---|---|
| ATOM | 585 | O | GLN | 218 | 108.335 | 33.103 | 7.328 | 1.00 | 19.60 | A O |
| ATOM | 586 | N | ARG | 219 | 109.622 | 32.464 | 5.604 | 1.00 | 16.04 | A N |
| ATOM | 587 | CA | ARG | 219 | 108.599 | 31.602 | 5.005 | 1.00 | 15.69 | A C |
| ATOM | 588 | CB | ARG | 219 | 108.595 | 31.786 | 3.489 | 1.00 | 43.49 | A C |
| ATOM | 589 | CG | ARG | 219 | 109.053 | 33.163 | 3.054 | 1.00 | 43.49 | A C |
| ATOM | 590 | CD | ARG | 219 | 108.719 | 33.421 | 1.606 | 1.00 | 43.49 | A C |
| ATOM | 591 | NE | ARG | 219 | 107.365 | 33.952 | 1.454 | 1.00 | 43.49 | A N |
| ATOM | 592 | CZ | ARG | 219 | 107.042 | 35.232 | 1.606 | 1.00 | 43.49 | A C |
| ATOM | 593 | NH1 | ARG | 219 | 107.978 | 36.122 | 1.915 | 1.00 | 43.49 | A N |
| ATOM | 594 | NH2 | ARG | 219 | 105.786 | 35.621 | 1.443 | 1.00 | 43.49 | A N |
| ATOM | 595 | C | ARG | 219 | 108.814 | 30.127 | 5.350 | 1.00 | 16.90 | A C |
| ATOM | 596 | O | ARG | 219 | 108.073 | 29.253 | 4.886 | 1.00 | 16.91 | A O |
| ATOM | 597 | N | GLY | 220 | 109.838 | 29.867 | 6.160 | 1.00 | 9.58 | A N |
| ATOM | 598 | CA | GLY | 220 | 110.148 | 28.513 | 6.567 | 1.00 | 9.19 | A C |
| ATOM | 599 | C | GLY | 220 | 110.442 | 27.562 | 5.422 | 1.00 | 8.86 | A C |
| ATOM | 600 | O | GLY | 220 | 110.682 | 27.993 | 4.288 | 1.00 | 7.20 | A O |
| ATOM | 601 | N | GLY | 221 | 110.435 | 26.266 | 5.730 | 1.00 | 16.50 | A N |
| ATOM | 602 | CA | GLY | 221 | 110.682 | 25.265 | 4.718 | 1.00 | 15.07 | A C |
| ATOM | 603 | C | GLY | 221 | 111.117 | 23.954 | 5.314 | 1.00 | 15.49 | A C |
| ATOM | 604 | O | GLY | 221 | 112.038 | 23.928 | 6.124 | 1.00 | 12.29 | A O |
| ATOM | 605 | N | ARG | 222 | 110.459 | 22.865 | 4.927 | 1.00 | 35.34 | A N |
| ATOM | 606 | CA | ARG | 222 | 110.815 | 21.543 | 5.433 | 1.00 | 36.05 | A C |
| ATOM | 607 | CB | ARG | 222 | 109.652 | 20.567 | 5.235 | 1.00 | 22.30 | A C |
| ATOM | 608 | CG | ARG | 222 | 108.505 | 20.791 | 6.201 | 1.00 | 22.30 | A C |
| ATOM | 609 | CD | ARG | 222 | 107.252 | 20.047 | 5.779 | 1.00 | 22.30 | A C |
| ATOM | 610 | NE | ARG | 222 | 106.621 | 20.647 | 4.614 | 1.00 | 22.30 | A N |
| ATOM | 611 | CZ | ARG | 222 | 105.459 | 20.247 | 4.103 | 1.00 | 22.30 | A C |
| ATOM | 612 | NH1 | ARG | 222 | 104.795 | 19.241 | 4.654 | 1.00 | 22.30 | A N |
| ATOM | 613 | NH2 | ARG | 222 | 104.951 | 20.857 | 3.042 | 1.00 | 22.30 | A N |
| ATOM | 614 | C | ARG | 222 | 112.062 | 21.036 | 4.723 | 1.00 | 36.10 | A C |
| ATOM | 615 | O | ARG | 222 | 112.626 | 20.017 | 5.107 | 1.00 | 36.87 | A O |
| ATOM | 616 | N | GLN | 223 | 112.473 | 21.750 | 3.678 | 1.00 | 27.48 | A N |
| ATOM | 617 | CA | GLN | 223 | 113.672 | 21.428 | 2.912 | 1.00 | 25.77 | A C |
| ATOM | 618 | CB | GLN | 223 | 113.328 | 20.858 | 1.535 | 1.00 | 13.17 | A C |
| ATOM | 619 | CG | GLN | 223 | 112.830 | 19.417 | 1.508 | 1.00 | 14.61 | A C |
| ATOM | 620 | CD | GLN | 223 | 111.346 | 19.312 | 1.790 | 1.00 | 15.02 | A C |
| ATOM | 621 | OE1 | GLN | 223 | 110.533 | 20.016 | 1.190 | 1.00 | 15.42 | A O |
| ATOM | 622 | NE2 | GLN | 223 | 110.981 | 18.417 | 2.698 | 1.00 | 15.46 | A N |
| ATOM | 623 | C | GLN | 223 | 114.498 | 22.706 | 2.724 | 1.00 | 26.51 | A C |
| ATOM | 624 | O | GLN | 223 | 114.057 | 23.799 | 3.069 | 1.00 | 25.99 | A O |
| ATOM | 625 | N | THR | 224 | 115.696 | 22.567 | 2.172 | 1.00 | 24.40 | A N |
| ATOM | 626 | CA | THR | 224 | 116.581 | 23.704 | 1.948 | 1.00 | 22.28 | A C |
| ATOM | 627 | CB | THR | 224 | 117.795 | 23.633 | 2.897 | 1.00 | 14.98 | A C |
| ATOM | 628 | OG1 | THR | 224 | 117.328 | 23.565 | 4.246 | 1.00 | 14.97 | A O |
| ATOM | 629 | CG2 | THR | 224 | 118.683 | 24.849 | 2.747 | 1.00 | 11.28 | A C |
| ATOM | 630 | C | THR | 224 | 117.061 | 23.662 | 0.500 | 1.00 | 19.29 | A C |
| ATOM | 631 | O | THR | 224 | 118.122 | 23.129 | 0.202 | 1.00 | 15.78 | A O |
| ATOM | 632 | N | MET | 225 | 116.272 | 24.234 | -0.395 | 1.00 | 14.15 | A N |
| ATOM | 633 | CA | MET | 225 | 116.607 | 24.236 | -1.810 | 1.00 | 15.04 | A C |
| ATOM | 634 | CB | MET | 225 | 115.346 | 24.481 | -2.636 | 1.00 | 22.98 | A C |
| ATOM | 635 | CG | MET | 225 | 114.183 | 23.602 | -2.267 | 1.00 | 20.41 | A C |
| ATOM | 636 | SD | MET | 225 | 114.421 | 21.883 | -2.704 | 1.00 | 28.15 | A S |
| ATOM | 637 | CE | MET | 225 | 112.675 | 21.302 | -2.554 | 1.00 | 24.73 | A C |
| ATOM | 638 | C | MET | 225 | 117.653 | 25.275 | -2.204 | 1.00 | 16.07 | A C |
| ATOM | 639 | O | MET | 225 | 117.426 | 26.054 | -3.136 | 1.00 | 17.53 | A O |
| ATOM | 640 | N | THR | 226 | 118.791 | 25.297 | -1.513 | 1.00 | 16.19 | A N |
| ATOM | 641 | CA | THR | 226 | 119.841 | 26.259 | -1.840 | 1.00 | 15.66 | A C |
| ATOM | 642 | CB | THR | 226 | 121.155 | 25.905 | -1.129 | 1.00 | 25.30 | A C |
| ATOM | 643 | OG1 | THR | 226 | 120.925 | 25.825 | 0.284 | 1.00 | 27.32 | A O |
| ATOM | 644 | CG2 | THR | 226 | 122.216 | 26.959 | -1.414 | 1.00 | 23.02 | A C |
| ATOM | 645 | C | THR | 226 | 120.100 | 26.337 | -3.356 | 1.00 | 14.26 | A C |
| ATOM | 646 | O | THR | 226 | 120.229 | 27.418 | -3.917 | 1.00 | 8.95 | A O |
| ATOM | 647 | N | ALA | 227 | 120.158 | 25.190 | -4.019 | 1.00 | 9.41 | A N |
| ATOM | 648 | CA | ALA | 227 | 120.408 | 25.162 | -5.448 | 1.00 | 8.35 | A C |
| ATOM | 649 | CB | ALA | 227 | 120.422 | 23.738 | -5.939 | 1.00 | 23.80 | A C |
| ATOM | 650 | C | ALA | 227 | 119.342 | 25.951 | -6.188 | 1.00 | 9.01 | A C |
| ATOM | 651 | O | ALA | 227 | 119.644 | 26.759 | -7.067 | 1.00 | 9.81 | A O |
| ATOM | 652 | N | LEU | 228 | 118.085 | 25.711 | -5.842 | 1.00 | 28.18 | A N |
| ATOM | 653 | CA | LEU | 228 | 116.985 | 26.410 | -6.489 | 1.00 | 26.62 | A C |
| ATOM | 654 | CB | LEU | 228 | 115.649 | 25.860 | -5.988 | 1.00 | 14.81 | A C |
| ATOM | 655 | CG | LEU | 228 | 114.372 | 26.485 | -6.557 | 1.00 | 22.70 | A C |
| ATOM | 656 | CD1 | LEU | 228 | 114.356 | 26.363 | -8.080 | 1.00 | 20.29 | A C |
| ATOM | 657 | CD2 | LEU | 228 | 113.163 | 25.801 | -5.947 | 1.00 | 19.75 | A C |

FIG. 19A-10

```
ATOM    658  C    LEU  228     117.067  27.909  -6.221  1.00  25.80  A  C
ATOM    659  O    LEU  228     116.885  28.719  -7.129  1.00  28.78  A  O
ATOM    660  N    GLY  229     117.341  28.274  -4.971  1.00  23.50  A  N
ATOM    661  CA   GLY  229     117.449  29.679  -4.624  1.00  25.86  A  C
ATOM    662  C    GLY  229     118.464  30.407  -5.495  1.00  28.42  A  C
ATOM    663  O    GLY  229     118.149  31.428  -6.108  1.00  29.01  A  O
ATOM    664  N    ILE  230     119.682  29.876  -5.562  1.00  20.49  A  N
ATOM    665  CA   ILE  230     120.736  30.498  -6.354  1.00  21.82  A  C
ATOM    666  CB   ILE  230     122.096  29.779  -6.195  1.00   2.66  A  C
ATOM    667  CG2  ILE  230     123.168  30.546  -6.953  1.00   2.66  A  C
ATOM    668  CG1  ILE  230     122.486  29.692  -4.720  1.00   2.66  A  C
ATOM    669  CD1  ILE  230     123.773  28.920  -4.474  1.00   2.66  A  C
ATOM    670  C    ILE  230     120.386  30.508  -7.830  1.00  22.08  A  C
ATOM    671  O    ILE  230     120.614  31.498  -8.511  1.00  20.01  A  O
ATOM    672  N    ASP  231     119.841  29.409  -8.333  1.00  32.19  A  N
ATOM    673  CA   ASP  231     119.473  29.352  -9.743  1.00  30.59  A  C
ATOM    674  CB   ASP  231     118.959  27.958 -10.103  1.00  35.41  A  C
ATOM    675  CG   ASP  231     118.860  27.739 -11.604  1.00  42.41  A  C
ATOM    676  OD1  ASP  231     119.910  27.778 -12.281  1.00  41.17  A  O
ATOM    677  OD2  ASP  231     117.735  27.525 -12.103  1.00  45.95  A  O
ATOM    678  C    ASP  231     118.392  30.395 -10.048  1.00  31.57  A  C
ATOM    679  O    ASP  231     118.429  31.048 -11.090  1.00  28.79  A  O
ATOM    680  N    THR  232     117.443  30.554  -9.126  1.00  18.29  A  N
ATOM    681  CA   THR  232     116.347  31.510  -9.296  1.00  17.08  A  C
ATOM    682  CB   THR  232     115.287  31.347  -8.194  1.00  20.70  A  C
ATOM    683  OG1  THR  232     114.714  30.041  -8.279  1.00  19.21  A  O
ATOM    684  CG2  THR  232     114.191  32.370  -8.358  1.00  14.24  A  C
ATOM    685  C    THR  232     116.859  32.937  -9.264  1.00  17.71  A  C
ATOM    686  O    THR  232     116.390  33.801 -10.010  1.00  17.88  A  O
ATOM    687  N    ALA  233     117.815  33.187  -8.379  1.00  19.66  A  N
ATOM    688  CA   ALA  233     118.395  34.517  -8.270  1.00  22.31  A  C
ATOM    689  CB   ALA  233     119.364  34.580  -7.099  1.00  15.15  A  C
ATOM    690  C    ALA  233     119.125  34.796  -9.575  1.00  24.62  A  C
ATOM    691  O    ALA  233     119.187  35.929 -10.031  1.00  26.53  A  O
ATOM    692  N    ARG  234     119.666  33.746 -10.180  1.00  30.19  A  N
ATOM    693  CA   ARG  234     120.390  33.879 -11.434  1.00  33.29  A  C
ATOM    694  CB   ARG  234     121.241  32.637 -11.693  1.00  15.32  A  C
ATOM    695  CG   ARG  234     122.345  32.875 -12.693  1.00  15.32  A  C
ATOM    696  CD   ARG  234     122.760  31.617 -13.460  1.00  15.32  A  C
ATOM    697  NE   ARG  234     121.839  31.311 -14.554  1.00  15.32  A  N
ATOM    698  CZ   ARG  234     120.875  30.405 -14.481  1.00  15.32  A  C
ATOM    699  NH1  ARG  234     120.708  29.713 -13.368  1.00  15.32  A  N
ATOM    700  NH2  ARG  234     120.078  30.188 -15.511  1.00  15.32  A  N
ATOM    701  C    ARG  234     119.446  34.083 -12.619  1.00  35.42  A  C
ATOM    702  O    ARG  234     119.409  35.153 -13.215  1.00  35.47  A  O
ATOM    703  N    LYS  235     118.666  33.057 -12.941  1.00  67.48  A  N
ATOM    704  CA   LYS  235     117.767  33.124 -14.085  1.00  67.43  A  C
ATOM    705  CB   LYS  235     117.204  31.730 -14.397  1.00  53.18  A  C
ATOM    706  CG   LYS  235     115.965  31.308 -13.615  1.00  54.33  A  C
ATOM    707  CD   LYS  235     115.583  29.867 -13.970  1.00  54.15  A  C
ATOM    708  CE   LYS  235     114.146  29.517 -13.590  1.00  54.95  A  C
ATOM    709  NZ   LYS  235     113.873  29.660 -12.135  1.00  55.71  A  N
ATOM    710  C    LYS  235     116.628  34.134 -14.017  1.00  67.57  A  C
ATOM    711  O    LYS  235     116.074  34.500 -15.054  1.00  67.91  A  O
ATOM    712  N    GLU  236     116.277  34.596 -12.822  1.00  98.68  A  N
ATOM    713  CA   GLU  236     115.186  35.558 -12.693  1.00 100.30  A  C
ATOM    714  CB   GLU  236     114.087  34.999 -11.781  1.00  50.64  A  C
ATOM    715  CG   GLU  236     113.008  34.192 -12.510  1.00  53.41  A  C
ATOM    716  CD   GLU  236     112.199  33.276 -11.582  1.00  55.89  A  C
ATOM    717  OE1  GLU  236     111.660  33.760 -10.565  1.00  55.98  A  O
ATOM    718  OE2  GLU  236     112.098  32.065 -11.875  1.00  55.73  A  O
ATOM    719  C    GLU  236     115.627  36.917 -12.174  1.00  98.85  A  C
ATOM    720  O    GLU  236     115.638  37.900 -12.912  1.00 100.28  A  O
ATOM    721  N    ALA  237     115.991  36.969 -10.899  1.00  71.25  A  N
ATOM    722  CA   ALA  237     116.405  38.218 -10.276  1.00  68.72  A  C
ATOM    723  CB   ALA  237     117.046  37.934  -8.932  1.00  56.85  A  C
ATOM    724  C    ALA  237     117.349  39.046 -11.139  1.00  67.56  A  C
ATOM    725  O    ALA  237     117.225  40.267 -11.200  1.00  65.98  A  O
ATOM    726  N    PHE  238     118.283  38.385 -11.812  1.00  41.81  A  N
ATOM    727  CA   PHE  238     119.256  39.080 -12.651  1.00  41.24  A  C
ATOM    728  CB   PHE  238     120.606  38.369 -12.591  1.00  47.57  A  C
ATOM    729  CG   PHE  238     121.413  38.696 -11.378  1.00  46.60  A  C
ATOM    730  CD1  PHE  238     121.686  37.725 -10.419  1.00  47.83  A  C
```

FIG. 19A-11

| ATOM | 731 | CD2 | PHE | 238 | 121.931 | 39.970 | -11.208 | 1.00 | 44.20 | A | C |
| ATOM | 732 | CE1 | PHE | 238 | 122.476 | 38.023 | -9.298 | 1.00 | 45.63 | A | C |
| ATOM | 733 | CE2 | PHE | 238 | 122.719 | 40.282 | -10.094 | 1.00 | 50.51 | A | C |
| ATOM | 734 | CZ | PHE | 238 | 122.993 | 39.305 | -9.137 | 1.00 | 51.93 | A | C |
| ATOM | 735 | C | PHE | 238 | 118.861 | 39.252 | -14.116 | 1.00 | 43.09 | A | C |
| ATOM | 736 | O | PHE | 238 | 119.699 | 39.129 | -15.017 | 1.00 | 43.19 | A | O |
| ATOM | 737 | N | THR | 239 | 117.586 | 39.520 | -14.362 | 1.00 | 28.84 | A | N |
| ATOM | 738 | CA | THR | 239 | 117.117 | 39.744 | -15.724 | 1.00 | 32.78 | A | C |
| ATOM | 739 | CB | THR | 239 | 115.952 | 38.821 | -16.086 | 1.00 | 22.29 | A | C |
| ATOM | 740 | OG1 | THR | 239 | 114.866 | 39.059 | -15.191 | 1.00 | 20.25 | A | O |
| ATOM | 741 | CG2 | THR | 239 | 116.363 | 37.382 | -15.988 | 1.00 | 25.20 | A | C |
| ATOM | 742 | C | THR | 239 | 116.655 | 41.202 | -15.798 | 1.00 | 33.04 | A | C |
| ATOM | 743 | O | THR | 239 | 115.955 | 41.695 | -14.902 | 1.00 | 33.54 | A | O |
| ATOM | 744 | N | GLU | 240 | 117.067 | 41.881 | -16.868 | 1.00 | 73.11 | A | N |
| ATOM | 745 | CA | GLU | 240 | 116.755 | 43.291 | -17.085 | 1.00 | 73.36 | A | C |
| ATOM | 746 | CB | GLU | 240 | 116.995 | 43.654 | -18.549 | 1.00 | 97.49 | A | C |
| ATOM | 747 | CG | GLU | 240 | 117.147 | 45.141 | -18.793 | 1.00 | 102.13 | A | C |
| ATOM | 748 | CD | GLU | 240 | 117.738 | 45.441 | -20.152 | 1.00 | 105.04 | A | C |
| ATOM | 749 | OE1 | GLU | 240 | 118.794 | 44.858 | -20.483 | 1.00 | 105.14 | A | O |
| ATOM | 750 | OE2 | GLU | 240 | 117.151 | 46.263 | -20.885 | 1.00 | 105.11 | A | O |
| ATOM | 751 | C | GLU | 240 | 115.336 | 43.665 | -16.689 | 1.00 | 74.71 | A | C |
| ATOM | 752 | O | GLU | 240 | 115.083 | 44.772 | -16.210 | 1.00 | 75.92 | A | O |
| ATOM | 753 | N | ALA | 241 | 114.417 | 42.730 | -16.885 | 1.00 | 32.59 | A | N |
| ATOM | 754 | CA | ALA | 241 | 113.016 | 42.952 | -16.552 | 1.00 | 33.44 | A | C |
| ATOM | 755 | CB | ALA | 241 | 112.170 | 41.769 | -17.051 | 1.00 | 4.05 | A | C |
| ATOM | 756 | C | ALA | 241 | 112.802 | 43.165 | -15.044 | 1.00 | 32.91 | A | C |
| ATOM | 757 | O | ALA | 241 | 111.809 | 43.759 | -14.622 | 1.00 | 34.37 | A | O |
| ATOM | 758 | N | ARG | 242 | 113.725 | 42.678 | -14.223 | 1.00 | 31.60 | A | N |
| ATOM | 759 | CA | ARG | 242 | 113.585 | 42.851 | -12.786 | 1.00 | 31.34 | A | C |
| ATOM | 760 | CB | ARG | 242 | 113.757 | 41.500 | -12.079 | 1.00 | 27.81 | A | C |
| ATOM | 761 | CG | ARG | 242 | 112.489 | 40.658 | -12.052 | 1.00 | 28.01 | A | C |
| ATOM | 762 | CD | ARG | 242 | 112.669 | 39.440 | -11.160 | 1.00 | 28.87 | A | C |
| ATOM | 763 | NE | ARG | 242 | 111.425 | 39.010 | -10.515 | 1.00 | 30.07 | A | N |
| ATOM | 764 | CZ | ARG | 242 | 110.582 | 38.106 | -11.011 | 1.00 | 29.27 | A | C |
| ATOM | 765 | NH1 | ARG | 242 | 110.846 | 37.525 | -12.176 | 1.00 | 28.32 | A | N |
| ATOM | 766 | NH2 | ARG | 242 | 109.485 | 37.769 | -10.334 | 1.00 | 31.29 | A | N |
| ATOM | 767 | C | ARG | 242 | 114.557 | 43.898 | -12.231 | 1.00 | 32.54 | A | C |
| ATOM | 768 | O | ARG | 242 | 114.824 | 43.954 | -11.026 | 1.00 | 35.55 | A | O |
| ATOM | 769 | N | GLY | 243 | 115.080 | 44.733 | -13.122 | 1.00 | 38.70 | A | N |
| ATOM | 770 | CA | GLY | 243 | 115.996 | 45.775 | -12.706 | 1.00 | 36.85 | A | C |
| ATOM | 771 | C | GLY | 243 | 117.468 | 45.462 | -12.890 | 1.00 | 35.13 | A | C |
| ATOM | 772 | O | GLY | 243 | 118.318 | 46.139 | -12.308 | 1.00 | 34.75 | A | O |
| ATOM | 773 | N | ALA | 244 | 117.792 | 44.447 | -13.683 | 1.00 | 32.25 | A | N |
| ATOM | 774 | CA | ALA | 244 | 119.190 | 44.119 | -13.896 | 1.00 | 30.25 | A | C |
| ATOM | 775 | CB | ALA | 244 | 119.326 | 42.709 | -14.442 | 1.00 | 67.28 | A | C |
| ATOM | 776 | C | ALA | 244 | 119.750 | 45.130 | -14.886 | 1.00 | 32.13 | A | C |
| ATOM | 777 | O | ALA | 244 | 119.437 | 45.088 | -16.068 | 1.00 | 31.59 | A | O |
| ATOM | 778 | N | ARG | 245 | 120.566 | 46.054 | -14.401 | 1.00 | 18.96 | A | N |
| ATOM | 779 | CA | ARG | 245 | 121.154 | 47.074 | -15.258 | 1.00 | 19.79 | A | C |
| ATOM | 780 | CB | ARG | 245 | 121.853 | 48.130 | -14.399 | 1.00 | 36.60 | A | C |
| ATOM | 781 | CG | ARG | 245 | 120.888 | 49.043 | -13.655 | 1.00 | 39.07 | A | C |
| ATOM | 782 | CD | ARG | 245 | 121.614 | 49.991 | -12.741 | 1.00 | 39.28 | A | C |
| ATOM | 783 | NE | ARG | 245 | 122.309 | 49.254 | -11.701 | 1.00 | 33.70 | A | N |
| ATOM | 784 | CZ | ARG | 245 | 122.997 | 49.824 | -10.726 | 1.00 | 33.52 | A | C |
| ATOM | 785 | NH1 | ARG | 245 | 123.084 | 51.145 | -10.662 | 1.00 | 32.72 | A | N |
| ATOM | 786 | NH2 | ARG | 245 | 123.590 | 49.075 | -9.810 | 1.00 | 30.81 | A | N |
| ATOM | 787 | C | ARG | 245 | 122.131 | 46.493 | -16.266 | 1.00 | 18.16 | A | C |
| ATOM | 788 | O | ARG | 245 | 123.003 | 45.710 | -15.911 | 1.00 | 14.27 | A | O |
| ATOM | 789 | N | ARG | 246 | 121.985 | 46.896 | -17.525 | 1.00 | 55.16 | A | N |
| ATOM | 790 | CA | ARG | 246 | 122.848 | 46.429 | -18.607 | 1.00 | 57.95 | A | C |
| ATOM | 791 | CB | ARG | 246 | 122.447 | 47.078 | -19.928 | 1.00 | 115.62 | A | C |
| ATOM | 792 | CG | ARG | 246 | 123.405 | 46.764 | -21.067 | 1.00 | 120.98 | A | C |
| ATOM | 793 | CD | ARG | 246 | 123.057 | 47.546 | -22.318 | 1.00 | 126.90 | A | C |
| ATOM | 794 | NE | ARG | 246 | 121.637 | 47.444 | -22.641 | 1.00 | 129.81 | A | N |
| ATOM | 795 | CZ | ARG | 246 | 120.981 | 46.298 | -22.804 | 1.00 | 132.92 | A | C |
| ATOM | 796 | NH1 | ARG | 246 | 121.615 | 45.138 | -22.676 | 1.00 | 132.61 | A | N |
| ATOM | 797 | NH2 | ARG | 246 | 119.685 | 46.314 | -23.094 | 1.00 | 133.70 | A | N |
| ATOM | 798 | C | ARG | 246 | 124.313 | 46.736 | -18.364 | 1.00 | 55.77 | A | C |
| ATOM | 799 | O | ARG | 246 | 124.671 | 47.879 | -18.092 | 1.00 | 58.40 | A | O |
| ATOM | 800 | N | GLY | 247 | 125.151 | 45.711 | -18.475 | 1.00 | 47.75 | A | N |
| ATOM | 801 | CA | GLY | 247 | 126.587 | 45.878 | -18.302 | 1.00 | 50.33 | A | C |
| ATOM | 802 | C | GLY | 247 | 127.097 | 46.294 | -16.934 | 1.00 | 50.40 | A | C |
| ATOM | 803 | O | GLY | 247 | 128.129 | 46.958 | -16.824 | 1.00 | 53.36 | A | O |

FIG. 19A-12

| | | | | | | | | | | | |
|---|---|---|---|---|---|---|---|---|---|---|---|
| ATOM | 804 | N | VAL | 248 | 126.382 | 45.911 | -15.887 | 1.00 | 40.38 | A | N |
| ATOM | 805 | CA | VAL | 248 | 126.790 | 46.248 | -14.535 | 1.00 | 38.39 | A | C |
| ATOM | 806 | CB | VAL | 248 | 125.653 | 46.928 | -13.780 | 1.00 | 41.70 | A | C |
| ATOM | 807 | CG1 | VAL | 248 | 126.049 | 47.136 | -12.331 | 1.00 | 39.35 | A | C |
| ATOM | 808 | CG2 | VAL | 248 | 125.331 | 48.250 | -14.436 | 1.00 | 33.47 | A | C |
| ATOM | 809 | C | VAL | 248 | 127.173 | 44.970 | -13.807 | 1.00 | 41.41 | A | C |
| ATOM | 810 | O | VAL | 248 | 126.530 | 43.936 | -13.993 | 1.00 | 45.46 | A | O |
| ATOM | 811 | N | LYS | 249 | 128.208 | 45.036 | -12.975 | 1.00 | 30.45 | A | N |
| ATOM | 812 | CA | LYS | 249 | 128.645 | 43.852 | -12.250 | 1.00 | 31.36 | A | C |
| ATOM | 813 | CB | LYS | 249 | 129.799 | 44.186 | -11.299 | 1.00 | 85.59 | A | C |
| ATOM | 814 | CG | LYS | 249 | 130.426 | 42.940 | -10.690 | 1.00 | 91.11 | A | C |
| ATOM | 815 | CD | LYS | 249 | 130.844 | 41.943 | -11.782 | 1.00 | 92.18 | A | C |
| ATOM | 816 | CE | LYS | 249 | 131.040 | 40.539 | -11.224 | 1.00 | 94.54 | A | C |
| ATOM | 817 | NZ | LYS | 249 | 131.548 | 39.546 | -12.218 | 1.00 | 97.36 | A | N |
| ATOM | 818 | C | LYS | 249 | 127.503 | 43.190 | -11.473 | 1.00 | 30.02 | A | C |
| ATOM | 819 | O | LYS | 249 | 126.706 | 43.862 | -10.815 | 1.00 | 29.84 | A | O |
| ATOM | 820 | N | LYS | 250 | 127.432 | 41.864 | -11.559 | 1.00 | 29.51 | A | N |
| ATOM | 821 | CA | LYS | 250 | 126.396 | 41.110 | -10.879 | 1.00 | 29.16 | A | C |
| ATOM | 822 | CB | LYS | 250 | 125.763 | 40.134 | -11.871 | 1.00 | 45.59 | A | C |
| ATOM | 823 | CG | LYS | 250 | 125.050 | 40.864 | -12.996 | 1.00 | 44.19 | A | C |
| ATOM | 824 | CD | LYS | 250 | 124.892 | 40.022 | -14.263 | 1.00 | 45.74 | A | C |
| ATOM | 825 | CE | LYS | 250 | 123.827 | 38.928 | -14.135 | 1.00 | 44.90 | A | C |
| ATOM | 826 | NZ | LYS | 250 | 123.513 | 38.274 | -15.453 | 1.00 | 46.72 | A | N |
| ATOM | 827 | C | LYS | 250 | 126.979 | 40.391 | -9.663 | 1.00 | 28.51 | A | C |
| ATOM | 828 | O | LYS | 250 | 127.849 | 39.541 | -9.804 | 1.00 | 28.19 | A | O |
| ATOM | 829 | N | VAL | 251 | 126.493 | 40.754 | -8.474 | 1.00 | 23.05 | A | N |
| ATOM | 830 | CA | VAL | 251 | 126.954 | 40.173 | -7.219 | 1.00 | 22.96 | A | C |
| ATOM | 831 | CB | VAL | 251 | 127.504 | 41.263 | -6.307 | 1.00 | 28.85 | A | C |
| ATOM | 832 | CG1 | VAL | 251 | 127.901 | 40.676 | -4.959 | 1.00 | 27.00 | A | C |
| ATOM | 833 | CG2 | VAL | 251 | 128.678 | 41.928 | -6.974 | 1.00 | 30.06 | A | C |
| ATOM | 834 | C | VAL | 251 | 125.863 | 39.421 | -6.451 | 1.00 | 21.44 | A | C |
| ATOM | 835 | O | VAL | 251 | 124.778 | 39.945 | -6.232 | 1.00 | 17.44 | A | O |
| ATOM | 836 | N | MET | 252 | 126.168 | 38.199 | -6.023 | 1.00 | 19.32 | A | N |
| ATOM | 837 | CA | MET | 252 | 125.212 | 37.383 | -5.278 | 1.00 | 20.30 | A | C |
| ATOM | 838 | CB | MET | 252 | 124.949 | 36.073 | -6.024 | 1.00 | 19.49 | A | C |
| ATOM | 839 | CG | MET | 252 | 123.850 | 35.212 | -5.425 | 1.00 | 18.18 | A | C |
| ATOM | 840 | SD | MET | 252 | 123.556 | 33.701 | -6.379 | 1.00 | 22.23 | A | S |
| ATOM | 841 | CE | MET | 252 | 123.009 | 34.366 | -7.960 | 1.00 | 13.54 | A | C |
| ATOM | 842 | C | MET | 252 | 125.730 | 37.072 | -3.875 | 1.00 | 19.32 | A | C |
| ATOM | 843 | O | MET | 252 | 126.880 | 36.675 | -3.704 | 1.00 | 21.69 | A | O |
| ATOM | 844 | N | VAL | 253 | 124.886 | 37.261 | -2.869 | 1.00 | 11.70 | A | N |
| ATOM | 845 | CA | VAL | 253 | 125.286 | 36.971 | -1.505 | 1.00 | 12.85 | A | C |
| ATOM | 846 | CB | VAL | 253 | 125.173 | 38.221 | -0.593 | 1.00 | 5.67 | A | C |
| ATOM | 847 | CG1 | VAL | 253 | 125.508 | 37.856 | 0.842 | 1.00 | 7.09 | A | C |
| ATOM | 848 | CG2 | VAL | 253 | 126.118 | 39.310 | -1.079 | 1.00 | 5.31 | A | C |
| ATOM | 849 | C | VAL | 253 | 124.370 | 35.881 | -0.974 | 1.00 | 12.42 | A | C |
| ATOM | 850 | O | VAL | 253 | 123.166 | 36.093 | -0.870 | 1.00 | 10.86 | A | O |
| ATOM | 851 | N | ILE | 254 | 124.936 | 34.716 | -0.649 | 1.00 | 26.88 | A | N |
| ATOM | 852 | CA | ILE | 254 | 124.142 | 33.597 | -0.126 | 1.00 | 23.78 | A | C |
| ATOM | 853 | CB | ILE | 254 | 124.457 | 32.266 | -0.847 | 1.00 | 10.72 | A | C |
| ATOM | 854 | CG2 | ILE | 254 | 123.584 | 31.171 | -0.294 | 1.00 | 7.19 | A | C |
| ATOM | 855 | CG1 | ILE | 254 | 124.220 | 32.397 | -2.352 | 1.00 | 9.30 | A | C |
| ATOM | 856 | CD1 | ILE | 254 | 125.307 | 33.140 | -3.078 | 1.00 | 8.93 | A | C |
| ATOM | 857 | C | ILE | 254 | 124.379 | 33.370 | 1.359 | 1.00 | 21.87 | A | C |
| ATOM | 858 | O | ILE | 254 | 125.508 | 33.431 | 1.833 | 1.00 | 23.74 | A | O |
| ATOM | 859 | N | VAL | 255 | 123.300 | 33.105 | 2.084 | 1.00 | 38.19 | A | N |
| ATOM | 860 | CA | VAL | 255 | 123.379 | 32.858 | 3.516 | 1.00 | 36.93 | A | C |
| ATOM | 861 | CB | VAL | 255 | 122.733 | 33.994 | 4.328 | 1.00 | 13.80 | A | C |
| ATOM | 862 | CG1 | VAL | 255 | 123.224 | 33.949 | 5.753 | 1.00 | 12.25 | A | C |
| ATOM | 863 | CG2 | VAL | 255 | 123.056 | 35.325 | 3.713 | 1.00 | 14.44 | A | C |
| ATOM | 864 | C | VAL | 255 | 122.592 | 31.594 | 3.798 | 1.00 | 34.68 | A | C |
| ATOM | 865 | O | VAL | 255 | 121.431 | 31.491 | 3.403 | 1.00 | 36.68 | A | O |
| ATOM | 866 | N | THR | 256 | 123.210 | 30.632 | 4.474 | 1.00 | 19.22 | A | N |
| ATOM | 867 | CA | THR | 256 | 122.514 | 29.387 | 4.798 | 1.00 | 20.04 | A | C |
| ATOM | 868 | CB | THR | 256 | 122.477 | 28.457 | 3.566 | 1.00 | 10.08 | A | C |
| ATOM | 869 | OG1 | THR | 256 | 122.032 | 27.147 | 3.952 | 1.00 | 6.12 | A | O |
| ATOM | 870 | CG2 | THR | 256 | 123.851 | 28.387 | 2.926 | 1.00 | 8.93 | A | C |
| ATOM | 871 | C | THR | 256 | 123.128 | 28.650 | 5.995 | 1.00 | 23.52 | A | C |
| ATOM | 872 | O | THR | 256 | 124.303 | 28.831 | 6.310 | 1.00 | 19.68 | A | O |
| ATOM | 873 | N | ASP | 257 | 122.323 | 27.829 | 6.663 | 1.00 | 46.58 | A | N |
| ATOM | 874 | CA | ASP | 257 | 122.794 | 27.097 | 7.830 | 1.00 | 46.96 | A | C |
| ATOM | 875 | CB | ASP | 257 | 122.069 | 27.585 | 9.091 | 1.00 | 21.89 | A | C |
| ATOM | 876 | CG | ASP | 257 | 120.655 | 27.009 | 9.225 | 1.00 | 27.25 | A | C |

FIG. 19A-13

```
ATOM    877  OD1 ASP 257     120.089  26.573   8.191  1.00   27.72      A  O
ATOM    878  OD2 ASP 257     120.110  27.006  10.362  1.00   32.52      A  O
ATOM    879  C   ASP 257     122.599  25.596   7.693  1.00   43.55      A  C
ATOM    880  O   ASP 257     122.525  24.883   8.695  1.00   42.79      A  O
ATOM    881  N   GLY 258     122.510  25.106   6.461  1.00   42.38      A  N
ATOM    882  CA  GLY 258     122.330  23.678   6.283  1.00   44.80      A  C
ATOM    883  C   GLY 258     122.618  23.150   4.896  1.00   48.62      A  C
ATOM    884  O   GLY 258     122.523  23.871   3.903  1.00   44.34      A  O
ATOM    885  N   GLU 259     122.984  21.876   4.832  1.00   88.78      A  N
ATOM    886  CA  GLU 259     123.265  21.230   3.562  1.00   90.66      A  C
ATOM    887  CB  GLU 259     123.650  19.770   3.782  1.00   87.02      A  C
ATOM    888  CG  GLU 259     124.983  19.588   4.461  1.00   94.80      A  C
ATOM    889  CD  GLU 259     125.130  18.214   5.070  1.00   98.61      A  C
ATOM    890  OE1 GLU 259     126.256  17.861   5.481  1.00  105.36      A  O
ATOM    891  OE2 GLU 259     124.115  17.490   5.147  1.00   98.63      A  O
ATOM    892  C   GLU 259     122.004  21.298   2.727  1.00   89.52      A  C
ATOM    893  O   GLU 259     120.927  20.906   3.174  1.00   86.69      A  O
ATOM    894  N   SER 260     122.140  21.815   1.517  1.00   31.72      A  N
ATOM    895  CA  SER 260     121.007  21.922   0.615  1.00   34.88      A  C
ATOM    896  CB  SER 260     121.435  22.606  -0.685  1.00  104.64      A  C
ATOM    897  OG  SER 260     122.467  21.872  -1.325  1.00  105.15      A  O
ATOM    898  C   SER 260     120.489  20.526   0.304  1.00   34.78      A  C
ATOM    899  O   SER 260     121.257  19.571   0.315  1.00   30.81      A  O
ATOM    900  N   HIS 261     119.192  20.409   0.039  1.00  119.42      A  N
ATOM    901  CA  HIS 261     118.609  19.114  -0.284  1.00  123.77      A  C
ATOM    902  CB  HIS 261     117.107  19.116   0.020  1.00   89.56      A  C
ATOM    903  CG  HIS 261     116.789  19.030   1.482  1.00   92.76      A  C
ATOM    904  CD2 HIS 261     116.610  19.997   2.413  1.00   91.87      A  C
ATOM    905  ND1 HIS 261     116.648  17.830   2.147  1.00   94.24      A  N
ATOM    906  CE1 HIS 261     116.393  18.065   3.422  1.00   94.31      A  C
ATOM    907  NE2 HIS 261     116.365  19.372   3.610  1.00   91.58      A  N
ATOM    908  C   HIS 261     118.866  18.815  -1.754  1.00  124.83      A  C
ATOM    909  O   HIS 261     118.732  17.676  -2.203  1.00  122.05      A  O
ATOM    910  N   ASP 262     119.251  19.850  -2.495  1.00   94.20      A  N
ATOM    911  CA  ASP 262     119.556  19.709  -3.913  1.00   99.17      A  C
ATOM    912  CB  ASP 262     118.838  20.798  -4.732  1.00   77.35      A  C
ATOM    913  CG  ASP 262     118.558  22.065  -3.929  1.00   77.35      A  C
ATOM    914  OD1 ASP 262     119.382  22.429  -3.067  1.00   77.35      A  O
ATOM    915  OD2 ASP 262     117.515  22.708  -4.179  1.00   77.35      A  O
ATOM    916  C   ASP 262     121.065  19.758  -4.191  1.00   99.22      A  C
ATOM    917  O   ASP 262     121.510  20.456  -5.104  1.00   99.08      A  O
ATOM    918  N   ASN 263     121.842  19.009  -3.406  1.00   48.33      A  N
ATOM    919  CA  ASN 263     123.300  18.956  -3.558  1.00   49.50      A  C
ATOM    920  CB  ASN 263     123.896  17.820  -2.719  1.00   78.20      A  C
ATOM    921  CG  ASN 263     123.359  17.781  -1.303  1.00   82.57      A  C
ATOM    922  OD1 ASN 263     123.578  18.703  -0.511  1.00   84.07      A  O
ATOM    923  ND2 ASN 263     122.651  16.702  -0.974  1.00   77.07      A  N
ATOM    924  C   ASN 263     123.657  18.684  -5.012  1.00   50.14      A  C
ATOM    925  O   ASN 263     124.574  19.286  -5.572  1.00   49.04      A  O
ATOM    926  N   TYR 264     122.915  17.754  -5.601  1.00   83.05      A  N
ATOM    927  CA  TYR 264     123.112  17.330  -6.976  1.00   80.90      A  C
ATOM    928  CB  TYR 264     121.905  16.512  -7.431  1.00  165.37      A  C
ATOM    929  CG  TYR 264     121.684  15.297  -6.568  1.00  165.37      A  C
ATOM    930  CD1 TYR 264     121.294  15.427  -5.234  1.00  165.37      A  C
ATOM    931  CE1 TYR 264     121.137  14.312  -4.419  1.00  165.37      A  C
ATOM    932  CD2 TYR 264     121.909  14.016  -7.067  1.00  165.37      A  C
ATOM    933  CE2 TYR 264     121.753  12.892  -6.262  1.00  165.37      A  C
ATOM    934  CZ  TYR 264     121.369  13.048  -4.939  1.00  165.37      A  C
ATOM    935  OH  TYR 264     121.224  11.940  -4.139  1.00  165.37      A  O
ATOM    936  C   TYR 264     123.396  18.439  -7.977  1.00   79.55      A  C
ATOM    937  O   TYR 264     124.509  18.536  -8.498  1.00   76.68      A  O
ATOM    938  N   ARG 265     122.406  19.283  -8.245  1.00   83.26      A  N
ATOM    939  CA  ARG 265     122.605  20.340  -9.224  1.00   82.16      A  C
ATOM    940  CB  ARG 265     121.297  20.636  -9.957  1.00   36.62      A  C
ATOM    941  CG  ARG 265     120.182  21.225  -9.142  1.00   37.07      A  C
ATOM    942  CD  ARG 265     119.267  21.953 -10.110  1.00   38.90      A  C
ATOM    943  NE  ARG 265     118.140  22.620  -9.464  1.00   44.29      A  N
ATOM    944  CZ  ARG 265     117.562  23.714  -9.947  1.00   44.46      A  C
ATOM    945  NH1 ARG 265     118.016  24.257 -11.071  1.00   49.09      A  N
ATOM    946  NH2 ARG 265     116.528  24.258  -9.321  1.00   48.43      A  N
ATOM    947  C   ARG 265     123.211  21.644  -8.720  1.00   81.41      A  C
ATOM    948  O   ARG 265     123.137  22.668  -9.396  1.00   82.72      A  O
ATOM    949  N   LEU 266     123.819  21.614  -7.543  1.00   27.19      A  N
```

FIG. 19A-14

```
ATOM    950  CA  LEU  266     124.435  22.815  -7.003  1.00  28.76  A  C
ATOM    951  CB  LEU  266     124.798  22.601  -5.539  1.00   4.24  A  C
ATOM    952  CG  LEU  266     125.336  23.820  -4.797  1.00   3.45  A  C
ATOM    953  CD1 LEU  266     124.393  24.999  -4.976  1.00   5.79  A  C
ATOM    954  CD2 LEU  266     125.502  23.466  -3.320  1.00   1.87  A  C
ATOM    955  C   LEU  266     125.684  23.084  -7.828  1.00  31.58  A  C
ATOM    956  O   LEU  266     126.086  24.226  -8.022  1.00  31.46  A  O
ATOM    957  N   LYS  267     126.286  22.007  -8.317  1.00  45.65  A  N
ATOM    958  CA  LYS  267     127.479  22.088  -9.149  1.00  47.96  A  C
ATOM    959  CB  LYS  267     127.949  20.673  -9.497  1.00  72.30  A  C
ATOM    960  CG  LYS  267     129.239  20.583 -10.298  1.00  72.30  A  C
ATOM    961  CD  LYS  267     130.428  20.277  -9.403  1.00  72.30  A  C
ATOM    962  CE  LYS  267     131.649  19.894 -10.230  1.00  72.30  A  C
ATOM    963  NZ  LYS  267     132.793  19.452  -9.381  1.00  72.30  A  N
ATOM    964  C   LYS  267     127.103  22.842 -10.427  1.00  47.45  A  C
ATOM    965  O   LYS  267     127.763  23.810 -10.809  1.00  46.97  A  O
ATOM    966  N   GLN  268     126.032  22.389 -11.074  1.00  32.65  A  N
ATOM    967  CA  GLN  268     125.553  22.999 -12.303  1.00  31.62  A  C
ATOM    968  CB  GLN  268     124.292  22.295 -12.798  1.00  88.56  A  C
ATOM    969  CG  GLN  268     124.449  20.845 -13.182  1.00  88.56  A  C
ATOM    970  CD  GLN  268     123.119  20.227 -13.576  1.00  88.56  A  C
ATOM    971  OE1 GLN  268     123.059  19.078 -14.010  1.00  88.56  A  O
ATOM    972  NE2 GLN  268     122.041  20.992 -13.423  1.00  88.56  A  N
ATOM    973  C   GLN  268     125.221  24.474 -12.100  1.00  27.37  A  C
ATOM    974  O   GLN  268     125.678  25.332 -12.851  1.00  28.55  A  O
ATOM    975  N   VAL  269     124.410  24.767 -11.089  1.00  11.19  A  N
ATOM    976  CA  VAL  269     124.007  26.140 -10.830  1.00   8.94  A  C
ATOM    977  CB  VAL  269     123.088  26.223  -9.598  1.00  22.95  A  C
ATOM    978  CG1 VAL  269     122.650  27.667  -9.374  1.00  18.60  A  C
ATOM    979  CG2 VAL  269     121.872  25.334  -9.801  1.00  20.81  A  C
ATOM    980  C   VAL  269     125.198  27.076 -10.649  1.00   8.53  A  C
ATOM    981  O   VAL  269     125.286  28.093 -11.318  1.00  11.37  A  O
ATOM    982  N   ILE  270     126.114  26.744  -9.746  1.00   5.57  A  N
ATOM    983  CA  ILE  270     127.291  27.585  -9.535  1.00   6.19  A  C
ATOM    984  CB  ILE  270     128.281  26.944  -8.533  1.00  12.81  A  C
ATOM    985  CG2 ILE  270     129.592  27.731  -8.504  1.00   7.43  A  C
ATOM    986  CG1 ILE  270     127.671  26.926  -7.135  1.00  10.37  A  C
ATOM    987  CD1 ILE  270     127.367  28.317  -6.591  1.00  11.49  A  C
ATOM    988  C   ILE  270     128.001  27.775 -10.870  1.00  10.06  A  C
ATOM    989  O   ILE  270     128.549  28.838 -11.140  1.00   8.84  A  O
ATOM    990  N   GLN  271     127.981  26.729 -11.696  1.00   7.96  A  N
ATOM    991  CA  GLN  271     128.605  26.751 -13.011  1.00  10.02  A  C
ATOM    992  CB  GLN  271     128.434  25.394 -13.698  1.00  84.89  A  C
ATOM    993  CG  GLN  271     129.267  25.214 -14.947  1.00  86.79  A  C
ATOM    994  CD  GLN  271     130.744  25.366 -14.665  1.00  89.29  A  C
ATOM    995  OE1 GLN  271     131.244  26.477 -14.506  1.00  89.62  A  O
ATOM    996  NE2 GLN  271     131.451  24.243 -14.583  1.00  90.86  A  N
ATOM    997  C   GLN  271     127.962  27.842 -13.860  1.00  12.48  A  C
ATOM    998  O   GLN  271     128.644  28.733 -14.348  1.00  15.17  A  O
ATOM    999  N   ASP  272     126.648  27.770 -14.031  1.00  33.57  A  N
ATOM   1000  CA  ASP  272     125.929  28.758 -14.818  1.00  34.85  A  C
ATOM   1001  CB  ASP  272     124.430  28.459 -14.786  1.00  74.39  A  C
ATOM   1002  CG  ASP  272     124.084  27.142 -15.454  1.00  76.01  A  C
ATOM   1003  OD1 ASP  272     123.000  26.589 -15.163  1.00  78.08  A  O
ATOM   1004  OD2 ASP  272     124.893  26.665 -16.278  1.00  82.27  A  O
ATOM   1005  C   ASP  272     126.194  30.163 -14.283  1.00  35.65  A  C
ATOM   1006  O   ASP  272     126.190  31.131 -15.042  1.00  33.10  A  O
ATOM   1007  N   CYS  273     126.426  30.280 -12.978  1.00  42.88  A  N
ATOM   1008  CA  CYS  273     126.698  31.582 -12.387  1.00  41.31  A  C
ATOM   1009  CB  CYS  273     126.630  31.516 -10.862  1.00  24.14  A  C
ATOM   1010  SG  CYS  273     124.940  31.489 -10.191  1.00  22.24  A  S
ATOM   1011  C   CYS  273     128.059  32.090 -12.826  1.00  41.68  A  C
ATOM   1012  O   CYS  273     128.244  33.288 -13.008  1.00  35.99  A  O
ATOM   1013  N   GLU  274     129.010  31.178 -12.994  1.00  20.07  A  N
ATOM   1014  CA  GLU  274     130.364  31.531 -13.440  1.00  22.87  A  C
ATOM   1015  CB  GLU  274     131.317  30.338 -13.298  1.00  39.18  A  C
ATOM   1016  CG  GLU  274     132.090  30.309 -11.989  1.00  44.30  A  C
ATOM   1017  CD  GLU  274     133.041  31.490 -11.836  1.00  49.41  A  C
ATOM   1018  OE1 GLU  274     133.622  31.659 -10.740  1.00  51.28  A  O
ATOM   1019  OE2 GLU  274     133.212  32.251 -12.812  1.00  53.97  A  O
ATOM   1020  C   GLU  274     130.345  31.984 -14.893  1.00  25.29  A  C
ATOM   1021  O   GLU  274     131.031  32.931 -15.266  1.00  27.49  A  O
ATOM   1022  N   ASP  275     129.550  31.298 -15.707  1.00  41.03  A  N
```

FIG. 19A-15

| | | | | | | | | | | |
|---|---|---|---|---|---|---|---|---|---|---|
| ATOM | 1023 | CA | ASP | 275 | 129.421 | 31.625 | -17.119 | 1.00 | 39.77 | A | C |
| ATOM | 1024 | CB | ASP | 275 | 128.538 | 30.594 | -17.822 | 1.00 | 63.42 | A | C |
| ATOM | 1025 | CG | ASP | 275 | 129.106 | 29.203 | -17.757 | 1.00 | 64.69 | A | C |
| ATOM | 1026 | OD1 | ASP | 275 | 129.987 | 28.959 | -16.906 | 1.00 | 68.39 | A | O |
| ATOM | 1027 | OD2 | ASP | 275 | 128.657 | 28.352 | -18.551 | 1.00 | 66.35 | A | O |
| ATOM | 1028 | C | ASP | 275 | 128.789 | 32.996 | -17.295 | 1.00 | 38.76 | A | C |
| ATOM | 1029 | O | ASP | 275 | 128.883 | 33.595 | -18.367 | 1.00 | 34.31 | A | O |
| ATOM | 1030 | N | GLU | 276 | 128.137 | 33.485 | -16.247 | 1.00 | 28.36 | A | N |
| ATOM | 1031 | CA | GLU | 276 | 127.479 | 34.771 | -16.328 | 1.00 | 28.01 | A | C |
| ATOM | 1032 | CB | GLU | 276 | 126.019 | 34.617 | -15.913 | 1.00 | 53.33 | A | C |
| ATOM | 1033 | CG | GLU | 276 | 125.310 | 33.520 | -16.700 | 1.00 | 53.20 | A | C |
| ATOM | 1034 | CD | GLU | 276 | 123.807 | 33.493 | -16.487 | 1.00 | 54.30 | A | C |
| ATOM | 1035 | OE1 | GLU | 276 | 123.150 | 32.629 | -17.102 | 1.00 | 55.01 | A | O |
| ATOM | 1036 | OE2 | GLU | 276 | 123.280 | 34.330 | -15.717 | 1.00 | 51.24 | A | O |
| ATOM | 1037 | C | GLU | 276 | 128.172 | 35.841 | -15.504 | 1.00 | 26.84 | A | C |
| ATOM | 1038 | O | GLU | 276 | 127.621 | 36.919 | -15.288 | 1.00 | 27.95 | A | O |
| ATOM | 1039 | N | ASN | 277 | 129.382 | 35.535 | -15.050 | 1.00 | 28.50 | A | N |
| ATOM | 1040 | CA | ASN | 277 | 130.185 | 36.472 | -14.268 | 1.00 | 28.47 | A | C |
| ATOM | 1041 | CB | ASN | 277 | 130.607 | 37.655 | -15.140 | 1.00 | 86.35 | A | C |
| ATOM | 1042 | CG | ASN | 277 | 131.230 | 37.218 | -16.439 | 1.00 | 91.27 | A | C |
| ATOM | 1043 | OD1 | ASN | 277 | 132.263 | 36.548 | -16.451 | 1.00 | 91.09 | A | O |
| ATOM | 1044 | ND2 | ASN | 277 | 130.601 | 37.589 | -17.550 | 1.00 | 90.23 | A | N |
| ATOM | 1045 | C | ASN | 277 | 129.493 | 37.014 | -13.018 | 1.00 | 24.82 | A | C |
| ATOM | 1046 | O | ASN | 277 | 129.476 | 38.226 | -12.790 | 1.00 | 25.80 | A | O |
| ATOM | 1047 | N | ILE | 278 | 128.925 | 36.127 | -12.207 | 1.00 | 15.37 | A | N |
| ATOM | 1048 | CA | ILE | 278 | 128.261 | 36.560 | -10.989 | 1.00 | 15.82 | A | C |
| ATOM | 1049 | CB | ILE | 278 | 126.963 | 35.773 | -10.747 | 1.00 | 17.43 | A | C |
| ATOM | 1050 | CG2 | ILE | 278 | 126.304 | 36.243 | -9.454 | 1.00 | 18.82 | A | C |
| ATOM | 1051 | CG1 | ILE | 278 | 126.016 | 35.949 | -11.932 | 1.00 | 14.88 | A | C |
| ATOM | 1052 | CD1 | ILE | 278 | 124.742 | 35.153 | -11.796 | 1.00 | 17.16 | A | C |
| ATOM | 1053 | C | ILE | 278 | 129.168 | 36.345 | -9.780 | 1.00 | 16.42 | A | C |
| ATOM | 1054 | O | ILE | 278 | 129.363 | 35.212 | -9.354 | 1.00 | 16.76 | A | O |
| ATOM | 1055 | N | GLN | 279 | 129.737 | 37.426 | -9.244 | 1.00 | 26.25 | A | N |
| ATOM | 1056 | CA | GLN | 279 | 130.578 | 37.335 | -8.053 | 1.00 | 25.85 | A | C |
| ATOM | 1057 | CB | GLN | 279 | 131.035 | 38.716 | -7.605 | 1.00 | 41.76 | A | C |
| ATOM | 1058 | CG | GLN | 279 | 131.959 | 39.382 | -8.574 | 1.00 | 47.54 | A | C |
| ATOM | 1059 | CD | GLN | 279 | 133.158 | 38.524 | -8.894 | 1.00 | 51.46 | A | C |
| ATOM | 1060 | OE1 | GLN | 279 | 133.992 | 38.255 | -8.023 | 1.00 | 45.70 | A | O |
| ATOM | 1061 | NE2 | GLN | 279 | 133.252 | 38.078 | -10.146 | 1.00 | 51.05 | A | N |
| ATOM | 1062 | C | GLN | 279 | 129.716 | 36.736 | -6.958 | 1.00 | 23.72 | A | C |
| ATOM | 1063 | O | GLN | 279 | 128.609 | 37.216 | -6.692 | 1.00 | 20.64 | A | O |
| ATOM | 1064 | N | ARG | 280 | 130.214 | 35.697 | -6.310 | 1.00 | 16.06 | A | N |
| ATOM | 1065 | CA | ARG | 280 | 129.440 | 35.054 | -5.258 | 1.00 | 17.58 | A | C |
| ATOM | 1066 | CB | ARG | 280 | 129.107 | 33.620 | -5.661 | 1.00 | 19.51 | A | C |
| ATOM | 1067 | CG | ARG | 280 | 128.413 | 33.488 | -6.997 | 1.00 | 18.14 | A | C |
| ATOM | 1068 | CD | ARG | 280 | 128.274 | 32.021 | -7.371 | 1.00 | 17.81 | A | C |
| ATOM | 1069 | NE | ARG | 280 | 129.576 | 31.365 | -7.441 | 1.00 | 14.86 | A | N |
| ATOM | 1070 | CZ | ARG | 280 | 130.427 | 31.489 | -8.452 | 1.00 | 18.77 | A | C |
| ATOM | 1071 | NH1 | ARG | 280 | 130.131 | 32.241 | -9.493 | 1.00 | 21.69 | A | N |
| ATOM | 1072 | NH2 | ARG | 280 | 131.579 | 30.846 | -8.422 | 1.00 | 23.71 | A | N |
| ATOM | 1073 | C | ARG | 280 | 130.123 | 35.037 | -3.892 | 1.00 | 17.24 | A | C |
| ATOM | 1074 | O | ARG | 280 | 131.269 | 34.592 | -3.750 | 1.00 | 16.97 | A | O |
| ATOM | 1075 | N | PHE | 281 | 129.406 | 35.539 | -2.894 | 1.00 | 21.33 | A | N |
| ATOM | 1076 | CA | PHE | 281 | 129.889 | 35.538 | -1.527 | 1.00 | 23.32 | A | C |
| ATOM | 1077 | CB | PHE | 281 | 129.848 | 36.933 | -0.924 | 1.00 | 12.67 | A | C |
| ATOM | 1078 | CG | PHE | 281 | 130.754 | 37.900 | -1.603 | 1.00 | 15.70 | A | C |
| ATOM | 1079 | CD1 | PHE | 281 | 130.419 | 38.434 | -2.837 | 1.00 | 19.55 | A | C |
| ATOM | 1080 | CD2 | PHE | 281 | 131.968 | 38.250 | -1.024 | 1.00 | 17.43 | A | C |
| ATOM | 1081 | CE1 | PHE | 281 | 131.281 | 39.305 | -3.487 | 1.00 | 19.61 | A | C |
| ATOM | 1082 | CE2 | PHE | 281 | 132.842 | 39.120 | -1.665 | 1.00 | 15.16 | A | C |
| ATOM | 1083 | CZ | PHE | 281 | 132.498 | 39.650 | -2.900 | 1.00 | 16.59 | A | C |
| ATOM | 1084 | C | PHE | 281 | 128.925 | 34.646 | -0.785 | 1.00 | 24.03 | A | C |
| ATOM | 1085 | O | PHE | 281 | 127.710 | 34.867 | -0.821 | 1.00 | 26.40 | A | O |
| ATOM | 1086 | N | SER | 282 | 129.449 | 33.613 | -0.141 | 1.00 | 13.47 | A | N |
| ATOM | 1087 | CA | SER | 282 | 128.594 | 32.705 | 0.602 | 1.00 | 15.32 | A | C |
| ATOM | 1088 | CB | SER | 282 | 128.746 | 31.272 | 0.084 | 1.00 | 11.38 | A | C |
| ATOM | 1089 | OG | SER | 282 | 130.081 | 30.816 | 0.216 | 1.00 | 7.93 | A | O |
| ATOM | 1090 | C | SER | 282 | 128.947 | 32.782 | 2.069 | 1.00 | 17.20 | A | C |
| ATOM | 1091 | O | SER | 282 | 130.066 | 33.135 | 2.435 | 1.00 | 21.06 | A | O |
| ATOM | 1092 | N | ILE | 283 | 127.969 | 32.477 | 2.908 | 1.00 | 24.08 | A | N |
| ATOM | 1093 | CA | ILE | 283 | 128.164 | 32.504 | 4.343 | 1.00 | 22.00 | A | C |
| ATOM | 1094 | CB | ILE | 283 | 127.517 | 33.733 | 4.968 | 1.00 | 17.91 | A | C |
| ATOM | 1095 | CG2 | ILE | 283 | 127.843 | 33.791 | 6.442 | 1.00 | 18.72 | A | C |

FIG. 19A-16

| | | | | | | | | | | |
|---|---|---|---|---|---|---|---|---|---|---|
| ATOM | 1096 | CG1 | ILE | 283 | 128.045 | 34.986 | 4.281 | 1.00 | 14.38 | A C |
| ATOM | 1097 | CD1 | ILE | 283 | 127.103 | 36.171 | 4.383 | 1.00 | 17.94 | A C |
| ATOM | 1098 | C | ILE | 283 | 127.510 | 31.273 | 4.912 | 1.00 | 21.07 | A C |
| ATOM | 1099 | O | ILE | 283 | 126.394 | 30.917 | 4.536 | 1.00 | 20.93 | A O |
| ATOM | 1100 | N | ALA | 284 | 128.204 | 30.618 | 5.823 | 1.00 | 29.93 | A N |
| ATOM | 1101 | CA | ALA | 284 | 127.663 | 29.421 | 6.412 | 1.00 | 29.95 | A C |
| ATOM | 1102 | CB | ALA | 284 | 128.548 | 28.253 | 6.070 | 1.00 | 1.87 | A C |
| ATOM | 1103 | C | ALA | 284 | 127.507 | 29.536 | 7.920 | 1.00 | 28.08 | A C |
| ATOM | 1104 | O | ALA | 284 | 128.482 | 29.740 | 8.641 | 1.00 | 26.74 | A O |
| ATOM | 1105 | N | ILE | 285 | 126.270 | 29.422 | 8.389 | 1.00 | 31.23 | A N |
| ATOM | 1106 | CA | ILE | 285 | 125.997 | 29.457 | 9.817 | 1.00 | 25.43 | A C |
| ATOM | 1107 | CB | ILE | 285 | 124.529 | 29.859 | 10.107 | 1.00 | 43.54 | A C |
| ATOM | 1108 | CG2 | ILE | 285 | 124.187 | 29.569 | 11.555 | 1.00 | 38.36 | A C |
| ATOM | 1109 | CG1 | ILE | 285 | 124.306 | 31.344 | 9.791 | 1.00 | 38.87 | A C |
| ATOM | 1110 | CD1 | ILE | 285 | 124.206 | 31.670 | 8.315 | 1.00 | 40.01 | A C |
| ATOM | 1111 | C | ILE | 285 | 126.227 | 28.022 | 10.296 | 1.00 | 28.75 | A C |
| ATOM | 1112 | O | ILE | 285 | 125.523 | 27.106 | 9.872 | 1.00 | 30.49 | A O |
| ATOM | 1113 | N | LEU | 286 | 127.205 | 27.818 | 11.169 | 1.00 | 38.23 | A N |
| ATOM | 1114 | CA | LEU | 286 | 127.497 | 26.471 | 11.649 | 1.00 | 38.71 | A C |
| ATOM | 1115 | CB | LEU | 286 | 128.999 | 26.313 | 11.876 | 1.00 | 50.51 | A C |
| ATOM | 1116 | CG | LEU | 286 | 129.917 | 26.722 | 10.727 | 1.00 | 53.33 | A C |
| ATOM | 1117 | CD1 | LEU | 286 | 131.340 | 26.363 | 11.105 | 1.00 | 55.89 | A C |
| ATOM | 1118 | CD2 | LEU | 286 | 129.513 | 26.019 | 9.441 | 1.00 | 55.00 | A C |
| ATOM | 1119 | C | LEU | 286 | 126.760 | 26.069 | 12.923 | 1.00 | 39.16 | A C |
| ATOM | 1120 | O | LEU | 286 | 127.068 | 25.036 | 13.517 | 1.00 | 40.00 | A O |
| ATOM | 1121 | N | GLY | 287 | 125.789 | 26.875 | 13.339 | 1.00 | 72.80 | A N |
| ATOM | 1122 | CA | GLY | 287 | 125.042 | 26.579 | 14.551 | 1.00 | 71.58 | A C |
| ATOM | 1123 | C | GLY | 287 | 124.586 | 25.139 | 14.700 | 1.00 | 69.16 | A C |
| ATOM | 1124 | O | GLY | 287 | 125.056 | 24.419 | 15.583 | 1.00 | 73.26 | A O |
| ATOM | 1125 | N | THR | 296 | 131.112 | 19.210 | 10.542 | 1.00 | 87.02 | A N |
| ATOM | 1126 | CA | THR | 296 | 130.609 | 20.333 | 9.766 | 1.00 | 87.06 | A C |
| ATOM | 1127 | CB | THR | 296 | 130.702 | 21.652 | 10.554 | 1.00 | 100.17 | A C |
| ATOM | 1128 | OG1 | THR | 296 | 132.071 | 21.903 | 10.895 | 1.00 | 105.23 | A O |
| ATOM | 1129 | CG2 | THR | 296 | 129.861 | 21.592 | 11.817 | 1.00 | 100.04 | A C |
| ATOM | 1130 | C | THR | 296 | 131.387 | 20.535 | 8.479 | 1.00 | 88.04 | A C |
| ATOM | 1131 | O | THR | 296 | 130.985 | 21.331 | 7.631 | 1.00 | 86.85 | A O |
| ATOM | 1132 | N | GLU | 297 | 132.497 | 19.825 | 8.322 | 1.00 | 78.34 | A N |
| ATOM | 1133 | CA | GLU | 297 | 133.304 | 20.020 | 7.128 | 1.00 | 81.80 | A C |
| ATOM | 1134 | CB | GLU | 297 | 134.577 | 19.171 | 7.169 | 1.00 | 125.47 | A C |
| ATOM | 1135 | CG | GLU | 297 | 134.403 | 17.709 | 6.851 | 1.00 | 132.50 | A C |
| ATOM | 1136 | CD | GLU | 297 | 135.690 | 17.103 | 6.342 | 1.00 | 133.75 | A C |
| ATOM | 1137 | OE1 | GLU | 297 | 135.709 | 15.886 | 6.067 | 1.00 | 135.24 | A O |
| ATOM | 1138 | OE2 | GLU | 297 | 136.682 | 17.853 | 6.212 | 1.00 | 137.19 | A O |
| ATOM | 1139 | C | GLU | 297 | 132.550 | 19.770 | 5.832 | 1.00 | 79.84 | A C |
| ATOM | 1140 | O | GLU | 297 | 132.581 | 20.609 | 4.931 | 1.00 | 79.34 | A O |
| ATOM | 1141 | N | LYS | 298 | 131.865 | 18.638 | 5.728 | 1.00 | 42.69 | A N |
| ATOM | 1142 | CA | LYS | 298 | 131.125 | 18.352 | 4.505 | 1.00 | 42.69 | A C |
| ATOM | 1143 | CB | LYS | 298 | 130.281 | 17.087 | 4.678 | 1.00 | 102.63 | A C |
| ATOM | 1144 | CG | LYS | 298 | 129.695 | 16.562 | 3.376 | 1.00 | 111.34 | A C |
| ATOM | 1145 | CD | LYS | 298 | 129.117 | 15.166 | 3.545 | 1.00 | 113.06 | A C |
| ATOM | 1146 | CE | LYS | 298 | 130.167 | 14.187 | 4.057 | 1.00 | 116.88 | A C |
| ATOM | 1147 | NZ | LYS | 298 | 131.378 | 14.159 | 3.195 | 1.00 | 121.20 | A N |
| ATOM | 1148 | C | LYS | 298 | 130.228 | 19.547 | 4.143 | 1.00 | 40.29 | A C |
| ATOM | 1149 | O | LYS | 298 | 130.032 | 19.853 | 2.964 | 1.00 | 41.17 | A O |
| ATOM | 1150 | N | PHE | 299 | 129.700 | 20.218 | 5.167 | 1.00 | 38.43 | A N |
| ATOM | 1151 | CA | PHE | 299 | 128.839 | 21.380 | 4.978 | 1.00 | 36.67 | A C |
| ATOM | 1152 | CB | PHE | 299 | 128.100 | 21.712 | 6.283 | 1.00 | 55.97 | A C |
| ATOM | 1153 | CG | PHE | 299 | 127.256 | 22.967 | 6.209 | 1.00 | 48.41 | A C |
| ATOM | 1154 | CD1 | PHE | 299 | 126.319 | 23.146 | 5.186 | 1.00 | 44.86 | A C |
| ATOM | 1155 | CD2 | PHE | 299 | 127.400 | 23.970 | 7.160 | 1.00 | 46.14 | A C |
| ATOM | 1156 | CE1 | PHE | 299 | 125.545 | 24.307 | 5.117 | 1.00 | 44.27 | A C |
| ATOM | 1157 | CE2 | PHE | 299 | 126.627 | 25.132 | 7.095 | 1.00 | 40.55 | A C |
| ATOM | 1158 | CZ | PHE | 299 | 125.701 | 25.299 | 6.073 | 1.00 | 39.06 | A C |
| ATOM | 1159 | C | PHE | 299 | 129.684 | 22.573 | 4.544 | 1.00 | 37.02 | A C |
| ATOM | 1160 | O | PHE | 299 | 129.439 | 23.190 | 3.504 | 1.00 | 32.83 | A O |
| ATOM | 1161 | N | VAL | 300 | 130.682 | 22.896 | 5.352 | 1.00 | 13.94 | A N |
| ATOM | 1162 | CA | VAL | 300 | 131.551 | 24.010 | 5.034 | 1.00 | 18.89 | A C |
| ATOM | 1163 | CB | VAL | 300 | 132.752 | 24.068 | 5.993 | 1.00 | 40.51 | A C |
| ATOM | 1164 | CG1 | VAL | 300 | 133.769 | 25.076 | 5.493 | 1.00 | 44.08 | A C |
| ATOM | 1165 | CG2 | VAL | 300 | 132.282 | 24.451 | 7.382 | 1.00 | 44.52 | A C |
| ATOM | 1166 | C | VAL | 300 | 132.061 | 23.893 | 3.607 | 1.00 | 17.53 | A C |
| ATOM | 1167 | O | VAL | 300 | 132.177 | 24.889 | 2.906 | 1.00 | 18.03 | A O |
| ATOM | 1168 | N | GLU | 301 | 132.365 | 22.679 | 3.164 | 1.00 | 18.30 | A N |

FIG. 19A-17

| ATOM | 1169 | CA | GLU | 301 | 132.866 | 22.513 | 1.808 | 1.00 | 18.96 | A | C |
| --- | --- | --- | --- | --- | --- | --- | --- | --- | --- | --- | --- |
| ATOM | 1170 | CB | GLU | 301 | 133.407 | 21.094 | 1.605 | 1.00 | 40.16 | A | C |
| ATOM | 1171 | CG | GLU | 301 | 134.058 | 20.854 | 0.243 | 1.00 | 42.43 | A | C |
| ATOM | 1172 | CD | GLU | 301 | 135.049 | 21.943 | -0.155 | 1.00 | 48.24 | A | C |
| ATOM | 1173 | OE1 | GLU | 301 | 135.956 | 22.267 | 0.645 | 1.00 | 47.79 | A | O |
| ATOM | 1174 | OE2 | GLU | 301 | 134.918 | 22.469 | -1.282 | 1.00 | 50.51 | A | O |
| ATOM | 1175 | C | GLU | 301 | 131.770 | 22.832 | 0.791 | 1.00 | 17.53 | A | C |
| ATOM | 1176 | O | GLU | 301 | 132.034 | 23.458 | -0.242 | 1.00 | 15.61 | A | O |
| ATOM | 1177 | N | GLU | 302 | 130.541 | 22.420 | 1.097 | 1.00 | 32.12 | A | N |
| ATOM | 1178 | CA | GLU | 302 | 129.412 | 22.667 | 0.210 | 1.00 | 31.93 | A | C |
| ATOM | 1179 | CB | GLU | 302 | 128.127 | 22.084 | 0.801 | 1.00 | 76.04 | A | C |
| ATOM | 1180 | CG | GLU | 302 | 126.894 | 22.274 | -0.071 | 1.00 | 75.79 | A | C |
| ATOM | 1181 | CD | GLU | 302 | 125.659 | 21.594 | 0.501 | 1.00 | 72.72 | A | C |
| ATOM | 1182 | OE1 | GLU | 302 | 125.651 | 20.349 | 0.584 | 1.00 | 72.70 | A | O |
| ATOM | 1183 | OE2 | GLU | 302 | 124.698 | 22.302 | 0.872 | 1.00 | 77.14 | A | O |
| ATOM | 1184 | C | GLU | 302 | 129.237 | 24.158 | -0.033 | 1.00 | 35.00 | A | C |
| ATOM | 1185 | O | GLU | 302 | 129.040 | 24.580 | -1.170 | 1.00 | 34.26 | A | O |
| ATOM | 1186 | N | ILE | 303 | 129.334 | 24.953 | 1.031 | 1.00 | 23.69 | A | N |
| ATOM | 1187 | CA | ILE | 303 | 129.171 | 26.405 | 0.936 | 1.00 | 23.74 | A | C |
| ATOM | 1188 | CB | ILE | 303 | 128.933 | 27.019 | 2.326 | 1.00 | 28.42 | A | C |
| ATOM | 1189 | CG2 | ILE | 303 | 128.556 | 28.480 | 2.199 | 1.00 | 23.60 | A | C |
| ATOM | 1190 | CG1 | ILE | 303 | 127.823 | 26.245 | 3.046 | 1.00 | 26.02 | A | C |
| ATOM | 1191 | CD1 | ILE | 303 | 126.599 | 25.926 | 2.183 | 1.00 | 22.48 | A | C |
| ATOM | 1192 | C | ILE | 303 | 130.340 | 27.129 | 0.267 | 1.00 | 25.77 | A | C |
| ATOM | 1193 | O | ILE | 303 | 130.133 | 28.036 | -0.553 | 1.00 | 28.26 | A | O |
| ATOM | 1194 | N | LYS | 304 | 131.564 | 26.740 | 0.612 | 1.00 | 28.18 | A | N |
| ATOM | 1195 | CA | LYS | 304 | 132.733 | 27.363 | 0.003 | 1.00 | 28.98 | A | C |
| ATOM | 1196 | CB | LYS | 304 | 134.018 | 26.713 | 0.501 | 1.00 | 31.11 | A | C |
| ATOM | 1197 | CG | LYS | 304 | 134.415 | 27.051 | 1.915 | 1.00 | 37.78 | A | C |
| ATOM | 1198 | CD | LYS | 304 | 135.810 | 26.502 | 2.190 | 1.00 | 39.31 | A | C |
| ATOM | 1199 | CE | LYS | 304 | 136.298 | 26.803 | 3.599 | 1.00 | 42.04 | A | C |
| ATOM | 1200 | NZ | LYS | 304 | 137.673 | 26.262 | 3.857 | 1.00 | 44.22 | A | N |
| ATOM | 1201 | C | LYS | 304 | 132.665 | 27.210 | -1.512 | 1.00 | 25.07 | A | C |
| ATOM | 1202 | O | LYS | 304 | 133.033 | 28.118 | -2.252 | 1.00 | 29.15 | A | O |
| ATOM | 1203 | N | SER | 305 | 132.195 | 26.054 | -1.965 | 1.00 | 30.32 | A | N |
| ATOM | 1204 | CA | SER | 305 | 132.100 | 25.785 | -3.386 | 1.00 | 27.48 | A | C |
| ATOM | 1205 | CB | SER | 305 | 131.702 | 24.329 | -3.635 | 1.00 | 18.09 | A | C |
| ATOM | 1206 | OG | SER | 305 | 130.352 | 24.088 | -3.293 | 1.00 | 14.77 | A | O |
| ATOM | 1207 | C | SER | 305 | 131.094 | 26.709 | -4.044 | 1.00 | 28.00 | A | C |
| ATOM | 1208 | O | SER | 305 | 131.137 | 26.917 | -5.263 | 1.00 | 30.57 | A | O |
| ATOM | 1209 | N | ILE | 306 | 130.181 | 27.258 | -3.247 | 1.00 | 37.08 | A | N |
| ATOM | 1210 | CA | ILE | 306 | 129.180 | 28.176 | -3.783 | 1.00 | 33.83 | A | C |
| ATOM | 1211 | CB | ILE | 306 | 127.990 | 28.319 | -2.831 | 1.00 | 15.00 | A | C |
| ATOM | 1212 | CG2 | ILE | 306 | 127.190 | 29.565 | -3.167 | 1.00 | 15.73 | A | C |
| ATOM | 1213 | CG1 | ILE | 306 | 127.118 | 27.069 | -2.929 | 1.00 | 17.63 | A | C |
| ATOM | 1214 | CD1 | ILE | 306 | 125.993 | 27.029 | -1.916 | 1.00 | 15.34 | A | C |
| ATOM | 1215 | C | ILE | 306 | 129.812 | 29.544 | -4.008 | 1.00 | 31.59 | A | C |
| ATOM | 1216 | O | ILE | 306 | 129.361 | 30.333 | -4.851 | 1.00 | 32.12 | A | O |
| ATOM | 1217 | N | ALA | 307 | 130.874 | 29.805 | -3.251 | 1.00 | 20.26 | A | N |
| ATOM | 1218 | CA | ALA | 307 | 131.584 | 31.062 | -3.349 | 1.00 | 22.45 | A | C |
| ATOM | 1219 | CB | ALA | 307 | 132.444 | 31.260 | -2.118 | 1.00 | 5.65 | A | C |
| ATOM | 1220 | C | ALA | 307 | 132.441 | 31.113 | -4.611 | 1.00 | 22.11 | A | C |
| ATOM | 1221 | O | ALA | 307 | 132.622 | 30.103 | -5.302 | 1.00 | 21.10 | A | O |
| ATOM | 1222 | N | SER | 308 | 132.953 | 32.307 | -4.906 | 1.00 | 24.29 | A | N |
| ATOM | 1223 | CA | SER | 308 | 133.796 | 32.533 | -6.072 | 1.00 | 27.22 | A | C |
| ATOM | 1224 | CB | SER | 308 | 133.489 | 33.899 | -6.700 | 1.00 | 15.61 | A | C |
| ATOM | 1225 | OG | SER | 308 | 132.299 | 33.860 | -7.460 | 1.00 | 19.00 | A | O |
| ATOM | 1226 | C | SER | 308 | 135.264 | 32.482 | -5.690 | 1.00 | 30.87 | A | C |
| ATOM | 1227 | O | SER | 308 | 135.625 | 32.797 | -4.555 | 1.00 | 28.21 | A | O |
| ATOM | 1228 | N | GLU | 309 | 136.103 | 32.069 | -6.640 | 1.00 | 26.43 | A | N |
| ATOM | 1229 | CA | GLU | 309 | 137.542 | 32.008 | -6.418 | 1.00 | 29.92 | A | C |
| ATOM | 1230 | CB | GLU | 309 | 138.224 | 31.266 | -7.569 | 1.00 | 73.14 | A | C |
| ATOM | 1231 | CG | GLU | 309 | 137.811 | 29.809 | -7.737 | 1.00 | 78.51 | A | C |
| ATOM | 1232 | CD | GLU | 309 | 138.181 | 28.950 | -6.541 | 1.00 | 81.27 | A | C |
| ATOM | 1233 | OE1 | GLU | 309 | 138.103 | 27.708 | -6.651 | 1.00 | 83.60 | A | O |
| ATOM | 1234 | OE2 | GLU | 309 | 138.544 | 29.514 | -5.487 | 1.00 | 85.42 | A | O |
| ATOM | 1235 | C | GLU | 309 | 138.009 | 33.461 | -6.396 | 1.00 | 30.67 | A | C |
| ATOM | 1236 | O | GLU | 309 | 137.580 | 34.257 | -7.230 | 1.00 | 32.32 | A | O |
| ATOM | 1237 | N | PRO | 310 | 138.882 | 33.834 | -5.442 | 1.00 | 19.51 | A | N |
| ATOM | 1238 | CD | PRO | 310 | 139.395 | 35.217 | -5.381 | 1.00 | 49.07 | A | C |
| ATOM | 1239 | CA | PRO | 310 | 139.483 | 33.029 | -4.377 | 1.00 | 19.70 | A | C |
| ATOM | 1240 | CB | PRO | 310 | 140.703 | 33.851 | -3.982 | 1.00 | 50.90 | A | C |
| ATOM | 1241 | CG | PRO | 310 | 140.182 | 35.231 | -4.065 | 1.00 | 50.46 | A | C |

FIG. 19A-18

| ATOM | 1242 | C   | PRO | 310 | 138.569 | 32.751 | -3.178 | 1.00 | 20.19  | A | C |
|------|------|-----|-----|-----|---------|--------|--------|------|--------|---|---|
| ATOM | 1243 | O   | PRO | 310 | 138.229 | 33.654 | -2.394 | 1.00 | 16.98  | A | O |
| ATOM | 1244 | N   | THR | 311 | 138.197 | 31.483 | -3.043 | 1.00 | 25.93  | A | N |
| ATOM | 1245 | CA  | THR | 311 | 137.352 | 31.013 | -1.957 | 1.00 | 26.80  | A | C |
| ATOM | 1246 | CB  | THR | 311 | 137.618 | 29.521 | -1.695 | 1.00 | 73.61  | A | C |
| ATOM | 1247 | OG1 | THR | 311 | 137.053 | 29.145 | -0.434 | 1.00 | 77.77  | A | O |
| ATOM | 1248 | CG2 | THR | 311 | 139.118 | 29.244 | -1.696 | 1.00 | 76.69  | A | C |
| ATOM | 1249 | C   | THR | 311 | 137.521 | 31.781 | -0.643 | 1.00 | 28.67  | A | C |
| ATOM | 1250 | O   | THR | 311 | 136.535 | 32.173 | -0.025 | 1.00 | 29.84  | A | O |
| ATOM | 1251 | N   | GLU | 312 | 138.759 | 32.009 | -0.223 | 1.00 | 47.89  | A | N |
| ATOM | 1252 | CA  | GLU | 312 | 139.007 | 32.713 | 1.029  | 1.00 | 46.51  | A | C |
| ATOM | 1253 | CB  | GLU | 312 | 140.506 | 32.751 | 1.340  | 1.00 | 98.24  | A | C |
| ATOM | 1254 | CG  | GLU | 312 | 141.354 | 33.411 | 0.268  | 1.00 | 100.00 | A | C |
| ATOM | 1255 | CD  | GLU | 312 | 142.621 | 34.031 | 0.825  | 1.00 | 99.11  | A | C |
| ATOM | 1256 | OE1 | GLU | 312 | 143.491 | 34.431 | 0.024  | 1.00 | 102.46 | A | O |
| ATOM | 1257 | OE2 | GLU | 312 | 142.742 | 34.130 | 2.065  | 1.00 | 99.98  | A | O |
| ATOM | 1258 | C   | GLU | 312 | 138.453 | 34.134 | 1.092  | 1.00 | 45.13  | A | C |
| ATOM | 1259 | O   | GLU | 312 | 137.997 | 34.576 | 2.147  | 1.00 | 45.09  | A | O |
| ATOM | 1260 | N   | LYS | 313 | 138.490 | 34.856 | -0.021 | 1.00 | 49.11  | A | N |
| ATOM | 1261 | CA  | LYS | 313 | 137.990 | 36.226 | -0.024 | 1.00 | 48.31  | A | C |
| ATOM | 1262 | CB  | LYS | 313 | 138.797 | 37.091 | -1.000 | 1.00 | 91.02  | A | C |
| ATOM | 1263 | CG  | LYS | 313 | 140.171 | 37.508 | -0.486 | 1.00 | 90.90  | A | C |
| ATOM | 1264 | CD  | LYS | 313 | 140.081 | 38.565 | 0.620  | 1.00 | 87.20  | A | C |
| ATOM | 1265 | CE  | LYS | 313 | 139.966 | 39.982 | 0.066  | 1.00 | 89.24  | A | C |
| ATOM | 1266 | NZ  | LYS | 313 | 138.804 | 40.159 | -0.842 | 1.00 | 93.72  | A | N |
| ATOM | 1267 | C   | LYS | 313 | 136.511 | 36.307 | -0.374 | 1.00 | 49.46  | A | C |
| ATOM | 1268 | O   | LYS | 313 | 135.973 | 37.397 | -0.580 | 1.00 | 51.78  | A | O |
| ATOM | 1269 | N   | HIS | 314 | 135.849 | 35.159 | -0.427 | 1.00 | 27.67  | A | N |
| ATOM | 1270 | CA  | HIS | 314 | 134.437 | 35.137 | -0.775 | 1.00 | 28.52  | A | C |
| ATOM | 1271 | CB  | HIS | 314 | 134.274 | 34.652 | -2.212 | 1.00 | 32.51  | A | C |
| ATOM | 1272 | CG  | HIS | 314 | 134.872 | 35.574 | -3.224 | 1.00 | 29.37  | A | C |
| ATOM | 1273 | CD2 | HIS | 314 | 136.073 | 35.552 | -3.849 | 1.00 | 28.84  | A | C |
| ATOM | 1274 | ND1 | HIS | 314 | 134.220 | 36.697 | -3.683 | 1.00 | 28.95  | A | N |
| ATOM | 1275 | CE1 | HIS | 314 | 134.992 | 37.326 | -4.551 | 1.00 | 28.24  | A | C |
| ATOM | 1276 | NE2 | HIS | 314 | 136.122 | 36.652 | -4.669 | 1.00 | 28.63  | A | N |
| ATOM | 1277 | C   | HIS | 314 | 133.587 | 34.277 | 0.141  | 1.00 | 28.65  | A | C |
| ATOM | 1278 | O   | HIS | 314 | 132.366 | 34.238 | -0.008 | 1.00 | 32.05  | A | O |
| ATOM | 1279 | N   | PHE | 315 | 134.230 | 33.591 | 1.081  | 1.00 | 32.99  | A | N |
| ATOM | 1280 | CA  | PHE | 315 | 133.519 | 32.723 | 2.013  | 1.00 | 32.79  | A | C |
| ATOM | 1281 | CB  | PHE | 315 | 134.045 | 31.294 | 1.878  | 1.00 | 35.38  | A | C |
| ATOM | 1282 | CG  | PHE | 315 | 133.476 | 30.339 | 2.884  | 1.00 | 30.36  | A | C |
| ATOM | 1283 | CD1 | PHE | 315 | 132.123 | 30.026 | 2.877  | 1.00 | 32.20  | A | C |
| ATOM | 1284 | CD2 | PHE | 315 | 134.298 | 29.749 | 3.839  | 1.00 | 28.44  | A | C |
| ATOM | 1285 | CE1 | PHE | 315 | 131.592 | 29.144 | 3.800  | 1.00 | 27.15  | A | C |
| ATOM | 1286 | CE2 | PHE | 315 | 133.783 | 28.866 | 4.769  | 1.00 | 29.14  | A | C |
| ATOM | 1287 | CZ  | PHE | 315 | 132.421 | 28.560 | 4.749  | 1.00 | 30.81  | A | C |
| ATOM | 1288 | C   | PHE | 315 | 133.640 | 33.198 | 3.466  | 1.00 | 33.51  | A | C |
| ATOM | 1289 | O   | PHE | 315 | 134.706 | 33.643 | 3.896  | 1.00 | 34.91  | A | O |
| ATOM | 1290 | N   | PHE | 316 | 132.539 | 33.104 | 4.210  | 1.00 | 26.09  | A | N |
| ATOM | 1291 | CA  | PHE | 316 | 132.513 | 33.516 | 5.610  | 1.00 | 23.14  | A | C |
| ATOM | 1292 | CB  | PHE | 316 | 131.707 | 34.803 | 5.780  | 1.00 | 27.51  | A | C |
| ATOM | 1293 | CG  | PHE | 316 | 132.343 | 36.008 | 5.155  | 1.00 | 31.13  | A | C |
| ATOM | 1294 | CD1 | PHE | 316 | 132.125 | 36.312 | 3.822  | 1.00 | 26.72  | A | C |
| ATOM | 1295 | CD2 | PHE | 316 | 133.182 | 36.827 | 5.903  | 1.00 | 27.98  | A | C |
| ATOM | 1296 | CE1 | PHE | 316 | 132.737 | 37.420 | 3.237  | 1.00 | 29.29  | A | C |
| ATOM | 1297 | CE2 | PHE | 316 | 133.799 | 37.931 | 5.334  | 1.00 | 31.09  | A | C |
| ATOM | 1298 | CZ  | PHE | 316 | 133.577 | 38.230 | 3.998  | 1.00 | 31.32  | A | C |
| ATOM | 1299 | C   | PHE | 316 | 131.909 | 32.438 | 6.497  | 1.00 | 21.07  | A | C |
| ATOM | 1300 | O   | PHE | 316 | 130.901 | 31.831 | 6.153  | 1.00 | 20.31  | A | O |
| ATOM | 1301 | N   | ASN | 317 | 132.533 | 32.220 | 7.647  | 1.00 | 37.16  | A | N |
| ATOM | 1302 | CA  | ASN | 317 | 132.093 | 31.214 | 8.599  | 1.00 | 38.38  | A | C |
| ATOM | 1303 | CB  | ASN | 317 | 133.288 | 30.385 | 9.047  | 1.00 | 74.28  | A | C |
| ATOM | 1304 | CG  | ASN | 317 | 133.055 | 28.919 | 8.888  | 1.00 | 77.27  | A | C |
| ATOM | 1305 | OD1 | ASN | 317 | 131.954 | 28.433 | 9.138  | 1.00 | 79.20  | A | O |
| ATOM | 1306 | ND2 | ASN | 317 | 134.088 | 28.190 | 8.478  | 1.00 | 75.53  | A | N |
| ATOM | 1307 | C   | ASN | 317 | 131.487 | 31.893 | 9.817  | 1.00 | 39.34  | A | C |
| ATOM | 1308 | O   | ASN | 317 | 132.001 | 32.902 | 10.285 | 1.00 | 40.20  | A | O |
| ATOM | 1309 | N   | VAL | 318 | 130.398 | 31.348 | 10.336 | 1.00 | 30.64  | A | N |
| ATOM | 1310 | CA  | VAL | 318 | 129.763 | 31.924 | 11.521 | 1.00 | 29.27  | A | C |
| ATOM | 1311 | CB  | VAL | 318 | 128.531 | 32.778 | 11.144 | 1.00 | 70.89  | A | C |
| ATOM | 1312 | CG1 | VAL | 318 | 127.896 | 33.349 | 12.386 | 1.00 | 71.02  | A | C |
| ATOM | 1313 | CG2 | VAL | 318 | 128.942 | 33.899 | 10.223 | 1.00 | 70.87  | A | C |
| ATOM | 1314 | C   | VAL | 318 | 129.331 | 30.808 | 12.482 | 1.00 | 24.42  | A | C |

FIG. 19A-19

| | | | | | | | | | | |
|---|---|---|---|---|---|---|---|---|---|---|
| ATOM | 1315 | O | VAL | 318 | 128.872 | 29.744 | 12.053 | 1.00 | 25.09 | A O |
| ATOM | 1316 | N | SER | 319 | 129.482 | 31.045 | 13.779 | 1.00 | 32.47 | A N |
| ATOM | 1317 | CA | SER | 319 | 129.108 | 30.035 | 14.752 | 1.00 | 31.73 | A C |
| ATOM | 1318 | CB | SER | 319 | 129.669 | 30.384 | 16.134 | 1.00 | 29.19 | A C |
| ATOM | 1319 | OG | SER | 319 | 129.289 | 31.687 | 16.538 | 1.00 | 41.14 | A O |
| ATOM | 1320 | C | SER | 319 | 127.600 | 29.840 | 14.831 | 1.00 | 30.33 | A C |
| ATOM | 1321 | O | SER | 319 | 127.132 | 28.716 | 14.963 | 1.00 | 28.40 | A O |
| ATOM | 1322 | N | ASP | 320 | 126.839 | 30.926 | 14.741 | 1.00 | 32.33 | A N |
| ATOM | 1323 | CA | ASP | 320 | 125.382 | 30.846 | 14.816 | 1.00 | 32.31 | A C |
| ATOM | 1324 | CB | ASP | 320 | 124.934 | 30.632 | 16.275 | 1.00 | 63.91 | A C |
| ATOM | 1325 | CG | ASP | 320 | 125.369 | 31.760 | 17.209 | 1.00 | 62.36 | A C |
| ATOM | 1326 | OD1 | ASP | 320 | 126.586 | 31.992 | 17.364 | 1.00 | 61.04 | A O |
| ATOM | 1327 | OD2 | ASP | 320 | 124.486 | 32.412 | 17.801 | 1.00 | 62.91 | A O |
| ATOM | 1328 | C | ASP | 320 | 124.698 | 32.088 | 14.237 | 1.00 | 30.68 | A C |
| ATOM | 1329 | O | ASP | 320 | 125.367 | 33.072 | 13.905 | 1.00 | 30.46 | A O |
| ATOM | 1330 | N | GLU | 321 | 123.371 | 32.042 | 14.110 | 1.00 | 35.58 | A N |
| ATOM | 1331 | CA | GLU | 321 | 122.614 | 33.173 | 13.569 | 1.00 | 36.56 | A C |
| ATOM | 1332 | CB | GLU | 321 | 121.126 | 33.029 | 13.889 | 1.00 | 84.00 | A C |
| ATOM | 1333 | CG | GLU | 321 | 120.285 | 32.398 | 12.796 | 1.00 | 77.84 | A C |
| ATOM | 1334 | CD | GLU | 321 | 120.602 | 30.938 | 12.569 | 1.00 | 77.59 | A C |
| ATOM | 1335 | OE1 | GLU | 321 | 120.595 | 30.164 | 13.549 | 1.00 | 79.02 | A O |
| ATOM | 1336 | OE2 | GLU | 321 | 120.849 | 30.565 | 11.404 | 1.00 | 81.63 | A O |
| ATOM | 1337 | C | GLU | 321 | 123.101 | 34.500 | 14.134 | 1.00 | 40.55 | A C |
| ATOM | 1338 | O | GLU | 321 | 123.278 | 35.475 | 13.397 | 1.00 | 37.31 | A O |
| ATOM | 1339 | N | LEU | 322 | 123.323 | 34.519 | 15.447 | 1.00 | 25.97 | A N |
| ATOM | 1340 | CA | LEU | 322 | 123.769 | 35.717 | 16.155 | 1.00 | 28.66 | A C |
| ATOM | 1341 | CB | LEU | 322 | 123.925 | 35.407 | 17.648 | 1.00 | 49.06 | A C |
| ATOM | 1342 | CG | LEU | 322 | 122.646 | 35.281 | 18.477 | 1.00 | 47.69 | A C |
| ATOM | 1343 | CD1 | LEU | 322 | 121.935 | 36.625 | 18.486 | 1.00 | 49.43 | A C |
| ATOM | 1344 | CD2 | LEU | 322 | 121.745 | 34.194 | 17.917 | 1.00 | 52.74 | A C |
| ATOM | 1345 | C | LEU | 322 | 125.052 | 36.368 | 15.644 | 1.00 | 30.25 | A C |
| ATOM | 1346 | O | LEU | 322 | 125.106 | 37.580 | 15.459 | 1.00 | 33.60 | A O |
| ATOM | 1347 | N | ALA | 323 | 126.080 | 35.558 | 15.424 | 1.00 | 27.12 | A N |
| ATOM | 1348 | CA | ALA | 323 | 127.358 | 36.071 | 14.965 | 1.00 | 27.55 | A C |
| ATOM | 1349 | CB | ALA | 323 | 128.420 | 34.994 | 15.112 | 1.00 | 20.92 | A C |
| ATOM | 1350 | C | ALA | 323 | 127.368 | 36.631 | 13.539 | 1.00 | 27.96 | A C |
| ATOM | 1351 | O | ALA | 323 | 128.363 | 37.227 | 13.120 | 1.00 | 27.98 | A O |
| ATOM | 1352 | N | LEU | 324 | 126.280 | 36.451 | 12.794 | 1.00 | 44.60 | A N |
| ATOM | 1353 | CA | LEU | 324 | 126.231 | 36.961 | 11.427 | 1.00 | 43.08 | A C |
| ATOM | 1354 | CB | LEU | 324 | 124.807 | 36.875 | 10.867 | 1.00 | 12.96 | A C |
| ATOM | 1355 | CG | LEU | 324 | 124.398 | 35.546 | 10.215 | 1.00 | 11.69 | A C |
| ATOM | 1356 | CD1 | LEU | 324 | 122.900 | 35.547 | 9.935 | 1.00 | 10.83 | A C |
| ATOM | 1357 | CD2 | LEU | 324 | 125.197 | 35.331 | 8.938 | 1.00 | 9.62 | A C |
| ATOM | 1358 | C | LEU | 324 | 126.734 | 38.400 | 11.346 | 1.00 | 46.61 | A C |
| ATOM | 1359 | O | LEU | 324 | 127.545 | 38.735 | 10.484 | 1.00 | 43.15 | A O |
| ATOM | 1360 | N | VAL | 325 | 126.257 | 39.244 | 12.252 | 1.00 | 37.14 | A N |
| ATOM | 1361 | CA | VAL | 325 | 126.657 | 40.645 | 12.297 | 1.00 | 40.67 | A C |
| ATOM | 1362 | CB | VAL | 325 | 126.111 | 41.328 | 13.549 | 1.00 | 15.02 | A C |
| ATOM | 1363 | CG1 | VAL | 325 | 124.613 | 41.517 | 13.425 | 1.00 | 15.13 | A C |
| ATOM | 1364 | CG2 | VAL | 325 | 126.453 | 40.503 | 14.773 | 1.00 | 18.41 | A C |
| ATOM | 1365 | C | VAL | 325 | 128.168 | 40.840 | 12.304 | 1.00 | 43.49 | A C |
| ATOM | 1366 | O | VAL | 325 | 128.706 | 41.663 | 11.560 | 1.00 | 45.55 | A O |
| ATOM | 1367 | N | THR | 326 | 128.844 | 40.080 | 13.161 | 1.00 | 37.74 | A N |
| ATOM | 1368 | CA | THR | 326 | 130.289 | 40.164 | 13.286 | 1.00 | 39.15 | A C |
| ATOM | 1369 | CB | THR | 326 | 130.768 | 39.218 | 14.391 | 1.00 | 28.63 | A C |
| ATOM | 1370 | OG1 | THR | 326 | 130.648 | 37.863 | 13.944 | 1.00 | 30.54 | A O |
| ATOM | 1371 | CG2 | THR | 326 | 129.911 | 39.398 | 15.643 | 1.00 | 31.00 | A C |
| ATOM | 1372 | C | THR | 326 | 130.996 | 39.790 | 11.985 | 1.00 | 39.16 | A C |
| ATOM | 1373 | O | THR | 326 | 132.105 | 39.268 | 12.005 | 1.00 | 37.98 | A O |
| ATOM | 1374 | N | ILE | 327 | 130.358 | 40.065 | 10.854 | 1.00 | 29.50 | A N |
| ATOM | 1375 | CA | ILE | 327 | 130.922 | 39.739 | 9.552 | 1.00 | 29.69 | A C |
| ATOM | 1376 | CB | ILE | 327 | 130.407 | 38.343 | 9.098 | 1.00 | 36.77 | A C |
| ATOM | 1377 | CG2 | ILE | 327 | 129.867 | 38.372 | 7.679 | 1.00 | 37.54 | A C |
| ATOM | 1378 | CG1 | ILE | 327 | 131.539 | 37.335 | 9.199 | 1.00 | 37.13 | A C |
| ATOM | 1379 | CD1 | ILE | 327 | 131.100 | 35.928 | 8.903 | 1.00 | 36.80 | A C |
| ATOM | 1380 | C | ILE | 327 | 130.572 | 40.816 | 8.520 | 1.00 | 30.20 | A C |
| ATOM | 1381 | O | ILE | 327 | 131.284 | 41.008 | 7.530 | 1.00 | 30.45 | A O |
| ATOM | 1382 | N | VAL | 328 | 129.478 | 41.527 | 8.766 | 1.00 | 25.26 | A N |
| ATOM | 1383 | CA | VAL | 328 | 129.040 | 42.565 | 7.851 | 1.00 | 27.40 | A C |
| ATOM | 1384 | CB | VAL | 328 | 127.851 | 43.363 | 8.436 | 1.00 | 56.37 | A C |
| ATOM | 1385 | CG1 | VAL | 328 | 126.752 | 42.408 | 8.838 | 1.00 | 58.32 | A C |
| ATOM | 1386 | CG2 | VAL | 328 | 128.301 | 44.197 | 9.626 | 1.00 | 57.64 | A C |
| ATOM | 1387 | C | VAL | 328 | 130.159 | 43.539 | 7.485 | 1.00 | 27.32 | A C |

FIG. 19A-20

```
ATOM   1388  O    VAL   328     130.220  44.017   6.355  1.00   26.60    A  O
ATOM   1389  N    LYS   329     131.047  43.837   8.426  1.00   32.39    A  N
ATOM   1390  CA   LYS   329     132.121  44.773   8.124  1.00   31.60    A  C
ATOM   1391  CB   LYS   329     132.949  45.076   9.378  1.00   67.11    A  C
ATOM   1392  CG   LYS   329     133.861  46.291   9.242  1.00   68.66    A  C
ATOM   1393  CD   LYS   329     134.737  46.454  10.474  1.00   70.98    A  C
ATOM   1394  CE   LYS   329     135.540  47.746  10.437  1.00   74.02    A  C
ATOM   1395  NZ   LYS   329     134.660  48.952  10.496  1.00   77.70    A  N
ATOM   1396  C    LYS   329     133.014  44.194   7.036  1.00   29.77    A  C
ATOM   1397  O    LYS   329     133.205  44.802   5.978  1.00   30.98    A  O
ATOM   1398  N    ALA   330     133.551  43.008   7.293  1.00   29.12    A  N
ATOM   1399  CA   ALA   330     134.425  42.365   6.331  1.00   29.15    A  C
ATOM   1400  CB   ALA   330     134.997  41.091   6.922  1.00   30.19    A  C
ATOM   1401  C    ALA   330     133.681  42.056   5.043  1.00   30.30    A  C
ATOM   1402  O    ALA   330     134.207  42.269   3.955  1.00   30.20    A  O
ATOM   1403  N    LEU   331     132.457  41.551   5.168  1.00   22.22    A  N
ATOM   1404  CA   LEU   331     131.661  41.206   3.994  1.00   19.86    A  C
ATOM   1405  CB   LEU   331     130.284  40.667   4.403  1.00   36.97    A  C
ATOM   1406  CG   LEU   331     129.567  39.761   3.389  1.00   33.39    A  C
ATOM   1407  CD1  LEU   331     128.110  39.600   3.787  1.00   35.02    A  C
ATOM   1408  CD2  LEU   331     129.658  40.343   1.996  1.00   29.08    A  C
ATOM   1409  C    LEU   331     131.483  42.467   3.162  1.00   19.89    A  C
ATOM   1410  O    LEU   331     131.741  42.468   1.961  1.00   19.24    A  O
ATOM   1411  N    GLY   332     131.045  43.535   3.830  1.00   15.82    A  N
ATOM   1412  CA   GLY   332     130.824  44.811   3.179  1.00   16.92    A  C
ATOM   1413  C    GLY   332     132.024  45.309   2.402  1.00   17.18    A  C
ATOM   1414  O    GLY   332     131.911  45.651   1.224  1.00   21.05    A  O
ATOM   1415  N    GLU   333     133.185  45.347   3.045  1.00   34.74    A  N
ATOM   1416  CA   GLU   333     134.369  45.831   2.362  1.00   32.80    A  C
ATOM   1417  CB   GLU   333     135.472  46.165   3.371  1.00   75.29    A  C
ATOM   1418  CG   GLU   333     136.139  44.968   4.005  1.00   73.66    A  C
ATOM   1419  CD   GLU   333     137.251  45.363   4.959  1.00   73.68    A  C
ATOM   1420  OE1  GLU   333     137.953  44.459   5.456  1.00   75.73    A  O
ATOM   1421  OE2  GLU   333     137.421  46.575   5.215  1.00   67.80    A  O
ATOM   1422  C    GLU   333     134.888  44.841   1.322  1.00   31.78    A  C
ATOM   1423  O    GLU   333     135.370  45.236   0.261  1.00   31.40    A  O
ATOM   1424  N    ARG   334     134.781  43.552   1.610  1.00   50.02    A  N
ATOM   1425  CA   ARG   334     135.275  42.563   0.669  1.00   53.40    A  C
ATOM   1426  CB   ARG   334     135.064  41.152   1.215  1.00   83.27    A  C
ATOM   1427  CG   ARG   334     136.000  40.123   0.607  1.00   82.56    A  C
ATOM   1428  CD   ARG   334     136.564  39.198   1.677  1.00   81.32    A  C
ATOM   1429  NE   ARG   334     137.441  39.901   2.612  1.00   76.87    A  N
ATOM   1430  CZ   ARG   334     137.888  39.383   3.753  1.00   80.96    A  C
ATOM   1431  NH1  ARG   334     137.537  38.148   4.108  1.00   77.70    A  N
ATOM   1432  NH2  ARG   334     138.686  40.097   4.539  1.00   87.10    A  N
ATOM   1433  C    ARG   334     134.556  42.757  -0.654  1.00   54.70    A  C
ATOM   1434  O    ARG   334     135.170  42.716  -1.716  1.00   51.62    A  O
ATOM   1435  N    ILE   335     133.253  42.988  -0.591  1.00   36.48    A  N
ATOM   1436  CA   ILE   335     132.473  43.214  -1.803  1.00   36.41    A  C
ATOM   1437  CB   ILE   335     130.940  42.967  -1.539  1.00   33.09    A  C
ATOM   1438  CG2  ILE   335     130.524  43.522  -0.203  1.00   35.87    A  C
ATOM   1439  CG1  ILE   335     130.094  43.611  -2.630  1.00   34.31    A  C
ATOM   1440  CD1  ILE   335     128.612  43.520  -2.368  1.00   37.10    A  C
ATOM   1441  C    ILE   335     132.742  44.663  -2.215  1.00   34.70    A  C
ATOM   1442  O    ILE   335     132.421  45.092  -3.326  1.00   37.30    A  O
ATOM   1443  N    PHE   336     133.392  45.377  -1.299  1.00  108.43    A  N
ATOM   1444  CA   PHE   336     133.744  46.789  -1.419  1.00  108.06    A  C
ATOM   1445  CB   PHE   336     135.092  46.989  -2.157  1.00   57.00    A  C
ATOM   1446  CG   PHE   336     135.114  46.540  -3.601  1.00   53.32    A  C
ATOM   1447  CD1  PHE   336     134.135  46.941  -4.508  1.00   52.74    A  C
ATOM   1448  CD2  PHE   336     136.178  45.779  -4.073  1.00   51.27    A  C
ATOM   1449  CE1  PHE   336     134.219  46.589  -5.868  1.00   43.07    A  C
ATOM   1450  CE2  PHE   336     136.271  45.426  -5.422  1.00   45.63    A  C
ATOM   1451  CZ   PHE   336     135.292  45.832  -6.319  1.00   46.09    A  C
ATOM   1452  C    PHE   336     132.662  47.670  -2.020  1.00  108.09    A  C
ATOM   1453  O    PHE   336     131.623  47.131  -2.453  1.00   87.71    A  O
ATOM   1454  OXT  PHE   336     132.864  48.902  -2.024  1.00   40.49    A  O
ATOM   1455  CB   GLU     1     119.537  12.185  27.786  1.00   88.08    H  C
ATOM   1456  CG   GLU     1     118.650  11.120  28.419  1.00   88.08    H  C
ATOM   1457  CD   GLU     1     119.399  10.237  29.409  1.00   88.08    H  C
ATOM   1458  OE1  GLU     1     120.127  10.777  30.271  1.00   88.08    H  O
ATOM   1459  OE2  GLU     1     119.251   8.998  29.324  1.00   88.08    H  O
ATOM   1460  C    GLU     1     118.366  14.360  28.176  1.00   62.78    H  C
```

FIG. 19A-21

| ATOM | 1461 | O | GLU | 1 | 117.763 | 15.033 | 29.012 | 1.00 | 62.78 | H | O |
|---|---|---|---|---|---|---|---|---|---|---|---|
| ATOM | 1462 | N | GLU | 1 | 119.687 | 13.262 | 30.016 | 1.00 | 62.78 | H | N |
| ATOM | 1463 | CA | GLU | 1 | 119.580 | 13.515 | 28.553 | 1.00 | 62.78 | H | C |
| ATOM | 1464 | N | VAL | 2 | 118.019 | 14.312 | 26.896 | 1.00 | 44.26 | H | N |
| ATOM | 1465 | CA | VAL | 2 | 116.896 | 15.064 | 26.359 | 1.00 | 44.26 | H | C |
| ATOM | 1466 | CB | VAL | 2 | 117.154 | 15.460 | 24.909 | 1.00 | 15.14 | H | C |
| ATOM | 1467 | CG1 | VAL | 2 | 118.610 | 15.840 | 24.732 | 1.00 | 15.14 | H | C |
| ATOM | 1468 | CG2 | VAL | 2 | 116.807 | 14.309 | 23.997 | 1.00 | 15.14 | H | C |
| ATOM | 1469 | C | VAL | 2 | 115.677 | 14.174 | 26.353 | 1.00 | 44.26 | H | C |
| ATOM | 1470 | O | VAL | 2 | 115.803 | 12.951 | 26.347 | 1.00 | 44.26 | H | O |
| ATOM | 1471 | N | GLN | 3 | 114.497 | 14.780 | 26.340 | 1.00 | 25.45 | H | N |
| ATOM | 1472 | CA | GLN | 3 | 113.280 | 13.984 | 26.288 | 1.00 | 25.45 | H | C |
| ATOM | 1473 | CB | GLN | 3 | 113.191 | 13.046 | 27.494 | 1.00 | 105.15 | H | C |
| ATOM | 1474 | CG | GLN | 3 | 113.307 | 13.707 | 28.841 | 1.00 | 105.15 | H | C |
| ATOM | 1475 | CD | GLN | 3 | 113.015 | 12.733 | 29.961 | 1.00 | 105.15 | H | C |
| ATOM | 1476 | OE1 | GLN | 3 | 113.554 | 11.623 | 29.990 | 1.00 | 105.15 | H | O |
| ATOM | 1477 | NE2 | GLN | 3 | 112.157 | 13.139 | 30.892 | 1.00 | 105.15 | H | N |
| ATOM | 1478 | C | GLN | 3 | 111.961 | 14.708 | 26.119 | 1.00 | 25.45 | H | C |
| ATOM | 1479 | O | GLN | 3 | 111.809 | 15.887 | 26.438 | 1.00 | 25.45 | H | O |
| ATOM | 1480 | N | LEU | 4 | 111.009 | 13.959 | 25.588 | 1.00 | 27.88 | H | N |
| ATOM | 1481 | CA | LEU | 4 | 109.668 | 14.446 | 25.339 | 1.00 | 27.88 | H | C |
| ATOM | 1482 | CB | LEU | 4 | 109.347 | 14.369 | 23.842 | 1.00 | 33.14 | H | C |
| ATOM | 1483 | CG | LEU | 4 | 110.367 | 14.924 | 22.847 | 1.00 | 33.14 | H | C |
| ATOM | 1484 | CD1 | LEU | 4 | 109.821 | 14.772 | 21.438 | 1.00 | 33.14 | H | C |
| ATOM | 1485 | CD2 | LEU | 4 | 110.646 | 16.385 | 23.155 | 1.00 | 33.14 | H | C |
| ATOM | 1486 | C | LEU | 4 | 108.755 | 13.507 | 26.095 | 1.00 | 27.88 | H | C |
| ATOM | 1487 | O | LEU | 4 | 108.871 | 12.282 | 25.960 | 1.00 | 27.88 | H | O |
| ATOM | 1488 | N | VAL | 5 | 107.858 | 14.061 | 26.901 | 1.00 | 26.47 | H | N |
| ATOM | 1489 | CA | VAL | 5 | 106.942 | 13.215 | 27.656 | 1.00 | 26.47 | H | C |
| ATOM | 1490 | CB | VAL | 5 | 107.176 | 13.329 | 29.197 | 1.00 | 25.39 | H | C |
| ATOM | 1491 | CG1 | VAL | 5 | 107.281 | 14.772 | 29.606 | 1.00 | 25.39 | H | C |
| ATOM | 1492 | CG2 | VAL | 5 | 106.046 | 12.654 | 29.947 | 1.00 | 25.39 | H | C |
| ATOM | 1493 | C | VAL | 5 | 105.520 | 13.578 | 27.297 | 1.00 | 26.47 | H | C |
| ATOM | 1494 | O | VAL | 5 | 105.031 | 14.664 | 27.635 | 1.00 | 26.47 | H | O |
| ATOM | 1495 | N | GLU | 6 | 104.868 | 12.650 | 26.601 | 1.00 | 23.78 | H | N |
| ATOM | 1496 | CA | GLU | 6 | 103.495 | 12.835 | 26.133 | 1.00 | 23.78 | H | C |
| ATOM | 1497 | CB | GLU | 6 | 103.258 | 11.995 | 24.885 | 1.00 | 29.58 | H | C |
| ATOM | 1498 | CG | GLU | 6 | 104.409 | 12.017 | 23.933 | 1.00 | 29.58 | H | C |
| ATOM | 1499 | CD | GLU | 6 | 104.188 | 11.109 | 22.756 | 1.00 | 29.58 | H | C |
| ATOM | 1500 | OE1 | GLU | 6 | 105.194 | 10.664 | 22.168 | 1.00 | 29.58 | H | O |
| ATOM | 1501 | OE2 | GLU | 6 | 103.013 | 10.846 | 22.413 | 1.00 | 29.58 | H | O |
| ATOM | 1502 | C | GLU | 6 | 102.429 | 12.485 | 27.155 | 1.00 | 23.78 | H | C |
| ATOM | 1503 | O | GLU | 6 | 102.680 | 11.740 | 28.101 | 1.00 | 23.78 | H | O |
| ATOM | 1504 | N | SER | 7 | 101.242 | 13.047 | 26.937 | 1.00 | 26.30 | H | N |
| ATOM | 1505 | CA | SER | 7 | 100.061 | 12.823 | 27.766 | 1.00 | 26.30 | H | C |
| ATOM | 1506 | CB | SER | 7 | 100.177 | 13.535 | 29.102 | 1.00 | 32.56 | H | C |
| ATOM | 1507 | OG | SER | 7 | 100.574 | 14.871 | 28.906 | 1.00 | 32.56 | H | O |
| ATOM | 1508 | C | SER | 7 | 98.886 | 13.381 | 26.998 | 1.00 | 26.30 | H | C |
| ATOM | 1509 | O | SER | 7 | 99.060 | 14.248 | 26.136 | 1.00 | 26.30 | H | O |
| ATOM | 1510 | N | GLY | 8 | 97.693 | 12.872 | 27.287 | 1.00 | 41.74 | H | N |
| ATOM | 1511 | CA | GLY | 8 | 96.514 | 13.360 | 26.598 | 1.00 | 41.74 | H | C |
| ATOM | 1512 | C | GLY | 8 | 95.807 | 12.321 | 25.752 | 1.00 | 41.74 | H | C |
| ATOM | 1513 | O | GLY | 8 | 94.745 | 12.603 | 25.201 | 1.00 | 41.74 | H | O |
| ATOM | 1514 | N | GLY | 9 | 96.383 | 11.127 | 25.637 | 1.00 | 47.50 | H | N |
| ATOM | 1515 | CA | GLY | 9 | 95.751 | 10.079 | 24.851 | 1.00 | 47.50 | H | C |
| ATOM | 1516 | C | GLY | 9 | 94.431 | 9.601 | 25.446 | 1.00 | 47.50 | H | C |
| ATOM | 1517 | O | GLY | 9 | 94.038 | 10.020 | 26.536 | 1.00 | 47.50 | H | O |
| ATOM | 1518 | N | GLY | 10 | 93.732 | 8.723 | 24.735 | 1.00 | 16.50 | H | N |
| ATOM | 1519 | CA | GLY | 10 | 92.469 | 8.225 | 25.244 | 1.00 | 16.50 | H | C |
| ATOM | 1520 | C | GLY | 10 | 91.485 | 7.806 | 24.169 | 1.00 | 16.50 | H | C |
| ATOM | 1521 | O | GLY | 10 | 91.830 | 7.701 | 22.990 | 1.00 | 16.50 | H | O |
| ATOM | 1522 | N | LEU | 11 | 90.251 | 7.559 | 24.595 | 1.00 | 37.61 | H | N |
| ATOM | 1523 | CA | LEU | 11 | 89.175 | 7.137 | 23.710 | 1.00 | 37.61 | H | C |
| ATOM | 1524 | CB | LEU | 11 | 88.388 | 6.003 | 24.365 | 1.00 | 18.32 | H | C |
| ATOM | 1525 | CG | LEU | 11 | 86.959 | 5.715 | 23.885 | 1.00 | 18.32 | H | C |
| ATOM | 1526 | CD1 | LEU | 11 | 86.962 | 5.148 | 22.463 | 1.00 | 18.32 | H | C |
| ATOM | 1527 | CD2 | LEU | 11 | 86.313 | 4.729 | 24.856 | 1.00 | 18.32 | H | C |
| ATOM | 1528 | C | LEU | 11 | 88.235 | 8.292 | 23.436 | 1.00 | 37.61 | H | C |
| ATOM | 1529 | O | LEU | 11 | 87.769 | 8.943 | 24.365 | 1.00 | 37.61 | H | O |
| ATOM | 1530 | N | VAL | 12 | 87.961 | 8.550 | 22.165 | 1.00 | 31.23 | H | N |
| ATOM | 1531 | CA | VAL | 12 | 87.048 | 9.624 | 21.792 | 1.00 | 31.23 | H | C |
| ATOM | 1532 | CB | VAL | 12 | 87.794 | 10.800 | 21.144 | 1.00 | 52.64 | H | C |
| ATOM | 1533 | CG1 | VAL | 12 | 88.609 | 11.532 | 22.192 | 1.00 | 52.64 | H | C |

FIG. 19A-22

| | | | | | | | | | | | |
|---|---|---|---|---|---|---|---|---|---|---|---|
| ATOM | 1534 | CG2 | VAL | 12 | 88.699 | 10.290 | 20.039 | 1.00 | 52.64 | H | C |
| ATOM | 1535 | C | VAL | 12 | 86.062 | 9.045 | 20.794 | 1.00 | 31.23 | H | C |
| ATOM | 1536 | O | VAL | 12 | 86.365 | 8.057 | 20.138 | 1.00 | 31.23 | H | O |
| ATOM | 1537 | N | GLN | 13 | 84.882 | 9.640 | 20.681 | 1.00 | 27.32 | H | N |
| ATOM | 1538 | CA | GLN | 13 | 83.894 | 9.126 | 19.741 | 1.00 | 27.32 | H | C |
| ATOM | 1539 | CB | GLN | 13 | 82.493 | 9.391 | 20.270 | 1.00 | 92.40 | H | C |
| ATOM | 1540 | CG | GLN | 13 | 82.206 | 8.652 | 21.553 | 1.00 | 92.40 | H | C |
| ATOM | 1541 | CD | GLN | 13 | 80.808 | 8.906 | 22.056 | 1.00 | 92.40 | H | C |
| ATOM | 1542 | OE1 | GLN | 13 | 79.836 | 8.766 | 21.310 | 1.00 | 92.40 | H | O |
| ATOM | 1543 | NE2 | GLN | 13 | 80.693 | 9.276 | 23.329 | 1.00 | 92.40 | H | N |
| ATOM | 1544 | C | GLN | 13 | 84.063 | 9.747 | 18.356 | 1.00 | 27.32 | H | C |
| ATOM | 1545 | O | GLN | 13 | 84.400 | 10.924 | 18.227 | 1.00 | 27.32 | H | O |
| ATOM | 1546 | N | PRO | 14 | 83.834 | 8.955 | 17.298 | 1.00 | 39.48 | H | N |
| ATOM | 1547 | CD | PRO | 14 | 83.418 | 7.539 | 17.302 | 1.00 | 31.44 | H | C |
| ATOM | 1548 | CA | PRO | 14 | 83.971 | 9.452 | 15.929 | 1.00 | 39.48 | H | C |
| ATOM | 1549 | CB | PRO | 14 | 83.219 | 8.406 | 15.118 | 1.00 | 31.44 | H | C |
| ATOM | 1550 | CG | PRO | 14 | 83.584 | 7.145 | 15.837 | 1.00 | 31.44 | H | C |
| ATOM | 1551 | C | PRO | 14 | 83.401 | 10.849 | 15.766 | 1.00 | 39.48 | H | C |
| ATOM | 1552 | O | PRO | 14 | 82.235 | 11.076 | 16.053 | 1.00 | 39.48 | H | O |
| ATOM | 1553 | N | GLY | 15 | 84.233 | 11.784 | 15.319 | 1.00 | 28.44 | H | N |
| ATOM | 1554 | CA | GLY | 15 | 83.788 | 13.154 | 15.130 | 1.00 | 28.44 | H | C |
| ATOM | 1555 | C | GLY | 15 | 84.048 | 14.065 | 16.323 | 1.00 | 28.44 | H | C |
| ATOM | 1556 | O | GLY | 15 | 83.759 | 15.265 | 16.269 | 1.00 | 28.44 | H | O |
| ATOM | 1557 | N | GLY | 16 | 84.588 | 13.496 | 17.401 | 1.00 | 22.09 | H | N |
| ATOM | 1558 | CA | GLY | 16 | 84.880 | 14.266 | 18.601 | 1.00 | 22.09 | H | C |
| ATOM | 1559 | C | GLY | 16 | 86.286 | 14.826 | 18.571 | 1.00 | 22.09 | H | C |
| ATOM | 1560 | O | GLY | 16 | 86.900 | 14.912 | 17.507 | 1.00 | 22.09 | H | O |
| ATOM | 1561 | N | SER | 17 | 86.819 | 15.202 | 19.726 | 1.00 | 31.69 | H | N |
| ATOM | 1562 | CA | SER | 17 | 88.161 | 15.762 | 19.749 | 1.00 | 31.69 | H | C |
| ATOM | 1563 | CB | SER | 17 | 88.085 | 17.272 | 19.592 | 1.00 | 54.23 | H | C |
| ATOM | 1564 | OG | SER | 17 | 87.308 | 17.829 | 20.625 | 1.00 | 54.23 | H | O |
| ATOM | 1565 | C | SER | 17 | 88.953 | 15.416 | 21.000 | 1.00 | 31.69 | H | C |
| ATOM | 1566 | O | SER | 17 | 88.427 | 14.824 | 21.944 | 1.00 | 31.69 | H | O |
| ATOM | 1567 | N | LEU | 18 | 90.227 | 15.794 | 20.995 | 1.00 | 31.76 | H | N |
| ATOM | 1568 | CA | LEU | 18 | 91.132 | 15.515 | 22.105 | 1.00 | 31.76 | H | C |
| ATOM | 1569 | CB | LEU | 18 | 91.452 | 14.019 | 22.124 | 1.00 | 63.56 | H | C |
| ATOM | 1570 | CG | LEU | 18 | 92.462 | 13.465 | 23.124 | 1.00 | 63.56 | H | C |
| ATOM | 1571 | CD1 | LEU | 18 | 92.121 | 13.932 | 24.536 | 1.00 | 63.56 | H | C |
| ATOM | 1572 | CD2 | LEU | 18 | 92.462 | 11.942 | 23.017 | 1.00 | 63.56 | H | C |
| ATOM | 1573 | C | LEU | 18 | 92.407 | 16.334 | 21.899 | 1.00 | 31.76 | H | C |
| ATOM | 1574 | O | LEU | 18 | 92.622 | 16.884 | 20.815 | 1.00 | 31.76 | H | O |
| ATOM | 1575 | N | ARG | 19 | 93.243 | 16.443 | 22.928 | 1.00 | 39.26 | H | N |
| ATOM | 1576 | CA | ARG | 19 | 94.475 | 17.207 | 22.781 | 1.00 | 39.26 | H | C |
| ATOM | 1577 | CB | ARG | 19 | 94.303 | 18.650 | 23.258 | 1.00 | 32.50 | H | C |
| ATOM | 1578 | CG | ARG | 19 | 95.571 | 19.474 | 23.063 | 1.00 | 32.50 | H | C |
| ATOM | 1579 | CD | ARG | 19 | 95.481 | 20.862 | 23.667 | 1.00 | 32.50 | H | C |
| ATOM | 1580 | NE | ARG | 19 | 95.387 | 20.846 | 25.125 | 1.00 | 32.50 | H | N |
| ATOM | 1581 | CZ | ARG | 19 | 95.262 | 21.936 | 25.879 | 1.00 | 32.50 | H | C |
| ATOM | 1582 | NH1 | ARG | 19 | 95.220 | 23.138 | 25.322 | 1.00 | 32.50 | H | N |
| ATOM | 1583 | NH2 | ARG | 19 | 95.162 | 21.824 | 27.193 | 1.00 | 32.50 | H | N |
| ATOM | 1584 | C | ARG | 19 | 95.668 | 16.606 | 23.500 | 1.00 | 39.26 | H | C |
| ATOM | 1585 | O | ARG | 19 | 95.687 | 16.469 | 24.732 | 1.00 | 39.26 | H | O |
| ATOM | 1586 | N | LEU | 20 | 96.677 | 16.266 | 22.709 | 1.00 | 36.74 | H | N |
| ATOM | 1587 | CA | LEU | 20 | 97.896 | 15.695 | 23.241 | 1.00 | 36.74 | H | C |
| ATOM | 1588 | CB | LEU | 20 | 98.534 | 14.737 | 22.222 | 1.00 | 31.69 | H | C |
| ATOM | 1589 | CG | LEU | 20 | 97.601 | 13.846 | 21.390 | 1.00 | 31.69 | H | C |
| ATOM | 1590 | CD1 | LEU | 20 | 98.426 | 12.870 | 20.555 | 1.00 | 31.69 | H | C |
| ATOM | 1591 | CD2 | LEU | 20 | 96.659 | 13.093 | 22.292 | 1.00 | 31.69 | H | C |
| ATOM | 1592 | C | LEU | 20 | 98.854 | 16.838 | 23.533 | 1.00 | 36.74 | H | C |
| ATOM | 1593 | O | LEU | 20 | 98.866 | 17.856 | 22.840 | 1.00 | 36.74 | H | O |
| ATOM | 1594 | N | SER | 21 | 99.638 | 16.664 | 24.584 | 1.00 | 25.68 | H | N |
| ATOM | 1595 | CA | SER | 21 | 100.635 | 17.640 | 24.974 | 1.00 | 25.68 | H | C |
| ATOM | 1596 | CB | SER | 21 | 100.273 | 18.278 | 26.307 | 1.00 | 13.03 | H | C |
| ATOM | 1597 | OG | SER | 21 | 99.718 | 17.320 | 27.175 | 1.00 | 13.03 | H | O |
| ATOM | 1598 | C | SER | 21 | 101.901 | 16.838 | 25.099 | 1.00 | 25.68 | H | C |
| ATOM | 1599 | O | SER | 21 | 101.851 | 15.635 | 25.336 | 1.00 | 25.68 | H | O |
| ATOM | 1600 | N | CYS | 22 | 103.036 | 17.498 | 24.931 | 1.00 | 22.18 | H | N |
| ATOM | 1601 | CA | CYS | 22 | 104.321 | 16.822 | 25.008 | 1.00 | 22.18 | H | C |
| ATOM | 1602 | C | CYS | 22 | 105.255 | 17.765 | 25.713 | 1.00 | 22.18 | H | C |
| ATOM | 1603 | O | CYS | 22 | 105.491 | 18.863 | 25.229 | 1.00 | 22.18 | H | O |
| ATOM | 1604 | CB | CYS | 22 | 104.804 | 16.543 | 23.603 | 1.00 | 57.35 | H | C |
| ATOM | 1605 | SG | CYS | 22 | 106.473 | 15.867 | 23.383 | 1.00 | 57.35 | H | S |
| ATOM | 1606 | N | ALA | 23 | 105.769 | 17.349 | 26.867 | 1.00 | 26.87 | H | N |

FIG. 19A-23

| | | | | | | | | | | | |
|---|---|---|---|---|---|---|---|---|---|---|---|
| ATOM | 1607 | CA | ALA | 23 | 106.669 | 18.191 | 27.654 | 1.00 | 26.87 | H | C |
| ATOM | 1608 | CB | ALA | 23 | 106.470 | 17.937 | 29.141 | 1.00 | 9.84 | H | C |
| ATOM | 1609 | C | ALA | 23 | 108.125 | 17.989 | 27.284 | 1.00 | 26.87 | H | C |
| ATOM | 1610 | O | ALA | 23 | 108.683 | 16.899 | 27.437 | 1.00 | 26.87 | H | O |
| ATOM | 1611 | N | ALA | 24 | 108.738 | 19.058 | 26.800 | 1.00 | 13.29 | H | N |
| ATOM | 1612 | CA | ALA | 24 | 110.124 | 18.988 | 26.409 | 1.00 | 13.29 | H | C |
| ATOM | 1613 | CB | ALA | 24 | 110.357 | 19.851 | 25.183 | 1.00 | 45.62 | H | C |
| ATOM | 1614 | C | ALA | 24 | 111.023 | 19.432 | 27.552 | 1.00 | 13.29 | H | C |
| ATOM | 1615 | O | ALA | 24 | 110.664 | 20.304 | 28.356 | 1.00 | 13.29 | H | O |
| ATOM | 1616 | N | SER | 25 | 112.194 | 18.819 | 27.617 | 1.00 | 22.11 | H | N |
| ATOM | 1617 | CA | SER | 25 | 113.168 | 19.152 | 28.634 | 1.00 | 22.11 | H | C |
| ATOM | 1618 | CB | SER | 25 | 112.731 | 18.582 | 29.982 | 1.00 | 51.20 | H | C |
| ATOM | 1619 | OG | SER | 25 | 112.401 | 17.214 | 29.862 | 1.00 | 51.20 | H | O |
| ATOM | 1620 | C | SER | 25 | 114.526 | 18.591 | 28.232 | 1.00 | 22.11 | H | C |
| ATOM | 1621 | O | SER | 25 | 114.614 | 17.539 | 27.590 | 1.00 | 22.11 | H | O |
| ATOM | 1622 | N | GLY | 26 | 115.582 | 19.306 | 28.591 | 1.00 | 10.76 | H | N |
| ATOM | 1623 | CA | GLY | 26 | 116.914 | 18.844 | 28.263 | 1.00 | 10.76 | H | C |
| ATOM | 1624 | C | GLY | 26 | 117.553 | 19.585 | 27.107 | 1.00 | 10.76 | H | C |
| ATOM | 1625 | O | GLY | 26 | 118.728 | 19.367 | 26.809 | 1.00 | 10.76 | H | O |
| ATOM | 1626 | N | PHE | 27 | 116.794 | 20.458 | 26.448 | 1.00 | 18.08 | H | N |
| ATOM | 1627 | CA | PHE | 27 | 117.325 | 21.207 | 25.318 | 1.00 | 18.08 | H | C |
| ATOM | 1628 | CB | PHE | 27 | 117.241 | 20.373 | 24.031 | 1.00 | 16.53 | H | C |
| ATOM | 1629 | CG | PHE | 27 | 115.842 | 19.974 | 23.651 | 1.00 | 16.53 | H | C |
| ATOM | 1630 | CD1 | PHE | 27 | 115.089 | 19.140 | 24.476 | 1.00 | 16.53 | H | C |
| ATOM | 1631 | CD2 | PHE | 27 | 115.269 | 20.448 | 22.476 | 1.00 | 16.53 | H | C |
| ATOM | 1632 | CE1 | PHE | 27 | 113.770 | 18.782 | 24.137 | 1.00 | 16.53 | H | C |
| ATOM | 1633 | CE2 | PHE | 27 | 113.958 | 20.101 | 22.125 | 1.00 | 16.53 | H | C |
| ATOM | 1634 | CZ | PHE | 27 | 113.203 | 19.268 | 22.954 | 1.00 | 16.53 | H | C |
| ATOM | 1635 | C | PHE | 27 | 116.592 | 22.528 | 25.135 | 1.00 | 18.08 | H | C |
| ATOM | 1636 | O | PHE | 27 | 115.566 | 22.780 | 25.763 | 1.00 | 18.08 | H | O |
| ATOM | 1637 | N | THR | 28 | 117.139 | 23.377 | 24.276 | 1.00 | 42.88 | H | N |
| ATOM | 1638 | CA | THR | 28 | 116.544 | 24.672 | 24.017 | 1.00 | 42.88 | H | C |
| ATOM | 1639 | CB | THR | 28 | 117.575 | 25.604 | 23.381 | 1.00 | 53.65 | H | C |
| ATOM | 1640 | OG1 | THR | 28 | 118.841 | 25.399 | 24.018 | 1.00 | 53.65 | H | O |
| ATOM | 1641 | CG2 | THR | 28 | 117.168 | 27.056 | 23.561 | 1.00 | 53.65 | H | C |
| ATOM | 1642 | C | THR | 28 | 115.369 | 24.463 | 23.074 | 1.00 | 42.88 | H | C |
| ATOM | 1643 | O | THR | 28 | 115.484 | 24.666 | 21.868 | 1.00 | 42.88 | H | O |
| ATOM | 1644 | N | PHE | 29 | 114.239 | 24.051 | 23.644 | 1.00 | 29.92 | H | N |
| ATOM | 1645 | CA | PHE | 29 | 113.004 | 23.772 | 22.901 | 1.00 | 29.92 | H | C |
| ATOM | 1646 | CB | PHE | 29 | 111.855 | 23.614 | 23.906 | 1.00 | 3.95 | H | C |
| ATOM | 1647 | CG | PHE | 29 | 110.503 | 23.347 | 23.276 | 1.00 | 3.95 | H | C |
| ATOM | 1648 | CD1 | PHE | 29 | 110.208 | 22.102 | 22.696 | 1.00 | 3.95 | H | C |
| ATOM | 1649 | CD2 | PHE | 29 | 109.504 | 24.336 | 23.283 | 1.00 | 3.95 | H | C |
| ATOM | 1650 | CE1 | PHE | 29 | 108.939 | 21.852 | 22.139 | 1.00 | 3.95 | H | C |
| ATOM | 1651 | CE2 | PHE | 29 | 108.234 | 24.092 | 22.727 | 1.00 | 3.95 | H | C |
| ATOM | 1652 | CZ | PHE | 29 | 107.953 | 22.860 | 22.160 | 1.00 | 3.95 | H | C |
| ATOM | 1653 | C | PHE | 29 | 112.611 | 24.777 | 21.797 | 1.00 | 29.92 | H | C |
| ATOM | 1654 | O | PHE | 29 | 112.390 | 24.389 | 20.647 | 1.00 | 29.92 | H | O |
| ATOM | 1655 | N | SER | 30 | 112.539 | 26.058 | 22.144 | 1.00 | 32.50 | H | N |
| ATOM | 1656 | CA | SER | 30 | 112.139 | 27.105 | 21.199 | 1.00 | 32.50 | H | C |
| ATOM | 1657 | CB | SER | 30 | 112.335 | 28.473 | 21.852 | 1.00 | 67.50 | H | C |
| ATOM | 1658 | OG | SER | 30 | 113.644 | 28.591 | 22.372 | 1.00 | 67.50 | H | O |
| ATOM | 1659 | C | SER | 30 | 112.799 | 27.107 | 19.812 | 1.00 | 32.50 | H | C |
| ATOM | 1660 | O | SER | 30 | 112.191 | 27.504 | 18.816 | 1.00 | 32.50 | H | O |
| ATOM | 1661 | N | ARG | 31 | 114.037 | 26.649 | 19.751 | 1.00 | 18.89 | H | N |
| ATOM | 1662 | CA | ARG | 31 | 114.801 | 26.636 | 18.515 | 1.00 | 18.89 | H | C |
| ATOM | 1663 | CB | ARG | 31 | 116.292 | 26.604 | 18.886 | 1.00 | 48.17 | H | C |
| ATOM | 1664 | CG | ARG | 31 | 117.217 | 25.955 | 17.887 | 1.00 | 48.17 | H | C |
| ATOM | 1665 | CD | ARG | 31 | 118.650 | 26.425 | 18.112 | 1.00 | 48.17 | H | C |
| ATOM | 1666 | NE | ARG | 31 | 119.135 | 26.203 | 19.476 | 1.00 | 48.17 | H | N |
| ATOM | 1667 | CZ | ARG | 31 | 120.228 | 26.777 | 19.980 | 1.00 | 48.17 | H | C |
| ATOM | 1668 | NH1 | ARG | 31 | 120.950 | 27.608 | 19.238 | 1.00 | 48.17 | H | N |
| ATOM | 1669 | NH2 | ARG | 31 | 120.604 | 26.524 | 21.226 | 1.00 | 48.17 | H | N |
| ATOM | 1670 | C | ARG | 31 | 114.463 | 25.523 | 17.521 | 1.00 | 18.89 | H | C |
| ATOM | 1671 | O | ARG | 31 | 114.520 | 25.723 | 16.313 | 1.00 | 18.89 | H | O |
| ATOM | 1672 | N | TYR | 32 | 114.095 | 24.353 | 18.027 | 1.00 | 15.47 | H | N |
| ATOM | 1673 | CA | TYR | 32 | 113.791 | 23.200 | 17.179 | 1.00 | 15.47 | H | C |
| ATOM | 1674 | CB | TYR | 32 | 113.949 | 21.922 | 17.996 | 1.00 | 6.03 | H | C |
| ATOM | 1675 | CG | TYR | 32 | 115.367 | 21.653 | 18.426 | 1.00 | 6.03 | H | C |
| ATOM | 1676 | CD1 | TYR | 32 | 115.934 | 22.336 | 19.500 | 1.00 | 6.03 | H | C |
| ATOM | 1677 | CE1 | TYR | 32 | 117.249 | 22.097 | 19.889 | 1.00 | 6.03 | H | C |
| ATOM | 1678 | CD2 | TYR | 32 | 116.153 | 20.722 | 17.747 | 1.00 | 6.03 | H | C |
| ATOM | 1679 | CE2 | TYR | 32 | 117.467 | 20.477 | 18.122 | 1.00 | 6.03 | H | C |

FIG. 19A-24

```
ATOM   1680  CZ   TYR  32   118.013  21.165  19.198  1.00   6.03  H  C
ATOM   1681  OH   TYR  32   119.317  20.907  19.597  1.00   6.03  H  O
ATOM   1682  C    TYR  32   112.426  23.184  16.534  1.00  15.47  H  C
ATOM   1683  O    TYR  32   111.480  23.748  17.058  1.00  15.47  H  O
ATOM   1684  N    THR  33   112.309  22.545  15.382  1.00  10.91  H  N
ATOM   1685  CA   THR  33   110.988  22.451  14.792  1.00  10.91  H  C
ATOM   1686  CB   THR  33   111.032  22.556  13.230  1.00  11.96  H  C
ATOM   1687  OG1  THR  33   111.079  21.259  12.639  1.00  11.96  H  O
ATOM   1688  CG2  THR  33   112.251  23.338  12.786  1.00  11.96  H  C
ATOM   1689  C    THR  33   110.501  21.082  15.303  1.00  10.91  H  C
ATOM   1690  O    THR  33   111.188  20.061  15.157  1.00  10.91  H  O
ATOM   1691  N    MET  34   109.348  21.070  15.960  1.00  21.14  H  N
ATOM   1692  CA   MET  34   108.815  19.835  16.518  1.00  21.14  H  C
ATOM   1693  CB   MET  34   108.188  20.094  17.888  1.00  16.88  H  C
ATOM   1694  CG   MET  34   109.035  20.899  18.847  1.00  16.88  H  C
ATOM   1695  SD   MET  34   110.603  20.131  19.122  1.00  16.88  H  S
ATOM   1696  CE   MET  34   110.155  18.770  20.240  1.00  16.88  H  C
ATOM   1697  C    MET  34   107.760  19.218  15.614  1.00  21.14  H  C
ATOM   1698  O    MET  34   107.160  19.905  14.781  1.00  21.14  H  O
ATOM   1699  N    SER  35   107.519  17.925  15.802  1.00  15.88  H  N
ATOM   1700  CA   SER  35   106.533  17.232  14.997  1.00  15.88  H  C
ATOM   1701  CB   SER  35   107.205  16.581  13.794  1.00  13.53  H  C
ATOM   1702  OG   SER  35   107.895  17.550  13.034  1.00  13.53  H  O
ATOM   1703  C    SER  35   105.767  16.168  15.763  1.00  15.88  H  C
ATOM   1704  O    SER  35   106.058  15.867  16.926  1.00  15.88  H  O
ATOM   1705  N    TRP  36   104.765  15.617  15.087  1.00  13.73  H  N
ATOM   1706  CA   TRP  36   103.948  14.556  15.626  1.00  13.73  H  C
ATOM   1707  CB   TRP  36   102.510  15.023  15.849  1.00  20.04  H  C
ATOM   1708  CG   TRP  36   102.337  15.903  17.039  1.00  20.04  H  C
ATOM   1709  CD2  TRP  36   102.259  15.489  18.406  1.00  20.04  H  C
ATOM   1710  CE2  TRP  36   102.112  16.654  19.186  1.00  20.04  H  C
ATOM   1711  CE3  TRP  36   102.301  14.248  19.046  1.00  20.04  H  C
ATOM   1712  CD1  TRP  36   102.236  17.255  17.045  1.00  20.04  H  C
ATOM   1713  NE1  TRP  36   102.100  17.716  18.329  1.00  20.04  H  N
ATOM   1714  CZ2  TRP  36   102.004  16.622  20.576  1.00  20.04  H  C
ATOM   1715  CZ3  TRP  36   102.192  14.211  20.442  1.00  20.04  H  C
ATOM   1716  CH2  TRP  36   102.044  15.396  21.190  1.00  20.04  H  C
ATOM   1717  C    TRP  36   103.978  13.470  14.565  1.00  13.73  H  C
ATOM   1718  O    TRP  36   103.879  13.769  13.373  1.00  13.73  H  O
ATOM   1719  N    VAL  37   104.138  12.221  15.006  1.00  21.09  H  N
ATOM   1720  CA   VAL  37   104.179  11.054  14.125  1.00  21.09  H  C
ATOM   1721  CB   VAL  37   105.622  10.464  14.053  1.00   6.36  H  C
ATOM   1722  CG1  VAL  37   105.591   9.017  13.642  1.00   6.36  H  C
ATOM   1723  CG2  VAL  37   106.461  11.253  13.057  1.00   6.36  H  C
ATOM   1724  C    VAL  37   103.229  10.041  14.748  1.00  21.09  H  C
ATOM   1725  O    VAL  37   103.144   9.940  15.963  1.00  21.09  H  O
ATOM   1726  N    ARG  38   102.508   9.294  13.929  1.00  17.98  H  N
ATOM   1727  CA   ARG  38   101.562   8.309  14.454  1.00  17.98  H  C
ATOM   1728  CB   ARG  38   100.133   8.697  14.058  1.00  13.99  H  C
ATOM   1729  CG   ARG  38   100.106   9.210  12.633  1.00  13.99  H  C
ATOM   1730  CD   ARG  38    98.899   8.817  11.839  1.00  13.99  H  C
ATOM   1731  NE   ARG  38    97.664   9.434  12.289  1.00  13.99  H  N
ATOM   1732  CZ   ARG  38    96.652   9.707  11.470  1.00  13.99  H  C
ATOM   1733  NH1  ARG  38    96.744   9.432  10.171  1.00  13.99  H  N
ATOM   1734  NH2  ARG  38    95.533  10.224  11.960  1.00  13.99  H  N
ATOM   1735  C    ARG  38   101.856   6.925  13.895  1.00  17.98  H  C
ATOM   1736  O    ARG  38   102.468   6.785  12.840  1.00  17.98  H  O
ATOM   1737  N    GLN  39   101.386   5.909  14.604  1.00  17.63  H  N
ATOM   1738  CA   GLN  39   101.560   4.521  14.200  1.00  17.63  H  C
ATOM   1739  CB   GLN  39   102.659   3.866  15.051  1.00  12.11  H  C
ATOM   1740  CG   GLN  39   102.976   2.424  14.712  1.00  12.11  H  C
ATOM   1741  CD   GLN  39   104.396   2.025  15.134  1.00  12.11  H  C
ATOM   1742  OE1  GLN  39   104.811   2.262  16.272  1.00  12.11  H  O
ATOM   1743  NE2  GLN  39   105.143   1.414  14.212  1.00  12.11  H  N
ATOM   1744  C    GLN  39   100.206   3.847  14.429  1.00  17.63  H  C
ATOM   1745  O    GLN  39    99.712   3.770  15.562  1.00  17.63  H  O
ATOM   1746  N    ALA  40    99.590   3.399  13.344  1.00  55.11  H  N
ATOM   1747  CA   ALA  40    98.300   2.737  13.436  1.00  55.11  H  C
ATOM   1748  CB   ALA  40    97.605   2.754  12.088  1.00  43.12  H  C
ATOM   1749  C    ALA  40    98.536   1.302  13.881  1.00  55.11  H  C
ATOM   1750  O    ALA  40    99.626   0.762  13.687  1.00  55.11  H  O
ATOM   1751  N    PRO  41    97.517   0.670  14.491  1.00  55.83  H  N
ATOM   1752  CD   PRO  41    96.189   1.237  14.782  1.00  86.02  H  C
```

FIG. 19A-25

| | | | | | | | | | | | |
|---|---|---|---|---|---|---|---|---|---|---|---|
| ATOM | 1753 | CA | PRO | 41 | 97.600 | -0.712 | 14.969 | 1.00 | 55.83 | H | C |
| ATOM | 1754 | CB | PRO | 41 | 96.169 | -1.009 | 15.400 | 1.00 | 86.02 | H | C |
| ATOM | 1755 | CG | PRO | 41 | 95.681 | 0.315 | 15.859 | 1.00 | 86.02 | H | C |
| ATOM | 1756 | C | PRO | 41 | 98.057 | -1.624 | 13.838 | 1.00 | 55.83 | H | C |
| ATOM | 1757 | O | PRO | 41 | 97.423 | -1.670 | 12.781 | 1.00 | 55.83 | H | O |
| ATOM | 1758 | N | GLY | 42 | 99.160 | -2.335 | 14.061 | 1.00 | 43.01 | H | N |
| ATOM | 1759 | CA | GLY | 42 | 99.684 | -3.227 | 13.042 | 1.00 | 43.01 | H | C |
| ATOM | 1760 | C | GLY | 42 | 100.227 | -2.529 | 11.800 | 1.00 | 43.01 | H | C |
| ATOM | 1761 | O | GLY | 42 | 100.480 | -3.175 | 10.775 | 1.00 | 43.01 | H | O |
| ATOM | 1762 | N | LYS | 43 | 100.415 | -1.212 | 11.882 | 1.00 | 46.16 | H | N |
| ATOM | 1763 | CA | LYS | 43 | 100.922 | -0.446 | 10.750 | 1.00 | 46.16 | H | C |
| ATOM | 1764 | CB | LYS | 43 | 99.896 | 0.612 | 10.334 | 1.00 | 59.60 | H | C |
| ATOM | 1765 | CG | LYS | 43 | 98.800 | 0.081 | 9.421 | 1.00 | 59.60 | H | C |
| ATOM | 1766 | CD | LYS | 43 | 98.003 | -1.023 | 10.079 | 1.00 | 59.60 | H | C |
| ATOM | 1767 | CE | LYS | 43 | 97.230 | -1.831 | 9.047 | 1.00 | 59.60 | H | C |
| ATOM | 1768 | NZ | LYS | 43 | 98.125 | -2.590 | 8.124 | 1.00 | 59.60 | H | N |
| ATOM | 1769 | C | LYS | 43 | 102.278 | 0.215 | 10.994 | 1.00 | 46.16 | H | C |
| ATOM | 1770 | O | LYS | 43 | 102.889 | 0.060 | 12.063 | 1.00 | 46.16 | H | O |
| ATOM | 1771 | N | GLY | 44 | 102.742 | 0.942 | 9.976 | 1.00 | 50.42 | H | N |
| ATOM | 1772 | CA | GLY | 44 | 104.016 | 1.631 | 10.054 | 1.00 | 50.42 | H | C |
| ATOM | 1773 | C | GLY | 44 | 103.916 | 3.004 | 10.691 | 1.00 | 50.42 | H | C |
| ATOM | 1774 | O | GLY | 44 | 103.001 | 3.281 | 11.462 | 1.00 | 50.42 | H | O |
| ATOM | 1775 | N | LEU | 45 | 104.862 | 3.870 | 10.347 | 1.00 | 25.59 | H | N |
| ATOM | 1776 | CA | LEU | 45 | 104.933 | 5.229 | 10.883 | 1.00 | 25.59 | H | C |
| ATOM | 1777 | CB | LEU | 45 | 106.387 | 5.544 | 11.224 | 1.00 | 8.94 | H | C |
| ATOM | 1778 | CG | LEU | 45 | 107.011 | 4.480 | 12.118 | 1.00 | 8.94 | H | C |
| ATOM | 1779 | CD1 | LEU | 45 | 108.520 | 4.578 | 12.054 | 1.00 | 8.94 | H | C |
| ATOM | 1780 | CD2 | LEU | 45 | 106.481 | 4.638 | 13.541 | 1.00 | 8.94 | H | C |
| ATOM | 1781 | C | LEU | 45 | 104.394 | 6.259 | 9.893 | 1.00 | 25.59 | H | C |
| ATOM | 1782 | O | LEU | 45 | 104.613 | 6.142 | 8.684 | 1.00 | 25.59 | H | O |
| ATOM | 1783 | N | GLU | 46 | 103.698 | 7.268 | 10.411 | 1.00 | 28.67 | H | N |
| ATOM | 1784 | CA | GLU | 46 | 103.111 | 8.308 | 9.569 | 1.00 | 28.67 | H | C |
| ATOM | 1785 | CB | GLU | 46 | 101.617 | 8.045 | 9.370 | 1.00 | 21.38 | H | C |
| ATOM | 1786 | CG | GLU | 46 | 100.977 | 8.902 | 8.304 | 1.00 | 21.38 | H | C |
| ATOM | 1787 | CD | GLU | 46 | 99.555 | 8.471 | 7.972 | 1.00 | 21.38 | H | C |
| ATOM | 1788 | OE1 | GLU | 46 | 98.711 | 8.399 | 8.903 | 1.00 | 21.38 | H | O |
| ATOM | 1789 | OE2 | GLU | 46 | 99.283 | 8.214 | 6.776 | 1.00 | 21.38 | H | O |
| ATOM | 1790 | C | GLU | 46 | 103.304 | 9.698 | 10.152 | 1.00 | 28.67 | H | C |
| ATOM | 1791 | O | GLU | 46 | 102.942 | 9.962 | 11.301 | 1.00 | 28.67 | H | O |
| ATOM | 1792 | N | TRP | 47 | 103.887 | 10.579 | 9.347 | 1.00 | 2.61 | H | N |
| ATOM | 1793 | CA | TRP | 47 | 104.132 | 11.944 | 9.758 | 1.00 | 2.61 | H | C |
| ATOM | 1794 | CB | TRP | 47 | 105.055 | 12.618 | 8.757 | 1.00 | 14.19 | H | C |
| ATOM | 1795 | CG | TRP | 47 | 105.068 | 14.095 | 8.904 | 1.00 | 14.19 | H | C |
| ATOM | 1796 | CD2 | TRP | 47 | 104.446 | 15.035 | 8.036 | 1.00 | 14.19 | H | C |
| ATOM | 1797 | CE2 | TRP | 47 | 104.681 | 16.323 | 8.578 | 1.00 | 14.19 | H | C |
| ATOM | 1798 | CE3 | TRP | 47 | 103.709 | 14.919 | 6.852 | 1.00 | 14.19 | H | C |
| ATOM | 1799 | CD1 | TRP | 47 | 105.644 | 14.824 | 9.914 | 1.00 | 14.19 | H | C |
| ATOM | 1800 | NE1 | TRP | 47 | 105.418 | 16.161 | 9.723 | 1.00 | 14.19 | H | N |
| ATOM | 1801 | CZ2 | TRP | 47 | 104.201 | 17.490 | 7.969 | 1.00 | 14.19 | H | C |
| ATOM | 1802 | CZ3 | TRP | 47 | 103.233 | 16.074 | 6.248 | 1.00 | 14.19 | H | C |
| ATOM | 1803 | CH2 | TRP | 47 | 103.480 | 17.344 | 6.808 | 1.00 | 14.19 | H | C |
| ATOM | 1804 | C | TRP | 47 | 102.791 | 12.673 | 9.802 | 1.00 | 2.61 | H | C |
| ATOM | 1805 | O | TRP | 47 | 102.083 | 12.752 | 8.796 | 1.00 | 2.61 | H | O |
| ATOM | 1806 | N | VAL | 48 | 102.443 | 13.215 | 10.962 | 1.00 | 34.26 | H | N |
| ATOM | 1807 | CA | VAL | 48 | 101.165 | 13.895 | 11.114 | 1.00 | 34.26 | H | C |
| ATOM | 1808 | CB | VAL | 48 | 100.576 | 13.639 | 12.523 | 1.00 | 16.29 | H | C |
| ATOM | 1809 | CG1 | VAL | 48 | 99.137 | 14.148 | 12.623 | 1.00 | 16.29 | H | C |
| ATOM | 1810 | CG2 | VAL | 48 | 100.624 | 12.187 | 12.812 | 1.00 | 16.29 | H | C |
| ATOM | 1811 | C | VAL | 48 | 101.246 | 15.393 | 10.884 | 1.00 | 34.26 | H | C |
| ATOM | 1812 | O | VAL | 48 | 100.563 | 15.932 | 10.015 | 1.00 | 34.26 | H | O |
| ATOM | 1813 | N | ALA | 49 | 102.078 | 16.068 | 11.665 | 1.00 | 19.79 | H | N |
| ATOM | 1814 | CA | ALA | 49 | 102.198 | 17.505 | 11.533 | 1.00 | 19.79 | H | C |
| ATOM | 1815 | CB | ALA | 49 | 101.052 | 18.193 | 12.288 | 1.00 | 1.87 | H | C |
| ATOM | 1816 | C | ALA | 49 | 103.542 | 17.994 | 12.041 | 1.00 | 19.79 | H | C |
| ATOM | 1817 | O | ALA | 49 | 104.295 | 17.244 | 12.645 | 1.00 | 19.79 | H | O |
| ATOM | 1818 | N | THR | 50 | 103.816 | 19.271 | 11.795 | 1.00 | 29.76 | H | N |
| ATOM | 1819 | CA | THR | 50 | 105.067 | 19.906 | 12.184 | 1.00 | 29.76 | H | C |
| ATOM | 1820 | CB | THR | 50 | 106.142 | 19.637 | 11.127 | 1.00 | 20.69 | H | C |
| ATOM | 1821 | OG1 | THR | 50 | 106.390 | 18.232 | 11.065 | 1.00 | 20.69 | H | O |
| ATOM | 1822 | CG2 | THR | 50 | 107.422 | 20.357 | 11.460 | 1.00 | 20.69 | H | C |
| ATOM | 1823 | C | THR | 50 | 104.897 | 21.416 | 12.327 | 1.00 | 29.76 | H | C |
| ATOM | 1824 | O | THR | 50 | 104.113 | 22.035 | 11.616 | 1.00 | 29.76 | H | O |
| ATOM | 1825 | N | ILE | 51 | 105.649 | 21.994 | 13.258 | 1.00 | 20.54 | H | N |

FIG. 19A-26

| | | | | | | | | | | |
|---|---|---|---|---|---|---|---|---|---|---|
| ATOM | 1826 | CA | ILE | 51 | 105.626 | 23.424 | 13.530 | 1.00 | 20.54 | H C |
| ATOM | 1827 | CB | ILE | 51 | 104.824 | 23.714 | 14.816 | 1.00 | 27.11 | H C |
| ATOM | 1828 | CG2 | ILE | 51 | 105.430 | 22.955 | 15.975 | 1.00 | 27.11 | H C |
| ATOM | 1829 | CG1 | ILE | 51 | 104.805 | 25.217 | 15.108 | 1.00 | 27.11 | H C |
| ATOM | 1830 | CD1 | ILE | 51 | 104.073 | 25.593 | 16.389 | 1.00 | 27.11 | H C |
| ATOM | 1831 | C | ILE | 51 | 107.090 | 23.813 | 13.723 | 1.00 | 20.54 | H C |
| ATOM | 1832 | O | ILE | 51 | 107.781 | 23.208 | 14.533 | 1.00 | 20.54 | H O |
| ATOM | 1833 | N | SER | 52 | 107.565 | 24.803 | 12.970 | 1.00 | 28.49 | H N |
| ATOM | 1834 | CA | SER | 52 | 108.962 | 25.234 | 13.047 | 1.00 | 28.49 | H C |
| ATOM | 1835 | CB | SER | 52 | 109.356 | 26.018 | 11.797 | 1.00 | 35.37 | H C |
| ATOM | 1836 | OG | SER | 52 | 108.819 | 27.332 | 11.832 | 1.00 | 35.37 | H O |
| ATOM | 1837 | C | SER | 52 | 109.236 | 26.105 | 14.256 | 1.00 | 28.49 | H C |
| ATOM | 1838 | O | SER | 52 | 108.316 | 26.461 | 14.994 | 1.00 | 28.49 | H O |
| ATOM | 1839 | N | GLY | 53 | 110.509 | 26.452 | 14.451 | 1.00 | 16.74 | H N |
| ATOM | 1840 | CA | GLY | 53 | 110.864 | 27.295 | 15.568 | 1.00 | 16.74 | H C |
| ATOM | 1841 | C | GLY | 53 | 110.203 | 28.651 | 15.410 | 1.00 | 16.74 | H C |
| ATOM | 1842 | O | GLY | 53 | 110.093 | 29.412 | 16.369 | 1.00 | 16.74 | H O |
| ATOM | 1843 | N | GLY | 54 | 109.746 | 28.939 | 14.192 | 1.00 | 26.55 | H N |
| ATOM | 1844 | CA | GLY | 54 | 109.120 | 30.218 | 13.907 | 1.00 | 26.55 | H C |
| ATOM | 1845 | C | GLY | 54 | 107.605 | 30.253 | 13.815 | 1.00 | 26.55 | H C |
| ATOM | 1846 | O | GLY | 54 | 107.020 | 31.317 | 13.607 | 1.00 | 26.55 | H O |
| ATOM | 1847 | N | GLY | 55 | 106.953 | 29.105 | 13.948 | 1.00 | 34.83 | H N |
| ATOM | 1848 | CA | GLY | 55 | 105.505 | 29.105 | 13.889 | 1.00 | 34.83 | H C |
| ATOM | 1849 | C | GLY | 55 | 104.878 | 28.610 | 12.604 | 1.00 | 34.83 | H C |
| ATOM | 1850 | O | GLY | 55 | 103.657 | 28.663 | 12.458 | 1.00 | 34.83 | H O |
| ATOM | 1851 | N | HIS | 56 | 105.683 | 28.149 | 11.655 | 1.00 | 20.17 | H N |
| ATOM | 1852 | CA | HIS | 56 | 105.091 | 27.643 | 10.426 | 1.00 | 20.17 | H C |
| ATOM | 1853 | CB | HIS | 56 | 106.117 | 27.522 | 9.302 | 1.00 | 75.35 | H C |
| ATOM | 1854 | CG | HIS | 56 | 106.829 | 28.797 | 8.996 | 1.00 | 75.35 | H C |
| ATOM | 1855 | CD2 | HIS | 56 | 106.561 | 29.773 | 8.096 | 1.00 | 75.35 | H C |
| ATOM | 1856 | ND1 | HIS | 56 | 107.959 | 29.201 | 9.677 | 1.00 | 75.35 | H N |
| ATOM | 1857 | CE1 | HIS | 56 | 108.356 | 30.370 | 9.209 | 1.00 | 75.35 | H C |
| ATOM | 1858 | NE2 | HIS | 56 | 107.525 | 30.739 | 8.250 | 1.00 | 75.35 | H N |
| ATOM | 1859 | C | HIS | 56 | 104.585 | 26.266 | 10.774 | 1.00 | 20.17 | H C |
| ATOM | 1860 | O | HIS | 56 | 105.309 | 25.465 | 11.350 | 1.00 | 20.17 | H O |
| ATOM | 1861 | N | THR | 57 | 103.331 | 25.994 | 10.458 | 1.00 | 9.30 | H N |
| ATOM | 1862 | CA | THR | 57 | 102.793 | 24.676 | 10.728 | 1.00 | 9.30 | H C |
| ATOM | 1863 | CB | THR | 57 | 101.437 | 24.766 | 11.475 | 1.00 | 25.93 | H C |
| ATOM | 1864 | OG1 | THR | 57 | 100.483 | 25.493 | 10.691 | 1.00 | 25.93 | H O |
| ATOM | 1865 | CG2 | THR | 57 | 101.624 | 25.460 | 12.821 | 1.00 | 25.93 | H C |
| ATOM | 1866 | C | THR | 57 | 102.657 | 23.911 | 9.403 | 1.00 | 9.30 | H C |
| ATOM | 1867 | O | THR | 57 | 102.437 | 24.503 | 8.348 | 1.00 | 9.30 | H O |
| ATOM | 1868 | N | TYR | 58 | 102.849 | 22.598 | 9.463 | 1.00 | 10.35 | H N |
| ATOM | 1869 | CA | TYR | 58 | 102.739 | 21.729 | 8.293 | 1.00 | 10.35 | H C |
| ATOM | 1870 | CB | TYR | 58 | 104.115 | 21.217 | 7.912 | 1.00 | 22.31 | H C |
| ATOM | 1871 | CG | TYR | 58 | 105.023 | 22.324 | 7.485 | 1.00 | 22.31 | H C |
| ATOM | 1872 | CD1 | TYR | 58 | 105.051 | 22.744 | 6.167 | 1.00 | 22.31 | H C |
| ATOM | 1873 | CE1 | TYR | 58 | 105.871 | 23.765 | 5.768 | 1.00 | 22.31 | H C |
| ATOM | 1874 | CD2 | TYR | 58 | 105.843 | 22.967 | 8.399 | 1.00 | 22.31 | H C |
| ATOM | 1875 | CE2 | TYR | 58 | 106.667 | 23.997 | 8.007 | 1.00 | 22.31 | H C |
| ATOM | 1876 | CZ | TYR | 58 | 106.674 | 24.388 | 6.689 | 1.00 | 22.31 | H C |
| ATOM | 1877 | OH | TYR | 58 | 107.478 | 25.419 | 6.279 | 1.00 | 22.31 | H O |
| ATOM | 1878 | C | TYR | 58 | 101.812 | 20.565 | 8.635 | 1.00 | 10.35 | H C |
| ATOM | 1879 | O | TYR | 58 | 101.699 | 20.164 | 9.801 | 1.00 | 10.35 | H O |
| ATOM | 1880 | N | TYR | 59 | 101.147 | 20.007 | 7.634 | 1.00 | 15.64 | H N |
| ATOM | 1881 | CA | TYR | 59 | 100.219 | 18.936 | 7.931 | 1.00 | 15.64 | H C |
| ATOM | 1882 | CB | TYR | 59 | 98.843 | 19.542 | 8.203 | 1.00 | 11.32 | H C |
| ATOM | 1883 | CG | TYR | 59 | 98.803 | 20.511 | 9.360 | 1.00 | 11.32 | H C |
| ATOM | 1884 | CD1 | TYR | 59 | 98.625 | 20.058 | 10.661 | 1.00 | 11.32 | H C |
| ATOM | 1885 | CE1 | TYR | 59 | 98.540 | 20.942 | 11.731 | 1.00 | 11.32 | H C |
| ATOM | 1886 | CD2 | TYR | 59 | 98.912 | 21.886 | 9.148 | 1.00 | 11.32 | H C |
| ATOM | 1887 | CE2 | TYR | 59 | 98.835 | 22.783 | 10.208 | 1.00 | 11.32 | H C |
| ATOM | 1888 | CZ | TYR | 59 | 98.640 | 22.302 | 11.502 | 1.00 | 11.32 | H C |
| ATOM | 1889 | OH | TYR | 59 | 98.498 | 23.177 | 12.557 | 1.00 | 11.32 | H O |
| ATOM | 1890 | C | TYR | 59 | 100.071 | 17.883 | 6.856 | 1.00 | 15.64 | H C |
| ATOM | 1891 | O | TYR | 59 | 100.150 | 18.182 | 5.666 | 1.00 | 15.64 | H O |
| ATOM | 1892 | N | LEU | 60 | 99.854 | 16.644 | 7.286 | 1.00 | 33.81 | H N |
| ATOM | 1893 | CA | LEU | 60 | 99.616 | 15.539 | 6.366 | 1.00 | 33.81 | H C |
| ATOM | 1894 | CB | LEU | 60 | 99.625 | 14.217 | 7.135 | 1.00 | 13.27 | H C |
| ATOM | 1895 | CG | LEU | 60 | 99.371 | 12.896 | 6.406 | 1.00 | 13.27 | H C |
| ATOM | 1896 | CD1 | LEU | 60 | 100.681 | 12.371 | 5.800 | 1.00 | 13.27 | H C |
| ATOM | 1897 | CD2 | LEU | 60 | 98.804 | 11.882 | 7.397 | 1.00 | 13.27 | H C |
| ATOM | 1898 | C | LEU | 60 | 98.198 | 15.861 | 5.869 | 1.00 | 33.81 | H C |

FIG. 19A-27

| ATOM | 1899 | O | LEU | 60 | 97.329 | 16.255 | 6.659 | 1.00 | 33.81 | H | O |
|---|---|---|---|---|---|---|---|---|---|---|---|
| ATOM | 1900 | N | ASP | 61 | 97.962 | 15.710 | 4.573 | 1.00 | 24.56 | H | N |
| ATOM | 1901 | CA | ASP | 61 | 96.659 | 16.028 | 3.991 | 1.00 | 24.56 | H | C |
| ATOM | 1902 | CB | ASP | 61 | 96.639 | 15.579 | 2.530 | 1.00 | 55.35 | H | C |
| ATOM | 1903 | CG | ASP | 61 | 97.719 | 16.260 | 1.708 | 1.00 | 55.35 | H | C |
| ATOM | 1904 | OD1 | ASP | 61 | 98.919 | 16.083 | 2.023 | 1.00 | 55.35 | H | O |
| ATOM | 1905 | OD2 | ASP | 61 | 97.374 | 16.981 | 0.754 | 1.00 | 55.35 | H | O |
| ATOM | 1906 | C | ASP | 61 | 95.436 | 15.495 | 4.731 | 1.00 | 24.56 | H | C |
| ATOM | 1907 | O | ASP | 61 | 94.515 | 16.254 | 5.043 | 1.00 | 24.56 | H | O |
| ATOM | 1908 | N | SER | 62 | 95.432 | 14.198 | 5.024 | 1.00 | 20.78 | H | N |
| ATOM | 1909 | CA | SER | 62 | 94.317 | 13.567 | 5.717 | 1.00 | 20.78 | H | C |
| ATOM | 1910 | CB | SER | 62 | 94.630 | 12.085 | 5.955 | 1.00 | 31.68 | H | C |
| ATOM | 1911 | OG | SER | 62 | 95.820 | 11.902 | 6.708 | 1.00 | 31.68 | H | O |
| ATOM | 1912 | C | SER | 62 | 93.882 | 14.216 | 7.044 | 1.00 | 20.78 | H | C |
| ATOM | 1913 | O | SER | 62 | 92.732 | 14.053 | 7.475 | 1.00 | 20.78 | H | O |
| ATOM | 1914 | N | VAL | 63 | 94.779 | 14.949 | 7.695 | 1.00 | 24.27 | H | N |
| ATOM | 1915 | CA | VAL | 63 | 94.439 | 15.567 | 8.968 | 1.00 | 24.27 | H | C |
| ATOM | 1916 | CB | VAL | 63 | 95.478 | 15.202 | 10.049 | 1.00 | 45.54 | H | C |
| ATOM | 1917 | CG1 | VAL | 63 | 95.642 | 13.698 | 10.110 | 1.00 | 45.54 | H | C |
| ATOM | 1918 | CG2 | VAL | 63 | 96.812 | 15.873 | 9.752 | 1.00 | 45.54 | H | C |
| ATOM | 1919 | C | VAL | 63 | 94.374 | 17.083 | 8.839 | 1.00 | 24.27 | H | C |
| ATOM | 1920 | O | VAL | 63 | 94.112 | 17.812 | 9.823 | 1.00 | 24.27 | H | O |
| ATOM | 1921 | N | LYS | 64 | 94.611 | 17.556 | 7.618 | 1.00 | 38.99 | H | N |
| ATOM | 1922 | CA | LYS | 64 | 94.611 | 18.985 | 7.348 | 1.00 | 38.99 | H | C |
| ATOM | 1923 | CB | LYS | 64 | 94.983 | 19.235 | 5.889 | 1.00 | 39.16 | H | C |
| ATOM | 1924 | CG | LYS | 64 | 95.736 | 20.528 | 5.671 | 1.00 | 39.16 | H | C |
| ATOM | 1925 | CD | LYS | 64 | 96.417 | 20.521 | 4.309 | 1.00 | 39.16 | H | C |
| ATOM | 1926 | CE | LYS | 64 | 97.432 | 19.380 | 4.176 | 1.00 | 39.16 | H | C |
| ATOM | 1927 | NZ | LYS | 64 | 98.011 | 19.296 | 2.803 | 1.00 | 39.16 | H | N |
| ATOM | 1928 | C | LYS | 64 | 93.262 | 19.607 | 7.667 | 1.00 | 38.99 | H | C |
| ATOM | 1929 | O | LYS | 64 | 92.240 | 19.212 | 7.121 | 1.00 | 38.99 | H | O |
| ATOM | 1930 | N | GLY | 65 | 93.263 | 20.577 | 8.567 | 1.00 | 28.42 | H | N |
| ATOM | 1931 | CA | GLY | 65 | 92.019 | 21.219 | 8.918 | 1.00 | 28.42 | H | C |
| ATOM | 1932 | C | GLY | 65 | 91.277 | 20.501 | 10.021 | 1.00 | 28.42 | H | C |
| ATOM | 1933 | O | GLY | 65 | 90.271 | 21.005 | 10.509 | 1.00 | 28.42 | H | O |
| ATOM | 1934 | N | ARG | 66 | 91.751 | 19.324 | 10.414 | 1.00 | 48.07 | H | N |
| ATOM | 1935 | CA | ARG | 66 | 91.098 | 18.588 | 11.488 | 1.00 | 48.07 | H | C |
| ATOM | 1936 | CB | ARG | 66 | 90.783 | 17.154 | 11.064 | 1.00 | 36.61 | H | C |
| ATOM | 1937 | CG | ARG | 66 | 89.845 | 17.052 | 9.887 | 1.00 | 36.61 | H | C |
| ATOM | 1938 | CD | ARG | 66 | 89.484 | 15.608 | 9.571 | 1.00 | 36.61 | H | C |
| ATOM | 1939 | NE | ARG | 66 | 90.654 | 14.750 | 9.346 | 1.00 | 36.61 | H | N |
| ATOM | 1940 | CZ | ARG | 66 | 91.133 | 13.877 | 10.236 | 1.00 | 36.61 | H | C |
| ATOM | 1941 | NH1 | ARG | 66 | 90.545 | 13.739 | 11.421 | 1.00 | 36.61 | H | N |
| ATOM | 1942 | NH2 | ARG | 66 | 92.203 | 13.144 | 9.944 | 1.00 | 36.61 | H | N |
| ATOM | 1943 | C | ARG | 66 | 92.018 | 18.568 | 12.687 | 1.00 | 48.07 | H | C |
| ATOM | 1944 | O | ARG | 66 | 91.584 | 18.312 | 13.808 | 1.00 | 48.07 | H | O |
| ATOM | 1945 | N | PHE | 67 | 93.296 | 18.839 | 12.438 | 1.00 | 31.81 | H | N |
| ATOM | 1946 | CA | PHE | 67 | 94.304 | 18.854 | 13.490 | 1.00 | 31.81 | H | C |
| ATOM | 1947 | CB | PHE | 67 | 95.372 | 17.802 | 13.211 | 1.00 | 34.94 | H | C |
| ATOM | 1948 | CG | PHE | 67 | 94.937 | 16.394 | 13.444 | 1.00 | 34.94 | H | C |
| ATOM | 1949 | CD1 | PHE | 67 | 93.763 | 15.907 | 12.902 | 1.00 | 34.94 | H | C |
| ATOM | 1950 | CD2 | PHE | 67 | 95.748 | 15.530 | 14.158 | 1.00 | 34.94 | H | C |
| ATOM | 1951 | CE1 | PHE | 67 | 93.400 | 14.564 | 13.063 | 1.00 | 34.94 | H | C |
| ATOM | 1952 | CE2 | PHE | 67 | 95.400 | 14.192 | 14.326 | 1.00 | 34.94 | H | C |
| ATOM | 1953 | CZ | PHE | 67 | 94.222 | 13.706 | 13.777 | 1.00 | 34.94 | H | C |
| ATOM | 1954 | C | PHE | 67 | 94.989 | 20.209 | 13.520 | 1.00 | 31.81 | H | C |
| ATOM | 1955 | O | PHE | 67 | 95.054 | 20.899 | 12.501 | 1.00 | 31.81 | H | O |
| ATOM | 1956 | N | THR | 68 | 95.511 | 20.587 | 14.683 | 1.00 | 27.20 | H | N |
| ATOM | 1957 | CA | THR | 68 | 96.233 | 21.851 | 14.804 | 1.00 | 27.20 | H | C |
| ATOM | 1958 | CB | THR | 68 | 95.344 | 22.998 | 15.384 | 1.00 | 14.56 | H | C |
| ATOM | 1959 | OG1 | THR | 68 | 94.400 | 23.434 | 14.399 | 1.00 | 14.56 | H | O |
| ATOM | 1960 | CG2 | THR | 68 | 96.196 | 24.192 | 15.758 | 1.00 | 14.56 | H | C |
| ATOM | 1961 | C | THR | 68 | 97.466 | 21.680 | 15.689 | 1.00 | 27.20 | H | C |
| ATOM | 1962 | O | THR | 68 | 97.355 | 21.393 | 16.882 | 1.00 | 27.20 | H | O |
| ATOM | 1963 | N | ILE | 69 | 98.643 | 21.847 | 15.099 | 1.00 | 22.74 | H | N |
| ATOM | 1964 | CA | ILE | 69 | 99.869 | 21.718 | 15.861 | 1.00 | 22.74 | H | C |
| ATOM | 1965 | CB | ILE | 69 | 100.991 | 21.084 | 15.020 | 1.00 | 13.28 | H | C |
| ATOM | 1966 | CG2 | ILE | 69 | 101.417 | 22.022 | 13.933 | 1.00 | 13.28 | H | C |
| ATOM | 1967 | CG1 | ILE | 69 | 102.188 | 20.736 | 15.908 | 1.00 | 13.28 | H | C |
| ATOM | 1968 | CD1 | ILE | 69 | 103.226 | 19.848 | 15.206 | 1.00 | 13.28 | H | C |
| ATOM | 1969 | C | ILE | 69 | 100.287 | 23.096 | 16.336 | 1.00 | 22.74 | H | C |
| ATOM | 1970 | O | ILE | 69 | 100.282 | 24.065 | 15.578 | 1.00 | 22.74 | H | O |
| ATOM | 1971 | N | SER | 70 | 100.632 | 23.188 | 17.608 | 1.00 | 15.22 | H | N |

FIG. 19A-28

| | | | | | | | | | | |
|---|---|---|---|---|---|---|---|---|---|---|
| ATOM | 1972 | CA | SER | 70 | 101.032 | 24.460 | 18.183 | 1.00 | 15.22 | H | C |
| ATOM | 1973 | CB | SER | 70 | 99.834 | 25.147 | 18.851 | 1.00 | 3.12 | H | C |
| ATOM | 1974 | OG | SER | 70 | 99.588 | 24.606 | 20.144 | 1.00 | 3.12 | H | O |
| ATOM | 1975 | C | SER | 70 | 102.088 | 24.203 | 19.235 | 1.00 | 15.22 | H | C |
| ATOM | 1976 | O | SER | 70 | 102.392 | 23.053 | 19.557 | 1.00 | 15.22 | H | O |
| ATOM | 1977 | N | ARG | 71 | 102.636 | 25.281 | 19.780 | 1.00 | 42.13 | H | N |
| ATOM | 1978 | CA | ARG | 71 | 103.640 | 25.158 | 20.813 | 1.00 | 42.13 | H | C |
| ATOM | 1979 | CB | ARG | 71 | 105.039 | 25.089 | 20.210 | 1.00 | 12.52 | H | C |
| ATOM | 1980 | CG | ARG | 71 | 105.417 | 26.296 | 19.388 | 1.00 | 12.52 | H | C |
| ATOM | 1981 | CD | ARG | 71 | 106.906 | 26.507 | 19.436 | 1.00 | 12.52 | H | C |
| ATOM | 1982 | NE | ARG | 71 | 107.644 | 25.627 | 18.540 | 1.00 | 12.52 | H | N |
| ATOM | 1983 | CZ | ARG | 71 | 108.844 | 25.114 | 18.816 | 1.00 | 12.52 | H | C |
| ATOM | 1984 | NH1 | ARG | 71 | 109.444 | 25.380 | 19.970 | 1.00 | 12.52 | H | N |
| ATOM | 1985 | NH2 | ARG | 71 | 109.456 | 24.354 | 17.924 | 1.00 | 12.52 | H | N |
| ATOM | 1986 | C | ARG | 71 | 103.568 | 26.341 | 21.739 | 1.00 | 42.13 | H | C |
| ATOM | 1987 | O | ARG | 71 | 103.115 | 27.416 | 21.352 | 1.00 | 42.13 | H | O |
| ATOM | 1988 | N | ASP | 72 | 104.003 | 26.131 | 22.973 | 1.00 | 26.38 | H | N |
| ATOM | 1989 | CA | ASP | 72 | 104.034 | 27.197 | 23.954 | 1.00 | 26.38 | H | C |
| ATOM | 1990 | CB | ASP | 72 | 102.949 | 27.026 | 25.007 | 1.00 | 47.03 | H | C |
| ATOM | 1991 | CG | ASP | 72 | 103.003 | 28.108 | 26.050 | 1.00 | 47.03 | H | C |
| ATOM | 1992 | OD1 | ASP | 72 | 102.157 | 28.112 | 26.964 | 1.00 | 47.03 | H | O |
| ATOM | 1993 | OD2 | ASP | 72 | 103.907 | 28.959 | 25.953 | 1.00 | 47.03 | H | O |
| ATOM | 1994 | C | ASP | 72 | 105.402 | 27.159 | 24.607 | 1.00 | 26.38 | H | C |
| ATOM | 1995 | O | ASP | 72 | 105.618 | 26.508 | 25.633 | 1.00 | 26.38 | H | O |
| ATOM | 1996 | N | ASN | 73 | 106.325 | 27.868 | 23.979 | 1.00 | 50.64 | H | N |
| ATOM | 1997 | CA | ASN | 73 | 107.692 | 27.939 | 24.441 | 1.00 | 50.64 | H | C |
| ATOM | 1998 | CB | ASN | 73 | 108.522 | 28.747 | 23.446 | 1.00 | 30.24 | H | C |
| ATOM | 1999 | CG | ASN | 73 | 108.584 | 28.091 | 22.086 | 1.00 | 30.24 | H | C |
| ATOM | 2000 | OD1 | ASN | 73 | 109.170 | 28.625 | 21.149 | 1.00 | 30.24 | H | O |
| ATOM | 2001 | ND2 | ASN | 73 | 107.984 | 26.917 | 21.974 | 1.00 | 30.24 | H | N |
| ATOM | 2002 | C | ASN | 73 | 107.827 | 28.516 | 25.841 | 1.00 | 50.64 | H | C |
| ATOM | 2003 | O | ASN | 73 | 108.898 | 28.436 | 26.438 | 1.00 | 50.64 | H | O |
| ATOM | 2004 | N | SER | 74 | 106.758 | 29.097 | 26.376 | 1.00 | 33.75 | H | N |
| ATOM | 2005 | CA | SER | 74 | 106.848 | 29.644 | 27.723 | 1.00 | 33.75 | H | C |
| ATOM | 2006 | CB | SER | 74 | 105.593 | 30.429 | 28.093 | 1.00 | 48.57 | H | C |
| ATOM | 2007 | OG | SER | 74 | 104.534 | 29.556 | 28.444 | 1.00 | 48.57 | H | O |
| ATOM | 2008 | C | SER | 74 | 106.979 | 28.456 | 28.653 | 1.00 | 33.75 | H | C |
| ATOM | 2009 | O | SER | 74 | 107.681 | 28.530 | 29.660 | 1.00 | 33.75 | H | O |
| ATOM | 2010 | N | LYS | 75 | 106.312 | 27.354 | 28.302 | 1.00 | 39.57 | H | N |
| ATOM | 2011 | CA | LYS | 75 | 106.352 | 26.142 | 29.119 | 1.00 | 39.57 | H | C |
| ATOM | 2012 | CB | LYS | 75 | 104.973 | 25.889 | 29.732 | 1.00 | 42.48 | H | C |
| ATOM | 2013 | CG | LYS | 75 | 103.842 | 25.924 | 28.731 | 1.00 | 42.48 | H | C |
| ATOM | 2014 | CD | LYS | 75 | 102.482 | 25.985 | 29.418 | 1.00 | 42.48 | H | C |
| ATOM | 2015 | CE | LYS | 75 | 102.156 | 27.393 | 29.918 | 1.00 | 42.48 | H | C |
| ATOM | 2016 | NZ | LYS | 75 | 103.090 | 27.928 | 30.963 | 1.00 | 42.48 | H | N |
| ATOM | 2017 | C | LYS | 75 | 106.843 | 24.894 | 28.380 | 1.00 | 39.57 | H | C |
| ATOM | 2018 | O | LYS | 75 | 106.497 | 23.767 | 28.744 | 1.00 | 39.57 | H | O |
| ATOM | 2019 | N | ASN | 76 | 107.660 | 25.110 | 27.353 | 1.00 | 44.84 | H | N |
| ATOM | 2020 | CA | ASN | 76 | 108.245 | 24.043 | 26.539 | 1.00 | 44.84 | H | C |
| ATOM | 2021 | CB | ASN | 76 | 109.572 | 23.608 | 27.139 | 1.00 | 31.30 | H | C |
| ATOM | 2022 | CG | ASN | 76 | 110.528 | 24.766 | 27.312 | 1.00 | 31.30 | H | C |
| ATOM | 2023 | OD1 | ASN | 76 | 111.666 | 24.593 | 27.739 | 1.00 | 31.30 | H | O |
| ATOM | 2024 | ND2 | ASN | 76 | 110.067 | 25.965 | 26.979 | 1.00 | 31.30 | H | N |
| ATOM | 2025 | C | ASN | 76 | 107.362 | 22.827 | 26.322 | 1.00 | 44.84 | H | C |
| ATOM | 2026 | O | ASN | 76 | 107.793 | 21.681 | 26.479 | 1.00 | 44.84 | H | O |
| ATOM | 2027 | N | THR | 77 | 106.121 | 23.090 | 25.941 | 1.00 | 30.42 | H | N |
| ATOM | 2028 | CA | THR | 77 | 105.181 | 22.032 | 25.686 | 1.00 | 30.42 | H | C |
| ATOM | 2029 | CB | THR | 77 | 103.989 | 22.131 | 26.628 | 1.00 | 46.49 | H | C |
| ATOM | 2030 | OG1 | THR | 77 | 104.446 | 21.977 | 27.974 | 1.00 | 46.49 | H | O |
| ATOM | 2031 | CG2 | THR | 77 | 102.975 | 21.045 | 26.319 | 1.00 | 46.49 | H | C |
| ATOM | 2032 | C | THR | 77 | 104.708 | 22.182 | 24.254 | 1.00 | 30.42 | H | C |
| ATOM | 2033 | O | THR | 77 | 104.488 | 23.291 | 23.786 | 1.00 | 30.42 | H | O |
| ATOM | 2034 | N | LEU | 78 | 104.583 | 21.056 | 23.563 | 1.00 | 20.66 | H | N |
| ATOM | 2035 | CA | LEU | 78 | 104.135 | 21.017 | 22.185 | 1.00 | 20.66 | H | C |
| ATOM | 2036 | CB | LEU | 78 | 104.978 | 20.024 | 21.394 | 1.00 | 19.59 | H | C |
| ATOM | 2037 | CG | LEU | 78 | 104.550 | 19.758 | 19.953 | 1.00 | 19.59 | H | C |
| ATOM | 2038 | CD1 | LEU | 78 | 104.575 | 21.055 | 19.166 | 1.00 | 19.59 | H | C |
| ATOM | 2039 | CD2 | LEU | 78 | 105.470 | 18.731 | 19.320 | 1.00 | 19.59 | H | C |
| ATOM | 2040 | C | LEU | 78 | 102.716 | 20.520 | 22.298 | 1.00 | 20.66 | H | C |
| ATOM | 2041 | O | LEU | 78 | 102.368 | 19.921 | 23.312 | 1.00 | 20.66 | H | O |
| ATOM | 2042 | N | TYR | 79 | 101.902 | 20.753 | 21.271 | 1.00 | 30.75 | H | N |
| ATOM | 2043 | CA | TYR | 79 | 100.498 | 20.333 | 21.294 | 1.00 | 30.75 | H | C |
| ATOM | 2044 | CB | TYR | 79 | 99.591 | 21.494 | 21.728 | 1.00 | 47.95 | H | C |

FIG. 19A-29

| | | | | | | | | | | |
|---|---|---|---|---|---|---|---|---|---|---|
| ATOM | 2045 | CG | TYR | 79 | 99.809 | 22.008 | 23.119 | 1.00 | 47.95 | H | C |
| ATOM | 2046 | CD1 | TYR | 79 | 99.166 | 21.430 | 24.205 | 1.00 | 47.95 | H | C |
| ATOM | 2047 | CE1 | TYR | 79 | 99.357 | 21.916 | 25.491 | 1.00 | 47.95 | H | C |
| ATOM | 2048 | CD2 | TYR | 79 | 100.655 | 23.085 | 23.349 | 1.00 | 47.95 | H | C |
| ATOM | 2049 | CE2 | TYR | 79 | 100.857 | 23.579 | 24.628 | 1.00 | 47.95 | H | C |
| ATOM | 2050 | CZ | TYR | 79 | 100.204 | 22.991 | 25.695 | 1.00 | 47.95 | H | C |
| ATOM | 2051 | OH | TYR | 79 | 100.404 | 23.493 | 26.958 | 1.00 | 47.95 | H | O |
| ATOM | 2052 | C | TYR | 79 | 99.966 | 19.863 | 19.950 | 1.00 | 30.75 | H | C |
| ATOM | 2053 | O | TYR | 79 | 100.418 | 20.316 | 18.898 | 1.00 | 30.75 | H | O |
| ATOM | 2054 | N | LEU | 80 | 98.981 | 18.969 | 20.003 | 1.00 | 19.83 | H | N |
| ATOM | 2055 | CA | LEU | 80 | 98.308 | 18.472 | 18.811 | 1.00 | 19.83 | H | C |
| ATOM | 2056 | CB | LEU | 80 | 98.776 | 17.070 | 18.397 | 1.00 | 5.08 | H | C |
| ATOM | 2057 | CG | LEU | 80 | 98.132 | 16.598 | 17.076 | 1.00 | 5.08 | H | C |
| ATOM | 2058 | CD1 | LEU | 80 | 98.706 | 17.386 | 15.914 | 1.00 | 5.08 | H | C |
| ATOM | 2059 | CD2 | LEU | 80 | 98.352 | 15.111 | 16.874 | 1.00 | 5.08 | H | C |
| ATOM | 2060 | C | LEU | 80 | 96.838 | 18.411 | 19.182 | 1.00 | 19.83 | H | C |
| ATOM | 2061 | O | LEU | 80 | 96.398 | 17.503 | 19.879 | 1.00 | 19.83 | H | O |
| ATOM | 2062 | N | GLN | 81 | 96.091 | 19.412 | 18.742 | 1.00 | 24.43 | H | N |
| ATOM | 2063 | CA | GLN | 81 | 94.671 | 19.463 | 19.004 | 1.00 | 24.43 | H | C |
| ATOM | 2064 | CB | GLN | 81 | 94.169 | 20.911 | 18.966 | 1.00 | 60.73 | H | C |
| ATOM | 2065 | CG | GLN | 81 | 92.710 | 21.093 | 19.399 | 1.00 | 60.73 | H | C |
| ATOM | 2066 | CD | GLN | 81 | 92.505 | 20.974 | 20.911 | 1.00 | 60.73 | H | C |
| ATOM | 2067 | OE1 | GLN | 81 | 92.981 | 21.810 | 21.691 | 1.00 | 60.73 | H | O |
| ATOM | 2068 | NE2 | GLN | 81 | 91.787 | 19.935 | 21.328 | 1.00 | 60.73 | H | N |
| ATOM | 2069 | C | GLN | 81 | 94.064 | 18.672 | 17.867 | 1.00 | 24.43 | H | C |
| ATOM | 2070 | O | GLN | 81 | 94.376 | 18.921 | 16.698 | 1.00 | 24.43 | H | O |
| ATOM | 2071 | N | MET | 82 | 93.205 | 17.718 | 18.210 | 1.00 | 35.69 | H | N |
| ATOM | 2072 | CA | MET | 82 | 92.559 | 16.878 | 17.211 | 1.00 | 35.69 | H | C |
| ATOM | 2073 | CB | MET | 82 | 92.989 | 15.424 | 17.383 | 1.00 | 24.95 | H | C |
| ATOM | 2074 | CG | MET | 82 | 94.481 | 15.209 | 17.363 | 1.00 | 24.95 | H | C |
| ATOM | 2075 | SD | MET | 82 | 94.896 | 13.491 | 17.609 | 1.00 | 24.95 | H | S |
| ATOM | 2076 | CE | MET | 82 | 94.985 | 13.427 | 19.373 | 1.00 | 24.95 | H | C |
| ATOM | 2077 | C | MET | 82 | 91.051 | 16.957 | 17.316 | 1.00 | 35.69 | H | C |
| ATOM | 2078 | O | MET | 82 | 90.479 | 16.599 | 18.338 | 1.00 | 35.69 | H | O |
| ATOM | 2079 | N | ASN | 83 | 90.414 | 17.416 | 16.247 | 1.00 | 28.29 | H | N |
| ATOM | 2080 | CA | ASN | 83 | 88.968 | 17.536 | 16.204 | 1.00 | 28.29 | H | C |
| ATOM | 2081 | CB | ASN | 83 | 88.550 | 18.989 | 15.985 | 1.00 | 66.28 | H | C |
| ATOM | 2082 | CG | ASN | 83 | 89.274 | 19.943 | 16.899 | 1.00 | 66.28 | H | C |
| ATOM | 2083 | OD1 | ASN | 83 | 89.213 | 19.819 | 18.121 | 1.00 | 66.28 | H | O |
| ATOM | 2084 | ND2 | ASN | 83 | 89.970 | 20.910 | 16.309 | 1.00 | 66.28 | H | N |
| ATOM | 2085 | C | ASN | 83 | 88.502 | 16.728 | 15.025 | 1.00 | 28.29 | H | C |
| ATOM | 2086 | O | ASN | 83 | 89.306 | 16.348 | 14.185 | 1.00 | 28.29 | H | O |
| ATOM | 2087 | N | SER | 84 | 87.199 | 16.486 | 14.954 | 1.00 | 57.41 | H | N |
| ATOM | 2088 | CA | SER | 84 | 86.618 | 15.739 | 13.847 | 1.00 | 57.41 | H | C |
| ATOM | 2089 | CB | SER | 84 | 86.648 | 16.584 | 12.574 | 1.00 | 29.12 | H | C |
| ATOM | 2090 | OG | SER | 84 | 86.027 | 17.836 | 12.786 | 1.00 | 29.12 | H | O |
| ATOM | 2091 | C | SER | 84 | 87.374 | 14.450 | 13.603 | 1.00 | 57.41 | H | C |
| ATOM | 2092 | O | SER | 84 | 87.642 | 14.085 | 12.456 | 1.00 | 57.41 | H | O |
| ATOM | 2093 | N | LEU | 85 | 87.725 | 13.769 | 14.687 | 1.00 | 32.34 | H | N |
| ATOM | 2094 | CA | LEU | 85 | 88.452 | 12.513 | 14.595 | 1.00 | 32.34 | H | C |
| ATOM | 2095 | CB | LEU | 85 | 88.818 | 12.009 | 15.990 | 1.00 | 15.22 | H | C |
| ATOM | 2096 | CG | LEU | 85 | 89.913 | 12.880 | 16.600 | 1.00 | 15.22 | H | C |
| ATOM | 2097 | CD1 | LEU | 85 | 90.082 | 12.594 | 18.078 | 1.00 | 15.22 | H | C |
| ATOM | 2098 | CD2 | LEU | 85 | 91.204 | 12.636 | 15.828 | 1.00 | 15.22 | H | C |
| ATOM | 2099 | C | LEU | 85 | 87.641 | 11.460 | 13.877 | 1.00 | 32.34 | H | C |
| ATOM | 2100 | O | LEU | 85 | 86.434 | 11.369 | 14.050 | 1.00 | 32.34 | H | O |
| ATOM | 2101 | N | ARG | 86 | 88.319 | 10.680 | 13.049 | 1.00 | 24.27 | H | N |
| ATOM | 2102 | CA | ARG | 86 | 87.686 | 9.604 | 12.316 | 1.00 | 24.27 | H | C |
| ATOM | 2103 | CB | ARG | 86 | 87.858 | 9.801 | 10.815 | 1.00 | 51.87 | H | C |
| ATOM | 2104 | CG | ARG | 86 | 87.146 | 11.026 | 10.286 | 1.00 | 51.87 | H | C |
| ATOM | 2105 | CD | ARG | 86 | 86.864 | 10.887 | 8.808 | 1.00 | 51.87 | H | C |
| ATOM | 2106 | NE | ARG | 86 | 87.237 | 12.088 | 8.076 | 1.00 | 51.87 | H | N |
| ATOM | 2107 | CZ | ARG | 86 | 88.470 | 12.581 | 8.043 | 1.00 | 51.87 | H | C |
| ATOM | 2108 | NH1 | ARG | 86 | 89.444 | 11.967 | 8.707 | 1.00 | 51.87 | H | N |
| ATOM | 2109 | NH2 | ARG | 86 | 88.733 | 13.676 | 7.334 | 1.00 | 51.87 | H | N |
| ATOM | 2110 | C | ARG | 86 | 88.387 | 8.343 | 12.769 | 1.00 | 24.27 | H | C |
| ATOM | 2111 | O | ARG | 86 | 89.367 | 8.416 | 13.514 | 1.00 | 24.27 | H | O |
| ATOM | 2112 | N | ALA | 87 | 87.894 | 7.191 | 12.335 | 1.00 | 40.98 | H | N |
| ATOM | 2113 | CA | ALA | 87 | 88.499 | 5.928 | 12.733 | 1.00 | 40.98 | H | C |
| ATOM | 2114 | CB | ALA | 87 | 87.678 | 4.763 | 12.196 | 1.00 | 28.01 | H | C |
| ATOM | 2115 | C | ALA | 87 | 89.937 | 5.833 | 12.242 | 1.00 | 40.98 | H | C |
| ATOM | 2116 | O | ALA | 87 | 90.824 | 5.425 | 12.989 | 1.00 | 40.98 | H | O |
| ATOM | 2117 | N | GLU | 88 | 90.169 | 6.222 | 10.993 | 1.00 | 32.24 | H | N |

FIG. 19A-30

| | | | | | | | | | | | |
|---|---|---|---|---|---|---|---|---|---|---|---|
| ATOM | 2118 | CA | GLU | 88 | 91.511 | 6.157 | 10.433 | 1.00 | 32.24 | H | C |
| ATOM | 2119 | CB | GLU | 88 | 91.583 | 6.890 | 9.094 | 1.00 | 72.38 | H | C |
| ATOM | 2120 | CG | GLU | 88 | 90.432 | 6.614 | 8.169 | 1.00 | 72.38 | H | C |
| ATOM | 2121 | CD | GLU | 88 | 89.327 | 7.623 | 8.336 | 1.00 | 72.38 | H | C |
| ATOM | 2122 | OE1 | GLU | 88 | 89.529 | 8.792 | 7.937 | 1.00 | 72.38 | H | O |
| ATOM | 2123 | OE2 | GLU | 88 | 88.265 | 7.246 | 8.874 | 1.00 | 72.38 | H | O |
| ATOM | 2124 | C | GLU | 88 | 92.529 | 6.780 | 11.372 | 1.00 | 32.24 | H | C |
| ATOM | 2125 | O | GLU | 88 | 93.691 | 6.370 | 11.417 | 1.00 | 32.24 | H | O |
| ATOM | 2126 | N | ASP | 89 | 92.080 | 7.772 | 12.128 | 1.00 | 18.63 | H | N |
| ATOM | 2127 | CA | ASP | 89 | 92.935 | 8.497 | 13.054 | 1.00 | 18.63 | H | C |
| ATOM | 2128 | CB | ASP | 89 | 92.212 | 9.764 | 13.507 | 1.00 | 29.25 | H | C |
| ATOM | 2129 | CG | ASP | 89 | 92.073 | 10.775 | 12.392 | 1.00 | 29.25 | H | C |
| ATOM | 2130 | OD1 | ASP | 89 | 91.297 | 11.732 | 12.553 | 1.00 | 29.25 | H | O |
| ATOM | 2131 | OD2 | ASP | 89 | 92.748 | 10.622 | 11.355 | 1.00 | 29.25 | H | O |
| ATOM | 2132 | C | ASP | 89 | 93.434 | 7.724 | 14.268 | 1.00 | 18.63 | H | C |
| ATOM | 2133 | O | ASP | 89 | 94.391 | 8.149 | 14.922 | 1.00 | 18.63 | H | O |
| ATOM | 2134 | N | THR | 90 | 92.817 | 6.588 | 14.575 | 1.00 | 29.66 | H | N |
| ATOM | 2135 | CA | THR | 90 | 93.261 | 5.845 | 15.749 | 1.00 | 29.66 | H | C |
| ATOM | 2136 | CB | THR | 90 | 92.303 | 4.668 | 16.113 | 1.00 | 30.61 | H | C |
| ATOM | 2137 | OG1 | THR | 90 | 92.601 | 3.537 | 15.293 | 1.00 | 30.61 | H | O |
| ATOM | 2138 | CG2 | THR | 90 | 90.828 | 5.072 | 15.903 | 1.00 | 30.61 | H | C |
| ATOM | 2139 | C | THR | 90 | 94.664 | 5.311 | 15.527 | 1.00 | 29.66 | H | C |
| ATOM | 2140 | O | THR | 90 | 94.961 | 4.727 | 14.492 | 1.00 | 29.66 | H | O |
| ATOM | 2141 | N | ALA | 91 | 95.532 | 5.553 | 16.499 | 1.00 | 11.25 | H | N |
| ATOM | 2142 | CA | ALA | 91 | 96.918 | 5.094 | 16.451 | 1.00 | 11.25 | H | C |
| ATOM | 2143 | CB | ALA | 91 | 97.629 | 5.690 | 15.259 | 1.00 | 1.87 | H | C |
| ATOM | 2144 | C | ALA | 91 | 97.611 | 5.536 | 17.729 | 1.00 | 11.25 | H | C |
| ATOM | 2145 | O | ALA | 91 | 96.972 | 6.044 | 18.646 | 1.00 | 11.25 | H | O |
| ATOM | 2146 | N | VAL | 92 | 98.915 | 5.312 | 17.797 | 1.00 | 22.44 | H | N |
| ATOM | 2147 | CA | VAL | 92 | 99.694 | 5.755 | 18.947 | 1.00 | 22.44 | H | C |
| ATOM | 2148 | CB | VAL | 92 | 100.654 | 4.665 | 19.465 | 1.00 | 21.44 | H | C |
| ATOM | 2149 | CG1 | VAL | 92 | 101.306 | 3.966 | 18.298 | 1.00 | 21.44 | H | C |
| ATOM | 2150 | CG2 | VAL | 92 | 101.716 | 5.284 | 20.346 | 1.00 | 21.44 | H | C |
| ATOM | 2151 | C | VAL | 92 | 100.482 | 6.913 | 18.363 | 1.00 | 22.44 | H | C |
| ATOM | 2152 | O | VAL | 92 | 101.107 | 6.771 | 17.310 | 1.00 | 22.44 | H | O |
| ATOM | 2153 | N | TYR | 93 | 100.413 | 8.066 | 19.019 | 1.00 | 21.58 | H | N |
| ATOM | 2154 | CA | TYR | 93 | 101.105 | 9.261 | 18.538 | 1.00 | 21.58 | H | C |
| ATOM | 2155 | CB | TYR | 93 | 100.161 | 10.470 | 18.585 | 1.00 | 12.38 | H | C |
| ATOM | 2156 | CG | TYR | 93 | 99.000 | 10.385 | 17.624 | 1.00 | 12.38 | H | C |
| ATOM | 2157 | CD1 | TYR | 93 | 98.023 | 9.399 | 17.759 | 1.00 | 12.38 | H | C |
| ATOM | 2158 | CE1 | TYR | 93 | 96.975 | 9.287 | 16.836 | 1.00 | 12.38 | H | C |
| ATOM | 2159 | CD2 | TYR | 93 | 98.899 | 11.264 | 16.553 | 1.00 | 12.38 | H | C |
| ATOM | 2160 | CE2 | TYR | 93 | 97.863 | 11.165 | 15.634 | 1.00 | 12.38 | H | C |
| ATOM | 2161 | CZ | TYR | 93 | 96.908 | 10.173 | 15.773 | 1.00 | 12.38 | H | C |
| ATOM | 2162 | OH | TYR | 93 | 95.915 | 10.043 | 14.827 | 1.00 | 12.38 | H | O |
| ATOM | 2163 | C | TYR | 93 | 102.384 | 9.577 | 19.312 | 1.00 | 21.58 | H | C |
| ATOM | 2164 | O | TYR | 93 | 102.466 | 9.401 | 20.531 | 1.00 | 21.58 | H | O |
| ATOM | 2165 | N | TYR | 94 | 103.381 | 10.049 | 18.579 | 1.00 | 19.04 | H | N |
| ATOM | 2166 | CA | TYR | 94 | 104.668 | 10.409 | 19.151 | 1.00 | 19.04 | H | C |
| ATOM | 2167 | CB | TYR | 94 | 105.789 | 9.576 | 18.533 | 1.00 | 29.80 | H | C |
| ATOM | 2168 | CG | TYR | 94 | 105.548 | 8.101 | 18.431 | 1.00 | 29.80 | H | C |
| ATOM | 2169 | CD1 | TYR | 94 | 105.948 | 7.237 | 19.454 | 1.00 | 29.80 | H | C |
| ATOM | 2170 | CE1 | TYR | 94 | 105.768 | 5.876 | 19.345 | 1.00 | 29.80 | H | C |
| ATOM | 2171 | CD2 | TYR | 94 | 104.958 | 7.563 | 17.298 | 1.00 | 29.80 | H | C |
| ATOM | 2172 | CE2 | TYR | 94 | 104.773 | 6.204 | 17.177 | 1.00 | 29.80 | H | C |
| ATOM | 2173 | CZ | TYR | 94 | 105.179 | 5.363 | 18.202 | 1.00 | 29.80 | H | C |
| ATOM | 2174 | OH | TYR | 94 | 104.996 | 4.007 | 18.071 | 1.00 | 29.80 | H | O |
| ATOM | 2175 | C | TYR | 94 | 104.991 | 11.853 | 18.805 | 1.00 | 19.04 | H | C |
| ATOM | 2176 | O | TYR | 94 | 104.867 | 12.244 | 17.642 | 1.00 | 19.04 | H | O |
| ATOM | 2177 | N | CYS | 95 | 105.383 | 12.654 | 19.791 | 1.00 | 25.07 | H | N |
| ATOM | 2178 | CA | CYS | 95 | 105.806 | 14.000 | 19.466 | 1.00 | 25.07 | H | C |
| ATOM | 2179 | C | CYS | 95 | 107.228 | 13.689 | 19.096 | 1.00 | 25.07 | H | C |
| ATOM | 2180 | O | CYS | 95 | 107.716 | 12.584 | 19.342 | 1.00 | 25.07 | H | O |
| ATOM | 2181 | CB | CYS | 95 | 105.784 | 14.942 | 20.647 | 1.00 | 46.53 | H | C |
| ATOM | 2182 | SG | CYS | 95 | 106.112 | 14.206 | 22.267 | 1.00 | 46.53 | H | S |
| ATOM | 2183 | N | THR | 96 | 107.931 | 14.657 | 18.549 | 1.00 | 31.61 | H | N |
| ATOM | 2184 | CA | THR | 96 | 109.253 | 14.331 | 18.115 | 1.00 | 31.61 | H | C |
| ATOM | 2185 | CB | THR | 96 | 109.088 | 13.445 | 16.861 | 1.00 | 32.15 | H | C |
| ATOM | 2186 | OG1 | THR | 96 | 110.331 | 12.862 | 16.494 | 1.00 | 32.15 | H | O |
| ATOM | 2187 | CG2 | THR | 96 | 108.554 | 14.260 | 15.708 | 1.00 | 32.15 | H | C |
| ATOM | 2188 | C | THR | 96 | 110.045 | 15.591 | 17.830 | 1.00 | 31.61 | H | C |
| ATOM | 2189 | O | THR | 96 | 109.530 | 16.548 | 17.260 | 1.00 | 31.61 | H | O |
| ATOM | 2190 | N | ARG | 97 | 111.292 | 15.610 | 18.270 | 1.00 | 26.02 | H | N |

FIG. 19A-31

| ATOM | 2191 | CA | ARG | 97 | 112.135 | 16.759 | 17.996 | 1.00 | 26.02 | H | C |
| ATOM | 2192 | CB | ARG | 97 | 113.220 | 16.959 | 19.053 | 1.00 | 22.53 | H | C |
| ATOM | 2193 | CG | ARG | 97 | 114.076 | 18.184 | 18.766 | 1.00 | 22.53 | H | C |
| ATOM | 2194 | CD | ARG | 97 | 115.204 | 18.345 | 19.764 | 1.00 | 22.53 | H | C |
| ATOM | 2195 | NE | ARG | 97 | 116.357 | 17.532 | 19.411 | 1.00 | 22.53 | H | N |
| ATOM | 2196 | CZ | ARG | 97 | 117.494 | 17.509 | 20.099 | 1.00 | 22.53 | H | C |
| ATOM | 2197 | NH1 | ARG | 97 | 117.635 | 18.257 | 21.183 | 1.00 | 22.53 | H | N |
| ATOM | 2198 | NH2 | ARG | 97 | 118.494 | 16.739 | 19.704 | 1.00 | 22.53 | H | N |
| ATOM | 2199 | C | ARG | 97 | 112.799 | 16.473 | 16.665 | 1.00 | 26.02 | H | C |
| ATOM | 2200 | O | ARG | 97 | 113.145 | 15.322 | 16.357 | 1.00 | 26.02 | H | O |
| ATOM | 2201 | N | GLY | 98 | 112.980 | 17.528 | 15.882 | 1.00 | 13.43 | H | N |
| ATOM | 2202 | CA | GLY | 98 | 113.586 | 17.367 | 14.582 | 1.00 | 13.43 | H | C |
| ATOM | 2203 | C | GLY | 98 | 114.947 | 17.995 | 14.496 | 1.00 | 13.43 | H | C |
| ATOM | 2204 | O | GLY | 98 | 115.308 | 18.850 | 15.281 | 1.00 | 13.43 | H | O |
| ATOM | 2205 | N | PHE | 99 | 115.719 | 17.537 | 13.534 | 1.00 | 20.13 | H | N |
| ATOM | 2206 | CA | PHE | 99 | 117.038 | 18.065 | 13.315 | 1.00 | 20.13 | H | C |
| ATOM | 2207 | CB | PHE | 99 | 118.018 | 16.902 | 13.211 | 1.00 | 25.23 | H | C |
| ATOM | 2208 | CG | PHE | 99 | 119.338 | 17.271 | 12.628 | 1.00 | 25.23 | H | C |
| ATOM | 2209 | CD1 | PHE | 99 | 119.587 | 17.079 | 11.279 | 1.00 | 25.23 | H | C |
| ATOM | 2210 | CD2 | PHE | 99 | 120.326 | 17.828 | 13.420 | 1.00 | 25.23 | H | C |
| ATOM | 2211 | CE1 | PHE | 99 | 120.804 | 17.437 | 10.721 | 1.00 | 25.23 | H | C |
| ATOM | 2212 | CE2 | PHE | 99 | 121.543 | 18.191 | 12.875 | 1.00 | 25.23 | H | C |
| ATOM | 2213 | CZ | PHE | 99 | 121.784 | 17.994 | 11.517 | 1.00 | 25.23 | H | C |
| ATOM | 2214 | C | PHE | 99 | 116.887 | 18.819 | 11.996 | 1.00 | 20.13 | H | C |
| ATOM | 2215 | O | PHE | 99 | 115.950 | 18.551 | 11.241 | 1.00 | 20.13 | H | O |
| ATOM | 2216 | N | GLY | 100 | 117.768 | 19.774 | 11.719 | 1.00 | 15.08 | H | N |
| ATOM | 2217 | CA | GLY | 100 | 117.655 | 20.513 | 10.469 | 1.00 | 15.08 | H | C |
| ATOM | 2218 | C | GLY | 100 | 116.285 | 21.139 | 10.274 | 1.00 | 15.08 | H | C |
| ATOM | 2219 | O | GLY | 100 | 115.682 | 21.636 | 11.216 | 1.00 | 15.08 | H | O |
| ATOM | 2220 | N | ASP | 101 | 115.779 | 21.128 | 9.050 | 1.00 | 7.89 | H | N |
| ATOM | 2221 | CA | ASP | 101 | 114.462 | 21.692 | 8.812 | 1.00 | 7.89 | H | C |
| ATOM | 2222 | CB | ASP | 101 | 114.195 | 21.848 | 7.302 | 1.00 | 13.13 | H | C |
| ATOM | 2223 | CG | ASP | 101 | 115.328 | 22.587 | 6.564 | 1.00 | 13.13 | H | C |
| ATOM | 2224 | OD1 | ASP | 101 | 115.921 | 23.558 | 7.105 | 1.00 | 13.13 | H | O |
| ATOM | 2225 | OD2 | ASP | 101 | 115.616 | 22.190 | 5.417 | 1.00 | 13.13 | H | O |
| ATOM | 2226 | C | ASP | 101 | 113.406 | 20.785 | 9.460 | 1.00 | 7.89 | H | C |
| ATOM | 2227 | O | ASP | 101 | 112.222 | 20.844 | 9.124 | 1.00 | 7.89 | H | O |
| ATOM | 2228 | N | GLY | 102 | 113.854 | 19.924 | 10.374 | 1.00 | 22.31 | H | N |
| ATOM | 2229 | CA | GLY | 102 | 112.952 | 19.043 | 11.100 | 1.00 | 22.31 | H | C |
| ATOM | 2230 | C | GLY | 102 | 112.588 | 17.674 | 10.562 | 1.00 | 22.31 | H | C |
| ATOM | 2231 | O | GLY | 102 | 111.927 | 16.915 | 11.263 | 1.00 | 22.31 | H | O |
| ATOM | 2232 | N | GLY | 103 | 113.001 | 17.347 | 9.343 | 1.00 | 25.09 | H | N |
| ATOM | 2233 | CA | GLY | 103 | 112.662 | 16.054 | 8.772 | 1.00 | 25.09 | H | C |
| ATOM | 2234 | C | GLY | 103 | 113.342 | 14.844 | 9.403 | 1.00 | 25.09 | H | C |
| ATOM | 2235 | O | GLY | 103 | 112.948 | 13.703 | 9.156 | 1.00 | 25.09 | H | O |
| ATOM | 2236 | N | TYR | 104 | 114.376 | 15.071 | 10.202 | 1.00 | 22.52 | H | N |
| ATOM | 2237 | CA | TYR | 104 | 115.070 | 13.961 | 10.844 | 1.00 | 22.52 | H | C |
| ATOM | 2238 | CB | TYR | 104 | 116.578 | 14.114 | 10.715 | 1.00 | 15.87 | H | C |
| ATOM | 2239 | CG | TYR | 104 | 117.342 | 13.175 | 11.599 | 1.00 | 15.87 | H | C |
| ATOM | 2240 | CD1 | TYR | 104 | 118.507 | 13.600 | 12.233 | 1.00 | 15.87 | H | C |
| ATOM | 2241 | CE1 | TYR | 104 | 119.198 | 12.776 | 13.100 | 1.00 | 15.87 | H | C |
| ATOM | 2242 | CD2 | TYR | 104 | 116.884 | 11.880 | 11.844 | 1.00 | 15.87 | H | C |
| ATOM | 2243 | CE2 | TYR | 104 | 117.575 | 11.034 | 12.713 | 1.00 | 15.87 | H | C |
| ATOM | 2244 | CZ | TYR | 104 | 118.734 | 11.498 | 13.343 | 1.00 | 15.87 | H | C |
| ATOM | 2245 | OH | TYR | 104 | 119.417 | 10.713 | 14.239 | 1.00 | 15.87 | H | O |
| ATOM | 2246 | C | TYR | 104 | 114.665 | 13.991 | 12.296 | 1.00 | 22.52 | H | C |
| ATOM | 2247 | O | TYR | 104 | 114.933 | 14.956 | 13.001 | 1.00 | 22.52 | H | O |
| ATOM | 2248 | N | PHE | 105 | 114.036 | 12.909 | 12.733 | 1.00 | 16.00 | H | N |
| ATOM | 2249 | CA | PHE | 105 | 113.501 | 12.806 | 14.073 | 1.00 | 16.00 | H | C |
| ATOM | 2250 | CB | PHE | 105 | 112.292 | 11.890 | 14.031 | 1.00 | 16.01 | H | C |
| ATOM | 2251 | CG | PHE | 105 | 111.269 | 12.327 | 13.020 | 1.00 | 16.01 | H | C |
| ATOM | 2252 | CD1 | PHE | 105 | 110.782 | 13.627 | 13.038 | 1.00 | 16.01 | H | C |
| ATOM | 2253 | CD2 | PHE | 105 | 110.827 | 11.459 | 12.023 | 1.00 | 16.01 | H | C |
| ATOM | 2254 | CE1 | PHE | 105 | 109.880 | 14.059 | 12.091 | 1.00 | 16.01 | H | C |
| ATOM | 2255 | CE2 | PHE | 105 | 109.918 | 11.885 | 11.067 | 1.00 | 16.01 | H | C |
| ATOM | 2256 | CZ | PHE | 105 | 109.443 | 13.190 | 11.101 | 1.00 | 16.01 | H | C |
| ATOM | 2257 | C | PHE | 105 | 114.442 | 12.433 | 15.179 | 1.00 | 16.00 | H | C |
| ATOM | 2258 | O | PHE | 105 | 114.543 | 11.283 | 15.595 | 1.00 | 16.00 | H | O |
| ATOM | 2259 | N | ASP | 106 | 115.105 | 13.481 | 15.642 | 1.00 | 29.40 | H | N |
| ATOM | 2260 | CA | ASP | 106 | 116.089 | 13.519 | 16.714 | 1.00 | 29.40 | H | C |
| ATOM | 2261 | CB | ASP | 106 | 116.251 | 14.976 | 17.117 | 1.00 | 39.43 | H | C |
| ATOM | 2262 | CG | ASP | 106 | 117.656 | 15.400 | 17.133 | 1.00 | 39.43 | H | C |
| ATOM | 2263 | OD1 | ASP | 106 | 118.492 | 14.528 | 17.433 | 1.00 | 39.43 | H | O |

FIG. 19A-32

```
ATOM   2264  OD2 ASP  106   117.922  16.591  16.859  1.00  39.43  H  O
ATOM   2265  C   ASP  106   115.797  12.728  17.993  1.00  29.40  H  C
ATOM   2266  O   ASP  106   116.567  11.861  18.396  1.00  29.40  H  O
ATOM   2267  N   VAL  107   114.687  13.094  18.635  1.00   7.69  H  N
ATOM   2268  CA  VAL  107   114.248  12.533  19.906  1.00   7.69  H  C
ATOM   2269  CB  VAL  107   114.402  13.600  21.026  1.00  10.61  H  C
ATOM   2270  CG1 VAL  107   113.985  13.045  22.374  1.00  10.61  H  C
ATOM   2271  CG2 VAL  107   115.838  14.116  21.048  1.00  10.61  H  C
ATOM   2272  C   VAL  107   112.778  12.199  19.765  1.00   7.69  H  C
ATOM   2273  O   VAL  107   112.107  12.835  18.970  1.00   7.69  H  O
ATOM   2274  N   TRP  108   112.285  11.224  20.540  1.00  26.84  H  N
ATOM   2275  CA  TRP  108   110.871  10.795  20.510  1.00  26.84  H  C
ATOM   2276  CB  TRP  108   110.729   9.405  19.868  1.00   1.87  H  C
ATOM   2277  CG  TRP  108   111.201   9.329  18.468  1.00   1.87  H  C
ATOM   2278  CD2 TRP  108   110.431   8.950  17.328  1.00   1.87  H  C
ATOM   2279  CE2 TRP  108   111.287   9.020  16.201  1.00   1.87  H  C
ATOM   2280  CE3 TRP  108   109.102   8.557  17.142  1.00   1.87  H  C
ATOM   2281  CD1 TRP  108   112.460   9.606  18.008  1.00   1.87  H  C
ATOM   2282  NE1 TRP  108   112.520   9.422  16.648  1.00   1.87  H  N
ATOM   2283  CZ2 TRP  108   110.854   8.710  14.904  1.00   1.87  H  C
ATOM   2284  CZ3 TRP  108   108.667   8.244  15.836  1.00   1.87  H  C
ATOM   2285  CH2 TRP  108   109.547   8.325  14.742  1.00   1.87  H  C
ATOM   2286  C   TRP  108   110.204  10.724  21.881  1.00  26.84  H  C
ATOM   2287  O   TRP  108   110.859  10.503  22.899  1.00  26.84  H  O
ATOM   2288  N   GLY  109   108.889  10.907  21.889  1.00  15.55  H  N
ATOM   2289  CA  GLY  109   108.134  10.811  23.125  1.00  15.55  H  C
ATOM   2290  C   GLY  109   107.896   9.331  23.386  1.00  15.55  H  C
ATOM   2291  O   GLY  109   108.170   8.502  22.511  1.00  15.55  H  O
ATOM   2292  N   GLN  110   107.393   8.971  24.563  1.00  21.92  H  N
ATOM   2293  CA  GLN  110   107.161   7.554  24.852  1.00  21.92  H  C
ATOM   2294  CB  GLN  110   106.800   7.338  26.325  1.00  44.26  H  C
ATOM   2295  CG  GLN  110   105.404   7.798  26.703  1.00  44.26  H  C
ATOM   2296  CD  GLN  110   105.321   9.283  26.957  1.00  44.26  H  C
ATOM   2297  OE1 GLN  110   105.573  10.102  26.071  1.00  44.26  H  O
ATOM   2298  NE2 GLN  110   104.967   9.642  28.181  1.00  44.26  H  N
ATOM   2299  C   GLN  110   106.051   6.979  23.973  1.00  21.92  H  C
ATOM   2300  O   GLN  110   106.054   5.798  23.651  1.00  21.92  H  O
ATOM   2301  N   GLY  111   105.114   7.824  23.574  1.00  22.63  H  N
ATOM   2302  CA  GLY  111   104.014   7.361  22.761  1.00  22.63  H  C
ATOM   2303  C   GLY  111   102.758   7.463  23.597  1.00  22.63  H  C
ATOM   2304  O   GLY  111   102.834   7.414  24.827  1.00  22.63  H  O
ATOM   2305  N   THR  112   101.611   7.619  22.938  1.00  17.52  H  N
ATOM   2306  CA  THR  112   100.333   7.740  23.630  1.00  17.52  H  C
ATOM   2307  CB  THR  112   100.058   9.211  24.030  1.00  34.98  H  C
ATOM   2308  OG1 THR  112    98.958   9.261  24.939  1.00  34.98  H  O
ATOM   2309  CG2 THR  112    99.734  10.055  22.809  1.00  34.98  H  C
ATOM   2310  C   THR  112    99.228   7.203  22.717  1.00  17.52  H  C
ATOM   2311  O   THR  112    99.133   7.559  21.533  1.00  17.52  H  O
ATOM   2312  N   LEU  113    98.396   6.340  23.292  1.00  32.82  H  N
ATOM   2313  CA  LEU  113    97.318   5.668  22.576  1.00  32.82  H  C
ATOM   2314  CB  LEU  113    96.953   4.374  23.328  1.00  26.98  H  C
ATOM   2315  CG  LEU  113    95.842   3.431  22.856  1.00  26.98  H  C
ATOM   2316  CD1 LEU  113    94.455   4.057  23.105  1.00  26.98  H  C
ATOM   2317  CD2 LEU  113    96.055   3.115  21.392  1.00  26.98  H  C
ATOM   2318  C   LEU  113    96.073   6.498  22.354  1.00  32.82  H  C
ATOM   2319  O   LEU  113    95.448   6.964  23.299  1.00  32.82  H  O
ATOM   2320  N   VAL  114    95.708   6.671  21.094  1.00  38.48  H  N
ATOM   2321  CA  VAL  114    94.506   7.419  20.767  1.00  38.48  H  C
ATOM   2322  CB  VAL  114    94.809   8.658  19.870  1.00  53.69  H  C
ATOM   2323  CG1 VAL  114    93.518   9.420  19.571  1.00  53.69  H  C
ATOM   2324  CG2 VAL  114    95.798   9.575  20.562  1.00  53.69  H  C
ATOM   2325  C   VAL  114    93.557   6.484  20.022  1.00  38.48  H  C
ATOM   2326  O   VAL  114    93.859   6.003  18.928  1.00  38.48  H  O
ATOM   2327  N   THR  115    92.411   6.216  20.629  1.00  29.76  H  N
ATOM   2328  CA  THR  115    91.414   5.356  20.012  1.00  29.76  H  C
ATOM   2329  CB  THR  115    91.081   4.125  20.916  1.00  30.84  H  C
ATOM   2330  OG1 THR  115    92.292   3.453  21.300  1.00  30.84  H  O
ATOM   2331  CG2 THR  115    90.180   3.151  20.170  1.00  30.84  H  C
ATOM   2332  C   THR  115    90.133   6.164  19.803  1.00  29.76  H  C
ATOM   2333  O   THR  115    89.700   6.905  20.694  1.00  29.76  H  O
ATOM   2334  N   VAL  116    89.543   6.056  18.619  1.00  38.29  H  N
ATOM   2335  CA  VAL  116    88.289   6.747  18.371  1.00  38.29  H  C
ATOM   2336  CB  VAL  116    88.395   7.822  17.240  1.00  10.28  H  C
```

FIG. 19A-33

```
ATOM   2337  CG1 VAL  116      89.861    8.088   16.922  1.00   10.28      H  C
ATOM   2338  CG2 VAL  116      87.575    7.415   15.994  1.00   10.28      H  C
ATOM   2339  C   VAL  116      87.303    5.656   17.996  1.00   38.29      H  C
ATOM   2340  O   VAL  116      87.545    4.888   17.063  1.00   38.29      H  O
ATOM   2341  N   SER  117      86.207    5.579   18.746  1.00   41.53      H  N
ATOM   2342  CA  SER  117      85.193    4.565   18.517  1.00   41.53      H  C
ATOM   2343  CB  SER  117      85.768    3.182   18.851  1.00   61.62      H  C
ATOM   2344  OG  SER  117      84.788    2.165   18.751  1.00   61.62      H  O
ATOM   2345  C   SER  117      83.959    4.815   19.366  1.00   41.53      H  C
ATOM   2346  O   SER  117      84.049    5.336   20.482  1.00   41.53      H  O
ATOM   2347  N   SER  118      82.808    4.431   18.828  1.00   36.79      H  N
ATOM   2348  CA  SER  118      81.538    4.581   19.525  1.00   36.79      H  C
ATOM   2349  CB  SER  118      80.401    4.226   18.579  1.00   49.30      H  C
ATOM   2350  OG  SER  118      80.598    2.919   18.069  1.00   49.30      H  O
ATOM   2351  C   SER  118      81.510    3.649   20.740  1.00   36.79      H  C
ATOM   2352  O   SER  118      80.753    3.853   21.685  1.00   35.84      H  O
ATOM   2353  N   ALA  119      82.339    2.616   20.707  1.00   26.31      H  N
ATOM   2354  CA  ALA  119      82.412    1.679   21.815  1.00   26.31      H  C
ATOM   2355  CB  ALA  119      83.569    0.707   21.617  1.00   20.55      H  C
ATOM   2356  C   ALA  119      82.611    2.461   23.100  1.00   26.31      H  C
ATOM   2357  O   ALA  119      83.319    3.477   23.124  1.00   26.31      H  O
ATOM   2358  N   SER  120      81.988    1.975   24.166  1.00   39.08      H  N
ATOM   2359  CA  SER  120      82.074    2.621   25.462  1.00   39.08      H  C
ATOM   2360  CB  SER  120      80.711    2.597   26.151  1.00   57.76      H  C
ATOM   2361  OG  SER  120      79.720    3.179   25.329  1.00   57.76      H  O
ATOM   2362  C   SER  120      83.086    1.938   26.353  1.00   39.08      H  C
ATOM   2363  O   SER  120      83.194    0.715   26.362  1.00   39.08      H  O
ATOM   2364  N   THR  121      83.837    2.734   27.100  1.00   26.62      H  N
ATOM   2365  CA  THR  121      84.813    2.188   28.023  1.00   25.63      H  C
ATOM   2366  CB  THR  121      85.274    3.267   29.002  1.00   27.79      H  C
ATOM   2367  OG1 THR  121      85.860    4.353   28.268  1.00   32.58      H  O
ATOM   2368  CG2 THR  121      86.273    2.691   30.007  1.00   25.52      H  C
ATOM   2369  C   THR  121      84.108    1.078   28.801  1.00   26.35      H  C
ATOM   2370  O   THR  121      82.919    1.189   29.098  1.00   29.95      H  O
ATOM   2371  N   LYS  122      84.828    0.007   29.116  1.00   53.26      H  N
ATOM   2372  CA  LYS  122      84.243   -1.102   29.864  1.00   50.64      H  C
ATOM   2373  CB  LYS  122      83.333   -1.930   28.947  1.00   42.70      H  C
ATOM   2374  CG  LYS  122      83.009   -3.347   29.437  1.00   44.07      H  C
ATOM   2375  CD  LYS  122      82.469   -3.373   30.864  1.00   47.16      H  C
ATOM   2376  CE  LYS  122      82.216   -4.805   31.337  1.00   51.36      H  C
ATOM   2377  NZ  LYS  122      81.986   -4.880   32.809  1.00   50.23      H  N
ATOM   2378  C   LYS  122      85.301   -1.991   30.496  1.00   52.40      H  C
ATOM   2379  O   LYS  122      86.154   -2.548   29.809  1.00   54.02      H  O
ATOM   2380  N   GLY  123      85.240   -2.114   31.817  1.00   42.56      H  N
ATOM   2381  CA  GLY  123      86.188   -2.952   32.530  1.00   42.89      H  C
ATOM   2382  C   GLY  123      86.213   -4.396   32.035  1.00   44.35      H  C
ATOM   2383  O   GLY  123      85.222   -4.907   31.503  1.00   40.33      H  O
ATOM   2384  N   PRO  124      87.346   -5.090   32.198  1.00   44.81      H  N
ATOM   2385  CD  PRO  124      88.680   -4.632   32.633  1.00   21.78      H  C
ATOM   2386  CA  PRO  124      87.397   -6.472   31.731  1.00   46.19      H  C
ATOM   2387  CB  PRO  124      88.868   -6.668   31.439  1.00   22.93      H  C
ATOM   2388  CG  PRO  124      89.504   -5.905   32.561  1.00   22.69      H  C
ATOM   2389  C   PRO  124      86.899   -7.461   32.764  1.00   45.69      H  C
ATOM   2390  O   PRO  124      86.854   -7.170   33.961  1.00   46.94      H  O
ATOM   2391  N   SER  125      86.507   -8.631   32.287  1.00   43.49      H  N
ATOM   2392  CA  SER  125      86.053   -9.678   33.176  1.00   38.23      H  C
ATOM   2393  CB  SER  125      84.858  -10.416   32.579  1.00   23.34      H  C
ATOM   2394  OG  SER  125      83.756   -9.544   32.402  1.00   25.34      H  O
ATOM   2395  C   SER  125      87.262  -10.576   33.200  1.00   33.52      H  C
ATOM   2396  O   SER  125      87.738  -10.972   32.139  1.00   32.91      H  O
ATOM   2397  N   VAL  126      87.787  -10.873   34.386  1.00   23.96      H  N
ATOM   2398  CA  VAL  126      88.962  -11.727   34.452  1.00   20.86      H  C
ATOM   2399  CB  VAL  126      90.135  -11.003   35.174  1.00   22.19      H  C
ATOM   2400  CG1 VAL  126      89.894   -9.504   35.113  1.00   17.46      H  C
ATOM   2401  CG2 VAL  126      90.331  -11.507   36.597  1.00   22.90      H  C
ATOM   2402  C   VAL  126      88.666  -13.091   35.065  1.00   20.51      H  C
ATOM   2403  O   VAL  126      88.382  -13.227   36.256  1.00   24.79      H  O
ATOM   2404  N   PHE  127      88.713  -14.105   34.213  1.00   27.15      H  N
ATOM   2405  CA  PHE  127      88.443  -15.464   34.625  1.00   29.56      H  C
ATOM   2406  CB  PHE  127      87.628  -16.167   33.544  1.00   16.06      H  C
ATOM   2407  CG  PHE  127      86.392  -15.419   33.141  1.00   12.41      H  C
ATOM   2408  CD1 PHE  127      85.380  -15.167   34.071  1.00   11.21      H  C
ATOM   2409  CD2 PHE  127      86.255  -14.922   31.840  1.00   10.06      H  C
```

FIG. 19A-34

```
ATOM   2410  CE1  PHE  127      84.254  -14.428  33.721  1.00   12.93  H  C
ATOM   2411  CE2  PHE  127      85.126  -14.174  31.470  1.00    6.89  H  C
ATOM   2412  CZ   PHE  127      84.125  -13.925  32.413  1.00    6.94  H  C
ATOM   2413  C    PHE  127      89.763  -16.183  34.825  1.00   31.37  H  C
ATOM   2414  O    PHE  127      90.806  -15.733  34.351  1.00   34.05  H  O
ATOM   2415  N    PRO  128      89.743  -17.310  35.540  1.00   21.35  H  N
ATOM   2416  CD   PRO  128      88.681  -17.812  36.434  1.00   32.37  H  C
ATOM   2417  CA   PRO  128      90.996  -18.039  35.752  1.00   22.25  H  C
ATOM   2418  CB   PRO  128      90.823  -18.577  37.161  1.00   34.03  H  C
ATOM   2419  CG   PRO  128      89.358  -18.983  37.130  1.00   33.18  H  C
ATOM   2420  C    PRO  128      91.198  -19.176  34.739  1.00   21.65  H  C
ATOM   2421  O    PRO  128      90.235  -19.770  34.244  1.00   21.29  H  O
ATOM   2422  N    LEU  129      92.457  -19.457  34.432  1.00   17.17  H  N
ATOM   2423  CA   LEU  129      92.811  -20.557  33.545  1.00   19.61  H  C
ATOM   2424  CB   LEU  129      93.683  -20.061  32.396  1.00   18.81  H  C
ATOM   2425  CG   LEU  129      93.086  -18.872  31.635  1.00   18.17  H  C
ATOM   2426  CD1  LEU  129      94.115  -18.254  30.696  1.00   16.12  H  C
ATOM   2427  CD2  LEU  129      91.886  -19.341  30.870  1.00   11.94  H  C
ATOM   2428  C    LEU  129      93.601  -21.457  34.497  1.00   23.45  H  C
ATOM   2429  O    LEU  129      94.824  -21.481  34.499  1.00   25.82  H  O
ATOM   2430  N    ALA  130      92.870  -22.179  35.332  1.00   16.93  H  N
ATOM   2431  CA   ALA  130      93.455  -23.046  36.341  1.00   18.97  H  C
ATOM   2432  CB   ALA  130      92.363  -23.561  37.256  1.00   49.82  H  C
ATOM   2433  C    ALA  130      94.280  -24.219  35.846  1.00   18.88  H  C
ATOM   2434  O    ALA  130      93.928  -24.876  34.869  1.00   20.61  H  O
ATOM   2435  N    PRO  131      95.401  -24.490  36.534  1.00   29.98  H  N
ATOM   2436  CD   PRO  131      95.929  -23.703  37.665  1.00   16.68  H  C
ATOM   2437  CA   PRO  131      96.301  -25.595  36.198  1.00   27.20  H  C
ATOM   2438  CB   PRO  131      97.453  -25.424  37.196  1.00   12.88  H  C
ATOM   2439  CG   PRO  131      96.815  -24.691  38.354  1.00   15.86  H  C
ATOM   2440  C    PRO  131      95.534  -26.897  36.405  1.00   26.68  H  C
ATOM   2441  O    PRO  131      94.666  -26.978  37.274  1.00   27.16  H  O
ATOM   2442  N    SER  132      95.838  -27.912  35.607  1.00   64.88  H  N
ATOM   2443  CA   SER  132      95.138  -29.187  35.720  1.00   67.56  H  C
ATOM   2444  CB   SER  132      93.745  -29.075  35.086  1.00   44.77  H  C
ATOM   2445  OG   SER  132      93.824  -28.747  33.704  1.00   46.53  H  O
ATOM   2446  C    SER  132      95.918  -30.284  35.020  1.00   69.15  H  C
ATOM   2447  O    SER  132      97.107  -30.139  34.757  1.00   69.80  H  O
ATOM   2448  N    SER  133      95.247  -31.391  34.732  1.00   58.75  H  N
ATOM   2449  CA   SER  133      95.894  -32.483  34.024  1.00   61.13  H  C
ATOM   2450  CB   SER  133      95.007  -33.738  34.068  1.00   91.14  H  C
ATOM   2451  OG   SER  133      93.668  -33.456  33.684  1.00  100.88  H  O
ATOM   2452  C    SER  133      96.121  -32.017  32.576  1.00   60.76  H  C
ATOM   2453  O    SER  133      97.091  -32.413  31.927  1.00   61.01  H  O
ATOM   2454  N    LYS  134      95.220  -31.156  32.095  1.00  101.65  H  N
ATOM   2455  CA   LYS  134      95.285  -30.605  30.739  1.00  102.79  H  C
ATOM   2456  CB   LYS  134      93.951  -29.962  30.341  1.00   44.82  H  C
ATOM   2457  CG   LYS  134      92.703  -30.784  30.609  1.00   52.94  H  C
ATOM   2458  CD   LYS  134      92.058  -30.452  31.959  1.00   55.86  H  C
ATOM   2459  CE   LYS  134      90.686  -31.127  32.091  1.00   53.71  H  C
ATOM   2460  NZ   LYS  134      89.988  -30.792  33.367  1.00   52.28  H  N
ATOM   2461  C    LYS  134      96.364  -29.531  30.655  1.00  102.96  H  C
ATOM   2462  O    LYS  134      96.932  -29.284  29.589  1.00  104.03  H  O
ATOM   2463  N    SER  135      96.619  -28.885  31.791  1.00   77.03  H  N
ATOM   2464  CA   SER  135      97.611  -27.818  31.896  1.00   76.76  H  C
ATOM   2465  CB   SER  135      97.069  -26.698  32.784  1.00   81.66  H  C
ATOM   2466  OG   SER  135      95.726  -26.390  32.443  1.00   81.07  H  O
ATOM   2467  C    SER  135      98.911  -28.358  32.488  1.00   71.98  H  C
ATOM   2468  O    SER  135      99.733  -27.601  33.006  1.00   72.29  H  O
ATOM   2469  N    THR  136      99.075  -29.676  32.418  1.00   86.02  H  N
ATOM   2470  CA   THR  136     100.262  -30.351  32.932  1.00   86.44  H  C
ATOM   2471  CB   THR  136      99.897  -31.391  34.036  1.00   47.16  H  C
ATOM   2472  OG1  THR  136      99.491  -30.715  35.237  1.00   47.25  H  O
ATOM   2473  CG2  THR  136     101.096  -32.281  34.354  1.00   50.70  H  C
ATOM   2474  C    THR  136     100.977  -31.072  31.788  1.00   86.90  H  C
ATOM   2475  O    THR  136     100.334  -31.615  30.885  1.00   85.81  H  O
ATOM   2476  N    SER  137     102.309  -31.059  31.836  1.00   82.54  H  N
ATOM   2477  CA   SER  137     103.164  -31.700  30.834  1.00   82.34  H  C
ATOM   2478  CB   SER  137     103.113  -30.942  29.495  1.00   65.40  H  C
ATOM   2479  OG   SER  137     101.863  -31.097  28.841  1.00   66.87  H  O
ATOM   2480  C    SER  137     104.600  -31.715  31.352  1.00   82.68  H  C
ATOM   2481  O    SER  137     105.321  -30.722  31.244  1.00   84.11  H  O
ATOM   2482  N    GLY  138     105.016  -32.845  31.911  1.00   62.73  H  N
```

FIG. 19A-35

| ATOM | 2483 | CA | GLY | 138 | 106.361 | -32.941 | 32.438 | 1.00 | 62.79 | H | C |
|---|---|---|---|---|---|---|---|---|---|---|---|
| ATOM | 2484 | C | GLY | 138 | 106.394 | -32.371 | 33.840 | 1.00 | 65.01 | H | C |
| ATOM | 2485 | O | GLY | 138 | 105.392 | -32.410 | 34.555 | 1.00 | 65.52 | H | O |
| ATOM | 2486 | N | GLY | 139 | 107.537 | -31.827 | 34.237 | 1.00 | 45.62 | H | N |
| ATOM | 2487 | CA | GLY | 139 | 107.645 | -31.267 | 35.570 | 1.00 | 45.97 | H | C |
| ATOM | 2488 | C | GLY | 139 | 107.037 | -29.884 | 35.680 | 1.00 | 46.52 | H | C |
| ATOM | 2489 | O | GLY | 139 | 107.020 | -29.297 | 36.762 | 1.00 | 50.66 | H | O |
| ATOM | 2490 | N | THR | 140 | 106.527 | -29.365 | 34.568 | 1.00 | 41.37 | H | N |
| ATOM | 2491 | CA | THR | 140 | 105.941 | -28.030 | 34.571 | 1.00 | 35.80 | H | C |
| ATOM | 2492 | CB | THR | 140 | 106.626 | -27.108 | 33.533 | 1.00 | 32.97 | H | C |
| ATOM | 2493 | OG1 | THR | 140 | 105.886 | -27.138 | 32.311 | 1.00 | 30.01 | H | O |
| ATOM | 2494 | CG2 | THR | 140 | 108.052 | -27.574 | 33.250 | 1.00 | 33.92 | H | C |
| ATOM | 2495 | C | THR | 140 | 104.434 | -27.993 | 34.299 | 1.00 | 32.68 | H | C |
| ATOM | 2496 | O | THR | 140 | 103.884 | -28.820 | 33.560 | 1.00 | 31.27 | H | O |
| ATOM | 2497 | N | ALA | 141 | 103.777 | -27.013 | 34.914 | 1.00 | 23.19 | H | N |
| ATOM | 2498 | CA | ALA | 141 | 102.350 | -26.817 | 34.752 | 1.00 | 23.90 | H | C |
| ATOM | 2499 | CB | ALA | 141 | 101.647 | -26.986 | 36.087 | 1.00 | 31.87 | H | C |
| ATOM | 2500 | C | ALA | 141 | 102.121 | -25.408 | 34.206 | 1.00 | 24.06 | H | C |
| ATOM | 2501 | O | ALA | 141 | 102.930 | -24.498 | 34.415 | 1.00 | 28.34 | H | O |
| ATOM | 2502 | N | ALA | 142 | 101.022 | -25.239 | 33.487 | 1.00 | 36.28 | H | N |
| ATOM | 2503 | CA | ALA | 142 | 100.685 | -23.948 | 32.924 | 1.00 | 31.12 | H | C |
| ATOM | 2504 | CB | ALA | 142 | 100.507 | -24.062 | 31.419 | 1.00 | 1.87 | H | C |
| ATOM | 2505 | C | ALA | 142 | 99.389 | -23.519 | 33.588 | 1.00 | 29.11 | H | C |
| ATOM | 2506 | O | ALA | 142 | 98.565 | -24.359 | 33.961 | 1.00 | 33.50 | H | O |
| ATOM | 2507 | N | LEU | 143 | 99.233 | -22.211 | 33.751 | 1.00 | 27.06 | H | N |
| ATOM | 2508 | CA | LEU | 143 | 98.054 | -21.611 | 34.372 | 1.00 | 31.22 | H | C |
| ATOM | 2509 | CB | LEU | 143 | 98.154 | -21.670 | 35.900 | 1.00 | 28.24 | H | C |
| ATOM | 2510 | CG | LEU | 143 | 99.269 | -20.865 | 36.582 | 1.00 | 30.55 | H | C |
| ATOM | 2511 | CD1 | LEU | 143 | 98.702 | -19.526 | 36.991 | 1.00 | 23.14 | H | C |
| ATOM | 2512 | CD2 | LEU | 143 | 99.817 | -21.596 | 37.809 | 1.00 | 37.29 | H | C |
| ATOM | 2513 | C | LEU | 143 | 98.068 | -20.169 | 33.913 | 1.00 | 34.46 | H | C |
| ATOM | 2514 | O | LEU | 143 | 99.069 | -19.700 | 33.364 | 1.00 | 32.14 | H | O |
| ATOM | 2515 | N | GLY | 144 | 96.970 | -19.458 | 34.128 | 1.00 | 25.78 | H | N |
| ATOM | 2516 | CA | GLY | 144 | 96.922 | -18.074 | 33.694 | 1.00 | 28.57 | H | C |
| ATOM | 2517 | C | GLY | 144 | 95.578 | -17.425 | 33.896 | 1.00 | 31.81 | H | C |
| ATOM | 2518 | O | GLY | 144 | 94.693 | -17.985 | 34.543 | 1.00 | 35.57 | H | O |
| ATOM | 2519 | N | CYS | 145 | 95.420 | -16.235 | 33.335 | 1.00 | 24.76 | H | N |
| ATOM | 2520 | CA | CYS | 145 | 94.177 | -15.501 | 33.471 | 1.00 | 23.67 | H | C |
| ATOM | 2521 | C | CYS | 145 | 93.665 | -15.071 | 32.122 | 1.00 | 21.65 | H | C |
| ATOM | 2522 | O | CYS | 145 | 94.437 | -14.868 | 31.188 | 1.00 | 22.23 | H | O |
| ATOM | 2523 | CB | CYS | 145 | 94.385 | -14.273 | 34.363 | 1.00 | 28.67 | H | C |
| ATOM | 2524 | SG | CYS | 145 | 94.354 | -14.658 | 36.141 | 1.00 | 36.96 | H | S |
| ATOM | 2525 | N | LEU | 146 | 92.351 | -14.940 | 32.024 | 1.00 | 43.52 | H | N |
| ATOM | 2526 | CA | LEU | 146 | 91.712 | -14.512 | 30.792 | 1.00 | 43.76 | H | C |
| ATOM | 2527 | CB | LEU | 146 | 90.715 | -15.580 | 30.314 | 1.00 | 38.89 | H | C |
| ATOM | 2528 | CG | LEU | 146 | 89.754 | -15.245 | 29.164 | 1.00 | 28.77 | H | C |
| ATOM | 2529 | CD1 | LEU | 146 | 90.519 | -14.669 | 27.982 | 1.00 | 25.69 | H | C |
| ATOM | 2530 | CD2 | LEU | 146 | 88.989 | -16.489 | 28.755 | 1.00 | 35.84 | H | C |
| ATOM | 2531 | C | LEU | 146 | 90.997 | -13.188 | 31.055 | 1.00 | 45.61 | H | C |
| ATOM | 2532 | O | LEU | 146 | 89.943 | -13.160 | 31.690 | 1.00 | 45.79 | H | O |
| ATOM | 2533 | N | VAL | 147 | 91.609 | -12.098 | 30.593 | 1.00 | 12.91 | H | N |
| ATOM | 2534 | CA | VAL | 147 | 91.069 | -10.732 | 30.716 | 1.00 | 12.94 | H | C |
| ATOM | 2535 | CB | VAL | 147 | 92.231 | -9.696 | 30.638 | 1.00 | 24.21 | H | C |
| ATOM | 2536 | CG1 | VAL | 147 | 91.703 | -8.291 | 30.722 | 1.00 | 25.32 | H | C |
| ATOM | 2537 | CG2 | VAL | 147 | 93.212 | -9.947 | 31.778 | 1.00 | 13.52 | H | C |
| ATOM | 2538 | C | VAL | 147 | 90.101 | -10.563 | 29.532 | 1.00 | 18.31 | H | C |
| ATOM | 2539 | O | VAL | 147 | 90.532 | -10.460 | 28.381 | 1.00 | 18.59 | H | O |
| ATOM | 2540 | N | LYS | 148 | 88.798 | -10.519 | 29.806 | 1.00 | 25.16 | H | N |
| ATOM | 2541 | CA | LYS | 148 | 87.835 | -10.467 | 28.709 | 1.00 | 29.22 | H | C |
| ATOM | 2542 | CB | LYS | 148 | 87.140 | -11.827 | 28.609 | 1.00 | 15.56 | H | C |
| ATOM | 2543 | CG | LYS | 148 | 86.353 | -12.032 | 27.348 | 1.00 | 22.92 | H | C |
| ATOM | 2544 | CD | LYS | 148 | 85.731 | -13.405 | 27.355 | 1.00 | 22.16 | H | C |
| ATOM | 2545 | CE | LYS | 148 | 84.795 | -13.570 | 26.190 | 1.00 | 24.54 | H | C |
| ATOM | 2546 | NZ | LYS | 148 | 85.514 | -13.308 | 24.928 | 1.00 | 22.92 | H | N |
| ATOM | 2547 | C | LYS | 148 | 86.777 | -9.372 | 28.646 | 1.00 | 32.79 | H | C |
| ATOM | 2548 | O | LYS | 148 | 86.332 | -8.844 | 29.664 | 1.00 | 33.18 | H | O |
| ATOM | 2549 | N | ASP | 149 | 86.387 | -9.069 | 27.409 | 1.00 | 55.13 | H | N |
| ATOM | 2550 | CA | ASP | 149 | 85.381 | -8.070 | 27.078 | 1.00 | 53.92 | H | C |
| ATOM | 2551 | CB | ASP | 149 | 83.993 | -8.595 | 27.429 | 1.00 | 38.49 | H | C |
| ATOM | 2552 | CG | ASP | 149 | 83.635 | -9.853 | 26.661 | 1.00 | 42.52 | H | C |
| ATOM | 2553 | OD1 | ASP | 149 | 83.797 | -9.882 | 25.421 | 1.00 | 46.52 | H | O |
| ATOM | 2554 | OD2 | ASP | 149 | 83.181 | -10.817 | 27.305 | 1.00 | 41.08 | H | O |
| ATOM | 2555 | C | ASP | 149 | 85.585 | -6.690 | 27.698 | 1.00 | 56.06 | H | C |

FIG. 19A-36

| | | | | | | | | | | |
|---|---|---|---|---|---|---|---|---|---|---|
| ATOM | 2556 | O | ASP | 149 | 84.720 | -6.175 | 28.415 | 1.00 | 57.30 | H | O |
| ATOM | 2557 | N | TYR | 150 | 86.734 | -6.091 | 27.399 | 1.00 | 33.00 | H | N |
| ATOM | 2558 | CA | TYR | 150 | 87.072 | -4.770 | 27.897 | 1.00 | 33.34 | H | C |
| ATOM | 2559 | CB | TYR | 150 | 88.306 | -4.844 | 28.797 | 1.00 | 39.19 | H | C |
| ATOM | 2560 | CG | TYR | 150 | 89.622 | -5.155 | 28.097 | 1.00 | 44.75 | H | C |
| ATOM | 2561 | CD1 | TYR | 150 | 90.405 | -4.137 | 27.556 | 1.00 | 44.06 | H | C |
| ATOM | 2562 | CE1 | TYR | 150 | 91.653 | -4.401 | 26.994 | 1.00 | 46.40 | H | C |
| ATOM | 2563 | CD2 | TYR | 150 | 90.121 | -6.457 | 28.046 | 1.00 | 44.23 | H | C |
| ATOM | 2564 | CE2 | TYR | 150 | 91.369 | -6.730 | 27.483 | 1.00 | 43.19 | H | C |
| ATOM | 2565 | CZ | TYR | 150 | 92.130 | -5.694 | 26.963 | 1.00 | 45.07 | H | C |
| ATOM | 2566 | OH | TYR | 150 | 93.376 | -5.942 | 26.431 | 1.00 | 42.66 | H | O |
| ATOM | 2567 | C | TYR | 150 | 87.331 | -3.838 | 26.723 | 1.00 | 34.19 | H | C |
| ATOM | 2568 | O | TYR | 150 | 87.420 | -4.275 | 25.569 | 1.00 | 36.79 | H | O |
| ATOM | 2569 | N | PHE | 151 | 87.450 | -2.549 | 27.034 | 1.00 | 53.36 | H | N |
| ATOM | 2570 | CA | PHE | 151 | 87.686 | -1.522 | 26.034 | 1.00 | 51.06 | H | C |
| ATOM | 2571 | CB | PHE | 151 | 86.520 | -1.506 | 25.038 | 1.00 | 22.52 | H | C |
| ATOM | 2572 | CG | PHE | 151 | 86.663 | -0.500 | 23.923 | 1.00 | 22.34 | H | C |
| ATOM | 2573 | CD1 | PHE | 151 | 86.509 | 0.865 | 24.164 | 1.00 | 21.58 | H | C |
| ATOM | 2574 | CD2 | PHE | 151 | 86.896 | -0.923 | 22.616 | 1.00 | 24.08 | H | C |
| ATOM | 2575 | CE1 | PHE | 151 | 86.576 | 1.789 | 23.117 | 1.00 | 22.62 | H | C |
| ATOM | 2576 | CE2 | PHE | 151 | 86.968 | -0.003 | 21.558 | 1.00 | 25.39 | H | C |
| ATOM | 2577 | CZ | PHE | 151 | 86.805 | 1.351 | 21.809 | 1.00 | 25.56 | H | C |
| ATOM | 2578 | C | PHE | 151 | 87.819 | -0.175 | 26.734 | 1.00 | 48.17 | H | C |
| ATOM | 2579 | O | PHE | 151 | 87.161 | 0.084 | 27.737 | 1.00 | 47.45 | H | O |
| ATOM | 2580 | N | PRO | 152 | 88.712 | 0.685 | 26.232 | 1.00 | 46.09 | H | N |
| ATOM | 2581 | CD | PRO | 152 | 88.959 | 2.055 | 26.730 | 1.00 | 7.14 | H | C |
| ATOM | 2582 | CA | PRO | 152 | 89.554 | 0.388 | 25.065 | 1.00 | 47.66 | H | C |
| ATOM | 2583 | CB | PRO | 152 | 89.773 | 1.765 | 24.464 | 1.00 | 12.39 | H | C |
| ATOM | 2584 | CG | PRO | 152 | 90.017 | 2.594 | 25.730 | 1.00 | 9.55 | H | C |
| ATOM | 2585 | C | PRO | 152 | 90.835 | -0.199 | 25.636 | 1.00 | 47.42 | H | C |
| ATOM | 2586 | O | PRO | 152 | 90.826 | -0.716 | 26.748 | 1.00 | 49.63 | H | O |
| ATOM | 2587 | N | GLU | 153 | 91.933 | -0.128 | 24.894 | 1.00 | 48.37 | H | N |
| ATOM | 2588 | CA | GLU | 153 | 93.200 | -0.620 | 25.422 | 1.00 | 45.01 | H | C |
| ATOM | 2589 | CB | GLU | 153 | 94.232 | -0.788 | 24.308 | 1.00 | 35.76 | H | C |
| ATOM | 2590 | CG | GLU | 153 | 93.983 | -1.951 | 23.370 | 1.00 | 41.71 | H | C |
| ATOM | 2591 | CD | GLU | 153 | 94.465 | -3.279 | 23.920 | 1.00 | 49.73 | H | C |
| ATOM | 2592 | OE1 | GLU | 153 | 94.329 | -4.276 | 23.191 | 1.00 | 53.96 | H | O |
| ATOM | 2593 | OE2 | GLU | 153 | 94.979 | -3.337 | 25.062 | 1.00 | 49.06 | H | O |
| ATOM | 2594 | C | GLU | 153 | 93.667 | 0.487 | 26.355 | 1.00 | 40.62 | H | C |
| ATOM | 2595 | O | GLU | 153 | 93.160 | 1.611 | 26.288 | 1.00 | 43.09 | H | O |
| ATOM | 2596 | N | PRO | 154 | 94.626 | 0.193 | 27.242 | 1.00 | 31.67 | H | N |
| ATOM | 2597 | CD | PRO | 154 | 95.605 | 1.250 | 27.562 | 1.00 | 24.24 | H | C |
| ATOM | 2598 | CA | PRO | 154 | 95.266 | -1.107 | 27.404 | 1.00 | 32.01 | H | C |
| ATOM | 2599 | CB | PRO | 154 | 96.707 | -0.803 | 27.072 | 1.00 | 23.56 | H | C |
| ATOM | 2600 | CG | PRO | 154 | 96.899 | 0.447 | 27.855 | 1.00 | 23.31 | H | C |
| ATOM | 2601 | C | PRO | 154 | 95.127 | -1.577 | 28.846 | 1.00 | 37.33 | H | C |
| ATOM | 2602 | O | PRO | 154 | 94.929 | -0.788 | 29.770 | 1.00 | 40.93 | H | O |
| ATOM | 2603 | N | VAL | 155 | 95.270 | -2.874 | 29.029 | 1.00 | 27.89 | H | N |
| ATOM | 2604 | CA | VAL | 155 | 95.171 | -3.468 | 30.339 | 1.00 | 28.93 | H | C |
| ATOM | 2605 | CB | VAL | 155 | 94.167 | -4.647 | 30.309 | 1.00 | 32.63 | H | C |
| ATOM | 2606 | CG1 | VAL | 155 | 94.624 | -5.699 | 29.306 | 1.00 | 39.44 | H | C |
| ATOM | 2607 | CG2 | VAL | 155 | 94.030 | -5.243 | 31.690 | 1.00 | 38.09 | H | C |
| ATOM | 2608 | C | VAL | 155 | 96.561 | -3.969 | 30.715 | 1.00 | 29.75 | H | C |
| ATOM | 2609 | O | VAL | 155 | 97.319 | -4.427 | 29.856 | 1.00 | 34.58 | H | O |
| ATOM | 2610 | N | THR | 156 | 96.898 | -3.864 | 31.995 | 1.00 | 30.47 | H | N |
| ATOM | 2611 | CA | THR | 156 | 98.195 | -4.322 | 32.482 | 1.00 | 30.67 | H | C |
| ATOM | 2612 | CB | THR | 156 | 98.855 | -3.316 | 33.458 | 1.00 | 37.06 | H | C |
| ATOM | 2613 | OG1 | THR | 156 | 98.554 | -3.699 | 34.810 | 1.00 | 41.96 | H | O |
| ATOM | 2614 | CG2 | THR | 156 | 98.346 | -1.895 | 33.213 | 1.00 | 35.30 | H | C |
| ATOM | 2615 | C | THR | 156 | 97.956 | -5.589 | 33.276 | 1.00 | 28.26 | H | C |
| ATOM | 2616 | O | THR | 156 | 96.915 | -5.736 | 33.906 | 1.00 | 24.33 | H | O |
| ATOM | 2617 | N | VAL | 157 | 98.914 | -6.501 | 33.250 | 1.00 | 20.40 | H | N |
| ATOM | 2618 | CA | VAL | 157 | 98.784 | -7.731 | 34.014 | 1.00 | 23.86 | H | C |
| ATOM | 2619 | CB | VAL | 157 | 98.263 | -8.918 | 33.149 | 1.00 | 6.55 | H | C |
| ATOM | 2620 | CG1 | VAL | 157 | 98.307 | -10.191 | 33.970 | 1.00 | 2.70 | H | C |
| ATOM | 2621 | CG2 | VAL | 157 | 96.817 | -8.649 | 32.662 | 1.00 | 8.40 | H | C |
| ATOM | 2622 | C | VAL | 157 | 100.122 | -8.142 | 34.618 | 1.00 | 25.91 | H | C |
| ATOM | 2623 | O | VAL | 157 | 101.130 | -8.220 | 33.918 | 1.00 | 28.24 | H | O |
| ATOM | 2624 | N | SER | 158 | 100.127 | -8.401 | 35.918 | 1.00 | 37.92 | H | N |
| ATOM | 2625 | CA | SER | 158 | 101.333 | -8.840 | 36.606 | 1.00 | 38.42 | H | C |
| ATOM | 2626 | CB | SER | 158 | 101.852 | -7.738 | 37.521 | 1.00 | 26.79 | H | C |
| ATOM | 2627 | OG | SER | 158 | 101.008 | -7.591 | 38.648 | 1.00 | 29.78 | H | O |
| ATOM | 2628 | C | SER | 158 | 100.947 | -10.064 | 37.439 | 1.00 | 37.35 | H | C |

FIG. 19A-37

```
ATOM   2629  O    SER  158      99.765 -10.366  37.583  1.00  35.45  H  O
ATOM   2630  N    TRP  159     101.926 -10.772  37.989  1.00  38.23  H  N
ATOM   2631  CA   TRP  159     101.604 -11.945  38.790  1.00  38.96  H  C
ATOM   2632  CB   TRP  159     102.060 -13.224  38.074  1.00  33.06  H  C
ATOM   2633  CG   TRP  159     101.197 -13.555  36.899  1.00  30.80  H  C
ATOM   2634  CD2  TRP  159     100.089 -14.463  36.879  1.00  31.04  H  C
ATOM   2635  CE2  TRP  159      99.540 -14.423  35.577  1.00  29.21  H  C
ATOM   2636  CE3  TRP  159      99.507 -15.307  37.836  1.00  31.84  H  C
ATOM   2637  CD1  TRP  159     101.271 -13.015  35.649  1.00  26.46  H  C
ATOM   2638  NE1  TRP  159     100.280 -13.531  34.848  1.00  30.17  H  N
ATOM   2639  CZ2  TRP  159      98.439 -15.196  35.204  1.00  33.73  H  C
ATOM   2640  CZ3  TRP  159      98.407 -16.079  37.465  1.00  33.56  H  C
ATOM   2641  CH2  TRP  159      97.887 -16.018  36.158  1.00  34.95  H  C
ATOM   2642  C    TRP  159     102.166 -11.908  40.203  1.00  41.53  H  C
ATOM   2643  O    TRP  159     103.355 -11.670  40.412  1.00  40.45  H  O
ATOM   2644  N    ASN  160     101.295 -12.163  41.170  1.00  50.63  H  N
ATOM   2645  CA   ASN  160     101.699 -12.153  42.557  1.00  51.18  H  C
ATOM   2646  CB   ASN  160     102.753 -13.230  42.814  1.00  31.23  H  C
ATOM   2647  CG   ASN  160     102.145 -14.619  42.946  1.00  28.65  H  C
ATOM   2648  OD1  ASN  160     100.924 -14.784  42.911  1.00  22.55  H  O
ATOM   2649  ND2  ASN  160     103.000 -15.630  43.107  1.00  28.71  H  N
ATOM   2650  C    ASN  160     102.245 -10.777  42.891  1.00  53.56  H  C
ATOM   2651  O    ASN  160     103.277 -10.637  43.554  1.00  51.84  H  O
ATOM   2652  N    SER  161     101.548  -9.758  42.397  1.00  57.36  H  N
ATOM   2653  CA   SER  161     101.915  -8.372  42.651  1.00  58.07  H  C
ATOM   2654  CB   SER  161     101.833  -8.106  44.161  1.00  44.49  H  C
ATOM   2655  OG   SER  161     100.611  -8.586  44.713  1.00  48.26  H  O
ATOM   2656  C    SER  161     103.305  -7.997  42.118  1.00  57.98  H  C
ATOM   2657  O    SER  161     103.779  -6.883  42.329  1.00  58.91  H  O
ATOM   2658  N    GLY  162     103.957  -8.927  41.431  1.00  43.40  H  N
ATOM   2659  CA   GLY  162     105.271  -8.641  40.886  1.00  41.61  H  C
ATOM   2660  C    GLY  162     106.343  -9.670  41.195  1.00  41.13  H  C
ATOM   2661  O    GLY  162     107.340  -9.756  40.475  1.00  41.89  H  O
ATOM   2662  N    ALA  163     106.144 -10.460  42.248  1.00  32.79  H  N
ATOM   2663  CA   ALA  163     107.135 -11.462  42.644  1.00  33.15  H  C
ATOM   2664  CB   ALA  163     106.845 -11.956  44.065  1.00   7.75  H  C
ATOM   2665  C    ALA  163     107.265 -12.651  41.702  1.00  33.69  H  C
ATOM   2666  O    ALA  163     108.154 -13.473  41.868  1.00  36.52  H  O
ATOM   2667  N    LEU  164     106.378 -12.750  40.722  1.00  33.04  H  N
ATOM   2668  CA   LEU  164     106.412 -13.847  39.755  1.00  28.09  H  C
ATOM   2669  CB   LEU  164     105.146 -14.701  39.869  1.00  29.67  H  C
ATOM   2670  CG   LEU  164     105.008 -15.851  38.870  1.00  27.43  H  C
ATOM   2671  CD1  LEU  164     105.976 -16.963  39.215  1.00  24.01  H  C
ATOM   2672  CD2  LEU  164     103.605 -16.370  38.903  1.00  22.28  H  C
ATOM   2673  C    LEU  164     106.483 -13.227  38.370  1.00  26.00  H  C
ATOM   2674  O    LEU  164     105.492 -12.663  37.893  1.00  20.06  H  O
ATOM   2675  N    THR  165     107.656 -13.326  37.740  1.00  28.49  H  N
ATOM   2676  CA   THR  165     107.893 -12.758  36.410  1.00  32.54  H  C
ATOM   2677  CB   THR  165     108.927 -11.613  36.462  1.00  18.33  H  C
ATOM   2678  OG1  THR  165     110.114 -12.057  37.139  1.00  21.15  H  O
ATOM   2679  CG2  THR  165     108.348 -10.419  37.184  1.00  20.86  H  C
ATOM   2680  C    THR  165     108.394 -13.770  35.397  1.00  33.42  H  C
ATOM   2681  O    THR  165     108.028 -13.717  34.227  1.00  34.44  H  O
ATOM   2682  N    SER  166     109.244 -14.683  35.849  1.00  63.46  H  N
ATOM   2683  CA   SER  166     109.804 -15.702  34.973  1.00  62.93  H  C
ATOM   2684  CB   SER  166     110.901 -16.472  35.710  1.00  37.10  H  C
ATOM   2685  OG   SER  166     111.503 -17.442  34.870  1.00  42.11  H  O
ATOM   2686  C    SER  166     108.748 -16.678  34.458  1.00  60.85  H  C
ATOM   2687  O    SER  166     107.955 -17.226  35.227  1.00  60.31  H  O
ATOM   2688  N    GLY  167     108.744 -16.895  33.148  1.00  58.61  H  N
ATOM   2689  CA   GLY  167     107.784 -17.812  32.566  1.00  55.44  H  C
ATOM   2690  C    GLY  167     106.425 -17.181  32.332  1.00  49.55  H  C
ATOM   2691  O    GLY  167     105.462 -17.878  32.010  1.00  51.52  H  O
ATOM   2692  N    VAL  168     106.340 -15.864  32.491  1.00  12.32  H  N
ATOM   2693  CA   VAL  168     105.081 -15.183  32.280  1.00  12.04  H  C
ATOM   2694  CB   VAL  168     104.933 -13.970  33.190  1.00   2.74  H  C
ATOM   2695  CG1  VAL  168     103.590 -13.273  32.906  1.00   2.74  H  C
ATOM   2696  CG2  VAL  168     105.070 -14.398  34.630  1.00   2.83  H  C
ATOM   2697  C    VAL  168     104.965 -14.687  30.842  1.00  11.82  H  C
ATOM   2698  O    VAL  168     105.894 -14.087  30.319  1.00  11.28  H  O
ATOM   2699  N    HIS  169     103.807 -14.931  30.253  1.00  28.24  H  N
ATOM   2700  CA   HIS  169     103.518 -14.512  28.891  1.00  24.96  H  C
ATOM   2701  CB   HIS  169     103.566 -15.695  27.924  1.00   1.87  H  C
```

FIG. 19A-38

| ATOM | 2702 | CG | HIS | 169 | 104.935 | -16.209 | 27.634 | 1.00 | 1.87 | H | C |
|---|---|---|---|---|---|---|---|---|---|---|---|
| ATOM | 2703 | CD2 | HIS | 169 | 105.456 | -17.452 | 27.739 | 1.00 | 10.72 | H | C |
| ATOM | 2704 | ND1 | HIS | 169 | 105.935 | -15.415 | 27.114 | 1.00 | 4.04 | H | N |
| ATOM | 2705 | CE1 | HIS | 169 | 107.015 | -16.147 | 26.912 | 1.00 | 11.56 | H | C |
| ATOM | 2706 | NE2 | HIS | 169 | 106.750 | -17.387 | 27.282 | 1.00 | 3.03 | H | N |
| ATOM | 2707 | C | HIS | 169 | 102.106 | -13.934 | 28.818 | 1.00 | 26.88 | H | C |
| ATOM | 2708 | O | HIS | 169 | 101.143 | -14.679 | 28.610 | 1.00 | 27.44 | H | O |
| ATOM | 2709 | N | THR | 170 | 101.960 | -12.628 | 28.995 | 1.00 | 15.52 | H | N |
| ATOM | 2710 | CA | THR | 170 | 100.637 | -12.030 | 28.885 | 1.00 | 14.61 | H | C |
| ATOM | 2711 | CB | THR | 170 | 100.472 | -10.872 | 29.894 | 1.00 | 20.19 | H | C |
| ATOM | 2712 | OG1 | THR | 170 | 99.403 | -10.021 | 29.470 | 1.00 | 14.32 | H | O |
| ATOM | 2713 | CG2 | THR | 170 | 101.760 | -10.096 | 30.042 | 1.00 | 25.14 | H | C |
| ATOM | 2714 | C | THR | 170 | 100.487 | -11.553 | 27.433 | 1.00 | 15.32 | H | C |
| ATOM | 2715 | O | THR | 170 | 101.023 | -10.532 | 27.053 | 1.00 | 11.65 | H | O |
| ATOM | 2716 | N | PHE | 171 | 99.762 | -12.324 | 26.630 | 1.00 | 23.28 | H | N |
| ATOM | 2717 | CA | PHE | 171 | 99.587 | -12.046 | 25.206 | 1.00 | 17.85 | H | C |
| ATOM | 2718 | CB | PHE | 171 | 98.695 | -13.110 | 24.554 | 1.00 | 15.23 | H | C |
| ATOM | 2719 | CG | PHE | 171 | 99.138 | -14.521 | 24.806 | 1.00 | 7.97 | H | C |
| ATOM | 2720 | CD1 | PHE | 171 | 98.731 | -15.195 | 25.955 | 1.00 | 8.65 | H | C |
| ATOM | 2721 | CD2 | PHE | 171 | 99.978 | -15.174 | 23.903 | 1.00 | 7.84 | H | C |
| ATOM | 2722 | CE1 | PHE | 171 | 99.153 | -16.492 | 26.202 | 1.00 | 17.36 | H | C |
| ATOM | 2723 | CE2 | PHE | 171 | 100.407 | -16.473 | 24.144 | 1.00 | 15.22 | H | C |
| ATOM | 2724 | CZ | PHE | 171 | 99.993 | -17.133 | 25.295 | 1.00 | 16.34 | H | C |
| ATOM | 2725 | C | PHE | 171 | 99.032 | -10.692 | 24.793 | 1.00 | 18.20 | H | C |
| ATOM | 2726 | O | PHE | 171 | 98.344 | -10.015 | 25.552 | 1.00 | 23.73 | H | O |
| ATOM | 2727 | N | PRO | 172 | 99.341 | -10.278 | 23.557 | 1.00 | 21.77 | H | N |
| ATOM | 2728 | CD | PRO | 172 | 100.227 | -10.890 | 22.550 | 1.00 | 20.32 | H | C |
| ATOM | 2729 | CA | PRO | 172 | 98.827 | -8.999 | 23.088 | 1.00 | 23.20 | H | C |
| ATOM | 2730 | CB | PRO | 172 | 99.595 | -8.775 | 21.782 | 1.00 | 20.71 | H | C |
| ATOM | 2731 | CG | PRO | 172 | 99.834 | -10.148 | 21.287 | 1.00 | 18.82 | H | C |
| ATOM | 2732 | C | PRO | 172 | 97.339 | -9.235 | 22.876 | 1.00 | 25.11 | H | C |
| ATOM | 2733 | O | PRO | 172 | 96.916 | -10.364 | 22.645 | 1.00 | 23.46 | H | O |
| ATOM | 2734 | N | ALA | 173 | 96.551 | -8.172 | 22.960 | 1.00 | 24.67 | H | N |
| ATOM | 2735 | CA | ALA | 173 | 95.104 | -8.267 | 22.815 | 1.00 | 27.18 | H | C |
| ATOM | 2736 | CB | ALA | 173 | 94.439 | -7.079 | 23.498 | 1.00 | 1.87 | H | C |
| ATOM | 2737 | C | ALA | 173 | 94.604 | -8.379 | 21.391 | 1.00 | 30.18 | H | C |
| ATOM | 2738 | O | ALA | 173 | 95.304 | -8.080 | 20.426 | 1.00 | 32.13 | H | O |
| ATOM | 2739 | N | VAL | 174 | 93.365 | -8.820 | 21.277 | 1.00 | 21.72 | H | N |
| ATOM | 2740 | CA | VAL | 174 | 92.753 | -8.964 | 19.984 | 1.00 | 23.16 | H | C |
| ATOM | 2741 | CB | VAL | 174 | 92.841 | -10.406 | 19.511 | 1.00 | 28.95 | H | C |
| ATOM | 2742 | CG1 | VAL | 174 | 92.103 | -10.566 | 18.201 | 1.00 | 32.21 | H | C |
| ATOM | 2743 | CG2 | VAL | 174 | 94.305 | -10.797 | 19.356 | 1.00 | 26.32 | H | C |
| ATOM | 2744 | C | VAL | 174 | 91.302 | -8.508 | 20.058 | 1.00 | 25.36 | H | C |
| ATOM | 2745 | O | VAL | 174 | 90.611 | -8.718 | 21.069 | 1.00 | 25.35 | H | O |
| ATOM | 2746 | N | LEU | 175 | 90.860 | -7.856 | 18.987 | 1.00 | 41.55 | H | N |
| ATOM | 2747 | CA | LEU | 175 | 89.504 | -7.338 | 18.890 | 1.00 | 40.23 | H | C |
| ATOM | 2748 | CB | LEU | 175 | 89.443 | -6.276 | 17.787 | 1.00 | 23.29 | H | C |
| ATOM | 2749 | CG | LEU | 175 | 88.728 | -4.928 | 17.990 | 1.00 | 20.94 | H | C |
| ATOM | 2750 | CD1 | LEU | 175 | 88.634 | -4.511 | 19.463 | 1.00 | 21.45 | H | C |
| ATOM | 2751 | CD2 | LEU | 175 | 89.518 | -3.900 | 17.186 | 1.00 | 22.78 | H | C |
| ATOM | 2752 | C | LEU | 175 | 88.539 | -8.474 | 18.588 | 1.00 | 42.85 | H | C |
| ATOM | 2753 | O | LEU | 175 | 88.738 | -9.233 | 17.638 | 1.00 | 45.50 | H | O |
| ATOM | 2754 | N | GLN | 176 | 87.500 | -8.592 | 19.407 | 1.00 | 41.11 | H | N |
| ATOM | 2755 | CA | GLN | 176 | 86.514 | -9.645 | 19.228 | 1.00 | 42.33 | H | C |
| ATOM | 2756 | CB | GLN | 176 | 85.852 | -9.990 | 20.564 | 1.00 | 38.15 | H | C |
| ATOM | 2757 | CG | GLN | 176 | 86.817 | -10.276 | 21.703 | 1.00 | 37.93 | H | C |
| ATOM | 2758 | CD | GLN | 176 | 86.109 | -10.801 | 22.939 | 1.00 | 36.82 | H | C |
| ATOM | 2759 | OE1 | GLN | 176 | 85.562 | -11.899 | 22.923 | 1.00 | 36.67 | H | O |
| ATOM | 2760 | NE2 | GLN | 176 | 86.108 | -10.014 | 24.011 | 1.00 | 33.13 | H | N |
| ATOM | 2761 | C | GLN | 176 | 85.439 | -9.207 | 18.245 | 1.00 | 44.39 | H | C |
| ATOM | 2762 | O | GLN | 176 | 85.274 | -8.018 | 17.969 | 1.00 | 34.09 | H | O |
| ATOM | 2763 | N | SER | 177 | 84.708 | -10.182 | 17.718 | 1.00 | 59.83 | H | N |
| ATOM | 2764 | CA | SER | 177 | 83.624 | -9.902 | 16.790 | 1.00 | 58.61 | H | C |
| ATOM | 2765 | CB | SER | 177 | 82.804 | -11.177 | 16.558 | 1.00 | 104.21 | H | C |
| ATOM | 2766 | OG | SER | 177 | 81.708 | -10.945 | 15.689 | 1.00 | 104.01 | H | O |
| ATOM | 2767 | C | SER | 177 | 82.759 | -8.832 | 17.448 | 1.00 | 60.09 | H | C |
| ATOM | 2768 | O | SER | 177 | 82.169 | -7.985 | 16.778 | 1.00 | 62.26 | H | O |
| ATOM | 2769 | N | SER | 178 | 82.722 | -8.877 | 18.778 | 1.00 | 34.26 | H | N |
| ATOM | 2770 | CA | SER | 178 | 81.942 | -7.952 | 19.596 | 1.00 | 32.97 | H | C |
| ATOM | 2771 | CB | SER | 178 | 81.798 | -8.510 | 21.019 | 1.00 | 67.89 | H | C |
| ATOM | 2772 | OG | SER | 178 | 83.057 | -8.636 | 21.663 | 1.00 | 66.22 | H | O |
| ATOM | 2773 | C | SER | 178 | 82.538 | -6.554 | 19.671 | 1.00 | 32.95 | H | C |
| ATOM | 2774 | O | SER | 178 | 81.921 | -5.640 | 20.210 | 1.00 | 35.05 | H | O |

FIG. 19A-39

| ATOM | 2775 | N   | GLY | 179 | 83.738  | -6.382  | 19.135 | 1.00 | 43.45 | H | N |
|------|------|-----|-----|-----|---------|---------|--------|------|-------|---|---|
| ATOM | 2776 | CA  | GLY | 179 | 84.357  | -5.072  | 19.191 | 1.00 | 46.81 | H | C |
| ATOM | 2777 | C   | GLY | 179 | 84.972  | -4.821  | 20.552 | 1.00 | 50.21 | H | C |
| ATOM | 2778 | O   | GLY | 179 | 85.380  | -3.707  | 20.869 | 1.00 | 50.30 | H | O |
| ATOM | 2779 | N   | LEU | 180 | 85.020  | -5.862  | 21.369 | 1.00 | 30.24 | H | N |
| ATOM | 2780 | CA  | LEU | 180 | 85.620  | -5.749  | 22.686 | 1.00 | 32.27 | H | C |
| ATOM | 2781 | CB  | LEU | 180 | 84.706  | -6.380  | 23.730 | 1.00 | 33.41 | H | C |
| ATOM | 2782 | CG  | LEU | 180 | 83.485  | -5.524  | 24.054 | 1.00 | 32.78 | H | C |
| ATOM | 2783 | CD1 | LEU | 180 | 82.513  | -6.292  | 24.902 | 1.00 | 27.00 | H | C |
| ATOM | 2784 | CD2 | LEU | 180 | 83.943  | -4.278  | 24.781 | 1.00 | 32.58 | H | C |
| ATOM | 2785 | C   | LEU | 180 | 86.974  | -6.442  | 22.672 | 1.00 | 32.86 | H | C |
| ATOM | 2786 | O   | LEU | 180 | 87.135  | -7.488  | 22.054 | 1.00 | 36.18 | H | O |
| ATOM | 2787 | N   | TYR | 181 | 87.952  | -5.843  | 23.336 | 1.00 | 31.41 | H | N |
| ATOM | 2788 | CA  | TYR | 181 | 89.293  | -6.409  | 23.387 | 1.00 | 32.68 | H | C |
| ATOM | 2789 | CB  | TYR | 181 | 90.297  | -5.323  | 23.792 | 1.00 | 57.58 | H | C |
| ATOM | 2790 | CG  | TYR | 181 | 90.773  | -4.445  | 22.651 | 1.00 | 56.39 | H | C |
| ATOM | 2791 | CD1 | TYR | 181 | 91.591  | -4.961  | 21.647 | 1.00 | 57.58 | H | C |
| ATOM | 2792 | CE1 | TYR | 181 | 92.063  | -4.155  | 20.605 | 1.00 | 57.08 | H | C |
| ATOM | 2793 | CD2 | TYR | 181 | 90.430  | -3.092  | 22.585 | 1.00 | 56.67 | H | C |
| ATOM | 2794 | CE2 | TYR | 181 | 90.899  | -2.273  | 21.543 | 1.00 | 57.48 | H | C |
| ATOM | 2795 | CZ  | TYR | 181 | 91.717  | -2.816  | 20.559 | 1.00 | 58.33 | H | C |
| ATOM | 2796 | OH  | TYR | 181 | 92.202  | -2.033  | 19.533 | 1.00 | 62.35 | H | O |
| ATOM | 2797 | C   | TYR | 181 | 89.361  | -7.573  | 24.375 | 1.00 | 31.73 | H | C |
| ATOM | 2798 | O   | TYR | 181 | 88.581  | -7.638  | 25.324 | 1.00 | 32.08 | H | O |
| ATOM | 2799 | N   | SER | 182 | 90.287  | -8.499  | 24.149 | 1.00 | 35.13 | H | N |
| ATOM | 2800 | CA  | SER | 182 | 90.446  | -9.642  | 25.045 | 1.00 | 32.04 | H | C |
| ATOM | 2801 | CB  | SER | 182 | 89.439  | -10.741 | 24.700 | 1.00 | 65.40 | H | C |
| ATOM | 2802 | OG  | SER | 182 | 89.612  | -11.868 | 25.543 | 1.00 | 59.63 | H | O |
| ATOM | 2803 | C   | SER | 182 | 91.860  | -10.209 | 24.970 | 1.00 | 33.65 | H | C |
| ATOM | 2804 | O   | SER | 182 | 92.494  | -10.187 | 23.906 | 1.00 | 37.13 | H | O |
| ATOM | 2805 | N   | LEU | 183 | 92.351  | -10.713 | 26.101 | 1.00 | 28.98 | H | N |
| ATOM | 2806 | CA  | LEU | 183 | 93.689  | -11.290 | 26.152 | 1.00 | 24.91 | H | C |
| ATOM | 2807 | CB  | LEU | 183 | 94.753  | -10.179 | 26.189 | 1.00 | 31.36 | H | C |
| ATOM | 2808 | CG  | LEU | 183 | 94.913  | -9.263  | 27.414 | 1.00 | 23.12 | H | C |
| ATOM | 2809 | CD1 | LEU | 183 | 95.475  | -10.014 | 28.625 | 1.00 | 27.02 | H | C |
| ATOM | 2810 | CD2 | LEU | 183 | 95.849  | -8.148  | 27.036 | 1.00 | 19.84 | H | C |
| ATOM | 2811 | C   | LEU | 183 | 93.898  | -12.209 | 27.342 | 1.00 | 24.58 | H | C |
| ATOM | 2812 | O   | LEU | 183 | 93.179  | -12.135 | 28.326 | 1.00 | 18.76 | H | O |
| ATOM | 2813 | N   | SER | 184 | 94.894  | -13.077 | 27.250 | 1.00 | 26.13 | H | N |
| ATOM | 2814 | CA  | SER | 184 | 95.205  | -13.967 | 28.357 | 1.00 | 26.65 | H | C |
| ATOM | 2815 | CB  | SER | 184 | 95.000  | -15.445 | 27.968 | 1.00 | 16.60 | H | C |
| ATOM | 2816 | OG  | SER | 184 | 93.638  | -15.750 | 27.710 | 1.00 | 22.49 | H | O |
| ATOM | 2817 | C   | SER | 184 | 96.660  | -13.752 | 28.784 | 1.00 | 22.47 | H | C |
| ATOM | 2818 | O   | SER | 184 | 97.546  | -13.511 | 27.953 | 1.00 | 21.27 | H | O |
| ATOM | 2819 | N   | SER | 185 | 96.896  | -13.786 | 30.087 | 1.00 | 27.49 | H | N |
| ATOM | 2820 | CA  | SER | 185 | 98.251  | -13.670 | 30.575 | 1.00 | 25.55 | H | C |
| ATOM | 2821 | CB  | SER | 185 | 98.389  | -12.634 | 31.678 | 1.00 | 27.24 | H | C |
| ATOM | 2822 | OG  | SER | 185 | 99.760  | -12.516 | 32.031 | 1.00 | 25.68 | H | O |
| ATOM | 2823 | C   | SER | 185 | 98.460  | -15.060 | 31.123 | 1.00 | 23.97 | H | C |
| ATOM | 2824 | O   | SER | 185 | 97.652  | -15.551 | 31.912 | 1.00 | 25.28 | H | O |
| ATOM | 2825 | N   | VAL | 186 | 99.533  | -15.699 | 30.679 | 1.00 | 29.81 | H | N |
| ATOM | 2826 | CA  | VAL | 186 | 99.830  | -17.060 | 31.064 | 1.00 | 29.28 | H | C |
| ATOM | 2827 | CB  | VAL | 186 | 99.717  | -17.966 | 29.831 | 1.00 | 20.56 | H | C |
| ATOM | 2828 | CG1 | VAL | 186 | 100.305 | -19.306 | 30.112 | 1.00 | 20.80 | H | C |
| ATOM | 2829 | CG2 | VAL | 186 | 98.253  | -18.121 | 29.446 | 1.00 | 19.74 | H | C |
| ATOM | 2830 | C   | VAL | 186 | 101.204 | -17.193 | 31.664 | 1.00 | 30.42 | H | C |
| ATOM | 2831 | O   | VAL | 186 | 102.097 | -16.416 | 31.357 | 1.00 | 31.20 | H | O |
| ATOM | 2832 | N   | VAL | 187 | 101.359 | -18.179 | 32.540 | 1.00 | 29.47 | H | N |
| ATOM | 2833 | CA  | VAL | 187 | 102.645 | -18.457 | 33.178 | 1.00 | 26.42 | H | C |
| ATOM | 2834 | CB  | VAL | 187 | 102.739 | -17.797 | 34.586 | 1.00 | 27.93 | H | C |
| ATOM | 2835 | CG1 | VAL | 187 | 101.681 | -18.385 | 35.507 | 1.00 | 26.86 | H | C |
| ATOM | 2836 | CG2 | VAL | 187 | 104.134 | -17.994 | 35.180 | 1.00 | 26.29 | H | C |
| ATOM | 2837 | C   | VAL | 187 | 102.842 | -19.975 | 33.309 | 1.00 | 20.75 | H | C |
| ATOM | 2838 | O   | VAL | 187 | 101.882 | -20.743 | 33.316 | 1.00 | 22.47 | H | O |
| ATOM | 2839 | N   | THR | 188 | 104.098 | -20.397 | 33.377 | 1.00 | 5.29  | H | N |
| ATOM | 2840 | CA  | THR | 188 | 104.441 | -21.807 | 33.539 | 1.00 | 7.86  | H | C |
| ATOM | 2841 | CB  | THR | 188 | 105.280 | -22.327 | 32.366 | 1.00 | 35.20 | H | C |
| ATOM | 2842 | OG1 | THR | 188 | 106.425 | -21.487 | 32.194 | 1.00 | 33.26 | H | O |
| ATOM | 2843 | CG2 | THR | 188 | 104.453 | -22.337 | 31.078 | 1.00 | 39.96 | H | C |
| ATOM | 2844 | C   | THR | 188 | 105.270 | -21.870 | 34.802 | 1.00 | 13.86 | H | C |
| ATOM | 2845 | O   | THR | 188 | 106.194 | -21.077 | 34.975 | 1.00 | 18.45 | H | O |
| ATOM | 2846 | N   | VAL | 189 | 104.921 | -22.799 | 35.688 | 1.00 | 28.00 | H | N |
| ATOM | 2847 | CA  | VAL | 189 | 105.613 | -22.963 | 36.965 | 1.00 | 25.42 | H | C |

FIG. 19A-40

```
ATOM   2848  CB   VAL  189     104.755  -22.412  38.137  1.00  24.28      H  C
ATOM   2849  CG1  VAL  189     104.399  -20.951  37.904  1.00  17.23      H  C
ATOM   2850  CG2  VAL  189     103.478  -23.234  38.270  1.00  17.84      H  C
ATOM   2851  C    VAL  189     105.875  -24.439  37.242  1.00  32.15      H  C
ATOM   2852  O    VAL  189     105.386  -25.309  36.523  1.00  35.18      H  O
ATOM   2853  N    PRO  190     106.671   24.738  38.280  1.00  50.39      H  N
ATOM   2854  CD   PRO  190     107.545  -23.823  39.036  1.00  32.03      H  C
ATOM   2855  CA   PRO  190     106.962  -26.133  38.624  1.00  50.40      H  C
ATOM   2856  CB   PRO  190     107.911  -26.001  39.814  1.00  29.50      H  C
ATOM   2857  CG   PRO  190     108.651  -24.746  39.514  1.00  29.72      H  C
ATOM   2858  C    PRO  190     105.650  -26.801  39.018  1.00  50.46      H  C
ATOM   2859  O    PRO  190     104.899  -26.267  39.834  1.00  48.43      H  O
ATOM   2860  N    SER  191     105.357  -27.953  38.436  1.00  54.29      H  N
ATOM   2861  CA   SER  191     104.122  -28.638  38.774  1.00  60.79      H  C
ATOM   2862  CB   SER  191     104.111  -30.036  38.157  1.00  30.49      H  C
ATOM   2863  OG   SER  191     104.076  -29.980  36.740  1.00  31.07      H  O
ATOM   2864  C    SER  191     104.009  -28.730  40.297  1.00  63.91      H  C
ATOM   2865  O    SER  191     102.986  -28.361  40.882  1.00  66.82      H  O
ATOM   2866  N    SER  192     105.084  -29.201  40.924  1.00  39.50      H  N
ATOM   2867  CA   SER  192     105.177  -29.374  42.376  1.00  40.99      H  C
ATOM   2868  CB   SER  192     106.602  -29.776  42.739  1.00  41.75      H  C
ATOM   2869  OG   SER  192     107.475  -28.675  42.565  1.00  41.65      H  O
ATOM   2870  C    SER  192     104.795  -28.150  43.220  1.00  42.26      H  C
ATOM   2871  O    SER  192     104.403  -28.286  44.381  1.00  48.17      H  O
ATOM   2872  N    SER  193     104.923  -26.960  42.645  1.00  20.64      H  N
ATOM   2873  CA   SER  193     104.601  -25.733  43.365  1.00  22.36      H  C
ATOM   2874  CB   SER  193     105.396  -24.567  42.771  1.00  39.90      H  C
ATOM   2875  OG   SER  193     104.973  -24.284  41.447  1.00  36.65      H  O
ATOM   2876  C    SER  193     103.097  -25.380  43.392  1.00  22.92      H  C
ATOM   2877  O    SER  193     102.697  -24.363  43.963  1.00  25.84      H  O
ATOM   2878  N    LEU  194     102.268  -26.218  42.776  1.00  41.78      H  N
ATOM   2879  CA   LEU  194     100.827  -25.974  42.741  1.00  45.87      H  C
ATOM   2880  CB   LEU  194     100.172  -26.850  41.677  1.00  23.80      H  C
ATOM   2881  CG   LEU  194     100.533  -26.605  40.216  1.00  21.31      H  C
ATOM   2882  CD1  LEU  194      99.975  -27.739  39.377  1.00  19.27      H  C
ATOM   2883  CD2  LEU  194      99.973  -25.246  39.757  1.00  15.31      H  C
ATOM   2884  C    LEU  194     100.177  -26.276  44.080  1.00  49.01      H  C
ATOM   2885  O    LEU  194      99.209  -25.623  44.478  1.00  48.38      H  O
ATOM   2886  N    GLY  195     100.718  -27.272  44.770  1.00  65.65      H  N
ATOM   2887  CA   GLY  195     100.160  -27.676  46.043  1.00  68.76      H  C
ATOM   2888  C    GLY  195     100.625  -26.877  47.235  1.00  66.22      H  C
ATOM   2889  O    GLY  195     100.051  -26.992  48.314  1.00  68.30      H  O
ATOM   2890  N    THR  196     101.659  -26.067  47.053  1.00  33.26      H  N
ATOM   2891  CA   THR  196     102.175  -25.265  48.155  1.00  32.73      H  C
ATOM   2892  CB   THR  196     103.575  -25.763  48.585  1.00  30.77      H  C
ATOM   2893  OG1  THR  196     104.489  -25.676  47.478  1.00  28.63      H  O
ATOM   2894  CG2  THR  196     103.488  -27.213  49.071  1.00  27.23      H  C
ATOM   2895  C    THR  196     102.251  -23.786  47.813  1.00  35.97      H  C
ATOM   2896  O    THR  196     102.179  -22.933  48.695  1.00  36.72      H  O
ATOM   2897  N    GLN  197     102.389  -23.488  46.527  1.00  53.90      H  N
ATOM   2898  CA   GLN  197     102.478  -22.110  46.060  1.00  54.25      H  C
ATOM   2899  CB   GLN  197     103.480  -22.031  44.906  1.00  42.12      H  C
ATOM   2900  CG   GLN  197     104.561  -20.975  45.045  1.00  45.66      H  C
ATOM   2901  CD   GLN  197     104.051  -19.587  44.765  1.00  49.49      H  C
ATOM   2902  OE1  GLN  197     103.257  -19.032  45.528  1.00  50.05      H  O
ATOM   2903  NE2  GLN  197     104.500  -19.013  43.656  1.00  49.01      H  N
ATOM   2904  C    GLN  197     101.105  -21.617  45.604  1.00  52.98      H  C
ATOM   2905  O    GLN  197     100.314  -22.382  45.050  1.00  55.53      H  O
ATOM   2906  N    THR  198     100.829  -20.338  45.847  1.00  30.38      H  N
ATOM   2907  CA   THR  198      99.559  -19.719  45.470  1.00  29.29      H  C
ATOM   2908  CB   THR  198      98.922  -18.970  46.677  1.00  45.77      H  C
ATOM   2909  OG1  THR  198      97.546  -18.682  46.404  1.00  43.55      H  O
ATOM   2910  CG2  THR  198      99.643  -17.644  46.929  1.00  47.95      H  C
ATOM   2911  C    THR  198      99.811  -18.719  44.338  1.00  27.94      H  C
ATOM   2912  O    THR  198     100.722  -17.891  44.413  1.00  31.22      H  O
ATOM   2913  N    TYR  199      99.008  -18.789  43.285  1.00  40.84      H  N
ATOM   2914  CA   TYR  199      99.191  -17.874  42.168  1.00  31.26      H  C
ATOM   2915  CB   TYR  199      99.402  -18.681  40.880  1.00  39.46      H  C
ATOM   2916  CG   TYR  199     100.677  -19.496  40.904  1.00  33.83      H  C
ATOM   2917  CD1  TYR  199     101.911  -18.901  40.630  1.00  31.63      H  C
ATOM   2918  CE1  TYR  199     103.107  -19.626  40.735  1.00  31.28      H  C
ATOM   2919  CD2  TYR  199     100.662  -20.847  41.282  1.00  32.94      H  C
ATOM   2920  CE2  TYR  199     101.850  -21.590  41.392  1.00  33.91      H  C
```

FIG. 19A-41

```
ATOM   2921  CZ   TYR  199    103.069  -20.972   41.118  1.00  33.40   H  C
ATOM   2922  OH   TYR  199    104.244  -21.685   41.223  1.00  37.29   H  O
ATOM   2923  C    TYR  199     98.029  -16.897   42.014  1.00  31.50   H  C
ATOM   2924  O    TYR  199     96.876  -17.302   41.913  1.00  32.18   H  O
ATOM   2925  N    ILE  200     98.342  -15.605   42.026  1.00  38.61   H  N
ATOM   2926  CA   ILE  200     97.329  -14.566   41.858  1.00  39.11   H  C
ATOM   2927  CB   ILE  200     97.265  -13.574   43.051  1.00  27.10   H  C
ATOM   2928  CG2  ILE  200     96.185  -12.540   42.793  1.00  26.36   H  C
ATOM   2929  CG1  ILE  200     96.978  -14.301   44.363  1.00  30.59   H  C
ATOM   2930  CD1  ILE  200     98.119  -15.184   44.842  1.00  36.15   H  C
ATOM   2931  C    ILE  200     97.730  -13.736   40.649  1.00  41.59   H  C
ATOM   2932  O    ILE  200     98.916  -13.517   40.415  1.00  45.01   H  O
ATOM   2933  N    CYS  201     96.758  -13.283   39.867  1.00  30.01   H  N
ATOM   2934  CA   CYS  201     97.092  -12.434   38.735  1.00  27.23   H  C
ATOM   2935  C    CYS  201     96.476  -11.075   39.011  1.00  24.60   H  C
ATOM   2936  O    CYS  201     95.307  -10.967   39.386  1.00  22.36   H  O
ATOM   2937  CB   CYS  201     96.577  -12.997   37.394  1.00  42.80   H  C
ATOM   2938  SG   CYS  201     94.784  -12.909   37.090  1.00  39.16   H  S
ATOM   2939  N    ASN  202     97.282  -10.035   38.849  1.00  26.40   H  N
ATOM   2940  CA   ASN  202     96.819   -8.683   39.080  1.00  32.39   H  C
ATOM   2941  CB   ASN  202     97.884   -7.902   39.846  1.00  36.85   H  C
ATOM   2942  CG   ASN  202     98.507   -8.720   40.954  1.00  39.80   H  C
ATOM   2943  OD1  ASN  202     99.570   -9.314   40.779  1.00  38.11   H  O
ATOM   2944  ND2  ASN  202     97.837   -8.776   42.097  1.00  41.02   H  N
ATOM   2945  C    ASN  202     96.530   -8.025   37.743  1.00  36.08   H  C
ATOM   2946  O    ASN  202     97.419   -7.867   36.911  1.00  40.34   H  O
ATOM   2947  N    VAL  203     95.273   -7.668   37.533  1.00  28.99   H  N
ATOM   2948  CA   VAL  203     94.868   -7.017   36.295  1.00  29.18   H  C
ATOM   2949  CB   VAL  203     93.691   -7.781   35.624  1.00  21.70   H  C
ATOM   2950  CG1  VAL  203     93.321   -7.134   34.274  1.00  17.35   H  C
ATOM   2951  CG2  VAL  203     94.067   -9.236   35.450  1.00  25.16   H  C
ATOM   2952  C    VAL  203     94.443   -5.580   36.615  1.00  32.31   H  C
ATOM   2953  O    VAL  203     93.808   -5.320   37.643  1.00  27.84   H  O
ATOM   2954  N    ASN  204     94.799   -4.648   35.741  1.00  45.86   H  N
ATOM   2955  CA   ASN  204     94.442   -3.266   35.979  1.00  50.50   H  C
ATOM   2956  CB   ASN  204     95.565   -2.570   36.739  1.00  59.79   H  C
ATOM   2957  CG   ASN  204     95.186   -1.176   37.164  1.00  65.34   H  C
ATOM   2958  OD1  ASN  204     94.801   -0.347   36.338  1.00  69.10   H  O
ATOM   2959  ND2  ASN  204     95.287   -0.906   38.459  1.00  65.59   H  N
ATOM   2960  C    ASN  204     94.109   -2.486   34.709  1.00  51.54   H  C
ATOM   2961  O    ASN  204     94.985   -2.164   33.905  1.00  51.77   H  O
ATOM   2962  N    HIS  205     92.828   -2.176   34.550  1.00  30.40   H  N
ATOM   2963  CA   HIS  205     92.338   -1.431   33.396  1.00  29.10   H  C
ATOM   2964  CB   HIS  205     90.994   -1.998   32.957  1.00  20.87   H  C
ATOM   2965  CG   HIS  205     90.444   -1.371   31.718  1.00  25.68   H  C
ATOM   2966  CD2  HIS  205     89.209   -0.889   31.437  1.00  28.69   H  C
ATOM   2967  ND1  HIS  205     91.165   -1.282   30.548  1.00  23.44   H  N
ATOM   2968  CE1  HIS  205     90.396   -0.780   29.597  1.00  25.19   H  C
ATOM   2969  NE2  HIS  205     89.203   -0.534   30.110  1.00  28.16   H  N
ATOM   2970  C    HIS  205     92.157    0.022   33.793  1.00  30.12   H  C
ATOM   2971  O    HIS  205     91.057    0.429   34.173  1.00  28.02   H  O
ATOM   2972  N    LYS  206     93.228    0.805   33.714  1.00  50.94   H  N
ATOM   2973  CA   LYS  206     93.138    2.209   34.084  1.00  49.11   H  C
ATOM   2974  CB   LYS  206     94.486    2.906   33.867  1.00  50.82   H  C
ATOM   2975  CG   LYS  206     95.536    2.476   34.895  1.00  57.82   H  C
ATOM   2976  CD   LYS  206     96.809    3.325   34.857  1.00  61.64   H  C
ATOM   2977  CE   LYS  206     97.793    2.906   35.959  1.00  63.00   H  C
ATOM   2978  NZ   LYS  206     99.049    3.715   35.960  1.00  66.30   H  N
ATOM   2979  C    LYS  206     92.017    2.949   33.353  1.00  47.68   H  C
ATOM   2980  O    LYS  206     91.318    3.765   33.955  1.00  46.73   H  O
ATOM   2981  N    PRO  207     91.810    2.650   32.057  1.00  33.42   H  N
ATOM   2982  CD   PRO  207     92.613    1.722   31.239  1.00  21.52   H  C
ATOM   2983  CA   PRO  207     90.770    3.285   31.241  1.00  34.06   H  C
ATOM   2984  CB   PRO  207     90.831    2.501   29.936  1.00  21.18   H  C
ATOM   2985  CG   PRO  207     92.286    2.156   29.831  1.00  24.69   H  C
ATOM   2986  C    PRO  207     89.366    3.280   31.846  1.00  34.36   H  C
ATOM   2987  O    PRO  207     88.452    3.927   31.311  1.00  32.31   H  O
ATOM   2988  N    SER  208     89.190    2.545   32.944  1.00  25.18   H  N
ATOM   2989  CA   SER  208     87.893    2.481   33.628  1.00  28.11   H  C
ATOM   2990  CB   SER  208     87.055    1.320   33.094  1.00  29.27   H  C
ATOM   2991  OG   SER  208     87.724    0.096   33.315  1.00  27.44   H  O
ATOM   2992  C    SER  208     88.120    2.314   35.126  1.00  31.08   H  C
ATOM   2993  O    SER  208     87.266    1.789   35.846  1.00  34.78   H  O
```

FIG. 19A-42

| | | | | | | | | | | | |
|---|---|---|---|---|---|---|---|---|---|---|---|
| ATOM | 2994 | N | ASN | 209 | 89.284 | 2.777 | 35.573 | 1.00 | 68.02 | H | N |
| ATOM | 2995 | CA | ASN | 209 | 89.678 | 2.701 | 36.970 | 1.00 | 70.18 | H | C |
| ATOM | 2996 | CB | ASN | 209 | 89.073 | 3.879 | 37.741 | 1.00 | 49.77 | H | C |
| ATOM | 2997 | CG | ASN | 209 | 89.673 | 4.044 | 39.125 | 1.00 | 56.50 | H | C |
| ATOM | 2998 | OD1 | ASN | 209 | 90.885 | 3.963 | 39.301 | 1.00 | 62.08 | H | O |
| ATOM | 2999 | ND2 | ASN | 209 | 88.824 | 4.290 | 40.114 | 1.00 | 57.03 | H | N |
| ATOM | 3000 | C | ASN | 209 | 89.267 | 1.360 | 37.593 | 1.00 | 68.80 | H | C |
| ATOM | 3001 | O | ASN | 209 | 88.708 | 1.304 | 38.690 | 1.00 | 68.05 | H | O |
| ATOM | 3002 | N | THR | 210 | 89.555 | 0.282 | 36.871 | 1.00 | 35.45 | H | N |
| ATOM | 3003 | CA | THR | 210 | 89.246 | -1.061 | 37.322 | 1.00 | 37.08 | H | C |
| ATOM | 3004 | CB | THR | 210 | 88.640 | -1.883 | 36.201 | 1.00 | 55.80 | H | C |
| ATOM | 3005 | OG1 | THR | 210 | 87.416 | -1.273 | 35.787 | 1.00 | 56.14 | H | O |
| ATOM | 3006 | CG2 | THR | 210 | 88.367 | -3.303 | 36.668 | 1.00 | 57.05 | H | C |
| ATOM | 3007 | C | THR | 210 | 90.538 | -1.719 | 37.762 | 1.00 | 36.35 | H | C |
| ATOM | 3008 | O | THR | 210 | 91.613 | -1.388 | 37.266 | 1.00 | 34.79 | H | O |
| ATOM | 3009 | N | LYS | 211 | 90.426 | -2.655 | 38.692 | 1.00 | 33.96 | H | N |
| ATOM | 3010 | CA | LYS | 211 | 91.588 | -3.352 | 39.207 | 1.00 | 34.09 | H | C |
| ATOM | 3011 | CB | LYS | 211 | 92.366 | -2.422 | 40.154 | 1.00 | 52.60 | H | C |
| ATOM | 3012 | CG | LYS | 211 | 93.360 | -3.095 | 41.117 | 1.00 | 57.40 | H | C |
| ATOM | 3013 | CD | LYS | 211 | 94.338 | -4.040 | 40.416 | 1.00 | 62.07 | H | C |
| ATOM | 3014 | CE | LYS | 211 | 95.636 | -4.228 | 41.216 | 1.00 | 64.56 | H | C |
| ATOM | 3015 | NZ | LYS | 211 | 95.432 | -4.548 | 42.660 | 1.00 | 65.70 | H | N |
| ATOM | 3016 | C | LYS | 211 | 91.147 | -4.609 | 39.935 | 1.00 | 32.12 | H | C |
| ATOM | 3017 | O | LYS | 211 | 90.611 | -4.525 | 41.036 | 1.00 | 32.03 | H | O |
| ATOM | 3018 | N | VAL | 212 | 91.357 | -5.772 | 39.322 | 1.00 | 43.02 | H | N |
| ATOM | 3019 | CA | VAL | 212 | 90.971 | -7.017 | 39.973 | 1.00 | 37.80 | H | C |
| ATOM | 3020 | CB | VAL | 212 | 89.728 | -7.685 | 39.308 | 1.00 | 28.95 | H | C |
| ATOM | 3021 | CG1 | VAL | 212 | 88.671 | -6.639 | 39.021 | 1.00 | 26.33 | H | C |
| ATOM | 3022 | CG2 | VAL | 212 | 90.125 | -8.431 | 38.059 | 1.00 | 26.83 | H | C |
| ATOM | 3023 | C | VAL | 212 | 92.086 | -8.042 | 40.020 | 1.00 | 39.84 | H | C |
| ATOM | 3024 | O | VAL | 212 | 92.832 | -8.224 | 39.057 | 1.00 | 39.92 | H | O |
| ATOM | 3025 | N | ASP | 213 | 92.184 | -8.709 | 41.162 | 1.00 | 52.39 | H | N |
| ATOM | 3026 | CA | ASP | 213 | 93.177 | -9.743 | 41.376 | 1.00 | 49.02 | H | C |
| ATOM | 3027 | CB | ASP | 213 | 93.900 | -9.493 | 42.692 | 1.00 | 46.86 | H | C |
| ATOM | 3028 | CG | ASP | 213 | 94.548 | -8.128 | 42.740 | 1.00 | 52.80 | H | C |
| ATOM | 3029 | OD1 | ASP | 213 | 95.420 | -7.852 | 41.887 | 1.00 | 56.11 | H | O |
| ATOM | 3030 | OD2 | ASP | 213 | 94.182 | -7.329 | 43.626 | 1.00 | 57.38 | H | O |
| ATOM | 3031 | C | ASP | 213 | 92.433 | -11.067 | 41.423 | 1.00 | 46.03 | H | C |
| ATOM | 3032 | O | ASP | 213 | 91.537 | -11.248 | 42.236 | 1.00 | 45.16 | H | O |
| ATOM | 3033 | N | LYS | 214 | 92.796 | -11.993 | 40.548 | 1.00 | 33.42 | H | N |
| ATOM | 3034 | CA | LYS | 214 | 92.124 | -13.282 | 40.502 | 1.00 | 29.46 | H | C |
| ATOM | 3035 | CB | LYS | 214 | 91.732 | -13.602 | 39.055 | 0.00 | 52.86 | H | C |
| ATOM | 3036 | CG | LYS | 214 | 90.422 | -14.370 | 38.875 | 0.00 | 47.62 | H | C |
| ATOM | 3037 | CD | LYS | 214 | 90.398 | -15.699 | 39.614 | 0.00 | 43.68 | H | C |
| ATOM | 3038 | CE | LYS | 214 | 89.852 | -15.541 | 41.024 | 0.00 | 41.24 | H | C |
| ATOM | 3039 | NZ | LYS | 214 | 88.452 | -15.037 | 41.021 | 0.00 | 39.27 | H | N |
| ATOM | 3040 | C | LYS | 214 | 93.027 | -14.377 | 41.047 | 1.00 | 29.68 | H | C |
| ATOM | 3041 | O | LYS | 214 | 94.160 | -14.549 | 40.585 | 1.00 | 27.06 | H | O |
| ATOM | 3042 | N | LYS | 215 | 92.533 | -15.103 | 42.045 | 1.00 | 38.49 | H | N |
| ATOM | 3043 | CA | LYS | 215 | 93.289 | -16.207 | 42.617 | 1.00 | 34.59 | H | C |
| ATOM | 3044 | CB | LYS | 215 | 92.788 | -16.531 | 44.032 | 0.00 | 48.10 | H | C |
| ATOM | 3045 | CG | LYS | 215 | 92.812 | -15.343 | 44.987 | 0.00 | 42.43 | H | C |
| ATOM | 3046 | CD | LYS | 215 | 92.403 | -15.737 | 46.401 | 0.00 | 38.17 | H | C |
| ATOM | 3047 | CE | LYS | 215 | 93.458 | -16.597 | 47.089 | 0.00 | 35.48 | H | C |
| ATOM | 3048 | NZ | LYS | 215 | 93.695 | -17.895 | 46.397 | 0.00 | 33.32 | H | N |
| ATOM | 3049 | C | LYS | 215 | 93.042 | -17.391 | 41.675 | 1.00 | 36.50 | H | C |
| ATOM | 3050 | O | LYS | 215 | 91.901 | -17.770 | 41.413 | 1.00 | 38.63 | H | O |
| ATOM | 3051 | N | VAL | 216 | 94.113 | -17.939 | 41.122 | 1.00 | 32.15 | H | N |
| ATOM | 3052 | CA | VAL | 216 | 93.996 | -19.081 | 40.224 | 1.00 | 32.08 | H | C |
| ATOM | 3053 | CB | VAL | 216 | 94.801 | -18.850 | 38.923 | 1.00 | 21.03 | H | C |
| ATOM | 3054 | CG1 | VAL | 216 | 94.435 | -19.912 | 37.880 | 1.00 | 20.14 | H | C |
| ATOM | 3055 | CG2 | VAL | 216 | 94.482 | -17.480 | 38.375 | 1.00 | 18.92 | H | C |
| ATOM | 3056 | C | VAL | 216 | 94.504 | -20.334 | 40.948 | 1.00 | 33.21 | H | C |
| ATOM | 3057 | O | VAL | 216 | 95.696 | -20.441 | 41.248 | 1.00 | 33.32 | H | O |
| ATOM | 3058 | N | GLU | 217 | 93.586 | -21.269 | 41.219 | 1.00 | 45.06 | H | N |
| ATOM | 3059 | CA | GLU | 217 | 93.871 | -22.508 | 41.949 | 1.00 | 48.19 | H | C |
| ATOM | 3060 | CB | GLU | 217 | 93.065 | -22.532 | 43.250 | 1.00 | 91.11 | H | C |
| ATOM | 3061 | CG | GLU | 217 | 93.114 | -21.248 | 44.065 | 1.00 | 95.99 | H | C |
| ATOM | 3062 | CD | GLU | 217 | 91.872 | -21.005 | 44.901 | 1.00 | 101.94 | H | C |
| ATOM | 3063 | OE1 | GLU | 217 | 90.757 | -21.353 | 44.453 | 1.00 | 105.02 | H | O |
| ATOM | 3064 | OE2 | GLU | 217 | 92.013 | -20.475 | 46.029 | 1.00 | 105.37 | H | O |
| ATOM | 3065 | C | GLU | 217 | 93.426 | -23.720 | 41.109 | 1.00 | 48.96 | H | C |
| ATOM | 3066 | O | GLU | 217 | 92.500 | -23.643 | 40.332 | 1.00 | 51.24 | H | O |

FIG. 19A-43

| | | | | | | | | | | |
|---|---|---|---|---|---|---|---|---|---|---|
| ATOM | 3067 | N | PRO | 218 | 94.078 | -24.870 | 41.265 | 1.00 | 42.53 | H | N |
| ATOM | 3068 | CD | PRO | 218 | 95.339 | -25.074 | 41.993 | 1.00 | 48.02 | H | C |
| ATOM | 3069 | CA | PRO | 218 | 93.711 | -26.079 | 40.509 | 1.00 | 40.69 | H | C |
| ATOM | 3070 | CB | PRO | 218 | 94.962 | -26.924 | 40.609 | 1.00 | 42.70 | H | C |
| ATOM | 3071 | CG | PRO | 218 | 95.482 | -26.557 | 41.957 | 1.00 | 44.19 | H | C |
| ATOM | 3072 | C | PRO | 218 | 92.544 | -26.782 | 41.183 | 1.00 | 41.85 | H | C |
| ATOM | 3073 | O | PRO | 218 | 92.513 | -26.844 | 42.403 | 1.00 | 45.36 | H | O |
| ATOM | 3074 | N | LYS | 219 | 91.638 | -27.354 | 40.396 | 1.00 | 112.06 | H | N |
| ATOM | 3075 | CA | LYS | 219 | 90.475 | -28.045 | 40.934 | 1.00 | 111.92 | H | C |
| ATOM | 3076 | CB | LYS | 219 | 89.635 | -28.618 | 39.794 | 0.00 | 52.93 | H | C |
| ATOM | 3077 | CG | LYS | 219 | 89.522 | -27.658 | 38.654 | 0.00 | 47.21 | H | C |
| ATOM | 3078 | CD | LYS | 219 | 88.205 | -27.801 | 37.948 | 0.00 | 42.71 | H | C |
| ATOM | 3079 | CE | LYS | 219 | 88.174 | -26.793 | 36.845 | 0.00 | 39.84 | H | C |
| ATOM | 3080 | NZ | LYS | 219 | 86.847 | -26.599 | 36.249 | 0.00 | 37.57 | H | N |
| ATOM | 3081 | C | LYS | 219 | 90.867 | -29.169 | 41.892 | 1.00 | 116.73 | H | C |
| ATOM | 3082 | O | LYS | 219 | 90.330 | -29.223 | 43.021 | 1.00 | 116.18 | H | O |
| ATOM | 3083 | OXT | LYS | 219 | 91.705 | -30.007 | 41.503 | 1.00 | 36.39 | H | O |
| ATOM | 3084 | CB | ILE | 2 | 109.298 | 10.543 | -2.157 | 1.00 | 31.85 | L | C |
| ATOM | 3085 | CG2 | ILE | 2 | 110.285 | 9.382 | -2.130 | 1.00 | 31.85 | L | C |
| ATOM | 3086 | CG1 | ILE | 2 | 109.803 | 11.664 | -3.069 | 1.00 | 31.85 | L | C |
| ATOM | 3087 | CD1 | ILE | 2 | 111.143 | 12.240 | -2.656 | 1.00 | 31.85 | L | C |
| ATOM | 3088 | C | ILE | 2 | 107.518 | 8.858 | -1.778 | 1.00 | 41.66 | L | C |
| ATOM | 3089 | O | ILE | 2 | 107.155 | 9.019 | -0.613 | 1.00 | 41.66 | L | O |
| ATOM | 3090 | N | ILE | 2 | 106.898 | 11.133 | -2.646 | 1.00 | 41.66 | L | N |
| ATOM | 3091 | CA | ILE | 2 | 107.922 | 10.043 | -2.648 | 1.00 | 41.66 | L | C |
| ATOM | 3092 | N | GLN | 3 | 107.597 | 7.665 | -2.361 | 1.00 | 28.81 | L | N |
| ATOM | 3093 | CA | GLN | 3 | 107.244 | 6.433 | -1.669 | 1.00 | 28.81 | L | C |
| ATOM | 3094 | CB | GLN | 3 | 106.206 | 5.677 | -2.484 | 1.00 | 56.92 | L | C |
| ATOM | 3095 | CG | GLN | 3 | 105.708 | 4.412 | -1.837 | 1.00 | 56.92 | L | C |
| ATOM | 3096 | CD | GLN | 3 | 104.579 | 3.778 | -2.622 | 1.00 | 56.92 | L | C |
| ATOM | 3097 | OE1 | GLN | 3 | 104.124 | 2.681 | -2.298 | 1.00 | 56.92 | L | O |
| ATOM | 3098 | NE2 | GLN | 3 | 104.116 | 4.469 | -3.661 | 1.00 | 56.92 | L | N |
| ATOM | 3099 | C | GLN | 3 | 108.482 | 5.557 | -1.428 | 1.00 | 28.81 | L | C |
| ATOM | 3100 | O | GLN | 3 | 109.297 | 5.322 | -2.327 | 1.00 | 28.81 | L | O |
| ATOM | 3101 | N | LEU | 4 | 108.615 | 5.088 | -0.195 | 1.00 | 39.62 | L | N |
| ATOM | 3102 | CA | LEU | 4 | 109.744 | 4.260 | 0.198 | 1.00 | 39.62 | L | C |
| ATOM | 3103 | CB | LEU | 4 | 110.377 | 4.820 | 1.469 | 1.00 | 19.64 | L | C |
| ATOM | 3104 | CG | LEU | 4 | 111.546 | 5.792 | 1.348 | 1.00 | 19.64 | L | C |
| ATOM | 3105 | CD1 | LEU | 4 | 111.407 | 6.643 | 0.092 | 1.00 | 19.64 | L | C |
| ATOM | 3106 | CD2 | LEU | 4 | 111.614 | 6.640 | 2.617 | 1.00 | 19.64 | L | C |
| ATOM | 3107 | C | LEU | 4 | 109.323 | 2.823 | 0.445 | 1.00 | 39.62 | L | C |
| ATOM | 3108 | O | LEU | 4 | 108.470 | 2.548 | 1.289 | 1.00 | 39.62 | L | O |
| ATOM | 3109 | N | THR | 5 | 109.935 | 1.903 | -0.289 | 1.00 | 16.92 | L | N |
| ATOM | 3110 | CA | THR | 5 | 109.634 | 0.485 | -0.152 | 1.00 | 16.92 | L | C |
| ATOM | 3111 | CB | THR | 5 | 108.945 | -0.038 | -1.437 | 1.00 | 21.45 | L | C |
| ATOM | 3112 | OG1 | THR | 5 | 109.307 | -1.402 | -1.651 | 1.00 | 21.45 | L | O |
| ATOM | 3113 | CG2 | THR | 5 | 109.324 | 0.802 | -2.641 | 1.00 | 21.45 | L | C |
| ATOM | 3114 | C | THR | 5 | 110.908 | -0.312 | 0.186 | 1.00 | 16.92 | L | C |
| ATOM | 3115 | O | THR | 5 | 111.849 | -0.382 | -0.601 | 1.00 | 16.92 | L | O |
| ATOM | 3116 | N | GLN | 6 | 110.919 | -0.880 | 1.391 | 1.00 | 17.69 | L | N |
| ATOM | 3117 | CA | GLN | 6 | 112.040 | -1.661 | 1.933 | 1.00 | 17.69 | L | C |
| ATOM | 3118 | CB | GLN | 6 | 112.078 | -1.544 | 3.468 | 1.00 | 15.96 | L | C |
| ATOM | 3119 | CG | GLN | 6 | 111.898 | -0.138 | 4.014 | 1.00 | 15.96 | L | C |
| ATOM | 3120 | CD | GLN | 6 | 112.007 | -0.060 | 5.535 | 1.00 | 15.96 | L | C |
| ATOM | 3121 | OE1 | GLN | 6 | 111.626 | 0.944 | 6.139 | 1.00 | 15.96 | L | O |
| ATOM | 3122 | NE2 | GLN | 6 | 112.541 | -1.115 | 6.158 | 1.00 | 15.96 | L | N |
| ATOM | 3123 | C | GLN | 6 | 111.962 | -3.143 | 1.588 | 1.00 | 17.69 | L | C |
| ATOM | 3124 | O | GLN | 6 | 110.882 | -3.675 | 1.352 | 1.00 | 17.69 | L | O |
| ATOM | 3125 | N | SER | 7 | 113.107 | -3.814 | 1.595 | 1.00 | 44.56 | L | N |
| ATOM | 3126 | CA | SER | 7 | 113.148 | -5.238 | 1.293 | 1.00 | 44.56 | L | C |
| ATOM | 3127 | CB | SER | 7 | 113.109 | -5.470 | -0.214 | 1.00 | 33.18 | L | C |
| ATOM | 3128 | OG | SER | 7 | 114.194 | -4.813 | -0.837 | 1.00 | 33.18 | L | O |
| ATOM | 3129 | C | SER | 7 | 114.394 | -5.898 | 1.855 | 1.00 | 44.56 | L | C |
| ATOM | 3130 | O | SER | 7 | 115.480 | -5.328 | 1.811 | 1.00 | 44.56 | L | O |
| ATOM | 3131 | N | PRO | 8 | 114.246 | -7.107 | 2.415 | 1.00 | 19.10 | L | N |
| ATOM | 3132 | CD | PRO | 8 | 115.292 | -7.921 | 3.063 | 1.00 | 16.76 | L | C |
| ATOM | 3133 | CA | PRO | 8 | 112.945 | -7.771 | 2.494 | 1.00 | 19.10 | L | C |
| ATOM | 3134 | CB | PRO | 8 | 113.303 | -9.161 | 3.004 | 1.00 | 16.76 | L | C |
| ATOM | 3135 | CG | PRO | 8 | 114.481 | -8.882 | 3.905 | 1.00 | 16.76 | L | C |
| ATOM | 3136 | C | PRO | 8 | 112.068 | -7.023 | 3.479 | 1.00 | 19.10 | L | C |
| ATOM | 3137 | O | PRO | 8 | 112.517 | -6.069 | 4.125 | 1.00 | 19.10 | L | O |
| ATOM | 3138 | N | SER | 9 | 110.822 | -7.460 | 3.589 | 1.00 | 12.41 | L | N |
| ATOM | 3139 | CA | SER | 9 | 109.885 | -6.851 | 4.516 | 1.00 | 12.41 | L | C |

FIG. 19A-44

```
ATOM  3140  CB   SER   9   108.466  -7.059   4.023  1.00  25.43  L  C
ATOM  3141  OG   SER   9   108.345  -6.555   2.707  1.00  25.43  L  O
ATOM  3142  C    SER   9   110.083  -7.558   5.837  1.00  12.41  L  C
ATOM  3143  O    SER   9   109.904  -6.983   6.904  1.00  12.41  L  O
ATOM  3144  N    SER  10   110.492  -8.817   5.745  1.00  33.63  L  N
ATOM  3145  CA   SER  10   110.720  -9.645   6.910  1.00  33.63  L  C
ATOM  3146  CB   SER  10   109.490 -10.517   7.144  1.00  43.13  L  C
ATOM  3147  OG   SER  10   109.614 -11.248   8.338  1.00  43.13  L  O
ATOM  3148  C    SER  10   111.942 -10.504   6.624  1.00  33.63  L  C
ATOM  3149  O    SER  10   112.226 -10.814   5.470  1.00  33.63  L  O
ATOM  3150  N    LEU  11   112.677 -10.880   7.666  1.00  38.19  L  N
ATOM  3151  CA   LEU  11   113.867 -11.709   7.484  1.00  38.19  L  C
ATOM  3152  CB   LEU  11   115.020 -10.880   6.894  1.00  33.64  L  C
ATOM  3153  CG   LEU  11   115.721  -9.849   7.793  1.00  33.64  L  C
ATOM  3154  CD1  LEU  11   116.757 -10.532   8.667  1.00  33.64  L  C
ATOM  3155  CD2  LEU  11   116.401  -8.807   6.927  1.00  33.64  L  C
ATOM  3156  C    LEU  11   114.319 -12.335   8.792  1.00  38.19  L  C
ATOM  3157  O    LEU  11   114.365 -11.672   9.829  1.00  38.19  L  O
ATOM  3158  N    SER  12   114.661 -13.616   8.736  1.00  42.98  L  N
ATOM  3159  CA   SER  12   115.128 -14.320   9.916  1.00  42.98  L  C
ATOM  3160  CB   SER  12   114.334 -15.612  10.103  1.00  67.78  L  C
ATOM  3161  OG   SER  12   114.474 -16.092  11.426  1.00  67.78  L  O
ATOM  3162  C    SER  12   116.611 -14.628   9.738  1.00  42.98  L  C
ATOM  3163  O    SER  12   117.031 -15.118   8.697  1.00  42.98  L  O
ATOM  3164  N    ALA  13   117.407 -14.320  10.749  1.00  25.03  L  N
ATOM  3165  CA   ALA  13   118.836 -14.575  10.667  1.00  25.03  L  C
ATOM  3166  CB   ALA  13   119.556 -13.340  10.124  1.00  41.64  L  C
ATOM  3167  C    ALA  13   119.390 -14.952  12.037  1.00  25.03  L  C
ATOM  3168  O    ALA  13   118.829 -14.571  13.067  1.00  25.03  L  O
ATOM  3169  N    SER  14   120.493 -15.701  12.045  1.00  32.48  L  N
ATOM  3170  CA   SER  14   121.111 -16.132  13.294  1.00  32.48  L  C
ATOM  3171  CB   SER  14   121.594 -17.569  13.160  1.00  77.12  L  C
ATOM  3172  OG   SER  14   122.348 -17.721  11.975  1.00  77.12  L  O
ATOM  3173  C    SER  14   122.269 -15.231  13.691  1.00  32.48  L  C
ATOM  3174  O    SER  14   122.893 -14.595  12.841  1.00  32.48  L  O
ATOM  3175  N    VAL  15   122.545 -15.166  14.988  1.00  47.29  L  N
ATOM  3176  CA   VAL  15   123.637 -14.336  15.470  1.00  47.29  L  C
ATOM  3177  CB   VAL  15   123.996 -14.657  16.937  1.00  53.16  L  C
ATOM  3178  CG1  VAL  15   123.121 -13.847  17.881  1.00  53.16  L  C
ATOM  3179  CG2  VAL  15   123.808 -16.148  17.198  1.00  53.16  L  C
ATOM  3180  C    VAL  15   124.858 -14.575  14.606  1.00  47.29  L  C
ATOM  3181  O    VAL  15   125.164 -15.712  14.250  1.00  47.29  L  O
ATOM  3182  N    GLY  16   125.537 -13.495  14.247  1.00  32.44  L  N
ATOM  3183  CA   GLY  16   126.728 -13.615  13.431  1.00  32.44  L  C
ATOM  3184  C    GLY  16   126.506 -13.463  11.945  1.00  32.44  L  C
ATOM  3185  O    GLY  16   127.467 -13.306  11.191  1.00  32.44  L  O
ATOM  3186  N    ASP  17   125.255 -13.524  11.510  1.00  32.03  L  N
ATOM  3187  CA   ASP  17   124.959 -13.367  10.092  1.00  32.03  L  C
ATOM  3188  CB   ASP  17   123.533 -13.814   9.788  1.00  55.01  L  C
ATOM  3189  CG   ASP  17   123.344 -15.291   9.961  1.00  55.01  L  C
ATOM  3190  OD1  ASP  17   122.211 -15.771   9.739  1.00  55.01  L  O
ATOM  3191  OD2  ASP  17   124.331 -15.965  10.320  1.00  55.01  L  O
ATOM  3192  C    ASP  17   125.109 -11.905   9.677  1.00  32.03  L  C
ATOM  3193  O    ASP  17   125.041 -10.997  10.517  1.00  32.03  L  O
ATOM  3194  N    ARG  18   125.324 -11.680   8.385  1.00  40.86  L  N
ATOM  3195  CA   ARG  18   125.447 -10.325   7.875  1.00  40.86  L  C
ATOM  3196  CB   ARG  18   126.587 -10.231   6.865  1.00  78.37  L  C
ATOM  3197  CG   ARG  18   126.790  -8.842   6.293  1.00  78.37  L  C
ATOM  3198  CD   ARG  18   128.223  -8.662   5.812  1.00  78.37  L  C
ATOM  3199  NE   ARG  18   128.413  -7.408   5.087  1.00  78.37  L  N
ATOM  3200  CZ   ARG  18   127.841  -7.131   3.918  1.00  78.37  L  C
ATOM  3201  NH1  ARG  18   127.042  -8.021   3.336  1.00  78.37  L  N
ATOM  3202  NH2  ARG  18   128.064  -5.960   3.334  1.00  78.37  L  N
ATOM  3203  C    ARG  18   124.116  -9.986   7.220  1.00  40.86  L  C
ATOM  3204  O    ARG  18   123.690 -10.656   6.284  1.00  40.86  L  O
ATOM  3205  N    VAL  19   123.455  -8.948   7.721  1.00  26.42  L  N
ATOM  3206  CA   VAL  19   122.157  -8.549   7.193  1.00  26.42  L  C
ATOM  3207  CB   VAL  19   121.154  -8.426   8.335  1.00  32.94  L  C
ATOM  3208  CG1  VAL  19   119.768  -8.214   7.783  1.00  32.94  L  C
ATOM  3209  CG2  VAL  19   121.204  -9.678   9.194  1.00  32.94  L  C
ATOM  3210  C    VAL  19   122.200  -7.235   6.420  1.00  26.42  L  C
ATOM  3211  O    VAL  19   122.902  -6.306   6.798  1.00  26.42  L  O
ATOM  3212  N    THR  20   121.443  -7.160   5.333  1.00  42.24  L  N
```

FIG. 19A-45

| ATOM | 3213 | CA | THR | 20 | 121.408 | -5.950 | 4.519 | 1.00 | 42.24 | L | C |
|---|---|---|---|---|---|---|---|---|---|---|---|
| ATOM | 3214 | CB | THR | 20 | 122.310 | -6.097 | 3.289 | 1.00 | 29.90 | L | C |
| ATOM | 3215 | OG1 | THR | 20 | 123.680 | -6.127 | 3.714 | 1.00 | 29.90 | L | O |
| ATOM | 3216 | CG2 | THR | 20 | 122.099 | -4.944 | 2.326 | 1.00 | 29.90 | L | C |
| ATOM | 3217 | C | THR | 20 | 120.008 | -5.582 | 4.050 | 1.00 | 42.24 | L | C |
| ATOM | 3218 | O | THR | 20 | 119.477 | -6.202 | 3.127 | 1.00 | 42.24 | L | O |
| ATOM | 3219 | N | ILE | 21 | 119.418 | -4.568 | 4.683 | 1.00 | 13.95 | L | N |
| ATOM | 3220 | CA | ILE | 21 | 118.077 | -4.114 | 4.326 | 1.00 | 13.95 | L | C |
| ATOM | 3221 | CB | ILE | 21 | 117.349 | -3.486 | 5.541 | 1.00 | 24.11 | L | C |
| ATOM | 3222 | CG2 | ILE | 21 | 115.892 | -3.176 | 5.186 | 1.00 | 24.11 | L | C |
| ATOM | 3223 | CG1 | ILE | 21 | 117.390 | -4.457 | 6.720 | 1.00 | 24.11 | L | C |
| ATOM | 3224 | CD1 | ILE | 21 | 116.709 | -3.936 | 7.960 | 1.00 | 24.11 | L | C |
| ATOM | 3225 | C | ILE | 21 | 118.180 | -3.081 | 3.217 | 1.00 | 13.95 | L | C |
| ATOM | 3226 | O | ILE | 21 | 119.036 | -2.208 | 3.251 | 1.00 | 13.95 | L | O |
| ATOM | 3227 | N | THR | 22 | 117.305 | -3.190 | 2.230 | 1.00 | 27.07 | L | N |
| ATOM | 3228 | CA | THR | 22 | 117.304 | -2.266 | 1.107 | 1.00 | 27.07 | L | C |
| ATOM | 3229 | CB | THR | 22 | 117.335 | -3.022 | -0.239 | 1.00 | 29.03 | L | C |
| ATOM | 3230 | OG1 | THR | 22 | 118.613 | -3.642 | -0.404 | 1.00 | 29.03 | L | O |
| ATOM | 3231 | CG2 | THR | 22 | 117.084 | -2.084 | -1.391 | 1.00 | 29.03 | L | C |
| ATOM | 3232 | C | THR | 22 | 116.067 | -1.385 | 1.123 | 1.00 | 27.07 | L | C |
| ATOM | 3233 | O | THR | 22 | 114.951 | -1.871 | 1.313 | 1.00 | 27.07 | L | O |
| ATOM | 3234 | N | CYS | 23 | 116.281 | -0.089 | 0.916 | 1.00 | 32.83 | L | N |
| ATOM | 3235 | CA | CYS | 23 | 115.203 | 0.896 | 0.882 | 1.00 | 32.83 | L | C |
| ATOM | 3236 | C | CYS | 23 | 115.259 | 1.546 | -0.489 | 1.00 | 32.83 | L | C |
| ATOM | 3237 | O | CYS | 23 | 116.250 | 2.187 | -0.837 | 1.00 | 32.83 | L | O |
| ATOM | 3238 | CB | CYS | 23 | 115.424 | 1.947 | 1.973 | 1.00 | 18.66 | L | C |
| ATOM | 3239 | SG | CYS | 23 | 114.216 | 3.310 | 2.141 | 1.00 | 18.66 | L | S |
| ATOM | 3240 | N | SER | 24 | 114.199 | 1.355 | -1.268 | 1.00 | 11.34 | L | N |
| ATOM | 3241 | CA | SER | 24 | 114.110 | 1.924 | -2.612 | 1.00 | 11.34 | L | C |
| ATOM | 3242 | CB | SER | 24 | 113.696 | 0.853 | -3.614 | 1.00 | 28.67 | L | C |
| ATOM | 3243 | OG | SER | 24 | 114.642 | -0.190 | -3.632 | 1.00 | 28.67 | L | O |
| ATOM | 3244 | C | SER | 24 | 113.096 | 3.058 | -2.641 | 1.00 | 11.34 | L | C |
| ATOM | 3245 | O | SER | 24 | 111.971 | 2.910 | -2.154 | 1.00 | 11.34 | L | O |
| ATOM | 3246 | N | ALA | 25 | 113.496 | 4.186 | -3.217 | 1.00 | 32.05 | L | N |
| ATOM | 3247 | CA | ALA | 25 | 112.617 | 5.343 | -3.286 | 1.00 | 32.05 | L | C |
| ATOM | 3248 | CB | ALA | 25 | 113.312 | 6.567 | -2.707 | 1.00 | 44.86 | L | C |
| ATOM | 3249 | C | ALA | 25 | 112.139 | 5.633 | -4.699 | 1.00 | 32.05 | L | C |
| ATOM | 3250 | O | ALA | 25 | 112.918 | 5.619 | -5.658 | 1.00 | 32.05 | L | O |
| ATOM | 3251 | N | SER | 26 | 110.839 | 5.901 | -4.803 | 1.00 | 26.80 | L | N |
| ATOM | 3252 | CA | SER | 26 | 110.179 | 6.204 | -6.070 | 1.00 | 26.80 | L | C |
| ATOM | 3253 | CB | SER | 26 | 108.717 | 6.572 | -5.814 | 1.00 | 23.33 | L | C |
| ATOM | 3254 | OG | SER | 26 | 108.617 | 7.713 | -4.984 | 1.00 | 23.33 | L | O |
| ATOM | 3255 | C | SER | 26 | 110.866 | 7.338 | -6.813 | 1.00 | 26.80 | L | C |
| ATOM | 3256 | O | SER | 26 | 110.814 | 7.404 | -8.032 | 1.00 | 26.80 | L | O |
| ATOM | 3257 | N | SER | 27 | 111.496 | 8.234 | -6.066 | 1.00 | 22.71 | L | N |
| ATOM | 3258 | CA | SER | 27 | 112.210 | 9.363 | -6.644 | 1.00 | 22.71 | L | C |
| ATOM | 3259 | CB | SER | 27 | 111.439 | 10.661 | -6.406 | 1.00 | 47.74 | L | C |
| ATOM | 3260 | OG | SER | 27 | 110.105 | 10.552 | -6.862 | 1.00 | 47.74 | L | O |
| ATOM | 3261 | C | SER | 27 | 113.547 | 9.438 | -5.934 | 1.00 | 22.71 | L | C |
| ATOM | 3262 | O | SER | 27 | 113.666 | 8.982 | -4.805 | 1.00 | 22.71 | L | O |
| ATOM | 3263 | N | SER | 28 | 114.555 | 10.004 | -6.586 | 1.00 | 37.73 | L | N |
| ATOM | 3264 | CA | SER | 28 | 115.874 | 10.121 | -5.972 | 1.00 | 37.73 | L | C |
| ATOM | 3265 | CB | SER | 28 | 116.890 | 10.583 | -7.010 | 1.00 | 36.75 | L | C |
| ATOM | 3266 | OG | SER | 28 | 116.486 | 11.818 | -7.573 | 1.00 | 36.75 | L | O |
| ATOM | 3267 | C | SER | 28 | 115.846 | 11.106 | -4.804 | 1.00 | 37.73 | L | C |
| ATOM | 3268 | O | SER | 28 | 115.043 | 12.038 | -4.775 | 1.00 | 37.73 | L | O |
| ATOM | 3269 | N | VAL | 29 | 116.726 | 10.890 | -3.838 | 1.00 | 35.34 | L | N |
| ATOM | 3270 | CA | VAL | 29 | 116.807 | 11.753 | -2.669 | 1.00 | 35.34 | L | C |
| ATOM | 3271 | CB | VAL | 29 | 116.002 | 11.154 | -1.484 | 1.00 | 39.96 | L | C |
| ATOM | 3272 | CG1 | VAL | 29 | 114.521 | 11.097 | -1.842 | 1.00 | 39.96 | L | C |
| ATOM | 3273 | CG2 | VAL | 29 | 116.506 | 9.755 | -1.147 | 1.00 | 39.96 | L | C |
| ATOM | 3274 | C | VAL | 29 | 118.277 | 11.895 | -2.289 | 1.00 | 35.34 | L | C |
| ATOM | 3275 | O | VAL | 29 | 119.076 | 11.001 | -2.571 | 1.00 | 35.34 | L | O |
| ATOM | 3276 | N | ASN | 30 | 118.641 | 13.007 | -1.658 | 1.00 | 55.44 | L | N |
| ATOM | 3277 | CA | ASN | 30 | 120.033 | 13.236 | -1.278 | 1.00 | 55.44 | L | C |
| ATOM | 3278 | CB | ASN | 30 | 120.252 | 14.722 | -0.974 | 1.00 | 66.75 | L | C |
| ATOM | 3279 | CG | ASN | 30 | 119.176 | 15.292 | -0.071 | 1.00 | 66.75 | L | C |
| ATOM | 3280 | OD1 | ASN | 30 | 118.006 | 15.359 | -0.453 | 1.00 | 66.75 | L | O |
| ATOM | 3281 | ND2 | ASN | 30 | 119.561 | 15.694 | 1.138 | 1.00 | 66.75 | L | N |
| ATOM | 3282 | C | ASN | 30 | 120.510 | 12.386 | -0.095 | 1.00 | 55.44 | L | C |
| ATOM | 3283 | O | ASN | 30 | 121.705 | 12.099 | 0.033 | 1.00 | 55.44 | L | O |
| ATOM | 3284 | N | HIS | 31 | 119.586 | 11.985 | 0.770 | 1.00 | 34.66 | L | N |
| ATOM | 3285 | CA | HIS | 31 | 119.947 | 11.172 | 1.923 | 1.00 | 34.66 | L | C |

FIG. 19A-46

```
ATOM   3286  CB   HIS  31    120.290  12.049   3.132  1.00  51.96  L  C
ATOM   3287  CG   HIS  31    121.623  12.725   3.042  1.00  51.96  L  C
ATOM   3288  CD2  HIS  31    122.763  12.534   3.744  1.00  51.96  L  C
ATOM   3289  ND1  HIS  31    121.879  13.763   2.172  1.00  51.96  L  N
ATOM   3290  CE1  HIS  31    123.118  14.186   2.345  1.00  51.96  L  C
ATOM   3291  NE2  HIS  31    123.676  13.457   3.294  1.00  51.96  L  N
ATOM   3292  C    HIS  31    118.811  10.241   2.316  1.00  34.66  L  C
ATOM   3293  O    HIS  31    117.736  10.267   1.707  1.00  34.66  L  O
ATOM   3294  N    MET  32    119.070   9.415   3.332  1.00  24.85  L  N
ATOM   3295  CA   MET  32    118.081   8.489   3.864  1.00  24.85  L  C
ATOM   3296  CB   MET  32    118.189   7.126   3.187  1.00  22.87  L  C
ATOM   3297  CG   MET  32    116.961   6.226   3.394  1.00  22.87  L  C
ATOM   3298  SD   MET  32    115.381   6.922   2.757  1.00  22.87  L  S
ATOM   3299  CE   MET  32    115.727   7.028   1.012  1.00  22.87  L  C
ATOM   3300  C    MET  32    118.316   8.340   5.360  1.00  24.85  L  C
ATOM   3301  O    MET  32    119.454   8.377   5.831  1.00  24.85  L  O
ATOM   3302  N    PHE  33    117.244   8.180   6.118  1.00   7.47  L  N
ATOM   3303  CA   PHE  33    117.391   8.029   7.554  1.00   7.47  L  C
ATOM   3304  CB   PHE  33    116.693   9.171   8.285  1.00  11.22  L  C
ATOM   3305  CG   PHE  33    117.205  10.533   7.901  1.00  11.22  L  C
ATOM   3306  CD1  PHE  33    116.901  11.078   6.652  1.00  11.22  L  C
ATOM   3307  CD2  PHE  33    118.017  11.259   8.776  1.00  11.22  L  C
ATOM   3308  CE1  PHE  33    117.399  12.325   6.275  1.00  11.22  L  C
ATOM   3309  CE2  PHE  33    118.519  12.501   8.407  1.00  11.22  L  C
ATOM   3310  CZ   PHE  33    118.207  13.035   7.149  1.00  11.22  L  C
ATOM   3311  C    PHE  33    116.817   6.702   7.994  1.00   7.47  L  C
ATOM   3312  O    PHE  33    115.959   6.150   7.320  1.00   7.47  L  O
ATOM   3313  N    TRP  34    117.301   6.186   9.118  1.00  15.67  L  N
ATOM   3314  CA   TRP  34    116.815   4.912   9.618  1.00  15.67  L  C
ATOM   3315  CB   TRP  34    117.859   3.818   9.414  1.00  16.49  L  C
ATOM   3316  CG   TRP  34    118.217   3.590   7.992  1.00  16.49  L  C
ATOM   3317  CD2  TRP  34    117.671   2.592   7.123  1.00  16.49  L  C
ATOM   3318  CE2  TRP  34    118.315   2.732   5.872  1.00  16.49  L  C
ATOM   3319  CE3  TRP  34    116.702   1.596   7.279  1.00  16.49  L  C
ATOM   3320  CD1  TRP  34    119.137   4.278   7.259  1.00  16.49  L  C
ATOM   3321  NE1  TRP  34    119.205   3.767   5.984  1.00  16.49  L  N
ATOM   3322  CZ2  TRP  34    118.024   1.914   4.782  1.00  16.49  L  C
ATOM   3323  CZ3  TRP  34    116.409   0.780   6.194  1.00  16.49  L  C
ATOM   3324  CH2  TRP  34    117.069   0.945   4.960  1.00  16.49  L  C
ATOM   3325  C    TRP  34    116.459   4.960  11.086  1.00  15.67  L  C
ATOM   3326  O    TRP  34    117.149   5.593  11.882  1.00  15.67  L  O
ATOM   3327  N    TYR  35    115.370   4.288  11.437  1.00  19.71  L  N
ATOM   3328  CA   TYR  35    114.939   4.229  12.820  1.00  19.71  L  C
ATOM   3329  CB   TYR  35    113.591   4.922  13.007  1.00  25.75  L  C
ATOM   3330  CG   TYR  35    113.623   6.381  12.621  1.00  25.75  L  C
ATOM   3331  CD1  TYR  35    113.255   6.790  11.344  1.00  25.75  L  C
ATOM   3332  CE1  TYR  35    113.310   8.124  10.980  1.00  25.75  L  C
ATOM   3333  CD2  TYR  35    114.052   7.353  13.527  1.00  25.75  L  C
ATOM   3334  CE2  TYR  35    114.110   8.685  13.173  1.00  25.75  L  C
ATOM   3335  CZ   TYR  35    113.737   9.064  11.899  1.00  25.75  L  C
ATOM   3336  OH   TYR  35    113.776  10.384  11.540  1.00  25.75  L  O
ATOM   3337  C    TYR  35    114.821   2.781  13.207  1.00  19.71  L  C
ATOM   3338  O    TYR  35    114.508   1.937  12.373  1.00  19.71  L  O
ATOM   3339  N    GLN  36    115.100   2.491  14.468  1.00  30.18  L  N
ATOM   3340  CA   GLN  36    114.987   1.136  14.964  1.00  30.18  L  C
ATOM   3341  CB   GLN  36    116.292   0.659  15.597  1.00  33.56  L  C
ATOM   3342  CG   GLN  36    116.109  -0.625  16.387  1.00  33.56  L  C
ATOM   3343  CD   GLN  36    117.154  -0.806  17.464  1.00  33.56  L  C
ATOM   3344  OE1  GLN  36    118.296  -1.161  17.179  1.00  33.56  L  O
ATOM   3345  NE2  GLN  36    116.770  -0.550  18.716  1.00  33.56  L  N
ATOM   3346  C    GLN  36    113.902   1.124  16.017  1.00  30.18  L  C
ATOM   3347  O    GLN  36    113.986   1.852  17.008  1.00  30.18  L  O
ATOM   3348  N    GLN  37    112.877   0.311  15.803  1.00  31.84  L  N
ATOM   3349  CA   GLN  37    111.811   0.209  16.778  1.00  31.84  L  C
ATOM   3350  CB   GLN  37    110.467   0.599  16.162  1.00  26.28  L  C
ATOM   3351  CG   GLN  37    109.335   0.494  17.165  1.00  26.28  L  C
ATOM   3352  CD   GLN  37    108.003   0.979  16.632  1.00  26.28  L  C
ATOM   3353  OE1  GLN  37    107.573   0.597  15.537  1.00  26.28  L  O
ATOM   3354  NE2  GLN  37    107.328   1.819  17.417  1.00  26.28  L  N
ATOM   3355  C    GLN  37    111.729  -1.201  17.360  1.00  31.84  L  C
ATOM   3356  O    GLN  37    111.571  -2.189  16.637  1.00  31.84  L  O
ATOM   3357  N    LYS  38    111.861  -1.285  18.676  1.00  33.78  L  N
ATOM   3358  CA   LYS  38    111.776  -2.561  19.366  1.00  33.78  L  C
```

FIG. 19A-47

```
ATOM   3359  CB   LYS  38    112.784   -2.618   20.519  1.00   38.31   L   C
ATOM   3360  CG   LYS  38    114.209   -2.306   20.094  1.00   38.31   L   C
ATOM   3361  CD   LYS  38    115.224   -2.552   21.207  1.00   38.31   L   C
ATOM   3362  CE   LYS  38    115.494   -4.034   21.402  1.00   38.31   L   C
ATOM   3363  NZ   LYS  38    115.954   -4.720   20.154  1.00   38.31   L   N
ATOM   3364  C    LYS  38    110.346   -2.671   19.889  1.00   33.78   L   C
ATOM   3365  O    LYS  38    109.770   -1.690   20.354  1.00   33.78   L   O
ATOM   3366  N    PRO  39    109.757   -3.873   19.818  1.00   36.51   L   N
ATOM   3367  CD   PRO  39    110.419   -5.128   19.422  1.00   56.09   L   C
ATOM   3368  CA   PRO  39    108.389   -4.139   20.271  1.00   36.51   L   C
ATOM   3369  CB   PRO  39    108.376   -5.652   20.409  1.00   56.09   L   C
ATOM   3370  CG   PRO  39    109.254   -6.072   19.283  1.00   56.09   L   C
ATOM   3371  C    PRO  39    107.976   -3.434   21.559  1.00   36.51   L   C
ATOM   3372  O    PRO  39    108.664   -3.523   22.573  1.00   36.51   L   O
ATOM   3373  N    GLY  40    106.846   -2.735   21.503  1.00   29.94   L   N
ATOM   3374  CA   GLY  40    106.330   -2.036   22.667  1.00   29.94   L   C
ATOM   3375  C    GLY  40    107.025   -0.738   23.034  1.00   29.94   L   C
ATOM   3376  O    GLY  40    106.669   -0.119   24.037  1.00   29.94   L   O
ATOM   3377  N    LYS  41    108.019   -0.332   22.243  1.00   32.57   L   N
ATOM   3378  CA   LYS  41    108.754    0.903   22.503  1.00   32.57   L   C
ATOM   3379  CB   LYS  41    110.231    0.611   22.804  1.00   82.45   L   C
ATOM   3380  CG   LYS  41    110.466   -0.251   24.040  1.00   82.45   L   C
ATOM   3381  CD   LYS  41    111.905   -0.157   24.579  1.00   82.45   L   C
ATOM   3382  CE   LYS  41    112.977   -0.603   23.575  1.00   82.45   L   C
ATOM   3383  NZ   LYS  41    113.257    0.396   22.496  1.00   82.45   L   N
ATOM   3384  C    LYS  41    108.656    1.860   21.319  1.00   32.57   L   C
ATOM   3385  O    LYS  41    108.243    1.480   20.227  1.00   32.57   L   O
ATOM   3386  N    ALA  42    109.029    3.112   21.547  1.00   30.66   L   N
ATOM   3387  CA   ALA  42    108.990    4.126   20.502  1.00   30.66   L   C
ATOM   3388  CB   ALA  42    108.980    5.513   21.129  1.00   32.87   L   C
ATOM   3389  C    ALA  42    110.209    3.973   19.606  1.00   30.66   L   C
ATOM   3390  O    ALA  42    111.235    3.436   20.028  1.00   30.66   L   O
ATOM   3391  N    PRO  43    110.112    4.435   18.351  1.00   23.79   L   N
ATOM   3392  CD   PRO  43    108.939    4.976   17.647  1.00    7.10   L   C
ATOM   3393  CA   PRO  43    111.248    4.323   17.440  1.00   23.79   L   C
ATOM   3394  CB   PRO  43    110.727    4.980   16.170  1.00    7.10   L   C
ATOM   3395  CG   PRO  43    109.275    4.677   16.212  1.00    7.10   L   C
ATOM   3396  C    PRO  43    112.476    5.042   18.007  1.00   23.79   L   C
ATOM   3397  O    PRO  43    112.359    5.903   18.877  1.00   23.79   L   O
ATOM   3398  N    LYS  44    113.652    4.678   17.514  1.00   26.42   L   N
ATOM   3399  CA   LYS  44    114.888    5.283   17.972  1.00   26.42   L   C
ATOM   3400  CB   LYS  44    115.656    4.289   18.843  1.00   45.11   L   C
ATOM   3401  CG   LYS  44    115.840    4.724   20.288  1.00   45.11   L   C
ATOM   3402  CD   LYS  44    116.535    3.651   21.131  1.00   45.11   L   C
ATOM   3403  CE   LYS  44    115.656    2.400   21.338  1.00   45.11   L   C
ATOM   3404  NZ   LYS  44    115.359    1.613   20.087  1.00   45.11   L   N
ATOM   3405  C    LYS  44    115.741    5.673   16.767  1.00   26.42   L   C
ATOM   3406  O    LYS  44    115.898    4.888   15.829  1.00   26.42   L   O
ATOM   3407  N    PRO  45    116.287    6.902   16.764  1.00   19.50   L   N
ATOM   3408  CD   PRO  45    116.146    7.943   17.794  1.00    7.61   L   C
ATOM   3409  CA   PRO  45    117.132    7.362   15.649  1.00   19.50   L   C
ATOM   3410  CB   PRO  45    117.638    8.720   16.120  1.00    7.61   L   C
ATOM   3411  CG   PRO  45    116.547    9.180   17.041  1.00    7.61   L   C
ATOM   3412  C    PRO  45    118.273    6.367   15.542  1.00   19.50   L   C
ATOM   3413  O    PRO  45    118.925    6.082   16.549  1.00   19.50   L   O
ATOM   3414  N    TRP  46    118.521    5.848   14.342  1.00   23.41   L   N
ATOM   3415  CA   TRP  46    119.581    4.861   14.158  1.00   23.41   L   C
ATOM   3416  CB   TRP  46    118.980    3.559   13.643  1.00   20.77   L   C
ATOM   3417  CG   TRP  46    119.662    2.382   14.178  1.00   20.77   L   C
ATOM   3418  CD2  TRP  46    119.738    2.007   15.554  1.00   20.77   L   C
ATOM   3419  CE2  TRP  46    120.509    0.829   15.624  1.00   20.77   L   C
ATOM   3420  CE3  TRP  46    119.229    2.554   16.737  1.00   20.77   L   C
ATOM   3421  CD1  TRP  46    120.365    1.446   13.481  1.00   20.77   L   C
ATOM   3422  NE1  TRP  46    120.879    0.504   14.345  1.00   20.77   L   N
ATOM   3423  CZ2  TRP  46    120.786    0.191   16.834  1.00   20.77   L   C
ATOM   3424  CZ3  TRP  46    119.505    1.918   17.938  1.00   20.77   L   C
ATOM   3425  CH2  TRP  46    120.276    0.750   17.977  1.00   20.77   L   C
ATOM   3426  C    TRP  46    120.691    5.302   13.209  1.00   23.41   L   C
ATOM   3427  O    TRP  46    121.871    5.174   13.507  1.00   23.41   L   O
ATOM   3428  N    ILE  47    120.306    5.806   12.048  1.00   21.62   L   N
ATOM   3429  CA   ILE  47    121.275    6.248   11.073  1.00   21.62   L   C
ATOM   3430  CB   ILE  47    121.515    5.160   10.008  1.00   12.16   L   C
ATOM   3431  CG2  ILE  47    122.473    5.668    8.929  1.00   12.16   L   C
```

FIG. 19A-48

| ATOM | 3432 | CG1 | ILE | 47 | 122.067 | 3.902 | 10.670 | 1.00 | 12.16 | L | C |
|---|---|---|---|---|---|---|---|---|---|---|---|
| ATOM | 3433 | CD1 | ILE | 47 | 122.301 | 2.746 | 9.686 | 1.00 | 12.16 | L | C |
| ATOM | 3434 | C | ILE | 47 | 120.694 | 7.482 | 10.408 | 1.00 | 21.62 | L | C |
| ATOM | 3435 | O | ILE | 47 | 119.600 | 7.424 | 9.840 | 1.00 | 21.62 | L | O |
| ATOM | 3436 | N | TYR | 48 | 121.408 | 8.603 | 10.510 | 1.00 | 27.63 | L | N |
| ATOM | 3437 | CA | TYR | 48 | 120.961 | 9.842 | 9.887 | 1.00 | 27.63 | L | C |
| ATOM | 3438 | CB | TYR | 48 | 120.899 | 10.992 | 10.892 | 1.00 | 47.89 | L | C |
| ATOM | 3439 | CG | TYR | 48 | 122.206 | 11.318 | 11.564 | 1.00 | 47.89 | L | C |
| ATOM | 3440 | CD1 | TYR | 48 | 122.762 | 10.454 | 12.502 | 1.00 | 47.89 | L | C |
| ATOM | 3441 | CE1 | TYR | 48 | 123.961 | 10.766 | 13.143 | 1.00 | 47.89 | L | C |
| ATOM | 3442 | CD2 | TYR | 48 | 122.881 | 12.503 | 11.277 | 1.00 | 47.89 | L | C |
| ATOM | 3443 | CE2 | TYR | 48 | 124.078 | 12.827 | 11.907 | 1.00 | 47.89 | L | C |
| ATOM | 3444 | CZ | TYR | 48 | 124.617 | 11.957 | 12.843 | 1.00 | 47.89 | L | C |
| ATOM | 3445 | OH | TYR | 48 | 125.803 | 12.269 | 13.483 | 1.00 | 47.89 | L | O |
| ATOM | 3446 | C | TYR | 48 | 121.922 | 10.181 | 8.766 | 1.00 | 27.63 | L | C |
| ATOM | 3447 | O | TYR | 48 | 122.992 | 9.575 | 8.646 | 1.00 | 27.63 | L | O |
| ATOM | 3448 | N | LEU | 49 | 121.535 | 11.150 | 7.948 | 1.00 | 28.95 | L | N |
| ATOM | 3449 | CA | LEU | 49 | 122.344 | 11.550 | 6.811 | 1.00 | 28.95 | L | C |
| ATOM | 3450 | CB | LEU | 49 | 123.421 | 12.568 | 7.232 | 1.00 | 11.18 | L | C |
| ATOM | 3451 | CG | LEU | 49 | 123.051 | 14.040 | 7.473 | 1.00 | 11.18 | L | C |
| ATOM | 3452 | CD1 | LEU | 49 | 122.174 | 14.552 | 6.344 | 1.00 | 11.18 | L | C |
| ATOM | 3453 | CD2 | LEU | 49 | 122.333 | 14.178 | 8.780 | 1.00 | 11.18 | L | C |
| ATOM | 3454 | C | LEU | 49 | 122.997 | 10.350 | 6.117 | 1.00 | 28.95 | L | C |
| ATOM | 3455 | O | LEU | 49 | 124.204 | 10.323 | 5.920 | 1.00 | 28.95 | L | O |
| ATOM | 3456 | N | THR | 50 | 122.192 | 9.351 | 5.777 | 1.00 | 29.56 | L | N |
| ATOM | 3457 | CA | THR | 50 | 122.666 | 8.165 | 5.072 | 1.00 | 29.56 | L | C |
| ATOM | 3458 | CB | THR | 50 | 123.352 | 8.566 | 3.770 | 1.00 | 23.05 | L | C |
| ATOM | 3459 | OG1 | THR | 50 | 122.490 | 9.434 | 3.040 | 1.00 | 23.05 | L | O |
| ATOM | 3460 | CG2 | THR | 50 | 123.647 | 7.335 | 2.923 | 1.00 | 23.05 | L | C |
| ATOM | 3461 | C | THR | 50 | 123.582 | 7.152 | 5.767 | 1.00 | 29.56 | L | C |
| ATOM | 3462 | O | THR | 50 | 123.229 | 5.976 | 5.888 | 1.00 | 29.56 | L | O |
| ATOM | 3463 | N | SER | 51 | 124.757 | 7.586 | 6.203 | 1.00 | 25.90 | L | N |
| ATOM | 3464 | CA | SER | 51 | 125.697 | 6.670 | 6.839 | 1.00 | 25.90 | L | C |
| ATOM | 3465 | CB | SER | 51 | 126.976 | 6.594 | 6.003 | 1.00 | 41.07 | L | C |
| ATOM | 3466 | OG | SER | 51 | 127.467 | 7.893 | 5.715 | 1.00 | 41.07 | L | O |
| ATOM | 3467 | C | SER | 51 | 126.049 | 6.998 | 8.287 | 1.00 | 25.90 | L | C |
| ATOM | 3468 | O | SER | 51 | 126.578 | 6.160 | 9.015 | 1.00 | 25.90 | L | O |
| ATOM | 3469 | N | ASN | 52 | 125.749 | 8.211 | 8.712 | 1.00 | 36.32 | L | N |
| ATOM | 3470 | CA | ASN | 52 | 126.050 | 8.615 | 10.075 | 1.00 | 36.32 | L | C |
| ATOM | 3471 | CB | ASN | 52 | 125.741 | 10.092 | 10.247 | 1.00 | 35.00 | L | C |
| ATOM | 3472 | CG | ASN | 52 | 126.708 | 10.954 | 9.499 | 1.00 | 35.00 | L | C |
| ATOM | 3473 | OD1 | ASN | 52 | 127.881 | 11.022 | 9.857 | 1.00 | 35.00 | L | O |
| ATOM | 3474 | ND2 | ASN | 52 | 126.236 | 11.608 | 8.439 | 1.00 | 35.00 | L | N |
| ATOM | 3475 | C | ASN | 52 | 125.288 | 7.815 | 11.109 | 1.00 | 36.32 | L | C |
| ATOM | 3476 | O | ASN | 52 | 124.059 | 7.766 | 11.078 | 1.00 | 36.32 | L | O |
| ATOM | 3477 | N | LEU | 53 | 126.018 | 7.190 | 12.027 | 1.00 | 27.25 | L | N |
| ATOM | 3478 | CA | LEU | 53 | 125.387 | 6.408 | 13.080 | 1.00 | 27.25 | L | C |
| ATOM | 3479 | CB | LEU | 53 | 126.355 | 5.366 | 13.631 | 1.00 | 36.82 | L | C |
| ATOM | 3480 | CG | LEU | 53 | 126.949 | 4.324 | 12.682 | 1.00 | 36.82 | L | C |
| ATOM | 3481 | CD1 | LEU | 53 | 127.640 | 3.266 | 13.531 | 1.00 | 36.82 | L | C |
| ATOM | 3482 | CD2 | LEU | 53 | 125.876 | 3.674 | 11.822 | 1.00 | 36.82 | L | C |
| ATOM | 3483 | C | LEU | 53 | 124.938 | 7.312 | 14.219 | 1.00 | 27.25 | L | C |
| ATOM | 3484 | O | LEU | 53 | 125.643 | 8.241 | 14.581 | 1.00 | 27.25 | L | O |
| ATOM | 3485 | N | ALA | 54 | 123.763 | 7.043 | 14.779 | 1.00 | 46.43 | L | N |
| ATOM | 3486 | CA | ALA | 54 | 123.251 | 7.827 | 15.897 | 1.00 | 46.43 | L | C |
| ATOM | 3487 | CB | ALA | 54 | 121.938 | 7.272 | 16.373 | 1.00 | 9.56 | L | C |
| ATOM | 3488 | C | ALA | 54 | 124.267 | 7.728 | 17.008 | 1.00 | 46.43 | L | C |
| ATOM | 3489 | O | ALA | 54 | 125.380 | 7.254 | 16.794 | 1.00 | 46.43 | L | O |
| ATOM | 3490 | N | SER | 55 | 123.891 | 8.140 | 18.208 | 1.00 | 82.41 | L | N |
| ATOM | 3491 | CA | SER | 55 | 124.847 | 8.081 | 19.290 | 1.00 | 82.41 | L | C |
| ATOM | 3492 | CB | SER | 55 | 124.439 | 9.036 | 20.406 | 1.00 | 85.12 | L | C |
| ATOM | 3493 | OG | SER | 55 | 125.561 | 9.342 | 21.215 | 1.00 | 85.12 | L | O |
| ATOM | 3494 | C | SER | 55 | 125.049 | 6.675 | 19.850 | 1.00 | 82.41 | L | C |
| ATOM | 3495 | O | SER | 55 | 126.187 | 6.226 | 20.004 | 1.00 | 82.41 | L | O |
| ATOM | 3496 | N | GLY | 56 | 123.957 | 5.970 | 20.137 | 1.00 | 57.94 | L | N |
| ATOM | 3497 | CA | GLY | 56 | 124.074 | 4.632 | 20.701 | 1.00 | 57.94 | L | C |
| ATOM | 3498 | C | GLY | 56 | 124.408 | 3.486 | 19.758 | 1.00 | 57.94 | L | C |
| ATOM | 3499 | O | GLY | 56 | 125.101 | 2.545 | 20.136 | 1.00 | 57.94 | L | O |
| ATOM | 3500 | N | VAL | 57 | 123.914 | 3.562 | 18.530 | 1.00 | 69.56 | L | N |
| ATOM | 3501 | CA | VAL | 57 | 124.131 | 2.519 | 17.530 | 1.00 | 69.56 | L | C |
| ATOM | 3502 | CB | VAL | 57 | 123.809 | 3.053 | 16.108 | 1.00 | 49.85 | L | C |
| ATOM | 3503 | CG1 | VAL | 57 | 123.682 | 1.898 | 15.128 | 1.00 | 49.85 | L | C |
| ATOM | 3504 | CG2 | VAL | 57 | 122.529 | 3.875 | 16.139 | 1.00 | 49.85 | L | C |

FIG. 19A-49

| | | | | | | | | | | | |
|---|---|---|---|---|---|---|---|---|---|---|---|
| ATOM | 3505 | C | VAL | 57 | 125.544 | 1.929 | 17.513 | 1.00 | 69.56 | L | C |
| ATOM | 3506 | O | VAL | 57 | 126.515 | 2.637 | 17.244 | 1.00 | 69.56 | L | O |
| ATOM | 3507 | N | PRO | 58 | 125.674 | 0.618 | 17.799 | 1.00 | 24.22 | L | N |
| ATOM | 3508 | CD | PRO | 58 | 124.609 | -0.342 | 18.141 | 1.00 | 44.23 | L | C |
| ATOM | 3509 | CA | PRO | 58 | 126.978 | -0.046 | 17.802 | 1.00 | 24.22 | L | C |
| ATOM | 3510 | CB | PRO | 58 | 126.638 | -1.472 | 18.237 | 1.00 | 44.23 | L | C |
| ATOM | 3511 | CG | PRO | 58 | 125.244 | -1.653 | 17.772 | 1.00 | 44.23 | L | C |
| ATOM | 3512 | C | PRO | 58 | 127.609 | 0.017 | 16.415 | 1.00 | 24.22 | L | C |
| ATOM | 3513 | O | PRO | 58 | 126.903 | -0.083 | 15.400 | 1.00 | 24.22 | L | O |
| ATOM | 3514 | N | SER | 59 | 128.935 | 0.174 | 16.381 | 1.00 | 54.17 | L | N |
| ATOM | 3515 | CA | SER | 59 | 129.691 | 0.295 | 15.134 | 1.00 | 54.17 | L | C |
| ATOM | 3516 | CB | SER | 59 | 131.184 | 0.489 | 15.438 | 1.00 | 118.98 | L | C |
| ATOM | 3517 | OG | SER | 59 | 131.729 | -0.615 | 16.139 | 1.00 | 118.98 | L | O |
| ATOM | 3518 | C | SER | 59 | 129.528 | -0.815 | 14.096 | 1.00 | 54.17 | L | C |
| ATOM | 3519 | O | SER | 59 | 130.015 | -0.672 | 12.970 | 1.00 | 54.17 | L | O |
| ATOM | 3520 | N | ARG | 60 | 128.861 | -1.914 | 14.449 | 1.00 | 62.94 | L | N |
| ATOM | 3521 | CA | ARG | 60 | 128.659 | -2.983 | 13.473 | 1.00 | 62.94 | L | C |
| ATOM | 3522 | CB | ARG | 60 | 128.247 | -4.291 | 14.159 | 1.00 | 67.90 | L | C |
| ATOM | 3523 | CG | ARG | 60 | 127.110 | -4.165 | 15.136 | 1.00 | 67.90 | L | C |
| ATOM | 3524 | CD | ARG | 60 | 126.572 | -5.533 | 15.506 | 1.00 | 67.90 | L | C |
| ATOM | 3525 | NE | ARG | 60 | 125.638 | -5.453 | 16.621 | 1.00 | 67.90 | L | N |
| ATOM | 3526 | CZ | ARG | 60 | 125.978 | -5.050 | 17.840 | 1.00 | 67.90 | L | C |
| ATOM | 3527 | NH1 | ARG | 60 | 127.230 | -4.696 | 18.093 | 1.00 | 67.90 | L | N |
| ATOM | 3528 | NH2 | ARG | 60 | 125.070 | -5.002 | 18.807 | 1.00 | 67.90 | L | N |
| ATOM | 3529 | C | ARG | 60 | 127.596 | -2.555 | 12.459 | 1.00 | 62.94 | L | C |
| ATOM | 3530 | O | ARG | 60 | 127.471 | -3.146 | 11.382 | 1.00 | 62.94 | L | O |
| ATOM | 3531 | N | PHE | 61 | 126.839 | -1.517 | 12.814 | 1.00 | 65.80 | L | N |
| ATOM | 3532 | CA | PHE | 61 | 125.799 | -0.979 | 11.943 | 1.00 | 65.80 | L | C |
| ATOM | 3533 | CB | PHE | 61 | 124.718 | -0.270 | 12.752 | 1.00 | 20.54 | L | C |
| ATOM | 3534 | CG | PHE | 61 | 123.650 | -1.177 | 13.278 | 1.00 | 20.54 | L | C |
| ATOM | 3535 | CD1 | PHE | 61 | 123.613 | -1.519 | 14.628 | 1.00 | 20.54 | L | C |
| ATOM | 3536 | CD2 | PHE | 61 | 122.656 | -1.662 | 12.428 | 1.00 | 20.54 | L | C |
| ATOM | 3537 | CE1 | PHE | 61 | 122.593 | -2.330 | 15.133 | 1.00 | 20.54 | L | C |
| ATOM | 3538 | CE2 | PHE | 61 | 121.627 | -2.476 | 12.914 | 1.00 | 20.54 | L | C |
| ATOM | 3539 | CZ | PHE | 61 | 121.594 | -2.809 | 14.270 | 1.00 | 20.54 | L | C |
| ATOM | 3540 | C | PHE | 61 | 126.389 | 0.019 | 10.964 | 1.00 | 65.80 | L | C |
| ATOM | 3541 | O | PHE | 61 | 127.300 | 0.773 | 11.300 | 1.00 | 65.80 | L | O |
| ATOM | 3542 | N | SER | 62 | 125.851 | 0.030 | 9.754 | 1.00 | 31.43 | L | N |
| ATOM | 3543 | CA | SER | 62 | 126.317 | 0.941 | 8.722 | 1.00 | 31.43 | L | C |
| ATOM | 3544 | CB | SER | 62 | 127.530 | 0.355 | 8.001 | 1.00 | 48.53 | L | C |
| ATOM | 3545 | OG | SER | 62 | 127.212 | -0.890 | 7.412 | 1.00 | 48.53 | L | O |
| ATOM | 3546 | C | SER | 62 | 125.211 | 1.216 | 7.714 | 1.00 | 31.43 | L | C |
| ATOM | 3547 | O | SER | 62 | 124.402 | 0.340 | 7.395 | 1.00 | 31.43 | L | O |
| ATOM | 3548 | N | GLY | 63 | 125.177 | 2.443 | 7.216 | 1.00 | 26.27 | L | N |
| ATOM | 3549 | CA | GLY | 63 | 124.168 | 2.802 | 6.244 | 1.00 | 26.27 | L | C |
| ATOM | 3550 | C | GLY | 63 | 124.870 | 3.245 | 4.988 | 1.00 | 26.27 | L | C |
| ATOM | 3551 | O | GLY | 63 | 126.032 | 3.634 | 5.044 | 1.00 | 26.27 | L | O |
| ATOM | 3552 | N | SER | 64 | 124.177 | 3.201 | 3.860 | 1.00 | 35.51 | L | N |
| ATOM | 3553 | CA | SER | 64 | 124.789 | 3.605 | 2.610 | 1.00 | 35.51 | L | C |
| ATOM | 3554 | CB | SER | 64 | 125.824 | 2.565 | 2.193 | 1.00 | 33.46 | L | C |
| ATOM | 3555 | OG | SER | 64 | 126.422 | 2.920 | 0.964 | 1.00 | 33.46 | L | O |
| ATOM | 3556 | C | SER | 64 | 123.772 | 3.783 | 1.495 | 1.00 | 35.51 | L | C |
| ATOM | 3557 | O | SER | 64 | 122.614 | 3.371 | 1.622 | 1.00 | 35.51 | L | O |
| ATOM | 3558 | N | GLY | 65 | 124.209 | 4.401 | 0.401 | 1.00 | 29.14 | L | N |
| ATOM | 3559 | CA | GLY | 65 | 123.318 | 4.594 | -0.727 | 1.00 | 29.14 | L | C |
| ATOM | 3560 | C | GLY | 65 | 123.334 | 5.963 | -1.370 | 1.00 | 29.14 | L | C |
| ATOM | 3561 | O | GLY | 65 | 124.127 | 6.837 | -1.024 | 1.00 | 29.14 | L | O |
| ATOM | 3562 | N | SER | 66 | 122.439 | 6.137 | -2.329 | 1.00 | 15.93 | L | N |
| ATOM | 3563 | CA | SER | 66 | 122.305 | 7.389 | -3.052 | 1.00 | 15.93 | L | C |
| ATOM | 3564 | CB | SER | 66 | 123.623 | 7.750 | -3.741 | 1.00 | 32.28 | L | C |
| ATOM | 3565 | OG | SER | 66 | 124.127 | 6.657 | -4.482 | 1.00 | 32.28 | L | O |
| ATOM | 3566 | C | SER | 66 | 121.171 | 7.264 | -4.076 | 1.00 | 15.93 | L | C |
| ATOM | 3567 | O | SER | 66 | 120.609 | 6.184 | -4.284 | 1.00 | 15.93 | L | O |
| ATOM | 3568 | N | GLY | 67 | 120.812 | 8.378 | -4.690 | 1.00 | 33.97 | L | N |
| ATOM | 3569 | CA | GLY | 67 | 119.751 | 8.349 | -5.673 | 1.00 | 33.97 | L | C |
| ATOM | 3570 | C | GLY | 67 | 118.469 | 7.706 | -5.194 | 1.00 | 33.97 | L | C |
| ATOM | 3571 | O | GLY | 67 | 117.757 | 8.262 | -4.361 | 1.00 | 33.97 | L | O |
| ATOM | 3572 | N | THR | 68 | 118.182 | 6.521 | -5.715 | 1.00 | 25.46 | L | N |
| ATOM | 3573 | CA | THR | 68 | 116.954 | 5.828 | -5.366 | 1.00 | 25.46 | L | C |
| ATOM | 3574 | CB | THR | 68 | 116.176 | 5.455 | -6.633 | 1.00 | 47.05 | L | C |
| ATOM | 3575 | OG1 | THR | 68 | 117.003 | 4.636 | -7.471 | 1.00 | 47.05 | L | O |
| ATOM | 3576 | CG2 | THR | 68 | 115.772 | 6.704 | -7.395 | 1.00 | 47.05 | L | C |
| ATOM | 3577 | C | THR | 68 | 117.132 | 4.559 | -4.539 | 1.00 | 25.46 | L | C |

FIG. 19A-50

| ATOM | 3578 | O | THR | 68 | 116.144 | 3.963 | -4.103 | 1.00 | 25.46 | L | O |
|---|---|---|---|---|---|---|---|---|---|---|---|
| ATOM | 3579 | N | ASP | 69 | 118.374 | 4.134 | -4.327 | 1.00 | 17.04 | L | N |
| ATOM | 3580 | CA | ASP | 69 | 118.614 | 2.921 | -3.554 | 1.00 | 17.04 | L | C |
| ATOM | 3581 | CB | ASP | 69 | 119.156 | 1.812 | -4.463 | 1.00 | 63.22 | L | C |
| ATOM | 3582 | CG | ASP | 69 | 118.129 | 1.354 | -5.490 | 1.00 | 63.22 | L | C |
| ATOM | 3583 | OD1 | ASP | 69 | 117.087 | 0.791 | -5.083 | 1.00 | 63.22 | L | O |
| ATOM | 3584 | OD2 | ASP | 69 | 118.356 | 1.565 | -6.703 | 1.00 | 63.22 | L | O |
| ATOM | 3585 | C | ASP | 69 | 119.544 | 3.146 | -2.372 | 1.00 | 17.04 | L | C |
| ATOM | 3586 | O | ASP | 69 | 120.684 | 3.567 | -2.535 | 1.00 | 17.04 | L | O |
| ATOM | 3587 | N | TYR | 70 | 119.030 | 2.866 | -1.177 | 1.00 | 19.76 | L | N |
| ATOM | 3588 | CA | TYR | 70 | 119.778 | 3.037 | 0.061 | 1.00 | 19.76 | L | C |
| ATOM | 3589 | CB | TYR | 70 | 119.130 | 4.151 | 0.895 | 1.00 | 24.73 | L | C |
| ATOM | 3590 | CG | TYR | 70 | 119.424 | 5.544 | 0.369 | 1.00 | 24.73 | L | C |
| ATOM | 3591 | CD1 | TYR | 70 | 120.547 | 6.255 | 0.809 | 1.00 | 24.73 | L | C |
| ATOM | 3592 | CE1 | TYR | 70 | 120.865 | 7.511 | 0.281 | 1.00 | 24.73 | L | C |
| ATOM | 3593 | CD2 | TYR | 70 | 118.620 | 6.129 | -0.616 | 1.00 | 24.73 | L | C |
| ATOM | 3594 | CE2 | TYR | 70 | 118.931 | 7.384 | -1.153 | 1.00 | 24.73 | L | C |
| ATOM | 3595 | CZ | TYR | 70 | 120.053 | 8.062 | -0.700 | 1.00 | 24.73 | L | C |
| ATOM | 3596 | OH | TYR | 70 | 120.371 | 9.275 | -1.247 | 1.00 | 24.73 | L | O |
| ATOM | 3597 | C | TYR | 70 | 119.812 | 1.727 | 0.840 | 1.00 | 19.76 | L | C |
| ATOM | 3598 | O | TYR | 70 | 118.997 | 0.828 | 0.599 | 1.00 | 19.76 | L | O |
| ATOM | 3599 | N | THR | 71 | 120.751 | 1.603 | 1.772 | 1.00 | 26.87 | L | N |
| ATOM | 3600 | CA | THR | 71 | 120.837 | 0.366 | 2.535 | 1.00 | 26.87 | L | C |
| ATOM | 3601 | CB | THR | 71 | 121.754 | -0.661 | 1.828 | 1.00 | 34.85 | L | C |
| ATOM | 3602 | OG1 | THR | 71 | 123.107 | -0.192 | 1.860 | 1.00 | 34.85 | L | O |
| ATOM | 3603 | CG2 | THR | 71 | 121.329 | -0.863 | 0.376 | 1.00 | 34.85 | L | C |
| ATOM | 3604 | C | THR | 71 | 121.333 | 0.483 | 3.977 | 1.00 | 26.87 | L | C |
| ATOM | 3605 | O | THR | 71 | 122.160 | 1.335 | 4.306 | 1.00 | 26.87 | L | O |
| ATOM | 3606 | N | LEU | 72 | 120.800 | -0.385 | 4.829 | 1.00 | 24.40 | L | N |
| ATOM | 3607 | CA | LEU | 72 | 121.204 | -0.467 | 6.222 | 1.00 | 24.40 | L | C |
| ATOM | 3608 | CB | LEU | 72 | 119.987 | -0.412 | 7.150 | 1.00 | 25.91 | L | C |
| ATOM | 3609 | CG | LEU | 72 | 120.183 | -0.827 | 8.614 | 1.00 | 25.91 | L | C |
| ATOM | 3610 | CD1 | LEU | 72 | 121.539 | -0.387 | 9.105 | 1.00 | 25.91 | L | C |
| ATOM | 3611 | CD2 | LEU | 72 | 119.097 | -0.207 | 9.470 | 1.00 | 25.91 | L | C |
| ATOM | 3612 | C | LEU | 72 | 121.875 | -1.837 | 6.296 | 1.00 | 24.40 | L | C |
| ATOM | 3613 | O | LEU | 72 | 121.386 | -2.803 | 5.707 | 1.00 | 24.40 | L | O |
| ATOM | 3614 | N | THR | 73 | 123.000 | -1.930 | 6.990 | 1.00 | 38.15 | L | N |
| ATOM | 3615 | CA | THR | 73 | 123.695 | -3.204 | 7.066 | 1.00 | 38.15 | L | C |
| ATOM | 3616 | CB | THR | 73 | 124.907 | -3.217 | 6.110 | 1.00 | 35.63 | L | C |
| ATOM | 3617 | OG1 | THR | 73 | 124.556 | -2.566 | 4.885 | 1.00 | 35.63 | L | O |
| ATOM | 3618 | CG2 | THR | 73 | 125.328 | -4.649 | 5.797 | 1.00 | 35.63 | L | C |
| ATOM | 3619 | C | THR | 73 | 124.189 | -3.542 | 8.467 | 1.00 | 38.15 | L | C |
| ATOM | 3620 | O | THR | 73 | 124.719 | -2.690 | 9.177 | 1.00 | 38.15 | L | O |
| ATOM | 3621 | N | ILE | 74 | 123.997 | -4.791 | 8.866 | 1.00 | 31.55 | L | N |
| ATOM | 3622 | CA | ILE | 74 | 124.467 | -5.246 | 10.158 | 1.00 | 31.55 | L | C |
| ATOM | 3623 | CB | ILE | 74 | 123.342 | -5.884 | 10.988 | 1.00 | 39.02 | L | C |
| ATOM | 3624 | CG2 | ILE | 74 | 123.734 | -5.878 | 12.461 | 1.00 | 39.02 | L | C |
| ATOM | 3625 | CG1 | ILE | 74 | 122.041 | -5.099 | 10.821 | 1.00 | 39.02 | L | C |
| ATOM | 3626 | CD1 | ILE | 74 | 120.870 | -5.663 | 11.635 | 1.00 | 39.02 | L | C |
| ATOM | 3627 | C | ILE | 74 | 125.504 | -6.313 | 9.814 | 1.00 | 31.55 | L | C |
| ATOM | 3628 | O | ILE | 74 | 125.146 | -7.434 | 9.440 | 1.00 | 31.55 | L | O |
| ATOM | 3629 | N | SER | 75 | 126.782 | -5.951 | 9.921 | 1.00 | 48.74 | L | N |
| ATOM | 3630 | CA | SER | 75 | 127.888 | -6.857 | 9.605 | 1.00 | 48.74 | L | C |
| ATOM | 3631 | CB | SER | 75 | 129.209 | -6.106 | 9.727 | 1.00 | 44.70 | L | C |
| ATOM | 3632 | OG | SER | 75 | 129.306 | -5.485 | 10.994 | 1.00 | 44.70 | L | O |
| ATOM | 3633 | C | SER | 75 | 127.940 | -8.129 | 10.456 | 1.00 | 48.74 | L | C |
| ATOM | 3634 | O | SER | 75 | 128.346 | -9.184 | 9.970 | 1.00 | 48.74 | L | O |
| ATOM | 3635 | N | SER | 76 | 127.544 | -8.021 | 11.722 | 1.00 | 53.77 | L | N |
| ATOM | 3636 | CA | SER | 76 | 127.530 | -9.165 | 12.635 | 1.00 | 53.77 | L | C |
| ATOM | 3637 | CB | SER | 76 | 128.773 | -9.166 | 13.521 | 1.00 | 79.21 | L | C |
| ATOM | 3638 | OG | SER | 76 | 128.707 | -10.224 | 14.463 | 1.00 | 79.21 | L | O |
| ATOM | 3639 | C | SER | 76 | 126.288 | -9.102 | 13.515 | 1.00 | 53.77 | L | C |
| ATOM | 3640 | O | SER | 76 | 126.306 | -8.533 | 14.604 | 1.00 | 53.77 | L | O |
| ATOM | 3641 | N | LEU | 77 | 125.211 | -9.704 | 13.036 | 1.00 | 35.38 | L | N |
| ATOM | 3642 | CA | LEU | 77 | 123.946 | -9.691 | 13.756 | 1.00 | 35.38 | L | C |
| ATOM | 3643 | CB | LEU | 77 | 122.955 | -10.639 | 13.085 | 1.00 | 37.68 | L | C |
| ATOM | 3644 | CG | LEU | 77 | 121.514 | -10.154 | 12.995 | 1.00 | 37.68 | L | C |
| ATOM | 3645 | CD1 | LEU | 77 | 120.623 | -11.329 | 12.638 | 1.00 | 37.68 | L | C |
| ATOM | 3646 | CD2 | LEU | 77 | 121.080 | -9.548 | 14.317 | 1.00 | 37.68 | L | C |
| ATOM | 3647 | C | LEU | 77 | 124.096 | -10.080 | 15.215 | 1.00 | 35.38 | L | C |
| ATOM | 3648 | O | LEU | 77 | 124.714 | -11.086 | 15.531 | 1.00 | 35.38 | L | O |
| ATOM | 3649 | N | GLN | 78 | 123.527 | -9.279 | 16.105 | 1.00 | 50.91 | L | N |
| ATOM | 3650 | CA | GLN | 78 | 123.589 | -9.577 | 17.527 | 1.00 | 50.91 | L | C |

FIG. 19A-51

| ATOM | 3651 | CB | GLN | 78 | 124.201 | -8.408 | 18.290 | 1.00 | 82.93 | L | C |
|---|---|---|---|---|---|---|---|---|---|---|---|
| ATOM | 3652 | CG | GLN | 78 | 125.653 | -8.159 | 17.938 | 1.00 | 82.93 | L | C |
| ATOM | 3653 | CD | GLN | 78 | 126.525 | -9.385 | 18.135 | 1.00 | 82.93 | L | C |
| ATOM | 3654 | OE1 | GLN | 78 | 126.509 | -10.007 | 19.200 | 1.00 | 82.93 | L | O |
| ATOM | 3655 | NE2 | GLN | 78 | 127.299 | -9.736 | 17.109 | 1.00 | 82.93 | L | N |
| ATOM | 3656 | C | GLN | 78 | 122.192 | -9.880 | 18.062 | 1.00 | 50.91 | L | C |
| ATOM | 3657 | O | GLN | 78 | 121.197 | -9.411 | 17.519 | 1.00 | 50.91 | L | O |
| ATOM | 3658 | N | PRO | 79 | 122.104 | -10.680 | 19.135 | 1.00 | 74.65 | L | N |
| ATOM | 3659 | CD | PRO | 79 | 123.228 | -11.171 | 19.952 | 1.00 | 43.98 | L | C |
| ATOM | 3660 | CA | PRO | 79 | 120.821 | -11.049 | 19.743 | 1.00 | 74.65 | L | C |
| ATOM | 3661 | CB | PRO | 79 | 121.243 | -11.963 | 20.887 | 1.00 | 43.98 | L | C |
| ATOM | 3662 | CG | PRO | 79 | 122.577 | -11.373 | 21.284 | 1.00 | 43.98 | L | C |
| ATOM | 3663 | C | PRO | 79 | 120.033 | -9.830 | 20.224 | 1.00 | 74.65 | L | C |
| ATOM | 3664 | O | PRO | 79 | 118.855 | -9.922 | 20.577 | 1.00 | 74.65 | L | O |
| ATOM | 3665 | N | GLU | 80 | 120.697 | -8.685 | 20.221 | 1.00 | 42.25 | L | N |
| ATOM | 3666 | CA | GLU | 80 | 120.080 | -7.451 | 20.659 | 1.00 | 42.25 | L | C |
| ATOM | 3667 | CB | GLU | 80 | 121.085 | -6.697 | 21.527 | 1.00 | 40.93 | L | C |
| ATOM | 3668 | CG | GLU | 80 | 122.485 | -6.700 | 20.958 | 1.00 | 40.93 | L | C |
| ATOM | 3669 | CD | GLU | 80 | 123.424 | -5.786 | 21.726 | 1.00 | 40.93 | L | C |
| ATOM | 3670 | OE1 | GLU | 80 | 123.013 | -4.648 | 22.033 | 1.00 | 40.93 | L | O |
| ATOM | 3671 | OE2 | GLU | 80 | 124.572 | -6.197 | 22.009 | 1.00 | 40.93 | L | O |
| ATOM | 3672 | C | GLU | 80 | 119.602 | -6.575 | 19.489 | 1.00 | 42.25 | L | C |
| ATOM | 3673 | O | GLU | 80 | 118.723 | -5.726 | 19.656 | 1.00 | 42.25 | L | O |
| ATOM | 3674 | N | ASP | 81 | 120.189 | -6.787 | 18.312 | 1.00 | 42.48 | L | N |
| ATOM | 3675 | CA | ASP | 81 | 119.835 | -6.037 | 17.108 | 1.00 | 42.48 | L | C |
| ATOM | 3676 | CB | ASP | 81 | 120.867 | -6.254 | 16.005 | 1.00 | 43.12 | L | C |
| ATOM | 3677 | CG | ASP | 81 | 122.262 | -5.914 | 16.441 | 1.00 | 43.12 | L | C |
| ATOM | 3678 | OD1 | ASP | 81 | 122.422 | -5.003 | 17.281 | 1.00 | 43.12 | L | O |
| ATOM | 3679 | OD2 | ASP | 81 | 123.205 | -6.549 | 15.924 | 1.00 | 43.12 | L | O |
| ATOM | 3680 | C | ASP | 81 | 118.495 | -6.488 | 16.564 | 1.00 | 42.48 | L | C |
| ATOM | 3681 | O | ASP | 81 | 118.086 | -6.063 | 15.488 | 1.00 | 42.48 | L | O |
| ATOM | 3682 | N | PHE | 82 | 117.810 | -7.351 | 17.299 | 1.00 | 48.53 | L | N |
| ATOM | 3683 | CA | PHE | 82 | 116.544 | -7.856 | 16.822 | 1.00 | 48.53 | L | C |
| ATOM | 3684 | CB | PHE | 82 | 116.337 | -9.265 | 17.368 | 1.00 | 189.91 | L | C |
| ATOM | 3685 | CG | PHE | 82 | 117.320 | -10.260 | 16.810 | 1.00 | 189.91 | L | C |
| ATOM | 3686 | CD1 | PHE | 82 | 117.227 | -10.676 | 15.485 | 1.00 | 189.91 | L | C |
| ATOM | 3687 | CD2 | PHE | 82 | 118.369 | -10.741 | 17.587 | 1.00 | 189.91 | L | C |
| ATOM | 3688 | CE1 | PHE | 82 | 118.164 | -11.554 | 14.940 | 1.00 | 189.91 | L | C |
| ATOM | 3689 | CE2 | PHE | 82 | 119.311 | -11.622 | 17.048 | 1.00 | 189.91 | L | C |
| ATOM | 3690 | CZ | PHE | 82 | 119.207 | -12.027 | 15.725 | 1.00 | 189.91 | L | C |
| ATOM | 3691 | C | PHE | 82 | 115.359 | -6.953 | 17.094 | 1.00 | 48.53 | L | C |
| ATOM | 3692 | O | PHE | 82 | 114.857 | -6.863 | 18.216 | 1.00 | 48.53 | L | O |
| ATOM | 3693 | N | ALA | 83 | 114.939 | -6.271 | 16.032 | 1.00 | 31.52 | L | N |
| ATOM | 3694 | CA | ALA | 83 | 113.813 | -5.350 | 16.052 | 1.00 | 31.52 | L | C |
| ATOM | 3695 | CB | ALA | 83 | 114.217 | -4.051 | 16.723 | 1.00 | 63.37 | L | C |
| ATOM | 3696 | C | ALA | 83 | 113.398 | -5.090 | 14.605 | 1.00 | 31.52 | L | C |
| ATOM | 3697 | O | ALA | 83 | 113.816 | -5.808 | 13.693 | 1.00 | 31.52 | L | O |
| ATOM | 3698 | N | THR | 84 | 112.565 | -4.075 | 14.395 | 1.00 | 28.09 | L | N |
| ATOM | 3699 | CA | THR | 84 | 112.124 | -3.733 | 13.045 | 1.00 | 28.09 | L | C |
| ATOM | 3700 | CB | THR | 84 | 110.572 | -3.799 | 12.928 | 1.00 | 15.50 | L | C |
| ATOM | 3701 | OG1 | THR | 84 | 110.127 | -3.002 | 11.822 | 1.00 | 15.50 | L | O |
| ATOM | 3702 | CG2 | THR | 84 | 109.922 | -3.332 | 14.207 | 1.00 | 15.50 | L | C |
| ATOM | 3703 | C | THR | 84 | 112.664 | -2.346 | 12.659 | 1.00 | 28.09 | L | C |
| ATOM | 3704 | O | THR | 84 | 112.505 | -1.373 | 13.400 | 1.00 | 28.09 | L | O |
| ATOM | 3705 | N | TYR | 85 | 113.316 | -2.282 | 11.496 | 1.00 | 21.31 | L | N |
| ATOM | 3706 | CA | TYR | 85 | 113.935 | -1.055 | 11.000 | 1.00 | 21.31 | L | C |
| ATOM | 3707 | CB | TYR | 85 | 115.367 | -1.338 | 10.517 | 1.00 | 19.63 | L | C |
| ATOM | 3708 | CG | TYR | 85 | 116.240 | -1.976 | 11.566 | 1.00 | 19.63 | L | C |
| ATOM | 3709 | CD1 | TYR | 85 | 115.988 | -3.279 | 12.021 | 1.00 | 19.63 | L | C |
| ATOM | 3710 | CE1 | TYR | 85 | 116.718 | -3.834 | 13.061 | 1.00 | 19.63 | L | C |
| ATOM | 3711 | CD2 | TYR | 85 | 117.255 | -1.259 | 12.174 | 1.00 | 19.63 | L | C |
| ATOM | 3712 | CE2 | TYR | 85 | 117.990 | -1.807 | 13.217 | 1.00 | 19.63 | L | C |
| ATOM | 3713 | CZ | TYR | 85 | 117.711 | -3.087 | 13.655 | 1.00 | 19.63 | L | C |
| ATOM | 3714 | OH | TYR | 85 | 118.405 | -3.592 | 14.722 | 1.00 | 19.63 | L | O |
| ATOM | 3715 | C | TYR | 85 | 113.173 | -0.365 | 9.882 | 1.00 | 21.31 | L | C |
| ATOM | 3716 | O | TYR | 85 | 112.768 | -0.996 | 8.900 | 1.00 | 21.31 | L | O |
| ATOM | 3717 | N | TYR | 86 | 113.015 | 0.948 | 10.046 | 1.00 | 18.01 | L | N |
| ATOM | 3718 | CA | TYR | 86 | 112.321 | 1.806 | 9.090 | 1.00 | 18.01 | L | C |
| ATOM | 3719 | CB | TYR | 86 | 111.242 | 2.632 | 9.790 | 1.00 | 24.73 | L | C |
| ATOM | 3720 | CG | TYR | 86 | 110.130 | 1.846 | 10.421 | 1.00 | 24.73 | L | C |
| ATOM | 3721 | CD1 | TYR | 86 | 109.020 | 1.459 | 9.679 | 1.00 | 24.73 | L | C |
| ATOM | 3722 | CE1 | TYR | 86 | 107.971 | 0.756 | 10.278 | 1.00 | 24.73 | L | C |
| ATOM | 3723 | CD2 | TYR | 86 | 110.177 | 1.508 | 11.773 | 1.00 | 24.73 | L | C |

FIG. 19A-52

| ATOM | 3724 | CE2 | TYR | 86 | 109.140 | 0.804 | 12.378 | 1.00 | 24.73 | L | C |
| --- | --- | --- | --- | --- | --- | --- | --- | --- | --- | --- | --- |
| ATOM | 3725 | CZ | TYR | 86 | 108.042 | 0.438 | 11.628 | 1.00 | 24.73 | L | C |
| ATOM | 3726 | OH | TYR | 86 | 107.002 | -0.204 | 12.238 | 1.00 | 24.73 | L | O |
| ATOM | 3727 | C | TYR | 86 | 113.280 | 2.798 | 8.465 | 1.00 | 18.01 | L | C |
| ATOM | 3728 | O | TYR | 86 | 114.110 | 3.378 | 9.158 | 1.00 | 18.01 | L | O |
| ATOM | 3729 | N | CYS | 87 | 113.170 | 2.996 | 7.158 | 1.00 | 20.53 | L | N |
| ATOM | 3730 | CA | CYS | 87 | 113.989 | 3.999 | 6.494 | 1.00 | 20.53 | L | C |
| ATOM | 3731 | C | CYS | 87 | 113.021 | 5.156 | 6.335 | 1.00 | 20.53 | L | C |
| ATOM | 3732 | O | CYS | 87 | 111.806 | 4.954 | 6.351 | 1.00 | 20.53 | L | O |
| ATOM | 3733 | CB | CYS | 87 | 114.509 | 3.527 | 5.133 | 1.00 | 17.33 | L | C |
| ATOM | 3734 | SG | CYS | 87 | 113.306 | 2.900 | 3.921 | 1.00 | 17.33 | L | S |
| ATOM | 3735 | N | GLN | 88 | 113.545 | 6.363 | 6.212 | 1.00 | 10.63 | L | N |
| ATOM | 3736 | CA | GLN | 88 | 112.696 | 7.534 | 6.083 | 1.00 | 10.63 | L | C |
| ATOM | 3737 | CB | GLN | 88 | 112.393 | 8.083 | 7.482 | 1.00 | 18.09 | L | C |
| ATOM | 3738 | CG | GLN | 88 | 111.509 | 9.303 | 7.525 | 1.00 | 18.09 | L | C |
| ATOM | 3739 | CD | GLN | 88 | 112.256 | 10.547 | 7.971 | 1.00 | 18.09 | L | C |
| ATOM | 3740 | OE1 | GLN | 88 | 112.946 | 10.539 | 8.987 | 1.00 | 18.09 | L | O |
| ATOM | 3741 | NE2 | GLN | 88 | 112.106 | 11.627 | 7.219 | 1.00 | 18.09 | L | N |
| ATOM | 3742 | C | GLN | 88 | 113.390 | 8.583 | 5.219 | 1.00 | 10.63 | L | C |
| ATOM | 3743 | O | GLN | 88 | 114.626 | 8.680 | 5.198 | 1.00 | 10.63 | L | O |
| ATOM | 3744 | N | GLN | 89 | 112.600 | 9.357 | 4.483 | 1.00 | 11.94 | L | N |
| ATOM | 3745 | CA | GLN | 89 | 113.171 | 10.386 | 3.625 | 1.00 | 11.94 | L | C |
| ATOM | 3746 | CB | GLN | 89 | 112.877 | 10.073 | 2.152 | 1.00 | 25.01 | L | C |
| ATOM | 3747 | CG | GLN | 89 | 111.407 | 10.008 | 1.776 | 1.00 | 25.01 | L | C |
| ATOM | 3748 | CD | GLN | 89 | 110.786 | 11.377 | 1.579 | 1.00 | 25.01 | L | C |
| ATOM | 3749 | OE1 | GLN | 89 | 111.373 | 12.247 | 0.935 | 1.00 | 25.01 | L | O |
| ATOM | 3750 | NE2 | GLN | 89 | 109.591 | 11.571 | 2.119 | 1.00 | 25.01 | L | N |
| ATOM | 3751 | C | GLN | 89 | 112.606 | 11.732 | 4.023 | 1.00 | 11.94 | L | C |
| ATOM | 3752 | O | GLN | 89 | 111.498 | 11.802 | 4.552 | 1.00 | 11.94 | L | O |
| ATOM | 3753 | N | TRP | 90 | 113.375 | 12.794 | 3.792 | 1.00 | 19.62 | L | N |
| ATOM | 3754 | CA | TRP | 90 | 112.948 | 14.144 | 4.145 | 1.00 | 19.62 | L | C |
| ATOM | 3755 | CB | TRP | 90 | 113.773 | 14.667 | 5.336 | 1.00 | 17.27 | L | C |
| ATOM | 3756 | CG | TRP | 90 | 115.220 | 15.018 | 5.023 | 1.00 | 17.27 | L | C |
| ATOM | 3757 | CD2 | TRP | 90 | 116.174 | 15.611 | 5.918 | 1.00 | 17.27 | L | C |
| ATOM | 3758 | CE2 | TRP | 90 | 117.373 | 15.797 | 5.189 | 1.00 | 17.27 | L | C |
| ATOM | 3759 | CE3 | TRP | 90 | 116.132 | 16.005 | 7.267 | 1.00 | 17.27 | L | C |
| ATOM | 3760 | CD1 | TRP | 90 | 115.869 | 14.867 | 3.823 | 1.00 | 17.27 | L | C |
| ATOM | 3761 | NE1 | TRP | 90 | 117.156 | 15.334 | 3.918 | 1.00 | 17.27 | L | N |
| ATOM | 3762 | CZ2 | TRP | 90 | 118.522 | 16.363 | 5.759 | 1.00 | 17.27 | L | C |
| ATOM | 3763 | CZ3 | TRP | 90 | 117.284 | 16.570 | 7.839 | 1.00 | 17.27 | L | C |
| ATOM | 3764 | CH2 | TRP | 90 | 118.462 | 16.741 | 7.080 | 1.00 | 17.27 | L | C |
| ATOM | 3765 | C | TRP | 90 | 113.074 | 15.093 | 2.947 | 1.00 | 19.62 | L | C |
| ATOM | 3766 | O | TRP | 90 | 112.783 | 16.289 | 3.048 | 1.00 | 19.62 | L | O |
| ATOM | 3767 | N | SER | 91 | 113.494 | 14.552 | 1.807 | 1.00 | 12.71 | L | N |
| ATOM | 3768 | CA | SER | 91 | 113.662 | 15.359 | 0.600 | 1.00 | 12.71 | L | C |
| ATOM | 3769 | CB | SER | 91 | 114.504 | 14.587 | -0.414 | 1.00 | 23.55 | L | C |
| ATOM | 3770 | OG | SER | 91 | 115.762 | 14.248 | 0.137 | 1.00 | 23.55 | L | O |
| ATOM | 3771 | C | SER | 91 | 112.344 | 15.800 | -0.054 | 1.00 | 12.71 | L | C |
| ATOM | 3772 | O | SER | 91 | 112.284 | 16.860 | -0.680 | 1.00 | 12.71 | L | O |
| ATOM | 3773 | N | GLY | 92 | 111.297 | 14.986 | 0.096 | 1.00 | 23.24 | L | N |
| ATOM | 3774 | CA | GLY | 92 | 110.008 | 15.310 | -0.493 | 1.00 | 23.24 | L | C |
| ATOM | 3775 | C | GLY | 92 | 108.867 | 15.347 | 0.509 | 1.00 | 23.24 | L | C |
| ATOM | 3776 | O | GLY | 92 | 108.931 | 14.718 | 1.567 | 1.00 | 23.24 | L | O |
| ATOM | 3777 | N | ASN | 93 | 107.811 | 16.078 | 0.169 | 1.00 | 31.94 | L | N |
| ATOM | 3778 | CA | ASN | 93 | 106.663 | 16.206 | 1.048 | 1.00 | 31.94 | L | C |
| ATOM | 3779 | CB | ASN | 93 | 106.307 | 17.670 | 1.203 | 1.00 | 23.71 | L | C |
| ATOM | 3780 | CG | ASN | 93 | 107.400 | 18.448 | 1.896 | 1.00 | 23.71 | L | C |
| ATOM | 3781 | OD1 | ASN | 93 | 107.790 | 19.525 | 1.445 | 1.00 | 23.71 | L | O |
| ATOM | 3782 | ND2 | ASN | 93 | 107.905 | 17.905 | 3.006 | 1.00 | 23.71 | L | N |
| ATOM | 3783 | C | ASN | 93 | 105.478 | 15.454 | 0.507 | 1.00 | 31.94 | L | C |
| ATOM | 3784 | O | ASN | 93 | 105.227 | 15.478 | -0.692 | 1.00 | 31.94 | L | O |
| ATOM | 3785 | N | PRO | 94 | 104.724 | 14.779 | 1.386 | 1.00 | 29.10 | L | N |
| ATOM | 3786 | CD | PRO | 94 | 103.575 | 13.939 | 1.009 | 1.00 | 1.87 | L | C |
| ATOM | 3787 | CA | PRO | 94 | 104.950 | 14.713 | 2.830 | 1.00 | 29.10 | L | C |
| ATOM | 3788 | CB | PRO | 94 | 103.651 | 14.113 | 3.340 | 1.00 | 1.87 | L | C |
| ATOM | 3789 | CG | PRO | 94 | 103.336 | 13.137 | 2.269 | 1.00 | 1.87 | L | C |
| ATOM | 3790 | C | PRO | 94 | 106.131 | 13.823 | 3.167 | 1.00 | 29.10 | L | C |
| ATOM | 3791 | O | PRO | 94 | 106.516 | 12.987 | 2.361 | 1.00 | 29.10 | L | O |
| ATOM | 3792 | N | TRP | 95 | 106.711 | 14.011 | 4.349 | 1.00 | 16.41 | L | N |
| ATOM | 3793 | CA | TRP | 95 | 107.810 | 13.155 | 4.772 | 1.00 | 16.41 | L | C |
| ATOM | 3794 | CB | TRP | 95 | 108.425 | 13.629 | 6.094 | 1.00 | 13.37 | L | C |
| ATOM | 3795 | CG | TRP | 95 | 109.201 | 14.906 | 5.979 | 1.00 | 13.37 | L | C |
| ATOM | 3796 | CD2 | TRP | 95 | 109.284 | 15.950 | 6.954 | 1.00 | 13.37 | L | C |

FIG. 19A-53

| | | | | | | | | | | | |
|---|---|---|---|---|---|---|---|---|---|---|---|
| ATOM | 3797 | CE2 | TRP | 95 | 110.104 | 16.960 | 6.412 | 1.00 | 13.37 | L | C |
| ATOM | 3798 | CE3 | TRP | 95 | 108.743 | 16.132 | 8.229 | 1.00 | 13.37 | L | C |
| ATOM | 3799 | CD1 | TRP | 95 | 109.963 | 15.312 | 4.917 | 1.00 | 13.37 | L | C |
| ATOM | 3800 | NE1 | TRP | 95 | 110.504 | 16.543 | 5.168 | 1.00 | 13.37 | L | N |
| ATOM | 3801 | CZ2 | TRP | 95 | 110.394 | 18.144 | 7.107 | 1.00 | 13.37 | L | C |
| ATOM | 3802 | CZ3 | TRP | 95 | 109.030 | 17.305 | 8.919 | 1.00 | 13.37 | L | C |
| ATOM | 3803 | CH2 | TRP | 95 | 109.845 | 18.297 | 8.358 | 1.00 | 13.37 | L | C |
| ATOM | 3804 | C | TRP | 95 | 107.226 | 11.751 | 4.942 | 1.00 | 16.41 | L | C |
| ATOM | 3805 | O | TRP | 95 | 106.136 | 11.575 | 5.484 | 1.00 | 16.41 | L | O |
| ATOM | 3806 | N | THR | 96 | 107.956 | 10.748 | 4.481 | 1.00 | 6.71 | L | N |
| ATOM | 3807 | CA | THR | 96 | 107.465 | 9.388 | 4.563 | 1.00 | 6.71 | L | C |
| ATOM | 3808 | CB | THR | 96 | 106.963 | 8.932 | 3.172 | 1.00 | 11.59 | L | C |
| ATOM | 3809 | OG1 | THR | 96 | 108.045 | 8.991 | 2.235 | 1.00 | 11.59 | L | O |
| ATOM | 3810 | CG2 | THR | 96 | 105.859 | 9.852 | 2.674 | 1.00 | 11.59 | L | C |
| ATOM | 3811 | C | THR | 96 | 108.489 | 8.369 | 5.087 | 1.00 | 6.71 | L | C |
| ATOM | 3812 | O | THR | 96 | 109.703 | 8.621 | 5.121 | 1.00 | 6.71 | L | O |
| ATOM | 3813 | N | PHE | 97 | 107.966 | 7.222 | 5.513 | 1.00 | 24.36 | L | N |
| ATOM | 3814 | CA | PHE | 97 | 108.777 | 6.119 | 6.013 | 1.00 | 24.36 | L | C |
| ATOM | 3815 | CB | PHE | 97 | 108.327 | 5.689 | 7.418 | 1.00 | 11.10 | L | C |
| ATOM | 3816 | CG | PHE | 97 | 108.422 | 6.762 | 8.461 | 1.00 | 11.10 | L | C |
| ATOM | 3817 | CD1 | PHE | 97 | 107.541 | 7.831 | 8.460 | 1.00 | 11.10 | L | C |
| ATOM | 3818 | CD2 | PHE | 97 | 109.391 | 6.685 | 9.470 | 1.00 | 11.10 | L | C |
| ATOM | 3819 | CE1 | PHE | 97 | 107.612 | 8.821 | 9.453 | 1.00 | 11.10 | L | C |
| ATOM | 3820 | CE2 | PHE | 97 | 109.475 | 7.665 | 10.468 | 1.00 | 11.10 | L | C |
| ATOM | 3821 | CZ | PHE | 97 | 108.577 | 8.738 | 10.456 | 1.00 | 11.10 | L | C |
| ATOM | 3822 | C | PHE | 97 | 108.532 | 4.950 | 5.062 | 1.00 | 24.36 | L | C |
| ATOM | 3823 | O | PHE | 97 | 107.613 | 4.990 | 4.241 | 1.00 | 24.36 | L | O |
| ATOM | 3824 | N | GLY | 98 | 109.362 | 3.919 | 5.168 | 1.00 | 21.54 | L | N |
| ATOM | 3825 | CA | GLY | 98 | 109.183 | 2.727 | 4.350 | 1.00 | 21.54 | L | C |
| ATOM | 3826 | C | GLY | 98 | 108.266 | 1.849 | 5.184 | 1.00 | 21.54 | L | C |
| ATOM | 3827 | O | GLY | 98 | 107.977 | 2.196 | 6.339 | 1.00 | 21.54 | L | O |
| ATOM | 3828 | N | GLN | 99 | 107.796 | 0.728 | 4.645 | 1.00 | 11.59 | L | N |
| ATOM | 3829 | CA | GLN | 99 | 106.894 | -0.114 | 5.442 | 1.00 | 11.59 | L | C |
| ATOM | 3830 | CB | GLN | 99 | 106.211 | -1.197 | 4.593 | 1.00 | 37.88 | L | C |
| ATOM | 3831 | CG | GLN | 99 | 106.810 | -1.403 | 3.238 | 1.00 | 37.88 | L | C |
| ATOM | 3832 | CD | GLN | 99 | 108.266 | -1.748 | 3.319 | 1.00 | 37.88 | L | C |
| ATOM | 3833 | OE1 | GLN | 99 | 108.638 | -2.821 | 3.796 | 1.00 | 37.88 | L | O |
| ATOM | 3834 | NE2 | GLN | 99 | 109.110 | -0.832 | 2.866 | 1.00 | 37.88 | L | N |
| ATOM | 3835 | C | GLN | 99 | 107.586 | -0.758 | 6.634 | 1.00 | 11.59 | L | C |
| ATOM | 3836 | O | GLN | 99 | 106.943 | -1.317 | 7.508 | 1.00 | 11.59 | L | O |
| ATOM | 3837 | N | GLY | 100 | 108.902 | -0.640 | 6.684 | 1.00 | 24.72 | L | N |
| ATOM | 3838 | CA | GLY | 100 | 109.633 | -1.225 | 7.785 | 1.00 | 24.72 | L | C |
| ATOM | 3839 | C | GLY | 100 | 110.055 | -2.630 | 7.425 | 1.00 | 24.72 | L | C |
| ATOM | 3840 | O | GLY | 100 | 109.402 | -3.279 | 6.606 | 1.00 | 24.72 | L | O |
| ATOM | 3841 | N | THR | 101 | 111.157 | -3.084 | 8.017 | 1.00 | 23.77 | L | N |
| ATOM | 3842 | CA | THR | 101 | 111.685 | -4.424 | 7.780 | 1.00 | 23.77 | L | C |
| ATOM | 3843 | CB | THR | 101 | 113.019 | -4.382 | 7.040 | 1.00 | 10.18 | L | C |
| ATOM | 3844 | OG1 | THR | 101 | 112.790 | -4.076 | 5.659 | 1.00 | 10.18 | L | O |
| ATOM | 3845 | CG2 | THR | 101 | 113.735 | -5.716 | 7.173 | 1.00 | 10.18 | L | C |
| ATOM | 3846 | C | THR | 101 | 111.908 | -5.076 | 9.129 | 1.00 | 23.77 | L | C |
| ATOM | 3847 | O | THR | 101 | 112.689 | -4.582 | 9.942 | 1.00 | 23.77 | L | O |
| ATOM | 3848 | N | LYS | 102 | 111.223 | -6.188 | 9.365 | 1.00 | 19.34 | L | N |
| ATOM | 3849 | CA | LYS | 102 | 111.347 | -6.858 | 10.641 | 1.00 | 19.34 | L | C |
| ATOM | 3850 | CB | LYS | 102 | 110.009 | -7.496 | 11.027 | 1.00 | 36.70 | L | C |
| ATOM | 3851 | CG | LYS | 102 | 109.872 | -7.774 | 12.521 | 1.00 | 36.70 | L | C |
| ATOM | 3852 | CD | LYS | 102 | 108.464 | -8.244 | 12.876 | 1.00 | 36.70 | L | C |
| ATOM | 3853 | CE | LYS | 102 | 108.313 | -8.467 | 14.372 | 1.00 | 36.70 | L | C |
| ATOM | 3854 | NZ | LYS | 102 | 108.632 | -7.218 | 15.120 | 1.00 | 36.70 | L | N |
| ATOM | 3855 | C | LYS | 102 | 112.449 | -7.907 | 10.608 | 1.00 | 19.34 | L | C |
| ATOM | 3856 | O | LYS | 102 | 112.530 | -8.703 | 9.661 | 1.00 | 19.34 | L | O |
| ATOM | 3857 | N | VAL | 103 | 113.304 | -7.894 | 11.634 | 1.00 | 20.01 | L | N |
| ATOM | 3858 | CA | VAL | 103 | 114.378 | -8.868 | 11.714 | 1.00 | 20.01 | L | C |
| ATOM | 3859 | CB | VAL | 103 | 115.793 | -8.188 | 11.567 | 1.00 | 24.69 | L | C |
| ATOM | 3860 | CG1 | VAL | 103 | 115.696 | -6.991 | 10.636 | 1.00 | 24.69 | L | C |
| ATOM | 3861 | CG2 | VAL | 103 | 116.361 | -7.780 | 12.908 | 1.00 | 24.69 | L | C |
| ATOM | 3862 | C | VAL | 103 | 114.280 | -9.654 | 13.031 | 1.00 | 20.01 | L | C |
| ATOM | 3863 | O | VAL | 103 | 114.380 | -9.075 | 14.117 | 1.00 | 20.01 | L | O |
| ATOM | 3864 | N | GLU | 104 | 114.047 | -10.969 | 12.927 | 1.00 | 25.78 | L | N |
| ATOM | 3865 | CA | GLU | 104 | 113.948 | -11.831 | 14.106 | 1.00 | 25.78 | L | C |
| ATOM | 3866 | CB | GLU | 104 | 112.662 | -12.666 | 14.098 | 1.00 | 117.28 | L | C |
| ATOM | 3867 | CG | GLU | 104 | 112.589 | -13.728 | 13.022 | 1.00 | 117.28 | L | C |
| ATOM | 3868 | CD | GLU | 104 | 112.095 | -13.176 | 11.705 | 1.00 | 117.28 | L | C |
| ATOM | 3869 | OE1 | GLU | 104 | 112.047 | -13.942 | 10.717 | 1.00 | 117.28 | L | O |

FIG. 19A-54

| | | | | | | | | | | |
|---|---|---|---|---|---|---|---|---|---|---|
| ATOM | 3870 | OE2 | GLU | 104 | 111.747 | -11.975 | 11.660 | 1.00 | 117.28 | L | O |
| ATOM | 3871 | C | GLU | 104 | 115.148 | -12.759 | 14.179 | 1.00 | 25.78 | L | C |
| ATOM | 3872 | O | GLU | 104 | 115.852 | -12.955 | 13.185 | 1.00 | 25.78 | L | O |
| ATOM | 3873 | N | ILE | 105 | 115.368 | -13.324 | 15.365 | 1.00 | 16.82 | L | N |
| ATOM | 3874 | CA | ILE | 105 | 116.489 | -14.228 | 15.621 | 1.00 | 16.82 | L | C |
| ATOM | 3875 | CB | ILE | 105 | 116.771 | -14.386 | 17.124 | 1.00 | 41.57 | L | C |
| ATOM | 3876 | CG2 | ILE | 105 | 118.226 | -14.701 | 17.335 | 1.00 | 41.57 | L | C |
| ATOM | 3877 | CG1 | ILE | 105 | 116.372 | -13.111 | 17.873 | 1.00 | 41.57 | L | C |
| ATOM | 3878 | CD1 | ILE | 105 | 116.594 | -13.151 | 19.385 | 1.00 | 41.57 | L | C |
| ATOM | 3879 | C | ILE | 105 | 116.204 | -15.611 | 15.102 | 1.00 | 16.82 | L | C |
| ATOM | 3880 | O | ILE | 105 | 115.251 | -16.250 | 15.543 | 1.00 | 16.82 | L | O |
| ATOM | 3881 | N | LYS | 106 | 117.008 | -16.076 | 14.153 | 1.00 | 39.65 | L | N |
| ATOM | 3882 | CA | LYS | 106 | 116.807 | -17.422 | 13.653 | 1.00 | 39.65 | L | C |
| ATOM | 3883 | CB | LYS | 106 | 117.310 | -17.587 | 12.217 | 1.00 | 48.57 | L | C |
| ATOM | 3884 | CG | LYS | 106 | 116.947 | -18.952 | 11.631 | 1.00 | 48.57 | L | C |
| ATOM | 3885 | CD | LYS | 106 | 117.401 | -19.148 | 10.179 | 1.00 | 48.57 | L | C |
| ATOM | 3886 | CE | LYS | 106 | 117.087 | -20.579 | 9.702 | 1.00 | 48.57 | L | C |
| ATOM | 3887 | NZ | LYS | 106 | 117.672 | -20.948 | 8.369 | 1.00 | 48.57 | L | N |
| ATOM | 3888 | C | LYS | 106 | 117.598 | -18.310 | 14.600 | 1.00 | 39.65 | L | C |
| ATOM | 3889 | O | LYS | 106 | 118.804 | -18.122 | 14.782 | 1.00 | 38.70 | L | O |
| ATOM | 3890 | N | ARG | 107 | 116.894 | -19.242 | 15.235 | 1.00 | 14.86 | L | N |
| ATOM | 3891 | CA | ARG | 107 | 117.492 | -20.178 | 16.174 | 1.00 | 14.86 | L | C |
| ATOM | 3892 | CB | ARG | 107 | 117.158 | -19.771 | 17.605 | 1.00 | 20.96 | L | C |
| ATOM | 3893 | CG | ARG | 107 | 115.687 | -19.532 | 17.832 | 1.00 | 20.96 | L | C |
| ATOM | 3894 | CD | ARG | 107 | 115.296 | -19.930 | 19.239 | 1.00 | 20.96 | L | C |
| ATOM | 3895 | NE | ARG | 107 | 115.615 | -21.335 | 19.502 | 1.00 | 20.96 | L | N |
| ATOM | 3896 | CZ | ARG | 107 | 115.513 | -21.910 | 20.692 | 1.00 | 20.96 | L | C |
| ATOM | 3897 | NH1 | ARG | 107 | 115.096 | -21.206 | 21.732 | 1.00 | 20.96 | L | N |
| ATOM | 3898 | NH2 | ARG | 107 | 115.843 | -23.182 | 20.840 | 1.00 | 20.96 | L | N |
| ATOM | 3899 | C | ARG | 107 | 116.986 | -21.595 | 15.899 | 1.00 | 14.86 | L | C |
| ATOM | 3900 | O | ARG | 107 | 116.062 | -21.796 | 15.107 | 1.00 | 14.86 | L | O |
| ATOM | 3901 | N | THR | 108 | 117.606 | -22.575 | 16.545 | 1.00 | 15.74 | L | N |
| ATOM | 3902 | CA | THR | 108 | 117.220 | -23.963 | 16.354 | 1.00 | 15.74 | L | C |
| ATOM | 3903 | CB | THR | 108 | 118.025 | -24.921 | 17.260 | 1.00 | 26.88 | L | C |
| ATOM | 3904 | OG1 | THR | 108 | 118.232 | -24.320 | 18.548 | 1.00 | 26.88 | L | O |
| ATOM | 3905 | CG2 | THR | 108 | 119.347 | -25.257 | 16.618 | 1.00 | 26.88 | L | C |
| ATOM | 3906 | C | THR | 108 | 115.756 | -24.161 | 16.653 | 1.00 | 15.74 | L | C |
| ATOM | 3907 | O | THR | 108 | 115.179 | -23.450 | 17.481 | 1.00 | 15.74 | L | O |
| ATOM | 3908 | N | VAL | 109 | 115.170 | -25.134 | 15.963 | 1.00 | 14.98 | L | N |
| ATOM | 3909 | CA | VAL | 109 | 113.775 | -25.469 | 16.136 | 1.00 | 12.60 | L | C |
| ATOM | 3910 | CB | VAL | 109 | 113.368 | -26.593 | 15.189 | 1.00 | 15.46 | L | C |
| ATOM | 3911 | CG1 | VAL | 109 | 111.987 | -27.105 | 15.527 | 1.00 | 14.41 | L | C |
| ATOM | 3912 | CG2 | VAL | 109 | 113.383 | -26.074 | 13.789 | 1.00 | 13.59 | L | C |
| ATOM | 3913 | C | VAL | 109 | 113.517 | -25.909 | 17.565 | 1.00 | 13.54 | L | C |
| ATOM | 3914 | O | VAL | 109 | 114.393 | -26.477 | 18.236 | 1.00 | 21.28 | L | O |
| ATOM | 3915 | N | ALA | 110 | 112.313 | -25.637 | 18.036 | 1.00 | 11.81 | L | N |
| ATOM | 3916 | CA | ALA | 110 | 111.953 | -26.001 | 19.383 | 1.00 | 12.99 | L | C |
| ATOM | 3917 | CB | ALA | 110 | 112.312 | -24.878 | 20.330 | 1.00 | 8.30 | L | C |
| ATOM | 3918 | C | ALA | 110 | 110.463 | -26.281 | 19.426 | 1.00 | 13.63 | L | C |
| ATOM | 3919 | O | ALA | 110 | 109.654 | -25.390 | 19.158 | 1.00 | 15.92 | L | O |
| ATOM | 3920 | N | ALA | 111 | 110.112 | -27.525 | 19.758 | 1.00 | 25.70 | L | N |
| ATOM | 3921 | CA | ALA | 111 | 108.715 | -27.951 | 19.838 | 1.00 | 26.75 | L | C |
| ATOM | 3922 | CB | ALA | 111 | 108.641 | -29.446 | 20.087 | 1.00 | 23.32 | L | C |
| ATOM | 3923 | C | ALA | 111 | 107.981 | -27.198 | 20.936 | 1.00 | 25.59 | L | C |
| ATOM | 3924 | O | ALA | 111 | 108.525 | -26.926 | 22.008 | 1.00 | 29.44 | L | O |
| ATOM | 3925 | N | PRO | 112 | 106.720 | -26.857 | 20.686 | 1.00 | 20.76 | L | N |
| ATOM | 3926 | CD | PRO | 112 | 105.901 | -27.063 | 19.477 | 1.00 | 26.01 | L | C |
| ATOM | 3927 | CA | PRO | 112 | 105.975 | -26.125 | 21.707 | 1.00 | 26.81 | L | C |
| ATOM | 3928 | CB | PRO | 112 | 104.938 | -25.381 | 20.882 | 1.00 | 26.37 | L | C |
| ATOM | 3929 | CG | PRO | 112 | 104.550 | -26.457 | 19.876 | 1.00 | 24.71 | L | C |
| ATOM | 3930 | C | PRO | 112 | 105.322 | -27.058 | 22.703 | 1.00 | 30.67 | L | C |
| ATOM | 3931 | O | PRO | 112 | 104.936 | -28.166 | 22.353 | 1.00 | 31.28 | L | O |
| ATOM | 3932 | N | SER | 113 | 105.220 | -26.618 | 23.947 | 1.00 | 12.97 | L | N |
| ATOM | 3933 | CA | SER | 113 | 104.530 | -27.410 | 24.944 | 1.00 | 16.57 | L | C |
| ATOM | 3934 | CB | SER | 113 | 105.027 | -27.079 | 26.334 | 1.00 | 14.96 | L | C |
| ATOM | 3935 | OG | SER | 113 | 106.427 | -27.168 | 26.370 | 1.00 | 27.37 | L | O |
| ATOM | 3936 | C | SER | 113 | 103.099 | -26.913 | 24.815 | 1.00 | 15.10 | L | C |
| ATOM | 3937 | O | SER | 113 | 102.884 | -25.708 | 24.770 | 1.00 | 12.98 | L | O |
| ATOM | 3938 | N | VAL | 114 | 102.111 | -27.792 | 24.731 | 1.00 | 10.23 | L | N |
| ATOM | 3939 | CA | VAL | 114 | 100.766 | -27.258 | 24.630 | 1.00 | 9.98 | L | C |
| ATOM | 3940 | CB | VAL | 114 | 99.989 | -27.808 | 23.413 | 1.00 | 7.82 | L | C |
| ATOM | 3941 | CG1 | VAL | 114 | 100.921 | -27.972 | 22.212 | 1.00 | 4.17 | L | C |
| ATOM | 3942 | CG2 | VAL | 114 | 99.331 | -29.100 | 23.777 | 1.00 | 9.35 | L | C |

FIG. 19A-55

| ATOM | 3943 | C | VAL | 114 | 99.992 | -27.558 | 25.899 | 1.00 | 9.84 | L | C |
|---|---|---|---|---|---|---|---|---|---|---|---|
| ATOM | 3944 | O | VAL | 114 | 100.318 | -28.494 | 26.628 | 1.00 | 12.49 | L | O |
| ATOM | 3945 | N | PHE | 115 | 98.981 | -26.728 | 26.153 | 1.00 | 26.11 | L | N |
| ATOM | 3946 | CA | PHE | 115 | 98.109 | -26.840 | 27.318 | 1.00 | 30.12 | L | C |
| ATOM | 3947 | CB | PHE | 115 | 98.581 | -25.896 | 28.416 | 1.00 | 36.06 | L | C |
| ATOM | 3948 | CG | PHE | 115 | 100.030 | -26.015 | 28.706 | 1.00 | 35.84 | L | C |
| ATOM | 3949 | CD1 | PHE | 115 | 100.505 | -27.040 | 29.513 | 1.00 | 38.16 | L | C |
| ATOM | 3950 | CD2 | PHE | 115 | 100.935 | -25.146 | 28.115 | 1.00 | 34.45 | L | C |
| ATOM | 3951 | CE1 | PHE | 115 | 101.854 | -27.203 | 29.723 | 1.00 | 41.30 | L | C |
| ATOM | 3952 | CE2 | PHE | 115 | 102.287 | -25.302 | 28.319 | 1.00 | 38.56 | L | C |
| ATOM | 3953 | CZ | PHE | 115 | 102.749 | -26.335 | 29.126 | 1.00 | 39.82 | L | C |
| ATOM | 3954 | C | PHE | 115 | 96.727 | -26.410 | 26.873 | 1.00 | 32.06 | L | C |
| ATOM | 3955 | O | PHE | 115 | 96.590 | -25.543 | 26.017 | 1.00 | 32.56 | L | O |
| ATOM | 3956 | N | ILE | 116 | 95.694 | -27.018 | 27.432 | 1.00 | 24.34 | L | N |
| ATOM | 3957 | CA | ILE | 116 | 94.354 | -26.608 | 27.069 | 1.00 | 18.54 | L | C |
| ATOM | 3958 | CB | ILE | 116 | 93.606 | -27.735 | 26.309 | 1.00 | 15.62 | L | C |
| ATOM | 3959 | CG2 | ILE | 116 | 93.239 | -28.855 | 27.249 | 1.00 | 4.34 | L | C |
| ATOM | 3960 | CG1 | ILE | 116 | 92.377 | -27.145 | 25.615 | 1.00 | 12.45 | L | C |
| ATOM | 3961 | CD1 | ILE | 116 | 91.695 | -28.089 | 24.646 | 1.00 | 4.28 | L | C |
| ATOM | 3962 | C | ILE | 116 | 93.661 | -26.233 | 28.371 | 1.00 | 19.64 | L | C |
| ATOM | 3963 | O | ILE | 116 | 93.931 | -26.834 | 29.412 | 1.00 | 19.05 | L | O |
| ATOM | 3964 | N | PHE | 117 | 92.802 | -25.217 | 28.308 | 1.00 | 17.52 | L | N |
| ATOM | 3965 | CA | PHE | 117 | 92.066 | -24.715 | 29.475 | 1.00 | 21.17 | L | C |
| ATOM | 3966 | CB | PHE | 117 | 92.501 | -23.295 | 29.828 | 1.00 | 22.98 | L | C |
| ATOM | 3967 | CG | PHE | 117 | 93.922 | -23.177 | 30.280 | 1.00 | 26.62 | L | C |
| ATOM | 3968 | CD1 | PHE | 117 | 94.293 | -23.562 | 31.559 | 1.00 | 29.31 | L | C |
| ATOM | 3969 | CD2 | PHE | 117 | 94.882 | -22.653 | 29.433 | 1.00 | 28.01 | L | C |
| ATOM | 3970 | CE1 | PHE | 117 | 95.599 | -23.421 | 31.988 | 1.00 | 28.27 | L | C |
| ATOM | 3971 | CE2 | PHE | 117 | 96.186 | -22.511 | 29.854 | 1.00 | 26.58 | L | C |
| ATOM | 3972 | CZ | PHE | 117 | 96.550 | -22.895 | 31.134 | 1.00 | 28.58 | L | C |
| ATOM | 3973 | C | PHE | 117 | 90.585 | -24.642 | 29.194 | 1.00 | 24.71 | L | C |
| ATOM | 3974 | O | PHE | 117 | 90.167 | -23.964 | 28.261 | 1.00 | 29.18 | L | O |
| ATOM | 3975 | N | PRO | 118 | 89.768 | -25.323 | 30.007 | 1.00 | 23.78 | L | N |
| ATOM | 3976 | CD | PRO | 118 | 90.235 | -26.376 | 30.926 | 1.00 | 9.40 | L | C |
| ATOM | 3977 | CA | PRO | 118 | 88.300 | -25.354 | 29.883 | 1.00 | 26.26 | L | C |
| ATOM | 3978 | CB | PRO | 118 | 87.907 | -26.568 | 30.718 | 1.00 | 9.92 | L | C |
| ATOM | 3979 | CG | PRO | 118 | 89.159 | -27.404 | 30.763 | 1.00 | 12.26 | L | C |
| ATOM | 3980 | C | PRO | 118 | 87.660 | -24.081 | 30.455 | 1.00 | 29.72 | L | C |
| ATOM | 3981 | O | PRO | 118 | 88.231 | -23.440 | 31.338 | 1.00 | 31.19 | L | O |
| ATOM | 3982 | N | PRO | 119 | 86.464 | -23.699 | 29.966 | 1.00 | 9.50 | L | N |
| ATOM | 3983 | CD | PRO | 119 | 85.678 | -24.330 | 28.892 | 1.00 | 26.21 | L | C |
| ATOM | 3984 | CA | PRO | 119 | 85.787 | -22.493 | 30.479 | 1.00 | 9.82 | L | C |
| ATOM | 3985 | CB | PRO | 119 | 84.413 | -22.555 | 29.826 | 1.00 | 24.20 | L | C |
| ATOM | 3986 | CG | PRO | 119 | 84.703 | -23.219 | 28.519 | 1.00 | 27.52 | L | C |
| ATOM | 3987 | C | PRO | 119 | 85.682 | -22.566 | 32.001 | 1.00 | 15.21 | L | C |
| ATOM | 3988 | O | PRO | 119 | 85.463 | -23.630 | 32.561 | 1.00 | 17.89 | L | O |
| ATOM | 3989 | N | SER | 120 | 85.843 | -21.435 | 32.665 | 1.00 | 31.09 | L | N |
| ATOM | 3990 | CA | SER | 120 | 85.765 | -21.378 | 34.118 | 1.00 | 35.08 | L | C |
| ATOM | 3991 | CB | SER | 120 | 86.299 | -20.027 | 34.586 | 1.00 | 17.54 | L | C |
| ATOM | 3992 | OG | SER | 120 | 85.709 | -18.983 | 33.832 | 1.00 | 27.86 | L | O |
| ATOM | 3993 | C | SER | 120 | 84.334 | -21.550 | 34.623 | 1.00 | 35.73 | L | C |
| ATOM | 3994 | O | SER | 120 | 83.370 | -21.381 | 33.869 | 1.00 | 35.32 | L | O |
| ATOM | 3995 | N | ASP | 121 | 84.185 | -21.896 | 35.897 | 1.00 | 24.20 | L | N |
| ATOM | 3996 | CA | ASP | 121 | 82.842 | -22.015 | 36.465 | 1.00 | 27.07 | L | C |
| ATOM | 3997 | CB | ASP | 121 | 82.897 | -22.458 | 37.937 | 1.00 | 55.35 | L | C |
| ATOM | 3998 | CG | ASP | 121 | 83.160 | -23.950 | 38.101 | 1.00 | 60.98 | L | C |
| ATOM | 3999 | OD1 | ASP | 121 | 82.573 | -24.736 | 37.331 | 1.00 | 62.35 | L | O |
| ATOM | 4000 | OD2 | ASP | 121 | 83.934 | -24.337 | 39.008 | 1.00 | 63.66 | L | O |
| ATOM | 4001 | C | ASP | 121 | 82.194 | -20.627 | 36.384 | 1.00 | 26.11 | L | C |
| ATOM | 4002 | O | ASP | 121 | 81.053 | -20.474 | 35.941 | 1.00 | 23.12 | L | O |
| ATOM | 4003 | N | GLU | 122 | 82.954 | -19.617 | 36.794 | 1.00 | 48.87 | L | N |
| ATOM | 4004 | CA | GLU | 122 | 82.490 | -18.234 | 36.797 | 1.00 | 47.43 | L | C |
| ATOM | 4005 | CB | GLU | 122 | 83.596 | -17.328 | 37.348 | 1.00 | 56.26 | L | C |
| ATOM | 4006 | CG | GLU | 122 | 83.180 | -15.870 | 37.529 | 1.00 | 59.80 | L | C |
| ATOM | 4007 | CD | GLU | 122 | 84.328 | -14.966 | 37.984 | 1.00 | 63.49 | L | C |
| ATOM | 4008 | OE1 | GLU | 122 | 84.099 | -13.741 | 38.109 | 1.00 | 64.12 | L | O |
| ATOM | 4009 | OE2 | GLU | 122 | 85.453 | -15.472 | 38.213 | 1.00 | 63.98 | L | O |
| ATOM | 4010 | C | GLU | 122 | 82.018 | -17.703 | 35.434 | 1.00 | 47.22 | L | C |
| ATOM | 4011 | O | GLU | 122 | 80.884 | -17.232 | 35.303 | 1.00 | 45.96 | L | O |
| ATOM | 4012 | N | GLN | 123 | 82.881 | -17.774 | 34.424 | 1.00 | 34.52 | L | N |
| ATOM | 4013 | CA | GLN | 123 | 82.523 | -17.273 | 33.102 | 1.00 | 32.32 | L | C |
| ATOM | 4014 | CB | GLN | 123 | 83.643 | -17.511 | 32.097 | 1.00 | 23.68 | L | C |
| ATOM | 4015 | CG | GLN | 123 | 83.286 | -17.000 | 30.723 | 1.00 | 24.85 | L | C |

FIG. 19A-56

```
ATOM   4016  CD   GLN  123     84.089  -17.644  29.635  1.00   26.94  L  C
ATOM   4017  OE1  GLN  123     83.877  -17.369  28.463  1.00   23.36  L  O
ATOM   4018  NE2  GLN  123     85.017  -18.511  30.010  1.00   24.66  L  N
ATOM   4019  C    GLN  123     81.256  -17.909  32.565  1.00   32.32  L  C
ATOM   4020  O    GLN  123     80.424  -17.233  31.969  1.00   29.27  L  O
ATOM   4021  N    LEU  124     81.128  -19.218  32.745  1.00   36.22  L  N
ATOM   4022  CA   LEU  124     79.938  -19.926  32.288  1.00   37.57  L  C
ATOM   4023  CB   LEU  124     80.075  -21.425  32.570  1.00   20.16  L  C
ATOM   4024  CG   LEU  124     80.878  -22.173  31.498  1.00   19.96  L  C
ATOM   4025  CD1  LEU  124     81.099  -23.623  31.892  1.00   15.21  L  C
ATOM   4026  CD2  LEU  124     80.123  -22.085  30.176  1.00   18.53  L  C
ATOM   4027  C    LEU  124     78.722  -19.355  33.003  1.00   41.33  L  C
ATOM   4028  O    LEU  124     77.648  -19.204  32.417  1.00   43.14  L  O
ATOM   4029  N    LYS  125     78.912  -19.022  34.274  1.00  101.23  L  N
ATOM   4030  CA   LYS  125     77.856  -18.441  35.090  1.00  102.45  L  C
ATOM   4031  CB   LYS  125     78.355  -18.285  36.534  1.00   60.11  L  C
ATOM   4032  CG   LYS  125     77.286  -18.376  37.612  1.00   62.95  L  C
ATOM   4033  CD   LYS  125     76.737  -19.797  37.713  1.00   68.67  L  C
ATOM   4034  CE   LYS  125     75.726  -19.942  38.847  1.00   73.14  L  C
ATOM   4035  NZ   LYS  125     75.101  -21.299  38.895  1.00   74.11  L  N
ATOM   4036  C    LYS  125     77.545  -17.065  34.494  1.00  104.22  L  C
ATOM   4037  O    LYS  125     77.004  -16.195  35.168  1.00  105.97  L  O
ATOM   4038  N    SER  126     77.892  -16.880  33.222  1.00   44.02  L  N
ATOM   4039  CA   SER  126     77.693  -15.614  32.522  1.00   43.14  L  C
ATOM   4040  CB   SER  126     79.045  -14.925  32.308  1.00   48.89  L  C
ATOM   4041  OG   SER  126     78.953  -13.915  31.324  1.00   52.18  L  O
ATOM   4042  C    SER  126     76.995  -15.769  31.176  1.00   41.22  L  C
ATOM   4043  O    SER  126     76.469  -14.802  30.631  1.00   40.32  L  O
ATOM   4044  N    GLY  127     77.007  -16.978  30.626  1.00   29.57  L  N
ATOM   4045  CA   GLY  127     76.340  -17.190  29.355  1.00   30.30  L  C
ATOM   4046  C    GLY  127     77.266  -17.332  28.168  1.00   29.68  L  C
ATOM   4047  O    GLY  127     76.818  -17.391  27.022  1.00   30.41  L  O
ATOM   4048  N    THR  128     78.564  -17.375  28.432  1.00   60.53  L  N
ATOM   4049  CA   THR  128     79.530  -17.531  27.360  1.00   57.77  L  C
ATOM   4050  CB   THR  128     80.105  -16.180  26.921  1.00   55.78  L  C
ATOM   4051  OG1  THR  128     79.080  -15.424  26.264  1.00   56.94  L  O
ATOM   4052  CG2  THR  128     81.259  -16.381  25.960  1.00   54.81  L  C
ATOM   4053  C    THR  128     80.643  -18.434  27.830  1.00   56.24  L  C
ATOM   4054  O    THR  128     80.979  -18.446  29.015  1.00   51.99  L  O
ATOM   4055  N    ALA  129     81.201  -19.203  26.901  1.00   18.93  L  N
ATOM   4056  CA   ALA  129     82.275  -20.125  27.232  1.00   17.83  L  C
ATOM   4057  CB   ALA  129     81.779  -21.558  27.108  1.00   65.23  L  C
ATOM   4058  C    ALA  129     83.512  -19.937  26.374  1.00   17.59  L  C
ATOM   4059  O    ALA  129     83.443  -19.993  25.148  1.00   23.96  L  O
ATOM   4060  N    SER  130     84.652  -19.729  27.020  1.00   24.31  L  N
ATOM   4061  CA   SER  130     85.905  -19.560  26.298  1.00   19.76  L  C
ATOM   4062  CB   SER  130     86.565  -18.256  26.741  1.00   18.21  L  C
ATOM   4063  OG   SER  130     85.724  -17.142  26.477  1.00   20.32  L  O
ATOM   4064  C    SER  130     86.835  -20.755  26.573  1.00   16.63  L  C
ATOM   4065  O    SER  130     87.037  -21.141  27.732  1.00   19.43  L  O
ATOM   4066  N    VAL  131     87.370  -21.371  25.521  1.00   11.62  L  N
ATOM   4067  CA   VAL  131     88.294  -22.502  25.686  1.00    9.15  L  C
ATOM   4068  CB   VAL  131     87.848  -23.743  24.872  1.00   17.04  L  C
ATOM   4069  CG1  VAL  131     88.738  -24.927  25.196  1.00   21.32  L  C
ATOM   4070  CG2  VAL  131     86.413  -24.081  25.180  1.00   16.62  L  C
ATOM   4071  C    VAL  131     89.647  -22.030  25.156  1.00    9.42  L  C
ATOM   4072  O    VAL  131     89.731  -21.557  24.025  1.00   13.02  L  O
ATOM   4073  N    VAL  132     90.704  -22.146  25.956  1.00   21.24  L  N
ATOM   4074  CA   VAL  132     92.011  -21.677  25.501  1.00   16.30  L  C
ATOM   4075  CB   VAL  132     92.573  -20.538  26.414  1.00   43.77  L  C
ATOM   4076  CG1  VAL  132     93.958  -20.122  25.934  1.00   47.77  L  C
ATOM   4077  CG2  VAL  132     91.645  -19.324  26.393  1.00   44.24  L  C
ATOM   4078  C    VAL  132     93.081  -22.743  25.374  1.00   17.14  L  C
ATOM   4079  O    VAL  132     93.372  -23.482  26.320  1.00   14.49  L  O
ATOM   4080  N    CYS  133     93.662  -22.793  24.178  1.00   23.86  L  N
ATOM   4081  CA   CYS  133     94.737  -23.713  23.822  1.00   24.13  L  C
ATOM   4082  C    CYS  133     96.034  -22.880  23.891  1.00   24.10  L  C
ATOM   4083  O    CYS  133     96.072  -21.744  23.425  1.00   27.83  L  O
ATOM   4084  CB   CYS  133     94.486  -24.219  22.399  1.00   19.56  L  C
ATOM   4085  SG   CYS  133     95.558  -25.537  21.738  1.00   32.96  L  S
ATOM   4086  N    LEU  134     97.085  -23.432  24.482  1.00   36.02  L  N
ATOM   4087  CA   LEU  134     98.343  -22.709  24.591  1.00   34.35  L  C
ATOM   4088  CB   LEU  134     98.658  -22.383  26.058  1.00   16.71  L  C
```

FIG. 19A-57

```
ATOM   4089  CG   LEU  134    100.079 -21.843  26.376  1.00  12.52  L  C
ATOM   4090  CD1  LEU  134    100.297 -20.468  25.729  1.00   9.26  L  C
ATOM   4091  CD2  LEU  134    100.275 -21.746  27.892  1.00   9.75  L  C
ATOM   4092  C    LEU  134     99.532 -23.457  24.001  1.00  33.88  L  C
ATOM   4093  O    LEU  134     99.820 -24.595  24.378  1.00  33.96  L  O
ATOM   4094  N    LEU  135    100.206 -22.802  23.060  1.00  23.69  L  N
ATOM   4095  CA   LEU  135    101.406 -23.336  22.441  1.00  29.22  L  C
ATOM   4096  CB   LEU  135    101.353 -23.150  20.926  1.00   1.87  L  C
ATOM   4097  CG   LEU  135    100.337 -24.016  20.168  1.00   4.32  L  C
ATOM   4098  CD1  LEU  135     98.962 -23.751  20.672  1.00   5.12  L  C
ATOM   4099  CD2  LEU  135    100.392 -23.713  18.681  1.00   3.70  L  C
ATOM   4100  C    LEU  135    102.454 -22.437  23.097  1.00  29.43  L  C
ATOM   4101  O    LEU  135    102.401 -21.216  22.977  1.00  30.81  L  O
ATOM   4102  N    ASN  136    103.394 -23.047  23.810  1.00  17.75  L  N
ATOM   4103  CA   ASN  136    104.393 -22.299  24.550  1.00  20.05  L  C
ATOM   4104  CB   ASN  136    104.179 -22.576  26.016  1.00  15.03  L  C
ATOM   4105  CG   ASN  136    104.905 -21.615  26.885  1.00  19.57  L  C
ATOM   4106  OD1  ASN  136    105.767 -22.017  27.666  1.00  25.01  L  O
ATOM   4107  ND2  ASN  136    104.569 -20.327  26.769  1.00  19.54  L  N
ATOM   4108  C    ASN  136    105.856 -22.526  24.212  1.00  18.78  L  C
ATOM   4109  O    ASN  136    106.283 -23.651  23.963  1.00  17.25  L  O
ATOM   4110  N    ASN  137    106.619 -21.436  24.240  1.00  28.11  L  N
ATOM   4111  CA   ASN  137    108.053 -21.425  23.950  1.00  27.19  L  C
ATOM   4112  CB   ASN  137    108.869 -21.844  25.173  1.00  13.82  L  C
ATOM   4113  CG   ASN  137    108.594 -20.986  26.387  1.00  24.17  L  C
ATOM   4114  OD1  ASN  137    108.027 -19.901  26.281  1.00  19.30  L  O
ATOM   4115  ND2  ASN  137    109.009 -21.468  27.558  1.00  29.25  L  N
ATOM   4116  C    ASN  137    108.486 -22.292  22.783  1.00  25.42  L  C
ATOM   4117  O    ASN  137    109.125 -23.324  22.977  1.00  28.31  L  O
ATOM   4118  N    PHE  138    108.152 -21.880  21.571  1.00  45.01  L  N
ATOM   4119  CA   PHE  138    108.557 -22.652  20.412  1.00  41.21  L  C
ATOM   4120  CB   PHE  138    107.362 -23.361  19.777  1.00  23.11  L  C
ATOM   4121  CG   PHE  138    106.230 -22.452  19.442  1.00  20.89  L  C
ATOM   4122  CD1  PHE  138    105.342 -22.043  20.433  1.00  18.63  L  C
ATOM   4123  CD2  PHE  138    106.055 -21.993  18.137  1.00  19.93  L  C
ATOM   4124  CE1  PHE  138    104.289 -21.189  20.134  1.00  11.59  L  C
ATOM   4125  CE2  PHE  138    105.010 -21.138  17.818  1.00  16.52  L  C
ATOM   4126  CZ   PHE  138    104.118 -20.730  18.818  1.00  14.07  L  C
ATOM   4127  C    PHE  138    109.248 -21.794  19.369  1.00  36.81  L  C
ATOM   4128  O    PHE  138    109.456 -20.594  19.559  1.00  35.37  L  O
ATOM   4129  N    TYR  139    109.606 -22.437  18.267  1.00  17.70  L  N
ATOM   4130  CA   TYR  139    110.283 -21.797  17.159  1.00  20.93  L  C
ATOM   4131  CB   TYR  139    111.660 -21.300  17.579  1.00  31:56  L  C
ATOM   4132  CG   TYR  139    112.317 -20.472  16.502  1.00  31.46  L  C
ATOM   4133  CD1  TYR  139    112.207 -19.083  16.502  1.00  26.49  L  C
ATOM   4134  CE1  TYR  139    112.725 -18.327  15.462  1.00  25.20  L  C
ATOM   4135  CD2  TYR  139    112.974 -21.083  15.428  1.00  25.20  L  C
ATOM   4136  CE2  TYR  139    113.490 -20.336  14.386  1.00  25.20  L  C
ATOM   4137  CZ   TYR  139    113.358 -18.960  14.407  1.00  25.20  L  C
ATOM   4138  OH   TYR  139    113.820 -18.216  13.353  1.00  28.00  L  O
ATOM   4139  C    TYR  139    110.447 -22.917  16.166  1.00  20.32  L  C
ATOM   4140  O    TYR  139    110.798 -24.022  16.550  1.00  25.25  L  O
ATOM   4141  N    PRO  140    110.223 -22.662  14.876  1.00  34.32  L  N
ATOM   4142  CD   PRO  140    110.342 -23.783  13.937  1.00   6.42  L  C
ATOM   4143  CA   PRO  140    109.824 -21.443  14.171  1.00  30.02  L  C
ATOM   4144  CB   PRO  140    109.691 -21.901  12.723  1.00   2.76  L  C
ATOM   4145  CG   PRO  140    110.570 -23.070  12.643  1.00   4.42  L  C
ATOM   4146  C    PRO  140    108.502 -20.939  14.685  1.00  31.53  L  C
ATOM   4147  O    PRO  140    107.830 -21.612  15.466  1.00  29.36  L  O
ATOM   4148  N    ARG  141    108.119 -19.764  14.203  1.00  22.83  L  N
ATOM   4149  CA   ARG  141    106.871 -19.115  14.588  1.00  27.99  L  C
ATOM   4150  CB   ARG  141    106.931 -17.657  14.148  1.00  21.70  L  C
ATOM   4151  CG   ARG  141    105.753 -16.783  14.473  1.00  25.87  L  C
ATOM   4152  CD   ARG  141    106.157 -15.358  14.129  1.00  37.20  L  C
ATOM   4153  NE   ARG  141    105.187 -14.366  14.564  1.00  43.19  L  N
ATOM   4154  CZ   ARG  141    104.001 -14.188  13.995  1.00  43.90  L  C
ATOM   4155  NH1  ARG  141    103.642 -14.941  12.960  1.00  39.57  L  N
ATOM   4156  NH2  ARG  141    103.173 -13.262  14.464  1.00  42.44  L  N
ATOM   4157  C    ARG  141    105.668 -19.798  13.960  1.00  30.81  L  C
ATOM   4158  O    ARG  141    104.585 -19.815  14.537  1.00  34.71  L  O
ATOM   4159  N    GLU  142    105.860 -20.365  12.776  1.00  28.20  L  N
ATOM   4160  CA   GLU  142    104.756 -21.013  12.091  1.00  24.33  L  C
ATOM   4161  CB   GLU  142    105.171 -21.552  10.725  1.00   7.98  L  C
```

FIG. 19A-58

| | | | | | | | | | | |
|---|---|---|---|---|---|---|---|---|---|---|
| ATOM | 4162 | CG | GLU | 142 | 105.741 | -20.523 | 9.781 | 1.00 | 19.00 | L | C |
| ATOM | 4163 | CD | GLU | 142 | 107.096 | -20.051 | 10.217 | 1.00 | 27.12 | L | C |
| ATOM | 4164 | OE1 | GLU | 142 | 107.152 | -18.970 | 10.837 | 1.00 | 31.02 | L | O |
| ATOM | 4165 | OE2 | GLU | 142 | 108.095 | -20.772 | 9.952 | 1.00 | 33.88 | L | O |
| ATOM | 4166 | C | GLU | 142 | 104.154 | -22.151 | 12.878 | 1.00 | 22.94 | L | C |
| ATOM | 4167 | O | GLU | 142 | 104.753 | -23.220 | 13.021 | 1.00 | 26.95 | L | O |
| ATOM | 4168 | N | ALA | 143 | 102.958 | -21.909 | 13.386 | 1.00 | 30.55 | L | N |
| ATOM | 4169 | CA | ALA | 143 | 102.238 | -22.914 | 14.130 | 1.00 | 32.81 | L | C |
| ATOM | 4170 | CB | ALA | 143 | 102.260 | -22.593 | 15.640 | 1.00 | 21.32 | L | C |
| ATOM | 4171 | C | ALA | 143 | 100.819 | -22.862 | 13.579 | 1.00 | 34.94 | L | C |
| ATOM | 4172 | O | ALA | 143 | 100.373 | -21.832 | 13.058 | 1.00 | 38.69 | L | O |
| ATOM | 4173 | N | LYS | 144 | 100.120 | -23.981 | 13.677 | 1.00 | 46.96 | L | N |
| ATOM | 4174 | CA | LYS | 144 | 98.761 | -24.047 | 13.197 | 1.00 | 49.64 | L | C |
| ATOM | 4175 | CB | LYS | 144 | 98.734 | -24.807 | 11.870 | 1.00 | 34.36 | L | C |
| ATOM | 4176 | CG | LYS | 144 | 97.631 | -24.370 | 10.922 | 1.00 | 44.31 | L | C |
| ATOM | 4177 | CD | LYS | 144 | 97.441 | -25.358 | 9.772 | 1.00 | 55.06 | L | C |
| ATOM | 4178 | CE | LYS | 144 | 96.888 | -26.699 | 10.279 | 1.00 | 57.35 | L | C |
| ATOM | 4179 | NZ | LYS | 144 | 96.807 | -27.761 | 9.225 | 1.00 | 58.76 | L | N |
| ATOM | 4180 | C | LYS | 144 | 97.934 | -24.771 | 14.266 | 1.00 | 52.97 | L | C |
| ATOM | 4181 | O | LYS | 144 | 98.340 | -25.822 | 14.775 | 1.00 | 51.55 | L | O |
| ATOM | 4182 | N | VAL | 145 | 96.791 | -24.194 | 14.630 | 1.00 | 15.87 | L | N |
| ATOM | 4183 | CA | VAL | 145 | 95.927 | -24.813 | 15.629 | 1.00 | 21.71 | L | C |
| ATOM | 4184 | CB | VAL | 145 | 95.790 | -23.937 | 16.905 | 1.00 | 8.53 | L | C |
| ATOM | 4185 | CG1 | VAL | 145 | 94.817 | -24.597 | 17.889 | 1.00 | 7.53 | L | C |
| ATOM | 4186 | CG2 | VAL | 145 | 97.151 | -23.769 | 17.570 | 1.00 | 8.28 | L | C |
| ATOM | 4187 | C | VAL | 145 | 94.536 | -25.074 | 15.073 | 1.00 | 25.32 | L | C |
| ATOM | 4188 | O | VAL | 145 | 93.909 | -24.193 | 14.497 | 1.00 | 27.49 | L | O |
| ATOM | 4189 | N | GLN | 146 | 94.055 | -26.296 | 15.231 | 1.00 | 39.17 | L | N |
| ATOM | 4190 | CA | GLN | 146 | 92.729 | -26.611 | 14.743 | 1.00 | 38.70 | L | C |
| ATOM | 4191 | CB | GLN | 146 | 92.798 | -27.679 | 13.653 | 1.00 | 72.09 | L | C |
| ATOM | 4192 | CG | GLN | 146 | 93.678 | -27.281 | 12.482 | 1.00 | 76.00 | L | C |
| ATOM | 4193 | CD | GLN | 146 | 93.630 | -28.276 | 11.339 | 1.00 | 75.94 | L | C |
| ATOM | 4194 | OE1 | GLN | 146 | 92.616 | -28.399 | 10.654 | 1.00 | 76.92 | L | O |
| ATOM | 4195 | NE2 | GLN | 146 | 94.730 | -28.997 | 11.130 | 1.00 | 77.33 | L | N |
| ATOM | 4196 | C | GLN | 146 | 91.880 | -27.094 | 15.904 | 1.00 | 37.70 | L | C |
| ATOM | 4197 | O | GLN | 146 | 92.302 | -27.965 | 16.667 | 1.00 | 34.46 | L | O |
| ATOM | 4198 | N | TRP | 147 | 90.699 | -26.498 | 16.048 | 1.00 | 30.86 | L | N |
| ATOM | 4199 | CA | TRP | 147 | 89.777 | -26.878 | 17.102 | 1.00 | 30.91 | L | C |
| ATOM | 4200 | CB | TRP | 147 | 88.947 | -25.687 | 17.556 | 1.00 | 36.68 | L | C |
| ATOM | 4201 | CG | TRP | 147 | 89.689 | -24.788 | 18.432 | 1.00 | 34.29 | L | C |
| ATOM | 4202 | CD2 | TRP | 147 | 89.927 | -24.969 | 19.825 | 1.00 | 32.37 | L | C |
| ATOM | 4203 | CE2 | TRP | 147 | 90.723 | -23.885 | 20.258 | 1.00 | 33.31 | L | C |
| ATOM | 4204 | CE3 | TRP | 147 | 89.552 | -25.943 | 20.752 | 1.00 | 31.13 | L | C |
| ATOM | 4205 | CD1 | TRP | 147 | 90.326 | -23.641 | 18.077 | 1.00 | 36.68 | L | C |
| ATOM | 4206 | NE1 | TRP | 147 | 90.951 | -23.086 | 19.168 | 1.00 | 33.41 | L | N |
| ATOM | 4207 | CZ2 | TRP | 147 | 91.150 | -23.747 | 21.587 | 1.00 | 31.66 | L | C |
| ATOM | 4208 | CZ3 | TRP | 147 | 89.977 | -25.808 | 22.073 | 1.00 | 33.39 | L | C |
| ATOM | 4209 | CH2 | TRP | 147 | 90.767 | -24.716 | 22.476 | 1.00 | 33.58 | L | C |
| ATOM | 4210 | C | TRP | 147 | 88.844 | -27.963 | 16.611 | 1.00 | 33.36 | L | C |
| ATOM | 4211 | O | TRP | 147 | 88.440 | -27.968 | 15.453 | 1.00 | 34.42 | L | O |
| ATOM | 4212 | N | LYS | 148 | 88.495 | -28.877 | 17.501 | 1.00 | 28.86 | L | N |
| ATOM | 4213 | CA | LYS | 148 | 87.609 | -29.958 | 17.147 | 1.00 | 29.96 | L | C |
| ATOM | 4214 | CB | LYS | 148 | 88.431 | -31.196 | 16.787 | 1.00 | 35.94 | L | C |
| ATOM | 4215 | CG | LYS | 148 | 88.353 | -31.585 | 15.320 | 1.00 | 39.31 | L | C |
| ATOM | 4216 | CD | LYS | 148 | 89.726 | -31.865 | 14.715 | 1.00 | 45.24 | L | C |
| ATOM | 4217 | CE | LYS | 148 | 90.421 | -33.078 | 15.337 | 1.00 | 45.54 | L | .C |
| ATOM | 4218 | NZ | LYS | 148 | 91.826 | -33.267 | 14.818 | 1.00 | 44.96 | L | N |
| ATOM | 4219 | C | LYS | 148 | 86.712 | -30.227 | 18.340 | 1.00 | 32.40 | L | C |
| ATOM | 4220 | O | LYS | 148 | 87.197 | -30.505 | 19.438 | 1.00 | 31.51 | L | O |
| ATOM | 4221 | N | VAL | 149 | 85.404 | -30.124 | 18.118 | 1.00 | 22.85 | L | N |
| ATOM | 4222 | CA | VAL | 149 | 84.406 | -30.352 | 19.161 | 1.00 | 20.04 | L | C |
| ATOM | 4223 | CB | VAL | 149 | 83.453 | -29.167 | 19.269 | 1.00 | 1.90 | L | C |
| ATOM | 4224 | CG1 | VAL | 149 | 82.408 | -29.440 | 20.364 | 1.00 | 1.90 | L | C |
| ATOM | 4225 | CG2 | VAL | 149 | 84.242 | -27.899 | 19.563 | 1.00 | 1.90 | L | C |
| ATOM | 4226 | C | VAL | 149 | 83.580 | -31.605 | 18.862 | 1.00 | 23.24 | L | C |
| ATOM | 4227 | O | VAL | 149 | 82.835 | -31.642 | 17.883 | 1.00 | 24.43 | L | O |
| ATOM | 4228 | N | ASP | 150 | 83.679 | -32.611 | 19.731 | 1.00 | 18.00 | L | N |
| ATOM | 4229 | CA | ASP | 150 | 82.974 | -33.863 | 19.502 | 1.00 | 21.30 | L | C |
| ATOM | 4230 | CB | ASP | 150 | 81.464 | -33.661 | 19.459 | 1.00 | 45.33 | L | C |
| ATOM | 4231 | CG | ASP | 150 | 80.862 | -33.543 | 20.840 | 1.00 | 50.39 | L | C |
| ATOM | 4232 | OD1 | ASP | 150 | 81.334 | -34.248 | 21.760 | 1.00 | 51.76 | L | O |
| ATOM | 4233 | OD2 | ASP | 150 | 79.910 | -32.756 | 21.007 | 1.00 | 53.67 | L | O |
| ATOM | 4234 | C | ASP | 150 | 83.487 | -34.293 | 18.152 | 1.00 | 22.51 | L | C |

FIG. 19A-59

| | | | | | | | | | | |
|---|---|---|---|---|---|---|---|---|---|---|
| ATOM | 4235 | O | ASP | 150 | 82.737 | -34.683 | 17.268 | 1.00 | 23.76 | L | O |
| ATOM | 4236 | N | ASN | 151 | 84.800 | -34.161 | 18.007 | 1.00 | 36.79 | L | N |
| ATOM | 4237 | CA | ASN | 151 | 85.493 | -34.524 | 16.789 | 1.00 | 39.62 | L | C |
| ATOM | 4238 | CB | ASN | 151 | 85.425 | -36.041 | 16.614 | 1.00 | 29.22 | L | C |
| ATOM | 4239 | CG | ASN | 151 | 86.220 | -36.776 | 17.683 | 1.00 | 38.58 | L | C |
| ATOM | 4240 | OD1 | ASN | 151 | 87.450 | -36.736 | 17.686 | 1.00 | 42.16 | L | O |
| ATOM | 4241 | ND2 | ASN | 151 | 85.522 | -37.430 | 18.608 | 1.00 | 39.63 | L | N |
| ATOM | 4242 | C | ASN | 151 | 84.985 | -33.778 | 15.557 | 1.00 | 37.90 | L | C |
| ATOM | 4243 | O | ASN | 151 | 85.224 | -34.183 | 14.425 | 1.00 | 41.98 | L | O |
| ATOM | 4244 | N | ALA | 152 | 84.293 | -32.672 | 15.793 | 1.00 | 26.76 | L | N |
| ATOM | 4245 | CA | ALA | 152 | 83.802 | -31.838 | 14.703 | 1.00 | 29.16 | L | C |
| ATOM | 4246 | CB | ALA | 152 | 82.421 | -31.261 | 15.034 | 1.00 | 1.87 | L | C |
| ATOM | 4247 | C | ALA | 152 | 84.801 | -30.698 | 14.501 | 1.00 | 30.47 | L | C |
| ATOM | 4248 | O | ALA | 152 | 84.940 | -29.813 | 15.355 | 1.00 | 32.16 | L | O |
| ATOM | 4249 | N | LEU | 153 | 85.502 | -30.724 | 13.375 | 1.00 | 37.66 | L | N |
| ATOM | 4250 | CA | LEU | 153 | 86.470 | -29.684 | 13.073 | 1.00 | 38.47 | L | C |
| ATOM | 4251 | CB | LEU | 153 | 87.021 | -29.896 | 11.656 | 1.00 | 33.69 | L | C |
| ATOM | 4252 | CG | LEU | 153 | 87.944 | -28.864 | 11.005 | 1.00 | 36.76 | L | C |
| ATOM | 4253 | CD1 | LEU | 153 | 87.112 | -27.705 | 10.466 | 1.00 | 35.54 | L | C |
| ATOM | 4254 | CD2 | LEU | 153 | 88.999 | -28.394 | 12.004 | 1.00 | 35.80 | L | C |
| ATOM | 4255 | C | LEU | 153 | 85.796 | -28.315 | 13.206 | 1.00 | 37.05 | L | C |
| ATOM | 4256 | O | LEU | 153 | 84.632 | -28.150 | 12.870 | 1.00 | 37.53 | L | O |
| ATOM | 4257 | N | GLN | 154 | 86.524 | -27.342 | 13.732 | 1.00 | 42.87 | L | N |
| ATOM | 4258 | CA | GLN | 154 | 85.984 | -26.006 | 13.885 | 1.00 | 41.76 | L | C |
| ATOM | 4259 | CB | GLN | 154 | 86.346 | -25.438 | 15.255 | 1.00 | 24.84 | L | C |
| ATOM | 4260 | CG | GLN | 154 | 85.653 | -26.133 | 16.403 | 1.00 | 25.94 | L | C |
| ATOM | 4261 | CD | GLN | 154 | 84.146 | -26.162 | 16.225 | 1.00 | 28.42 | L | C |
| ATOM | 4262 | OE1 | GLN | 154 | 83.495 | -25.115 | 16.127 | 1.00 | 30.98 | L | O |
| ATOM | 4263 | NE2 | GLN | 154 | 83.584 | -27.365 | 16.176 | 1.00 | 27.76 | L | N |
| ATOM | 4264 | C | GLN | 154 | 86.574 | -25.139 | 12.793 | 1.00 | 40.20 | L | C |
| ATOM | 4265 | O | GLN | 154 | 87.702 | -25.363 | 12.350 | 1.00 | 39.24 | L | O |
| ATOM | 4266 | N | SER | 155 | 85.813 | -24.146 | 12.359 | 1.00 | 42.27 | L | N |
| ATOM | 4267 | CA | SER | 155 | 86.269 | -23.257 | 11.306 | 1.00 | 44.34 | L | C |
| ATOM | 4268 | CB | SER | 155 | 85.770 | -23.768 | 9.952 | 1.00 | 47.84 | L | C |
| ATOM | 4269 | OG | SER | 155 | 86.319 | -23.035 | 8.872 | 1.00 | 49.98 | L | O |
| ATOM | 4270 | C | SER | 155 | 85.693 | -21.888 | 11.600 | 1.00 | 40.94 | L | C |
| ATOM | 4271 | O | SER | 155 | 86.208 | -20.864 | 11.160 | 1.00 | 39.18 | L | O |
| ATOM | 4272 | N | GLY | 156 | 84.621 | -21.877 | 12.374 | 1.00 | 21.85 | L | N |
| ATOM | 4273 | CA | GLY | 156 | 83.986 | -20.619 | 12.702 | 1.00 | 22.33 | L | C |
| ATOM | 4274 | C | GLY | 156 | 84.732 | -19.585 | 13.544 | 1.00 | 22.19 | L | C |
| ATOM | 4275 | O | GLY | 156 | 85.518 | -18.793 | 13.032 | 1.00 | 19.16 | L | O |
| ATOM | 4276 | N | ASN | 157 | 84.484 | -19.595 | 14.850 | 1.00 | 39.06 | L | N |
| ATOM | 4277 | CA | ASN | 157 | 85.088 | -18.595 | 15.697 | 1.00 | 40.50 | L | C |
| ATOM | 4278 | CB | ASN | 157 | 83.992 | -17.700 | 16.281 | 1.00 | 106.22 | L | C |
| ATOM | 4279 | CG | ASN | 157 | 83.201 | -16.977 | 15.200 | 1.00 | 109.22 | L | C |
| ATOM | 4280 | OD1 | ASN | 157 | 83.779 | -16.402 | 14.277 | 1.00 | 109.54 | L | O |
| ATOM | 4281 | ND2 | ASN | 157 | 81.874 | -16.999 | 15.313 | 1.00 | 114.95 | L | N |
| ATOM | 4282 | C | ASN | 157 | 86.059 | -18.997 | 16.790 | 1.00 | 41.01 | L | C |
| ATOM | 4283 | O | ASN | 157 | 85.713 | -19.566 | 17.827 | 1.00 | 40.41 | L | O |
| ATOM | 4284 | N | SER | 158 | 87.299 | -18.635 | 16.520 | 1.00 | 42.44 | L | N |
| ATOM | 4285 | CA | SER | 158 | 88.409 | -18.862 | 17.405 | 1.00 | 35.84 | L | C |
| ATOM | 4286 | CB | SER | 158 | 89.078 | -20.173 | 17.047 | 1.00 | 10.55 | L | C |
| ATOM | 4287 | OG | SER | 158 | 89.643 | -20.069 | 15.757 | 1.00 | 10.12 | L | O |
| ATOM | 4288 | C | SER | 158 | 89.326 | -17.691 | 17.059 | 1.00 | 34.29 | L | C |
| ATOM | 4289 | O | SER | 158 | 89.197 | -17.092 | 15.992 | 1.00 | 32.27 | L | O |
| ATOM | 4290 | N | GLN | 159 | 90.238 | -17.345 | 17.952 | 1.00 | 34.35 | L | N |
| ATOM | 4291 | CA | GLN | 159 | 91.133 | -16.250 | 17.652 | 1.00 | 31.73 | L | C |
| ATOM | 4292 | CB | GLN | 159 | 90.538 | -14.932 | 18.130 | 1.00 | 20.18 | L | C |
| ATOM | 4293 | CG | GLN | 159 | 89.399 | -14.413 | 17.266 | 1.00 | 21.46 | L | C |
| ATOM | 4294 | CD | GLN | 159 | 89.053 | -12.981 | 17.608 | 1.00 | 25.67 | L | C |
| ATOM | 4295 | OE1 | GLN | 159 | 88.796 | -12.658 | 18.762 | 1.00 | 28.88 | L | O |
| ATOM | 4296 | NE2 | GLN | 159 | 89.051 | -12.114 | 16.606 | 1.00 | 25.13 | L | N |
| ATOM | 4297 | C | GLN | 159 | 92.502 | -16.452 | 18.255 | 1.00 | 29.74 | L | C |
| ATOM | 4298 | O | GLN | 159 | 92.647 | -16.711 | 19.449 | 1.00 | 28.24 | L | O |
| ATOM | 4299 | N | GLU | 160 | 93.514 | -16.327 | 17.414 | 1.00 | 31.36 | L | N |
| ATOM | 4300 | CA | GLU | 160 | 94.872 | -16.510 | 17.865 | 1.00 | 24.49 | L | C |
| ATOM | 4301 | CB | GLU | 160 | 95.646 | -17.316 | 16.834 | 1.00 | 58.94 | L | C |
| ATOM | 4302 | CG | GLU | 160 | 94.977 | -18.617 | 16.476 | 1.00 | 59.06 | L | C |
| ATOM | 4303 | CD | GLU | 160 | 95.890 | -19.506 | 15.678 | 1.00 | 67.10 | L | C |
| ATOM | 4304 | OE1 | GLU | 160 | 95.463 | -20.619 | 15.285 | 1.00 | 71.37 | L | O |
| ATOM | 4305 | OE2 | GLU | 160 | 97.043 | -19.078 | 15.452 | 1.00 | 65.02 | L | O |
| ATOM | 4306 | C | GLU | 160 | 95.591 | -15.199 | 18.140 | 1.00 | 20.89 | L | C |
| ATOM | 4307 | O | GLU | 160 | 95.211 | -14.141 | 17.654 | 1.00 | 14.39 | L | O |

FIG. 19A-60

```
ATOM   4308  N    SER  161     96.639  -15.293  18.941  1.00  19.35  L  N
ATOM   4309  CA   SER  161     97.456  -14.151  19.310  1.00  16.36  L  C
ATOM   4310  CB   SER  161     96.953  -13.486  20.597  1.00  26.12  L  C
ATOM   4311  OG   SER  161     97.935  -12.623  21.157  1.00  26.54  L  O
ATOM   4312  C    SER  161     98.811  -14.751  19.556  1.00  11.36  L  C
ATOM   4313  O    SER  161     98.934  -15.799  20.191  1.00  11.86  L  O
ATOM   4314  N    VAL  162     99.833  -14.086  19.053  1.00  21.19  L  N
ATOM   4315  CA   VAL  162    101.170  -14.592  19.215  1.00  22.81  L  C
ATOM   4316  CB   VAL  162    101.764  -14.965  17.832  1.00  29.37  L  C
ATOM   4317  CG1  VAL  162    101.449  -13.865  16.834  1.00  33.68  L  C
ATOM   4318  CG2  VAL  162    103.270  -15.178  17.933  1.00  33.85  L  C
ATOM   4319  C    VAL  162    101.997  -13.524  19.877  1.00  25.31  L  C
ATOM   4320  O    VAL  162    101.835  -12.349  19.566  1.00  32.55  L  O
ATOM   4321  N    THR  163    102.861  -13.928  20.805  1.00  22.97  L  N
ATOM   4322  CA   THR  163    103.735  -12.975  21.475  1.00  21.36  L  C
ATOM   4323  CB   THR  163    104.424  -13.567  22.719  1.00   4.31  L  C
ATOM   4324  OG1  THR  163    105.214  -14.705  22.342  1.00  10.67  L  O
ATOM   4325  CG2  THR  163    103.411  -13.966  23.748  1.00   4.70  L  C
ATOM   4326  C    THR  163    104.842  -12.550  20.520  1.00  20.43  L  C
ATOM   4327  O    THR  163    104.880  -12.951  19.350  1.00  20.01  L  O
ATOM   4328  N    GLU  164    105.741  -11.722  21.022  1.00  16.64  L  N
ATOM   4329  CA   GLU  164    106.844  -11.283  20.211  1.00  24.33  L  C
ATOM   4330  CB   GLU  164    107.182   -9.828  20.515  1.00  53.60  L  C
ATOM   4331  CG   GLU  164    107.982   -9.187  19.415  1.00  64.34  L  C
ATOM   4332  CD   GLU  164    107.202   -9.144  18.126  1.00  70.19  L  C
ATOM   4333  OE1  GLU  164    106.337   -8.252  17.994  1.00  69.97  L  O
ATOM   4334  OE2  GLU  164    107.442  -10.011  17.257  1.00  73.61  L  O
ATOM   4335  C    GLU  164    107.989  -12.190  20.635  1.00  22.81  L  C
ATOM   4336  O    GLU  164    107.990  -12.697  21.765  1.00  25.48  L  O
ATOM   4337  N    GLN  165    108.948  -12.407  19.734  1.00  26.35  L  N
ATOM   4338  CA   GLN  165    110.100  -13.261  20.018  1.00  31.24  L  C
ATOM   4339  CB   GLN  165    111.181  -13.024  18.967  1.00  24.53  L  C
ATOM   4340  CG   GLN  165    111.927  -14.274  18.584  1.00  20.02  L  C
ATOM   4341  CD   GLN  165    112.911  -14.054  17.454  1.00  22.62  L  C
ATOM   4342  OE1  GLN  165    113.487  -15.005  16.930  1.00  23.83  L  O
ATOM   4343  NE2  GLN  165    113.118  -12.794  17.080  1.00  19.11  L  N
ATOM   4344  C    GLN  165    110.633  -12.941  21.412  1.00  35.11  L  C
ATOM   4345  O    GLN  165    110.857  -11.783  21.739  1.00  31.98  L  O
ATOM   4346  N    ASP  166    110.826  -13.963  22.236  1.00  20.85  L  N
ATOM   4347  CA   ASP  166    111.311  -13.741  23.592  1.00  27.22  L  C
ATOM   4348  CB   ASP  166    111.206  -15.030  24.402  1.00  40.40  L  C
ATOM   4349  CG   ASP  166    111.513  -14.813  25.872  1.00  48.39  L  C
ATOM   4350  OD1  ASP  166    112.706  -14.808  26.246  1.00  51.89  L  O
ATOM   4351  OD2  ASP  166    110.555  -14.631  26.655  1.00  52.06  L  O
ATOM   4352  C    ASP  166    112.741  -13.205  23.656  1.00  29.80  L  C
ATOM   4353  O    ASP  166    113.659  -13.787  23.079  1.00  33.62  L  O
ATOM   4354  N    SER  167    112.923  -12.098  24.371  1.00  40.62  L  N
ATOM   4355  CA   SER  167    114.238  -11.463  24.521  1.00  38.35  L  C
ATOM   4356  CB   SER  167    114.089  -10.092  25.191  1.00  42.38  L  C
ATOM   4357  OG   SER  167    113.564  -10.221  26.499  1.00  53.10  L  O
ATOM   4358  C    SER  167    115.229  -12.312  25.325  1.00  40.21  L  C
ATOM   4359  O    SER  167    116.373  -11.913  25.544  1.00  45.86  L  O
ATOM   4360  N    LYS  168    114.777  -13.475  25.782  1.00  39.00  L  N
ATOM   4361  CA   LYS  168    115.637  -14.383  26.527  1.00  40.59  L  C
ATOM   4362  CB   LYS  168    114.968  -14.809  27.837  1.00  73.78  L  C
ATOM   4363  CG   LYS  168    115.002  -13.726  28.916  1.00  80.02  L  C
ATOM   4364  CD   LYS  168    114.141  -12.523  28.554  1.00  89.23  L  C
ATOM   4365  CE   LYS  168    112.663  -12.805  28.778  1.00  96.32  L  C
ATOM   4366  NZ   LYS  168    112.355  -13.017  30.222  1.00  95.77  L  N
ATOM   4367  C    LYS  168    115.959  -15.597  25.650  1.00  39.39  L  C
ATOM   4368  O    LYS  168    117.046  -15.671  25.077  1.00  43.53  L  O
ATOM   4369  N    ASP  169    115.011  -16.522  25.506  1.00  18.93  L  N
ATOM   4370  CA   ASP  169    115.240  -17.716  24.686  1.00  15.08  L  C
ATOM   4371  CB   ASP  169    114.476  -18.913  25.262  1.00  29.81  L  C
ATOM   4372  CG   ASP  169    112.992  -18.648  25.407  1.00  32.60  L  C
ATOM   4373  OD1  ASP  169    112.397  -18.049  24.488  1.00  27.93  L  O
ATOM   4374  OD2  ASP  169    112.415  -19.054  26.441  1.00  29.85  L  O
ATOM   4375  C    ASP  169    114.914  -17.596  23.193  1.00  15.61  L  C
ATOM   4376  O    ASP  169    115.038  -18.571  22.459  1.00   9.73  L  O
ATOM   4377  N    SER  170    114.490  -16.418  22.747  1.00  28.98  L  N
ATOM   4378  CA   SER  170    114.170  -16.202  21.331  1.00  26.94  L  C
ATOM   4379  CB   SER  170    115.401  -16.487  20.433  1.00  15.64  L  C
ATOM   4380  OG   SER  170    116.466  -15.560  20.636  1.00  17.90  L  O
```

FIG. 19A-61

```
ATOM   4381  C    SER  170     112.995  -17.042   20.825  1.00  25.42      L  C
ATOM   4382  O    SER  170     112.916  -17.345   19.636  1.00  25.18      L  O
ATOM   4383  N    THR  171     112.071  -17.411   21.702  1.00  22.07      L  N
ATOM   4384  CA   THR  171     110.946  -18.222   21.247  1.00  22.16      L  C
ATOM   4385  CB   THR  171     110.658  -19.406   22.212  1.00  16.53      L  C
ATOM   4386  OG1  THR  171     110.127  -18.911   23.452  1.00  18.93      L  O
ATOM   4387  CG2  THR  171     111.939  -20.191   22.471  1.00  18.13      L  C
ATOM   4388  C    THR  171     109.657  -17.437   21.064  1.00  26.03      L  C
ATOM   4389  O    THR  171     109.601  -16.235   21.327  1.00  31.48      L  O
ATOM   4390  N    TYR  172     108.633  -18.147   20.596  1.00   7.82      L  N
ATOM   4391  CA   TYR  172     107.297  -17.600   20.373  1.00   6.45      L  C
ATOM   4392  CB   TYR  172     106.934  -17.706   18.894  1.00  43.65      L  C
ATOM   4393  CG   TYR  172     107.809  -16.890   17.974  1.00  37.38      L  C
ATOM   4394  CD1  TYR  172     107.652  -15.507   17.865  1.00  32.97      L  C
ATOM   4395  CE1  TYR  172     108.438  -14.759   16.977  1.00  32.97      L  C
ATOM   4396  CD2  TYR  172     108.776  -17.508   17.181  1.00  37.97      L  C
ATOM   4397  CE2  TYR  172     109.565  -16.774   16.296  1.00  34.76      L  C
ATOM   4398  CZ   TYR  172     109.391  -15.405   16.194  1.00  32.97      L  C
ATOM   4399  OH   TYR  172     110.163  -14.703   15.294  1.00  32.97      L  O
ATOM   4400  C    TYR  172     106.255  -18.364   21.212  1.00   6.45      L  C
ATOM   4401  O    TYR  172     106.431  -19.539   21.528  1.00   9.78      L  O
ATOM   4402  N    SER  173     105.183  -17.687   21.600  1.00  23.67      L  N
ATOM   4403  CA   SER  173     104.123  -18.323   22.370  1.00  25.48      L  C
ATOM   4404  CB   SER  173     104.165  -17.902   23.834  1.00  31.18      L  C
ATOM   4405  OG   SER  173     105.281  -18.492   24.468  1.00  25.15      L  O
ATOM   4406  C    SER  173     102.836  -17.886   21.728  1.00  26.94      L  C
ATOM   4407  O    SER  173     102.611  -16.699   21.473  1.00  27.36      L  O
ATOM   4408  N    LEU  174     101.980  -18.857   21.474  1.00  22.39      L  N
ATOM   4409  CA   LEU  174     100.734  -18.593   20.791  1.00  25.49      L  C
ATOM   4410  CB   LEU  174     100.836  -19.238   19.399  1.00  22.33      L  C
ATOM   4411  CG   LEU  174      99.682  -19.165   18.422  1.00  13.39      L  C
ATOM   4412  CD1  LEU  174     100.207  -19.296   17.013  1.00  17.21      L  C
ATOM   4413  CD2  LEU  174      98.663  -20.257   18.769  1.00  10.23      L  C
ATOM   4414  C    LEU  174      99.510  -19.075   21.562  1.00  27.64      L  C
ATOM   4415  O    LEU  174      99.542  -20.111   22.229  1.00  30.82      L  O
ATOM   4416  N    SER  175      98.433  -18.306   21.470  1.00  22.56      L  N
ATOM   4417  CA   SER  175      97.200  -18.651   22.162  1.00  25.61      L  C
ATOM   4418  CB   SER  175      96.913  -17.644   23.292  1.00  28.99      L  C
ATOM   4419  OG   SER  175      96.487  -16.378   22.794  1.00  32.45      L  O
ATOM   4420  C    SER  175      96.009  -18.693   21.214  1.00  29.48      L  C
ATOM   4421  O    SER  175      95.733  -17.718   20.511  1.00  30.81      L  O
ATOM   4422  N    SER  176      95.316  -19.829   21.181  1.00  31.99      L  N
ATOM   4423  CA   SER  176      94.125  -19.957   20.346  1.00  32.77      L  C
ATOM   4424  CB   SER  176      94.154  -21.247   19.514  1.00  10.71      L  C
ATOM   4425  OG   SER  176      93.247  -21.176   18.421  1.00  10.34      L  O
ATOM   4426  C    SER  176      92.985  -19.991   21.352  1.00  29.41      L  C
ATOM   4427  O    SER  176      93.042  -20.712   22.350  1.00  29.56      L  O
ATOM   4428  N    THR  177      91.963  -19.183   21.118  1.00  38.41      L  N
ATOM   4429  CA   THR  177      90.846  -19.136   22.042  1.00  37.60      L  C
ATOM   4430  CB   THR  177      90.742  -17.741   22.706  1.00   7.23      L  C
ATOM   4431  OG1  THR  177      92.000  -17.399   23.318  1.00  10.12      L  O
ATOM   4432  CG2  THR  177      89.631  -17.728   23.773  1.00   2.94      L  C
ATOM   4433  C    THR  177      89.551  -19.455   21.311  1.00  35.94      L  C
ATOM   4434  O    THR  177      89.133  -18.709   20.425  1.00  37.02      L  O
ATOM   4435  N    LEU  178      88.941  -20.584   21.669  1.00  33.89      L  N
ATOM   4436  CA   LEU  178      87.682  -21.015   21.072  1.00  32.44      L  C
ATOM   4437  CB   LEU  178      87.587  -22.542   21.069  1.00  26.21      L  C
ATOM   4438  CG   LEU  178      86.291  -23.170   20.539  1.00  27.24      L  C
ATOM   4439  CD1  LEU  178      86.077  -22.824   19.070  1.00  27.77      L  C
ATOM   4440  CD2  LEU  178      86.367  -24.683   20.730  1.00  15.35      L  C
ATOM   4441  C    LEU  178      86.552  -20.412   21.901  1.00  32.70      L  C
ATOM   4442  O    LEU  178      86.476  -20.589   23.120  1.00  29.14      L  O
ATOM   4443  N    THR  179      85.669  -19.683   21.244  1.00  21.74      L  N
ATOM   4444  CA   THR  179      84.598  -19.059   21.983  1.00  27.65      L  C
ATOM   4445  CB   THR  179      84.804  -17.547   22.031  1.00  33.66      L  C
ATOM   4446  OG1  THR  179      83.651  -16.929   22.608  1.00  34.46      L  O
ATOM   4447  CG2  THR  179      85.056  -17.005   20.633  1.00  33.07      L  C
ATOM   4448  C    THR  179      83.223  -19.377   21.430  1.00  32.00      L  C
ATOM   4449  O    THR  179      82.928  -19.104   20.271  1.00  32.92      L  O
ATOM   4450  N    LEU  180      82.398  -19.981   22.278  1.00  32.07      L  N
ATOM   4451  CA   LEU  180      81.035  -20.349   21.922  1.00  33.73      L  C
ATOM   4452  CB   LEU  180      80.936  -21.831   21.528  1.00  30.85      L  C
ATOM   4453  CG   LEU  180      82.059  -22.804   21.881  1.00  33.56      L  C
```

FIG. 19A-62

| | | | | | | | | | | |
|---|---|---|---|---|---|---|---|---|---|---|
| ATOM | 4454 | CD1 | LEU | 180 | 82.518 | -22.589 | 23.309 | 1.00 | 36.03 | L C |
| ATOM | 4455 | CD2 | LEU | 180 | 81.552 | -24.220 | 21.697 | 1.00 | 34.15 | L C |
| ATOM | 4456 | C | LEU | 180 | 80.093 | -20.062 | 23.084 | 1.00 | 37.58 | L C |
| ATOM | 4457 | O | LEU | 180 | 80.526 | -19.899 | 24.229 | 1.00 | 37.41 | L O |
| ATOM | 4458 | N | SER | 181 | 78.801 | -20.000 | 22.772 | 1.00 | 28.10 | L N |
| ATOM | 4459 | CA | SER | 181 | 77.778 | -19.711 | 23.770 | 1.00 | 31.26 | L C |
| ATOM | 4460 | CB | SER | 181 | 76.433 | -19.537 | 23.087 | 1.00 | 22.13 | L C |
| ATOM | 4461 | OG | SER | 181 | 76.019 | -20.764 | 22.513 | 1.00 | 25.39 | L O |
| ATOM | 4462 | C | SER | 181 | 77.655 | -20.802 | 24.815 | 1.00 | 33.74 | L C |
| ATOM | 4463 | O | SER | 181 | 77.917 | -21.978 | 24.533 | 1.00 | 33.98 | L O |
| ATOM | 4464 | N | LYS | 182 | 77.247 | -20.402 | 26.019 | 1.00 | 29.35 | L N |
| ATOM | 4465 | CA | LYS | 182 | 77.060 | -21.339 | 27.120 | 1.00 | 30.58 | L C |
| ATOM | 4466 | CB | LYS | 182 | 76.375 | -20.647 | 28.307 | 1.00 | 27.86 | L C |
| ATOM | 4467 | CG | LYS | 182 | 76.341 | -21.446 | 29.627 | 1.00 | 29.57 | L C |
| ATOM | 4468 | CD | LYS | 182 | 74.912 | -21.752 | 30.107 | 1.00 | 31.50 | L C |
| ATOM | 4469 | CE | LYS | 182 | 74.863 | -22.027 | 31.619 | 1.00 | 34.15 | L C |
| ATOM | 4470 | NZ | LYS | 182 | 73.622 | -22.756 | 32.099 | 1.00 | 38.40 | L N |
| ATOM | 4471 | C | LYS | 182 | 76.167 | -22.438 | 26.573 | 1.00 | 28.49 | L C |
| ATOM | 4472 | O | LYS | 182 | 76.358 | -23.618 | 26.878 | 1.00 | 20.36 | L O |
| ATOM | 4473 | N | ALA | 183 | 75.206 | -22.030 | 25.743 | 1.00 | 42.67 | L N |
| ATOM | 4474 | CA | ALA | 183 | 74.252 | -22.937 | 25.108 | 1.00 | 43.14 | L C |
| ATOM | 4475 | CB | ALA | 183 | 73.319 | -22.150 | 24.203 | 1.00 | 20.20 | L C |
| ATOM | 4476 | C | ALA | 183 | 74.929 | -24.053 | 24.313 | 1.00 | 42.26 | L C |
| ATOM | 4477 | O | ALA | 183 | 74.645 | -25.229 | 24.531 | 1.00 | 43.50 | L O |
| ATOM | 4478 | N | ASP | 184 | 75.820 | -23.691 | 23.395 | 1.00 | 37.65 | L N |
| ATOM | 4479 | CA | ASP | 184 | 76.523 | -24.692 | 22.587 | 1.00 | 39.98 | L C |
| ATOM | 4480 | CB | ASP | 184 | 77.271 | -24.023 | 21.434 | 1.00 | 60.24 | L C |
| ATOM | 4481 | CG | ASP | 184 | 76.362 | -23.219 | 20.545 | 1.00 | 66.97 | L C |
| ATOM | 4482 | OD1 | ASP | 184 | 75.360 | -23.784 | 20.055 | 1.00 | 70.29 | L O |
| ATOM | 4483 | OD2 | ASP | 184 | 76.653 | -22.023 | 20.335 | 1.00 | 70.50 | L O |
| ATOM | 4484 | C | ASP | 184 | 77.519 | -25.525 | 23.395 | 1.00 | 38.91 | L C |
| ATOM | 4485 | O | ASP | 184 | 77.531 | -26.753 | 23.308 | 1.00 | 36.50 | L O |
| ATOM | 4486 | N | TYR | 185 | 78.362 | -24.849 | 24.167 | 1.00 | 50.74 | L N |
| ATOM | 4487 | CA | TYR | 185 | 79.352 | -25.544 | 24.972 | 1.00 | 51.74 | L C |
| ATOM | 4488 | CB | TYR | 185 | 80.011 | -24.589 | 25.965 | 1.00 | 23.76 | L C |
| ATOM | 4489 | CG | TYR | 185 | 81.104 | -25.256 | 26.771 | 1.00 | 21.08 | L C |
| ATOM | 4490 | CD1 | TYR | 185 | 82.328 | -25.552 | 26.192 | 1.00 | 16.43 | L C |
| ATOM | 4491 | CE1 | TYR | 185 | 83.332 | -26.186 | 26.915 | 1.00 | 15.99 | L C |
| ATOM | 4492 | CD2 | TYR | 185 | 80.905 | -25.613 | 28.104 | 1.00 | 17.64 | L C |
| ATOM | 4493 | CE2 | TYR | 185 | 81.902 | -26.244 | 28.839 | 1.00 | 14.97 | L C |
| ATOM | 4494 | CZ | TYR | 185 | 83.118 | -26.526 | 28.235 | 1.00 | 14.93 | L C |
| ATOM | 4495 | OH | TYR | 185 | 84.141 | -27.119 | 28.944 | 1.00 | 16.56 | L O |
| ATOM | 4496 | C | TYR | 185 | 78.729 | -26.695 | 25.756 | 1.00 | 52.88 | L C |
| ATOM | 4497 | O | TYR | 185 | 79.364 | -27.728 | 25.978 | 1.00 | 52.42 | L O |
| ATOM | 4498 | N | GLU | 186 | 77.484 | -26.505 | 26.177 | 1.00 | 52.93 | L N |
| ATOM | 4499 | CA | GLU | 186 | 76.787 | -27.509 | 26.965 | 1.00 | 54.71 | L C |
| ATOM | 4500 | CB | GLU | 186 | 75.643 | -26.870 | 27.748 | 1.00 | 28.62 | L C |
| ATOM | 4501 | CG | GLU | 186 | 76.067 | -26.060 | 28.955 | 1.00 | 35.11 | L C |
| ATOM | 4502 | CD | GLU | 186 | 74.876 | -25.493 | 29.702 | 1.00 | 38.66 | L C |
| ATOM | 4503 | OE1 | GLU | 186 | 75.089 | -24.850 | 30.746 | 1.00 | 41.21 | L O |
| ATOM | 4504 | OE2 | GLU | 186 | 73.725 | -25.689 | 29.245 | 1.00 | 36.89 | L O |
| ATOM | 4505 | C | GLU | 186 | 76.242 | -28.694 | 26.190 | 1.00 | 52.40 | L C |
| ATOM | 4506 | O | GLU | 186 | 76.029 | -29.755 | 26.769 | 1.00 | 48.88 | L O |
| ATOM | 4507 | N | LYS | 187 | 76.004 | -28.538 | 24.895 | 1.00 | 35.74 | L N |
| ATOM | 4508 | CA | LYS | 187 | 75.472 | -29.662 | 24.147 | 1.00 | 37.64 | L C |
| ATOM | 4509 | CB | LYS | 187 | 74.507 | -29.173 | 23.057 | 1.00 | 53.22 | L C |
| ATOM | 4510 | CG | LYS | 187 | 75.138 | -28.512 | 21.849 | 1.00 | 54.27 | L C |
| ATOM | 4511 | CD | LYS | 187 | 74.055 | -27.941 | 20.930 | 1.00 | 53.80 | L C |
| ATOM | 4512 | CE | LYS | 187 | 74.665 | -27.203 | 19.740 | 1.00 | 49.76 | L C |
| ATOM | 4513 | NZ | LYS | 187 | 73.707 | -26.272 | 19.069 | 1.00 | 48.24 | L N |
| ATOM | 4514 | C | LYS | 187 | 76.568 | -30.553 | 23.549 | 1.00 | 36.73 | L C |
| ATOM | 4515 | O | LYS | 187 | 76.287 | -31.436 | 22.732 | 1.00 | 37.96 | L O |
| ATOM | 4516 | N | HIS | 188 | 77.813 | -30.339 | 23.972 | 1.00 | 23.77 | L N |
| ATOM | 4517 | CA | HIS | 188 | 78.934 | -31.124 | 23.468 | 1.00 | 21.36 | L C |
| ATOM | 4518 | CB | HIS | 188 | 79.811 | -30.257 | 22.562 | 1.00 | 41.13 | L C |
| ATOM | 4519 | CG | HIS | 188 | 79.099 | -29.774 | 21.338 | 1.00 | 42.53 | L C |
| ATOM | 4520 | CD2 | HIS | 188 | 78.800 | -28.524 | 20.913 | 1.00 | 44.25 | L C |
| ATOM | 4521 | ND1 | HIS | 188 | 78.562 | -30.633 | 20.405 | 1.00 | 41.45 | L N |
| ATOM | 4522 | CE1 | HIS | 188 | 77.961 | -29.935 | 19.458 | 1.00 | 45.45 | L C |
| ATOM | 4523 | NE2 | HIS | 188 | 78.090 | -28.652 | 19.743 | 1.00 | 43.75 | L N |
| ATOM | 4524 | C | HIS | 188 | 79.743 | -31.715 | 24.610 | 1.00 | 19.53 | L C |
| ATOM | 4525 | O | HIS | 188 | 79.648 | -31.253 | 25.751 | 1.00 | 19.70 | L O |
| ATOM | 4526 | N | LYS | 189 | 80.521 | -32.747 | 24.294 | 1.00 | 33.83 | L N |

FIG. 19A-63

| | | | | | | | | | | |
|---|---|---|---|---|---|---|---|---|---|---|
| ATOM | 4527 | CA | LYS | 189 | 81.334 | -33.445 | 25.281 | 1.00 | 33.86 | L | C |
| ATOM | 4528 | CB | LYS | 189 | 81.136 | -34.957 | 25.152 | 1.00 | 43.10 | L | C |
| ATOM | 4529 | CG | LYS | 189 | 79.898 | -35.516 | 25.815 | 1.00 | 47.03 | L | C |
| ATOM | 4530 | CD | LYS | 189 | 79.974 | -37.041 | 25.887 | 1.00 | 53.76 | L | C |
| ATOM | 4531 | CE | LYS | 189 | 79.997 | -37.680 | 24.505 | 1.00 | 59.30 | L | C |
| ATOM | 4532 | NZ | LYS | 189 | 78.694 | -37.545 | 23.794 | 1.00 | 59.64 | L | N |
| ATOM | 4533 | C | LYS | 189 | 82.831 | -33.155 | 25.201 | 1.00 | 33.18 | L | C |
| ATOM | 4534 | O | LYS | 189 | 83.435 | -32.657 | 26.155 | 1.00 | 36.85 | L | O |
| ATOM | 4535 | N | VAL | 190 | 83.435 | -33.482 | 24.069 | 1.00 | 39.67 | L | N |
| ATOM | 4536 | CA | VAL | 190 | 84.860 | -33.260 | 23.916 | 1.00 | 35.33 | L | C |
| ATOM | 4537 | CB | VAL | 190 | 85.516 | -34.439 | 23.214 | 1.00 | 33.71 | L | C |
| ATOM | 4538 | CG1 | VAL | 190 | 85.356 | -35.648 | 24.059 | 1.00 | 26.86 | L | C |
| ATOM | 4539 | CG2 | VAL | 190 | 84.880 | -34.657 | 21.855 | 1.00 | 36.79 | L | C |
| ATOM | 4540 | C | VAL | 190 | 85.249 | -31.992 | 23.170 | 1.00 | 35.17 | L | C |
| ATOM | 4541 | O | VAL | 190 | 84.656 | -31.641 | 22.141 | 1.00 | 36.62 | L | O |
| ATOM | 4542 | N | TYR | 191 | 86.256 | -31.319 | 23.718 | 1.00 | 27.65 | L | N |
| ATOM | 4543 | CA | TYR | 191 | 86.811 | -30.105 | 23.152 | 1.00 | 26.85 | L | C |
| ATOM | 4544 | CB | TYR | 191 | 86.554 | -28.934 | 24.095 | 1.00 | 16.61 | L | C |
| ATOM | 4545 | CG | TYR | 191 | 85.109 | -28.475 | 24.056 | 1.00 | 23.44 | L | C |
| ATOM | 4546 | CD1 | TYR | 191 | 84.654 | -27.650 | 23.030 | 1.00 | 27.57 | L | C |
| ATOM | 4547 | CE1 | TYR | 191 | 83.322 | -27.300 | 22.929 | 1.00 | 29.06 | L | C |
| ATOM | 4548 | CD2 | TYR | 191 | 84.178 | -28.937 | 24.991 | 1.00 | 24.37 | L | C |
| ATOM | 4549 | CE2 | TYR | 191 | 82.838 | -28.592 | 24.894 | 1.00 | 25.88 | L | C |
| ATOM | 4550 | CZ | TYR | 191 | 82.419 | -27.773 | 23.859 | 1.00 | 28.22 | L | C |
| ATOM | 4551 | OH | TYR | 191 | 81.097 | -27.419 | 23.745 | 1.00 | 30.91 | L | O |
| ATOM | 4552 | C | TYR | 191 | 88.295 | -30.381 | 23.010 | 1.00 | 28.07 | L | C |
| ATOM | 4553 | O | TYR | 191 | 88.946 | -30.821 | 23.960 | 1.00 | 29.13 | L | O |
| ATOM | 4554 | N | ALA | 192 | 88.837 | -30.159 | 21.822 | 1.00 | 17.93 | L | N |
| ATOM | 4555 | CA | ALA | 192 | 90.246 | -30.425 | 21.621 | 1.00 | 13.94 | L | C |
| ATOM | 4556 | CB | ALA | 192 | 90.424 | -31.850 | 21.160 | 1.00 | 12.32 | L | C |
| ATOM | 4557 | C | ALA | 192 | 90.921 | -29.489 | 20.640 | 1.00 | 14.27 | L | C |
| ATOM | 4558 | O | ALA | 192 | 90.271 | -28.885 | 19.784 | 1.00 | 14.89 | L | O |
| ATOM | 4559 | N | CYS | 193 | 92.234 | -29.362 | 20.787 | 1.00 | 20.91 | L | N |
| ATOM | 4560 | CA | CYS | 193 | 93.015 | -28.544 | 19.883 | 1.00 | 19.50 | L | C |
| ATOM | 4561 | C | CYS | 193 | 94.268 | -29.301 | 19.502 | 1.00 | 17.29 | L | C |
| ATOM | 4562 | O | CYS | 193 | 95.057 | -29.729 | 20.352 | 1.00 | 15.43 | L | O |
| ATOM | 4563 | CB | CYS | 193 | 93.361 | -27.183 | 20.490 | 1.00 | 44.80 | L | C |
| ATOM | 4564 | SG | CYS | 193 | 94.412 | -27.194 | 21.962 | 1.00 | 52.58 | L | S |
| ATOM | 4565 | N | GLU | 194 | 94.411 | -29.480 | 18.195 | 1.00 | 24.90 | L | N |
| ATOM | 4566 | CA | GLU | 194 | 95.522 | -30.193 | 17.600 | 1.00 | 25.90 | L | C |
| ATOM | 4567 | CB | GLU | 194 | 95.004 | -30.956 | 16.384 | 1.00 | 66.26 | L | C |
| ATOM | 4568 | CG | GLU | 194 | 95.979 | -31.887 | 15.718 | 1.00 | 77.97 | L | C |
| ATOM | 4569 | CD | GLU | 194 | 95.392 | -32.479 | 14.461 | 1.00 | 83.25 | L | C |
| ATOM | 4570 | OE1 | GLU | 194 | 95.276 | -31.738 | 13.462 | 1.00 | 80.00 | L | O |
| ATOM | 4571 | OE2 | GLU | 194 | 95.028 | -33.674 | 14.477 | 1.00 | 89.05 | L | O |
| ATOM | 4572 | C | GLU | 194 | 96.546 | -29.158 | 17.175 | 1.00 | 25.27 | L | C |
| ATOM | 4573 | O | GLU | 194 | 96.204 | -28.171 | 16.538 | 1.00 | 23.30 | L | O |
| ATOM | 4574 | N | VAL | 195 | 97.798 | -29.373 | 17.537 | 1.00 | 38.95 | L | N |
| ATOM | 4575 | CA | VAL | 195 | 98.850 | -28.443 | 17.168 | 1.00 | 34.83 | L | C |
| ATOM | 4576 | CB | VAL | 195 | 99.715 | -28.048 | 18.403 | 1.00 | 15.18 | L | C |
| ATOM | 4577 | CG1 | VAL | 195 | 100.911 | -27.210 | 17.971 | 1.00 | 11.26 | L | C |
| ATOM | 4578 | CG2 | VAL | 195 | 98.869 | -27.268 | 19.395 | 1.00 | 16.15 | L | C |
| ATOM | 4579 | C | VAL | 195 | 99.730 | -29.115 | 16.126 | 1.00 | 34.14 | L | C |
| ATOM | 4580 | O | VAL | 195 | 99.964 | -30.319 | 16.180 | 1.00 | 32.63 | L | O |
| ATOM | 4581 | N | THR | 196 | 100.190 | -28.340 | 15.157 | 1.00 | 43.12 | L | N |
| ATOM | 4582 | CA | THR | 196 | 101.063 | -28.876 | 14.135 | 1.00 | 42.44 | L | C |
| ATOM | 4583 | CB | THR | 196 | 100.411 | -28.867 | 12.764 | 1.00 | 26.65 | L | C |
| ATOM | 4584 | OG1 | THR | 196 | 99.001 | -28.673 | 12.909 | 1.00 | 36.35 | L | O |
| ATOM | 4585 | CG2 | THR | 196 | 100.671 | -30.180 | 12.067 | 1.00 | 28.65 | L | C |
| ATOM | 4586 | C | THR | 196 | 102.233 | -27.927 | 14.121 | 1.00 | 42.04 | L | C |
| ATOM | 4587 | O | THR | 196 | 102.049 | -26.710 | 14.053 | 1.00 | 37.83 | L | O |
| ATOM | 4588 | N | HIS | 197 | 103.437 | -28.479 | 14.186 | 1.00 | 32.41 | L | N |
| ATOM | 4589 | CA | HIS | 197 | 104.623 | -27.653 | 14.217 | 1.00 | 27.77 | L | C |
| ATOM | 4590 | CB | HIS | 197 | 104.867 | -27.172 | 15.651 | 1.00 | 21.71 | L | C |
| ATOM | 4591 | CG | HIS | 197 | 105.914 | -26.113 | 15.762 | 1.00 | 23.27 | L | C |
| ATOM | 4592 | CD2 | HIS | 197 | 105.817 | -24.761 | 15.753 | 1.00 | 17.64 | L | C |
| ATOM | 4593 | ND1 | HIS | 197 | 107.257 | -26.402 | 15.868 | 1.00 | 25.39 | L | N |
| ATOM | 4594 | CE1 | HIS | 197 | 107.944 | -25.274 | 15.923 | 1.00 | 22.67 | L | C |
| ATOM | 4595 | NE2 | HIS | 197 | 107.093 | -24.264 | 15.854 | 1.00 | 24.76 | L | N |
| ATOM | 4596 | C | HIS | 197 | 105.825 | -28.417 | 13.708 | 1.00 | 24.98 | L | C |
| ATOM | 4597 | O | HIS | 197 | 105.932 | -29.629 | 13.885 | 1.00 | 29.24 | L | O |
| ATOM | 4598 | N | GLN | 198 | 106.728 | -27.687 | 13.070 | 1.00 | 28.46 | L | N |
| ATOM | 4599 | CA | GLN | 198 | 107.944 | -28.252 | 12.515 | 1.00 | 26.49 | L | C |

FIG. 19A-64

```
ATOM   4600  CB   GLN  198     108.840  -27.114  12.048  1.00  34.42      L  C
ATOM   4601  CG   GLN  198     110.091  -27.549  11.333  1.00  36.17      L  C
ATOM   4602  CD   GLN  198     110.868  -26.365  10.821  1.00  48.65      L  C
ATOM   4603  OE1  GLN  198     110.286  -25.414  10.299  1.00  57.22      L  O
ATOM   4604  NE2  GLN  198     112.185  -26.414  10.956  1.00  51.65      L  N
ATOM   4605  C    GLN  198     108.681  -29.107  13.541  1.00  29.43      L  C
ATOM   4606  O    GLN  198     109.331  -30.088  13.182  1.00  31.15      L  O
ATOM   4607  N    GLY  199     108.568  -28.728  14.815  1.00  31.39      L  N
ATOM   4608  CA   GLY  199     109.234  -29.452  15.887  1.00  36.65      L  C
ATOM   4609  C    GLY  199     108.465  -30.636  16.444  1.00  39.08      L  C
ATOM   4610  O    GLY  199     108.880  -31.244  17.425  1.00  43.81      L  O
ATOM   4611  N    LEU  200     107.339  -30.961  15.823  1.00  25.48      L  N
ATOM   4612  CA   LEU  200     106.510  -32.087  16.247  1.00  22.67      L  C
ATOM   4613  CB   LEU  200     105.094  -31.597  16.570  1.00  31.49      L  C
ATOM   4614  CG   LEU  200     104.868  -31.002  17.964  1.00  34.60      L  C
ATOM   4615  CD1  LEU  200     106.036  -30.149  18.361  1.00  37.97      L  C
ATOM   4616  CD2  LEU  200     103.592  -30.188  17.967  1.00  34.28      L  C
ATOM   4617  C    LEU  200     106.463  -33.152  15.144  1.00  23.29      L  C
ATOM   4618  O    LEU  200     106.089  -32.869  14.003  1.00  24.15      L  O
ATOM   4619  N    SER  201     106.860  -34.372  15.499  1.00  21.11      L  N
ATOM   4620  CA   SER  201     106.886  -35.503  14.570  1.00  24.08      L  C
ATOM   4621  CB   SER  201     107.367  -36.747  15.311  1.00  27.13      L  C
ATOM   4622  OG   SER  201     106.702  -36.875  16.561  1.00  28.99      L  O
ATOM   4623  C    SER  201     105.510  -35.761  13.957  1.00  24.14      L  C
ATOM   4624  O    SER  201     105.392  -36.267  12.835  1.00  25.49      L  O
ATOM   4625  N    SER  202     104.476  -35.405  14.717  1.00  17.09      L  N
ATOM   4626  CA   SER  202     103.086  -35.562  14.302  1.00  21.15      L  C
ATOM   4627  CB   SER  202     102.636  -37.010  14.522  1.00  43.22      L  C
ATOM   4628  OG   SER  202     103.011  -37.462  15.810  1.00  46.12      L  O
ATOM   4629  C    SER  202     102.265  -34.603  15.155  1.00  21.60      L  C
ATOM   4630  O    SER  202     102.656  -34.296  16.282  1.00  27.36      L  O
ATOM   4631  N    PRO  203     101.119  -34.121  14.636  1.00  22.94      L  N
ATOM   4632  CD   PRO  203     100.457  -34.478  13.368  1.00  32.35      L  C
ATOM   4633  CA   PRO  203     100.290  -33.187  15.407  1.00  18.89      L  C
ATOM   4634  CB   PRO  203      98.971  -33.177  14.643  1.00  26.47      L  C
ATOM   4635  CG   PRO  203      99.416  -33.370  13.223  1.00  29.48      L  C
ATOM   4636  C    PRO  203     100.128  -33.646  16.836  1.00  18.90      L  C
ATOM   4637  O    PRO  203     100.178  -34.842  17.100  1.00  21.86      L  O
ATOM   4638  N    VAL  204      99.980  -32.693  17.753  1.00  28.11      L  N
ATOM   4639  CA   VAL  204      99.794  -32.996  19.172  1.00  29.99      L  C
ATOM   4640  CB   VAL  204     100.759  -32.201  20.081  1.00  20.42      L  C
ATOM   4641  CG1  VAL  204     100.254  -32.204  21.512  1.00  20.30      L  C
ATOM   4642  CG2  VAL  204     102.141  -32.819  20.036  1.00  15.23      L  C
ATOM   4643  C    VAL  204      98.393  -32.574  19.514  1.00  33.93      L  C
ATOM   4644  O    VAL  204      97.887  -31.601  18.963  1.00  35.36      L  O
ATOM   4645  N    THR  205      97.755  -33.293  20.422  1.00  45.34      L  N
ATOM   4646  CA   THR  205      96.402  -32.933  20.787  1.00  46.97      L  C
ATOM   4647  CB   THR  205      95.386  -33.896  20.137  1.00  14.48      L  C
ATOM   4648  OG1  THR  205      95.275  -33.587  18.747  1.00  10.44      L  O
ATOM   4649  CG2  THR  205      94.013  -33.761  20.769  1.00  11.16      L  C
ATOM   4650  C    THR  205      96.169  -32.886  22.280  1.00  47.18      L  C
ATOM   4651  O    THR  205      96.596  -33.763  23.032  1.00  49.19      L  O
ATOM   4652  N    LYS  206      95.513  -31.822  22.709  1.00  22.09      L  N
ATOM   4653  CA   LYS  206      95.167  -31.681  24.108  1.00  26.52      L  C
ATOM   4654  CB   LYS  206      95.791  -30.422  24.710  1.00  41.08      L  C
ATOM   4655  CG   LYS  206      97.208  -30.641  25.215  1.00  44.88      L  C
ATOM   4656  CD   LYS  206      97.269  -31.688  26.312  1.00  47.36      L  C
ATOM   4657  CE   LYS  206      98.654  -31.760  26.957  1.00  49.27      L  C
ATOM   4658  NZ   LYS  206      99.723  -32.144  25.997  1.00  50.40      L  N
ATOM   4659  C    LYS  206      93.653  -31.602  24.100  1.00  29.29      L  C
ATOM   4660  O    LYS  206      93.063  -30.939  23.246  1.00  34.45      L  O
ATOM   4661  N    SER  207      93.026  -32.304  25.033  1.00  32.39      L  N
ATOM   4662  CA   SER  207      91.578  -32.324  25.083  1.00  29.18      L  C
ATOM   4663  CB   SER  207      91.046  -33.364  24.080  1.00  31.23      L  C
ATOM   4664  OG   SER  207      91.613  -34.655  24.294  1.00  31.62      L  O
ATOM   4665  C    SER  207      91.039  -32.624  26.476  1.00  28.78      L  C
ATOM   4666  O    SER  207      91.798  -32.938  27.397  1.00  29.47      L  O
ATOM   4667  N    PHE  208      89.719  -32.517  26.606  1.00  33.89      L  N
ATOM   4668  CA   PHE  208      89.013  -32.777  27.852  1.00  39.79      L  C
ATOM   4669  CB   PHE  208      89.217  -31.615  28.842  1.00  17.06      L  C
ATOM   4670  CG   PHE  208      88.662  -30.300  28.353  1.00  14.11      L  C
ATOM   4671  CD1  PHE  208      89.409  -29.482  27.499  1.00  18.84      L  C
ATOM   4672  CD2  PHE  208      87.376  -29.906  28.690  1.00  11.57      L  C
```

FIG. 19A-65

```
ATOM   4673  CE1 PHE   208      88.879 -28.298  26.990  1.00  19.93    L  C
ATOM   4674  CE2 PHE   208      86.846 -28.729  28.182  1.00  14.34    L  C
ATOM   4675  CZ  PHE   208      87.602 -27.925  27.330  1.00  20.99    L  C
ATOM   4676  C   PHE   208      87.536 -32.873  27.472  1.00  45.59    L  C
ATOM   4677  O   PHE   208      87.168 -32.576  26.335  1.00  47.78    L  O
ATOM   4678  N   ASN   209      86.703 -33.293  28.420  1.00  24.67    L  N
ATOM   4679  CA  ASN   209      85.257 -33.398  28.213  1.00  28.33    L  C
ATOM   4680  CB  ASN   209      84.751 -34.785  28.623  1.00  27.05    L  C
ATOM   4681  CG  ASN   209      85.664 -35.913  28.172  1.00  33.97    L  C
ATOM   4682  OD1 ASN   209      85.777 -36.941  28.841  1.00  34.19    L  O
ATOM   4683  ND2 ASN   209      86.304 -35.732  27.031  1.00  37.01    L  N
ATOM   4684  C   ASN   209      84.630 -32.370  29.160  1.00  29.95    L  C
ATOM   4685  O   ASN   209      85.203 -32.108  30.218  1.00  31.18    L  O
ATOM   4686  N   ARG   210      83.473 -31.800  28.805  1.00  15.88    L  N
ATOM   4687  CA  ARG   210      82.810 -30.829  29.687  1.00  19.72    L  C
ATOM   4688  CB  ARG   210      81.337 -30.721  29.371  1.00  31.19    L  C
ATOM   4689  CG  ARG   210      81.027 -29.666  28.361  1.00  32.77    L  C
ATOM   4690  CD  ARG   210      79.655 -29.104  28.627  1.00  36.35    L  C
ATOM   4691  NE  ARG   210      78.656 -30.166  28.633  1.00  41.72    L  N
ATOM   4692  CZ  ARG   210      77.502 -30.095  29.282  1.00  45.49    L  C
ATOM   4693  NH1 ARG   210      77.204 -29.008  29.981  1.00  46.04    L  N
ATOM   4694  NH2 ARG   210      76.655 -31.112  29.232  1.00  47.73    L  N
ATOM   4695  C   ARG   210      82.964 -31.252  31.137  1.00  22.05    L  C
ATOM   4696  O   ARG   210      82.962 -32.440  31.428  1.00  23.93    L  O
ATOM   4697  N   GLY   211      83.096 -30.291  32.048  1.00  53.99    L  N
ATOM   4698  CA  GLY   211      83.297 -30.638  33.447  1.00  53.99    L  C
ATOM   4699  C   GLY   211      84.740 -31.088  33.630  1.00  53.99    L  C
ATOM   4700  O   GLY   211      85.665 -30.312  33.387  1.00  53.99    L  O
ATOM   4701  N   GLU   212      84.942 -32.336  34.046  1.00  80.95    L  N
ATOM   4702  CA  GLU   212      86.287 -32.890  34.236  1.00  80.95    L  C
ATOM   4703  CB  GLU   212      86.995 -33.004  32.871  1.00  34.07    L  C
ATOM   4704  CG  GLU   212      88.259 -33.888  32.849  1.00  34.07    L  C
ATOM   4705  CD  GLU   212      88.691 -34.311  31.435  1.00  34.07    L  C
ATOM   4706  OE1 GLU   212      89.803 -34.863  31.296  1.00  34.07    L  O
ATOM   4707  OE2 GLU   212      87.923 -34.113  30.468  1.00  34.07    L  O
ATOM   4708  C   GLU   212      87.134 -32.080  35.227  1.00  80.95    L  C
ATOM   4709  O   GLU   212      86.690 -31.043  35.732  1.00  80.95    L  O
ATOM   4710  N   CYS   213      88.341 -32.566  35.516  1.00  81.74    L  N
ATOM   4711  CA  CYS   213      89.243 -31.893  36.450  1.00  81.74    L  C
ATOM   4712  CB  CYS   213      88.990 -32.374  37.883  1.00  54.42    L  C
ATOM   4713  SG  CYS   213      87.479 -31.701  38.656  1.00  54.42    L  S
ATOM   4714  C   CYS   213      90.715 -32.123  36.095  1.00  81.74    L  C
ATOM   4715  O   CYS   213      90.996 -32.758  35.051  1.00  81.74    L  O
ATOM   4716  OXT CYS   213      91.581 -31.647  36.863  1.00  72.88    L  O
ATOM   4717  MN  MN    400     117.831  24.682   6.345  1.00  34.24    M
ATOM   4718  CB  THR   145     114.226  73.843  15.327  1.00  72.71    B  C
ATOM   4719  OG1 THR   145     113.673  74.174  16.611  1.00  72.71    B  O
ATOM   4720  CG2 THR   145     114.208  75.069  14.426  1.00  72.71    B  C
ATOM   4721  C   THR   145     113.665  71.399  15.485  1.00 109.74    B  C
ATOM   4722  O   THR   145     113.590  70.290  14.948  1.00 110.14    B  O
ATOM   4723  N   THR   145     111.957  72.996  14.632  1.00 108.12    B  N
ATOM   4724  CA  THR   145     113.414  72.677  14.686  1.00 107.72    B  C
ATOM   4725  N   GLN   146     113.963  71.561  16.769  1.00  79.22    B  N
ATOM   4726  CA  GLN   146     114.224  70.425  17.633  1.00  77.37    B  C
ATOM   4727  CB  GLN   146     115.554  70.620  18.378  1.00  80.28    B  C
ATOM   4728  CG  GLN   146     115.640  71.886  19.208  1.00  80.28    B  C
ATOM   4729  CD  GLN   146     116.952  72.001  19.955  1.00  80.28    B  C
ATOM   4730  OE1 GLN   146     117.150  72.929  20.742  1.00  80.28    B  O
ATOM   4731  NE2 GLN   146     117.858  71.059  19.712  1.00  80.28    B  N
ATOM   4732  C   GLN   146     113.077  70.200  18.620  1.00  77.79    B  C
ATOM   4733  O   GLN   146     112.818  71.018  19.511  1.00  79.65    B  O
ATOM   4734  N   LEU   147     112.383  69.081  18.432  1.00  43.47    B  N
ATOM   4735  CA  LEU   147     111.265  68.710  19.288  1.00  42.60    B  C
ATOM   4736  CB  LEU   147     109.936  68.755  18.525  1.00  51.95    B  C
ATOM   4737  CG  LEU   147     109.450  69.952  17.707  1.00  52.14    B  C
ATOM   4738  CD1 LEU   147     110.464  70.296  16.632  1.00  47.35    B  C
ATOM   4739  CD2 LEU   147     108.114  69.607  17.060  1.00  51.99    B  C
ATOM   4740  C   LEU   147     111.461  67.281  19.756  1.00  41.58    B  C
ATOM   4741  O   LEU   147     112.077  66.470  19.058  1.00  42.88    B  O
ATOM   4742  N   ASP   148     110.944  66.988  20.945  1.00  31.29    B  N
ATOM   4743  CA  ASP   148     110.974  65.640  21.493  1.00  28.75    B  C
ATOM   4744  CB  ASP   148     111.394  65.642  22.960  1.00  32.78    B  C
ATOM   4745  CG  ASP   148     112.897  65.718  23.133  1.00  32.40    B  C
```

FIG. 19A-66

```
ATOM   4746  OD1 ASP   148    113.366  65.715  24.290  1.00  31.51  B  O
ATOM   4747  OD2 ASP   148    113.616  65.777  22.116  1.00  30.58  B  O
ATOM   4748  C   ASP   148    109.526  65.181  21.358  1.00  25.13  B  C
ATOM   4749  O   ASP   148    108.664  65.583  22.128  1.00  24.43  B  O
ATOM   4750  N   ILE   149    109.260  64.368  20.345  1.00  21.33  B  N
ATOM   4751  CA  ILE   149    107.918  63.885  20.105  1.00  20.27  B  C
ATOM   4752  CB  ILE   149    107.610  63.880  18.605  1.00  13.57  B  C
ATOM   4753  CG2 ILE   149    106.140  63.573  18.378  1.00   8.58  B  C
ATOM   4754  CG1 ILE   149    107.932  65.234  17.998  1.00   9.29  B  C
ATOM   4755  CD1 ILE   149    107.697  65.263  16.508  1.00  12.04  B  C
ATOM   4756  C   ILE   149    107.723  62.464  20.629  1.00  21.92  B  C
ATOM   4757  O   ILE   149    108.507  61.563  20.315  1.00  22.32  B  O
ATOM   4758  N   VAL   150    106.680  62.271  21.433  1.00  32.56  B  N
ATOM   4759  CA  VAL   150    106.357  60.950  21.956  1.00  34.12  B  C
ATOM   4760  CB  VAL   150    106.256  60.940  23.492  1.00  12.90  B  C
ATOM   4761  CG1 VAL   150    105.775  59.579  23.967  1.00  15.09  B  C
ATOM   4762  CG2 VAL   150    107.620  61.256  24.110  1.00  14.71  B  C
ATOM   4763  C   VAL   150    105.001  60.604  21.381  1.00  31.68  B  C
ATOM   4764  O   VAL   150    104.057  61.380  21.523  1.00  29.83  B  O
ATOM   4765  N   ILE   151    104.904  59.459  20.714  1.00  36.82  B  N
ATOM   4766  CA  ILE   151    103.640  59.037  20.115  1.00  35.62  B  C
ATOM   4767  CB  ILE   151    103.862  58.436  18.709  1.00  31.63  B  C
ATOM   4768  CG2 ILE   151    102.537  58.084  18.081  1.00  27.99  B  C
ATOM   4769  CG1 ILE   151    104.582  59.454  17.817  1.00  30.05  B  C
ATOM   4770  CD1 ILE   151    104.981  58.916  16.457  1.00  32.03  B  C
ATOM   4771  C   ILE   151    102.978  58.008  21.016  1.00  33.74  B  C
ATOM   4772  O   ILE   151    103.593  57.013  21.394  1.00  33.98  B  O
ATOM   4773  N   VAL   152    101.725  58.254  21.368  1.00  29.85  B  N
ATOM   4774  CA  VAL   152    100.996  57.347  22.243  1.00  30.70  B  C
ATOM   4775  CB  VAL   152    100.279  58.127  23.344  1.00  30.57  B  C
ATOM   4776  CG1 VAL   152     99.721  57.170  24.385  1.00  29.70  B  C
ATOM   4777  CG2 VAL   152    101.245  59.134  23.962  1.00  27.01  B  C
ATOM   4778  C   VAL   152     99.966  56.560  21.451  1.00  28.60  B  C
ATOM   4779  O   VAL   152     98.867  57.044  21.194  1.00  22.20  B  O
ATOM   4780  N   LEU   153    100.324  55.336  21.083  1.00  26.94  B  N
ATOM   4781  CA  LEU   153     99.451  54.479  20.289  1.00  27.05  B  C
ATOM   4782  CB  LEU   153    100.312  53.600  19.370  1.00  31.93  B  C
ATOM   4783  CG  LEU   153    100.518  54.010  17.910  1.00  33.71  B  C
ATOM   4784  CD1 LEU   153    100.287  55.490  17.732  1.00  34.22  B  C
ATOM   4785  CD2 LEU   153    101.914  53.616  17.481  1.00  36.25  B  C
ATOM   4786  C   LEU   153     98.475  53.597  21.058  1.00  28.11  B  C
ATOM   4787  O   LEU   153     98.837  52.930  22.035  1.00  27.11  B  O
ATOM   4788  N   ASP   154     97.228  53.602  20.604  1.00  33.48  B  N
ATOM   4789  CA  ASP   154     96.199  52.768  21.204  1.00  32.96  B  C
ATOM   4790  CB  ASP   154     94.809  53.341  20.911  1.00  34.05  B  C
ATOM   4791  CG  ASP   154     93.686  52.502  21.505  1.00  33.25  B  C
ATOM   4792  OD1 ASP   154     93.959  51.385  21.985  1.00  36.76  B  O
ATOM   4793  OD2 ASP   154     92.523  52.960  21.489  1.00  29.57  B  O
ATOM   4794  C   ASP   154     96.362  51.412  20.515  1.00  36.30  B  C
ATOM   4795  O   ASP   154     96.349  51.326  19.285  1.00  32.62  B  O
ATOM   4796  N   GLY   155     96.539  50.361  21.303  1.00  16.68  B  N
ATOM   4797  CA  GLY   155     96.700  49.039  20.732  1.00  18.75  B  C
ATOM   4798  C   GLY   155     95.706  48.058  21.321  1.00  20.01  B  C
ATOM   4799  O   GLY   155     95.856  46.845  21.177  1.00  22.50  B  O
ATOM   4800  N   SER   156     94.692  48.595  21.992  1.00  30.46  B  N
ATOM   4801  CA  SER   156     93.653  47.780  22.612  1.00  35.04  B  C
ATOM   4802  CB  SER   156     92.616  48.670  23.302  1.00  22.70  B  C
ATOM   4803  OG  SER   156     91.999  49.542  22.372  1.00  25.62  B  O
ATOM   4804  C   SER   156     92.962  46.891  21.584  1.00  32.03  B  C
ATOM   4805  O   SER   156     93.057  47.122  20.379  1.00  35.21  B  O
ATOM   4806  N   ASN   157     92.257  45.879  22.074  1.00  34.08  B  N
ATOM   4807  CA  ASN   157     91.565  44.927  21.216  1.00  31.16  B  C
ATOM   4808  CB  ASN   157     90.632  44.046  22.047  1.00  34.61  B  C
ATOM   4809  CG  ASN   157     91.378  42.971  22.811  1.00  36.10  B  C
ATOM   4810  OD1 ASN   157     90.795  42.270  23.638  1.00  33.17  B  O
ATOM   4811  ND2 ASN   157     92.672  42.832  22.536  1.00  33.38  B  N
ATOM   4812  C   ASN   157     90.783  45.529  20.069  1.00  29.13  B  C
ATOM   4813  O   ASN   157     90.806  45.003  18.956  1.00  27.11  B  O
ATOM   4814  N   SER   158     90.094  46.631  20.339  1.00  20.01  B  N
ATOM   4815  CA  SER   158     89.275  47.285  19.324  1.00  18.22  B  C
ATOM   4816  CB  SER   158     88.506  48.464  19.936  1.00  15.08  B  C
ATOM   4817  OG  SER   158     89.356  49.363  20.616  1.00  17.79  B  O
ATOM   4818  C   SER   158     90.035  47.739  18.087  1.00  18.99  B  C
```

FIG. 19A-67

| ATOM | 4819 | O | SER | 158 | 89.527 | 47.602 | 16.984 | 1.00 | 16.16 | B | O |
|---|---|---|---|---|---|---|---|---|---|---|---|
| ATOM | 4820 | N | ILE | 159 | 91.245 | 48.269 | 18.257 | 1.00 | 19.55 | B | N |
| ATOM | 4821 | CA | ILE | 159 | 92.033 | 48.722 | 17.110 | 1.00 | 24.15 | B | C |
| ATOM | 4822 | CB | ILE | 159 | 93.423 | 49.203 | 17.541 | 1.00 | 21.45 | B | C |
| ATOM | 4823 | CG2 | ILE | 159 | 94.256 | 49.546 | 16.307 | 1.00 | 21.36 | B | C |
| ATOM | 4824 | CG1 | ILE | 159 | 93.293 | 50.411 | 18.471 | 1.00 | 26.23 | B | C |
| ATOM | 4825 | CD1 | ILE | 159 | 92.779 | 51.664 | 17.787 | 1.00 | 31.39 | B | C |
| ATOM | 4826 | C | ILE | 159 | 92.204 | 47.597 | 16.089 | 1.00 | 28.46 | B | C |
| ATOM | 4827 | O | ILE | 159 | 92.638 | 46.502 | 16.434 | 1.00 | 27.87 | B | O |
| ATOM | 4828 | N | TYR | 160 | 91.863 | 47.876 | 14.832 | 1.00 | 56.09 | B | N |
| ATOM | 4829 | CA | TYR | 160 | 91.959 | 46.886 | 13.756 | 1.00 | 58.22 | B | C |
| ATOM | 4830 | CB | TYR | 160 | 90.931 | 45.768 | 13.980 | 1.00 | 40.50 | B | C |
| ATOM | 4831 | CG | TYR | 160 | 90.932 | 44.654 | 12.939 | 1.00 | 37.26 | B | C |
| ATOM | 4832 | CD1 | TYR | 160 | 91.606 | 43.449 | 13.172 | 1.00 | 39.68 | B | C |
| ATOM | 4833 | CE1 | TYR | 160 | 91.602 | 42.423 | 12.225 | 1.00 | 37.28 | B | C |
| ATOM | 4834 | CD2 | TYR | 160 | 90.254 | 44.803 | 11.722 | 1.00 | 34.91 | B | C |
| ATOM | 4835 | CE2 | TYR | 160 | 90.251 | 43.782 | 10.770 | 1.00 | 38.62 | B | C |
| ATOM | 4836 | CZ | TYR | 160 | 90.926 | 42.598 | 11.030 | 1.00 | 37.97 | B | C |
| ATOM | 4837 | OH | TYR | 160 | 90.922 | 41.597 | 10.095 | 1.00 | 42.97 | B | O |
| ATOM | 4838 | C | TYR | 160 | 91.696 | 47.533 | 12.400 | 1.00 | 59.94 | B | C |
| ATOM | 4839 | O | TYR | 160 | 90.730 | 48.276 | 12.232 | 1.00 | 65.86 | B | O |
| ATOM | 4840 | N | PRO | 161 | 92.548 | 47.241 | 11.407 | 1.00 | 26.83 | B | N |
| ATOM | 4841 | CD | PRO | 161 | 92.182 | 47.499 | 10.002 | 1.00 | 24.03 | B | C |
| ATOM | 4842 | CA | PRO | 161 | 93.721 | 46.362 | 11.479 | 1.00 | 25.11 | B | C |
| ATOM | 4843 | CB | PRO | 161 | 93.784 | 45.785 | 10.075 | 1.00 | 28.41 | B | C |
| ATOM | 4844 | CG | PRO | 161 | 93.364 | 46.960 | 9.239 | 1.00 | 31.57 | B | C |
| ATOM | 4845 | C | PRO | 161 | 95.008 | 47.109 | 11.857 | 1.00 | 23.77 | B | C |
| ATOM | 4846 | O | PRO | 161 | 95.234 | 48.238 | 11.413 | 1.00 | 23.09 | B | O |
| ATOM | 4847 | N | TRP | 162 | 95.856 | 46.463 | 12.654 | 1.00 | 23.22 | B | N |
| ATOM | 4848 | CA | TRP | 162 | 97.108 | 47.062 | 13.111 | 1.00 | 24.29 | B | C |
| ATOM | 4849 | CB | TRP | 162 | 97.922 | 46.022 | 13.878 | 1.00 | 29.42 | B | C |
| ATOM | 4850 | CG | TRP | 162 | 99.067 | 46.586 | 14.670 | 1.00 | 29.94 | B | C |
| ATOM | 4851 | CD2 | TRP | 162 | 99.004 | 47.603 | 15.676 | 1.00 | 24.78 | B | C |
| ATOM | 4852 | CE2 | TRP | 162 | 100.308 | 47.769 | 16.185 | 1.00 | 28.33 | B | C |
| ATOM | 4853 | CE3 | TRP | 162 | 97.973 | 48.389 | 16.201 | 1.00 | 24.19 | B | C |
| ATOM | 4854 | CD1 | TRP | 162 | 100.369 | 46.192 | 14.611 | 1.00 | 29.13 | B | C |
| ATOM | 4855 | NE1 | TRP | 162 | 101.123 | 46.898 | 15.516 | 1.00 | 31.00 | B | N |
| ATOM | 4856 | CZ2 | TRP | 162 | 100.607 | 48.687 | 17.195 | 1.00 | 26.87 | B | C |
| ATOM | 4857 | CZ3 | TRP | 162 | 98.274 | 49.303 | 17.208 | 1.00 | 22.52 | B | C |
| ATOM | 4858 | CH2 | TRP | 162 | 99.580 | 49.441 | 17.691 | 1.00 | 27.43 | B | C |
| ATOM | 4859 | C | TRP | 162 | 97.961 | 47.663 | 11.988 | 1.00 | 26.07 | B | C |
| ATOM | 4860 | O | TRP | 162 | 98.554 | 48.734 | 12.161 | 1.00 | 25.22 | B | O |
| ATOM | 4861 | N | GLU | 163 | 98.010 | 46.979 | 10.843 | 1.00 | 39.64 | B | N |
| ATOM | 4862 | CA | GLU | 163 | 98.797 | 47.432 | 9.693 | 1.00 | 41.42 | B | C |
| ATOM | 4863 | CB | GLU | 163 | 98.585 | 46.509 | 8.485 | 1.00 | 121.98 | B | C |
| ATOM | 4864 | CG | GLU | 163 | 97.219 | 46.612 | 7.826 | 1.00 | 128.29 | B | C |
| ATOM | 4865 | CD | GLU | 163 | 97.206 | 46.043 | 6.418 | 1.00 | 130.43 | B | C |
| ATOM | 4866 | OE1 | GLU | 163 | 97.894 | 46.611 | 5.541 | 1.00 | 132.14 | B | O |
| ATOM | 4867 | OE2 | GLU | 163 | 96.512 | 45.029 | 6.187 | 1.00 | 129.39 | B | O |
| ATOM | 4868 | C | GLU | 163 | 98.491 | 48.867 | 9.280 | 1.00 | 41.08 | B | C |
| ATOM | 4869 | O | GLU | 163 | 99.390 | 49.609 | 8.881 | 1.00 | 37.25 | B | O |
| ATOM | 4870 | N | SER | 164 | 97.225 | 49.262 | 9.368 | 1.00 | 24.58 | B | N |
| ATOM | 4871 | CA | SER | 164 | 96.850 | 50.620 | 8.989 | 1.00 | 21.77 | B | C |
| ATOM | 4872 | CB | SER | 164 | 95.320 | 50.772 | 8.984 | 1.00 | 53.34 | B | C |
| ATOM | 4873 | OG | SER | 164 | 94.722 | 49.950 | 7.992 | 1.00 | 59.23 | B | O |
| ATOM | 4874 | C | SER | 164 | 97.484 | 51.619 | 9.956 | 1.00 | 22.53 | B | C |
| ATOM | 4875 | O | SER | 164 | 97.993 | 52.661 | 9.536 | 1.00 | 25.73 | B | O |
| ATOM | 4876 | N | VAL | 165 | 97.451 | 51.286 | 11.247 | 1.00 | 28.47 | B | N |
| ATOM | 4877 | CA | VAL | 165 | 98.027 | 52.137 | 12.280 | 1.00 | 27.86 | B | C |
| ATOM | 4878 | CB | VAL | 165 | 97.841 | 51.525 | 13.680 | 1.00 | 11.01 | B | C |
| ATOM | 4879 | CG1 | VAL | 165 | 98.722 | 52.245 | 14.697 | 1.00 | 12.40 | B | C |
| ATOM | 4880 | CG2 | VAL | 165 | 96.376 | 51.622 | 14.089 | 1.00 | 14.01 | B | C |
| ATOM | 4881 | C | VAL | 165 | 99.509 | 52.334 | 12.028 | 1.00 | 29.02 | B | C |
| ATOM | 4882 | O | VAL | 165 | 100.032 | 53.444 | 12.137 | 1.00 | 30.84 | B | O |
| ATOM | 4883 | N | ILE | 166 | 100.184 | 51.248 | 11.678 | 1.00 | 20.94 | B | N |
| ATOM | 4884 | CA | ILE | 166 | 101.613 | 51.305 | 11.400 | 1.00 | 20.26 | B | C |
| ATOM | 4885 | CB | ILE | 166 | 102.211 | 49.894 | 11.330 | 1.00 | 40.92 | B | C |
| ATOM | 4886 | CG2 | ILE | 166 | 103.697 | 49.962 | 10.986 | 1.00 | 40.13 | B | C |
| ATOM | 4887 | CG1 | ILE | 166 | 102.017 | 49.214 | 12.687 | 1.00 | 40.78 | B | C |
| ATOM | 4888 | CD1 | ILE | 166 | 102.580 | 47.823 | 12.762 | 1.00 | 37.18 | B | C |
| ATOM | 4889 | C | ILE | 166 | 101.920 | 52.073 | 10.121 | 1.00 | 19.71 | B | C |
| ATOM | 4890 | O | ILE | 166 | 102.909 | 52.792 | 10.059 | 1.00 | 21.46 | B | O |
| ATOM | 4891 | N | ALA | 167 | 101.076 | 51.927 | 9.106 | 1.00 | 22.08 | B | N |

FIG. 19A-68

```
ATOM   4892  CA   ALA  167   101.271  52.670   7.866  1.00   22.68  B  C
ATOM   4893  CB   ALA  167   100.207  52.309   6.859  1.00    1.87  B  C
ATOM   4894  C    ALA  167   101.165  54.150   8.224  1.00   23.89  B  C
ATOM   4895  O    ALA  167   101.881  54.989   7.684  1.00   20.49  B  O
ATOM   4896  N    PHE  168   100.261  54.458   9.147  1.00   25.99  B  N
ATOM   4897  CA   PHE  168   100.083  55.823   9.583  1.00   24.51  B  C
ATOM   4898  CB   PHE  168    98.964  55.902  10.623  1.00   28.51  B  C
ATOM   4899  CG   PHE  168    98.962  57.185  11.406  1.00   27.01  B  C
ATOM   4900  CD1  PHE  168    99.549  57.240  12.671  1.00   28.61  B  C
ATOM   4901  CD2  PHE  168    98.409  58.341  10.872  1.00   25.32  B  C
ATOM   4902  CE1  PHE  168    99.587  58.424  13.392  1.00   27.09  B  C
ATOM   4903  CE2  PHE  168    98.442  59.529  11.587  1.00   27.14  B  C
ATOM   4904  CZ   PHE  168    99.034  59.570  12.853  1.00   29.63  B  C
ATOM   4905  C    PHE  168   101.397  56.325  10.178  1.00   25.37  B  C
ATOM   4906  O    PHE  168   101.832  57.446   9.908  1.00   21.81  B  O
ATOM   4907  N    LEU  169   102.030  55.488  10.990  1.00   25.37  B  N
ATOM   4908  CA   LEU  169   103.286  55.867  11.611  1.00   27.96  B  C
ATOM   4909  CB   LEU  169   103.749  54.790  12.585  1.00   24.35  B  C
ATOM   4910  CG   LEU  169   103.127  54.723  13.977  1.00   23.51  B  C
ATOM   4911  CD1  LEU  169   103.983  53.810  14.831  1.00   19.97  B  C
ATOM   4912  CD2  LEU  169   103.079  56.105  14.609  1.00   20.37  B  C
ATOM   4913  C    LEU  169   104.357  56.081  10.555  1.00   30.26  B  C
ATOM   4914  O    LEU  169   105.055  57.095  10.555  1.00   31.69  B  O
ATOM   4915  N    ASN  170   104.488  55.115   9.655  1.00   28.40  B  N
ATOM   4916  CA   ASN  170   105.470  55.208   8.591  1.00   25.53  B  C
ATOM   4917  CB   ASN  170   105.243  54.077   7.580  1.00   72.75  B  C
ATOM   4918  CG   ASN  170   106.484  53.768   6.747  1.00   76.17  B  C
ATOM   4919  OD1  ASN  170   106.703  54.346   5.680  1.00   71.70  B  O
ATOM   4920  ND2  ASN  170   107.307  52.854   7.242  1.00   74.08  B  N
ATOM   4921  C    ASN  170   105.335  56.578   7.913  1.00   25.54  B  C
ATOM   4922  O    ASN  170   106.242  57.408   7.992  1.00   25.75  B  O
ATOM   4923  N    ASP  171   104.189  56.819   7.275  1.00   35.44  B  N
ATOM   4924  CA   ASP  171   103.940  58.079   6.581  1.00   37.56  B  C
ATOM   4925  CB   ASP  171   102.467  58.179   6.168  1.00   72.00  B  C
ATOM   4926  CG   ASP  171   102.163  57.427   4.880  1.00   79.65  B  C
ATOM   4927  OD1  ASP  171   102.448  56.213   4.805  1.00   81.87  B  O
ATOM   4928  OD2  ASP  171   101.635  58.055   3.937  1.00   81.51  B  O
ATOM   4929  C    ASP  171   104.309  59.289   7.418  1.00   39.05  B  C
ATOM   4930  O    ASP  171   104.975  60.202   6.937  1.00   37.77  B  O
ATOM   4931  N    LEU  172   103.881  59.289   8.674  1.00   36.54  B  N
ATOM   4932  CA   LEU  172   104.152  60.403   9.570  1.00   37.22  B  C
ATOM   4933  CB   LEU  172   103.410  60.204  10.891  1.00   36.27  B  C
ATOM   4934  CG   LEU  172   102.901  61.423  11.674  1.00   35.76  B  C
ATOM   4935  CD1  LEU  172   103.145  61.178  13.158  1.00   33.36  B  C
ATOM   4936  CD2  LEU  172   103.593  62.706  11.237  1.00   33.93  B  C
ATOM   4937  C    LEU  172   105.642  60.561   9.849  1.00   37.56  B  C
ATOM   4938  O    LEU  172   106.212  61.628   9.627  1.00   37.55  B  O
ATOM   4939  N    LEU  173   106.269  59.493  10.337  1.00   40.49  B  N
ATOM   4940  CA   LEU  173   107.692  59.520  10.669  1.00   43.24  B  C
ATOM   4941  CB   LEU  173   108.115  58.215  11.364  1.00   18.13  B  C
ATOM   4942  CG   LEU  173   107.801  57.866  12.826  1.00   19.48  B  C
ATOM   4943  CD1  LEU  173   108.033  59.060  13.729  1.00   23.00  B  C
ATOM   4944  CD2  LEU  173   106.380  57.395  12.943  1.00   20.03  B  C
ATOM   4945  C    LEU  173   108.650  59.772   9.503  1.00   44.67  B  C
ATOM   4946  O    LEU  173   109.601  60.537   9.642  1.00   41.39  B  O
ATOM   4947  N    LYS  174   108.409  59.135   8.360  1.00   37.56  B  N
ATOM   4948  CA   LYS  174   109.304  59.291   7.221  1.00   37.78  B  C
ATOM   4949  CB   LYS  174   108.836  58.421   6.047  1.00   42.14  B  C
ATOM   4950  CG   LYS  174   107.739  58.988   5.169  1.00   42.47  B  C
ATOM   4951  CD   LYS  174   107.472  58.022   4.008  1.00   41.72  B  C
ATOM   4952  CE   LYS  174   106.689  58.660   2.852  1.00   36.97  B  C
ATOM   4953  NZ   LYS  174   105.297  59.097   3.187  1.00   33.44  B  N
ATOM   4954  C    LYS  174   109.511  60.738   6.774  1.00   36.14  B  C
ATOM   4955  O    LYS  174   110.571  61.078   6.245  1.00   37.01  B  O
ATOM   4956  N    ARG  175   108.514  61.589   7.004  1.00   41.42  B  N
ATOM   4957  CA   ARG  175   108.587  63.006   6.635  1.00   43.65  B  C
ATOM   4958  CB   ARG  175   107.182  63.634   6.654  1.00  108.28  B  C
ATOM   4959  CG   ARG  175   106.189  63.149   5.589  1.00  115.21  B  C
ATOM   4960  CD   ARG  175   104.762  63.613   5.939  1.00  119.49  B  C
ATOM   4961  NE   ARG  175   103.895  63.818   4.775  1.00  124.39  B  N
ATOM   4962  CZ   ARG  175   103.454  62.856   3.969  1.00  127.97  B  C
ATOM   4963  NH1  ARG  175   103.793  61.593   4.182  1.00  128.17  B  N
ATOM   4964  NH2  ARG  175   102.666  63.162   2.945  1.00  128.87  B  N
```

FIG. 19A-69

```
ATOM   4965  C    ARG  175   109.471  63.798   7.611  1.00   41.18  B  C
ATOM   4966  O    ARG  175   109.696  64.986   7.411  1.00   41.02  B  O
ATOM   4967  N    MET  176   109.970  63.145   8.660  1.00   47.15  B  N
ATOM   4968  CA   MET  176   110.777  63.821   9.678  1.00   43.63  B  C
ATOM   4969  CB   MET  176   110.320  63.383  11.065  1.00   33.29  B  C
ATOM   4970  CG   MET  176   108.969  63.920  11.456  1.00   30.19  B  C
ATOM   4971  SD   MET  176   108.444  63.366  13.073  1.00   34.33  B  S
ATOM   4972  CE   MET  176   107.041  62.339  12.619  1.00   27.84  B  C
ATOM   4973  C    MET  176   112.284  63.663   9.611  1.00   47.14  B  C
ATOM   4974  O    MET  176   112.795  62.707   9.037  1.00   47.21  B  O
ATOM   4975  N    ASP  177   112.991  64.617  10.213  1.00   51.06  B  N
ATOM   4976  CA   ASP  177   114.451  64.590  10.276  1.00   53.55  B  C
ATOM   4977  CB   ASP  177   115.047  65.944   9.881  1.00  101.95  B  C
ATOM   4978  CG   ASP  177   115.065  66.158   8.381  1.00  104.90  B  C
ATOM   4979  OD1  ASP  177   115.635  67.174   7.934  1.00  104.57  B  O
ATOM   4980  OD2  ASP  177   114.511  65.310   7.647  1.00  106.55  B  O
ATOM   4981  C    ASP  177   114.851  64.249  11.706  1.00   53.47  B  C
ATOM   4982  O    ASP  177   115.107  65.133  12.519  1.00   53.19  B  O
ATOM   4983  N    ILE  178   114.888  62.954  12.003  1.00   55.91  B  N
ATOM   4984  CA   ILE  178   115.236  62.465  13.331  1.00   56.05  B  C
ATOM   4985  CB   ILE  178   114.719  61.004  13.543  1.00   33.37  B  C
ATOM   4986  CG2  ILE  178   115.323  60.410  14.790  1.00   31.65  B  C
ATOM   4987  CG1  ILE  178   113.191  60.985  13.665  1.00   34.43  B  C
ATOM   4988  CD1  ILE  178   112.464  60.671  12.376  1.00   36.27  B  C
ATOM   4989  C    ILE  178   116.743  62.502  13.583  1.00   55.19  B  C
ATOM   4990  O    ILE  178   117.543  62.224  12.686  1.00   57.18  B  O
ATOM   4991  N    GLY  179   117.117  62.846  14.812  1.00   23.09  B  N
ATOM   4992  CA   GLY  179   118.521  62.912  15.178  1.00   22.81  B  C
ATOM   4993  C    GLY  179   118.736  63.508  16.560  1.00   23.57  B  C
ATOM   4994  O    GLY  179   117.931  64.325  17.012  1.00   21.72  B  O
ATOM   4995  N    PRO  180   119.815  63.113  17.265  1.00   39.73  B  N
ATOM   4996  CD   PRO  180   120.782  62.068  16.873  1.00   73.51  B  C
ATOM   4997  CA   PRO  180   120.124  63.620  18.606  1.00   40.79  B  C
ATOM   4998  CB   PRO  180   121.542  63.113  18.840  1.00   72.35  B  C
ATOM   4999  CG   PRO  180   121.502  61.776  18.184  1.00   74.74  B  C
ATOM   5000  C    PRO  180   120.019  65.135  18.697  1.00   42.57  B  C
ATOM   5001  O    PRO  180   119.718  65.680  19.761  1.00   43.21  B  O
ATOM   5002  N    LYS  181   120.268  65.810  17.578  1.00   56.97  B  N
ATOM   5003  CA   LYS  181   120.186  67.265  17.534  1.00   57.39  B  C
ATOM   5004  CB   LYS  181   121.522  67.867  17.092  1.00   83.43  B  C
ATOM   5005  CG   LYS  181   122.677  67.613  18.052  1.00   84.03  B  C
ATOM   5006  CD   LYS  181   122.430  68.205  19.442  1.00   82.89  B  C
ATOM   5007  CE   LYS  181   123.580  67.868  20.394  1.00   85.41  B  C
ATOM   5008  NZ   LYS  181   123.351  68.348  21.790  1.00   84.98  B  N
ATOM   5009  C    LYS  181   119.070  67.736  16.597  1.00   56.74  B  C
ATOM   5010  O    LYS  181   118.973  68.917  16.274  1.00   55.06  B  O
ATOM   5011  N    GLN  182   118.225  66.804  16.167  1.00   33.36  B  N
ATOM   5012  CA   GLN  182   117.112  67.117  15.279  1.00   32.02  B  C
ATOM   5013  CB   GLN  182   117.152  66.219  14.044  1.00   74.94  B  C
ATOM   5014  CG   GLN  182   118.512  66.050  13.424  1.00   76.22  B  C
ATOM   5015  CD   GLN  182   119.037  67.334  12.850  1.00   77.84  B  C
ATOM   5016  OE1  GLN  182   119.266  68.305  13.573  1.00   78.68  B  O
ATOM   5017  NE2  GLN  182   119.230  67.356  11.537  1.00   79.20  B  N
ATOM   5018  C    GLN  182   115.831  66.826  16.046  1.00   30.93  B  C
ATOM   5019  O    GLN  182   115.638  67.278  17.173  1.00   35.26  B  O
ATOM   5020  N    THR  183   114.961  66.046  15.419  1.00   29.87  B  N
ATOM   5021  CA   THR  183   113.706  65.648  16.025  1.00   26.79  B  C
ATOM   5022  CB   THR  183   112.612  65.493  14.962  1.00   31.40  B  C
ATOM   5023  OG1  THR  183   112.484  66.721  14.231  1.00   27.85  B  O
ATOM   5024  CG2  THR  183   111.285  65.127  15.610  1.00   29.08  B  C
ATOM   5025  C    THR  183   113.957  64.288  16.666  1.00   26.45  B  C
ATOM   5026  O    THR  183   114.624  63.428  16.077  1.00   24.98  B  O
ATOM   5027  N    GLN  184   113.464  64.102  17.883  1.00   44.27  B  N
ATOM   5028  CA   GLN  184   113.619  62.822  18.546  1.00   39.92  B  C
ATOM   5029  CB   GLN  184   114.254  62.981  19.920  1.00   33.99  B  C
ATOM   5030  CG   GLN  184   115.752  63.197  19.878  1.00   33.74  B  C
ATOM   5031  CD   GLN  184   116.427  62.766  21.163  1.00   33.21  B  C
ATOM   5032  OE1  GLN  184   116.097  63.258  22.244  1.00   28.91  B  O
ATOM   5033  NE2  GLN  184   117.375  61.835  21.053  1.00   31.51  B  N
ATOM   5034  C    GLN  184   112.227  62.240  18.670  1.00   40.30  B  C
ATOM   5035  O    GLN  184   111.249  62.978  18.834  1.00   37.69  B  O
ATOM   5036  N    VAL  185   112.131  60.918  18.574  1.00   24.17  B  N
ATOM   5037  CA   VAL  185   110.837  60.255  18.649  1.00   22.54  B  C
```

FIG. 19A-70

```
ATOM   5038  CB   VAL  185   110.345  59.858  17.235  1.00  12.44  B  C
ATOM   5039  CG1  VAL  185   109.105  58.990  17.335  1.00  12.43  B  C
ATOM   5040  CG2  VAL  185   110.052  61.103  16.425  1.00   1.87  B  C
ATOM   5041  C    VAL  185   110.840  59.025  19.536  1.00  23.13  B  C
ATOM   5042  O    VAL  185   111.756  58.206  19.510  1.00  20.28  B  O
ATOM   5043  N    GLY  186   109.789  58.914  20.328  1.00  27.91  B  N
ATOM   5044  CA   GLY  186   109.630  57.782  21.213  1.00  29.54  B  C
ATOM   5045  C    GLY  186   108.200  57.319  21.045  1.00  27.52  B  C
ATOM   5046  O    GLY  186   107.308  58.138  20.839  1.00  32.88  B  O
ATOM   5047  N    ILE  187   107.970  56.017  21.105  1.00  20.77  B  N
ATOM   5048  CA   ILE  187   106.617  55.519  20.958  1.00  19.36  B  C
ATOM   5049  CB   ILE  187   106.460  54.729  19.642  1.00  17.70  B  C
ATOM   5050  CG2  ILE  187   105.081  54.079  19.577  1.00  15.03  B  C
ATOM   5051  CG1  ILE  187   106.639  55.676  18.454  1.00  18.22  B  C
ATOM   5052  CD1  ILE  187   106.437  55.033  17.100  1.00  19.27  B  C
ATOM   5053  C    ILE  187   106.160  54.674  22.143  1.00  18.65  B  C
ATOM   5054  O    ILE  187   106.852  53.763  22.590  1.00  17.55  B  O
ATOM   5055  N    VAL  188   104.984  55.015  22.649  1.00  23.72  B  N
ATOM   5056  CA   VAL  188   104.370  54.332  23.774  1.00  23.39  B  C
ATOM   5057  CB   VAL  188   104.053  55.333  24.911  1.00  24.28  B  C
ATOM   5058  CG1  VAL  188   103.055  54.728  25.896  1.00  19.55  B  C
ATOM   5059  CG2  VAL  188   105.320  55.715  25.625  1.00  24.70  B  C
ATOM   5060  C    VAL  188   103.055  53.702  23.303  1.00  21.93  B  C
ATOM   5061  O    VAL  188   102.274  54.341  22.591  1.00  21.34  B  O
ATOM   5062  N    GLN  189   102.815  52.453  23.686  1.00  21.90  B  N
ATOM   5063  CA   GLN  189   101.580  51.785  23.312  1.00  21.58  B  C
ATOM   5064  CB   GLN  189   101.857  50.545  22.463  1.00  19.75  B  C
ATOM   5065  CG   GLN  189   100.577  49.784  22.128  1.00  17.26  B  C
ATOM   5066  CD   GLN  189   100.819  48.495  21.377  1.00  17.97  B  C
ATOM   5067  OE1  GLN  189    99.930  47.647  21.283  1.00  19.19  B  O
ATOM   5068  NE2  GLN  189   102.022  48.340  20.831  1.00  19.01  B  N
ATOM   5069  C    GLN  189   100.820  51.386  24.572  1.00  18.57  B  C
ATOM   5070  O    GLN  189   101.423  50.980  25.567  1.00  16.93  B  O
ATOM   5071  N    TYR  190    99.494  51.500  24.524  1.00  20.56  B  N
ATOM   5072  CA   TYR  190    98.671  51.159  25.680  1.00  24.08  B  C
ATOM   5073  CB   TYR  190    98.255  52.432  26.418  1.00  22.72  B  C
ATOM   5074  CG   TYR  190    97.213  53.255  25.687  1.00  17.37  B  C
ATOM   5075  CD1  TYR  190    95.849  53.072  25.929  1.00  15.48  B  C
ATOM   5076  CE1  TYR  190    94.882  53.820  25.244  1.00  17.37  B  C
ATOM   5077  CD2  TYR  190    97.586  54.207  24.739  1.00  13.48  B  C
ATOM   5078  CE2  TYR  190    96.624  54.957  24.051  1.00  14.90  B  C
ATOM   5079  CZ   TYR  190    95.279  54.760  24.311  1.00  15.79  B  C
ATOM   5080  OH   TYR  190    94.340  55.527  23.663  1.00  14.38  B  O
ATOM   5081  C    TYR  190    97.428  50.342  25.344  1.00  25.93  B  C
ATOM   5082  O    TYR  190    97.000  50.260  24.195  1.00  26.01  B  O
ATOM   5083  N    GLY  191    96.860  49.746  26.385  1.00  24.69  B  N
ATOM   5084  CA   GLY  191    95.675  48.920  26.270  1.00  22.44  B  C
ATOM   5085  C    GLY  191    95.277  48.649  27.701  1.00  23.88  B  C
ATOM   5086  O    GLY  191    94.720  49.532  28.348  1.00  27.26  B  O
ATOM   5087  N    GLU  192    95.572  47.446  28.197  1.00  23.59  B  N
ATOM   5088  CA   GLU  192    95.284  47.084  29.584  1.00  25.60  B  C
ATOM   5089  CB   GLU  192    95.232  45.574  29.758  1.00  40.14  B  C
ATOM   5090  CG   GLU  192    94.135  44.871  29.002  1.00  40.52  B  C
ATOM   5091  CD   GLU  192    94.134  43.382  29.273  1.00  40.71  B  C
ATOM   5092  OE1  GLU  192    93.230  42.690  28.759  1.00  43.60  B  O
ATOM   5093  OE2  GLU  192    95.038  42.906  29.999  1.00  38.58  B  O
ATOM   5094  C    GLU  192    96.465  47.608  30.390  1.00  25.41  B  C
ATOM   5095  O    GLU  192    96.325  48.027  31.536  1.00  26.78  B  O
ATOM   5096  N    ASN  193    97.637  47.569  29.770  1.00  17.36  B  N
ATOM   5097  CA   ASN  193    98.862  48.041  30.395  1.00  18.57  B  C
ATOM   5098  CB   ASN  193    99.814  46.877  30.653  1.00  57.60  B  C
ATOM   5099  CG   ASN  193    99.159  45.755  31.418  1.00  60.77  B  C
ATOM   5100  OD1  ASN  193    98.225  45.115  30.933  1.00  64.88  B  O
ATOM   5101  ND2  ASN  193    99.644  45.509  32.626  1.00  62.88  B  N
ATOM   5102  C    ASN  193    99.510  49.007  29.425  1.00  16.75  B  C
ATOM   5103  O    ASN  193    98.917  49.360  28.413  1.00  17.75  B  O
ATOM   5104  N    VAL  194   100.735  49.418  29.728  1.00  23.63  B  N
ATOM   5105  CA   VAL  194   101.454  50.346  28.866  1.00  25.97  B  C
ATOM   5106  CB   VAL  194   101.516  51.750  29.490  1.00  24.85  B  C
ATOM   5107  CG1  VAL  194   102.014  52.745  28.459  1.00  25.88  B  C
ATOM   5108  CG2  VAL  194   100.153  52.147  30.032  1.00  22.12  B  C
ATOM   5109  C    VAL  194   102.887  49.864  28.661  1.00  23.74  B  C
ATOM   5110  O    VAL  194   103.535  49.384  29.597  1.00  21.86  B  O
```

FIG. 19A-71

| | | | | | | | | | | | |
|---|---|---|---|---|---|---|---|---|---|---|---|
| ATOM | 5111 | N | THR | 195 | 103.397 | 49.986 | 27.444 | 1.00 | 25.03 | B | N |
| ATOM | 5112 | CA | THR | 195 | 104.758 | 49.552 | 27.197 | 1.00 | 26.21 | B | C |
| ATOM | 5113 | CB | THR | 195 | 104.797 | 48.182 | 26.450 | 1.00 | 38.61 | B | C |
| ATOM | 5114 | OG1 | THR | 195 | 104.420 | 48.360 | 25.081 | 1.00 | 42.62 | B | O |
| ATOM | 5115 | CG2 | THR | 195 | 103.828 | 47.195 | 27.087 | 1.00 | 40.24 | B | C |
| ATOM | 5116 | C | THR | 195 | 105.511 | 50.599 | 26.391 | 1.00 | 27.05 | B | C |
| ATOM | 5117 | O | THR | 195 | 104.944 | 51.254 | 25.514 | 1.00 | 29.64 | B | O |
| ATOM | 5118 | N | HIS | 196 | 106.791 | 50.765 | 26.716 | 1.00 | 33.64 | B | N |
| ATOM | 5119 | CA | HIS | 196 | 107.656 | 51.713 | 26.029 | 1.00 | 33.74 | B | C |
| ATOM | 5120 | CB | HIS | 196 | 108.815 | 52.119 | 26.942 | 1.00 | 34.91 | B | C |
| ATOM | 5121 | CG | HIS | 196 | 108.417 | 53.011 | 28.079 | 1.00 | 31.41 | B | C |
| ATOM | 5122 | CD2 | HIS | 196 | 108.084 | 52.725 | 29.360 | 1.00 | 32.04 | B | C |
| ATOM | 5123 | ND1 | HIS | 196 | 108.322 | 54.382 | 27.955 | 1.00 | 30.06 | B | N |
| ATOM | 5124 | CE1 | HIS | 196 | 107.949 | 54.901 | 29.111 | 1.00 | 26.78 | B | C |
| ATOM | 5125 | NE2 | HIS | 196 | 107.797 | 53.918 | 29.979 | 1.00 | 24.99 | B | N |
| ATOM | 5126 | C | HIS | 196 | 108.219 | 51.017 | 24.806 | 1.00 | 33.60 | B | C |
| ATOM | 5127 | O | HIS | 196 | 109.201 | 50.289 | 24.932 | 1.00 | 32.26 | B | O |
| ATOM | 5128 | N | GLU | 197 | 107.609 | 51.216 | 23.636 | 1.00 | 34.73 | B | N |
| ATOM | 5129 | CA | GLU | 197 | 108.123 | 50.583 | 22.417 | 1.00 | 32.06 | B | C |
| ATOM | 5130 | CB | GLU | 197 | 107.313 | 50.999 | 21.193 | 1.00 | 45.57 | B | C |
| ATOM | 5131 | CG | GLU | 197 | 105.913 | 50.386 | 21.130 | 1.00 | 45.91 | B | C |
| ATOM | 5132 | CD | GLU | 197 | 105.911 | 48.876 | 21.303 | 1.00 | 44.98 | B | C |
| ATOM | 5133 | OE1 | GLU | 197 | 106.869 | 48.228 | 20.834 | 1.00 | 43.56 | B | O |
| ATOM | 5134 | OE2 | GLU | 197 | 104.949 | 48.331 | 21.892 | 1.00 | 46.64 | B | O |
| ATOM | 5135 | C | GLU | 197 | 109.595 | 50.958 | 22.245 | 1.00 | 29.53 | B | C |
| ATOM | 5136 | O | GLU | 197 | 110.447 | 50.081 | 22.151 | 1.00 | 34.73 | B | O |
| ATOM | 5137 | N | PHE | 198 | 109.898 | 52.254 | 22.203 | 1.00 | 32.40 | B | N |
| ATOM | 5138 | CA | PHE | 198 | 111.293 | 52.691 | 22.126 | 1.00 | 34.20 | B | C |
| ATOM | 5139 | CB | PHE | 198 | 111.881 | 52.501 | 20.714 | 1.00 | 23.77 | B | C |
| ATOM | 5140 | CG | PHE | 198 | 111.239 | 53.331 | 19.636 | 1.00 | 22.02 | B | C |
| ATOM | 5141 | CD1 | PHE | 198 | 111.379 | 54.711 | 19.614 | 1.00 | 28.16 | B | C |
| ATOM | 5142 | CD2 | PHE | 198 | 110.539 | 52.715 | 18.597 | 1.00 | 16.76 | B | C |
| ATOM | 5143 | CE1 | PHE | 198 | 110.837 | 55.468 | 18.571 | 1.00 | 24.19 | B | C |
| ATOM | 5144 | CE2 | PHE | 198 | 109.990 | 53.460 | 17.548 | 1.00 | 22.67 | B | C |
| ATOM | 5145 | CZ | PHE | 198 | 110.140 | 54.838 | 17.536 | 1.00 | 26.47 | B | C |
| ATOM | 5146 | C | PHE | 198 | 111.471 | 54.120 | 22.642 | 1.00 | 36.88 | B | C |
| ATOM | 5147 | O | PHE | 198 | 110.631 | 54.973 | 22.398 | 1.00 | 38.17 | B | O |
| ATOM | 5148 | N | ASN | 199 | 112.552 | 54.366 | 23.386 | 1.00 | 21.75 | B | N |
| ATOM | 5149 | CA | ASN | 199 | 112.810 | 55.686 | 23.971 | 1.00 | 22.04 | B | C |
| ATOM | 5150 | CB | ASN | 199 | 113.924 | 55.613 | 25.007 | 1.00 | 33.57 | B | C |
| ATOM | 5151 | CG | ASN | 199 | 113.636 | 54.633 | 26.105 | 1.00 | 34.83 | B | C |
| ATOM | 5152 | OD1 | ASN | 199 | 112.614 | 54.717 | 26.785 | 1.00 | 36.36 | B | O |
| ATOM | 5153 | ND2 | ASN | 199 | 114.549 | 53.688 | 26.295 | 1.00 | 33.71 | B | N |
| ATOM | 5154 | C | ASN | 199 | 113.159 | 56.792 | 22.996 | 1.00 | 24.50 | B | C |
| ATOM | 5155 | O | ASN | 199 | 113.569 | 56.546 | 21.862 | 1.00 | 22.31 | B | O |
| ATOM | 5156 | N | LEU | 200 | 113.004 | 58.023 | 23.473 | 1.00 | 27.41 | B | N |
| ATOM | 5157 | CA | LEU | 200 | 113.286 | 59.215 | 22.685 | 1.00 | 29.37 | B | C |
| ATOM | 5158 | CB | LEU | 200 | 113.094 | 60.467 | 23.542 | 1.00 | 22.93 | B | C |
| ATOM | 5159 | CG | LEU | 200 | 111.694 | 61.088 | 23.545 | 1.00 | 20.78 | B | C |
| ATOM | 5160 | CD1 | LEU | 200 | 111.613 | 62.208 | 24.578 | 1.00 | 25.90 | B | C |
| ATOM | 5161 | CD2 | LEU | 200 | 111.375 | 61.607 | 22.140 | 1.00 | 21.95 | B | C |
| ATOM | 5162 | C | LEU | 200 | 114.685 | 59.223 | 22.104 | 1.00 | 29.77 | B | C |
| ATOM | 5163 | O | LEU | 200 | 114.899 | 59.698 | 20.992 | 1.00 | 30.79 | B | O |
| ATOM | 5164 | N | ASN | 201 | 115.635 | 58.685 | 22.856 | 1.00 | 32.06 | B | N |
| ATOM | 5165 | CA | ASN | 201 | 117.027 | 58.660 | 22.426 | 1.00 | 33.91 | B | C |
| ATOM | 5166 | CB | ASN | 201 | 117.920 | 59.105 | 23.578 | 1.00 | 34.75 | B | C |
| ATOM | 5167 | CG | ASN | 201 | 117.838 | 58.168 | 24.769 | 1.00 | 37.03 | B | C |
| ATOM | 5168 | OD1 | ASN | 201 | 118.389 | 58.443 | 25.832 | 1.00 | 37.17 | B | O |
| ATOM | 5169 | ND2 | ASN | 201 | 117.147 | 57.052 | 24.592 | 1.00 | 34.87 | B | N |
| ATOM | 5170 | C | ASN | 201 | 117.517 | 57.309 | 21.936 | 1.00 | 33.96 | B | C |
| ATOM | 5171 | O | ASN | 201 | 118.723 | 57.111 | 21.825 | 1.00 | 29.86 | B | O |
| ATOM | 5172 | N | LYS | 202 | 116.603 | 56.382 | 21.653 | 1.00 | 35.80 | B | N |
| ATOM | 5173 | CA | LYS | 202 | 116.990 | 55.051 | 21.183 | 1.00 | 35.92 | B | C |
| ATOM | 5174 | CB | LYS | 202 | 115.786 | 54.107 | 21.160 | 1.00 | 34.30 | B | C |
| ATOM | 5175 | CG | LYS | 202 | 116.107 | 52.652 | 20.788 | 1.00 | 35.84 | B | C |
| ATOM | 5176 | CD | LYS | 202 | 116.841 | 51.929 | 21.898 | 1.00 | 37.75 | B | C |
| ATOM | 5177 | CE | LYS | 202 | 116.185 | 52.179 | 23.273 | 1.00 | 43.50 | B | C |
| ATOM | 5178 | NZ | LYS | 202 | 114.729 | 51.801 | 23.388 | 1.00 | 42.52 | B | N |
| ATOM | 5179 | C | LYS | 202 | 117.617 | 55.071 | 19.800 | 1.00 | 34.79 | B | C |
| ATOM | 5180 | O | LYS | 202 | 118.667 | 54.472 | 19.589 | 1.00 | 32.07 | B | O |
| ATOM | 5181 | N | TYR | 203 | 116.977 | 55.747 | 18.852 | 1.00 | 23.81 | B | N |
| ATOM | 5182 | CA | TYR | 203 | 117.509 | 55.815 | 17.491 | 1.00 | 23.49 | B | C |
| ATOM | 5183 | CB | TYR | 203 | 116.466 | 55.300 | 16.499 | 1.00 | 32.41 | B | C |

FIG. 19A-72

| | | | | | | | | | | |
|---|---|---|---|---|---|---|---|---|---|---|
| ATOM | 5184 | CG | TYR | 203 | 115.907 | 53.951 | 16.886 | 1.00 | 31.08 | B C |
| ATOM | 5185 | CD1 | TYR | 203 | 114.665 | 53.844 | 17.509 | 1.00 | 31.69 | B C |
| ATOM | 5186 | CE1 | TYR | 203 | 114.179 | 52.613 | 17.930 | 1.00 | 28.16 | B C |
| ATOM | 5187 | CD2 | TYR | 203 | 116.649 | 52.784 | 16.689 | 1.00 | 33.97 | B C |
| ATOM | 5188 | CE2 | TYR | 203 | 116.173 | 51.550 | 17.109 | 1.00 | 36.72 | B C |
| ATOM | 5189 | CZ | TYR | 203 | 114.940 | 51.474 | 17.730 | 1.00 | 36.34 | B C |
| ATOM | 5190 | OH | TYR | 203 | 114.466 | 50.262 | 18.169 | 1.00 | 41.34 | B O |
| ATOM | 5191 | C | TYR | 203 | 117.957 | 57.230 | 17.114 | 1.00 | 24.13 | B C |
| ATOM | 5192 | O | TYR | 203 | 117.268 | 58.211 | 17.387 | 1.00 | 22.30 | B O |
| ATOM | 5193 | N | SER | 204 | 119.122 | 57.323 | 16.484 | 1.00 | 32.64 | B N |
| ATOM | 5194 | CA | SER | 204 | 119.693 | 58.608 | 16.089 | 1.00 | 34.49 | B C |
| ATOM | 5195 | CB | SER | 204 | 121.199 | 58.588 | 16.320 | 1.00 | 50.27 | B C |
| ATOM | 5196 | OG | SER | 204 | 121.780 | 57.499 | 15.621 | 1.00 | 52.10 | B O |
| ATOM | 5197 | C | SER | 204 | 119.432 | 58.924 | 14.632 | 1.00 | 37.07 | B C |
| ATOM | 5198 | O | SER | 204 | 119.922 | 59.919 | 14.118 | 1.00 | 37.58 | B O |
| ATOM | 5199 | N | SER | 205 | 118.657 | 58.082 | 13.966 | 1.00 | 56.25 | B N |
| ATOM | 5200 | CA | SER | 205 | 118.379 | 58.289 | 12.558 | 1.00 | 55.91 | B C |
| ATOM | 5201 | CB | SER | 205 | 119.256 | 57.357 | 11.734 | 1.00 | 30.45 | B C |
| ATOM | 5202 | OG | SER | 205 | 118.818 | 57.302 | 10.393 | 1.00 | 35.94 | B O |
| ATOM | 5203 | C | SER | 205 | 116.918 | 58.067 | 12.195 | 1.00 | 54.04 | B C |
| ATOM | 5204 | O | SER | 205 | 116.208 | 57.320 | 12.866 | 1.00 | 50.30 | B O |
| ATOM | 5205 | N | THR | 206 | 116.477 | 58.718 | 11.122 | 1.00 | 22.26 | B N |
| ATOM | 5206 | CA | THR | 206 | 115.105 | 58.589 | 10.661 | 1.00 | 23.61 | B C |
| ATOM | 5207 | CB | THR | 206 | 114.799 | 59.611 | 9.560 | 1.00 | 36.04 | B C |
| ATOM | 5208 | OG1 | THR | 206 | 114.968 | 60.935 | 10.086 | 1.00 | 34.85 | B O |
| ATOM | 5209 | CG2 | THR | 206 | 113.364 | 59.438 | 9.047 | 1.00 | 34.41 | B C |
| ATOM | 5210 | C | THR | 206 | 114.780 | 57.188 | 10.144 | 1.00 | 24.20 | B C |
| ATOM | 5211 | O | THR | 206 | 113.676 | 56.683 | 10.363 | 1.00 | 26.99 | B O |
| ATOM | 5212 | N | GLU | 207 | 115.719 | 56.554 | 9.447 | 1.00 | 31.43 | B N |
| ATOM | 5213 | CA | GLU | 207 | 115.444 | 55.210 | 8.964 | 1.00 | 30.59 | B C |
| ATOM | 5214 | CB | GLU | 207 | 116.448 | 54.791 | 7.893 | 1.00 | 74.76 | B C |
| ATOM | 5215 | CG | GLU | 207 | 117.897 | 54.985 | 8.248 | 1.00 | 75.48 | B C |
| ATOM | 5216 | CD | GLU | 207 | 118.817 | 54.402 | 7.189 | 1.00 | 76.89 | B C |
| ATOM | 5217 | OE1 | GLU | 207 | 118.595 | 54.668 | 5.982 | 1.00 | 76.12 | B O |
| ATOM | 5218 | OE2 | GLU | 207 | 119.765 | 53.679 | 7.565 | 1.00 | 75.79 | B O |
| ATOM | 5219 | C | GLU | 207 | 115.462 | 54.237 | 10.141 | 1.00 | 31.09 | B C |
| ATOM | 5220 | O | GLU | 207 | 114.647 | 53.315 | 10.194 | 1.00 | 31.04 | B O |
| ATOM | 5221 | N | GLU | 208 | 116.373 | 54.449 | 11.093 | 1.00 | 40.73 | B N |
| ATOM | 5222 | CA | GLU | 208 | 116.441 | 53.584 | 12.267 | 1.00 | 42.46 | B C |
| ATOM | 5223 | CB | GLU | 208 | 117.542 | 54.038 | 13.230 | 1.00 | 57.02 | B C |
| ATOM | 5224 | CG | GLU | 208 | 118.951 | 53.899 | 12.682 | 1.00 | 54.49 | B C |
| ATOM | 5225 | CD | GLU | 208 | 120.022 | 54.254 | 13.703 | 1.00 | 54.01 | B C |
| ATOM | 5226 | OE1 | GLU | 208 | 121.217 | 54.253 | 13.333 | 1.00 | 59.78 | B O |
| ATOM | 5227 | OE2 | GLU | 208 | 119.669 | 54.533 | 14.873 | 1.00 | 52.73 | B O |
| ATOM | 5228 | C | GLU | 208 | 115.100 | 53.611 | 12.991 | 1.00 | 43.16 | B C |
| ATOM | 5229 | O | GLU | 208 | 114.637 | 52.584 | 13.489 | 1.00 | 44.16 | B O |
| ATOM | 5230 | N | VAL | 209 | 114.478 | 54.787 | 13.046 | 1.00 | 30.06 | B N |
| ATOM | 5231 | CA | VAL | 209 | 113.190 | 54.922 | 13.709 | 1.00 | 28.98 | B C |
| ATOM | 5232 | CB | VAL | 209 | 112.879 | 56.399 | 14.058 | 1.00 | 17.77 | B C |
| ATOM | 5233 | CG1 | VAL | 209 | 111.379 | 56.612 | 14.232 | 1.00 | 18.10 | B C |
| ATOM | 5234 | CG2 | VAL | 209 | 113.575 | 56.762 | 15.349 | 1.00 | 18.79 | B C |
| ATOM | 5235 | C | VAL | 209 | 112.098 | 54.359 | 12.820 | 1.00 | 27.00 | B C |
| ATOM | 5236 | O | VAL | 209 | 111.198 | 53.660 | 13.296 | 1.00 | 25.96 | B O |
| ATOM | 5237 | N | LEU | 210 | 112.187 | 54.655 | 11.529 | 1.00 | 33.19 | B N |
| ATOM | 5238 | CA | LEU | 210 | 111.207 | 54.164 | 10.570 | 1.00 | 33.52 | B C |
| ATOM | 5239 | CB | LEU | 210 | 111.557 | 54.643 | 9.168 | 1.00 | 15.67 | B C |
| ATOM | 5240 | CG | LEU | 210 | 110.629 | 55.672 | 8.535 | 1.00 | 15.91 | B C |
| ATOM | 5241 | CD1 | LEU | 210 | 111.182 | 55.981 | 7.171 | 1.00 | 12.46 | B C |
| ATOM | 5242 | CD2 | LEU | 210 | 109.191 | 55.157 | 8.437 | 1.00 | 9.36 | B C |
| ATOM | 5243 | C | LEU | 210 | 111.152 | 52.639 | 10.571 | 1.00 | 31.78 | B C |
| ATOM | 5244 | O | LEU | 210 | 110.090 | 52.042 | 10.382 | 1.00 | 32.55 | B O |
| ATOM | 5245 | N | VAL | 211 | 112.307 | 52.017 | 10.779 | 1.00 | 24.37 | B N |
| ATOM | 5246 | CA | VAL | 211 | 112.404 | 50.569 | 10.809 | 1.00 | 24.13 | B C |
| ATOM | 5247 | CB | VAL | 211 | 113.852 | 50.123 | 10.575 | 1.00 | 20.01 | B C |
| ATOM | 5248 | CG1 | VAL | 211 | 114.002 | 48.647 | 10.897 | 1.00 | 22.19 | B C |
| ATOM | 5249 | CG2 | VAL | 211 | 114.239 | 50.405 | 9.118 | 1.00 | 20.62 | B C |
| ATOM | 5250 | C | VAL | 211 | 111.913 | 49.997 | 12.129 | 1.00 | 23.38 | B C |
| ATOM | 5251 | O | VAL | 211 | 111.260 | 48.958 | 12.164 | 1.00 | 24.06 | B O |
| ATOM | 5252 | N | ALA | 212 | 112.230 | 50.674 | 13.221 | 1.00 | 40.83 | B N |
| ATOM | 5253 | CA | ALA | 212 | 111.803 | 50.203 | 14.526 | 1.00 | 39.81 | B C |
| ATOM | 5254 | CB | ALA | 212 | 112.489 | 51.000 | 15.612 | 1.00 | 28.52 | B C |
| ATOM | 5255 | C | ALA | 212 | 110.295 | 50.339 | 14.650 | 1.00 | 37.62 | B C |
| ATOM | 5256 | O | ALA | 212 | 109.626 | 49.493 | 15.256 | 1.00 | 37.56 | B O |

FIG. 19A-73

| ATOM | 5257 | N | ALA | 213 | 109.759 | 51.408 | 14.069 | 1.00 | 31.97 | B | N |
|---|---|---|---|---|---|---|---|---|---|---|---|
| ATOM | 5258 | CA | ALA | 213 | 108.324 | 51.658 | 14.122 | 1.00 | 33.14 | B | C |
| ATOM | 5259 | CB | ALA | 213 | 107.999 | 52.998 | 13.459 | 1.00 | 19.99 | B | C |
| ATOM | 5260 | C | ALA | 213 | 107.530 | 50.535 | 13.458 | 1.00 | 31.94 | B | C |
| ATOM | 5261 | O | ALA | 213 | 106.556 | 50.029 | 14.025 | 1.00 | 29.57 | B | O |
| ATOM | 5262 | N | ASN | 214 | 107.954 | 50.142 | 12.258 | 1.00 | 35.89 | B | N |
| ATOM | 5263 | CA | ASN | 214 | 107.264 | 49.091 | 11.524 | 1.00 | 39.76 | B | C |
| ATOM | 5264 | CB | ASN | 214 | 107.804 | 48.970 | 10.100 | 1.00 | 79.46 | B | C |
| ATOM | 5265 | CG | ASN | 214 | 107.278 | 50.049 | 9.190 | 1.00 | 81.19 | B | C |
| ATOM | 5266 | OD1 | ASN | 214 | 107.668 | 51.210 | 9.296 | 1.00 | 83.12 | B | O |
| ATOM | 5267 | ND2 | ASN | 214 | 106.379 | 49.676 | 8.289 | 1.00 | 81.61 | B | N |
| ATOM | 5268 | C | ASN | 214 | 107.348 | 47.738 | 12.207 | 1.00 | 42.15 | B | C |
| ATOM | 5269 | O | ASN | 214 | 106.583 | 46.829 | 11.891 | 1.00 | 42.87 | B | O |
| ATOM | 5270 | N | LYS | 215 | 108.271 | 47.596 | 13.148 | 1.00 | 30.37 | B | N |
| ATOM | 5271 | CA | LYS | 215 | 108.418 | 46.326 | 13.856 | 1.00 | 30.81 | B | C |
| ATOM | 5272 | CB | LYS | 215 | 109.892 | 46.059 | 14.209 | 1.00 | 46.54 | B | C |
| ATOM | 5273 | CG | LYS | 215 | 110.791 | 45.922 | 12.978 | 1.00 | 54.12 | B | C |
| ATOM | 5274 | CD | LYS | 215 | 112.062 | 45.124 | 13.256 | 1.00 | 57.66 | B | C |
| ATOM | 5275 | CE | LYS | 215 | 112.950 | 45.778 | 14.311 | 1.00 | 61.12 | B | C |
| ATOM | 5276 | NZ | LYS | 215 | 114.249 | 45.057 | 14.483 | 1.00 | 62.11 | B | N |
| ATOM | 5277 | C | LYS | 215 | 107.560 | 46.274 | 15.113 | 1.00 | 28.94 | B | C |
| ATOM | 5278 | O | LYS | 215 | 107.568 | 45.277 | 15.832 | 1.00 | 30.16 | B | O |
| ATOM | 5279 | N | ILE | 216 | 106.809 | 47.341 | 15.377 | 1.00 | 44.32 | B | N |
| ATOM | 5280 | CA | ILE | 216 | 105.945 | 47.362 | 16.553 | 1.00 | 41.14 | B | C |
| ATOM | 5281 | CB | ILE | 216 | 105.443 | 48.776 | 16.874 | 1.00 | 15.33 | B | C |
| ATOM | 5282 | CG2 | ILE | 216 | 104.492 | 48.730 | 18.038 | 1.00 | 12.11 | B | C |
| ATOM | 5283 | CG1 | ILE | 216 | 106.616 | 49.674 | 17.243 | 1.00 | 12.01 | B | C |
| ATOM | 5284 | CD1 | ILE | 216 | 106.191 | 51.073 | 17.602 | 1.00 | 10.70 | B | C |
| ATOM | 5285 | C | ILE | 216 | 104.740 | 46.447 | 16.369 | 1.00 | 39.58 | B | C |
| ATOM | 5286 | O | ILE | 216 | 104.035 | 46.498 | 15.361 | 1.00 | 40.28 | B | O |
| ATOM | 5287 | N | VAL | 217 | 104.524 | 45.611 | 17.372 | 1.00 | 36.13 | B | N |
| ATOM | 5288 | CA | VAL | 217 | 103.436 | 44.647 | 17.392 | 1.00 | 37.90 | B | C |
| ATOM | 5289 | CB | VAL | 217 | 103.949 | 43.284 | 17.887 | 1.00 | 59.95 | B | C |
| ATOM | 5290 | CG1 | VAL | 217 | 102.793 | 42.367 | 18.217 | 1.00 | 59.95 | B | C |
| ATOM | 5291 | CG2 | VAL | 217 | 104.837 | 42.666 | 16.829 | 1.00 | 59.95 | B | C |
| ATOM | 5292 | C | VAL | 217 | 102.316 | 45.111 | 18.311 | 1.00 | 39.06 | B | C |
| ATOM | 5293 | O | VAL | 217 | 102.565 | 45.725 | 19.352 | 1.00 | 38.52 | B | O |
| ATOM | 5294 | N | GLN | 218 | 101.084 | 44.809 | 17.914 | 1.00 | 32.14 | B | N |
| ATOM | 5295 | CA | GLN | 218 | 99.907 | 45.181 | 18.687 | 1.00 | 32.80 | B | C |
| ATOM | 5296 | CB | GLN | 218 | 98.646 | 44.976 | 17.850 | 1.00 | 28.44 | B | C |
| ATOM | 5297 | CG | GLN | 218 | 97.378 | 45.433 | 18.528 | 1.00 | 28.44 | B | C |
| ATOM | 5298 | CD | GLN | 218 | 96.153 | 45.273 | 17.644 | 1.00 | 28.44 | B | C |
| ATOM | 5299 | OE1 | GLN | 218 | 95.096 | 45.843 | 17.928 | 1.00 | 28.44 | B | O |
| ATOM | 5300 | NE2 | GLN | 218 | 96.283 | 44.490 | 16.571 | 1.00 | 28.44 | B | N |
| ATOM | 5301 | C | GLN | 218 | 99.856 | 44.288 | 19.913 | 1.00 | 32.25 | B | C |
| ATOM | 5302 | O | GLN | 218 | 99.948 | 43.079 | 19.792 | 1.00 | 36.00 | B | O |
| ATOM | 5303 | N | ARG | 219 | 99.709 | 44.883 | 21.091 | 1.00 | 14.17 | B | N |
| ATOM | 5304 | CA | ARG | 219 | 99.664 | 44.114 | 22.330 | 1.00 | 13.82 | B | C |
| ATOM | 5305 | CB | ARG | 219 | 100.490 | 44.828 | 23.394 | 1.00 | 43.11 | B | C |
| ATOM | 5306 | CG | ARG | 219 | 101.627 | 45.640 | 22.823 | 1.00 | 43.11 | B | C |
| ATOM | 5307 | CD | ARG | 219 | 102.594 | 46.039 | 23.901 | 1.00 | 43.11 | B | C |
| ATOM | 5308 | NE | ARG | 219 | 103.597 | 45.007 | 24.124 | 1.00 | 43.11 | B | N |
| ATOM | 5309 | CZ | ARG | 219 | 104.694 | 44.867 | 23.384 | 1.00 | 43.11 | B | C |
| ATOM | 5310 | NH1 | ARG | 219 | 104.921 | 45.705 | 22.369 | 1.00 | 43.11 | B | N |
| ATOM | 5311 | NH2 | ARG | 219 | 105.566 | 43.900 | 23.661 | 1.00 | 43.11 | B | N |
| ATOM | 5312 | C | ARG | 219 | 98.221 | 43.910 | 22.821 | 1.00 | 15.03 | B | C |
| ATOM | 5313 | O | ARG | 219 | 97.976 | 43.309 | 23.871 | 1.00 | 15.04 | B | O |
| ATOM | 5314 | N | GLY | 220 | 97.269 | 44.423 | 22.048 | 1.00 | 30.91 | B | N |
| ATOM | 5315 | CA | GLY | 220 | 95.868 | 44.283 | 22.402 | 1.00 | 30.52 | B | C |
| ATOM | 5316 | C | GLY | 220 | 95.495 | 44.884 | 23.742 | 1.00 | 30.19 | B | C |
| ATOM | 5317 | O | GLY | 220 | 96.246 | 45.674 | 24.327 | 1.00 | 28.53 | B | O |
| ATOM | 5318 | N | GLY | 221 | 94.316 | 44.511 | 24.222 | 1.00 | 22.15 | B | N |
| ATOM | 5319 | CA | GLY | 221 | 93.852 | 45.009 | 25.500 | 1.00 | 20.72 | B | C |
| ATOM | 5320 | C | GLY | 221 | 92.348 | 44.902 | 25.652 | 1.00 | 21.14 | B | C |
| ATOM | 5321 | O | GLY | 221 | 91.598 | 45.328 | 24.776 | 1.00 | 17.94 | B | O |
| ATOM | 5322 | N | ARG | 222 | 91.897 | 44.327 | 26.760 | 1.00 | 28.36 | B | N |
| ATOM | 5323 | CA | ARG | 222 | 90.467 | 44.199 | 27.011 | 1.00 | 29.07 | B | C |
| ATOM | 5324 | CB | ARG | 222 | 90.204 | 43.114 | 28.053 | 1.00 | 26.86 | B | C |
| ATOM | 5325 | CG | ARG | 222 | 90.365 | 41.713 | 27.491 | 1.00 | 26.86 | B | C |
| ATOM | 5326 | CD | ARG | 222 | 90.427 | 40.663 | 28.578 | 1.00 | 26.86 | B | C |
| ATOM | 5327 | NE | ARG | 222 | 91.679 | 40.734 | 29.316 | 1.00 | 26.86 | B | N |
| ATOM | 5328 | CZ | ARG | 222 | 92.021 | 39.885 | 30.274 | 1.00 | 26.86 | B | C |
| ATOM | 5329 | NH1 | ARG | 222 | 91.201 | 38.895 | 30.612 | 1.00 | 26.86 | B | N |

FIG. 19A-74

| | | | | | | | | | | | |
|---|---|---|---|---|---|---|---|---|---|---|---|
| ATOM | 5330 | NH2 | ARG | 222 | 93.184 | 40.027 | 30.893 | 1.00 | 26.86 | B | N |
| ATOM | 5331 | C | ARG | 222 | 89.899 | 45.529 | 27.482 | 1.00 | 29.12 | B | C |
| ATOM | 5332 | O | ARG | 222 | 88.686 | 45.686 | 27.599 | 1.00 | 29.89 | B | O |
| ATOM | 5333 | N | GLN | 223 | 90.792 | 46.477 | 27.756 | 1.00 | 34.74 | B | N |
| ATOM | 5334 | CA | GLN | 223 | 90.423 | 47.826 | 28.182 | 1.00 | 33.03 | B | C |
| ATOM | 5335 | CB | GLN | 223 | 90.700 | 48.050 | 29.677 | 1.00 | 36.16 | B | C |
| ATOM | 5336 | CG | GLN | 223 | 89.723 | 47.394 | 30.641 | 1.00 | 37.60 | B | C |
| ATOM | 5337 | CD | GLN | 223 | 90.065 | 45.957 | 30.915 | 1.00 | 38.01 | B | C |
| ATOM | 5338 | OE1 | GLN | 223 | 91.209 | 45.635 | 31.230 | 1.00 | 38.41 | B | O |
| ATOM | 5339 | NE2 | GLN | 223 | 89.075 | 45.080 | 30.811 | 1.00 | 38.45 | B | N |
| ATOM | 5340 | C | GLN | 223 | 91.221 | 48.849 | 27.372 | 1.00 | 33.77 | B | C |
| ATOM | 5341 | O | GLN | 223 | 92.122 | 48.487 | 26.619 | 1.00 | 33.25 | B | O |
| ATOM | 5342 | N | THR | 224 | 90.893 | 50.126 | 27.535 | 1.00 | 56.95 | B | N |
| ATOM | 5343 | CA | THR | 224 | 91.572 | 51.197 | 26.820 | 1.00 | 54.83 | B | C |
| ATOM | 5344 | CB | THR | 224 | 90.628 | 51.834 | 25.793 | 1.00 | 7.14 | B | C |
| ATOM | 5345 | OG1 | THR | 224 | 90.118 | 50.811 | 24.930 | 1.00 | 7.13 | B | O |
| ATOM | 5346 | CG2 | THR | 224 | 91.357 | 52.895 | 24.965 | 1.00 | 4.73 | B | C |
| ATOM | 5347 | C | THR | 224 | 92.002 | 52.252 | 27.829 | 1.00 | 51.84 | B | C |
| ATOM | 5348 | O | THR | 224 | 91.290 | 53.221 | 28.067 | 1.00 | 48.33 | B | O |
| ATOM | 5349 | N | MET | 225 | 93.175 | 52.061 | 28.419 | 1.00 | 27.08 | B | N |
| ATOM | 5350 | CA | MET | 225 | 93.679 | 52.980 | 29.426 | 1.00 | 27.97 | B | C |
| ATOM | 5351 | CB | MET | 225 | 94.712 | 52.269 | 30.301 | 1.00 | 32.79 | B | C |
| ATOM | 5352 | CG | MET | 225 | 94.280 | 50.904 | 30.804 | 1.00 | 30.22 | B | C |
| ATOM | 5353 | SD | MET | 225 | 92.971 | 50.963 | 31.995 | 1.00 | 37.96 | B | S |
| ATOM | 5354 | CE | MET | 225 | 93.153 | 49.343 | 32.760 | 1.00 | 34.54 | B | C |
| ATOM | 5355 | C | MET | 225 | 94.304 | 54.237 | 28.846 | 1.00 | 29.00 | B | C |
| ATOM | 5356 | O | MET | 225 | 95.442 | 54.561 | 29.180 | 1.00 | 30.46 | B | O |
| ATOM | 5357 | N | THR | 226 | 93.571 | 54.953 | 27.997 | 1.00 | 32.08 | B | N |
| ATOM | 5358 | CA | THR | 226 | 94.102 | 56.178 | 27.393 | 1.00 | 31.55 | B | C |
| ATOM | 5359 | CB | THR | 226 | 93.013 | 56.963 | 26.655 | 1.00 | 28.80 | B | C |
| ATOM | 5360 | OG1 | THR | 226 | 92.395 | 56.132 | 25.665 | 1.00 | 30.82 | B | O |
| ATOM | 5361 | CG2 | THR | 226 | 93.620 | 58.170 | 25.976 | 1.00 | 26.52 | B | C |
| ATOM | 5362 | C | THR | 226 | 94.735 | 57.104 | 28.438 | 1.00 | 30.15 | B | C |
| ATOM | 5363 | O | THR | 226 | 95.804 | 57.672 | 28.216 | 1.00 | 24.84 | B | O |
| ATOM | 5364 | N | ALA | 227 | 94.075 | 57.249 | 29.581 | 1.00 | 17.95 | B | N |
| ATOM | 5365 | CA | ALA | 227 | 94.594 | 58.094 | 30.645 | 1.00 | 16.89 | B | C |
| ATOM | 5366 | CB | ALA | 227 | 93.655 | 58.069 | 31.829 | 1.00 | 18.36 | B | C |
| ATOM | 5367 | C | ALA | 227 | 95.975 | 57.633 | 31.076 | 1.00 | 17.55 | B | C |
| ATOM | 5368 | O | ALA | 227 | 96.898 | 58.439 | 31.199 | 1.00 | 18.35 | B | O |
| ATOM | 5369 | N | LEU | 228 | 96.111 | 56.331 | 31.307 | 1.00 | 19.16 | B | N |
| ATOM | 5370 | CA | LEU | 228 | 97.384 | 55.752 | 31.728 | 1.00 | 17.60 | B | C |
| ATOM | 5371 | CB | LEU | 228 | 97.206 | 54.252 | 32.017 | 1.00 | 6.84 | B | C |
| ATOM | 5372 | CG | LEU | 228 | 98.453 | 53.498 | 32.483 | 1.00 | 14.73 | B | C |
| ATOM | 5373 | CD1 | LEU | 228 | 99.020 | 54.157 | 33.734 | 1.00 | 12.32 | B | C |
| ATOM | 5374 | CD2 | LEU | 228 | 98.097 | 52.064 | 32.732 | 1.00 | 11.78 | B | C |
| ATOM | 5375 | C | LEU | 228 | 98.463 | 55.955 | 30.662 | 1.00 | 16.78 | B | C |
| ATOM | 5376 | O | LEU | 228 | 99.605 | 56.321 | 30.971 | 1.00 | 19.76 | B | O |
| ATOM | 5377 | N | GLY | 229 | 98.094 | 55.713 | 29.408 | 1.00 | 21.79 | B | N |
| ATOM | 5378 | CA | GLY | 229 | 99.033 | 55.877 | 28.318 | 1.00 | 24.15 | B | C |
| ATOM | 5379 | C | GLY | 229 | 99.620 | 57.267 | 28.293 | 1.00 | 26.71 | B | C |
| ATOM | 5380 | O | GLY | 229 | 100.843 | 57.422 | 28.296 | 1.00 | 27.30 | B | O |
| ATOM | 5381 | N | ILE | 230 | 98.756 | 58.281 | 28.280 | 1.00 | 20.54 | B | N |
| ATOM | 5382 | CA | ILE | 230 | 99.216 | 59.666 | 28.259 | 1.00 | 21.87 | B | C |
| ATOM | 5383 | CB | ILE | 230 | 98.039 | 60.677 | 28.160 | 1.00 | 18.79 | B | C |
| ATOM | 5384 | CG2 | ILE | 230 | 98.595 | 62.090 | 28.034 | 1.00 | 18.79 | B | C |
| ATOM | 5385 | CG1 | ILE | 230 | 97.174 | 60.370 | 26.933 | 1.00 | 18.79 | B | C |
| ATOM | 5386 | CD1 | ILE | 230 | 95.945 | 61.225 | 26.807 | 1.00 | 18.79 | B | C |
| ATOM | 5387 | C | ILE | 230 | 100.042 | 60.007 | 29.505 | 1.00 | 22.13 | B | C |
| ATOM | 5388 | O | ILE | 230 | 101.101 | 60.634 | 29.402 | 1.00 | 20.06 | B | O |
| ATOM | 5389 | N | ASP | 231 | 99.566 | 59.595 | 30.677 | 1.00 | 30.92 | B | N |
| ATOM | 5390 | CA | ASP | 231 | 100.286 | 59.876 | 31.916 | 1.00 | 29.32 | B | C |
| ATOM | 5391 | CB | ASP | 231 | 99.494 | 59.354 | 33.116 | 1.00 | 27.91 | B | C |
| ATOM | 5392 | CG | ASP | 231 | 99.993 | 59.917 | 34.442 | 1.00 | 34.91 | B | C |
| ATOM | 5393 | OD1 | ASP | 231 | 99.939 | 61.155 | 34.644 | 1.00 | 33.67 | B | O |
| ATOM | 5394 | OD2 | ASP | 231 | 100.432 | 59.112 | 35.288 | 1.00 | 38.45 | B | O |
| ATOM | 5395 | C | ASP | 231 | 101.676 | 59.231 | 31.884 | 1.00 | 30.30 | B | C |
| ATOM | 5396 | O | ASP | 231 | 102.669 | 59.838 | 32.318 | 1.00 | 27.52 | B | O |
| ATOM | 5397 | N | THR | 232 | 101.741 | 58.007 | 31.361 | 1.00 | 43.37 | B | N |
| ATOM | 5398 | CA | THR | 232 | 102.998 | 57.276 | 31.260 | 1.00 | 42.16 | B | C |
| ATOM | 5399 | CB | THR | 232 | 102.768 | 55.830 | 30.801 | 1.00 | 59.43 | B | C |
| ATOM | 5400 | OG1 | THR | 232 | 101.963 | 55.148 | 31.771 | 1.00 | 57.94 | B | O |
| ATOM | 5401 | CG2 | THR | 232 | 104.097 | 55.098 | 30.645 | 1.00 | 52.97 | B | C |
| ATOM | 5402 | C | THR | 232 | 103.939 | 57.959 | 30.274 | 1.00 | 42.79 | B | C |

FIG. 19A-75

```
ATOM   5403  O    THR 232    105.153  58.050  30.509  1.00  42.96  B  O
ATOM   5404  N    ALA 233    103.383  58.427  29.161  1.00  22.02  B  N
ATOM   5405  CA   ALA 233    104.202  59.116  28.179  1.00  24.67  B  C
ATOM   5406  CB   ALA 233    103.373  59.472  26.961  1.00  49.88  B  C
ATOM   5407  C    ALA 233    104.752  60.385  28.836  1.00  26.98  B  C
ATOM   5408  O    ALA 233    105.862  60.834  28.532  1.00  28.89  B  O
ATOM   5409  N    ARG 234    103.967  60.947  29.751  1.00  50.27  B  N
ATOM   5410  CA   ARG 234    104.361  62.165  30.431  1.00  53.37  B  C
ATOM   5411  CB   ARG 234    103.146  62.842  31.077  1.00  50.29  B  C
ATOM   5412  CG   ARG 234    103.377  64.312  31.390  1.00  50.29  B  C
ATOM   5413  CD   ARG 234    102.536  64.816  32.561  1.00  50.29  B  C
ATOM   5414  NE   ARG 234    103.103  64.432  33.852  1.00  50.29  B  N
ATOM   5415  CZ   ARG 234    102.668  63.418  34.592  1.00  50.29  B  C
ATOM   5416  NH1  ARG 234    101.650  62.682  34.172  1.00  50.29  B  N
ATOM   5417  NH2  ARG 234    103.258  63.135  35.744  1.00  50.29  B  N
ATOM   5418  C    ARG 234    105.406  61.904  31.498  1.00  55.50  B  C
ATOM   5419  O    ARG 234    106.556  62.316  31.368  1.00  55.55  B  O
ATOM   5420  N    LYS 235    105.009  61.196  32.547  1.00  27.28  B  N
ATOM   5421  CA   LYS 235    105.914  60.939  33.660  1.00  27.23  B  C
ATOM   5422  CB   LYS 235    105.129  60.356  34.848  1.00  39.45  B  C
ATOM   5423  CG   LYS 235    104.888  58.857  34.831  1.00  40.60  B  C
ATOM   5424  CD   LYS 235    104.027  58.450  36.030  1.00  40.42  B  C
ATOM   5425  CE   LYS 235    104.119  56.955  36.346  1.00  41.22  B  C
ATOM   5426  NZ   LYS 235    103.715  56.073  35.205  1.00  41.98  B  N
ATOM   5427  C    LYS 235    107.149  60.078  33.375  1.00  27.37  B  C
ATOM   5428  O    LYS 235    108.112  60.118  34.130  1.00  27.71  B  O
ATOM   5429  N    GLU 236    107.133  59.313  32.290  1.00  28.33  B  N
ATOM   5430  CA   GLU 236    108.264  58.454  31.964  1.00  29.95  B  C
ATOM   5431  CB   GLU 236    107.803  56.992  31.884  1.00  47.54  B  C
ATOM   5432  CG   GLU 236    107.861  56.249  33.216  1.00  50.31  B  C
ATOM   5433  CD   GLU 236    107.031  54.965  33.245  1.00  52.79  B  C
ATOM   5434  OE1  GLU 236    107.194  54.118  32.342  1.00  52.88  B  O
ATOM   5435  OE2  GLU 236    106.219  54.797  34.184  1.00  52.63  B  O
ATOM   5436  C    GLU 236    108.966  58.840  30.670  1.00  28.50  B  C
ATOM   5437  O    GLU 236    110.092  59.336  30.684  1.00  29.93  B  O
ATOM   5438  N    ALA 237    108.287  58.617  29.552  1.00  22.73  B  N
ATOM   5439  CA   ALA 237    108.860  58.901  28.248  1.00  20.20  B  C
ATOM   5440  CB   ALA 237    107.783  58.831  27.180  1.00  41.37  B  C
ATOM   5441  C    ALA 237    109.562  60.233  28.187  1.00  19.04  B  C
ATOM   5442  O    ALA 237    110.636  60.344  27.589  1.00  17.46  B  O
ATOM   5443  N    PHE 238    108.962  61.242  28.810  1.00  29.57  B  N
ATOM   5444  CA   PHE 238    109.530  62.580  28.795  1.00  29.00  B  C
ATOM   5445  CB   PHE 238    108.419  63.620  28.752  1.00  35.30  B  C
ATOM   5446  CG   PHE 238    107.856  63.854  27.381  1.00  34.33  B  C
ATOM   5447  CD1  PHE 238    106.531  63.532  27.101  1.00  35.56  B  C
ATOM   5448  CD2  PHE 238    108.635  64.429  26.380  1.00  31.93  B  C
ATOM   5449  CE1  PHE 238    105.985  63.780  25.841  1.00  33.36  B  C
ATOM   5450  CE2  PHE 238    108.106  64.682  25.124  1.00  38.24  B  C
ATOM   5451  CZ   PHE 238    106.778  64.359  24.850  1.00  39.66  B  C
ATOM   5452  C    PHE 238    110.468  62.908  29.943  1.00  30.85  B  C
ATOM   5453  O    PHE 238    110.433  64.012  30.479  1.00  30.95  B  O
ATOM   5454  N    THR 239    111.303  61.951  30.325  1.00  29.27  B  N
ATOM   5455  CA   THR 239    112.266  62.182  31.391  1.00  33.21  B  C
ATOM   5456  CB   THR 239    112.113  61.150  32.520  1.00  23.55  B  C
ATOM   5457  OG1  THR 239    112.276  59.840  31.989  1.00  21.51  B  O
ATOM   5458  CG2  THR 239    110.745  61.242  33.153  1.00  26.46  B  C
ATOM   5459  C    THR 239    113.660  62.084  30.770  1.00  33.47  B  C
ATOM   5460  O    THR 239    113.930  61.177  29.980  1.00  33.97  B  O
ATOM   5461  N    GLU 240    114.531  63.030  31.117  1.00  17.24  B  N
ATOM   5462  CA   GLU 240    115.890  63.085  30.580  1.00  17.49  B  C
ATOM   5463  CB   GLU 240    116.748  64.003  31.444  1.00  74.12  B  C
ATOM   5464  CG   GLU 240    118.007  64.483  30.758  1.00  78.76  B  C
ATOM   5465  CD   GLU 240    118.634  65.654  31.479  1.00  81.67  B  C
ATOM   5466  OE1  GLU 240    117.904  66.627  31.774  1.00  81.77  B  O
ATOM   5467  OE2  GLU 240    119.853  65.605  31.746  1.00  81.74  B  O
ATOM   5468  C    GLU 240    116.555  61.712  30.465  1.00  18.84  B  C
ATOM   5469  O    GLU 240    117.323  61.444  29.530  1.00  20.05  B  O
ATOM   5470  N    ALA 241    116.234  60.839  31.415  1.00  54.75  B  N
ATOM   5471  CA   ALA 241    116.784  59.491  31.446  1.00  55.60  B  C
ATOM   5472  CB   ALA 241    116.331  58.783  32.723  1.00  26.00  B  C
ATOM   5473  C    ALA 241    116.387  58.678  30.212  1.00  55.07  B  C
ATOM   5474  O    ALA 241    117.093  57.751  29.823  1.00  56.53  B  O
ATOM   5475  N    ARG 242    115.259  59.024  29.598  1.00  25.17  B  N
```

FIG. 19A-76

| ATOM | 5476 | CA | ARG | 242 | 114.805 | 58.305 | 28.417 | 1.00 | 24.91 | B | C |
|------|------|------|------|-----|---------|--------|--------|------|-------|---|---|
| ATOM | 5477 | CB | ARG | 242 | 113.337 | 57.917 | 28.570 | 1.00 | 45.62 | B | C |
| ATOM | 5478 | CG | ARG | 242 | 113.136 | 56.644 | 29.392 | 1.00 | 45.82 | B | C |
| ATOM | 5479 | CD | ARG | 242 | 111.684 | 56.188 | 29.334 | 1.00 | 46.68 | B | C |
| ATOM | 5480 | NE | ARG | 242 | 111.525 | 54.733 | 29.424 | 1.00 | 47.88 | B | N |
| ATOM | 5481 | CZ | ARG | 242 | 111.348 | 54.055 | 30.557 | 1.00 | 47.08 | B | C |
| ATOM | 5482 | NH1 | ARG | 242 | 111.307 | 54.695 | 31.721 | 1.00 | 46.13 | B | N |
| ATOM | 5483 | NH2 | ARG | 242 | 111.187 | 52.738 | 30.526 | 1.00 | 49.10 | B | N |
| ATOM | 5484 | C | ARG | 242 | 115.039 | 59.088 | 27.120 | 1.00 | 26.11 | B | C |
| ATOM | 5485 | O | ARG | 242 | 114.450 | 58.796 | 26.076 | 1.00 | 29.12 | B | O |
| ATOM | 5486 | N | GLY | 243 | 115.919 | 60.079 | 27.194 | 1.00 | 41.48 | B | N |
| ATOM | 5487 | CA | GLY | 243 | 116.226 | 60.863 | 26.014 | 1.00 | 39.63 | B | C |
| ATOM | 5488 | C | GLY | 243 | 115.497 | 62.187 | 25.893 | 1.00 | 37.91 | B | C |
| ATOM | 5489 | O | GLY | 243 | 115.454 | 62.774 | 24.810 | 1.00 | 37.53 | B | O |
| ATOM | 5490 | N | ALA | 244 | 114.913 | 62.665 | 26.986 | 1.00 | 32.61 | B | N |
| ATOM | 5491 | CA | ALA | 244 | 114.209 | 63.941 | 26.939 | 1.00 | 30.61 | B | C |
| ATOM | 5492 | CB | ALA | 244 | 113.253 | 64.074 | 28.124 | 1.00 | 2.29 | B | C |
| ATOM | 5493 | C | ALA | 244 | 115.262 | 65.033 | 26.984 | 1.00 | 32.49 | B | C |
| ATOM | 5494 | O | ALA | 244 | 115.867 | 65.266 | 28.021 | 1.00 | 31.95 | B | O |
| ATOM | 5495 | N | ARG | 245 | 115.491 | 65.690 | 25.854 | 1.00 | 46.10 | B | N |
| ATOM | 5496 | CA | ARG | 245 | 116.482 | 66.760 | 25.768 | 1.00 | 46.93 | B | C |
| ATOM | 5497 | CB | ARG | 245 | 116.690 | 67.163 | 24.309 | 1.00 | 24.44 | B | C |
| ATOM | 5498 | CG | ARG | 245 | 117.460 | 66.126 | 23.503 | 1.00 | 26.91 | B | C |
| ATOM | 5499 | CD | ARG | 245 | 117.553 | 66.517 | 22.054 | 1.00 | 27.12 | B | C |
| ATOM | 5500 | NE | ARG | 245 | 116.229 | 66.560 | 21.457 | 1.00 | 21.54 | B | N |
| ATOM | 5501 | CZ | ARG | 245 | 115.999 | 66.826 | 20.179 | 1.00 | 21.36 | B | C |
| ATOM | 5502 | NH1 | ARG | 245 | 117.016 | 67.074 | 19.370 | 1.00 | 20.56 | B | N |
| ATOM | 5503 | NH2 | ARG | 245 | 114.756 | 66.834 | 19.708 | 1.00 | 18.65 | B | N |
| ATOM | 5504 | C | ARG | 245 | 116.101 | 67.986 | 26.585 | 1.00 | 45.30 | B | C |
| ATOM | 5505 | O | ARG | 245 | 114.975 | 68.480 | 26.496 | 1.00 | 41.41 | B | O |
| ATOM | 5506 | N | ARG | 246 | 117.051 | 68.476 | 27.376 | 1.00 | 48.54 | B | N |
| ATOM | 5507 | CA | ARG | 246 | 116.830 | 69.640 | 28.229 | 1.00 | 51.33 | B | C |
| ATOM | 5508 | CB | ARG | 246 | 118.096 | 69.982 | 29.012 | 1.00 | 83.48 | B | C |
| ATOM | 5509 | CG | ARG | 246 | 117.975 | 71.269 | 29.811 | 1.00 | 88.84 | B | C |
| ATOM | 5510 | CD | ARG | 246 | 119.295 | 71.647 | 30.449 | 1.00 | 94.76 | B | C |
| ATOM | 5511 | NE | ARG | 246 | 119.896 | 70.525 | 31.165 | 1.00 | 97.67 | B | N |
| ATOM | 5512 | CZ | ARG | 246 | 119.288 | 69.828 | 32.123 | 1.00 | 100.78 | B | C |
| ATOM | 5513 | NH1 | ARG | 246 | 118.047 | 70.132 | 32.491 | 1.00 | 100.47 | B | N |
| ATOM | 5514 | NH2 | ARG | 246 | 119.923 | 68.825 | 32.717 | 1.00 | 101.56 | B | N |
| ATOM | 5515 | C | ARG | 246 | 116.415 | 70.871 | 27.448 | 1.00 | 49.15 | B | C |
| ATOM | 5516 | O | ARG | 246 | 117.082 | 71.246 | 26.489 | 1.00 | 51.78 | B | O |
| ATOM | 5517 | N | GLY | 247 | 115.311 | 71.489 | 27.868 | 1.00 | 46.59 | B | N |
| ATOM | 5518 | CA | GLY | 247 | 114.825 | 72.705 | 27.233 | 1.00 | 49.17 | B | C |
| ATOM | 5519 | C | GLY | 247 | 114.381 | 72.609 | 25.787 | 1.00 | 49.24 | B | C |
| ATOM | 5520 | O | GLY | 247 | 114.531 | 73.560 | 25.019 | 1.00 | 52.20 | B | O |
| ATOM | 5521 | N | VAL | 248 | 113.836 | 71.462 | 25.407 | 1.00 | 57.57 | B | N |
| ATOM | 5522 | CA | VAL | 248 | 113.357 | 71.266 | 24.049 | 1.00 | 55.58 | B | C |
| ATOM | 5523 | CB | VAL | 248 | 114.012 | 70.043 | 23.407 | 1.00 | 22.85 | B | C |
| ATOM | 5524 | CG1 | VAL | 248 | 113.384 | 69.765 | 22.056 | 1.00 | 20.50 | B | C |
| ATOM | 5525 | CG2 | VAL | 248 | 115.499 | 70.287 | 23.266 | 1.00 | 14.62 | B | C |
| ATOM | 5526 | C | VAL | 248 | 111.855 | 71.056 | 24.094 | 1.00 | 58.60 | B | C |
| ATOM | 5527 | O | VAL | 248 | 111.343 | 70.403 | 25.005 | 1.00 | 62.65 | B | O |
| ATOM | 5528 | N | LYS | 249 | 111.147 | 71.607 | 23.115 | 1.00 | 37.34 | B | N |
| ATOM | 5529 | CA | LYS | 249 | 109.698 | 71.464 | 23.086 | 1.00 | 38.25 | B | C |
| ATOM | 5530 | CB | LYS | 249 | 109.115 | 72.122 | 21.832 | 1.00 | 57.29 | B | C |
| ATOM | 5531 | CG | LYS | 249 | 107.594 | 72.204 | 21.869 | 1.00 | 62.81 | B | C |
| ATOM | 5532 | CD | LYS | 249 | 107.103 | 72.892 | 23.155 | 1.00 | 63.88 | B | C |
| ATOM | 5533 | CE | LYS | 249 | 105.634 | 72.579 | 23.450 | 1.00 | 66.24 | B | C |
| ATOM | 5534 | NZ | LYS | 249 | 105.067 | 73.292 | 24.636 | 1.00 | 69.06 | B | N |
| ATOM | 5535 | C | LYS | 249 | 109.244 | 69.998 | 23.173 | 1.00 | 36.91 | B | C |
| ATOM | 5536 | O | LYS | 249 | 109.790 | 69.112 | 22.505 | 1.00 | 36.73 | B | O |
| ATOM | 5537 | N | LYS | 250 | 108.238 | 69.755 | 24.009 | 1.00 | 33.42 | B | N |
| ATOM | 5538 | CA | LYS | 250 | 107.706 | 68.419 | 24.208 | 1.00 | 33.07 | B | C |
| ATOM | 5539 | CB | LYS | 250 | 107.603 | 68.147 | 25.710 | 1.00 | 46.37 | B | C |
| ATOM | 5540 | CG | LYS | 250 | 108.970 | 68.151 | 26.374 | 1.00 | 44.97 | B | C |
| ATOM | 5541 | CD | LYS | 250 | 108.918 | 68.429 | 27.872 | 1.00 | 46.52 | B | C |
| ATOM | 5542 | CE | LYS | 250 | 108.389 | 67.256 | 28.686 | 1.00 | 45.68 | B | C |
| ATOM | 5543 | NZ | LYS | 250 | 108.578 | 67.474 | 30.157 | 1.00 | 47.50 | B | N |
| ATOM | 5544 | C | LYS | 250 | 106.355 | 68.263 | 23.506 | 1.00 | 32.42 | B | C |
| ATOM | 5545 | O | LYS | 250 | 105.380 | 68.931 | 23.842 | 1.00 | 32.10 | B | O |
| ATOM | 5546 | N | VAL | 251 | 106.320 | 67.372 | 22.519 | 1.00 | 37.83 | B | N |
| ATOM | 5547 | CA | VAL | 251 | 105.121 | 67.115 | 21.730 | 1.00 | 37.74 | B | C |
| ATOM | 5548 | CB | VAL | 251 | 105.403 | 67.373 | 20.248 | 1.00 | 28.71 | B | C |

FIG. 19A-77

| ATOM | 5549 | CG1 | VAL | 251 | 104.180 | 67.017 | 19.410 | 1.00 | 26.86 | B | C |
|------|------|-----|-----|-----|---------|--------|--------|------|-------|---|---|
| ATOM | 5550 | CG2 | VAL | 251 | 105.819 | 68.822 | 20.057 | 1.00 | 29.92 | B | C |
| ATOM | 5551 | C | VAL | 251 | 104.591 | 65.689 | 21.866 | 1.00 | 36.22 | B | C |
| ATOM | 5552 | O | VAL | 251 | 105.339 | 64.715 | 21.714 | 1.00 | 32.22 | B | O |
| ATOM | 5553 | N | MET | 252 | 103.289 | 65.572 | 22.122 | 1.00 | 42.57 | B | N |
| ATOM | 5554 | CA | MET | 252 | 102.651 | 64.269 | 22.275 | 1.00 | 43.55 | B | C |
| ATOM | 5555 | CB | MET | 252 | 102.013 | 64.160 | 23.660 | 1.00 | 27.32 | B | C |
| ATOM | 5556 | CG | MET | 252 | 101.440 | 62.787 | 23.998 | 1.00 | 26.01 | B | C |
| ATOM | 5557 | SD | MET | 252 | 100.740 | 62.725 | 25.675 | 1.00 | 30.06 | B | S |
| ATOM | 5558 | CE | MET | 252 | 102.222 | 63.011 | 26.691 | 1.00 | 21.37 | B | C |
| ATOM | 5559 | C | MET | 252 | 101.583 | 64.060 | 21.217 | 1.00 | 42.57 | B | C |
| ATOM | 5560 | O | MET | 252 | 100.761 | 64.937 | 20.982 | 1.00 | 44.94 | B | O |
| ATOM | 5561 | N | VAL | 253 | 101.604 | 62.900 | 20.573 | 1.00 | 21.89 | B | N |
| ATOM | 5562 | CA | VAL | 253 | 100.607 | 62.580 | 19.558 | 1.00 | 23.04 | B | C |
| ATOM | 5563 | CB | VAL | 253 | 101.267 | 62.281 | 18.187 | 1.00 | 9.79 | B | C |
| ATOM | 5564 | CG1 | VAL | 253 | 100.191 | 61.900 | 17.168 | 1.00 | 11.21 | B | C |
| ATOM | 5565 | CG2 | VAL | 253 | 102.044 | 63.490 | 17.701 | 1.00 | 9.43 | B | C |
| ATOM | 5566 | C | VAL | 253 | 99.819 | 61.353 | 20.015 | 1.00 | 22.61 | B | C |
| ATOM | 5567 | O | VAL | 253 | 100.383 | 60.276 | 20.161 | 1.00 | 21.05 | B | O |
| ATOM | 5568 | N | ILE | 254 | 98.522 | 61.516 | 20.252 | 1.00 | 29.50 | B | N |
| ATOM | 5569 | CA | ILE | 254 | 97.692 | 60.403 | 20.701 | 1.00 | 26.40 | B | C |
| ATOM | 5570 | CB | ILE | 254 | 96.820 | 60.777 | 21.925 | 1.00 | 25.01 | B | C |
| ATOM | 5571 | CG2 | ILE | 254 | 96.017 | 59.564 | 22.369 | 1.00 | 21.48 | B | C |
| ATOM | 5572 | CG1 | ILE | 254 | 97.697 | 61.256 | 23.089 | 1.00 | 23.59 | B | C |
| ATOM | 5573 | CD1 | ILE | 254 | 98.231 | 62.661 | 22.921 | 1.00 | 23.22 | B | C |
| ATOM | 5574 | C | ILE | 254 | 96.757 | 59.905 | 19.611 | 1.00 | 24.49 | B | C |
| ATOM | 5575 | O | ILE | 254 | 96.163 | 60.692 | 18.876 | 1.00 | 26.36 | B | O |
| ATOM | 5576 | N | VAL | 255 | 96.628 | 58.587 | 19.516 | 1.00 | 26.63 | B | N |
| ATOM | 5577 | CA | VAL | 255 | 95.758 | 57.981 | 18.521 | 1.00 | 25.37 | B | C |
| ATOM | 5578 | CB | VAL | 255 | 96.553 | 57.259 | 17.428 | 1.00 | 15.78 | B | C |
| ATOM | 5579 | CG1 | VAL | 255 | 95.672 | 57.064 | 16.198 | 1.00 | 14.23 | B | C |
| ATOM | 5580 | CG2 | VAL | 255 | 97.805 | 58.036 | 17.089 | 1.00 | 16.42 | B | C |
| ATOM | 5581 | C | VAL | 255 | 94.907 | 56.947 | 19.221 | 1.00 | 23.12 | B | C |
| ATOM | 5582 | O | VAL | 255 | 95.444 | 56.089 | 19.916 | 1.00 | 25.12 | B | O |
| ATOM | 5583 | N | THR | 256 | 93.591 | 57.012 | 19.036 | 1.00 | 8.41 | B | N |
| ATOM | 5584 | CA | THR | 256 | 92.709 | 56.052 | 19.689 | 1.00 | 8.83 | B | C |
| ATOM | 5585 | CB | THR | 256 | 92.529 | 56.416 | 21.189 | 1.00 | 19.33 | B | C |
| ATOM | 5586 | OG1 | THR | 256 | 91.459 | 55.645 | 21.755 | 1.00 | 15.37 | B | O |
| ATOM | 5587 | CG2 | THR | 256 | 92.255 | 57.908 | 21.344 | 1.00 | 18.18 | B | C |
| ATOM | 5588 | C | THR | 256 | 91.353 | 55.955 | 18.992 | 1.00 | 12.31 | B | C |
| ATOM | 5589 | O | THR | 256 | 90.941 | 56.881 | 18.308 | 1.00 | 8.47 | B | O |
| ATOM | 5590 | N | ASP | 257 | 90.673 | 54.824 | 19.162 | 1.00 | 17.26 | B | N |
| ATOM | 5591 | CA | ASP | 257 | 89.375 | 54.601 | 18.530 | 1.00 | 17.64 | B | C |
| ATOM | 5592 | CB | ASP | 257 | 89.491 | 53.474 | 17.491 | 1.00 | 29.20 | B | C |
| ATOM | 5593 | CG | ASP | 257 | 89.534 | 52.074 | 18.122 | 1.00 | 34.56 | B | C |
| ATOM | 5594 | OD1 | ASP | 257 | 89.894 | 51.957 | 19.313 | 1.00 | 35.03 | B | O |
| ATOM | 5595 | OD2 | ASP | 257 | 89.220 | 51.084 | 17.421 | 1.00 | 39.83 | B | O |
| ATOM | 5596 | C | ASP | 257 | 88.267 | 54.259 | 19.535 | 1.00 | 14.23 | B | C |
| ATOM | 5597 | O | ASP | 257 | 87.243 | 53.660 | 19.169 | 1.00 | 13.47 | B | O |
| ATOM | 5598 | N | GLY | 258 | 88.462 | 54.634 | 20.798 | 1.00 | 26.33 | B | N |
| ATOM | 5599 | CA | GLY | 258 | 87.450 | 54.331 | 21.793 | 1.00 | 28.75 | B | C |
| ATOM | 5600 | C | GLY | 258 | 87.546 | 55.109 | 23.088 | 1.00 | 32.57 | B | C |
| ATOM | 5601 | O | GLY | 258 | 88.615 | 55.601 | 23.476 | 1.00 | 28.29 | B | O |
| ATOM | 5602 | N | GLU | 259 | 86.404 | 55.231 | 23.755 | 1.00 | 39.52 | B | N |
| ATOM | 5603 | CA | GLU | 259 | 86.335 | 55.931 | 25.025 | 1.00 | 41.40 | B | C |
| ATOM | 5604 | CB | GLU | 259 | 84.905 | 55.925 | 25.555 | 1.00 | 36.52 | B | C |
| ATOM | 5605 | CG | GLU | 259 | 83.950 | 56.783 | 24.749 | 1.00 | 44.30 | B | C |
| ATOM | 5606 | CD | GLU | 259 | 82.509 | 56.415 | 24.994 | 1.00 | 48.11 | B | C |
| ATOM | 5607 | OE1 | GLU | 259 | 81.625 | 57.175 | 24.546 | 1.00 | 54.86 | B | O |
| ATOM | 5608 | OE2 | GLU | 259 | 82.262 | 55.360 | 25.626 | 1.00 | 48.13 | B | O |
| ATOM | 5609 | C | GLU | 259 | 87.240 | 55.210 | 26.003 | 1.00 | 40.26 | B | C |
| ATOM | 5610 | O | GLU | 259 | 87.125 | 53.999 | 26.194 | 1.00 | 37.43 | B | O |
| ATOM | 5611 | N | SER | 260 | 88.155 | 55.953 | 26.610 | 1.00 | 34.06 | B | N |
| ATOM | 5612 | CA | SER | 260 | 89.067 | 55.369 | 27.576 | 1.00 | 37.22 | B | C |
| ATOM | 5613 | CB | SER | 260 | 90.041 | 56.432 | 28.083 | 1.00 | 50.00 | B | C |
| ATOM | 5614 | OG | SER | 260 | 89.341 | 57.516 | 28.666 | 1.00 | 50.51 | B | O |
| ATOM | 5615 | C | SER | 260 | 88.261 | 54.814 | 28.740 | 1.00 | 37.12 | B | C |
| ATOM | 5616 | O | SER | 260 | 87.177 | 55.300 | 29.043 | 1.00 | 33.15 | B | O |
| ATOM | 5617 | N | HIS | 261 | 88.781 | 53.787 | 29.392 | 1.00 | 36.47 | B | N |
| ATOM | 5618 | CA | HIS | 261 | 88.084 | 53.212 | 30.527 | 1.00 | 40.82 | B | C |
| ATOM | 5619 | CB | HIS | 261 | 88.509 | 51.755 | 30.728 | 1.00 | 21.13 | B | C |
| ATOM | 5620 | CG | HIS | 261 | 87.908 | 50.809 | 29.732 | 1.00 | 24.33 | B | C |
| ATOM | 5621 | CD2 | HIS | 261 | 88.345 | 50.398 | 28.519 | 1.00 | 23.44 | B | C |

FIG. 19A-78

| | | | | | | | | | | |
|---|---|---|---|---|---|---|---|---|---|---|
| ATOM | 5622 | ND1 | HIS | 261 | 86.688 | 50.197 | 29.925 | 1.00 | 25.81 | B N |
| ATOM | 5623 | CE1 | HIS | 261 | 86.400 | 49.448 | 28.876 | 1.00 | 25.88 | B C |
| ATOM | 5624 | NE2 | HIS | 261 | 87.390 | 49.554 | 28.009 | 1.00 | 23.15 | B N |
| ATOM | 5625 | C | HIS | 261 | 88.394 | 54.045 | 31.761 | 1.00 | 41.88 | B C |
| ATOM | 5626 | O | HIS | 261 | 87.711 | 53.940 | 32.779 | 1.00 | 39.10 | B O |
| ATOM | 5627 | N | ASP | 262 | 89.425 | 54.880 | 31.657 | 1.00 | 49.36 | B N |
| ATOM | 5628 | CA | ASP | 262 | 89.825 | 55.758 | 32.753 | 1.00 | 54.33 | B C |
| ATOM | 5629 | CB | ASP | 262 | 91.343 | 55.676 | 32.985 | 1.00 | 33.92 | B C |
| ATOM | 5630 | CG | ASP | 262 | 92.124 | 55.281 | 31.733 | 1.00 | 33.92 | B C |
| ATOM | 5631 | OD1 | ASP | 262 | 91.724 | 55.659 | 30.611 | 1.00 | 33.92 | B O |
| ATOM | 5632 | OD2 | ASP | 262 | 93.162 | 54.600 | 31.875 | 1.00 | 33.92 | B O |
| ATOM | 5633 | C | ASP | 262 | 89.418 | 57.218 | 32.507 | 1.00 | 54.38 | B C |
| ATOM | 5634 | O | ASP | 262 | 90.221 | 58.134 | 32.700 | 1.00 | 54.24 | B O |
| ATOM | 5635 | N | ASN | 263 | 88.171 | 57.424 | 32.085 | 1.00 | 68.10 | B N |
| ATOM | 5636 | CA | ASN | 263 | 87.646 | 58.765 | 31.813 | 1.00 | 69.27 | B C |
| ATOM | 5637 | CB | ASN | 263 | 86.123 | 58.734 | 31.630 | 1.00 | 82.52 | B C |
| ATOM | 5638 | CG | ASN | 263 | 85.660 | 57.631 | 30.707 | 1.00 | 86.89 | B C |
| ATOM | 5639 | OD1 | ASN | 263 | 85.981 | 57.626 | 29.519 | 1.00 | 88.39 | B O |
| ATOM | 5640 | ND2 | ASN | 263 | 84.893 | 56.686 | 31.249 | 1.00 | 81.39 | B N |
| ATOM | 5641 | C | ASN | 263 | 87.948 | 59.670 | 32.998 | 1.00 | 69.91 | B C |
| ATOM | 5642 | O | ASN | 263 | 88.360 | 60.822 | 32.841 | 1.00 | 68.81 | B O |
| ATOM | 5643 | N | TYR | 264 | 87.732 | 59.122 | 34.187 | 1.00 | 59.82 | B N |
| ATOM | 5644 | CA | TYR | 264 | 87.925 | 59.837 | 35.432 | 1.00 | 57.67 | B C |
| ATOM | 5645 | CB | TYR | 264 | 87.914 | 58.853 | 36.590 | 1.00 | 108.49 | B C |
| ATOM | 5646 | CG | TYR | 264 | 86.626 | 58.083 | 36.660 | 1.00 | 108.49 | B C |
| ATOM | 5647 | CD1 | TYR | 264 | 86.284 | 57.171 | 35.663 | 1.00 | 108.49 | B C |
| ATOM | 5648 | CE1 | TYR | 264 | 85.074 | 56.490 | 35.698 | 1.00 | 108.49 | B C |
| ATOM | 5649 | CD2 | TYR | 264 | 85.723 | 58.292 | 37.699 | 1.00 | 108.49 | B C |
| ATOM | 5650 | CE2 | TYR | 264 | 84.509 | 57.615 | 37.744 | 1.00 | 108.49 | B C |
| ATOM | 5651 | CZ | TYR | 264 | 84.190 | 56.717 | 36.741 | 1.00 | 108.49 | B C |
| ATOM | 5652 | OH | TYR | 264 | 82.987 | 56.052 | 36.783 | 1.00 | 108.49 | B O |
| ATOM | 5653 | C | TYR | 264 | 89.156 | 60.710 | 35.512 | 1.00 | 56.32 | B C |
| ATOM | 5654 | O | TYR | 264 | 89.047 | 61.935 | 35.549 | 1.00 | 53.45 | B O |
| ATOM | 5655 | N | ARG | 265 | 90.331 | 60.098 | 35.527 | 1.00 | 41.74 | B N |
| ATOM | 5656 | CA | ARG | 265 | 91.544 | 60.892 | 35.641 | 1.00 | 40.64 | B C |
| ATOM | 5657 | CB | ARG | 265 | 92.610 | 60.127 | 36.427 | 1.00 | 58.89 | B C |
| ATOM | 5658 | CG | ARG | 265 | 93.152 | 58.875 | 35.779 | 1.00 | 59.34 | B C |
| ATOM | 5659 | CD | ARG | 265 | 94.501 | 58.614 | 36.400 | 1.00 | 61.17 | B C |
| ATOM | 5660 | NE | ARG | 265 | 95.183 | 57.456 | 35.851 | 1.00 | 66.56 | B N |
| ATOM | 5661 | CZ | ARG | 265 | 96.506 | 57.349 | 35.784 | 1.00 | 66.73 | B C |
| ATOM | 5662 | NH1 | ARG | 265 | 97.281 | 58.334 | 36.227 | 1.00 | 71.36 | B N |
| ATOM | 5663 | NH2 | ARG | 265 | 97.059 | 56.256 | 35.280 | 1.00 | 70.70 | B N |
| ATOM | 5664 | C | ARG | 265 | 92.147 | 61.423 | 34.347 | 1.00 | 39.89 | B C |
| ATOM | 5665 | O | ARG | 265 | 93.311 | 61.833 | 34.319 | 1.00 | 41.20 | B O |
| ATOM | 5666 | N | LEU | 266 | 91.360 | 61.433 | 33.278 | 1.00 | 45.12 | B N |
| ATOM | 5667 | CA | LEU | 266 | 91.855 | 61.947 | 32.007 | 1.00 | 46.69 | B C |
| ATOM | 5668 | CB | LEU | 266 | 90.885 | 61.580 | 30.886 | 1.00 | 30.69 | B C |
| ATOM | 5669 | CG | LEU | 266 | 91.357 | 61.919 | 29.480 | 1.00 | 29.90 | B C |
| ATOM | 5670 | CD1 | LEU | 266 | 92.760 | 61.369 | 29.232 | 1.00 | 32.24 | B C |
| ATOM | 5671 | CD2 | LEU | 266 | 90.347 | 61.344 | 28.500 | 1.00 | 26.36 | B C |
| ATOM | 5672 | C | LEU | 266 | 91.989 | 63.466 | 32.139 | 1.00 | 49.51 | B C |
| ATOM | 5673 | O | LEU | 266 | 92.861 | 64.093 | 31.541 | 1.00 | 49.39 | B O |
| ATOM | 5674 | N | LYS | 267 | 91.107 | 64.041 | 32.945 | 1.00 | 50.12 | B N |
| ATOM | 5675 | CA | LYS | 267 | 91.097 | 65.473 | 33.206 | 1.00 | 52.43 | B C |
| ATOM | 5676 | CB | LYS | 267 | 89.927 | 65.807 | 34.136 | 1.00 | 99.33 | B C |
| ATOM | 5677 | CG | LYS | 267 | 89.719 | 67.279 | 34.431 | 1.00 | 99.33 | B C |
| ATOM | 5678 | CD | LYS | 267 | 88.623 | 67.863 | 33.558 | 1.00 | 99.33 | B C |
| ATOM | 5679 | CE | LYS | 267 | 88.211 | 69.242 | 34.049 | 1.00 | 99.33 | B C |
| ATOM | 5680 | NZ | LYS | 267 | 87.044 | 69.788 | 33.293 | 1.00 | 99.33 | B N |
| ATOM | 5681 | C | LYS | 267 | 92.417 | 65.835 | 33.882 | 1.00 | 51.92 | B C |
| ATOM | 5682 | O | LYS | 267 | 93.126 | 66.738 | 33.440 | 1.00 | 51.44 | B O |
| ATOM | 5683 | N | GLN | 268 | 92.736 | 65.115 | 34.956 | 1.00 | 36.69 | B N |
| ATOM | 5684 | CA | GLN | 268 | 93.968 | 65.338 | 35.709 | 1.00 | 35.66 | B C |
| ATOM | 5685 | CB | GLN | 268 | 94.098 | 64.324 | 36.841 | 1.00 | 127.61 | B C |
| ATOM | 5686 | CG | GLN | 268 | 93.032 | 64.387 | 37.906 | 1.00 | 127.61 | B C |
| ATOM | 5687 | CD | GLN | 268 | 93.203 | 63.286 | 38.941 | 1.00 | 127.61 | B C |
| ATOM | 5688 | OE1 | GLN | 268 | 92.487 | 63.236 | 39.939 | 1.00 | 127.61 | B O |
| ATOM | 5689 | NE2 | GLN | 268 | 94.158 | 62.392 | 38.702 | 1.00 | 127.61 | B N |
| ATOM | 5690 | C | GLN | 268 | 95.203 | 65.210 | 34.824 | 1.00 | 31.41 | B C |
| ATOM | 5691 | O | GLN | 268 | 96.044 | 66.108 | 34.788 | 1.00 | 32.59 | B O |
| ATOM | 5692 | N | VAL | 269 | 95.308 | 64.085 | 34.114 | 1.00 | 29.89 | B N |
| ATOM | 5693 | CA | VAL | 269 | 96.457 | 63.831 | 33.256 | 1.00 | 27.64 | B C |
| ATOM | 5694 | CB | VAL | 269 | 96.321 | 62.467 | 32.516 | 1.00 | 26.10 | B C |

FIG. 19A-79

| ATOM | 5695 | CG1 | VAL | 269 | 97.551 | 62.215 | 31.663 | 1.00 | 21.75 | B | C |
| --- | --- | --- | --- | --- | --- | --- | --- | --- | --- | --- | --- |
| ATOM | 5696 | CG2 | VAL | 269 | 96.161 | 61.338 | 33.520 | 1.00 | 23.96 | B | C |
| ATOM | 5697 | C | VAL | 269 | 96.683 | 64.956 | 32.246 | 1.00 | 27.23 | B | C |
| ATOM | 5698 | O | VAL | 269 | 97.784 | 65.502 | 32.174 | 1.00 | 30.07 | B | O |
| ATOM | 5699 | N | ILE | 270 | 95.658 | 65.306 | 31.471 | 1.00 | 16.50 | B | N |
| ATOM | 5700 | CA | ILE | 270 | 95.797 | 66.379 | 30.487 | 1.00 | 17.12 | B | C |
| ATOM | 5701 | CB | ILE | 270 | 94.459 | 66.696 | 29.777 | 1.00 | 35.19 | B | C |
| ATOM | 5702 | CG2 | ILE | 270 | 94.594 | 67.973 | 28.937 | 1.00 | 29.81 | B | C |
| ATOM | 5703 | CG1 | ILE | 270 | 94.060 | 65.520 | 28.885 | 1.00 | 32.75 | B | C |
| ATOM | 5704 | CD1 | ILE | 270 | 95.062 | 65.231 | 27.778 | 1.00 | 33.87 | B | C |
| ATOM | 5705 | C | ILE | 270 | 96.275 | 67.631 | 31.210 | 1.00 | 20.99 | B | C |
| ATOM | 5706 | O | ILE | 270 | 97.060 | 68.413 | 30.670 | 1.00 | 19.77 | B | O |
| ATOM | 5707 | N | GLN | 271 | 95.802 | 67.796 | 32.444 | 1.00 | 57.05 | B | N |
| ATOM | 5708 | CA | GLN | 271 | 96.169 | 68.935 | 33.269 | 1.00 | 59.11 | B | C |
| ATOM | 5709 | CB | GLN | 271 | 95.440 | 68.865 | 34.610 | 1.00 | 85.78 | B | C |
| ATOM | 5710 | CG | GLN | 271 | 95.525 | 70.134 | 35.439 | 1.00 | 87.68 | B | C |
| ATOM | 5711 | CD | GLN | 271 | 94.967 | 71.338 | 34.708 | 1.00 | 90.18 | B | C |
| ATOM | 5712 | OE1 | GLN | 271 | 95.614 | 71.898 | 33.822 | 1.00 | 90.51 | B | O |
| ATOM | 5713 | NE2 | GLN | 271 | 93.752 | 71.735 | 35.065 | 1.00 | 91.75 | B | N |
| ATOM | 5714 | C | GLN | 271 | 97.673 | 68.932 | 33.495 | 1.00 | 61.57 | B | C |
| ATOM | 5715 | O | GLN | 271 | 98.359 | 69.896 | 33.172 | 1.00 | 64.26 | B | O |
| ATOM | 5716 | N | ASP | 272 | 98.184 | 67.837 | 34.042 | 1.00 | 39.03 | B | N |
| ATOM | 5717 | CA | ASP | 272 | 99.612 | 67.716 | 34.304 | 1.00 | 40.31 | B | C |
| ATOM | 5718 | CB | ASP | 272 | 99.922 | 66.338 | 34.890 | 1.00 | 54.12 | B | C |
| ATOM | 5719 | CG | ASP | 272 | 99.275 | 66.122 | 36.255 | 1.00 | 55.74 | B | C |
| ATOM | 5720 | OD1 | ASP | 272 | 99.087 | 64.949 | 36.647 | 1.00 | 57.81 | B | O |
| ATOM | 5721 | OD2 | ASP | 272 | 98.961 | 67.123 | 36.939 | 1.00 | 62.00 | B | O |
| ATOM | 5722 | C | ASP | 272 | 100.420 | 67.937 | 33.033 | 1.00 | 41.11 | B | C |
| ATOM | 5723 | O | ASP | 272 | 101.550 | 68.418 | 33.083 | 1.00 | 38.56 | B | O |
| ATOM | 5724 | N | CYS | 273 | 99.843 | 67.587 | 31.891 | 1.00 | 49.56 | B | N |
| ATOM | 5725 | CA | CYS | 273 | 100.538 | 67.776 | 30.629 | 1.00 | 47.99 | B | C |
| ATOM | 5726 | CB | CYS | 273 | 99.824 | 67.028 | 29.503 | 1.00 | 39.07 | B | C |
| ATOM | 5727 | SG | CYS | 273 | 100.050 | 65.235 | 29.538 | 1.00 | 37.17 | B | S |
| ATOM | 5728 | C | CYS | 273 | 100.628 | 69.257 | 30.291 | 1.00 | 48.36 | B | C |
| ATOM | 5729 | O | CYS | 273 | 101.602 | 69.695 | 29.686 | 1.00 | 42.67 | B | O |
| ATOM | 5730 | N | GLU | 274 | 99.609 | 70.022 | 30.682 | 1.00 | 40.12 | B | N |
| ATOM | 5731 | CA | GLU | 274 | 99.584 | 71.467 | 30.425 | 1.00 | 42.92 | B | C |
| ATOM | 5732 | CB | GLU | 274 | 98.187 | 72.055 | 30.703 | 1.00 | 40.77 | B | C |
| ATOM | 5733 | CG | GLU | 274 | 97.285 | 72.151 | 29.470 | 1.00 | 45.89 | B | C |
| ATOM | 5734 | CD | GLU | 274 | 97.830 | 73.108 | 28.405 | 1.00 | 51.00 | B | C |
| ATOM | 5735 | OE1 | GLU | 274 | 97.269 | 73.155 | 27.284 | 1.00 | 52.87 | B | O |
| ATOM | 5736 | OE2 | GLU | 274 | 98.816 | 73.818 | 28.691 | 1.00 | 55.56 | B | O |
| ATOM | 5737 | C | GLU | 274 | 100.615 | 72.172 | 31.293 | 1.00 | 45.34 | B | C |
| ATOM | 5738 | O | GLU | 274 | 101.309 | 73.081 | 30.842 | 1.00 | 47.54 | B | O |
| ATOM | 5739 | N | ASP | 275 | 100.711 | 71.735 | 32.542 | 1.00 | 77.40 | B | N |
| ATOM | 5740 | CA | ASP | 275 | 101.656 | 72.302 | 33.495 | 1.00 | 76.14 | B | C |
| ATOM | 5741 | CB | ASP | 275 | 101.456 | 71.665 | 34.871 | 1.00 | 72.98 | B | C |
| ATOM | 5742 | CG | ASP | 275 | 100.070 | 71.900 | 35.432 | 1.00 | 74.25 | B | C |
| ATOM | 5743 | OD1 | ASP | 275 | 99.160 | 72.258 | 34.656 | 1.00 | 77.95 | B | O |
| ATOM | 5744 | OD2 | ASP | 275 | 99.887 | 71.712 | 36.652 | 1.00 | 75.91 | B | O |
| ATOM | 5745 | C | ASP | 275 | 103.093 | 72.050 | 33.046 | 1.00 | 75.13 | B | C |
| ATOM | 5746 | O | ASP | 275 | 104.021 | 72.707 | 33.512 | 1.00 | 70.68 | B | O |
| ATOM | 5747 | N | GLU | 276 | 103.275 | 71.091 | 32.146 | 1.00 | 44.46 | B | N |
| ATOM | 5748 | CA | GLU | 276 | 104.606 | 70.757 | 31.668 | 1.00 | 44.11 | B | C |
| ATOM | 5749 | CB | GLU | 276 | 104.846 | 69.258 | 31.847 | 1.00 | 54.99 | B | C |
| ATOM | 5750 | CG | GLU | 276 | 104.556 | 68.799 | 33.266 | 1.00 | 54.86 | B | C |
| ATOM | 5751 | CD | GLU | 276 | 105.018 | 67.383 | 33.547 | 1.00 | 55.96 | B | C |
| ATOM | 5752 | OE1 | GLU | 276 | 104.861 | 66.934 | 34.705 | 1.00 | 56.67 | B | O |
| ATOM | 5753 | OE2 | GLU | 276 | 105.538 | 66.724 | 32.616 | 1.00 | 52.90 | B | O |
| ATOM | 5754 | C | GLU | 276 | 104.843 | 71.175 | 30.222 | 1.00 | 42.94 | B | C |
| ATOM | 5755 | O | GLU | 276 | 105.823 | 70.759 | 29.597 | 1.00 | 44.05 | B | O |
| ATOM | 5756 | N | ASN | 277 | 103.938 | 71.997 | 29.700 | 1.00 | 43.81 | B | N |
| ATOM | 5757 | CA | ASN | 277 | 104.043 | 72.505 | 28.338 | 1.00 | 43.78 | B | C |
| ATOM | 5758 | CB | ASN | 277 | 105.229 | 73.464 | 28.233 | 1.00 | 55.27 | B | C |
| ATOM | 5759 | CG | ASN | 277 | 105.219 | 74.514 | 29.311 | 1.00 | 60.19 | B | C |
| ATOM | 5760 | OD1 | ASN | 277 | 104.288 | 75.315 | 29.403 | 1.00 | 60.01 | B | O |
| ATOM | 5761 | ND2 | ASN | 277 | 106.256 | 74.518 | 30.145 | 1.00 | 59.15 | B | N |
| ATOM | 5762 | C | ASN | 277 | 104.188 | 71.428 | 27.261 | 1.00 | 40.13 | B | C |
| ATOM | 5763 | O | ASN | 277 | 105.083 | 71.515 | 26.416 | 1.00 | 41.11 | B | O |
| ATOM | 5764 | N | ILE | 278 | 103.309 | 70.427 | 27.278 | 1.00 | 17.87 | B | N |
| ATOM | 5765 | CA | ILE | 278 | 103.366 | 69.361 | 26.289 | 1.00 | 18.32 | B | C |
| ATOM | 5766 | CB | ILE | 278 | 103.110 | 67.975 | 26.928 | 1.00 | 22.06 | B | C |
| ATOM | 5767 | CG2 | ILE | 278 | 103.120 | 66.897 | 25.854 | 1.00 | 23.45 | B | C |

FIG. 19A-80

| ATOM | 5768 | CG1 | ILE | 278 | 104.172 | 67.675 | 27.987 | 1.00 | 19.51 | B | C |
|------|------|-----|-----|-----|---------|--------|--------|------|-------|---|---|
| ATOM | 5769 | CD1 | ILE | 278 | 103.941 | 66.373 | 28.707 | 1.00 | 21.79 | B | C |
| ATOM | 5770 | C   | ILE | 278 | 102.316 | 69.579 | 25.213 | 1.00 | 18.92 | B | C |
| ATOM | 5771 | O   | ILE | 278 | 101.132 | 69.378 | 25.463 | 1.00 | 19.26 | B | O |
| ATOM | 5772 | N   | GLN | 279 | 102.749 | 69.994 | 24.024 | 1.00 | 49.21 | B | N |
| ATOM | 5773 | CA  | GLN | 279 | 101.831 | 70.198 | 22.908 | 1.00 | 48.81 | B | C |
| ATOM | 5774 | CB  | GLN | 279 | 102.579 | 70.633 | 21.652 | 1.00 | 63.04 | B | C |
| ATOM | 5775 | CG  | GLN | 279 | 103.187 | 71.998 | 21.752 | 1.00 | 68.82 | B | C |
| ATOM | 5776 | CD  | GLN | 279 | 102.173 | 73.043 | 22.155 | 1.00 | 72.74 | B | C |
| ATOM | 5777 | OE1 | GLN | 279 | 101.233 | 73.328 | 21.410 | 1.00 | 66.98 | B | O |
| ATOM | 5778 | NE2 | GLN | 279 | 102.352 | 73.618 | 23.345 | 1.00 | 72.33 | B | N |
| ATOM | 5779 | C   | GLN | 279 | 101.175 | 68.864 | 22.640 | 1.00 | 46.68 | B | C |
| ATOM | 5780 | O   | GLN | 279 | 101.861 | 67.859 | 22.467 | 1.00 | 43.60 | B | O |
| ATOM | 5781 | N   | ARG | 280 | 99.851  | 68.848 | 22.595 | 1.00 | 28.30 | B | N |
| ATOM | 5782 | CA  | ARG | 280 | 99.138  | 67.605 | 22.363 | 1.00 | 29.82 | B | C |
| ATOM | 5783 | CB  | ARG | 280 | 98.276  | 67.277 | 23.575 | 1.00 | 38.67 | B | C |
| ATOM | 5784 | CG  | ARG | 280 | 99.036  | 67.225 | 24.874 | 1.00 | 37.30 | B | C |
| ATOM | 5785 | CD  | ARG | 280 | 98.068  | 67.012 | 26.018 | 1.00 | 36.97 | B | C |
| ATOM | 5786 | NE  | ARG | 280 | 97.070  | 68.075 | 26.073 | 1.00 | 34.02 | B | N |
| ATOM | 5787 | CZ  | ARG | 280 | 97.288  | 69.298 | 26.557 | 1.00 | 37.93 | B | C |
| ATOM | 5788 | NH1 | ARG | 280 | 98.483  | 69.627 | 27.041 | 1.00 | 40.85 | B | N |
| ATOM | 5789 | NH2 | ARG | 280 | 96.307  | 70.192 | 26.554 | 1.00 | 42.87 | B | N |
| ATOM | 5790 | C   | ARG | 280 | 98.264  | 67.579 | 21.111 | 1.00 | 29.48 | B | C |
| ATOM | 5791 | O   | ARG | 280 | 97.406  | 68.437 | 20.912 | 1.00 | 29.21 | B | O |
| ATOM | 5792 | N   | PHE | 281 | 98.501  | 66.582 | 20.266 | 1.00 | 31.71 | B | N |
| ATOM | 5793 | CA  | PHE | 281 | 97.713  | 66.392 | 19.066 | 1.00 | 33.70 | B | C |
| ATOM | 5794 | CB  | PHE | 281 | 98.594  | 66.335 | 17.826 | 1.00 | 18.70 | B | C |
| ATOM | 5795 | CG  | PHE | 281 | 99.324  | 67.604 | 17.555 | 1.00 | 21.73 | B | C |
| ATOM | 5796 | CD1 | PHE | 281 | 100.438 | 67.950 | 18.308 | 1.00 | 25.58 | B | C |
| ATOM | 5797 | CD2 | PHE | 281 | 98.887  | 68.469 | 16.551 | 1.00 | 23.46 | B | C |
| ATOM | 5798 | CE1 | PHE | 281 | 101.111 | 69.136 | 18.070 | 1.00 | 25.64 | B | C |
| ATOM | 5799 | CE2 | PHE | 281 | 99.554  | 69.665 | 16.301 | 1.00 | 21.19 | B | C |
| ATOM | 5800 | CZ  | PHE | 281 | 100.669 | 69.999 | 17.064 | 1.00 | 22.62 | B | C |
| ATOM | 5801 | C   | PHE | 281 | 97.025  | 65.060 | 19.266 | 1.00 | 34.41 | B | C |
| ATOM | 5802 | O   | PHE | 281 | 97.677  | 64.053 | 19.509 | 1.00 | 36.78 | B | O |
| ATOM | 5803 | N   | SER | 282 | 95.704  | 65.061 | 19.202 | 1.00 | 16.00 | B | N |
| ATOM | 5804 | CA  | SER | 282 | 94.962  | 63.835 | 19.374 | 1.00 | 17.85 | B | C |
| ATOM | 5805 | CB  | SER | 282 | 93.973  | 63.973 | 20.528 | 1.00 | 14.79 | B | C |
| ATOM | 5806 | OG  | SER | 282 | 93.036  | 64.997 | 20.286 | 1.00 | 11.34 | B | O |
| ATOM | 5807 | C   | SER | 282 | 94.231  | 63.507 | 18.093 | 1.00 | 19.73 | B | C |
| ATOM | 5808 | O   | SER | 282 | 93.909  | 64.389 | 17.306 | 1.00 | 23.59 | B | O |
| ATOM | 5809 | N   | ILE | 283 | 93.986  | 62.224 | 17.881 | 1.00 | 19.27 | B | N |
| ATOM | 5810 | CA  | ILE | 283 | 93.288  | 61.779 | 16.693 | 1.00 | 17.19 | B | C |
| ATOM | 5811 | CB  | ILE | 283 | 94.245  | 61.146 | 15.697 | 1.00 | 9.92  | B | C |
| ATOM | 5812 | CG2 | ILE | 283 | 93.501  | 60.806 | 14.425 | 1.00 | 10.73 | B | C |
| ATOM | 5813 | CG1 | ILE | 283 | 95.377  | 62.118 | 15.383 | 1.00 | 6.39  | B | C |
| ATOM | 5814 | CD1 | ILE | 283 | 96.630  | 61.446 | 14.894 | 1.00 | 9.95  | B | C |
| ATOM | 5815 | C   | ILE | 283 | 92.278  | 60.748 | 17.127 | 1.00 | 16.26 | B | C |
| ATOM | 5816 | O   | ILE | 283 | 92.574  | 59.886 | 17.947 | 1.00 | 16.12 | B | O |
| ATOM | 5817 | N   | ALA | 284 | 91.078  | 60.836 | 16.584 | 1.00 | 18.66 | B | N |
| ATOM | 5818 | CA  | ALA | 284 | 90.050  | 59.896 | 16.955 | 1.00 | 18.68 | B | C |
| ATOM | 5819 | CB  | ALA | 284 | 88.903  | 60.627 | 17.622 | 1.00 | 45.12 | B | C |
| ATOM | 5820 | C   | ALA | 284 | 89.542  | 59.107 | 15.759 | 1.00 | 16.81 | B | C |
| ATOM | 5821 | O   | ALA | 284 | 89.045  | 59.681 | 14.792 | 1.00 | 15.47 | B | O |
| ATOM | 5822 | N   | ILE | 285 | 89.691  | 57.788 | 15.826 | 1.00 | 23.61 | B | N |
| ATOM | 5823 | CA  | ILE | 285 | 89.205  | 56.922 | 14.772 | 1.00 | 17.81 | B | C |
| ATOM | 5824 | CB  | ILE | 285 | 89.960  | 55.564 | 14.741 | 1.00 | 12.20 | B | C |
| ATOM | 5825 | CG2 | ILE | 285 | 89.210  | 54.576 | 13.862 | 1.00 | 7.02  | B | C |
| ATOM | 5826 | CG1 | ILE | 285 | 91.380  | 55.738 | 14.204 | 1.00 | 7.53  | B | C |
| ATOM | 5827 | CD1 | ILE | 285 | 92.342  | 56.334 | 15.179 | 1.00 | 8.67  | B | C |
| ATOM | 5828 | C   | ILE | 285 | 87.745  | 56.678 | 15.148 | 1.00 | 21.13 | B | C |
| ATOM | 5829 | O   | ILE | 285 | 87.466  | 56.108 | 16.201 | 1.00 | 22.87 | B | O |
| ATOM | 5830 | N   | LEU | 286 | 86.820  | 57.112 | 14.297 | 1.00 | 18.22 | B | N |
| ATOM | 5831 | CA  | LEU | 286 | 85.399  | 56.937 | 14.581 | 1.00 | 18.70 | B | C |
| ATOM | 5832 | CB  | LEU | 286 | 84.615  | 58.129 | 14.039 | 1.00 | 27.86 | B | C |
| ATOM | 5833 | CG  | LEU | 286 | 85.105  | 59.512 | 14.456 | 1.00 | 30.68 | B | C |
| ATOM | 5834 | CD1 | LEU | 286 | 84.112  | 60.536 | 13.961 | 1.00 | 33.24 | B | C |
| ATOM | 5835 | CD2 | LEU | 286 | 85.249  | 59.599 | 15.963 | 1.00 | 32.35 | B | C |
| ATOM | 5836 | C   | LEU | 286 | 84.774  | 55.645 | 14.044 | 1.00 | 19.15 | B | C |
| ATOM | 5837 | O   | LEU | 286 | 83.552  | 55.458 | 14.122 | 1.00 | 19.99 | B | O |
| ATOM | 5838 | N   | GLY | 287 | 85.609  | 54.752 | 13.520 | 1.00 | 37.37 | B | N |
| ATOM | 5839 | CA  | GLY | 287 | 85.115  | 53.501 | 12.967 | 1.00 | 36.15 | B | C |
| ATOM | 5840 | C   | GLY | 287 | 84.059  | 52.745 | 13.760 | 1.00 | 33.73 | B | C |

FIG. 19A-81

```
ATOM   5841  O    GLY  287    82.899  52.681  13.367  1.00  37.83  B  O
ATOM   5842  N    HIS  288    84.464  52.162  14.878  1.00  34.79  B  N
ATOM   5843  CA   HIS  288    83.563  51.376  15.700  1.00  32.75  B  C
ATOM   5844  CB   HIS  288    84.272  51.016  16.996  1.00  68.63  B  C
ATOM   5845  CG   HIS  288    85.486  50.181  16.763  1.00  70.54  B  C
ATOM   5846  CD2  HIS  288    85.781  48.912  17.123  1.00  66.91  B  C
ATOM   5847  ND1  HIS  288    86.520  50.600  15.955  1.00  65.20  B  N
ATOM   5848  CE1  HIS  288    87.397  49.623  15.821  1.00  65.56  B  C
ATOM   5849  NE2  HIS  288    86.972  48.586  16.519  1.00  64.05  B  N
ATOM   5850  C    HIS  288    82.214  52.006  15.968  1.00  30.23  B  C
ATOM   5851  O    HIS  288    81.180  51.398  15.711  1.00  29.80  B  O
ATOM   5852  N    TYR  289    82.219  53.233  16.461  1.00  26.68  B  N
ATOM   5853  CA   TYR  289    80.982  53.912  16.754  1.00  27.59  B  C
ATOM   5854  CB   TYR  289    81.287  55.288  17.309  1.00  20.91  B  C
ATOM   5855  CG   TYR  289    81.803  55.203  18.717  1.00  23.71  B  C
ATOM   5856  CD1  TYR  289    83.163  55.293  18.997  1.00  24.30  B  C
ATOM   5857  CE1  TYR  289    83.633  55.127  20.281  1.00  27.49  B  C
ATOM   5858  CD2  TYR  289    80.928  54.947  19.764  1.00  26.60  B  C
ATOM   5859  CE2  TYR  289    81.381  54.776  21.047  1.00  21.41  B  C
ATOM   5860  CZ   TYR  289    82.733  54.866  21.303  1.00  23.14  B  C
ATOM   5861  OH   TYR  289    83.166  54.686  22.597  1.00  27.79  B  O
ATOM   5862  C    TYR  289    80.039  54.015  15.572  1.00  29.36  B  C
ATOM   5863  O    TYR  289    78.849  53.720  15.692  1.00  28.55  B  O
ATOM   5864  N    ASN  290    80.551  54.414  14.419  1.00  30.33  B  N
ATOM   5865  CA   ASN  290    79.681  54.538  13.264  1.00  29.82  B  C
ATOM   5866  CB   ASN  290    80.390  55.290  12.141  1.00  19.88  B  C
ATOM   5867  CG   ASN  290    80.582  56.750  12.466  1.00  23.09  B  C
ATOM   5868  OD1  ASN  290    79.681  57.395  13.005  1.00  24.51  B  O
ATOM   5869  ND2  ASN  290    81.748  57.286  12.133  1.00  26.61  B  N
ATOM   5870  C    ASN  290    79.142  53.214  12.746  1.00  28.65  B  C
ATOM   5871  O    ASN  290    78.008  53.153  12.264  1.00  35.25  B  O
ATOM   5872  N    ARG  291    79.944  52.155  12.842  1.00  46.80  B  N
ATOM   5873  CA   ARG  291    79.513  50.850  12.362  1.00  46.11  B  C
ATOM   5874  CB   ARG  291    80.694  49.867  12.337  1.00  45.84  B  C
ATOM   5875  CG   ARG  291    81.661  50.063  11.152  1.00  50.80  B  C
ATOM   5876  CD   ARG  291    82.722  48.943  11.054  1.00  54.88  B  C
ATOM   5877  NE   ARG  291    83.916  49.157  11.883  1.00  47.06  B  N
ATOM   5878  CZ   ARG  291    84.884  50.030  11.603  1.00  56.55  B  C
ATOM   5879  NH1  ARG  291    84.813  50.787  10.515  1.00  55.39  B  N
ATOM   5880  NH2  ARG  291    85.936  50.131  12.401  1.00  53.31  B  N
ATOM   5881  C    ARG  291    78.367  50.296  13.207  1.00  43.91  B  C
ATOM   5882  O    ARG  291    77.338  49.876  12.676  1.00  47.17  B  O
ATOM   5883  N    GLY  292    78.531  50.306  14.523  1.00  18.83  B  N
ATOM   5884  CA   GLY  292    77.476  49.795  15.374  1.00  19.08  B  C
ATOM   5885  C    GLY  292    76.427  50.857  15.628  1.00  26.45  B  C
ATOM   5886  O    GLY  292    75.874  50.947  16.722  1.00  32.58  B  O
ATOM   5887  N    ASN  293    76.151  51.664  14.610  1.00  32.56  B  N
ATOM   5888  CA   ASN  293    75.177  52.740  14.724  1.00  34.89  B  C
ATOM   5889  CB   ASN  293    73.785  52.239  14.339  1.00  18.98  B  C
ATOM   5890  CG   ASN  293    73.623  52.066  12.846  1.00  25.56  B  C
ATOM   5891  OD1  ASN  293    74.249  52.776  12.063  1.00  27.19  B  O
ATOM   5892  ND2  ASN  293    72.767  51.132  12.440  1.00  26.33  B  N
ATOM   5893  C    ASN  293    75.116  53.389  16.111  1.00  36.22  B  C
ATOM   5894  O    ASN  293    74.054  53.448  16.722  1.00  31.70  B  O
ATOM   5895  N    LEU  294    76.247  53.875  16.614  1.00  40.17  B  N
ATOM   5896  CA   LEU  294    76.260  54.525  17.921  1.00  39.32  B  C
ATOM   5897  CB   LEU  294    77.141  53.737  18.901  1.00  27.66  B  C
ATOM   5898  CG   LEU  294    76.633  52.343  19.291  1.00  26.48  B  C
ATOM   5899  CD1  LEU  294    77.463  51.781  20.440  1.00  27.02  B  C
ATOM   5900  CD2  LEU  294    75.175  52.437  19.714  1.00  27.39  B  C
ATOM   5901  C    LEU  294    76.730  55.985  17.823  1.00  41.69  B  C
ATOM   5902  O    LEU  294    77.579  56.314  16.984  1.00  40.35  B  O
ATOM   5903  N    SER  295    76.158  56.860  18.656  1.00  29.47  B  N
ATOM   5904  CA   SER  295    76.534  58.272  18.644  1.00  29.33  B  C
ATOM   5905  CB   SER  295    75.802  59.063  19.740  1.00  35.11  B  C
ATOM   5906  OG   SER  295    76.336  60.371  19.894  1.00  41.79  B  O
ATOM   5907  C    SER  295    78.022  58.329  18.890  1.00  25.45  B  C
ATOM   5908  O    SER  295    78.583  57.444  19.533  1.00  22.32  B  O
ATOM   5909  N    THR  296    78.661  59.379  18.401  1.00  28.05  B  N
ATOM   5910  CA   THR  296    80.096  59.500  18.559  1.00  28.09  B  C
ATOM   5911  CB   THR  296    80.786  59.452  17.191  1.00  44.94  B  C
ATOM   5912  OG1  THR  296    80.305  60.534  16.383  1.00  50.00  B  O
ATOM   5913  CG2  THR  296    80.485  58.150  16.487  1.00  44.81  B  C
```

FIG. 19A-82

| ATOM | 5914 | C | THR | 296 | 80.519 | 60.792 | 19.227 | 1.00 | 29.07 | B | C |
|---|---|---|---|---|---|---|---|---|---|---|---|
| ATOM | 5915 | O | THR | 296 | 81.695 | 60.971 | 19.535 | 1.00 | 27.88 | B | O |
| ATOM | 5916 | N | GLU | 297 | 79.581 | 61.705 | 19.451 | 1.00 | 50.64 | B | N |
| ATOM | 5917 | CA | GLU | 297 | 79.970 | 62.978 | 20.038 | 1.00 | 54.10 | B | C |
| ATOM | 5918 | CB | GLU | 297 | 78.781 | 63.943 | 20.111 | 1.00 | 93.12 | B | C |
| ATOM | 5919 | CG | GLU | 297 | 77.787 | 63.695 | 21.213 | 1.00 | 100.15 | B | C |
| ATOM | 5920 | CD | GLU | 297 | 77.036 | 64.960 | 21.569 | 1.00 | 101.40 | B | C |
| ATOM | 5921 | OE1 | GLU | 297 | 76.160 | 64.911 | 22.455 | 1.00 | 104.84 | B | O |
| ATOM | 5922 | OE2 | GLU | 297 | 77.333 | 66.010 | 20.964 | 1.00 | 102.89 | B | O |
| ATOM | 5923 | C | GLU | 297 | 80.639 | 62.849 | 21.399 | 1.00 | 52.14 | B | C |
| ATOM | 5924 | O | GLU | 297 | 81.715 | 63.406 | 21.612 | 1.00 | 51.64 | B | O |
| ATOM | 5925 | N | LYS | 298 | 80.029 | 62.104 | 22.315 | 1.00 | 35.40 | B | N |
| ATOM | 5926 | CA | LYS | 298 | 80.622 | 61.942 | 23.636 | 1.00 | 35.40 | B | C |
| ATOM | 5927 | CB | LYS | 298 | 79.837 | 60.916 | 24.443 | 1.00 | 37.32 | B | C |
| ATOM | 5928 | CG | LYS | 298 | 80.199 | 60.902 | 25.910 | 1.00 | 46.03 | B | C |
| ATOM | 5929 | CD | LYS | 298 | 79.201 | 60.085 | 26.727 | 1.00 | 47.75 | B | C |
| ATOM | 5930 | CE | LYS | 298 | 77.777 | 60.625 | 26.578 | 1.00 | 51.57 | B | C |
| ATOM | 5931 | NZ | LYS | 298 | 77.676 | 62.075 | 26.908 | 1.00 | 55.89 | B | N |
| ATOM | 5932 | C | LYS | 298 | 82.087 | 61.518 | 23.514 | 1.00 | 33.00 | B | C |
| ATOM | 5933 | O | LYS | 298 | 82.939 | 61.933 | 24.310 | 1.00 | 33.88 | B | O |
| ATOM | 5934 | N | PHE | 299 | 82.371 | 60.699 | 22.505 | 1.00 | 29.00 | B | N |
| ATOM | 5935 | CA | PHE | 299 | 83.729 | 60.226 | 22.244 | 1.00 | 27.24 | B | C |
| ATOM | 5936 | CB | PHE | 299 | 83.701 | 59.054 | 21.263 | 1.00 | 39.15 | B | C |
| ATOM | 5937 | CG | PHE | 299 | 85.065 | 58.571 | 20.851 | 1.00 | 31.59 | B | C |
| ATOM | 5938 | CD1 | PHE | 299 | 86.020 | 58.237 | 21.806 | 1.00 | 28.04 | B | C |
| ATOM | 5939 | CD2 | PHE | 299 | 85.396 | 58.435 | 19.505 | 1.00 | 29.32 | B | C |
| ATOM | 5940 | CE1 | PHE | 299 | 87.284 | 57.776 | 21.422 | 1.00 | 27.45 | B | C |
| ATOM | 5941 | CE2 | PHE | 299 | 86.667 | 57.970 | 19.119 | 1.00 | 23.73 | B | C |
| ATOM | 5942 | CZ | PHE | 299 | 87.603 | 57.643 | 20.078 | 1.00 | 22.24 | B | C |
| ATOM | 5943 | C | PHE | 299 | 84.562 | 61.361 | 21.662 | 1.00 | 27.59 | B | C |
| ATOM | 5944 | O | PHE | 299 | 85.625 | 61.702 | 22.183 | 1.00 | 23.40 | B | O |
| ATOM | 5945 | N | VAL | 300 | 84.077 | 61.946 | 20.576 | 1.00 | 13.78 | B | N |
| ATOM | 5946 | CA | VAL | 300 | 84.791 | 63.050 | 19.944 | 1.00 | 18.73 | B | C |
| ATOM | 5947 | CB | VAL | 300 | 83.954 | 63.701 | 18.822 | 1.00 | 24.12 | B | C |
| ATOM | 5948 | CG1 | VAL | 300 | 84.616 | 64.979 | 18.363 | 1.00 | 27.69 | B | C |
| ATOM | 5949 | CG2 | VAL | 300 | 83.814 | 62.731 | 17.646 | 1.00 | 28.13 | B | C |
| ATOM | 5950 | C | VAL | 300 | 85.142 | 64.119 | 20.966 | 1.00 | 17.37 | B | C |
| ATOM | 5951 | O | VAL | 300 | 86.209 | 64.715 | 20.906 | 1.00 | 17.87 | B | O |
| ATOM | 5952 | N | GLU | 301 | 84.248 | 64.359 | 21.914 | 1.00 | 33.19 | B | N |
| ATOM | 5953 | CA | GLU | 301 | 84.520 | 65.377 | 22.915 | 1.00 | 33.85 | B | C |
| ATOM | 5954 | CB | GLU | 301 | 83.255 | 65.707 | 23.706 | 1.00 | 133.49 | B | C |
| ATOM | 5955 | CG | GLU | 301 | 83.426 | 66.851 | 24.703 | 1.00 | 135.76 | B | C |
| ATOM | 5956 | CD | GLU | 301 | 84.115 | 68.077 | 24.108 | 1.00 | 141.57 | B | C |
| ATOM | 5957 | OE1 | GLU | 301 | 83.669 | 68.566 | 23.046 | 1.00 | 141.12 | B | O |
| ATOM | 5958 | OE2 | GLU | 301 | 85.102 | 68.555 | 24.713 | 1.00 | 143.84 | B | O |
| ATOM | 5959 | C | GLU | 301 | 85.634 | 64.925 | 23.847 | 1.00 | 32.42 | B | C |
| ATOM | 5960 | O | GLU | 301 | 86.495 | 65.723 | 24.239 | 1.00 | 30.50 | B | O |
| ATOM | 5961 | N | GLU | 302 | 85.628 | 63.642 | 24.190 | 1.00 | 18.71 | B | N |
| ATOM | 5962 | CA | GLU | 302 | 86.663 | 63.091 | 25.060 | 1.00 | 18.52 | B | C |
| ATOM | 5963 | CB | GLU | 302 | 86.420 | 61.596 | 25.293 | 1.00 | 49.27 | B | C |
| ATOM | 5964 | CG | GLU | 302 | 87.438 | 60.934 | 26.207 | 1.00 | 49.02 | B | C |
| ATOM | 5965 | CD | GLU | 302 | 87.100 | 59.486 | 26.491 | 1.00 | 45.95 | B | C |
| ATOM | 5966 | OE1 | GLU | 302 | 86.051 | 59.237 | 27.118 | 1.00 | 45.93 | B | O |
| ATOM | 5967 | OE2 | GLU | 302 | 87.875 | 58.594 | 26.084 | 1.00 | 50.37 | B | O |
| ATOM | 5968 | C | GLU | 302 | 88.046 | 63.301 | 24.456 | 1.00 | 21.59 | B | C |
| ATOM | 5969 | O | GLU | 302 | 88.964 | 63.720 | 25.150 | 1.00 | 20.85 | B | O |
| ATOM | 5970 | N | ILE | 303 | 88.188 | 63.031 | 23.159 | 1.00 | 30.73 | B | N |
| ATOM | 5971 | CA | ILE | 303 | 89.479 | 63.175 | 22.472 | 1.00 | 30.78 | B | C |
| ATOM | 5972 | CB | ILE | 303 | 89.470 | 62.431 | 21.112 | 1.00 | 21.11 | B | C |
| ATOM | 5973 | CG2 | ILE | 303 | 90.865 | 62.406 | 20.518 | 1.00 | 16.29 | B | C |
| ATOM | 5974 | CG1 | ILE | 303 | 88.932 | 61.003 | 21.306 | 1.00 | 18.71 | B | C |
| ATOM | 5975 | CD1 | ILE | 303 | 89.501 | 60.262 | 22.515 | 1.00 | 15.17 | B | C |
| ATOM | 5976 | C | ILE | 303 | 89.922 | 64.625 | 22.242 | 1.00 | 32.81 | B | C |
| ATOM | 5977 | O | ILE | 303 | 91.097 | 64.955 | 22.415 | 1.00 | 35.30 | B | O |
| ATOM | 5978 | N | LYS | 304 | 88.989 | 65.485 | 21.847 | 1.00 | 41.13 | B | N |
| ATOM | 5979 | CA | LYS | 304 | 89.321 | 66.881 | 21.624 | 1.00 | 41.93 | B | C |
| ATOM | 5980 | CB | LYS | 304 | 88.087 | 67.695 | 21.239 | 1.00 | 34.23 | B | C |
| ATOM | 5981 | CG | LYS | 304 | 87.578 | 67.484 | 19.837 | 1.00 | 40.90 | B | C |
| ATOM | 5982 | CD | LYS | 304 | 86.491 | 68.498 | 19.526 | 1.00 | 42.43 | B | C |
| ATOM | 5983 | CE | LYS | 304 | 85.937 | 68.312 | 18.122 | 1.00 | 45.16 | B | C |
| ATOM | 5984 | NZ | LYS | 304 | 84.893 | 69.323 | 17.799 | 1.00 | 47.34 | B | N |
| ATOM | 5985 | C | LYS | 304 | 89.892 | 67.455 | 22.906 | 1.00 | 38.02 | B | C |
| ATOM | 5986 | O | LYS | 304 | 90.833 | 68.240 | 22.871 | 1.00 | 42.10 | B | O |

FIG. 19A-83

| | | | | | | | | | | | |
|---|---|---|---|---|---|---|---|---|---|---|---|
| ATOM | 5987 | N | SER | 305 | 89.322 | 67.066 | 24.043 | 1.00 | 21.53 | B | N |
| ATOM | 5988 | CA | SER | 305 | 89.788 | 67.571 | 25.335 | 1.00 | 18.69 | B | C |
| ATOM | 5989 | CB | SER | 305 | 88.872 | 67.096 | 26.460 | 1.00 | 39.18 | B | C |
| ATOM | 5990 | OG | SER | 305 | 89.039 | 65.715 | 26.696 | 1.00 | 35.86 | B | O |
| ATOM | 5991 | C | SER | 305 | 91.223 | 67.134 | 25.622 | 1.00 | 19.21 | B | C |
| ATOM | 5992 | O | SER | 305 | 91.935 | 67.754 | 26.418 | 1.00 | 21.78 | B | O |
| ATOM | 5993 | N | ILE | 306 | 91.652 | 66.063 | 24.969 | 1.00 | 47.39 | B | N |
| ATOM | 5994 | CA | ILE | 306 | 93.005 | 65.582 | 25.158 | 1.00 | 44.14 | B | C |
| ATOM | 5995 | CB | ILE | 306 | 93.129 | 64.131 | 24.682 | 1.00 | 20.56 | B | C |
| ATOM | 5996 | CG2 | ILE | 306 | 94.584 | 63.769 | 24.454 | 1.00 | 21.29 | B | C |
| ATOM | 5997 | CG1 | ILE | 306 | 92.479 | 63.210 | 25.713 | 1.00 | 23.19 | B | C |
| ATOM | 5998 | CD1 | ILE | 306 | 92.459 | 61.762 | 25.302 | 1.00 | 20.90 | B | C |
| ATOM | 5999 | C | ILE | 306 | 93.966 | 66.469 | 24.378 | 1.00 | 41.90 | B | C |
| ATOM | 6000 | O | ILE | 306 | 95.146 | 66.583 | 24.717 | 1.00 | 42.43 | B | O |
| ATOM | 6001 | N | ALA | 307 | 93.445 | 67.103 | 23.334 | 1.00 | 47.34 | B | N |
| ATOM | 6002 | CA | ALA | 307 | 94.247 | 67.979 | 22.497 | 1.00 | 49.53 | B | C |
| ATOM | 6003 | CB | ALA | 307 | 93.538 | 68.236 | 21.181 | 1.00 | 34.34 | B | C |
| ATOM | 6004 | C | ALA | 307 | 94.526 | 69.296 | 23.200 | 1.00 | 49.19 | B | C |
| ATOM | 6005 | O | ALA | 307 | 93.952 | 69.595 | 24.253 | 1.00 | 48.18 | B | O |
| ATOM | 6006 | N | SER | 308 | 95.415 | 70.078 | 22.604 | 1.00 | 31.36 | B | N |
| ATOM | 6007 | CA | SER | 308 | 95.801 | 71.367 | 23.141 | 1.00 | 34.29 | B | C |
| ATOM | 6008 | CB | SER | 308 | 97.299 | 71.580 | 22.943 | 1.00 | 9.08 | B | C |
| ATOM | 6009 | OG | SER | 308 | 98.040 | 70.819 | 23.867 | 1.00 | 12.47 | B | O |
| ATOM | 6010 | C | SER | 308 | 95.054 | 72.489 | 22.446 | 1.00 | 37.94 | B | C |
| ATOM | 6011 | O | SER | 308 | 94.703 | 72.373 | 21.272 | 1.00 | 35.28 | B | O |
| ATOM | 6012 | N | GLU | 309 | 94.813 | 73.575 | 23.178 | 1.00 | 31.30 | B | N |
| ATOM | 6013 | CA | GLU | 309 | 94.137 | 74.735 | 22.614 | 1.00 | 34.79 | B | C |
| ATOM | 6014 | CB | GLU | 309 | 93.786 | 75.736 | 23.721 | 1.00 | 74.37 | B | C |
| ATOM | 6015 | CG | GLU | 309 | 92.834 | 75.203 | 24.787 | 1.00 | 79.74 | B | C |
| ATOM | 6016 | CD | GLU | 309 | 91.461 | 74.845 | 24.234 | 1.00 | 82.50 | B | C |
| ATOM | 6017 | OE1 | GLU | 309 | 90.533 | 74.618 | 25.043 | 1.00 | 84.83 | B | O |
| ATOM | 6018 | OE2 | GLU | 309 | 91.307 | 74.784 | 22.995 | 1.00 | 86.65 | B | O |
| ATOM | 6019 | C | GLU | 309 | 95.138 | 75.359 | 21.642 | 1.00 | 35.54 | B | C |
| ATOM | 6020 | O | GLU | 309 | 96.321 | 75.480 | 21.971 | 1.00 | 37.19 | B | O |
| ATOM | 6021 | N | PRO | 310 | 94.685 | 75.762 | 20.435 | 1.00 | 19.46 | B | N |
| ATOM | 6022 | CD | PRO | 310 | 95.588 | 76.399 | 19.457 | 1.00 | 19.32 | B | C |
| ATOM | 6023 | CA | PRO | 310 | 93.324 | 75.694 | 19.890 | 1.00 | 19.65 | B | C |
| ATOM | 6024 | CB | PRO | 310 | 93.362 | 76.729 | 18.770 | 1.00 | 21.15 | B | C |
| ATOM | 6025 | CG | PRO | 310 | 94.715 | 76.515 | 18.203 | 1.00 | 20.71 | B | C |
| ATOM | 6026 | C | PRO | 310 | 92.884 | 74.312 | 19.384 | 1.00 | 20.14 | B | C |
| ATOM | 6027 | O | PRO | 310 | 93.368 | 73.816 | 18.374 | 1.00 | 16.93 | B | O |
| ATOM | 6028 | N | THR | 311 | 91.945 | 73.714 | 20.101 | 1.00 | 34.98 | B | N |
| ATOM | 6029 | CA | THR | 311 | 91.410 | 72.410 | 19.764 | 1.00 | 35.85 | B | C |
| ATOM | 6030 | CB | THR | 311 | 89.985 | 72.276 | 20.321 | 1.00 | 54.06 | B | C |
| ATOM | 6031 | OG1 | THR | 311 | 89.327 | 71.159 | 19.711 | 1.00 | 58.22 | B | O |
| ATOM | 6032 | CG2 | THR | 311 | 89.195 | 73.556 | 20.052 | 1.00 | 57.14 | B | C |
| ATOM | 6033 | C | THR | 311 | 91.390 | 72.103 | 18.265 | 1.00 | 37.72 | B | C |
| ATOM | 6034 | O | THR | 311 | 91.801 | 71.022 | 17.847 | 1.00 | 38.89 | B | O |
| ATOM | 6035 | N | GLU | 312 | 90.929 | 73.049 | 17.451 | 1.00 | 45.13 | B | N |
| ATOM | 6036 | CA | GLU | 312 | 90.842 | 72.825 | 16.004 | 1.00 | 43.75 | B | C |
| ATOM | 6037 | CB | GLU | 312 | 90.160 | 74.008 | 15.309 | 1.00 | 94.13 | B | C |
| ATOM | 6038 | CG | GLU | 312 | 90.848 | 75.342 | 15.528 | 1.00 | 95.89 | B | C |
| ATOM | 6039 | CD | GLU | 312 | 90.633 | 76.309 | 14.376 | 1.00 | 95.00 | B | C |
| ATOM | 6040 | OE1 | GLU | 312 | 90.998 | 77.496 | 14.516 | 1.00 | 98.35 | B | O |
| ATOM | 6041 | OE2 | GLU | 312 | 90.109 | 75.880 | 13.327 | 1.00 | 95.87 | B | O |
| ATOM | 6042 | C | GLU | 312 | 92.168 | 72.547 | 15.310 | 1.00 | 42.37 | B | C |
| ATOM | 6043 | O | GLU | 312 | 92.219 | 71.771 | 14.367 | 1.00 | 42.33 | B | O |
| ATOM | 6044 | N | LYS | 313 | 93.240 | 73.180 | 15.763 | 1.00 | 62.67 | B | N |
| ATOM | 6045 | CA | LYS | 313 | 94.537 | 72.966 | 15.141 | 1.00 | 61.87 | B | C |
| ATOM | 6046 | CB | LYS | 313 | 95.368 | 74.255 | 15.192 | 1.00 | 80.35 | B | C |
| ATOM | 6047 | CG | LYS | 313 | 94.954 | 75.308 | 14.167 | 1.00 | 80.23 | B | C |
| ATOM | 6048 | CD | LYS | 313 | 95.351 | 74.917 | 12.745 | 1.00 | 76.53 | B | C |
| ATOM | 6049 | CE | LYS | 313 | 96.790 | 75.307 | 12.430 | 1.00 | 78.57 | B | C |
| ATOM | 6050 | NZ | LYS | 313 | 97.781 | 74.730 | 13.383 | 1.00 | 83.05 | B | N |
| ATOM | 6051 | C | LYS | 313 | 95.308 | 71.832 | 15.800 | 1.00 | 63.02 | B | C |
| ATOM | 6052 | O | LYS | 313 | 96.473 | 71.610 | 15.491 | 1.00 | 65.34 | B | O |
| ATOM | 6053 | N | HIS | 314 | 94.656 | 71.103 | 16.697 | 1.00 | 42.28 | B | N |
| ATOM | 6054 | CA | HIS | 314 | 95.326 | 70.011 | 17.391 | 1.00 | 43.13 | B | C |
| ATOM | 6055 | CB | HIS | 314 | 95.631 | 70.426 | 18.828 | 1.00 | 51.27 | B | C |
| ATOM | 6056 | CG | HIS | 314 | 96.611 | 71.551 | 18.938 | 1.00 | 48.13 | B | C |
| ATOM | 6057 | CD2 | HIS | 314 | 96.423 | 72.880 | 19.111 | 1.00 | 47.60 | B | C |
| ATOM | 6058 | ND1 | HIS | 314 | 97.973 | 71.364 | 18.847 | 1.00 | 47.71 | B | N |
| ATOM | 6059 | CE1 | HIS | 314 | 98.582 | 72.530 | 18.960 | 1.00 | 47.00 | B | C |

FIG. 19A-84

```
ATOM   6060  NE2  HIS  314    97.664  73.466  19.121  1.00  47.39  B  N
ATOM   6061  C    HIS  314    94.540  68.706  17.405  1.00  43.26  B  C
ATOM   6062  O    HIS  314    95.034  67.690  17.896  1.00  46.66  B  O
ATOM   6063  N    PHE  315    93.324  68.732  16.868  1.00  55.79  B  N
ATOM   6064  CA   PHE  315    92.475  67.546  16.835  1.00  55.59  B  C
ATOM   6065  CB   PHE  315    91.175  67.834  17.578  1.00  29.85  B  C
ATOM   6066  CG   PHE  315    90.175  66.731  17.499  1.00  24.83  B  C
ATOM   6067  CD1  PHE  315    90.445  65.490  18.057  1.00  26.67  B  C
ATOM   6068  CD2  PHE  315    88.944  66.942  16.890  1.00  22.91  B  C
ATOM   6069  CE1  PHE  315    89.503  64.473  18.016  1.00  21.62  B  C
ATOM   6070  CE2  PHE  315    87.989  65.939  16.838  1.00  23.61  B  C
ATOM   6071  CZ   PHE  315    88.268  64.700  17.404  1.00  25.28  B  C
ATOM   6072  C    PHE  315    92.172  67.086  15.412  1.00  56.31  B  C
ATOM   6073  O    PHE  315    91.948  67.903  14.516  1.00  57.71  B  O
ATOM   6074  N    PHE  316    92.170  65.772  15.212  1.00  44.89  B  N
ATOM   6075  CA   PHE  316    91.898  65.200  13.899  1.00  41.94  B  C
ATOM   6076  CB   PHE  316    93.175  64.621  13.282  1.00  20.23  B  C
ATOM   6077  CG   PHE  316    94.195  65.652  12.900  1.00  23.85  B  C
ATOM   6078  CD1  PHE  316    95.118  66.114  13.828  1.00  19.44  B  C
ATOM   6079  CD2  PHE  316    94.229  66.165  11.605  1.00  20.70  B  C
ATOM   6080  CE1  PHE  316    96.066  67.074  13.475  1.00  22.01  B  C
ATOM   6081  CE2  PHE  316    95.171  67.125  11.242  1.00  23.81  B  C
ATOM   6082  CZ   PHE  316    96.092  67.580  12.180  1.00  24.04  B  C
ATOM   6083  C    PHE  316    90.841  64.107  13.990  1.00  39.87  B  C
ATOM   6084  O    PHE  316    90.845  63.302  14.910  1.00  39.11  B  O
ATOM   6085  N    ASN  317    89.938  64.088  13.020  1.00  36.72  B  N
ATOM   6086  CA   ASN  317    88.863  63.110  12.978  1.00  37.94  B  C
ATOM   6087  CB   ASN  317    87.538  63.826  12.746  1.00  58.19  B  C
ATOM   6088  CG   ASN  317    86.496  63.443  13.752  1.00  61.18  B  C
ATOM   6089  OD1  ASN  317    86.408  62.284  14.144  1.00  63.11  B  O
ATOM   6090  ND2  ASN  317    85.688  64.411  14.176  1.00  59.44  B  N
ATOM   6091  C    ASN  317    89.102  62.140  11.831  1.00  38.90  B  C
ATOM   6092  O    ASN  317    89.519  62.549  10.757  1.00  39.76  B  O
ATOM   6093  N    VAL  318    88.840  60.858  12.045  1.00  40.86  B  N
ATOM   6094  CA   VAL  318    89.027  59.872  10.981  1.00  39.49  B  C
ATOM   6095  CB   VAL  318    90.348  59.096  11.156  1.00  59.32  B  C
ATOM   6096  CG1  VAL  318    90.497  58.075  10.065  1.00  59.45  B  C
ATOM   6097  CG2  VAL  318    91.519  60.052  11.111  1.00  59.30  B  C
ATOM   6098  C    VAL  318    87.861  58.894  10.987  1.00  34.64  B  C
ATOM   6099  O    VAL  318    87.363  58.523  12.050  1.00  35.31  B  O
ATOM   6100  N    SER  319    87.417  58.482   9.803  1.00  25.74  B  N
ATOM   6101  CA   SER  319    86.300  57.557   9.711  1.00  25.00  B  C
ATOM   6102  CB   SER  319    85.769  57.502   8.275  1.00  46.83  B  C
ATOM   6103  OG   SER  319    86.801  57.222   7.348  1.00  58.78  B  O
ATOM   6104  C    SER  319    86.672  56.161  10.195  1.00  23.60  B  C
ATOM   6105  O    SER  319    85.877  55.513  10.876  1.00  21.67  B  O
ATOM   6106  N    ASP  320    87.875  55.702   9.855  1.00  29.04  B  N
ATOM   6107  CA   ASP  320    88.342  54.377  10.272  1.00  29.02  B  C
ATOM   6108  CB   ASP  320    87.700  53.292   9.391  1.00  54.50  B  C
ATOM   6109  CG   ASP  320    88.036  53.455   7.907  1.00  52.95  B  C
ATOM   6110  OD1  ASP  320    87.708  54.505   7.318  1.00  51.63  B  O
ATOM   6111  OD2  ASP  320    88.628  52.525   7.324  1.00  53.50  B  O
ATOM   6112  C    ASP  320    89.878  54.249  10.227  1.00  27.39  B  C
ATOM   6113  O    ASP  320    90.574  55.142   9.734  1.00  27.17  B  O
ATOM   6114  N    GLU  321    90.403  53.140  10.745  1.00  32.71  B  N
ATOM   6115  CA   GLU  321    91.845  52.909  10.748  1.00  33.69  B  C
ATOM   6116  CB   GLU  321    92.152  51.430  11.018  1.00  76.40  B  C
ATOM   6117  CG   GLU  321    92.439  51.066  12.469  1.00  70.24  B  C
ATOM   6118  CD   GLU  321    91.229  51.194  13.373  1.00  69.99  B  C
ATOM   6119  OE1  GLU  321    90.159  50.621  13.053  1.00  71.42  B  O
ATOM   6120  OE2  GLU  321    91.357  51.862  14.418  1.00  74.03  B  O
ATOM   6121  C    GLU  321    92.476  53.300   9.412  1.00  37.68  B  C
ATOM   6122  O    GLU  321    93.529  53.943   9.369  1.00  34.44  B  O
ATOM   6123  N    LEU  322    91.820  52.905   8.323  1.00  34.24  B  N
ATOM   6124  CA   LEU  322    92.310  53.175   6.971  1.00  36.93  B  C
ATOM   6125  CB   LEU  322    91.345  52.598   5.937  1.00  67.00  B  C
ATOM   6126  CG   LEU  322    91.361  51.081   5.743  1.00  65.63  B  C
ATOM   6127  CD1  LEU  322    92.716  50.681   5.198  1.00  67.37  B  C
ATOM   6128  CD2  LEU  322    91.058  50.353   7.063  1.00  70.68  B  C
ATOM   6129  C    LEU  322    92.566  54.632   6.643  1.00  38.52  B  C
ATOM   6130  O    LEU  322    93.607  54.971   6.097  1.00  41.87  B  O
ATOM   6131  N    ALA  323    91.617  55.492   6.974  1.00  34.22  B  N
ATOM   6132  CA   ALA  323    91.759  56.908   6.687  1.00  34.65  B  C
```

FIG. 19A-85

| | | | | | | | | | | | |
|---|---|---|---|---|---|---|---|---|---|---|---|
| ATOM | 6133 | CB | ALA | 323 | 90.420 | 57.600 | 6.897 | 1.00 | 1.87 | B | C |
| ATOM | 6134 | C | ALA | 323 | 92.859 | 57.644 | 7.476 | 1.00 | 35.06 | B | C |
| ATOM | 6135 | O | ALA | 323 | 93.171 | 58.804 | 7.181 | 1.00 | 35.08 | B | O |
| ATOM | 6136 | N | LEU | 324 | 93.447 | 56.995 | 8.476 | 1.00 | 26.80 | B | N |
| ATOM | 6137 | CA | LEU | 324 | 94.492 | 57.652 | 9.256 | 1.00 | 25.28 | B | C |
| ATOM | 6138 | CB | LEU | 324 | 95.221 | 56.640 | 10.146 | 1.00 | 29.36 | B | C |
| ATOM | 6139 | CG | LEU | 324 | 94.590 | 56.344 | 11.516 | 1.00 | 28.09 | B | C |
| ATOM | 6140 | CD1 | LEU | 324 | 95.288 | 55.158 | 12.170 | 1.00 | 27.23 | B | C |
| ATOM | 6141 | CD2 | LEU | 324 | 94.676 | 57.580 | 12.406 | 1.00 | 26.02 | B | C |
| ATOM | 6142 | C | LEU | 324 | 95.495 | 58.366 | 8.354 | 1.00 | 28.81 | B | C |
| ATOM | 6143 | O | LEU | 324 | 95.822 | 59.521 | 8.588 | 1.00 | 25.35 | B | O |
| ATOM | 6144 | N | VAL | 325 | 95.966 | 57.679 | 7.317 | 1.00 | 52.77 | B | N |
| ATOM | 6145 | CA | VAL | 325 | 96.934 | 58.246 | 6.378 | 1.00 | 56.30 | B | C |
| ATOM | 6146 | CB | VAL | 325 | 97.153 | 57.321 | 5.185 | 1.00 | 36.74 | B | C |
| ATOM | 6147 | CG1 | VAL | 325 | 97.936 | 56.099 | 5.614 | 1.00 | 36.85 | B | C |
| ATOM | 6148 | CG2 | VAL | 325 | 95.810 | 56.923 | 4.599 | 1.00 | 40.13 | B | C |
| ATOM | 6149 | C | VAL | 325 | 96.524 | 59.598 | 5.818 | 1.00 | 59.12 | B | C |
| ATOM | 6150 | O | VAL | 325 | 97.324 | 60.529 | 5.761 | 1.00 | 61.18 | B | O |
| ATOM | 6151 | N | THR | 326 | 95.277 | 59.694 | 5.384 | 1.00 | 40.34 | B | N |
| ATOM | 6152 | CA | THR | 326 | 94.743 | 60.925 | 4.818 | 1.00 | 41.75 | B | C |
| ATOM | 6153 | CB | THR | 326 | 93.298 | 60.706 | 4.344 | 1.00 | 81.94 | B | C |
| ATOM | 6154 | OG1 | THR | 326 | 92.430 | 60.600 | 5.481 | 1.00 | 83.85 | B | O |
| ATOM | 6155 | CG2 | THR | 326 | 93.206 | 59.417 | 3.534 | 1.00 | 84.31 | B | C |
| ATOM | 6156 | C | THR | 326 | 94.744 | 62.070 | 5.836 | 1.00 | 41.76 | B | C |
| ATOM | 6157 | O | THR | 326 | 93.885 | 62.952 | 5.785 | 1.00 | 40.58 | B | O |
| ATOM | 6158 | N | ILE | 327 | 95.705 | 62.052 | 6.755 | 1.00 | 36.65 | B | N |
| ATOM | 6159 | CA | ILE | 327 | 95.812 | 63.075 | 7.792 | 1.00 | 36.84 | B | C |
| ATOM | 6160 | CB | ILE | 327 | 95.078 | 62.604 | 9.085 | 1.00 | 16.25 | B | C |
| ATOM | 6161 | CG2 | ILE | 327 | 95.934 | 62.757 | 10.328 | 1.00 | 17.02 | B | C |
| ATOM | 6162 | CG1 | ILE | 327 | 93.807 | 63.408 | 9.260 | 1.00 | 16.61 | B | C |
| ATOM | 6163 | CD1 | ILE | 327 | 92.943 | 62.878 | 10.372 | 1.00 | 16.28 | B | C |
| ATOM | 6164 | C | ILE | 327 | 97.272 | 63.402 | 8.093 | 1.00 | 37.35 | B | C |
| ATOM | 6165 | O | ILE | 327 | 97.590 | 64.494 | 8.559 | 1.00 | 37.60 | B | O |
| ATOM | 6166 | N | VAL | 328 | 98.158 | 62.455 | 7.804 | 1.00 | 43.89 | B | N |
| ATOM | 6167 | CA | VAL | 328 | 99.575 | 62.643 | 8.060 | 1.00 | 46.03 | B | C |
| ATOM | 6168 | CB | VAL | 328 | 100.407 | 61.469 | 7.510 | 1.00 | 54.81 | B | C |
| ATOM | 6169 | CG1 | VAL | 328 | 99.871 | 60.157 | 8.061 | 1.00 | 56.76 | B | C |
| ATOM | 6170 | CG2 | VAL | 328 | 100.381 | 61.480 | 5.997 | 1.00 | 56.08 | B | C |
| ATOM | 6171 | C | VAL | 328 | 100.121 | 63.943 | 7.481 | 1.00 | 45.95 | B | C |
| ATOM | 6172 | O | VAL | 328 | 100.998 | 64.563 | 8.075 | 1.00 | 45.23 | B | O |
| ATOM | 6173 | N | LYS | 329 | 99.611 | 64.366 | 6.331 | 1.00 | 44.51 | B | N |
| ATOM | 6174 | CA | LYS | 329 | 100.097 | 65.609 | 5.732 | 1.00 | 43.72 | B | C |
| ATOM | 6175 | CB | LYS | 329 | 99.471 | 65.824 | 4.356 | 1.00 | 45.34 | B | C |
| ATOM | 6176 | CG | LYS | 329 | 100.174 | 66.880 | 3.520 | 1.00 | 46.89 | B | C |
| ATOM | 6177 | CD | LYS | 329 | 99.423 | 67.129 | 2.220 | 1.00 | 49.21 | B | C |
| ATOM | 6178 | CE | LYS | 329 | 100.179 | 68.074 | 1.298 | 1.00 | 52.25 | B | C |
| ATOM | 6179 | NZ | LYS | 329 | 101.450 | 67.466 | 0.831 | 1.00 | 55.93 | B | N |
| ATOM | 6180 | C | LYS | 329 | 99.762 | 66.797 | 6.640 | 1.00 | 41.89 | B | C |
| ATOM | 6181 | O | LYS | 329 | 100.640 | 67.552 | 7.056 | 1.00 | 43.10 | B | O |
| ATOM | 6182 | N | ALA | 330 | 98.483 | 66.957 | 6.952 | 1.00 | 14.46 | B | N |
| ATOM | 6183 | CA | ALA | 330 | 98.053 | 68.043 | 7.814 | 1.00 | 14.49 | B | C |
| ATOM | 6184 | CB | ALA | 330 | 96.538 | 68.052 | 7.906 | 1.00 | 26.19 | B | C |
| ATOM | 6185 | C | ALA | 330 | 98.657 | 67.910 | 9.210 | 1.00 | 15.64 | B | C |
| ATOM | 6186 | O | ALA | 330 | 99.090 | 68.896 | 9.796 | 1.00 | 15.54 | B | O |
| ATOM | 6187 | N | LEU | 331 | 98.666 | 66.688 | 9.745 | 1.00 | 29.61 | B | N |
| ATOM | 6188 | CA | LEU | 331 | 99.200 | 66.447 | 11.078 | 1.00 | 27.25 | B | C |
| ATOM | 6189 | CB | LEU | 331 | 99.108 | 64.969 | 11.454 | 1.00 | 20.84 | B | C |
| ATOM | 6190 | CG | LEU | 331 | 99.086 | 64.642 | 12.958 | 1.00 | 17.26 | B | C |
| ATOM | 6191 | CD1 | LEU | 331 | 99.332 | 63.152 | 13.131 | 1.00 | 18.89 | B | C |
| ATOM | 6192 | CD2 | LEU | 331 | 100.130 | 65.436 | 13.722 | 1.00 | 12.95 | B | C |
| ATOM | 6193 | C | LEU | 331 | 100.647 | 66.860 | 11.070 | 1.00 | 27.28 | B | C |
| ATOM | 6194 | O | LEU | 331 | 101.090 | 67.613 | 11.931 | 1.00 | 26.63 | B | O |
| ATOM | 6195 | N | GLY | 332 | 101.374 | 66.358 | 10.079 | 1.00 | 36.12 | B | N |
| ATOM | 6196 | CA | GLY | 332 | 102.784 | 66.666 | 9.949 | 1.00 | 37.22 | B | C |
| ATOM | 6197 | C | GLY | 332 | 103.089 | 68.150 | 9.917 | 1.00 | 37.48 | B | C |
| ATOM | 6198 | O | GLY | 332 | 103.940 | 68.628 | 10.670 | 1.00 | 41.35 | B | O |
| ATOM | 6199 | N | GLU | 333 | 102.398 | 68.892 | 9.058 | 1.00 | 41.72 | B | N |
| ATOM | 6200 | CA | GLU | 333 | 102.653 | 70.317 | 8.967 | 1.00 | 39.78 | B | C |
| ATOM | 6201 | CB | GLU | 333 | 102.052 | 70.889 | 7.683 | 1.00 | 98.89 | B | C |
| ATOM | 6202 | CG | GLU | 333 | 100.546 | 70.988 | 7.678 | 1.00 | 97.26 | B | C |
| ATOM | 6203 | CD | GLU | 333 | 100.018 | 71.598 | 6.400 | 1.00 | 97.28 | B | C |
| ATOM | 6204 | OE1 | GLU | 333 | 98.795 | 71.849 | 6.322 | 1.00 | 99.33 | B | O |
| ATOM | 6205 | OE2 | GLU | 333 | 100.824 | 71.823 | 5.472 | 1.00 | 91.40 | B | O |

FIG. 19A-86

```
ATOM   6206  C    GLU  333    102.120  71.069  10.179  1.00   38.76  B  C
ATOM   6207  O    GLU  333    102.747  72.010  10.650  1.00   38.38  B  O
ATOM   6208  N    ARG  334    100.969  70.659  10.695  1.00   43.09  B  N
ATOM   6209  CA   ARG  334    100.398  71.340  11.847  1.00   46.47  B  C
ATOM   6210  CB   ARG  334     99.089  70.667  12.265  1.00   41.05  B  C
ATOM   6211  CG   ARG  334     98.167  71.568  13.056  1.00   40.34  B  C
ATOM   6212  CD   ARG  334     96.722  71.432  12.592  1.00   39.10  B  C
ATOM   6213  NE   ARG  334     96.544  71.911  11.222  1.00   34.65  B  N
ATOM   6214  CZ   ARG  334     95.446  71.721  10.488  1.00   38.74  B  C
ATOM   6215  NH1  ARG  334     94.407  71.052  10.987  1.00   35.48  B  N
ATOM   6216  NH2  ARG  334     95.388  72.197   9.246  1.00   44.88  B  N
ATOM   6217  C    ARG  334    101.419  71.321  12.980  1.00   47.77  B  C
ATOM   6218  O    ARG  334    101.633  72.329  13.643  1.00   44.69  B  O
ATOM   6219  N    ILE  335    102.060  70.177  13.192  1.00   95.68  B  N
ATOM   6220  CA   ILE  335    103.084  70.066  14.227  1.00   95.61  B  C
ATOM   6221  CB   ILE  335    103.349  68.565  14.599  1.00   69.44  B  C
ATOM   6222  CG2  ILE  335    103.371  67.701  13.359  1.00   72.22  B  C
ATOM   6223  CG1  ILE  335    104.671  68.420  15.350  1.00   70.66  B  C
ATOM   6224  CD1  ILE  335    105.043  66.983  15.628  1.00   73.45  B  C
ATOM   6225  C    ILE  335    104.346  70.716  13.653  1.00   93.90  B  C
ATOM   6226  O    ILE  335    105.317  70.979  14.364  1.00   96.50  B  O
ATOM   6227  N    PHE  336    104.273  71.011  12.356  1.00  144.26  B  N
ATOM   6228  CA   PHE  336    105.347  71.604  11.560  1.00  143.89  B  C
ATOM   6229  CB   PHE  336    105.336  73.156  11.625  1.00   83.50  B  C
ATOM   6230  CG   PHE  336    105.600  73.748  12.992  1.00   79.82  B  C
ATOM   6231  CD1  PHE  336    106.696  73.355  13.760  1.00   79.24  B  C
ATOM   6232  CD2  PHE  336    104.783  74.762  13.479  1.00   77.77  B  C
ATOM   6233  CE1  PHE  336    106.973  73.966  14.988  1.00   69.57  B  C
ATOM   6234  CE2  PHE  336    105.053  75.377  14.702  1.00   72.13  B  C
ATOM   6235  CZ   PHE  336    106.152  74.977  15.457  1.00   72.59  B  C
ATOM   6236  C    PHE  336    106.737  71.068  11.853  1.00  143.92  B  C
ATOM   6237  O    PHE  336    106.889  70.255  12.788  1.00  123.54  B  O
ATOM   6238  OXT  PHE  336    107.658  71.461  11.111  1.00   66.99  B  O
ATOM   6239  CB   GLU    1     68.990  38.972  10.337  1.00  143.47  X  C
ATOM   6240  CG   GLU    1     68.785  37.653  11.053  1.00  143.47  X  C
ATOM   6241  CD   GLU    1     68.300  36.572  10.118  1.00  143.47  X  C
ATOM   6242  OE1  GLU    1     69.012  36.278   9.134  1.00  143.47  X  O
ATOM   6243  OE2  GLU    1     67.209  36.019  10.363  1.00  143.47  X  O
ATOM   6244  C    GLU    1     71.024  39.462  11.710  1.00   74.19  X  C
ATOM   6245  O    GLU    1     71.492  38.415  11.265  1.00   74.19  X  O
ATOM   6246  N    GLU    1     69.921  41.257  10.328  1.00   74.19  X  N
ATOM   6247  CA   GLU    1     69.711  40.037  11.162  1.00   74.19  X  C
ATOM   6248  N    VAL    2     71.613  40.151  12.681  1.00   55.61  X  N
ATOM   6249  CA   VAL    2     72.858  39.694  13.284  1.00   55.61  X  C
ATOM   6250  CB   VAL    2     73.533  40.812  14.089  1.00   66.95  X  C
ATOM   6251  CG1  VAL    2     74.850  40.323  14.647  1.00   66.95  X  C
ATOM   6252  CG2  VAL    2     73.752  42.021  13.210  1.00   66.95  X  C
ATOM   6253  C    VAL    2     72.566  38.543  14.232  1.00   55.61  X  C
ATOM   6254  O    VAL    2     71.728  38.673  15.127  1.00   55.61  X  O
ATOM   6255  N    GLN    3     73.258  37.421  14.045  1.00   39.72  X  N
ATOM   6256  CA   GLN    3     73.044  36.261  14.908  1.00   39.72  X  C
ATOM   6257  CB   GLN    3     71.807  35.502  14.455  1.00  102.66  X  C
ATOM   6258  CG   GLN    3     71.852  35.144  13.002  1.00  102.66  X  C
ATOM   6259  CD   GLN    3     70.688  34.291  12.604  1.00  102.66  X  C
ATOM   6260  OE1  GLN    3     69.537  34.635  12.873  1.00  102.66  X  O
ATOM   6261  NE2  GLN    3     70.972  33.168  11.955  1.00  102.66  X  N
ATOM   6262  C    GLN    3     74.213  35.288  15.002  1.00   39.72  X  C
ATOM   6263  O    GLN    3     75.064  35.207  14.108  1.00   39.72  X  O
ATOM   6264  N    LEU    4     74.231  34.553  16.109  1.00   34.59  X  N
ATOM   6265  CA   LEU    4     75.260  33.555  16.389  1.00   34.59  X  C
ATOM   6266  CB   LEU    4     76.043  33.931  17.653  1.00   34.08  X  C
ATOM   6267  CG   LEU    4     77.107  35.040  17.665  1.00   34.08  X  C
ATOM   6268  CD1  LEU    4     77.119  35.820  16.353  1.00   34.08  X  C
ATOM   6269  CD2  LEU    4     76.844  35.950  18.863  1.00   34.08  X  C
ATOM   6270  C    LEU    4     74.581  32.212  16.615  1.00   34.59  X  C
ATOM   6271  O    LEU    4     73.737  32.080  17.503  1.00   34.59  X  O
ATOM   6272  N    VAL    5     74.933  31.218  15.806  1.00   36.99  X  N
ATOM   6273  CA   VAL    5     74.350  29.889  15.961  1.00   36.99  X  C
ATOM   6274  CB   VAL    5     73.536  29.456  14.698  1.00   37.13  X  C
ATOM   6275  CG1  VAL    5     74.285  29.815  13.430  1.00   37.13  X  C
ATOM   6276  CG2  VAL    5     73.264  27.963  14.744  1.00   37.13  X  C
ATOM   6277  C    VAL    5     75.429  28.861  16.277  1.00   36.99  X  C
ATOM   6278  O    VAL    5     76.163  28.404  15.398  1.00   36.99  X  O
```

FIG. 19A-87

| ATOM | 6279 | N | GLU | 6 | 75.519 | 28.517 | 17.555 | 1.00 | 44.32 | X | N |
|---|---|---|---|---|---|---|---|---|---|---|---|
| ATOM | 6280 | CA | GLU | 6 | 76.499 | 27.550 | 18.020 | 1.00 | 44.32 | X | C |
| ATOM | 6281 | CB | GLU | 6 | 76.924 | 27.884 | 19.457 | 1.00 | 53.96 | X | C |
| ATOM | 6282 | CG | GLU | 6 | 75.844 | 28.531 | 20.292 | 1.00 | 53.96 | X | C |
| ATOM | 6283 | CD | GLU | 6 | 76.340 | 28.943 | 21.659 | 1.00 | 53.96 | X | C |
| ATOM | 6284 | OE1 | GLU | 6 | 75.590 | 29.646 | 22.368 | 1.00 | 53.96 | X | O |
| ATOM | 6285 | OE2 | GLU | 6 | 77.472 | 28.561 | 22.028 | 1.00 | 53.96 | X | O |
| ATOM | 6286 | C | GLU | 6 | 76.029 | 26.095 | 17.930 | 1.00 | 44.32 | X | C |
| ATOM | 6287 | O | GLU | 6 | 74.856 | 25.813 | 17.668 | 1.00 | 44.32 | X | O |
| ATOM | 6288 | N | SER | 7 | 76.980 | 25.185 | 18.135 | 1.00 | 42.31 | X | N |
| ATOM | 6289 | CA | SER | 7 | 76.758 | 23.745 | 18.091 | 1.00 | 42.31 | X | C |
| ATOM | 6290 | CB | SER | 7 | 76.762 | 23.261 | 16.642 | 1.00 | 44.31 | X | C |
| ATOM | 6291 | OG | SER | 7 | 77.832 | 23.845 | 15.922 | 1.00 | 44.31 | X | O |
| ATOM | 6292 | C | SER | 7 | 77.919 | 23.123 | 18.848 | 1.00 | 42.31 | X | C |
| ATOM | 6293 | O | SER | 7 | 78.889 | 23.813 | 19.138 | 1.00 | 42.31 | X | O |
| ATOM | 6294 | N | GLY | 8 | 77.822 | 21.838 | 19.178 | 1.00 | 39.85 | X | N |
| ATOM | 6295 | CA | GLY | 8 | 78.908 | 21.177 | 19.893 | 1.00 | 39.85 | X | C |
| ATOM | 6296 | C | GLY | 8 | 78.569 | 20.747 | 21.313 | 1.00 | 39.85 | X | C |
| ATOM | 6297 | O | GLY | 8 | 79.330 | 20.016 | 21.962 | 1.00 | 39.85 | X | O |
| ATOM | 6298 | N | GLY | 9 | 77.417 | 21.199 | 21.795 | 1.00 | 54.13 | X | N |
| ATOM | 6299 | CA | GLY | 9 | 76.998 | 20.852 | 23.138 | 1.00 | 54.13 | X | C |
| ATOM | 6300 | C | GLY | 9 | 76.467 | 19.439 | 23.283 | 1.00 | 54.13 | X | C |
| ATOM | 6301 | O | GLY | 9 | 75.390 | 19.102 | 22.783 | 1.00 | 54.13 | X | O |
| ATOM | 6302 | N | GLY | 10 | 77.235 | 18.606 | 23.972 | 1.00 | 51.55 | X | N |
| ATOM | 6303 | CA | GLY | 10 | 76.825 | 17.236 | 24.195 | 1.00 | 51.55 | X | C |
| ATOM | 6304 | C | GLY | 10 | 77.359 | 16.807 | 25.544 | 1.00 | 51.55 | X | C |
| ATOM | 6305 | O | GLY | 10 | 77.723 | 17.651 | 26.370 | 1.00 | 51.55 | X | O |
| ATOM | 6306 | N | LEU | 11 | 77.409 | 15.500 | 25.776 | 1.00 | 54.73 | X | N |
| ATOM | 6307 | CA | LEU | 11 | 77.930 | 14.981 | 27.032 | 1.00 | 54.73 | X | C |
| ATOM | 6308 | CB | LEU | 11 | 76.994 | 13.903 | 27.583 | 1.00 | 40.69 | X | C |
| ATOM | 6309 | CG | LEU | 11 | 77.583 | 13.086 | 28.735 | 1.00 | 40.69 | X | C |
| ATOM | 6310 | CD1 | LEU | 11 | 78.170 | 14.011 | 29.795 | 1.00 | 40.69 | X | C |
| ATOM | 6311 | CD2 | LEU | 11 | 76.508 | 12.198 | 29.317 | 1.00 | 40.69 | X | C |
| ATOM | 6312 | C | LEU | 11 | 79.341 | 14.412 | 26.852 | 1.00 | 54.73 | X | C |
| ATOM | 6313 | O | LEU | 11 | 79.664 | 13.853 | 25.806 | 1.00 | 54.73 | X | O |
| ATOM | 6314 | N | VAL | 12 | 80.177 | 14.576 | 27.872 | 1.00 | 43.40 | X | N |
| ATOM | 6315 | CA | VAL | 12 | 81.552 | 14.079 | 27.848 | 1.00 | 43.40 | X | C |
| ATOM | 6316 | CB | VAL | 12 | 82.538 | 15.118 | 27.273 | 1.00 | 57.73 | X | C |
| ATOM | 6317 | CG1 | VAL | 12 | 82.222 | 15.388 | 25.812 | 1.00 | 57.73 | X | C |
| ATOM | 6318 | CG2 | VAL | 12 | 82.473 | 16.404 | 28.086 | 1.00 | 57.73 | X | C |
| ATOM | 6319 | C | VAL | 12 | 81.991 | 13.753 | 29.269 | 1.00 | 43.40 | X | C |
| ATOM | 6320 | O | VAL | 12 | 81.490 | 14.344 | 30.230 | 1.00 | 43.40 | X | O |
| ATOM | 6321 | N | GLN | 13 | 82.931 | 12.821 | 29.403 | 1.00 | 46.11 | X | N |
| ATOM | 6322 | CA | GLN | 13 | 83.404 | 12.420 | 30.720 | 1.00 | 46.11 | X | C |
| ATOM | 6323 | CB | GLN | 13 | 83.873 | 10.965 | 30.676 | 1.00 | 148.60 | X | C |
| ATOM | 6324 | CG | GLN | 13 | 82.843 | 10.015 | 30.094 | 1.00 | 148.60 | X | C |
| ATOM | 6325 | CD | GLN | 13 | 83.232 | 8.560 | 30.263 | 1.00 | 148.60 | X | C |
| ATOM | 6326 | OE1 | GLN | 13 | 84.322 | 8.145 | 29.868 | 1.00 | 148.60 | X | O |
| ATOM | 6327 | NE2 | GLN | 13 | 82.337 | 7.774 | 30.852 | 1.00 | 148.60 | X | N |
| ATOM | 6328 | C | GLN | 13 | 84.532 | 13.311 | 31.234 | 1.00 | 46.11 | X | C |
| ATOM | 6329 | O | GLN | 13 | 85.186 | 14.002 | 30.454 | 1.00 | 46.11 | X | O |
| ATOM | 6330 | N | PRO | 14 | 84.763 | 13.319 | 32.563 | 1.00 | 39.23 | X | N |
| ATOM | 6331 | CD | PRO | 14 | 83.989 | 12.657 | 33.630 | 1.00 | 55.62 | X | C |
| ATOM | 6332 | CA | PRO | 14 | 85.831 | 14.141 | 33.141 | 1.00 | 39.23 | X | C |
| ATOM | 6333 | CB | PRO | 14 | 85.902 | 13.648 | 34.581 | 1.00 | 55.62 | X | C |
| ATOM | 6334 | CG | PRO | 14 | 84.474 | 13.374 | 34.887 | 1.00 | 55.62 | X | C |
| ATOM | 6335 | C | PRO | 14 | 87.122 | 13.905 | 32.392 | 1.00 | 39.23 | X | C |
| ATOM | 6336 | O | PRO | 14 | 87.357 | 12.810 | 31.885 | 1.00 | 39.23 | X | O |
| ATOM | 6337 | N | GLY | 15 | 87.954 | 14.935 | 32.320 | 1.00 | 28.04 | X | N |
| ATOM | 6338 | CA | GLY | 15 | 89.220 | 14.816 | 31.616 | 1.00 | 28.04 | X | C |
| ATOM | 6339 | C | GLY | 15 | 89.037 | 14.807 | 30.109 | 1.00 | 28.04 | X | C |
| ATOM | 6340 | O | GLY | 15 | 89.990 | 14.979 | 29.352 | 1.00 | 28.04 | X | O |
| ATOM | 6341 | N | GLY | 16 | 87.801 | 14.613 | 29.672 | 1.00 | 22.75 | X | N |
| ATOM | 6342 | CA | GLY | 16 | 87.529 | 14.583 | 28.250 | 1.00 | 22.75 | X | C |
| ATOM | 6343 | C | GLY | 16 | 87.705 | 15.912 | 27.539 | 1.00 | 22.75 | X | C |
| ATOM | 6344 | O | GLY | 16 | 87.887 | 16.969 | 28.155 | 1.00 | 22.75 | X | O |
| ATOM | 6345 | N | SER | 17 | 87.633 | 15.845 | 26.217 | 1.00 | 36.95 | X | N |
| ATOM | 6346 | CA | SER | 17 | 87.789 | 17.014 | 25.371 | 1.00 | 36.95 | X | C |
| ATOM | 6347 | CB | SER | 17 | 88.962 | 16.795 | 24.417 | 1.00 | 47.78 | X | C |
| ATOM | 6348 | OG | SER | 17 | 89.203 | 17.952 | 23.645 | 1.00 | 47.78 | X | O |
| ATOM | 6349 | C | SER | 17 | 86.509 | 17.311 | 24.581 | 1.00 | 36.95 | X | C |
| ATOM | 6350 | O | SER | 17 | 85.817 | 16.402 | 24.106 | 1.00 | 36.95 | X | O |
| ATOM | 6351 | N | LEU | 18 | 86.199 | 18.593 | 24.429 | 1.00 | 50.75 | X | N |

FIG. 19A-88

```
ATOM   6352  CA   LEU  18    84.995  18.978  23.719  1.00  50.75  X  C
ATOM   6353  CB   LEU  18    83.833  18.944  24.701  1.00  37.38  X  C
ATOM   6354  CG   LEU  18    82.463  19.285  24.146  1.00  37.38  X  C
ATOM   6355  CD1  LEU  18    82.177  18.476  22.874  1.00  37.38  X  C
ATOM   6356  CD2  LEU  18    81.442  19.012  25.239  1.00  37.38  X  C
ATOM   6357  C    LEU  18    85.107  20.355  23.069  1.00  50.75  X  C
ATOM   6358  O    LEU  18    85.530  21.313  23.714  1.00  50.75  X  O
ATOM   6359  N    ARG  19    84.737  20.454  21.792  1.00  27.07  X  N
ATOM   6360  CA   ARG  19    84.805  21.739  21.097  1.00  27.07  X  C
ATOM   6361  CB   ARG  19    85.774  21.708  19.924  1.00  43.18  X  C
ATOM   6362  CG   ARG  19    85.825  23.068  19.238  1.00  43.18  X  C
ATOM   6363  CD   ARG  19    86.689  23.075  18.015  1.00  43.18  X  C
ATOM   6364  NE   ARG  19    86.060  22.389  16.896  1.00  43.18  X  N
ATOM   6365  CZ   ARG  19    86.564  22.371  15.666  1.00  43.18  X  C
ATOM   6366  NH1  ARG  19    87.708  23.006  15.407  1.00  43.18  X  N
ATOM   6367  NH2  ARG  19    85.924  21.725  14.696  1.00  43.18  X  N
ATOM   6368  C    ARG  19    83.501  22.302  20.558  1.00  27.07  X  C
ATOM   6369  O    ARG  19    82.895  21.745  19.625  1.00  27.07  X  O
ATOM   6370  N    LEU  20    83.109  23.438  21.135  1.00  30.57  X  N
ATOM   6371  CA   LEU  20    81.908  24.150  20.731  1.00  30.57  X  C
ATOM   6372  CB   LEU  20    81.354  24.965  21.896  1.00  36.53  X  C
ATOM   6373  CG   LEU  20    80.981  24.196  23.159  1.00  36.53  X  C
ATOM   6374  CD1  LEU  20    80.415  25.142  24.218  1.00  36.53  X  C
ATOM   6375  CD2  LEU  20    79.964  23.135  22.802  1.00  36.53  X  C
ATOM   6376  C    LEU  20    82.304  25.098  19.618  1.00  30.57  X  C
ATOM   6377  O    LEU  20    83.313  25.784  19.723  1.00  30.57  X  O
ATOM   6378  N    SER  21    81.527  25.122  18.544  1.00  31.77  X  N
ATOM   6379  CA   SER  21    81.789  26.024  17.426  1.00  31.77  X  C
ATOM   6380  CB   SER  21    81.876  25.252  16.117  1.00  32.65  X  C
ATOM   6381  OG   SER  21    80.580  24.896  15.682  1.00  32.65  X  O
ATOM   6382  C    SER  21    80.593  26.971  17.383  1.00  31.77  X  C
ATOM   6383  O    SER  21    79.591  26.738  18.057  1.00  31.77  X  O
ATOM   6384  N    CYS  22    80.673  28.024  16.585  1.00  49.03  X  N
ATOM   6385  CA   CYS  22    79.580  28.981  16.526  1.00  49.03  X  C
ATOM   6386  C    CYS  22    79.725  29.812  15.272  1.00  49.03  X  C
ATOM   6387  O    CYS  22    80.743  30.484  15.096  1.00  49.03  X  O
ATOM   6388  CB   CYS  22    79.643  29.849  17.788  1.00  49.62  X  C
ATOM   6389  SG   CYS  22    78.993  31.555  17.774  1.00  49.62  X  S
ATOM   6390  N    ALA  23    78.724  29.744  14.389  1.00  43.82  X  N
ATOM   6391  CA   ALA  23    78.742  30.509  13.136  1.00  43.82  X  C
ATOM   6392  CB   ALA  23    78.022  29.768  12.021  1.00   1.87  X  C
ATOM   6393  C    ALA  23    78.093  31.854  13.329  1.00  43.82  X  C
ATOM   6394  O    ALA  23    77.118  31.999  14.070  1.00  43.82  X  O
ATOM   6395  N    ALA  24    78.644  32.843  12.645  1.00  28.70  X  N
ATOM   6396  CA   ALA  24    78.129  34.190  12.735  1.00  28.70  X  C
ATOM   6397  CB   ALA  24    79.199  35.129  13.323  1.00  18.49  X  C
ATOM   6398  C    ALA  24    77.725  34.659  11.356  1.00  28.70  X  C
ATOM   6399  O    ALA  24    78.213  34.160  10.345  1.00  28.70  X  O
ATOM   6400  N    SER  25    76.816  35.620  11.338  1.00  39.45  X  N
ATOM   6401  CA   SER  25    76.338  36.218  10.108  1.00  39.45  X  C
ATOM   6402  CB   SER  25    75.279  35.322   9.443  1.00  48.28  X  C
ATOM   6403  OG   SER  25    74.163  35.090  10.287  1.00  48.28  X  O
ATOM   6404  C    SER  25    75.751  37.575  10.486  1.00  39.45  X  C
ATOM   6405  O    SER  25    75.425  37.819  11.656  1.00  39.45  X  O
ATOM   6406  N    GLY  26    75.651  38.464   9.506  1.00  15.13  X  N
ATOM   6407  CA   GLY  26    75.093  39.773   9.767  1.00  15.13  X  C
ATOM   6408  C    GLY  26    76.061  40.808  10.313  1.00  15.13  X  C
ATOM   6409  O    GLY  26    75.650  41.692  11.070  1.00  15.13  X  O
ATOM   6410  N    PHE  27    77.336  40.697   9.941  1.00  51.25  X  N
ATOM   6411  CA   PHE  27    78.375  41.638  10.358  1.00  51.25  X  C
ATOM   6412  CB   PHE  27    78.322  41.921  11.860  1.00  33.43  X  C
ATOM   6413  CG   PHE  27    78.647  40.736  12.720  1.00  33.43  X  C
ATOM   6414  CD1  PHE  27    77.696  39.749  12.958  1.00  33.43  X  C
ATOM   6415  CD2  PHE  27    79.891  40.629  13.337  1.00  33.43  X  C
ATOM   6416  CE1  PHE  27    77.978  38.673  13.810  1.00  33.43  X  C
ATOM   6417  CE2  PHE  27    80.186  39.558  14.190  1.00  33.43  X  C
ATOM   6418  CZ   PHE  27    79.227  38.581  14.428  1.00  33.43  X  C
ATOM   6419  C    PHE  27    79.748  41.100  10.012  1.00  51.25  X  C
ATOM   6420  O    PHE  27    79.966  39.894  10.027  1.00  51.25  X  O
ATOM   6421  N    THR  28    80.671  42.006   9.707  1.00  31.93  X  N
ATOM   6422  CA   THR  28    82.031  41.637   9.348  1.00  31.93  X  C
ATOM   6423  CB   THR  28    82.821  42.872   8.910  1.00  48.89  X  C
ATOM   6424  OG1  THR  28    82.126  43.520   7.836  1.00  48.89  X  O
```

FIG. 19A-89

```
ATOM   6425  CG2 THR   28      84.212  42.474   8.454  1.00  48.89      X  C
ATOM   6426  C   THR   28      82.744  40.981  10.519  1.00  31.93      X  C
ATOM   6427  O   THR   28      83.431  41.640  11.286  1.00  31.93      X  O
ATOM   6428  N   PHE   29      82.576  39.671  10.636  1.00  37.68      X  N
ATOM   6429  CA  PHE   29      83.166  38.876  11.712  1.00  37.68      X  C
ATOM   6430  CB  PHE   29      83.068  37.386  11.352  1.00  38.41      X  C
ATOM   6431  CG  PHE   29      83.484  36.454  12.462  1.00  38.41      X  C
ATOM   6432  CD1 PHE   29      82.795  36.440  13.676  1.00  38.41      X  C
ATOM   6433  CD2 PHE   29      84.570  35.587  12.296  1.00  38.41      X  C
ATOM   6434  CE1 PHE   29      83.183  35.577  14.709  1.00  38.41      X  C
ATOM   6435  CE2 PHE   29      84.967  34.718  13.324  1.00  38.41      X  C
ATOM   6436  CZ  PHE   29      84.272  34.715  14.530  1.00  38.41      X  C
ATOM   6437  C   PHE   29      84.616  39.225  12.021  1.00  37.68      X  C
ATOM   6438  O   PHE   29      84.958  39.552  13.160  1.00  37.68      X  O
ATOM   6439  N   SER   30      85.462  39.160  10.998  1.00  22.05      X  N
ATOM   6440  CA  SER   30      86.890  39.421  11.157  1.00  22.05      X  C
ATOM   6441  CB  SER   30      87.553  39.545   9.783  1.00  37.79      X  C
ATOM   6442  OG  SER   30      86.886  40.481   8.959  1.00  37.79      X  O
ATOM   6443  C   SER   30      87.270  40.622  12.014  1.00  22.05      X  C
ATOM   6444  O   SER   30      88.326  40.634  12.639  1.00  22.05      X  O
ATOM   6445  N   ARG   31      86.395  41.615  12.063  1.00  29.69      X  N
ATOM   6446  CA  ARG   31      86.651  42.846  12.801  1.00  29.69      X  C
ATOM   6447  CB  ARG   31      85.819  43.956  12.162  1.00  51.15      X  C
ATOM   6448  CG  ARG   31      86.068  45.323  12.719  1.00  51.15      X  C
ATOM   6449  CD  ARG   31      84.999  46.281  12.231  1.00  51.15      X  C
ATOM   6450  NE  ARG   31      84.964  46.383  10.772  1.00  51.15      X  N
ATOM   6451  CZ  ARG   31      85.899  46.974  10.038  1.00  51.15      X  C
ATOM   6452  NH1 ARG   31      86.959  47.523  10.621  1.00  51.15      X  N
ATOM   6453  NH2 ARG   31      85.764  47.027   8.722  1.00  51.15      X  N
ATOM   6454  C   ARG   31      86.425  42.833  14.329  1.00  29.69      X  C
ATOM   6455  O   ARG   31      87.226  43.399  15.080  1.00  29.69      X  O
ATOM   6456  N   TYR   32      85.352  42.185  14.785  1.00  39.46      X  N
ATOM   6457  CA  TYR   32      85.009  42.144  16.217  1.00  39.46      X  C
ATOM   6458  CB  TYR   32      83.506  41.880  16.409  1.00  51.56      X  C
ATOM   6459  CG  TYR   32      82.601  42.689  15.516  1.00  51.56      X  C
ATOM   6460  CD1 TYR   32      82.540  42.437  14.148  1.00  51.56      X  C
ATOM   6461  CE1 TYR   32      81.721  43.181  13.316  1.00  51.56      X  C
ATOM   6462  CD2 TYR   32      81.811  43.714  16.034  1.00  51.56      X  C
ATOM   6463  CE2 TYR   32      80.985  44.467  15.209  1.00  51.56      X  C
ATOM   6464  CZ  TYR   32      80.946  44.193  13.851  1.00  51.56      X  C
ATOM   6465  OH  TYR   32      80.135  44.929  13.015  1.00  51.56      X  O
ATOM   6466  C   TYR   32      85.761  41.108  17.037  1.00  39.46      X  C
ATOM   6467  O   TYR   32      86.159  40.072  16.515  1.00  39.46      X  O
ATOM   6468  N   THR   33      85.943  41.386  18.328  1.00  29.44      X  N
ATOM   6469  CA  THR   33      86.611  40.421  19.191  1.00  29.44      X  C
ATOM   6470  CB  THR   33      87.510  41.080  20.315  1.00  20.65      X  C
ATOM   6471  OG1 THR   33      86.749  41.242  21.514  1.00  20.65      X  O
ATOM   6472  CG2 THR   33      88.072  42.437  19.866  1.00  20.65      X  C
ATOM   6473  C   THR   33      85.483  39.614  19.835  1.00  29.44      X  C
ATOM   6474  O   THR   33      84.632  40.167  20.536  1.00  29.44      X  O
ATOM   6475  N   MET   34      85.484  38.307  19.568  1.00  30.35      X  N
ATOM   6476  CA  MET   34      84.474  37.391  20.084  1.00  30.35      X  C
ATOM   6477  CB  MET   34      84.235  36.284  19.067  1.00  43.39      X  C
ATOM   6478  CG  MET   34      84.070  36.798  17.652  1.00  43.39      X  C
ATOM   6479  SD  MET   34      82.775  38.029  17.525  1.00  43.39      X  S
ATOM   6480  CE  MET   34      81.376  37.024  17.198  1.00  43.39      X  C
ATOM   6481  C   MET   34      84.867  36.785  21.430  1.00  30.35      X  C
ATOM   6482  O   MET   34      86.049  36.761  21.790  1.00  30.35      X  O
ATOM   6483  N   SER   35      83.866  36.293  22.164  1.00  35.95      X  N
ATOM   6484  CA  SER   35      84.073  35.701  23.487  1.00  35.95      X  C
ATOM   6485  CB  SER   35      83.875  36.765  24.580  1.00  34.42      X  C
ATOM   6486  OG  SER   35      84.740  37.878  24.420  1.00  34.42      X  O
ATOM   6487  C   SER   35      83.105  34.548  23.761  1.00  35.95      X  C
ATOM   6488  O   SER   35      82.191  34.290  22.978  1.00  35.95      X  O
ATOM   6489  N   TRP   36      83.323  33.856  24.879  1.00  43.17      X  N
ATOM   6490  CA  TRP   36      82.457  32.758  25.309  1.00  43.17      X  C
ATOM   6491  CB  TRP   36      83.159  31.383  25.200  1.00  32.84      X  C
ATOM   6492  CG  TRP   36      83.355  30.875  23.782  1.00  32.84      X  C
ATOM   6493  CD2 TRP   36      82.419  30.118  22.998  1.00  32.84      X  C
ATOM   6494  CE2 TRP   36      82.982  29.957  21.711  1.00  32.84      X  C
ATOM   6495  CE3 TRP   36      81.153  29.564  23.257  1.00  32.84      X  C
ATOM   6496  CD1 TRP   36      84.419  31.124  22.962  1.00  32.84      X  C
ATOM   6497  NE1 TRP   36      84.201  30.579  21.716  1.00  32.84      X  N
```

FIG. 19A-90

```
ATOM   6498  CZ2  TRP  36    82.324  29.267  20.681  1.00  32.84   X  C
ATOM   6499  CZ3  TRP  36    80.495  28.877  22.228  1.00  32.84   X  C
ATOM   6500  CH2  TRP  36    81.086  28.738  20.957  1.00  32.84   X  C
ATOM   6501  C    TRP  36    82.056  33.022  26.764  1.00  43.17   X  C
ATOM   6502  O    TRP  36    82.908  33.298  27.615  1.00  43.17   X  O
ATOM   6503  N    VAL  37    80.751  32.958  27.026  1.00  29.19   X  N
ATOM   6504  CA   VAL  37    80.177  33.175  28.360  1.00  29.19   X  C
ATOM   6505  CB   VAL  37    79.213  34.419  28.353  1.00   8.00   X  C
ATOM   6506  CG1  VAL  37    78.350  34.467  29.621  1.00   8.00   X  C
ATOM   6507  CG2  VAL  37    80.026  35.689  28.240  1.00   8.00   X  C
ATOM   6508  C    VAL  37    79.412  31.907  28.760  1.00  29.19   X  C
ATOM   6509  O    VAL  37    78.629  31.381  27.971  1.00  29.19   X  O
ATOM   6510  N    ARG  38    79.651  31.415  29.974  1.00  61.80   X  N
ATOM   6511  CA   ARG  38    78.992  30.198  30.454  1.00  61.80   X  C
ATOM   6512  CB   ARG  38    80.036  29.167  30.899  1.00  27.50   X  C
ATOM   6513  CG   ARG  38    80.926  29.688  32.011  1.00  27.50   X  C
ATOM   6514  CD   ARG  38    81.370  28.603  32.965  1.00  27.50   X  C
ATOM   6515  NE   ARG  38    82.222  27.579  32.364  1.00  27.50   X  N
ATOM   6516  CZ   ARG  38    83.391  27.181  32.874  1.00  27.50   X  C
ATOM   6517  NH1  ARG  38    83.862  27.725  33.992  1.00  27.50   X  N
ATOM   6518  NH2  ARG  38    84.087  26.217  32.281  1.00  27.50   X  N
ATOM   6519  C    ARG  38    78.053  30.468  31.628  1.00  61.80   X  C
ATOM   6520  O    ARG  38    78.104  31.528  32.245  1.00  61.80   X  O
ATOM   6521  N    GLN  39    77.204  29.491  31.934  1.00  39.46   X  N
ATOM   6522  CA   GLN  39    76.269  29.597  33.049  1.00  39.46   X  C
ATOM   6523  CB   GLN  39    74.982  30.269  32.588  1.00  44.48   X  C
ATOM   6524  CG   GLN  39    73.997  30.530  33.708  1.00  44.48   X  C
ATOM   6525  CD   GLN  39    72.916  31.497  33.294  1.00  44.48   X  C
ATOM   6526  OE1  GLN  39    72.269  31.320  32.252  1.00  44.48   X  O
ATOM   6527  NE2  GLN  39    72.709  32.532  34.106  1.00  44.48   X  N
ATOM   6528  C    GLN  39    75.955  28.224  33.663  1.00  39.46   X  C
ATOM   6529  O    GLN  39    75.233  27.404  33.076  1.00  39.46   X  O
ATOM   6530  N    ALA  40    76.514  27.984  34.846  1.00  47.11   X  N
ATOM   6531  CA   ALA  40    76.324  26.727  35.558  1.00  47.11   X  C
ATOM   6532  CB   ALA  40    77.241  26.678  36.773  1.00  19.87   X  C
ATOM   6533  C    ALA  40    74.875  26.592  35.995  1.00  47.11   X  C
ATOM   6534  O    ALA  40    74.296  27.542  36.512  1.00  47.11   X  O
ATOM   6535  N    PRO  41    74.271  25.403  35.802  1.00  63.91   X  N
ATOM   6536  CD   PRO  41    74.879  24.157  35.299  1.00  66.56   X  C
ATOM   6537  CA   PRO  41    72.875  25.168  36.187  1.00  63.91   X  C
ATOM   6538  CB   PRO  41    72.793  23.649  36.244  1.00  66.56   X  C
ATOM   6539  CG   PRO  41    73.667  23.254  35.115  1.00  66.56   X  C
ATOM   6540  C    PRO  41    72.507  25.826  37.508  1.00  63.91   X  C
ATOM   6541  O    PRO  41    73.186  25.637  38.522  1.00  63.91   X  O
ATOM   6542  N    GLY  42    71.432  26.608  37.478  1.00  63.56   X  N
ATOM   6543  CA   GLY  42    70.979  27.297  38.671  1.00  63.56   X  C
ATOM   6544  C    GLY  42    71.963  28.342  39.165  1.00  63.56   X  C
ATOM   6545  O    GLY  42    71.920  28.732  40.334  1.00  63.56   X  O
ATOM   6546  N    LYS  43    72.846  28.793  38.276  1.00 103.79   X  N
ATOM   6547  CA   LYS  43    73.852  29.802  38.607  1.00 103.79   X  C
ATOM   6548  CB   LYS  43    75.248  29.168  38.641  1.00  95.84   X  C
ATOM   6549  CG   LYS  43    75.752  28.830  40.037  1.00  95.84   X  C
ATOM   6550  CD   LYS  43    74.840  27.853  40.755  1.00  95.84   X  C
ATOM   6551  CE   LYS  43    75.225  27.734  42.222  1.00  95.84   X  C
ATOM   6552  NZ   LYS  43    75.138  29.048  42.920  1.00  95.84   X  N
ATOM   6553  C    LYS  43    73.848  30.984  37.634  1.00 103.79   X  C
ATOM   6554  O    LYS  43    73.085  31.013  36.668  1.00 103.79   X  O
ATOM   6555  N    GLY  44    74.714  31.956  37.899  1.00  36.05   X  N
ATOM   6556  CA   GLY  44    74.796  33.131  37.055  1.00  36.05   X  C
ATOM   6557  C    GLY  44    75.710  33.025  35.845  1.00  36.05   X  C
ATOM   6558  O    GLY  44    76.150  31.931  35.477  1.00  36.05   X  O
ATOM   6559  N    LEU  45    76.003  34.186  35.249  1.00  24.14   X  N
ATOM   6560  CA   LEU  45    76.832  34.316  34.046  1.00  24.14   X  C
ATOM   6561  CB   LEU  45    76.343  35.504  33.214  1.00  15.59   X  C
ATOM   6562  CG   LEU  45    74.932  35.346  32.638  1.00  15.59   X  C
ATOM   6563  CD1  LEU  45    74.470  36.606  31.917  1.00  15.59   X  C
ATOM   6564  CD2  LEU  45    74.942  34.179  31.677  1.00  15.59   X  C
ATOM   6565  C    LEU  45    78.316  34.474  34.311  1.00  24.14   X  C
ATOM   6566  O    LEU  45    78.732  35.324  35.095  1.00  24.14   X  O
ATOM   6567  N    GLU  46    79.110  33.661  33.624  1.00  56.59   X  N
ATOM   6568  CA   GLU  46    80.557  33.686  33.774  1.00  56.59   X  C
ATOM   6569  CB   GLU  46    81.034  32.373  34.412  1.00  46.99   X  C
ATOM   6570  CG   GLU  46    82.536  32.308  34.666  1.00  46.99   X  C
```

FIG. 19A-91

| | | | | | | | | | | |
|---|---|---|---|---|---|---|---|---|---|---|
| ATOM | 6571 | CD | GLU | 46 | 82.953 | 31.066 | 35.438 | 1.00 | 46.99 | X | C |
| ATOM | 6572 | OE1 | GLU | 46 | 82.642 | 29.952 | 34.970 | 1.00 | 46.99 | X | O |
| ATOM | 6573 | OE2 | GLU | 46 | 83.594 | 31.201 | 36.508 | 1.00 | 46.99 | X | O |
| ATOM | 6574 | C | GLU | 46 | 81.272 | 33.904 | 32.439 | 1.00 | 56.59 | X | C |
| ATOM | 6575 | O | GLU | 46 | 80.821 | 33.433 | 31.393 | 1.00 | 56.59 | X | O |
| ATOM | 6576 | N | TRP | 47 | 82.385 | 34.632 | 32.489 | 1.00 | 30.60 | X | N |
| ATOM | 6577 | CA | TRP | 47 | 83.188 | 34.910 | 31.300 | 1.00 | 30.60 | X | C |
| ATOM | 6578 | CB | TRP | 47 | 83.889 | 36.273 | 31.426 | 1.00 | 23.41 | X | C |
| ATOM | 6579 | CG | TRP | 47 | 84.944 | 36.481 | 30.385 | 1.00 | 23.41 | X | C |
| ATOM | 6580 | CD2 | TRP | 47 | 86.358 | 36.500 | 30.601 | 1.00 | 23.41 | X | C |
| ATOM | 6581 | CE2 | TRP | 47 | 86.971 | 36.591 | 29.328 | 1.00 | 23.41 | X | C |
| ATOM | 6582 | CE3 | TRP | 47 | 87.170 | 36.441 | 31.746 | 1.00 | 23.41 | X | C |
| ATOM | 6583 | CD1 | TRP | 47 | 84.759 | 36.570 | 29.031 | 1.00 | 23.41 | X | C |
| ATOM | 6584 | NE1 | TRP | 47 | 85.969 | 36.633 | 28.392 | 1.00 | 23.41 | X | N |
| ATOM | 6585 | CZ2 | TRP | 47 | 88.365 | 36.622 | 29.165 | 1.00 | 23.41 | X | C |
| ATOM | 6586 | CZ3 | TRP | 47 | 88.553 | 36.470 | 31.587 | 1.00 | 23.41 | X | C |
| ATOM | 6587 | CH2 | TRP | 47 | 89.137 | 36.560 | 30.304 | 1.00 | 23.41 | X | C |
| ATOM | 6588 | C | TRP | 47 | 84.231 | 33.810 | 31.153 | 1.00 | 30.60 | X | C |
| ATOM | 6589 | O | TRP | 47 | 84.965 | 33.516 | 32.097 | 1.00 | 30.60 | X | O |
| ATOM | 6590 | N | VAL | 48 | 84.317 | 33.219 | 29.967 | 1.00 | 24.17 | X | N |
| ATOM | 6591 | CA | VAL | 48 | 85.270 | 32.128 | 29.755 | 1.00 | 24.17 | X | C |
| ATOM | 6592 | CB | VAL | 48 | 84.589 | 30.924 | 29.011 | 1.00 | 22.03 | X | C |
| ATOM | 6593 | CG1 | VAL | 48 | 85.589 | 29.786 | 28.790 | 1.00 | 22.03 | X | C |
| ATOM | 6594 | CG2 | VAL | 48 | 83.408 | 30.436 | 29.805 | 1.00 | 22.03 | X | C |
| ATOM | 6595 | C | VAL | 48 | 86.550 | 32.490 | 29.006 | 1.00 | 24.17 | X | C |
| ATOM | 6596 | O | VAL | 48 | 87.640 | 32.477 | 29.579 | 1.00 | 24.17 | X | O |
| ATOM | 6597 | N | ALA | 49 | 86.407 | 32.800 | 27.724 | 1.00 | 21.43 | X | N |
| ATOM | 6598 | CA | ALA | 49 | 87.550 | 33.118 | 26.885 | 1.00 | 21.43 | X | C |
| ATOM | 6599 | CB | ALA | 49 | 87.953 | 31.884 | 26.094 | 1.00 | 38.48 | X | C |
| ATOM | 6600 | C | ALA | 49 | 87.228 | 34.257 | 25.934 | 1.00 | 21.43 | X | C |
| ATOM | 6601 | O | ALA | 49 | 86.066 | 34.661 | 25.825 | 1.00 | 21.43 | X | O |
| ATOM | 6602 | N | THR | 50 | 88.257 | 34.745 | 25.235 | 1.00 | 24.70 | X | N |
| ATOM | 6603 | CA | THR | 50 | 88.115 | 35.856 | 24.286 | 1.00 | 24.70 | X | C |
| ATOM | 6604 | CB | THR | 50 | 87.952 | 37.202 | 25.048 | 1.00 | 38.80 | X | C |
| ATOM | 6605 | OG1 | THR | 50 | 86.711 | 37.215 | 25.763 | 1.00 | 38.80 | X | O |
| ATOM | 6606 | CG2 | THR | 50 | 87.981 | 38.369 | 24.087 | 1.00 | 38.80 | X | C |
| ATOM | 6607 | C | THR | 50 | 89.298 | 36.039 | 23.324 | 1.00 | 24.70 | X | C |
| ATOM | 6608 | O | THR | 50 | 90.456 | 35.935 | 23.738 | 1.00 | 24.70 | X | O |
| ATOM | 6609 | N | ILE | 51 | 89.010 | 36.300 | 22.047 | 1.00 | 32.54 | X | N |
| ATOM | 6610 | CA | ILE | 51 | 90.075 | 36.599 | 21.074 | 1.00 | 32.54 | X | C |
| ATOM | 6611 | CB | ILE | 51 | 90.333 | 35.495 | 19.998 | 1.00 | 54.98 | X | C |
| ATOM | 6612 | CG2 | ILE | 51 | 90.567 | 34.178 | 20.661 | 1.00 | 54.98 | X | C |
| ATOM | 6613 | CG1 | ILE | 51 | 89.180 | 35.415 | 18.997 | 1.00 | 54.98 | X | C |
| ATOM | 6614 | CD1 | ILE | 51 | 87.893 | 34.921 | 19.582 | 1.00 | 54.98 | X | C |
| ATOM | 6615 | C | ILE | 51 | 89.674 | 37.865 | 20.335 | 1.00 | 32.54 | X | C |
| ATOM | 6616 | O | ILE | 51 | 88.516 | 38.024 | 19.937 | 1.00 | 32.54 | X | O |
| ATOM | 6617 | N | SER | 52 | 90.628 | 38.774 | 20.167 | 1.00 | 43.61 | X | N |
| ATOM | 6618 | CA | SER | 52 | 90.361 | 40.024 | 19.477 | 1.00 | 43.61 | X | C |
| ATOM | 6619 | CB | SER | 52 | 91.374 | 41.081 | 19.910 | 1.00 | 24.33 | X | C |
| ATOM | 6620 | OG | SER | 52 | 92.684 | 40.702 | 19.528 | 1.00 | 24.33 | X | O |
| ATOM | 6621 | C | SER | 52 | 90.450 | 39.789 | 17.973 | 1.00 | 43.61 | X | C |
| ATOM | 6622 | O | SER | 52 | 90.677 | 38.663 | 17.533 | 1.00 | 43.61 | X | O |
| ATOM | 6623 | N | GLY | 53 | 90.243 | 40.843 | 17.187 | 1.00 | 34.59 | X | N |
| ATOM | 6624 | CA | GLY | 53 | 90.336 | 40.707 | 15.747 | 1.00 | 34.59 | X | C |
| ATOM | 6625 | C | GLY | 53 | 91.800 | 40.559 | 15.381 | 1.00 | 34.59 | X | C |
| ATOM | 6626 | O | GLY | 53 | 92.152 | 40.020 | 14.332 | 1.00 | 34.59 | X | O |
| ATOM | 6627 | N | GLY | 54 | 92.658 | 41.047 | 16.266 | 1.00 | 29.30 | X | N |
| ATOM | 6628 | CA | GLY | 54 | 94.079 | 40.949 | 16.033 | 1.00 | 29.30 | X | C |
| ATOM | 6629 | C | GLY | 54 | 94.555 | 39.550 | 16.359 | 1.00 | 29.30 | X | C |
| ATOM | 6630 | O | GLY | 54 | 95.642 | 39.135 | 15.954 | 1.00 | 29.30 | X | O |
| ATOM | 6631 | N | GLY | 55 | 93.747 | 38.811 | 17.103 | 1.00 | 15.27 | X | N |
| ATOM | 6632 | CA | GLY | 55 | 94.139 | 37.465 | 17.437 | 1.00 | 15.27 | X | C |
| ATOM | 6633 | C | GLY | 55 | 94.596 | 37.254 | 18.867 | 1.00 | 15.27 | X | C |
| ATOM | 6634 | O | GLY | 55 | 94.878 | 36.105 | 19.231 | 1.00 | 15.27 | X | O |
| ATOM | 6635 | N | HIS | 56 | 94.676 | 38.319 | 19.675 | 1.00 | 13.76 | X | N |
| ATOM | 6636 | CA | HIS | 56 | 95.101 | 38.181 | 21.076 | 1.00 | 13.76 | X | C |
| ATOM | 6637 | CB | HIS | 56 | 95.268 | 39.543 | 21.741 | 1.00 | 60.58 | X | C |
| ATOM | 6638 | CG | HIS | 56 | 96.115 | 40.490 | 20.957 | 1.00 | 60.58 | X | C |
| ATOM | 6639 | CD2 | HIS | 56 | 97.417 | 40.838 | 21.087 | 1.00 | 60.58 | X | C |
| ATOM | 6640 | ND1 | HIS | 56 | 95.638 | 41.180 | 19.862 | 1.00 | 60.58 | X | N |
| ATOM | 6641 | CE1 | HIS | 56 | 96.611 | 41.913 | 19.351 | 1.00 | 60.58 | X | C |
| ATOM | 6642 | NE2 | HIS | 56 | 97.701 | 41.724 | 20.075 | 1.00 | 60.58 | X | N |
| ATOM | 6643 | C | HIS | 56 | 94.071 | 37.383 | 21.857 | 1.00 | 13.76 | X | C |

FIG. 19A-92

| | | | | | | | | | | | |
|---|---|---|---|---|---|---|---|---|---|---|---|
| ATOM | 6644 | O | HIS | 56 | 92.864 | 37.621 | 21.736 | 1.00 | 13.76 | X | O |
| ATOM | 6645 | N | THR | 57 | 94.529 | 36.438 | 22.671 | 1.00 | 20.05 | X | N |
| ATOM | 6646 | CA | THR | 57 | 93.583 | 35.632 | 23.436 | 1.00 | 20.05 | X | C |
| ATOM | 6647 | CB | THR | 57 | 93.759 | 34.123 | 23.096 | 1.00 | 15.53 | X | C |
| ATOM | 6648 | OG1 | THR | 57 | 95.015 | 33.651 | 23.587 | 1.00 | 15.53 | X | O |
| ATOM | 6649 | CG2 | THR | 57 | 93.734 | 33.929 | 21.593 | 1.00 | 15.53 | X | C |
| ATOM | 6650 | C | THR | 57 | 93.655 | 35.876 | 24.952 | 1.00 | 20.05 | X | C |
| ATOM | 6651 | O | THR | 57 | 94.716 | 36.142 | 25.512 | 1.00 | 20.05 | X | O |
| ATOM | 6652 | N | TYR | 58 | 92.500 | 35.808 | 25.603 | 1.00 | 19.06 | X | N |
| ATOM | 6653 | CA | TYR | 58 | 92.410 | 36.037 | 27.040 | 1.00 | 19.06 | X | C |
| ATOM | 6654 | CB | TYR | 58 | 91.829 | 37.428 | 27.304 | 1.00 | 22.48 | X | C |
| ATOM | 6655 | CG | TYR | 58 | 92.614 | 38.542 | 26.661 | 1.00 | 22.48 | X | C |
| ATOM | 6656 | CD1 | TYR | 58 | 93.565 | 39.252 | 27.384 | 1.00 | 22.48 | X | C |
| ATOM | 6657 | CE1 | TYR | 58 | 94.308 | 40.265 | 26.788 | 1.00 | 22.48 | X | C |
| ATOM | 6658 | CD2 | TYR | 58 | 92.423 | 38.871 | 25.316 | 1.00 | 22.48 | X | C |
| ATOM | 6659 | CE2 | TYR | 58 | 93.167 | 39.886 | 24.703 | 1.00 | 22.48 | X | C |
| ATOM | 6660 | CZ | TYR | 58 | 94.105 | 40.580 | 25.447 | 1.00 | 22.48 | X | C |
| ATOM | 6661 | OH | TYR | 58 | 94.828 | 41.611 | 24.876 | 1.00 | 22.48 | X | O |
| ATOM | 6662 | C | TYR | 58 | 91.513 | 34.973 | 27.656 | 1.00 | 19.06 | X | C |
| ATOM | 6663 | O | TYR | 58 | 90.442 | 34.660 | 27.123 | 1.00 | 19.06 | X | O |
| ATOM | 6664 | N | TYR | 59 | 91.945 | 34.437 | 28.792 | 1.00 | 29.06 | X | N |
| ATOM | 6665 | CA | TYR | 59 | 91.199 | 33.378 | 29.456 | 1.00 | 29.06 | X | C |
| ATOM | 6666 | CB | TYR | 59 | 91.988 | 32.080 | 29.371 | 1.00 | 21.37 | X | C |
| ATOM | 6667 | CG | TYR | 59 | 92.252 | 31.641 | 27.969 | 1.00 | 21.37 | X | C |
| ATOM | 6668 | CD1 | TYR | 59 | 91.352 | 30.813 | 27.303 | 1.00 | 21.37 | X | C |
| ATOM | 6669 | CE1 | TYR | 59 | 91.573 | 30.428 | 25.988 | 1.00 | 21.37 | X | C |
| ATOM | 6670 | CD2 | TYR | 59 | 93.382 | 32.076 | 27.286 | 1.00 | 21.37 | X | C |
| ATOM | 6671 | CE2 | TYR | 59 | 93.608 | 31.698 | 25.968 | 1.00 | 21.37 | X | C |
| ATOM | 6672 | CZ | TYR | 59 | 92.697 | 30.874 | 25.330 | 1.00 | 21.37 | X | C |
| ATOM | 6673 | OH | TYR | 59 | 92.897 | 30.495 | 24.027 | 1.00 | 21.37 | X | O |
| ATOM | 6674 | C | TYR | 59 | 90.857 | 33.605 | 30.910 | 1.00 | 29.06 | X | C |
| ATOM | 6675 | O | TYR | 59 | 91.575 | 34.287 | 31.648 | 1.00 | 29.06 | X | O |
| ATOM | 6676 | N | LEU | 60 | 89.745 | 33.002 | 31.308 | 1.00 | 26.45 | X | N |
| ATOM | 6677 | CA | LEU | 60 | 89.309 | 33.048 | 32.689 | 1.00 | 26.45 | X | C |
| ATOM | 6678 | CB | LEU | 60 | 87.927 | 32.397 | 32.826 | 1.00 | 24.21 | X | C |
| ATOM | 6679 | CG | LEU | 60 | 87.411 | 32.193 | 34.252 | 1.00 | 24.21 | X | C |
| ATOM | 6680 | CD1 | LEU | 60 | 87.173 | 33.538 | 34.911 | 1.00 | 24.21 | X | C |
| ATOM | 6681 | CD2 | LEU | 60 | 86.135 | 31.380 | 34.223 | 1.00 | 24.21 | X | C |
| ATOM | 6682 | C | LEU | 60 | 90.382 | 32.189 | 33.360 | 1.00 | 26.45 | X | C |
| ATOM | 6683 | O | LEU | 60 | 90.822 | 31.191 | 32.781 | 1.00 | 26.45 | X | O |
| ATOM | 6684 | N | ASP | 61 | 90.822 | 32.570 | 34.553 | 1.00 | 64.06 | X | N |
| ATOM | 6685 | CA | ASP | 61 | 91.865 | 31.810 | 35.240 | 1.00 | 64.06 | X | C |
| ATOM | 6686 | CB | ASP | 61 | 92.297 | 32.556 | 36.502 | 1.00 | 60.41 | X | C |
| ATOM | 6687 | CG | ASP | 61 | 92.984 | 33.865 | 36.183 | 1.00 | 60.41 | X | C |
| ATOM | 6688 | OD1 | ASP | 61 | 93.262 | 34.650 | 37.114 | 1.00 | 60.41 | X | O |
| ATOM | 6689 | OD2 | ASP | 61 | 93.250 | 34.106 | 34.986 | 1.00 | 60.41 | X | O |
| ATOM | 6690 | C | ASP | 61 | 91.477 | 30.371 | 35.576 | 1.00 | 64.06 | X | C |
| ATOM | 6691 | O | ASP | 61 | 92.337 | 29.503 | 35.701 | 1.00 | 64.06 | X | O |
| ATOM | 6692 | N | SER | 62 | 90.181 | 30.122 | 35.707 | 1.00 | 57.78 | X | N |
| ATOM | 6693 | CA | SER | 62 | 89.681 | 28.791 | 36.028 | 1.00 | 57.78 | X | C |
| ATOM | 6694 | CB | SER | 62 | 88.196 | 28.868 | 36.386 | 1.00 | 42.55 | X | C |
| ATOM | 6695 | OG | SER | 62 | 87.643 | 27.575 | 36.556 | 1.00 | 42.55 | X | O |
| ATOM | 6696 | C | SER | 62 | 89.872 | 27.787 | 34.894 | 1.00 | 57.78 | X | C |
| ATOM | 6697 | O | SER | 62 | 90.000 | 26.590 | 35.142 | 1.00 | 57.78 | X | O |
| ATOM | 6698 | N | VAL | 63 | 89.890 | 28.269 | 33.655 | 1.00 | 47.11 | X | N |
| ATOM | 6699 | CA | VAL | 63 | 90.047 | 27.383 | 32.504 | 1.00 | 47.11 | X | C |
| ATOM | 6700 | CB | VAL | 63 | 88.796 | 27.464 | 31.555 | 1.00 | 39.29 | X | C |
| ATOM | 6701 | CG1 | VAL | 63 | 87.513 | 27.472 | 32.375 | 1.00 | 39.29 | X | C |
| ATOM | 6702 | CG2 | VAL | 63 | 88.863 | 28.700 | 30.679 | 1.00 | 39.29 | X | C |
| ATOM | 6703 | C | VAL | 63 | 91.318 | 27.660 | 31.686 | 1.00 | 47.11 | X | C |
| ATOM | 6704 | O | VAL | 63 | 91.504 | 27.093 | 30.603 | 1.00 | 47.11 | X | O |
| ATOM | 6705 | N | LYS | 64 | 92.200 | 28.511 | 32.208 | 1.00 | 47.01 | X | N |
| ATOM | 6706 | CA | LYS | 64 | 93.424 | 28.843 | 31.483 | 1.00 | 47.01 | X | C |
| ATOM | 6707 | CB | LYS | 64 | 94.116 | 30.063 | 32.107 | 1.00 | 84.46 | X | C |
| ATOM | 6708 | CG | LYS | 64 | 95.038 | 30.797 | 31.135 | 1.00 | 84.46 | X | C |
| ATOM | 6709 | CD | LYS | 64 | 95.670 | 32.025 | 31.766 | 1.00 | 84.46 | X | C |
| ATOM | 6710 | CE | LYS | 64 | 96.370 | 32.907 | 30.725 | 1.00 | 84.46 | X | C |
| ATOM | 6711 | NZ | LYS | 64 | 95.419 | 33.654 | 29.833 | 1.00 | 84.46 | X | N |
| ATOM | 6712 | C | LYS | 64 | 94.388 | 27.666 | 31.441 | 1.00 | 47.01 | X | C |
| ATOM | 6713 | O | LYS | 64 | 94.757 | 27.113 | 32.479 | 1.00 | 47.01 | X | O |
| ATOM | 6714 | N | GLY | 65 | 94.795 | 27.289 | 30.231 | 1.00 | 35.35 | X | N |
| ATOM | 6715 | CA | GLY | 65 | 95.704 | 26.167 | 30.073 | 1.00 | 35.35 | X | C |
| ATOM | 6716 | C | GLY | 65 | 94.953 | 24.919 | 29.652 | 1.00 | 35.35 | X | C |

FIG.19A-93

| | | | | | | | | | | |
|---|---|---|---|---|---|---|---|---|---|---|
| ATOM | 6717 | O | GLY | 65 | 95.547 | 23.945 | 29.195 | 1.00 | 35.35 | X | O |
| ATOM | 6718 | N | ARG | 66 | 93.634 | 24.956 | 29.809 | 1.00 | 33.32 | X | N |
| ATOM | 6719 | CA | ARG | 66 | 92.791 | 23.833 | 29.450 | 1.00 | 33.32 | X | C |
| ATOM | 6720 | CB | ARG | 66 | 91.881 | 23.470 | 30.616 | 1.00 | 43.17 | X | C |
| ATOM | 6721 | CG | ARG | 66 | 92.594 | 23.386 | 31.958 | 1.00 | 43.17 | X | C |
| ATOM | 6722 | CD | ARG | 66 | 91.684 | 22.813 | 33.050 | 1.00 | 43.17 | X | C |
| ATOM | 6723 | NE | ARG | 66 | 90.548 | 23.679 | 33.367 | 1.00 | 43.17 | X | N |
| ATOM | 6724 | CZ | ARG | 66 | 89.277 | 23.296 | 33.305 | 1.00 | 43.17 | X | C |
| ATOM | 6725 | NH1 | ARG | 66 | 88.973 | 22.061 | 32.932 | 1.00 | 43.17 | X | N |
| ATOM | 6726 | NH2 | ARG | 66 | 88.309 | 24.144 | 33.630 | 1.00 | 43.17 | X | N |
| ATOM | 6727 | C | ARG | 66 | 91.945 | 24.169 | 28.232 | 1.00 | 33.32 | X | C |
| ATOM | 6728 | O | ARG | 66 | 91.775 | 23.336 | 27.346 | 1.00 | 33.32 | X | O |
| ATOM | 6729 | N | PHE | 67 | 91.411 | 25.389 | 28.191 | 1.00 | 33.69 | X | N |
| ATOM | 6730 | CA | PHE | 67 | 90.567 | 25.834 | 27.074 | 1.00 | 33.69 | X | C |
| ATOM | 6731 | CB | PHE | 67 | 89.444 | 26.750 | 27.587 | 1.00 | 42.44 | X | C |
| ATOM | 6732 | CG | PHE | 67 | 88.346 | 26.030 | 28.330 | 1.00 | 42.44 | X | C |
| ATOM | 6733 | CD1 | PHE | 67 | 88.573 | 24.802 | 28.943 | 1.00 | 42.44 | X | C |
| ATOM | 6734 | CD2 | PHE | 67 | 87.074 | 26.594 | 28.426 | 1.00 | 42.44 | X | C |
| ATOM | 6735 | CE1 | PHE | 67 | 87.547 | 24.145 | 29.637 | 1.00 | 42.44 | X | C |
| ATOM | 6736 | CE2 | PHE | 67 | 86.038 | 25.940 | 29.122 | 1.00 | 42.44 | X | C |
| ATOM | 6737 | CZ | PHE | 67 | 86.278 | 24.717 | 29.724 | 1.00 | 42.44 | X | C |
| ATOM | 6738 | C | PHE | 67 | 91.393 | 26.578 | 26.027 | 1.00 | 33.69 | X | C |
| ATOM | 6739 | O | PHE | 67 | 92.405 | 27.194 | 26.344 | 1.00 | 33.69 | X | O |
| ATOM | 6740 | N | THR | 68 | 90.949 | 26.526 | 24.779 | 1.00 | 56.59 | X | N |
| ATOM | 6741 | CA | THR | 68 | 91.646 | 27.201 | 23.689 | 1.00 | 56.59 | X | C |
| ATOM | 6742 | CB | THR | 68 | 92.454 | 26.193 | 22.846 | 1.00 | 46.98 | X | C |
| ATOM | 6743 | OG1 | THR | 68 | 93.611 | 25.781 | 23.578 | 1.00 | 46.98 | X | O |
| ATOM | 6744 | CG2 | THR | 68 | 92.870 | 26.808 | 21.512 | 1.00 | 46.98 | X | C |
| ATOM | 6745 | C | THR | 68 | 90.661 | 27.913 | 22.768 | 1.00 | 56.59 | X | C |
| ATOM | 6746 | O | THR | 68 | 89.899 | 27.270 | 22.047 | 1.00 | 56.59 | X | O |
| ATOM | 6747 | N | ILE | 69 | 90.672 | 29.239 | 22.781 | 1.00 | 20.15 | X | N |
| ATOM | 6748 | CA | ILE | 69 | 89.760 | 29.975 | 21.918 | 1.00 | 20.15 | X | C |
| ATOM | 6749 | CB | ILE | 69 | 89.287 | 31.289 | 22.607 | 1.00 | 31.46 | X | C |
| ATOM | 6750 | CG2 | ILE | 69 | 90.480 | 32.153 | 22.953 | 1.00 | 31.46 | X | C |
| ATOM | 6751 | CG1 | ILE | 69 | 88.283 | 32.028 | 21.722 | 1.00 | 31.46 | X | C |
| ATOM | 6752 | CD1 | ILE | 69 | 87.574 | 33.159 | 22.446 | 1.00 | 31.46 | X | C |
| ATOM | 6753 | C | ILE | 69 | 90.464 | 30.262 | 20.591 | 1.00 | 20.15 | X | C |
| ATOM | 6754 | O | ILE | 69 | 91.672 | 30.481 | 20.559 | 1.00 | 20.15 | X | O |
| ATOM | 6755 | N | SER | 70 | 89.724 | 30.223 | 19.489 | 1.00 | 21.14 | X | N |
| ATOM | 6756 | CA | SER | 70 | 90.319 | 30.482 | 18.182 | 1.00 | 21.14 | X | C |
| ATOM | 6757 | CB | SER | 70 | 91.105 | 29.263 | 17.693 | 1.00 | 37.41 | X | C |
| ATOM | 6758 | OG | SER | 70 | 90.228 | 28.236 | 17.253 | 1.00 | 37.41 | X | O |
| ATOM | 6759 | C | SER | 70 | 89.242 | 30.824 | 17.163 | 1.00 | 21.14 | X | C |
| ATOM | 6760 | O | SER | 70 | 88.045 | 30.637 | 17.413 | 1.00 | 21.14 | X | O |
| ATOM | 6761 | N | ARG | 71 | 89.673 | 31.322 | 16.009 | 1.00 | 30.73 | X | N |
| ATOM | 6762 | CA | ARG | 71 | 88.734 | 31.687 | 14.966 | 1.00 | 30.73 | X | C |
| ATOM | 6763 | CB | ARG | 71 | 88.369 | 33.178 | 15.073 | 1.00 | 24.51 | X | C |
| ATOM | 6764 | CG | ARG | 71 | 89.546 | 34.139 | 14.901 | 1.00 | 24.51 | X | C |
| ATOM | 6765 | CD | ARG | 71 | 89.071 | 35.503 | 14.453 | 1.00 | 24.51 | X | C |
| ATOM | 6766 | NE | ARG | 71 | 88.464 | 36.278 | 15.534 | 1.00 | 24.51 | X | N |
| ATOM | 6767 | CZ | ARG | 71 | 87.604 | 37.283 | 15.351 | 1.00 | 24.51 | X | C |
| ATOM | 6768 | NH1 | ARG | 71 | 87.229 | 37.643 | 14.131 | 1.00 | 24.51 | X | N |
| ATOM | 6769 | NH2 | ARG | 71 | 87.132 | 37.948 | 16.391 | 1.00 | 24.51 | X | N |
| ATOM | 6770 | C | ARG | 71 | 89.259 | 31.393 | 13.560 | 1.00 | 30.73 | X | C |
| ATOM | 6771 | O | ARG | 71 | 90.464 | 31.415 | 13.301 | 1.00 | 30.73 | X | O |
| ATOM | 6772 | N | ASP | 72 | 88.326 | 31.106 | 12.663 | 1.00 | 55.72 | X | N |
| ATOM | 6773 | CA | ASP | 72 | 88.619 | 30.836 | 11.268 | 1.00 | 55.72 | X | C |
| ATOM | 6774 | CB | ASP | 72 | 88.219 | 29.405 | 10.902 | 1.00 | 83.09 | X | C |
| ATOM | 6775 | CG | ASP | 72 | 88.255 | 29.153 | 9.409 | 1.00 | 83.09 | X | C |
| ATOM | 6776 | OD1 | ASP | 72 | 89.282 | 29.466 | 8.773 | 1.00 | 83.09 | X | O |
| ATOM | 6777 | OD2 | ASP | 72 | 87.256 | 28.637 | 8.870 | 1.00 | 83.09 | X | O |
| ATOM | 6778 | C | ASP | 72 | 87.749 | 31.837 | 10.528 | 1.00 | 55.72 | X | C |
| ATOM | 6779 | O | ASP | 72 | 86.613 | 31.539 | 10.162 | 1.00 | 55.72 | X | O |
| ATOM | 6780 | N | ASN | 73 | 88.284 | 33.036 | 10.340 | 1.00 | 57.89 | X | N |
| ATOM | 6781 | CA | ASN | 73 | 87.552 | 34.098 | 9.673 | 1.00 | 57.89 | X | C |
| ATOM | 6782 | CB | ASN | 73 | 88.426 | 35.345 | 9.558 | 1.00 | 43.96 | X | C |
| ATOM | 6783 | CG | ASN | 73 | 88.777 | 35.928 | 10.912 | 1.00 | 43.96 | X | C |
| ATOM | 6784 | OD1 | ASN | 73 | 88.021 | 35.794 | 11.879 | 1.00 | 43.96 | X | O |
| ATOM | 6785 | ND2 | ASN | 73 | 89.919 | 36.593 | 10.986 | 1.00 | 43.96 | X | N |
| ATOM | 6786 | C | ASN | 73 | 87.020 | 33.715 | 8.306 | 1.00 | 57.89 | X | C |
| ATOM | 6787 | O | ASN | 73 | 85.949 | 34.173 | 7.903 | 1.00 | 57.89 | X | O |
| ATOM | 6788 | N | SER | 74 | 87.756 | 32.870 | 7.594 | 1.00 | 50.09 | X | N |
| ATOM | 6789 | CA | SER | 74 | 87.324 | 32.451 | 6.268 | 1.00 | 50.09 | X | C |

FIG. 19A-94

| ATOM | 6790 | CB | SER | 74 | 88.277 | 31.398 | 5.705 | 1.00 | 34.87 | X | C |
|---|---|---|---|---|---|---|---|---|---|---|---|
| ATOM | 6791 | OG | SER | 74 | 88.179 | 30.197 | 6.441 | 1.00 | 34.87 | X | O |
| ATOM | 6792 | C | SER | 74 | 85.910 | 31.880 | 6.303 | 1.00 | 50.09 | X | C |
| ATOM | 6793 | O | SER | 74 | 85.141 | 32.050 | 5.356 | 1.00 | 50.09 | X | O |
| ATOM | 6794 | N | LYS | 75 | 85.572 | 31.209 | 7.400 | 1.00 | 50.16 | X | N |
| ATOM | 6795 | CA | LYS | 75 | 84.257 | 30.597 | 7.551 | 1.00 | 50.16 | X | C |
| ATOM | 6796 | CB | LYS | 75 | 84.418 | 29.097 | 7.814 | 1.00 | 60.89 | X | C |
| ATOM | 6797 | CG | LYS | 75 | 85.206 | 28.372 | 6.729 | 1.00 | 60.89 | X | C |
| ATOM | 6798 | CD | LYS | 75 | 85.356 | 26.884 | 7.009 | 1.00 | 60.89 | X | C |
| ATOM | 6799 | CE | LYS | 75 | 86.046 | 26.195 | 5.840 | 1.00 | 60.89 | X | C |
| ATOM | 6800 | NZ | LYS | 75 | 85.341 | 26.459 | 4.551 | 1.00 | 60.89 | X | N |
| ATOM | 6801 | C | LYS | 75 | 83.423 | 31.226 | 8.663 | 1.00 | 50.16 | X | C |
| ATOM | 6802 | O | LYS | 75 | 82.470 | 30.618 | 9.142 | 1.00 | 50.16 | X | O |
| ATOM | 6803 | N | ASN | 76 | 83.786 | 32.441 | 9.066 | 1.00 | 54.49 | X | N |
| ATOM | 6804 | CA | ASN | 76 | 83.075 | 33.165 | 10.117 | 1.00 | 54.49 | X | C |
| ATOM | 6805 | CB | ASN | 76 | 81.812 | 33.818 | 9.559 | 1.00 | 41.29 | X | C |
| ATOM | 6806 | CG | ASN | 76 | 82.116 | 34.956 | 8.620 | 1.00 | 41.29 | X | C |
| ATOM | 6807 | OD1 | ASN | 76 | 81.399 | 35.956 | 8.592 | 1.00 | 41.29 | X | O |
| ATOM | 6808 | ND2 | ASN | 76 | 83.181 | 34.812 | 7.839 | 1.00 | 41.29 | X | N |
| ATOM | 6809 | C | ASN | 76 | 82.684 | 32.285 | 11.286 | 1.00 | 54.49 | X | C |
| ATOM | 6810 | O | ASN | 76 | 81.523 | 32.278 | 11.706 | 1.00 | 54.49 | X | O |
| ATOM | 6811 | N | THR | 77 | 83.645 | 31.550 | 11.827 | 1.00 | 48.88 | X | N |
| ATOM | 6812 | CA | THR | 77 | 83.325 | 30.675 | 12.938 | 1.00 | 48.88 | X | C |
| ATOM | 6813 | CB | THR | 77 | 83.321 | 29.215 | 12.481 | 1.00 | 67.62 | X | C |
| ATOM | 6814 | OG1 | THR | 77 | 82.318 | 29.048 | 11.469 | 1.00 | 67.62 | X | O |
| ATOM | 6815 | CG2 | THR | 77 | 83.028 | 28.284 | 13.653 | 1.00 | 67.62 | X | C |
| ATOM | 6816 | C | THR | 77 | 84.245 | 30.817 | 14.132 | 1.00 | 48.88 | X | C |
| ATOM | 6817 | O | THR | 77 | 85.463 | 30.858 | 13.990 | 1.00 | 48.88 | X | O |
| ATOM | 6818 | N | LEU | 78 | 83.641 | 30.900 | 15.313 | 1.00 | 25.08 | X | N |
| ATOM | 6819 | CA | LEU | 78 | 84.387 | 31.014 | 16.562 | 1.00 | 25.08 | X | C |
| ATOM | 6820 | CB | LEU | 78 | 83.739 | 32.047 | 17.488 | 1.00 | 24.57 | X | C |
| ATOM | 6821 | CG | LEU | 78 | 84.362 | 32.022 | 18.881 | 1.00 | 24.57 | X | C |
| ATOM | 6822 | CD1 | LEU | 78 | 85.757 | 32.625 | 18.789 | 1.00 | 24.57 | X | C |
| ATOM | 6823 | CD2 | LEU | 78 | 83.507 | 32.770 | 19.868 | 1.00 | 24.57 | X | C |
| ATOM | 6824 | C | LEU | 78 | 84.370 | 29.653 | 17.250 | 1.00 | 25.08 | X | C |
| ATOM | 6825 | O | LEU | 78 | 83.312 | 29.041 | 17.389 | 1.00 | 25.08 | X | O |
| ATOM | 6826 | N | TYR | 79 | 85.530 | 29.179 | 17.687 | 1.00 | 41.94 | X | N |
| ATOM | 6827 | CA | TYR | 79 | 85.595 | 27.880 | 18.344 | 1.00 | 41.94 | X | C |
| ATOM | 6828 | CB | TYR | 79 | 86.608 | 26.963 | 17.657 | 1.00 | 47.62 | X | C |
| ATOM | 6829 | CG | TYR | 79 | 86.328 | 26.619 | 16.226 | 1.00 | 47.62 | X | C |
| ATOM | 6830 | CD1 | TYR | 79 | 85.264 | 25.794 | 15.887 | 1.00 | 47.62 | X | C |
| ATOM | 6831 | CE1 | TYR | 79 | 85.008 | 25.460 | 14.559 | 1.00 | 47.62 | X | C |
| ATOM | 6832 | CD2 | TYR | 79 | 87.139 | 27.108 | 15.207 | 1.00 | 47.62 | X | C |
| ATOM | 6833 | CE2 | TYR | 79 | 86.896 | 26.784 | 13.878 | 1.00 | 47.62 | X | C |
| ATOM | 6834 | CZ | TYR | 79 | 85.826 | 25.959 | 13.559 | 1.00 | 47.62 | X | C |
| ATOM | 6835 | OH | TYR | 79 | 85.564 | 25.640 | 12.245 | 1.00 | 47.62 | X | O |
| ATOM | 6836 | C | TYR | 79 | 86.043 | 27.991 | 19.779 | 1.00 | 41.94 | X | C |
| ATOM | 6837 | O | TYR | 79 | 86.890 | 28.824 | 20.100 | 1.00 | 41.94 | X | O |
| ATOM | 6838 | N | LEU | 80 | 85.470 | 27.160 | 20.642 | 1.00 | 19.15 | X | N |
| ATOM | 6839 | CA | LEU | 80 | 85.917 | 27.110 | 22.022 | 1.00 | 19.15 | X | C |
| ATOM | 6840 | CB | LEU | 80 | 84.809 | 27.382 | 23.047 | 1.00 | 21.08 | X | C |
| ATOM | 6841 | CG | LEU | 80 | 85.271 | 27.127 | 24.510 | 1.00 | 21.08 | X | C |
| ATOM | 6842 | CD1 | LEU | 80 | 86.500 | 27.981 | 24.840 | 1.00 | 21.08 | X | C |
| ATOM | 6843 | CD2 | LEU | 80 | 84.142 | 27.412 | 25.503 | 1.00 | 21.08 | X | C |
| ATOM | 6844 | C | LEU | 80 | 86.342 | 25.671 | 22.129 | 1.00 | 19.15 | X | C |
| ATOM | 6845 | O | LEU | 80 | 85.517 | 24.769 | 21.941 | 1.00 | 19.15 | X | O |
| ATOM | 6846 | N | GLN | 81 | 87.631 | 25.455 | 22.395 | 1.00 | 31.28 | X | N |
| ATOM | 6847 | CA | GLN | 81 | 88.193 | 24.111 | 22.530 | 1.00 | 31.28 | X | C |
| ATOM | 6848 | CB | GLN | 81 | 89.497 | 24.015 | 21.738 | 1.00 | 68.87 | X | C |
| ATOM | 6849 | CG | GLN | 81 | 90.141 | 22.647 | 21.783 | 1.00 | 68.87 | X | C |
| ATOM | 6850 | CD | GLN | 81 | 89.318 | 21.580 | 21.075 | 1.00 | 68.87 | X | C |
| ATOM | 6851 | OE1 | GLN | 81 | 89.101 | 21.648 | 19.864 | 1.00 | 68.87 | X | O |
| ATOM | 6852 | NE2 | GLN | 81 | 88.857 | 20.588 | 21.831 | 1.00 | 68.87 | X | N |
| ATOM | 6853 | C | GLN | 81 | 88.448 | 23.775 | 24.001 | 1.00 | 31.28 | X | C |
| ATOM | 6854 | O | GLN | 81 | 89.402 | 24.260 | 24.604 | 1.00 | 31.28 | X | O |
| ATOM | 6855 | N | MET | 82 | 87.589 | 22.935 | 24.569 | 1.00 | 32.50 | X | N |
| ATOM | 6856 | CA | MET | 82 | 87.701 | 22.541 | 25.975 | 1.00 | 32.50 | X | C |
| ATOM | 6857 | CB | MET | 82 | 86.297 | 22.429 | 26.589 | 1.00 | 41.50 | X | C |
| ATOM | 6858 | CG | MET | 82 | 85.537 | 23.752 | 26.653 | 1.00 | 41.50 | X | C |
| ATOM | 6859 | SD | MET | 82 | 83.790 | 23.594 | 27.062 | 1.00 | 41.50 | X | S |
| ATOM | 6860 | CE | MET | 82 | 83.088 | 23.391 | 25.452 | 1.00 | 41.50 | X | C |
| ATOM | 6861 | C | MET | 82 | 88.463 | 21.230 | 26.188 | 1.00 | 32.50 | X | C |
| ATOM | 6862 | O | MET | 82 | 88.239 | 20.250 | 25.487 | 1.00 | 32.50 | X | O |

FIG. 19A-95

| | | | | | | | | | | |
|---|---|---|---|---|---|---|---|---|---|---|
| ATOM | 6863 | N | ASN | 83 | 89.369 | 21.224 | 27.160 | 1.00 | 43.69 | X | N |
| ATOM | 6864 | CA | ASN | 83 | 90.155 | 20.032 | 27.459 | 1.00 | 43.69 | X | C |
| ATOM | 6865 | CB | ASN | 83 | 91.574 | 20.157 | 26.883 | 1.00 | 34.50 | X | C |
| ATOM | 6866 | CG | ASN | 83 | 91.574 | 20.391 | 25.383 | 1.00 | 34.50 | X | C |
| ATOM | 6867 | OD1 | ASN | 83 | 90.920 | 19.670 | 24.636 | 1.00 | 34.50 | X | O |
| ATOM | 6868 | ND2 | ASN | 83 | 92.313 | 21.401 | 24.937 | 1.00 | 34.50 | X | N |
| ATOM | 6869 | C | ASN | 83 | 90.225 | 19.855 | 28.967 | 1.00 | 43.69 | X | C |
| ATOM | 6870 | O | ASN | 83 | 90.054 | 20.822 | 29.705 | 1.00 | 43.69 | X | O |
| ATOM | 6871 | N | SER | 84 | 90.480 | 18.625 | 29.416 | 1.00 | 47.01 | X | N |
| ATOM | 6872 | CA | SER | 84 | 90.560 | 18.322 | 30.843 | 1.00 | 47.01 | X | C |
| ATOM | 6873 | CB | SER | 84 | 91.748 | 19.045 | 31.482 | 1.00 | 36.84 | X | C |
| ATOM | 6874 | OG | SER | 84 | 92.963 | 18.623 | 30.892 | 1.00 | 36.84 | X | O |
| ATOM | 6875 | C | SER | 84 | 89.270 | 18.757 | 31.516 | 1.00 | 47.01 | X | C |
| ATOM | 6876 | O | SER | 84 | 89.272 | 19.261 | 32.644 | 1.00 | 47.01 | X | O |
| ATOM | 6877 | N | LEU | 85 | 88.170 | 18.548 | 30.804 | 1.00 | 35.88 | X | N |
| ATOM | 6878 | CA | LEU | 85 | 86.842 | 18.920 | 31.273 | 1.00 | 35.88 | X | C |
| ATOM | 6879 | CB | LEU | 85 | 85.800 | 18.466 | 30.250 | 1.00 | 45.16 | X | C |
| ATOM | 6880 | CG | LEU | 85 | 85.854 | 19.211 | 28.921 | 1.00 | 45.16 | X | C |
| ATOM | 6881 | CD1 | LEU | 85 | 84.875 | 18.608 | 27.936 | 1.00 | 45.16 | X | C |
| ATOM | 6882 | CD2 | LEU | 85 | 85.536 | 20.672 | 29.178 | 1.00 | 45.16 | X | C |
| ATOM | 6883 | C | LEU | 85 | 86.450 | 18.396 | 32.652 | 1.00 | 35.88 | X | C |
| ATOM | 6884 | O | LEU | 85 | 86.175 | 17.208 | 32.818 | 1.00 | 35.88 | X | O |
| ATOM | 6885 | N | ARG | 86 | 86.415 | 19.290 | 33.636 | 1.00 | 55.90 | X | N |
| ATOM | 6886 | CA | ARG | 86 | 86.022 | 18.907 | 34.985 | 1.00 | 55.90 | X | C |
| ATOM | 6887 | CB | ARG | 86 | 86.606 | 19.864 | 36.023 | 1.00 | 50.18 | X | C |
| ATOM | 6888 | CG | ARG | 86 | 88.108 | 20.015 | 35.994 | 1.00 | 50.18 | X | C |
| ATOM | 6889 | CD | ARG | 86 | 88.620 | 20.357 | 37.385 | 1.00 | 50.18 | X | C |
| ATOM | 6890 | NE | ARG | 86 | 89.970 | 20.904 | 37.355 | 1.00 | 50.18 | X | N |
| ATOM | 6891 | CZ | ARG | 86 | 90.256 | 22.185 | 37.133 | 1.00 | 50.18 | X | C |
| ATOM | 6892 | NH1 | ARG | 86 | 89.280 | 23.066 | 36.926 | 1.00 | 50.18 | X | N |
| ATOM | 6893 | NH2 | ARG | 86 | 91.524 | 22.587 | 37.109 | 1.00 | 50.18 | X | N |
| ATOM | 6894 | C | ARG | 86 | 84.501 | 18.954 | 35.069 | 1.00 | 55.90 | X | C |
| ATOM | 6895 | O | ARG | 86 | 83.818 | 19.086 | 34.055 | 1.00 | 55.90 | X | O |
| ATOM | 6896 | N | ALA | 87 | 83.974 | 18.856 | 36.282 | 1.00 | 39.09 | X | N |
| ATOM | 6897 | CA | ALA | 87 | 82.533 | 18.893 | 36.485 | 1.00 | 39.09 | X | C |
| ATOM | 6898 | CB | ALA | 87 | 82.164 | 18.133 | 37.750 | 1.00 | 69.79 | X | C |
| ATOM | 6899 | C | ALA | 87 | 82.028 | 20.325 | 36.578 | 1.00 | 39.09 | X | C |
| ATOM | 6900 | O | ALA | 87 | 80.885 | 20.607 | 36.219 | 1.00 | 39.09 | X | O |
| ATOM | 6901 | N | GLU | 88 | 82.876 | 21.228 | 37.066 | 1.00 | 49.44 | X | N |
| ATOM | 6902 | CA | GLU | 88 | 82.492 | 22.628 | 37.197 | 1.00 | 49.44 | X | C |
| ATOM | 6903 | CB | GLU | 88 | 83.586 | 23.435 | 37.899 | 1.00 | 57.40 | X | C |
| ATOM | 6904 | CG | GLU | 88 | 84.189 | 22.765 | 39.107 | 1.00 | 57.40 | X | C |
| ATOM | 6905 | CD | GLU | 88 | 85.178 | 21.691 | 38.724 | 1.00 | 57.40 | X | C |
| ATOM | 6906 | OE1 | GLU | 88 | 86.227 | 22.035 | 38.146 | 1.00 | 57.40 | X | O |
| ATOM | 6907 | OE2 | GLU | 88 | 84.906 | 20.504 | 38.993 | 1.00 | 57.40 | X | O |
| ATOM | 6908 | C | GLU | 88 | 82.242 | 23.242 | 35.824 | 1.00 | 49.44 | X | C |
| ATOM | 6909 | O | GLU | 88 | 81.474 | 24.195 | 35.687 | 1.00 | 49.44 | X | O |
| ATOM | 6910 | N | ASP | 89 | 82.892 | 22.698 | 34.803 | 1.00 | 49.12 | X | N |
| ATOM | 6911 | CA | ASP | 89 | 82.720 | 23.229 | 33.464 | 1.00 | 49.12 | X | C |
| ATOM | 6912 | CB | ASP | 89 | 83.818 | 22.698 | 32.549 | 1.00 | 52.75 | X | C |
| ATOM | 6913 | CG | ASP | 89 | 85.194 | 22.903 | 33.124 | 1.00 | 52.75 | X | C |
| ATOM | 6914 | OD1 | ASP | 89 | 85.430 | 23.960 | 33.752 | 1.00 | 52.75 | X | O |
| ATOM | 6915 | OD2 | ASP | 89 | 86.043 | 22.011 | 32.936 | 1.00 | 52.75 | X | O |
| ATOM | 6916 | C | ASP | 89 | 81.348 | 22.914 | 32.871 | 1.00 | 49.12 | X | C |
| ATOM | 6917 | O | ASP | 89 | 80.981 | 23.459 | 31.834 | 1.00 | 49.12 | X | O |
| ATOM | 6918 | N | THR | 90 | 80.590 | 22.034 | 33.517 | 1.00 | 33.14 | X | N |
| ATOM | 6919 | CA | THR | 90 | 79.265 | 21.686 | 33.012 | 1.00 | 33.14 | X | C |
| ATOM | 6920 | CB | THR | 90 | 78.652 | 20.480 | 33.766 | 1.00 | 40.77 | X | C |
| ATOM | 6921 | OG1 | THR | 90 | 78.585 | 20.770 | 35.162 | 1.00 | 40.77 | X | O |
| ATOM | 6922 | CG2 | THR | 90 | 79.498 | 19.257 | 33.590 | 1.00 | 40.77 | X | C |
| ATOM | 6923 | C | THR | 90 | 78.361 | 22.899 | 33.174 | 1.00 | 33.14 | X | C |
| ATOM | 6924 | O | THR | 90 | 78.260 | 23.486 | 34.263 | 1.00 | 33.14 | X | O |
| ATOM | 6925 | N | ALA | 91 | 77.718 | 23.276 | 32.076 | 1.00 | 55.37 | X | N |
| ATOM | 6926 | CA | ALA | 91 | 76.832 | 24.428 | 32.058 | 1.00 | 55.37 | X | C |
| ATOM | 6927 | CB | ALA | 91 | 77.527 | 25.625 | 32.692 | 1.00 | 7.95 | X | C |
| ATOM | 6928 | C | ALA | 91 | 76.504 | 24.732 | 30.609 | 1.00 | 55.37 | X | C |
| ATOM | 6929 | O | ALA | 91 | 77.073 | 24.128 | 29.698 | 1.00 | 55.37 | X | O |
| ATOM | 6930 | N | VAL | 92 | 75.579 | 25.656 | 30.387 | 1.00 | 44.83 | X | N |
| ATOM | 6931 | CA | VAL | 92 | 75.243 | 26.017 | 29.021 | 1.00 | 44.83 | X | C |
| ATOM | 6932 | CB | VAL | 92 | 73.747 | 26.429 | 28.878 | 1.00 | 41.51 | X | C |
| ATOM | 6933 | CG1 | VAL | 92 | 73.210 | 26.967 | 30.198 | 1.00 | 41.51 | X | C |
| ATOM | 6934 | CG2 | VAL | 92 | 73.596 | 27.460 | 27.769 | 1.00 | 41.51 | X | C |
| ATOM | 6935 | C | VAL | 92 | 76.182 | 27.145 | 28.591 | 1.00 | 44.83 | X | C |

FIG. 19A-96

| ATOM | 6936 | O | VAL | 92 | 76.446 | 28.085 | 29.354 | 1.00 | 44.83 | X | O |
|---|---|---|---|---|---|---|---|---|---|---|---|
| ATOM | 6937 | N | TYR | 93 | 76.701 | 27.019 | 27.371 | 1.00 | 51.76 | X | N |
| ATOM | 6938 | CA | TYR | 93 | 77.642 | 27.978 | 26.811 | 1.00 | 51.76 | X | C |
| ATOM | 6939 | CB | TYR | 93 | 78.838 | 27.241 | 26.227 | 1.00 | 15.58 | X | C |
| ATOM | 6940 | CG | TYR | 93 | 79.743 | 26.693 | 27.287 | 1.00 | 15.58 | X | C |
| ATOM | 6941 | CD1 | TYR | 93 | 79.520 | 25.443 | 27.841 | 1.00 | 15.58 | X | C |
| ATOM | 6942 | CE1 | TYR | 93 | 80.339 | 24.959 | 28.860 | 1.00 | 15.58 | X | C |
| ATOM | 6943 | CD2 | TYR | 93 | 80.802 | 27.454 | 27.777 | 1.00 | 15.58 | X | C |
| ATOM | 6944 | CE2 | TYR | 93 | 81.618 | 26.983 | 28.797 | 1.00 | 15.58 | X | C |
| ATOM | 6945 | CZ | TYR | 93 | 81.384 | 25.735 | 29.328 | 1.00 | 15.58 | X | C |
| ATOM | 6946 | OH | TYR | 93 | 82.223 | 25.253 | 30.297 | 1.00 | 15.58 | X | O |
| ATOM | 6947 | C | TYR | 93 | 77.091 | 28.908 | 25.757 | 1.00 | 51.76 | X | C |
| ATOM | 6948 | O | TYR | 93 | 76.223 | 28.534 | 24.972 | 1.00 | 51.76 | X | O |
| ATOM | 6949 | N | TYR | 94 | 77.633 | 30.121 | 25.729 | 1.00 | 29.82 | X | N |
| ATOM | 6950 | CA | TYR | 94 | 77.210 | 31.143 | 24.774 | 1.00 | 29.82 | X | C |
| ATOM | 6951 | CB | TYR | 94 | 76.448 | 32.267 | 25.489 | 1.00 | 45.66 | X | C |
| ATOM | 6952 | CG | TYR | 94 | 75.282 | 31.829 | 26.343 | 1.00 | 45.66 | X | C |
| ATOM | 6953 | CD1 | TYR | 94 | 74.053 | 31.494 | 25.771 | 1.00 | 45.66 | X | C |
| ATOM | 6954 | CE1 | TYR | 94 | 72.979 | 31.108 | 26.564 | 1.00 | 45.66 | X | C |
| ATOM | 6955 | CD2 | TYR | 94 | 75.405 | 31.763 | 27.733 | 1.00 | 45.66 | X | C |
| ATOM | 6956 | CE2 | TYR | 94 | 74.342 | 31.376 | 28.532 | 1.00 | 45.66 | X | C |
| ATOM | 6957 | CZ | TYR | 94 | 73.132 | 31.051 | 27.943 | 1.00 | 45.66 | X | C |
| ATOM | 6958 | OH | TYR | 94 | 72.082 | 30.665 | 28.743 | 1.00 | 45.66 | X | O |
| ATOM | 6959 | C | TYR | 94 | 78.389 | 31.799 | 24.074 | 1.00 | 29.82 | X | C |
| ATOM | 6960 | O | TYR | 94 | 79.360 | 32.174 | 24.727 | 1.00 | 29.82 | X | O |
| ATOM | 6961 | N | CYS | 95 | 78.332 | 31.923 | 22.752 | 1.00 | 22.64 | X | N |
| ATOM | 6962 | CA | CYS | 95 | 79.394 | 32.659 | 22.091 | 1.00 | 22.64 | X | C |
| ATOM | 6963 | C | CYS | 95 | 78.871 | 34.094 | 22.103 | 1.00 | 22.64 | X | C |
| ATOM | 6964 | O | CYS | 95 | 77.656 | 34.337 | 22.170 | 1.00 | 22.64 | X | O |
| ATOM | 6965 | CB | CYS | 95 | 79.660 | 32.185 | 20.660 | 1.00 | 55.79 | X | C |
| ATOM | 6966 | SG | CYS | 95 | 78.222 | 31.748 | 19.650 | 1.00 | 55.79 | X | S |
| ATOM | 6967 | N | THR | 96 | 79.778 | 35.057 | 22.067 | 1.00 | 43.77 | X | N |
| ATOM | 6968 | CA | THR | 96 | 79.337 | 36.435 | 22.107 | 1.00 | 43.77 | X | C |
| ATOM | 6969 | CB | THR | 96 | 79.387 | 36.985 | 23.556 | 1.00 | 38.47 | X | C |
| ATOM | 6970 | OG1 | THR | 96 | 80.723 | 36.865 | 24.069 | 1.00 | 38.47 | X | O |
| ATOM | 6971 | CG2 | THR | 96 | 78.421 | 36.220 | 24.453 | 1.00 | 38.47 | X | C |
| ATOM | 6972 | C | THR | 96 | 80.130 | 37.370 | 21.220 | 1.00 | 43.77 | X | C |
| ATOM | 6973 | O | THR | 96 | 81.328 | 37.174 | 20.987 | 1.00 | 43.77 | X | O |
| ATOM | 6974 | N | ARG | 97 | 79.432 | 38.379 | 20.709 | 1.00 | 52.60 | X | N |
| ATOM | 6975 | CA | ARG | 97 | 80.068 | 39.400 | 19.899 | 1.00 | 52.60 | X | C |
| ATOM | 6976 | CB | ARG | 97 | 79.237 | 39.799 | 18.689 | 1.00 | 26.06 | X | C |
| ATOM | 6977 | CG | ARG | 97 | 80.052 | 40.645 | 17.733 | 1.00 | 26.06 | X | C |
| ATOM | 6978 | CD | ARG | 97 | 79.235 | 41.249 | 16.624 | 1.00 | 26.06 | X | C |
| ATOM | 6979 | NE | ARG | 97 | 78.494 | 42.412 | 17.074 | 1.00 | 26.06 | X | N |
| ATOM | 6980 | CZ | ARG | 97 | 77.853 | 43.231 | 16.255 | 1.00 | 26.06 | X | C |
| ATOM | 6981 | NH1 | ARG | 97 | 77.873 | 43.004 | 14.948 | 1.00 | 26.06 | X | N |
| ATOM | 6982 | NH2 | ARG | 97 | 77.187 | 44.271 | 16.742 | 1.00 | 26.06 | X | N |
| ATOM | 6983 | C | ARG | 97 | 80.142 | 40.590 | 20.820 | 1.00 | 52.60 | X | C |
| ATOM | 6984 | O | ARG | 97 | 79.116 | 41.100 | 21.260 | 1.00 | 52.60 | X | O |
| ATOM | 6985 | N | GLY | 98 | 81.353 | 41.020 | 21.129 | 1.00 | 31.82 | X | N |
| ATOM | 6986 | CA | GLY | 98 | 81.505 | 42.162 | 22.004 | 1.00 | 31.82 | X | C |
| ATOM | 6987 | C | GLY | 98 | 81.635 | 43.450 | 21.225 | 1.00 | 31.82 | X | C |
| ATOM | 6988 | O | GLY | 98 | 81.903 | 43.452 | 20.020 | 1.00 | 31.82 | X | O |
| ATOM | 6989 | N | PHE | 99 | 81.416 | 44.558 | 21.913 | 1.00 | 20.36 | X | N |
| ATOM | 6990 | CA | PHE | 99 | 81.554 | 45.859 | 21.289 | 1.00 | 20.36 | X | C |
| ATOM | 6991 | CB | PHE | 99 | 80.358 | 46.753 | 21.621 | 1.00 | 37.93 | X | C |
| ATOM | 6992 | CG | PHE | 99 | 80.633 | 48.214 | 21.431 | 1.00 | 37.93 | X | C |
| ATOM | 6993 | CD1 | PHE | 99 | 80.968 | 49.015 | 22.517 | 1.00 | 37.93 | X | C |
| ATOM | 6994 | CD2 | PHE | 99 | 80.606 | 48.783 | 20.158 | 1.00 | 37.93 | X | C |
| ATOM | 6995 | CE1 | PHE | 99 | 81.276 | 50.355 | 22.339 | 1.00 | 37.93 | X | C |
| ATOM | 6996 | CE2 | PHE | 99 | 80.913 | 50.127 | 19.967 | 1.00 | 37.93 | X | C |
| ATOM | 6997 | CZ | PHE | 99 | 81.250 | 50.914 | 21.058 | 1.00 | 37.93 | X | C |
| ATOM | 6998 | C | PHE | 99 | 82.836 | 46.468 | 21.835 | 1.00 | 20.36 | X | C |
| ATOM | 6999 | O | PHE | 99 | 83.239 | 46.164 | 22.969 | 1.00 | 20.36 | X | O |
| ATOM | 7000 | N | GLY | 100 | 83.480 | 47.309 | 21.030 | 1.00 | 25.28 | X | N |
| ATOM | 7001 | CA | GLY | 100 | 84.704 | 47.954 | 21.469 | 1.00 | 25.28 | X | C |
| ATOM | 7002 | C | GLY | 100 | 85.850 | 46.983 | 21.672 | 1.00 | 25.28 | X | C |
| ATOM | 7003 | O | GLY | 100 | 86.390 | 46.466 | 20.700 | 1.00 | 25.28 | X | O |
| ATOM | 7004 | N | ASP | 101 | 86.231 | 46.744 | 22.926 | 1.00 | 27.39 | X | N |
| ATOM | 7005 | CA | ASP | 101 | 87.315 | 45.814 | 23.233 | 1.00 | 27.39 | X | C |
| ATOM | 7006 | CB | ASP | 101 | 88.175 | 46.338 | 24.396 | 1.00 | 32.17 | X | C |
| ATOM | 7007 | CG | ASP | 101 | 89.037 | 47.540 | 24.013 | 1.00 | 32.17 | X | C |
| ATOM | 7008 | OD1 | ASP | 101 | 89.287 | 47.744 | 22.812 | 1.00 | 32.17 | X | O |

FIG. 19A-97

```
ATOM   7009  OD2 ASP   101      89.483  48.274  24.920  1.00  32.17      X   O
ATOM   7010  C   ASP   101      86.773  44.418  23.596  1.00  27.39      X   C
ATOM   7011  O   ASP   101      87.549  43.518  23.929  1.00  27.39      X   O
ATOM   7012  N   GLY   102      85.449  44.250  23.538  1.00  18.22      X   N
ATOM   7013  CA  GLY   102      84.822  42.973  23.861  1.00  18.22      X   C
ATOM   7014  C   GLY   102      83.925  42.948  25.100  1.00  18.22      X   C
ATOM   7015  O   GLY   102      83.031  42.113  25.198  1.00  18.22      X   O
ATOM   7016  N   GLY   103      84.147  43.870  26.034  1.00  34.16      X   N
ATOM   7017  CA  GLY   103      83.370  43.915  27.268  1.00  34.16      X   C
ATOM   7018  C   GLY   103      81.850  43.964  27.216  1.00  34.16      X   C
ATOM   7019  O   GLY   103      81.182  43.416  28.087  1.00  34.16      X   O
ATOM   7020  N   TYR   104      81.290  44.649  26.230  1.00  25.31      X   N
ATOM   7021  CA  TYR   104      79.839  44.732  26.096  1.00  25.31      X   C
ATOM   7022  CB  TYR   104      79.433  46.131  25.639  1.00  26.21      X   C
ATOM   7023  CG  TYR   104      77.989  46.260  25.234  1.00  26.21      X   C
ATOM   7024  CD1 TYR   104      77.635  46.980  24.087  1.00  26.21      X   C
ATOM   7025  CE1 TYR   104      76.309  47.079  23.677  1.00  26.21      X   C
ATOM   7026  CD2 TYR   104      76.972  45.646  25.972  1.00  26.21      X   C
ATOM   7027  CE2 TYR   104      75.639  45.742  25.573  1.00  26.21      X   C
ATOM   7028  CZ  TYR   104      75.323  46.456  24.422  1.00  26.21      X   C
ATOM   7029  OH  TYR   104      74.025  46.523  23.995  1.00  26.21      X   O
ATOM   7030  C   TYR   104      79.484  43.700  25.037  1.00  25.31      X   C
ATOM   7031  O   TYR   104      79.905  43.810  23.886  1.00  25.31      X   O
ATOM   7032  N   PHE   105      78.728  42.686  25.432  1.00  17.54      X   N
ATOM   7033  CA  PHE   105      78.354  41.616  24.518  1.00  17.54      X   C
ATOM   7034  CB  PHE   105      78.088  40.337  25.309  1.00  20.12      X   C
ATOM   7035  CG  PHE   105      79.154  40.010  26.312  1.00  20.12      X   C
ATOM   7036  CD1 PHE   105      80.478  39.817  25.908  1.00  20.12      X   C
ATOM   7037  CD2 PHE   105      78.832  39.891  27.661  1.00  20.12      X   C
ATOM   7038  CE1 PHE   105      81.472  39.511  26.836  1.00  20.12      X   C
ATOM   7039  CE2 PHE   105      79.808  39.586  28.594  1.00  20.12      X   C
ATOM   7040  CZ  PHE   105      81.136  39.395  28.183  1.00  20.12      X   C
ATOM   7041  C   PHE   105      77.127  41.938  23.669  1.00  17.54      X   C
ATOM   7042  O   PHE   105      75.989  41.689  24.080  1.00  17.54      X   O
ATOM   7043  N   ASP   106      77.376  42.488  22.482  1.00  46.21      X   N
ATOM   7044  CA  ASP   106      76.327  42.840  21.532  1.00  46.21      X   C
ATOM   7045  CB  ASP   106      76.908  43.074  20.143  1.00  54.80      X   C
ATOM   7046  CG  ASP   106      77.456  44.442  19.976  1.00  54.80      X   C
ATOM   7047  OD1 ASP   106      76.774  45.384  20.429  1.00  54.80      X   O
ATOM   7048  OD2 ASP   106      78.552  44.576  19.387  1.00  54.80      X   O
ATOM   7049  C   ASP   106      75.355  41.705  21.399  1.00  46.21      X   C
ATOM   7050  O   ASP   106      74.281  41.707  21.974  1.00  46.21      X   O
ATOM   7051  N   VAL   107      75.769  40.732  20.603  1.00  33.04      X   N
ATOM   7052  CA  VAL   107      74.979  39.559  20.312  1.00  33.04      X   C
ATOM   7053  CB  VAL   107      75.180  39.152  18.858  1.00  31.62      X   C
ATOM   7054  CG1 VAL   107      74.156  38.100  18.457  1.00  31.62      X   C
ATOM   7055  CG2 VAL   107      75.092  40.388  17.980  1.00  31.62      X   C
ATOM   7056  C   VAL   107      75.322  38.379  21.197  1.00  33.04      X   C
ATOM   7057  O   VAL   107      76.413  38.296  21.763  1.00  33.04      X   O
ATOM   7058  N   TRP   108      74.359  37.474  21.306  1.00  37.95      X   N
ATOM   7059  CA  TRP   108      74.501  36.266  22.092  1.00  37.95      X   C
ATOM   7060  CB  TRP   108      73.674  36.351  23.372  1.00  32.89      X   C
ATOM   7061  CG  TRP   108      74.212  37.315  24.368  1.00  32.89      X   C
ATOM   7062  CD2 TRP   108      74.712  37.004  25.668  1.00  32.89      X   C
ATOM   7063  CE2 TRP   108      75.114  38.216  26.261  1.00  32.89      X   C
ATOM   7064  CE3 TRP   108      74.861  35.816  26.390  1.00  32.89      X   C
ATOM   7065  CD1 TRP   108      74.327  38.664  24.225  1.00  32.89      X   C
ATOM   7066  NE1 TRP   108      74.867  39.216  25.358  1.00  32.89      X   N
ATOM   7067  CZ2 TRP   108      75.655  38.278  27.543  1.00  32.89      X   C
ATOM   7068  CZ3 TRP   108      75.402  35.878  27.670  1.00  32.89      X   C
ATOM   7069  CH2 TRP   108      75.792  37.103  28.231  1.00  32.89      X   C
ATOM   7070  C   TRP   108      73.984  35.119  21.260  1.00  37.95      X   C
ATOM   7071  O   TRP   108      73.067  35.296  20.451  1.00  37.95      X   O
ATOM   7072  N   GLY   109      74.568  33.942  21.460  1.00  75.91      X   N
ATOM   7073  CA  GLY   109      74.124  32.770  20.732  1.00  75.91      X   C
ATOM   7074  C   GLY   109      72.791  32.307  21.288  1.00  75.91      X   C
ATOM   7075  O   GLY   109      71.997  33.114  21.780  1.00  75.91      X   O
ATOM   7076  N   GLN   110      72.537  31.007  21.207  1.00  35.37      X   N
ATOM   7077  CA  GLN   110      71.291  30.457  21.724  1.00  35.37      X   C
ATOM   7078  CB  GLN   110      70.652  29.498  20.714  1.00  98.79      X   C
ATOM   7079  CG  GLN   110      71.443  28.228  20.442  1.00  98.79      X   C
ATOM   7080  CD  GLN   110      72.597  28.441  19.485  1.00  98.79      X   C
ATOM   7081  OE1 GLN   110      73.318  27.502  19.152  1.00  98.79      X   O
```

FIG. 19A-98

```
ATOM   7082  NE2 GLN  110      72.775  29.675  19.031  1.00  98.79   X   N
ATOM   7083  C   GLN  110      71.610  29.708  23.004  1.00  35.37   X   C
ATOM   7084  O   GLN  110      70.793  29.626  23.918  1.00  35.37   X   O
ATOM   7085  N   GLY  111      72.831  29.194  23.067  1.00  45.85   X   N
ATOM   7086  CA  GLY  111      73.257  28.430  24.219  1.00  45.85   X   C
ATOM   7087  C   GLY  111      73.349  26.981  23.781  1.00  45.85   X   C
ATOM   7088  O   GLY  111      72.596  26.540  22.913  1.00  45.85   X   O
ATOM   7089  N   THR  112      74.281  26.243  24.369  1.00  30.06   X   N
ATOM   7090  CA  THR  112      74.480  24.840  24.040  1.00  30.06   X   C
ATOM   7091  CB  THR  112      75.550  24.696  22.962  1.00  24.67   X   C
ATOM   7092  OG1 THR  112      75.636  23.327  22.562  1.00  24.67   X   O
ATOM   7093  CG2 THR  112      76.903  25.177  23.487  1.00  24.67   X   C
ATOM   7094  C   THR  112      74.944  24.184  25.328  1.00  30.06   X   C
ATOM   7095  O   THR  112      75.883  24.658  25.960  1.00  30.06   X   O
ATOM   7096  N   LEU  113      74.292  23.102  25.725  1.00  42.99   X   N
ATOM   7097  CA  LEU  113      74.646  22.449  26.981  1.00  42.99   X   C
ATOM   7098  CB  LEU  113      73.434  21.652  27.499  1.00  32.90   X   C
ATOM   7099  CG  LEU  113      73.366  21.006  28.896  1.00  32.90   X   C
ATOM   7100  CD1 LEU  113      73.914  19.580  28.860  1.00  32.90   X   C
ATOM   7101  CD2 LEU  113      74.109  21.884  29.889  1.00  32.90   X   C
ATOM   7102  C   LEU  113      75.890  21.560  26.932  1.00  42.99   X   C
ATOM   7103  O   LEU  113      76.190  20.899  25.929  1.00  42.99   X   O
ATOM   7104  N   VAL  114      76.621  21.561  28.037  1.00  35.21   X   N
ATOM   7105  CA  VAL  114      77.815  20.754  28.141  1.00  35.21   X   C
ATOM   7106  CB  VAL  114      79.070  21.592  27.837  1.00  43.74   X   C
ATOM   7107  CG1 VAL  114      80.324  20.909  28.384  1.00  43.74   X   C
ATOM   7108  CG2 VAL  114      79.189  21.774  26.331  1.00  43.74   X   C
ATOM   7109  C   VAL  114      77.906  20.141  29.529  1.00  35.21   X   C
ATOM   7110  O   VAL  114      78.064  20.845  30.529  1.00  35.21   X   O
ATOM   7111  N   THR  115      77.788  18.819  29.575  1.00  58.81   X   N
ATOM   7112  CA  THR  115      77.855  18.099  30.829  1.00  58.81   X   C
ATOM   7113  CB  THR  115      76.717  17.098  30.956  1.00  63.66   X   C
ATOM   7114  OG1 THR  115      75.549  17.620  30.311  1.00  63.66   X   O
ATOM   7115  CG2 THR  115      76.412  16.849  32.422  1.00  63.66   X   C
ATOM   7116  C   THR  115      79.161  17.337  30.903  1.00  58.81   X   C
ATOM   7117  O   THR  115      79.831  17.121  29.893  1.00  58.81   X   O
ATOM   7118  N   VAL  116      79.516  16.933  32.114  1.00  73.79   X   N
ATOM   7119  CA  VAL  116      80.741  16.191  32.352  1.00  73.79   X   C
ATOM   7120  CB  VAL  116      81.899  17.135  32.747  1.00  46.90   X   C
ATOM   7121  CG1 VAL  116      83.172  16.339  32.941  1.00  46.90   X   C
ATOM   7122  CG2 VAL  116      82.101  18.194  31.667  1.00  46.90   X   C
ATOM   7123  C   VAL  116      80.478  15.202  33.482  1.00  73.79   X   C
ATOM   7124  O   VAL  116      80.382  15.584  34.649  1.00  73.79   X   O
ATOM   7125  N   SER  117      80.349  13.931  33.114  1.00  65.98   X   N
ATOM   7126  CA  SER  117      80.088  12.858  34.066  1.00  65.98   X   C
ATOM   7127  CB  SER  117      78.608  12.861  34.458  1.00  62.16   X   C
ATOM   7128  OG  SER  117      77.776  12.825  33.308  1.00  62.16   X   O
ATOM   7129  C   SER  117      80.454  11.521  33.427  1.00  65.98   X   C
ATOM   7130  O   SER  117      81.498  11.396  32.789  1.00  65.98   X   O
ATOM   7131  N   SER  118      79.587  10.524  33.594  1.00  80.64   X   N
ATOM   7132  CA  SER  118      79.828   9.208  33.014  1.00  80.64   X   C
ATOM   7133  CB  SER  118      80.556   8.329  34.031  1.00  66.12   X   C
ATOM   7134  OG  SER  118      81.771   8.944  34.438  1.00  66.12   X   O
ATOM   7135  C   SER  118      78.524   8.543  32.563  1.00  80.64   X   C
ATOM   7136  O   SER  118      77.445   9.021  32.973  1.00  79.69   X   O
ATOM   7137  OXT SER  118      78.594   7.553  31.804  1.00  65.17   X   O
ATOM   7138  CB  ILE    2      85.629  44.767  39.417  1.00  24.34   Y   C
ATOM   7139  CG2 ILE    2      84.329  45.456  39.830  1.00  24.34   Y   C
ATOM   7140  CG1 ILE    2      86.754  45.793  39.275  1.00  24.34   Y   C
ATOM   7141  CD1 ILE    2      86.473  46.861  38.237  1.00  24.34   Y   C
ATOM   7142  C   ILE    2      84.812  42.776  40.634  1.00  29.24   Y   C
ATOM   7143  O   ILE    2      84.508  41.962  39.756  1.00  29.24   Y   O
ATOM   7144  N   ILE    2      87.254  42.972  40.068  1.00  29.24   Y   N
ATOM   7145  CA  ILE    2      86.011  43.705  40.462  1.00  29.24   Y   C
ATOM   7146  N   GLN    3      84.122  42.926  41.761  1.00  42.94   Y   N
ATOM   7147  CA  GLN    3      82.960  42.107  42.070  1.00  42.94   Y   C
ATOM   7148  CB  GLN    3      83.156  41.435  43.434  1.00  85.86   Y   C
ATOM   7149  CG  GLN    3      82.045  40.492  43.850  1.00  85.86   Y   C
ATOM   7150  CD  GLN    3      82.371  39.747  45.131  1.00  85.86   Y   C
ATOM   7151  OE1 GLN    3      81.534  39.028  45.670  1.00  85.86   Y   O
ATOM   7152  NE2 GLN    3      83.597  39.911  45.621  1.00  85.86   Y   N
ATOM   7153  C   GLN    3      81.684  42.943  42.059  1.00  42.94   Y   C
ATOM   7154  O   GLN    3      81.626  44.026  42.645  1.00  42.94   Y   O
```

FIG. 19A-99

| ATOM | 7155 | N   | LEU | 4  | 80.666 | 42.426 | 41.380 | 1.00 | 33.35  | Y | N |
|------|------|-----|-----|----|--------|--------|--------|------|--------|---|---|
| ATOM | 7156 | CA  | LEU | 4  | 79.378 | 43.098 | 41.269 | 1.00 | 33.35  | Y | C |
| ATOM | 7157 | CB  | LEU | 4  | 78.954 | 43.160 | 39.800 | 1.00 | 47.12  | Y | C |
| ATOM | 7158 | CG  | LEU | 4  | 79.344 | 44.389 | 38.979 | 1.00 | 47.12  | Y | C |
| ATOM | 7159 | CD1 | LEU | 4  | 80.683 | 44.945 | 39.443 | 1.00 | 47.12  | Y | C |
| ATOM | 7160 | CD2 | LEU | 4  | 79.370 | 44.008 | 37.512 | 1.00 | 47.12  | Y | C |
| ATOM | 7161 | C   | LEU | 4  | 78.296 | 42.395 | 42.073 | 1.00 | 33.35  | Y | C |
| ATOM | 7162 | O   | LEU | 4  | 78.012 | 41.215 | 41.852 | 1.00 | 33.35  | Y | O |
| ATOM | 7163 | N   | THR | 5  | 77.691 | 43.129 | 43.001 | 1.00 | 42.53  | Y | N |
| ATOM | 7164 | CA  | THR | 5  | 76.628 | 42.586 | 43.833 | 1.00 | 42.53  | Y | C |
| ATOM | 7165 | CB  | THR | 5  | 77.100 | 42.482 | 45.315 | 1.00 | 37.95  | Y | C |
| ATOM | 7166 | OG1 | THR | 5  | 75.992 | 42.697 | 46.196 | 1.00 | 37.95  | Y | O |
| ATOM | 7167 | CG2 | THR | 5  | 78.209 | 43.479 | 45.604 | 1.00 | 37.95  | Y | C |
| ATOM | 7168 | C   | THR | 5  | 75.348 | 43.426 | 43.699 | 1.00 | 42.53  | Y | C |
| ATOM | 7169 | O   | THR | 5  | 75.306 | 44.593 | 44.089 | 1.00 | 42.53  | Y | O |
| ATOM | 7170 | N   | GLN | 6  | 74.318 | 42.806 | 43.119 | 1.00 | 44.79  | Y | N |
| ATOM | 7171 | CA  | GLN | 6  | 73.009 | 43.423 | 42.877 | 1.00 | 44.79  | Y | C |
| ATOM | 7172 | CB  | GLN | 6  | 72.340 | 42.791 | 41.641 | 1.00 | 23.30  | Y | C |
| ATOM | 7173 | CG  | GLN | 6  | 73.239 | 42.643 | 40.421 | 1.00 | 23.30  | Y | C |
| ATOM | 7174 | CD  | GLN | 6  | 72.520 | 42.055 | 39.195 | 1.00 | 23.30  | Y | C |
| ATOM | 7175 | OE1 | GLN | 6  | 73.163 | 41.628 | 38.231 | 1.00 | 23.30  | Y | O |
| ATOM | 7176 | NE2 | GLN | 6  | 71.193 | 42.046 | 39.226 | 1.00 | 23.30  | Y | N |
| ATOM | 7177 | C   | GLN | 6  | 72.050 | 43.274 | 44.061 | 1.00 | 44.79  | Y | C |
| ATOM | 7178 | O   | GLN | 6  | 72.195 | 42.370 | 44.883 | 1.00 | 44.79  | Y | O |
| ATOM | 7179 | N   | SER | 7  | 71.057 | 44.156 | 44.128 | 1.00 | 78.31  | Y | N |
| ATOM | 7180 | CA  | SER | 7  | 70.069 | 44.113 | 45.201 | 1.00 | 78.31  | Y | C |
| ATOM | 7181 | CB  | SER | 7  | 70.640 | 44.715 | 46.480 | 1.00 | 85.46  | Y | C |
| ATOM | 7182 | OG  | SER | 7  | 71.028 | 46.058 | 46.262 | 1.00 | 85.46  | Y | O |
| ATOM | 7183 | C   | SER | 7  | 68.797 | 44.855 | 44.824 | 1.00 | 78.31  | Y | C |
| ATOM | 7184 | O   | SER | 7  | 68.847 | 45.923 | 44.220 | 1.00 | 78.31  | Y | O |
| ATOM | 7185 | N   | PRO | 8  | 67.633 | 44.283 | 45.165 | 1.00 | 83.70  | Y | N |
| ATOM | 7186 | CD  | PRO | 8  | 66.277 | 44.777 | 44.863 | 1.00 | 54.81  | Y | C |
| ATOM | 7187 | CA  | PRO | 8  | 67.571 | 43.000 | 45.865 | 1.00 | 83.70  | Y | C |
| ATOM | 7188 | CB  | PRO | 8  | 66.097 | 42.880 | 46.226 | 1.00 | 54.81  | Y | C |
| ATOM | 7189 | CG  | PRO | 8  | 65.427 | 43.534 | 45.054 | 1.00 | 54.81  | Y | C |
| ATOM | 7190 | C   | PRO | 8  | 68.015 | 41.895 | 44.925 | 1.00 | 83.70  | Y | C |
| ATOM | 7191 | O   | PRO | 8  | 68.274 | 42.136 | 43.745 | 1.00 | 83.70  | Y | O |
| ATOM | 7192 | N   | SER | 9  | 68.111 | 40.685 | 45.455 | 1.00 | 47.38  | Y | N |
| ATOM | 7193 | CA  | SER | 9  | 68.504 | 39.541 | 44.651 | 1.00 | 47.38  | Y | C |
| ATOM | 7194 | CB  | SER | 9  | 69.145 | 38.481 | 45.543 | 1.00 | 74.91  | Y | C |
| ATOM | 7195 | OG  | SER | 9  | 70.214 | 39.045 | 46.283 | 1.00 | 74.91  | Y | O |
| ATOM | 7196 | C   | SER | 9  | 67.232 | 39.002 | 44.025 | 1.00 | 47.38  | Y | C |
| ATOM | 7197 | O   | SER | 9  | 67.237 | 38.434 | 42.936 | 1.00 | 47.38  | Y | O |
| ATOM | 7198 | N   | SER | 10 | 66.134 | 39.214 | 44.736 | 1.00 | 60.45  | Y | N |
| ATOM | 7199 | CA  | SER | 10 | 64.819 | 38.770 | 44.305 | 1.00 | 60.45  | Y | C |
| ATOM | 7200 | CB  | SER | 10 | 64.476 | 37.449 | 44.991 | 1.00 | 51.82  | Y | C |
| ATOM | 7201 | OG  | SER | 10 | 63.252 | 36.935 | 44.504 | 1.00 | 51.82  | Y | O |
| ATOM | 7202 | C   | SER | 10 | 63.797 | 39.840 | 44.691 | 1.00 | 60.45  | Y | C |
| ATOM | 7203 | O   | SER | 10 | 63.976 | 40.552 | 45.683 | 1.00 | 60.45  | Y | O |
| ATOM | 7204 | N   | LEU | 11 | 62.730 | 39.964 | 43.910 | 1.00 | 65.48  | Y | N |
| ATOM | 7205 | CA  | LEU | 11 | 61.710 | 40.964 | 44.206 | 1.00 | 65.48  | Y | C |
| ATOM | 7206 | CB  | LEU | 11 | 62.206 | 42.366 | 43.830 | 1.00 | 51.28  | Y | C |
| ATOM | 7207 | CG  | LEU | 11 | 62.310 | 42.727 | 42.342 | 1.00 | 51.28  | Y | C |
| ATOM | 7208 | CD1 | LEU | 11 | 60.949 | 43.139 | 41.803 | 1.00 | 51.28  | Y | C |
| ATOM | 7209 | CD2 | LEU | 11 | 63.294 | 43.877 | 42.168 | 1.00 | 51.28  | Y | C |
| ATOM | 7210 | C   | LEU | 11 | 60.413 | 40.680 | 43.473 | 1.00 | 65.48  | Y | C |
| ATOM | 7211 | O   | LEU | 11 | 60.412 | 40.363 | 42.282 | 1.00 | 65.48  | Y | O |
| ATOM | 7212 | N   | SER | 12 | 59.305 | 40.803 | 44.189 | 1.00 | 84.56  | Y | N |
| ATOM | 7213 | CA  | SER | 12 | 58.004 | 40.567 | 43.595 | 1.00 | 84.56  | Y | C |
| ATOM | 7214 | CB  | SER | 12 | 57.209 | 39.578 | 44.445 | 1.00 | 71.89  | Y | C |
| ATOM | 7215 | OG  | SER | 12 | 56.137 | 39.026 | 43.705 | 1.00 | 71.89  | Y | O |
| ATOM | 7216 | C   | SER | 12 | 57.273 | 41.902 | 43.507 | 1.00 | 84.56  | Y | C |
| ATOM | 7217 | O   | SER | 12 | 57.232 | 42.666 | 44.471 | 1.00 | 84.56  | Y | O |
| ATOM | 7218 | N   | ALA | 13 | 56.713 | 42.192 | 42.341 | 1.00 | 109.71 | Y | N |
| ATOM | 7219 | CA  | ALA | 13 | 55.997 | 43.442 | 42.152 | 1.00 | 109.71 | Y | C |
| ATOM | 7220 | CB  | ALA | 13 | 56.947 | 44.509 | 41.632 | 1.00 | 88.46  | Y | C |
| ATOM | 7221 | C   | ALA | 13 | 54.838 | 43.244 | 41.186 | 1.00 | 109.71 | Y | C |
| ATOM | 7222 | O   | ALA | 13 | 54.869 | 42.347 | 40.341 | 1.00 | 109.71 | Y | O |
| ATOM | 7223 | N   | SER | 14 | 53.816 | 44.084 | 41.315 | 1.00 | 66.55  | Y | N |
| ATOM | 7224 | CA  | SER | 14 | 52.632 | 44.000 | 40.461 | 1.00 | 66.55  | Y | C |
| ATOM | 7225 | CB  | SER | 14 | 51.370 | 44.265 | 41.290 | 1.00 | 62.23  | Y | C |
| ATOM | 7226 | OG  | SER | 14 | 51.506 | 45.449 | 42.059 | 1.00 | 62.23  | Y | O |
| ATOM | 7227 | C   | SER | 14 | 52.699 | 44.984 | 39.299 | 1.00 | 66.55  | Y | C |

FIG. 19A-100

| | | | | | | | | | | |
|---|---|---|---|---|---|---|---|---|---|---|
| ATOM | 7228 | O | SER | 14 | 53.362 | 46.015 | 39.394 | 1.00 | 66.55 | Y | O |
| ATOM | 7229 | N | VAL | 15 | 52.018 | 44.660 | 38.202 | 1.00 | 56.27 | Y | N |
| ATOM | 7230 | CA | VAL | 15 | 52.017 | 45.540 | 37.037 | 1.00 | 56.27 | Y | C |
| ATOM | 7231 | CB | VAL | 15 | 50.922 | 45.156 | 36.016 | 1.00 | 42.35 | Y | C |
| ATOM | 7232 | CG1 | VAL | 15 | 51.449 | 44.089 | 35.066 | 1.00 | 42.35 | Y | C |
| ATOM | 7233 | CG2 | VAL | 15 | 49.679 | 44.644 | 36.750 | 1.00 | 42.35 | Y | C |
| ATOM | 7234 | C | VAL | 15 | 51.773 | 46.964 | 37.492 | 1.00 | 56.27 | Y | C |
| ATOM | 7235 | O | VAL | 15 | 50.948 | 47.208 | 38.369 | 1.00 | 56.27 | Y | O |
| ATOM | 7236 | N | GLY | 16 | 52.509 | 47.903 | 36.911 | 1.00 | 54.44 | Y | N |
| ATOM | 7237 | CA | GLY | 16 | 52.343 | 49.296 | 37.280 | 1.00 | 54.44 | Y | C |
| ATOM | 7238 | C | GLY | 16 | 53.284 | 49.795 | 38.359 | 1.00 | 54.44 | Y | C |
| ATOM | 7239 | O | GLY | 16 | 53.419 | 51.000 | 38.542 | 1.00 | 54.44 | Y | O |
| ATOM | 7240 | N | ASP | 17 | 53.931 | 48.885 | 39.082 | 1.00 | 75.77 | Y | N |
| ATOM | 7241 | CA | ASP | 17 | 54.863 | 49.283 | 40.134 | 1.00 | 75.77 | Y | C |
| ATOM | 7242 | CB | ASP | 17 | 55.212 | 48.091 | 41.034 | 1.00 | 114.73 | Y | C |
| ATOM | 7243 | CG | ASP | 17 | 54.035 | 47.608 | 41.849 | 1.00 | 114.73 | Y | C |
| ATOM | 7244 | OD1 | ASP | 17 | 54.208 | 46.639 | 42.623 | 1.00 | 114.73 | Y | O |
| ATOM | 7245 | OD2 | ASP | 17 | 52.942 | 48.198 | 41.716 | 1.00 | 114.73 | Y | O |
| ATOM | 7246 | C | ASP | 17 | 56.149 | 49.824 | 39.525 | 1.00 | 75.77 | Y | C |
| ATOM | 7247 | O | ASP | 17 | 56.476 | 49.533 | 38.373 | 1.00 | 75.77 | Y | O |
| ATOM | 7248 | N | ARG | 18 | 56.873 | 50.616 | 40.304 | 1.00 | 69.15 | Y | N |
| ATOM | 7249 | CA | ARG | 18 | 58.139 | 51.161 | 39.844 | 1.00 | 69.15 | Y | C |
| ATOM | 7250 | CB | ARG | 18 | 58.263 | 52.634 | 40.225 | 1.00 | 52.23 | Y | C |
| ATOM | 7251 | CG | ARG | 18 | 59.557 | 53.291 | 39.779 | 1.00 | 52.23 | Y | C |
| ATOM | 7252 | CD | ARG | 18 | 59.365 | 54.788 | 39.625 | 1.00 | 52.23 | Y | C |
| ATOM | 7253 | NE | ARG | 18 | 60.622 | 55.478 | 39.370 | 1.00 | 52.23 | Y | N |
| ATOM | 7254 | CZ | ARG | 18 | 61.621 | 55.550 | 40.246 | 1.00 | 52.23 | Y | C |
| ATOM | 7255 | NH1 | ARG | 18 | 61.506 | 54.968 | 41.436 | 1.00 | 52.23 | Y | N |
| ATOM | 7256 | NH2 | ARG | 18 | 62.733 | 56.209 | 39.933 | 1.00 | 52.23 | Y | N |
| ATOM | 7257 | C | ARG | 18 | 59.232 | 50.346 | 40.514 | 1.00 | 69.15 | Y | C |
| ATOM | 7258 | O | ARG | 18 | 59.318 | 50.293 | 41.744 | 1.00 | 69.15 | Y | O |
| ATOM | 7259 | N | VAL | 19 | 60.064 | 49.706 | 39.701 | 1.00 | 58.62 | Y | N |
| ATOM | 7260 | CA | VAL | 19 | 61.132 | 48.871 | 40.221 | 1.00 | 58.62 | Y | C |
| ATOM | 7261 | CB | VAL | 19 | 61.068 | 47.477 | 39.567 | 1.00 | 74.00 | Y | C |
| ATOM | 7262 | CG1 | VAL | 19 | 62.050 | 46.531 | 40.235 | 1.00 | 74.00 | Y | C |
| ATOM | 7263 | CG2 | VAL | 19 | 59.651 | 46.938 | 39.664 | 1.00 | 74.00 | Y | C |
| ATOM | 7264 | C | VAL | 19 | 62.518 | 49.477 | 40.003 | 1.00 | 58.62 | Y | C |
| ATOM | 7265 | O | VAL | 19 | 62.782 | 50.096 | 38.975 | 1.00 | 58.62 | Y | O |
| ATOM | 7266 | N | THR | 20 | 63.399 | 49.297 | 40.978 | 1.00 | 54.75 | Y | N |
| ATOM | 7267 | CA | THR | 20 | 64.753 | 49.815 | 40.878 | 1.00 | 54.75 | Y | C |
| ATOM | 7268 | CB | THR | 20 | 64.883 | 51.148 | 41.639 | 1.00 | 56.43 | Y | C |
| ATOM | 7269 | OG1 | THR | 20 | 64.132 | 52.154 | 40.955 | 1.00 | 56.43 | Y | O |
| ATOM | 7270 | CG2 | THR | 20 | 66.337 | 51.586 | 41.726 | 1.00 | 56.43 | Y | C |
| ATOM | 7271 | C | THR | 20 | 65.806 | 48.834 | 41.401 | 1.00 | 54.75 | Y | C |
| ATOM | 7272 | O | THR | 20 | 65.963 | 48.663 | 42.611 | 1.00 | 54.75 | Y | O |
| ATOM | 7273 | N | ILE | 21 | 66.526 | 48.194 | 40.484 | 1.00 | 38.23 | Y | N |
| ATOM | 7274 | CA | ILE | 21 | 67.572 | 47.250 | 40.855 | 1.00 | 38.23 | Y | C |
| ATOM | 7275 | CB | ILE | 21 | 67.775 | 46.182 | 39.765 | 1.00 | 34.57 | Y | C |
| ATOM | 7276 | CG2 | ILE | 21 | 68.753 | 45.112 | 40.252 | 1.00 | 34.57 | Y | C |
| ATOM | 7277 | CG1 | ILE | 21 | 66.427 | 45.547 | 39.426 | 1.00 | 34.57 | Y | C |
| ATOM | 7278 | CD1 | ILE | 21 | 66.496 | 44.426 | 38.415 | 1.00 | 34.57 | Y | C |
| ATOM | 7279 | C | ILE | 21 | 68.877 | 48.006 | 41.047 | 1.00 | 38.23 | Y | C |
| ATOM | 7280 | O | ILE | 21 | 69.215 | 48.885 | 40.256 | 1.00 | 38.23 | Y | O |
| ATOM | 7281 | N | THR | 22 | 69.610 | 47.660 | 42.100 | 1.00 | 41.70 | Y | N |
| ATOM | 7282 | CA | THR | 22 | 70.880 | 48.312 | 42.396 | 1.00 | 41.70 | Y | C |
| ATOM | 7283 | CB | THR | 22 | 70.919 | 48.826 | 43.856 | 1.00 | 62.77 | Y | C |
| ATOM | 7284 | OG1 | THR | 22 | 69.986 | 49.903 | 44.017 | 1.00 | 62.77 | Y | O |
| ATOM | 7285 | CG2 | THR | 22 | 72.322 | 49.303 | 44.222 | 1.00 | 62.77 | Y | C |
| ATOM | 7286 | C | THR | 22 | 72.052 | 47.370 | 42.199 | 1.00 | 41.70 | Y | C |
| ATOM | 7287 | O | THR | 22 | 72.028 | 46.237 | 42.674 | 1.00 | 41.70 | Y | O |
| ATOM | 7288 | N | CYS | 23 | 73.077 | 47.852 | 41.500 | 1.00 | 52.46 | Y | N |
| ATOM | 7289 | CA | CYS | 23 | 74.289 | 47.076 | 41.247 | 1.00 | 52.46 | Y | C |
| ATOM | 7290 | C | CYS | 23 | 75.446 | 47.833 | 41.875 | 1.00 | 52.46 | Y | C |
| ATOM | 7291 | O | CYS | 23 | 75.749 | 48.957 | 41.476 | 1.00 | 52.46 | Y | O |
| ATOM | 7292 | CB | CYS | 23 | 74.522 | 46.938 | 39.744 | 1.00 | 61.15 | Y | C |
| ATOM | 7293 | SG | CYS | 23 | 75.983 | 45.982 | 39.184 | 1.00 | 61.15 | Y | S |
| ATOM | 7294 | N | SER | 24 | 76.079 | 47.219 | 42.866 | 1.00 | 43.95 | Y | N |
| ATOM | 7295 | CA | SER | 24 | 77.200 | 47.837 | 43.556 | 1.00 | 43.95 | Y | C |
| ATOM | 7296 | CB | SER | 24 | 76.992 | 47.751 | 45.072 | 1.00 | 58.07 | Y | C |
| ATOM | 7297 | OG | SER | 24 | 75.782 | 48.379 | 45.462 | 1.00 | 58.07 | Y | O |
| ATOM | 7298 | C | SER | 24 | 78.495 | 47.138 | 43.177 | 1.00 | 43.95 | Y | C |
| ATOM | 7299 | O | SER | 24 | 78.582 | 45.912 | 43.222 | 1.00 | 43.95 | Y | O |
| ATOM | 7300 | N | ALA | 25 | 79.503 | 47.924 | 42.814 | 1.00 | 35.63 | Y | N |

FIG. 19A-101

| ATOM | 7301 | CA | ALA | 25 | 80.796 | 47.373 | 42.427 | 1.00 | 35.63 | Y | C |
|---|---|---|---|---|---|---|---|---|---|---|---|
| ATOM | 7302 | CB | ALA | 25 | 81.214 | 47.920 | 41.068 | 1.00 | 50.18 | Y | C |
| ATOM | 7303 | C | ALA | 25 | 81.894 | 47.635 | 43.454 | 1.00 | 35.63 | Y | C |
| ATOM | 7304 | O | ALA | 25 | 82.050 | 48.754 | 43.959 | 1.00 | 35.63 | Y | O |
| ATOM | 7305 | N | SER | 26 | 82.650 | 46.579 | 43.742 | 1.00 | 37.44 | Y | N |
| ATOM | 7306 | CA | SER | 26 | 83.746 | 46.616 | 44.697 | 1.00 | 37.44 | Y | C |
| ATOM | 7307 | CB | SER | 26 | 84.492 | 45.280 | 44.672 | 1.00 | 31.41 | Y | C |
| ATOM | 7308 | OG | SER | 26 | 85.018 | 45.005 | 43.381 | 1.00 | 31.41 | Y | O |
| ATOM | 7309 | C | SER | 26 | 84.718 | 47.745 | 44.393 | 1.00 | 37.44 | Y | C |
| ATOM | 7310 | O | SER | 26 | 85.358 | 48.286 | 45.297 | 1.00 | 37.44 | Y | O |
| ATOM | 7311 | N | SER | 27 | 84.835 | 48.088 | 43.116 | 1.00 | 70.39 | Y | N |
| ATOM | 7312 | CA | SER | 27 | 85.726 | 49.157 | 42.687 | 1.00 | 70.39 | Y | C |
| ATOM | 7313 | CB | SER | 27 | 86.941 | 48.581 | 41.954 | 1.00 | 53.81 | Y | C |
| ATOM | 7314 | OG | SER | 27 | 87.574 | 47.567 | 42.716 | 1.00 | 53.81 | Y | O |
| ATOM | 7315 | C | SER | 27 | 84.922 | 50.023 | 41.736 | 1.00 | 70.39 | Y | C |
| ATOM | 7316 | O | SER | 27 | 83.960 | 49.545 | 41.139 | 1.00 | 70.39 | Y | O |
| ATOM | 7317 | N | SER | 28 | 85.306 | 51.290 | 41.595 | 1.00 | 30.73 | Y | N |
| ATOM | 7318 | CA | SER | 28 | 84.598 | 52.194 | 40.695 | 1.00 | 30.73 | Y | C |
| ATOM | 7319 | CB | SER | 28 | 85.060 | 53.628 | 40.920 | 1.00 | 55.81 | Y | C |
| ATOM | 7320 | OG | SER | 28 | 86.448 | 53.723 | 40.688 | 1.00 | 55.81 | Y | O |
| ATOM | 7321 | C | SER | 28 | 84.824 | 51.813 | 39.230 | 1.00 | 30.73 | Y | C |
| ATOM | 7322 | O | SER | 28 | 85.873 | 51.287 | 38.863 | 1.00 | 30.73 | Y | O |
| ATOM | 7323 | N | VAL | 29 | 83.832 | 52.092 | 38.398 | 1.00 | 34.83 | Y | N |
| ATOM | 7324 | CA | VAL | 29 | 83.909 | 51.780 | 36.983 | 1.00 | 34.83 | Y | C |
| ATOM | 7325 | CB | VAL | 29 | 83.173 | 50.443 | 36.682 | 1.00 | 24.96 | Y | C |
| ATOM | 7326 | CG1 | VAL | 29 | 83.891 | 49.286 | 37.382 | 1.00 | 24.96 | Y | C |
| ATOM | 7327 | CG2 | VAL | 29 | 81.717 | 50.518 | 37.153 | 1.00 | 24.96 | Y | C |
| ATOM | 7328 | C | VAL | 29 | 83.267 | 52.929 | 36.208 | 1.00 | 34.83 | Y | C |
| ATOM | 7329 | O | VAL | 29 | 82.397 | 53.621 | 36.738 | 1.00 | 34.83 | Y | O |
| ATOM | 7330 | N | ASN | 30 | 83.689 | 53.134 | 34.963 | 1.00 | 19.83 | Y | N |
| ATOM | 7331 | CA | ASN | 30 | 83.152 | 54.225 | 34.145 | 1.00 | 19.83 | Y | C |
| ATOM | 7332 | CB | ASN | 30 | 84.086 | 54.517 | 32.963 | 1.00 | 44.92 | Y | C |
| ATOM | 7333 | CG | ASN | 30 | 84.524 | 53.261 | 32.254 | 1.00 | 44.92 | Y | C |
| ATOM | 7334 | OD1 | ASN | 30 | 85.235 | 52.431 | 32.832 | 1.00 | 44.92 | Y | O |
| ATOM | 7335 | ND2 | ASN | 30 | 84.097 | 53.099 | 31.001 | 1.00 | 44.92 | Y | N |
| ATOM | 7336 | C | ASN | 30 | 81.740 | 53.976 | 33.634 | 1.00 | 19.83 | Y | C |
| ATOM | 7337 | O | ASN | 30 | 80.998 | 54.926 | 33.381 | 1.00 | 19.83 | Y | O |
| ATOM | 7338 | N | HIS | 31 | 81.367 | 52.708 | 33.475 | 1.00 | 24.55 | Y | N |
| ATOM | 7339 | CA | HIS | 31 | 80.031 | 52.373 | 32.991 | 1.00 | 24.55 | Y | C |
| ATOM | 7340 | CB | HIS | 31 | 80.003 | 52.259 | 31.459 | 1.00 | 41.70 | Y | C |
| ATOM | 7341 | CG | HIS | 31 | 80.061 | 53.572 | 30.737 | 1.00 | 41.70 | Y | C |
| ATOM | 7342 | CD2 | HIS | 31 | 79.124 | 54.233 | 30.016 | 1.00 | 41.70 | Y | C |
| ATOM | 7343 | ND1 | HIS | 31 | 81.196 | 54.351 | 30.692 | 1.00 | 41.70 | Y | N |
| ATOM | 7344 | CE1 | HIS | 31 | 80.958 | 55.435 | 29.973 | 1.00 | 41.70 | Y | C |
| ATOM | 7345 | NE2 | HIS | 31 | 79.708 | 55.387 | 29.551 | 1.00 | 41.70 | Y | N |
| ATOM | 7346 | C | HIS | 31 | 79.548 | 51.058 | 33.567 | 1.00 | 24.55 | Y | C |
| ATOM | 7347 | O | HIS | 31 | 80.274 | 50.392 | 34.305 | 1.00 | 24.55 | Y | O |
| ATOM | 7348 | N | MET | 32 | 78.312 | 50.698 | 33.227 | 1.00 | 16.59 | Y | N |
| ATOM | 7349 | CA | MET | 32 | 77.719 | 49.440 | 33.664 | 1.00 | 16.59 | Y | C |
| ATOM | 7350 | CB | MET | 32 | 76.944 | 49.624 | 34.971 | 1.00 | 29.77 | Y | C |
| ATOM | 7351 | CG | MET | 32 | 76.606 | 48.310 | 35.684 | 1.00 | 29.77 | Y | C |
| ATOM | 7352 | SD | MET | 32 | 78.097 | 47.369 | 36.143 | 1.00 | 29.77 | Y | S |
| ATOM | 7353 | CE | MET | 32 | 78.855 | 48.463 | 37.337 | 1.00 | 29.77 | Y | C |
| ATOM | 7354 | C | MET | 32 | 76.779 | 48.941 | 32.563 | 1.00 | 16.59 | Y | C |
| ATOM | 7355 | O | MET | 32 | 76.138 | 49.734 | 31.871 | 1.00 | 16.59 | Y | O |
| ATOM | 7356 | N | PHE | 33 | 76.706 | 47.629 | 32.383 | 1.00 | 41.04 | Y | N |
| ATOM | 7357 | CA | PHE | 33 | 75.830 | 47.089 | 31.358 | 1.00 | 41.04 | Y | C |
| ATOM | 7358 | CB | PHE | 33 | 76.639 | 46.329 | 30.315 | 1.00 | 16.08 | Y | C |
| ATOM | 7359 | CG | PHE | 33 | 77.695 | 47.161 | 29.657 | 1.00 | 16.08 | Y | C |
| ATOM | 7360 | CD1 | PHE | 33 | 78.846 | 47.528 | 30.354 | 1.00 | 16.08 | Y | C |
| ATOM | 7361 | CD2 | PHE | 33 | 77.524 | 47.609 | 28.350 | 1.00 | 16.08 | Y | C |
| ATOM | 7362 | CE1 | PHE | 33 | 79.810 | 48.328 | 29.763 | 1.00 | 16.08 | Y | C |
| ATOM | 7363 | CE2 | PHE | 33 | 78.484 | 48.414 | 27.745 | 1.00 | 16.08 | Y | C |
| ATOM | 7364 | CZ | PHE | 33 | 79.634 | 48.776 | 28.456 | 1.00 | 16.08 | Y | C |
| ATOM | 7365 | C | PHE | 33 | 74.803 | 46.175 | 31.985 | 1.00 | 41.04 | Y | C |
| ATOM | 7366 | O | PHE | 33 | 75.036 | 45.622 | 33.057 | 1.00 | 41.04 | Y | O |
| ATOM | 7367 | N | TRP | 34 | 73.664 | 46.020 | 31.322 | 1.00 | 26.10 | Y | N |
| ATOM | 7368 | CA | TRP | 34 | 72.604 | 45.168 | 31.843 | 1.00 | 26.10 | Y | C |
| ATOM | 7369 | CB | TRP | 34 | 71.438 | 46.009 | 32.364 | 1.00 | 47.27 | Y | C |
| ATOM | 7370 | CG | TRP | 34 | 71.807 | 46.935 | 33.466 | 1.00 | 47.27 | Y | C |
| ATOM | 7371 | CD2 | TRP | 34 | 71.660 | 46.692 | 34.868 | 1.00 | 47.27 | Y | C |
| ATOM | 7372 | CE2 | TRP | 34 | 72.145 | 47.836 | 35.542 | 1.00 | 47.27 | Y | C |
| ATOM | 7373 | CE3 | TRP | 34 | 71.167 | 45.621 | 35.622 | 1.00 | 47.27 | Y | C |

FIG. 19A-102

```
ATOM   7374  CD1  TRP  34   72.360  48.175  33.346  1.00  47.27  Y  C
ATOM   7375  NE1  TRP  34   72.567  48.725  34.589  1.00  47.27  Y  N
ATOM   7376  CZ2  TRP  34   72.150  47.939  36.940  1.00  47.27  Y  C
ATOM   7377  CZ3  TRP  34   71.172  45.725  37.013  1.00  47.27  Y  C
ATOM   7378  CH2  TRP  34   71.661  46.879  37.655  1.00  47.27  Y  C
ATOM   7379  C    TRP  34   72.067  44.187  30.812  1.00  26.10  Y  C
ATOM   7380  O    TRP  34   71.904  44.513  29.630  1.00  26.10  Y  O
ATOM   7381  N    TYR  35   71.793  42.972  31.267  1.00  43.42  Y  N
ATOM   7382  CA   TYR  35   71.248  41.964  30.381  1.00  43.42  Y  C
ATOM   7383  CB   TYR  35   72.230  40.808  30.189  1.00  22.29  Y  C
ATOM   7384  CG   TYR  35   73.549  41.240  29.596  1.00  22.29  Y  C
ATOM   7385  CD1  TYR  35   74.645  41.535  30.417  1.00  22.29  Y  C
ATOM   7386  CE1  TYR  35   75.841  41.962  29.881  1.00  22.29  Y  C
ATOM   7387  CD2  TYR  35   73.697  41.385  28.216  1.00  22.29  Y  C
ATOM   7388  CE2  TYR  35   74.898  41.808  27.670  1.00  22.29  Y  C
ATOM   7389  CZ   TYR  35   75.960  42.094  28.510  1.00  22.29  Y  C
ATOM   7390  OH   TYR  35   77.148  42.516  27.972  1.00  22.29  Y  O
ATOM   7391  C    TYR  35   69.966  41.449  30.991  1.00  43.42  Y  C
ATOM   7392  O    TYR  35   69.826  41.393  32.214  1.00  43.42  Y  O
ATOM   7393  N    GLN  36   69.015  41.107  30.136  1.00  45.64  Y  N
ATOM   7394  CA   GLN  36   67.760  40.567  30.607  1.00  45.64  Y  C
ATOM   7395  CB   GLN  36   66.574  41.346  30.054  1.00  37.71  Y  C
ATOM   7396  CG   GLN  36   65.259  40.610  30.277  1.00  37.71  Y  C
ATOM   7397  CD   GLN  36   64.189  41.002  29.287  1.00  37.71  Y  C
ATOM   7398  OE1  GLN  36   63.601  42.072  29.391  1.00  37.71  Y  O
ATOM   7399  NE2  GLN  36   63.936  40.137  28.314  1.00  37.71  Y  N
ATOM   7400  C    GLN  36   67.664  39.138  30.118  1.00  45.64  Y  C
ATOM   7401  O    GLN  36   67.725  38.881  28.910  1.00  45.64  Y  O
ATOM   7402  N    GLN  37   67.522  38.205  31.050  1.00  50.28  Y  N
ATOM   7403  CA   GLN  37   67.390  36.809  30.670  1.00  50.28  Y  C
ATOM   7404  CB   GLN  37   68.522  35.961  31.265  1.00  34.85  Y  C
ATOM   7405  CG   GLN  37   68.392  34.487  30.904  1.00  34.85  Y  C
ATOM   7406  CD   GLN  37   69.543  33.645  31.388  1.00  34.85  Y  C
ATOM   7407  OE1  GLN  37   69.925  33.699  32.565  1.00  34.85  Y  O
ATOM   7408  NE2  GLN  37   70.098  32.842  30.484  1.00  34.85  Y  N
ATOM   7409  C    GLN  37   66.042  36.248  31.108  1.00  50.28  Y  C
ATOM   7410  O    GLN  37   65.690  36.272  32.293  1.00  50.28  Y  O
ATOM   7411  N    LYS  38   65.284  35.763  30.133  1.00  68.24  Y  N
ATOM   7412  CA   LYS  38   63.983  35.175  30.403  1.00  68.24  Y  C
ATOM   7413  CB   LYS  38   62.991  35.530  29.291  1.00  55.54  Y  C
ATOM   7414  CG   LYS  38   62.893  37.031  29.023  1.00  55.54  Y  C
ATOM   7415  CD   LYS  38   61.764  37.382  28.056  1.00  55.54  Y  C
ATOM   7416  CE   LYS  38   60.394  37.298  28.726  1.00  55.54  Y  C
ATOM   7417  NZ   LYS  38   60.290  38.166  29.943  1.00  55.54  Y  N
ATOM   7418  C    LYS  38   64.198  33.667  30.473  1.00  68.24  Y  C
ATOM   7419  O    LYS  38   64.971  33.104  29.696  1.00  68.24  Y  O
ATOM   7420  N    PRO  39   63.520  32.994  31.412  1.00  67.87  Y  N
ATOM   7421  CD   PRO  39   62.478  33.563  32.282  1.00  58.47  Y  C
ATOM   7422  CA   PRO  39   63.621  31.546  31.614  1.00  67.87  Y  C
ATOM   7423  CB   PRO  39   62.368  31.234  32.417  1.00  58.47  Y  C
ATOM   7424  CG   PRO  39   62.247  32.446  33.271  1.00  58.47  Y  C
ATOM   7425  C    PRO  39   63.717  30.714  30.338  1.00  67.87  Y  C
ATOM   7426  O    PRO  39   62.898  30.859  29.425  1.00  67.87  Y  O
ATOM   7427  N    GLY  40   64.730  29.847  30.288  1.00  54.98  Y  N
ATOM   7428  CA   GLY  40   64.925  28.977  29.137  1.00  54.98  Y  C
ATOM   7429  C    GLY  40   65.488  29.625  27.882  1.00  54.98  Y  C
ATOM   7430  O    GLY  40   65.625  28.957  26.855  1.00  54.98  Y  O
ATOM   7431  N    LYS  41   65.801  30.918  27.955  1.00  83.28  Y  N
ATOM   7432  CA   LYS  41   66.364  31.641  26.816  1.00  83.28  Y  C
ATOM   7433  CB   LYS  41   65.414  32.754  26.354  1.00  72.06  Y  C
ATOM   7434  CG   LYS  41   64.045  32.271  25.882  1.00  72.06  Y  C
ATOM   7435  CD   LYS  41   63.316  33.311  25.008  1.00  72.06  Y  C
ATOM   7436  CE   LYS  41   63.035  34.642  25.726  1.00  72.06  Y  C
ATOM   7437  NZ   LYS  41   64.229  35.536  25.855  1.00  72.06  Y  N
ATOM   7438  C    LYS  41   67.727  32.245  27.160  1.00  83.28  Y  C
ATOM   7439  O    LYS  41   68.110  32.327  28.331  1.00  83.28  Y  O
ATOM   7440  N    ALA  42   68.458  32.666  26.133  1.00  55.60  Y  N
ATOM   7441  CA   ALA  42   69.776  33.261  26.326  1.00  55.60  Y  C
ATOM   7442  CB   ALA  42   70.561  33.194  25.041  1.00   1.87  Y  C
ATOM   7443  C    ALA  42   69.623  34.707  26.754  1.00  55.60  Y  C
ATOM   7444  O    ALA  42   68.607  35.337  26.462  1.00  55.60  Y  O
ATOM   7445  N    PRO  43   70.628  35.259  27.455  1.00  54.21  Y  N
ATOM   7446  CD   PRO  43   71.849  34.627  27.983  1.00  18.24  Y  C
```

FIG. 19A-103

| ATOM | 7447 | CA | PRO | 43 | 70.537 | 36.656 | 27.889 | 1.00 | 54.21 | Y | C |
| ATOM | 7448 | CB | PRO | 43 | 71.875 | 36.890 | 28.594 | 1.00 | 18.24 | Y | C |
| ATOM | 7449 | CG | PRO | 43 | 72.202 | 35.544 | 29.149 | 1.00 | 18.24 | Y | C |
| ATOM | 7450 | C | PRO | 43 | 70.349 | 37.584 | 26.689 | 1.00 | 54.21 | Y | C |
| ATOM | 7451 | O | PRO | 43 | 70.660 | 37.219 | 25.555 | 1.00 | 54.21 | Y | O |
| ATOM | 7452 | N | LYS | 44 | 69.837 | 38.782 | 26.946 | 1.00 | 55.44 | Y | N |
| ATOM | 7453 | CA | LYS | 44 | 69.618 | 39.764 | 25.892 | 1.00 | 55.44 | Y | C |
| ATOM | 7454 | CB | LYS | 44 | 68.120 | 39.894 | 25.601 | 1.00 | 46.11 | Y | C |
| ATOM | 7455 | CG | LYS | 44 | 67.705 | 39.473 | 24.199 | 1.00 | 46.11 | Y | C |
| ATOM | 7456 | CD | LYS | 44 | 66.189 | 39.520 | 24.018 | 1.00 | 46.11 | Y | C |
| ATOM | 7457 | CE | LYS | 44 | 65.457 | 38.464 | 24.865 | 1.00 | 46.11 | Y | C |
| ATOM | 7458 | NZ | LYS | 44 | 65.564 | 38.665 | 26.354 | 1.00 | 46.11 | Y | N |
| ATOM | 7459 | C | LYS | 44 | 70.172 | 41.117 | 26.328 | 1.00 | 55.44 | Y | C |
| ATOM | 7460 | O | LYS | 44 | 69.930 | 41.554 | 27.454 | 1.00 | 55.44 | Y | O |
| ATOM | 7461 | N | PRO | 45 | 70.946 | 41.785 | 25.451 | 1.00 | 21.39 | Y | N |
| ATOM | 7462 | CD | PRO | 45 | 71.303 | 41.365 | 24.085 | 1.00 | 11.37 | Y | C |
| ATOM | 7463 | CA | PRO | 45 | 71.523 | 43.103 | 25.772 | 1.00 | 21.39 | Y | C |
| ATOM | 7464 | CB | PRO | 45 | 72.159 | 43.539 | 24.457 | 1.00 | 11.37 | Y | C |
| ATOM | 7465 | CG | PRO | 45 | 72.485 | 42.234 | 23.795 | 1.00 | 11.37 | Y | C |
| ATOM | 7466 | C | PRO | 45 | 70.361 | 44.010 | 26.138 | 1.00 | 21.39 | Y | C |
| ATOM | 7467 | O | PRO | 45 | 69.407 | 44.103 | 25.383 | 1.00 | 21.39 | Y | O |
| ATOM | 7468 | N | TRP | 46 | 70.434 | 44.676 | 27.281 | 1.00 | 48.64 | Y | N |
| ATOM | 7469 | CA | TRP | 46 | 69.333 | 45.532 | 27.704 | 1.00 | 48.64 | Y | C |
| ATOM | 7470 | CB | TRP | 46 | 68.783 | 45.038 | 29.043 | 1.00 | 23.18 | Y | C |
| ATOM | 7471 | CG | TRP | 46 | 67.316 | 45.220 | 29.143 | 1.00 | 23.18 | Y | C |
| ATOM | 7472 | CD2 | TRP | 46 | 66.330 | 44.620 | 28.299 | 1.00 | 23.18 | Y | C |
| ATOM | 7473 | CE2 | TRP | 46 | 65.070 | 45.075 | 28.739 | 1.00 | 23.18 | Y | C |
| ATOM | 7474 | CE3 | TRP | 46 | 66.391 | 43.736 | 27.206 | 1.00 | 23.18 | Y | C |
| ATOM | 7475 | CD1 | TRP | 46 | 66.637 | 45.997 | 30.038 | 1.00 | 23.18 | Y | C |
| ATOM | 7476 | NE1 | TRP | 46 | 65.282 | 45.914 | 29.803 | 1.00 | 23.18 | Y | N |
| ATOM | 7477 | CZ2 | TRP | 46 | 63.881 | 44.679 | 28.126 | 1.00 | 23.18 | Y | C |
| ATOM | 7478 | CZ3 | TRP | 46 | 65.212 | 43.342 | 26.599 | 1.00 | 23.18 | Y | C |
| ATOM | 7479 | CH2 | TRP | 46 | 63.973 | 43.814 | 27.059 | 1.00 | 23.18 | Y | C |
| ATOM | 7480 | C | TRP | 46 | 69.694 | 47.007 | 27.826 | 1.00 | 48.64 | Y | C |
| ATOM | 7481 | O | TRP | 46 | 68.986 | 47.877 | 27.324 | 1.00 | 48.64 | Y | O |
| ATOM | 7482 | N | ILE | 47 | 70.785 | 47.283 | 28.523 | 1.00 | 42.06 | Y | N |
| ATOM | 7483 | CA | ILE | 47 | 71.238 | 48.644 | 28.717 | 1.00 | 42.06 | Y | C |
| ATOM | 7484 | CB | ILE | 47 | 70.801 | 49.172 | 30.099 | 1.00 | 37.03 | Y | C |
| ATOM | 7485 | CG2 | ILE | 47 | 71.345 | 50.580 | 30.325 | 1.00 | 37.03 | Y | C |
| ATOM | 7486 | CG1 | ILE | 47 | 69.275 | 49.168 | 30.198 | 1.00 | 37.03 | Y | C |
| ATOM | 7487 | CD1 | ILE | 47 | 68.749 | 49.670 | 31.538 | 1.00 | 37.03 | Y | C |
| ATOM | 7488 | C | ILE | 47 | 72.758 | 48.641 | 28.638 | 1.00 | 42.06 | Y | C |
| ATOM | 7489 | O | ILE | 47 | 73.417 | 47.951 | 29.414 | 1.00 | 42.06 | Y | O |
| ATOM | 7490 | N | TYR | 48 | 73.310 | 49.387 | 27.684 | 1.00 | 17.47 | Y | N |
| ATOM | 7491 | CA | TYR | 48 | 74.753 | 49.467 | 27.532 | 1.00 | 17.47 | Y | C |
| ATOM | 7492 | CB | TYR | 48 | 75.189 | 49.145 | 26.106 | 1.00 | 20.64 | Y | C |
| ATOM | 7493 | CG | TYR | 48 | 74.613 | 50.048 | 25.046 | 1.00 | 20.64 | Y | C |
| ATOM | 7494 | CD1 | TYR | 48 | 73.267 | 49.988 | 24.710 | 1.00 | 20.64 | Y | C |
| ATOM | 7495 | CE1 | TYR | 48 | 72.743 | 50.792 | 23.704 | 1.00 | 20.64 | Y | C |
| ATOM | 7496 | CD2 | TYR | 48 | 75.425 | 50.940 | 24.353 | 1.00 | 20.64 | Y | C |
| ATOM | 7497 | CE2 | TYR | 48 | 74.916 | 51.750 | 23.347 | 1.00 | 20.64 | Y | C |
| ATOM | 7498 | CZ | TYR | 48 | 73.573 | 51.671 | 23.028 | 1.00 | 20.64 | Y | C |
| ATOM | 7499 | OH | TYR | 48 | 73.051 | 52.476 | 22.045 | 1.00 | 20.64 | Y | O |
| ATOM | 7500 | C | TYR | 48 | 75.193 | 50.861 | 27.892 | 1.00 | 17.47 | Y | C |
| ATOM | 7501 | O | TYR | 48 | 74.365 | 51.754 | 28.021 | 1.00 | 17.47 | Y | O |
| ATOM | 7502 | N | LEU | 49 | 76.497 | 51.044 | 28.054 | 1.00 | 31.07 | Y | N |
| ATOM | 7503 | CA | LEU | 49 | 77.042 | 52.337 | 28.429 | 1.00 | 31.07 | Y | C |
| ATOM | 7504 | CB | LEU | 49 | 77.200 | 53.247 | 27.205 | 1.00 | 20.44 | Y | C |
| ATOM | 7505 | CG | LEU | 49 | 78.368 | 53.044 | 26.236 | 1.00 | 20.44 | Y | C |
| ATOM | 7506 | CD1 | LEU | 49 | 79.662 | 52.870 | 27.019 | 1.00 | 20.44 | Y | C |
| ATOM | 7507 | CD2 | LEU | 49 | 78.121 | 51.836 | 25.385 | 1.00 | 20.44 | Y | C |
| ATOM | 7508 | C | LEU | 49 | 76.173 | 53.037 | 29.475 | 1.00 | 31.07 | Y | C |
| ATOM | 7509 | O | LEU | 49 | 75.769 | 54.178 | 29.293 | 1.00 | 31.07 | Y | O |
| ATOM | 7510 | N | THR | 50 | 75.861 | 52.329 | 30.555 | 1.00 | 28.24 | Y | N |
| ATOM | 7511 | CA | THR | 50 | 75.083 | 52.870 | 31.670 | 1.00 | 28.24 | Y | C |
| ATOM | 7512 | CB | THR | 50 | 75.754 | 54.128 | 32.230 | 1.00 | 41.62 | Y | C |
| ATOM | 7513 | OG1 | THR | 50 | 77.134 | 53.847 | 32.495 | 1.00 | 41.62 | Y | O |
| ATOM | 7514 | CG2 | THR | 50 | 75.066 | 54.568 | 33.522 | 1.00 | 41.62 | Y | C |
| ATOM | 7515 | C | THR | 50 | 73.605 | 53.187 | 31.485 | 1.00 | 28.24 | Y | C |
| ATOM | 7516 | O | THR | 50 | 72.761 | 52.603 | 32.158 | 1.00 | 28.24 | Y | O |
| ATOM | 7517 | N | SER | 51 | 73.283 | 54.114 | 30.595 | 1.00 | 28.33 | Y | N |
| ATOM | 7518 | CA | SER | 51 | 71.889 | 54.496 | 30.402 | 1.00 | 28.33 | Y | C |
| ATOM | 7519 | CB | SER | 51 | 71.729 | 55.981 | 30.714 | 1.00 | 81.44 | Y | C |

FIG. 19A-104

| ATOM | 7520 | OG | SER | 51 | 72.714 | 56.738 | 30.034 | 1.00 | 81.44 | Y | O |
|------|------|----|-----|-----|--------|--------|--------|------|-------|---|---|
| ATOM | 7521 | C | SER | 51 | 71.312 | 54.190 | 29.019 | 1.00 | 28.33 | Y | C |
| ATOM | 7522 | O | SER | 51 | 70.092 | 54.174 | 28.831 | 1.00 | 28.33 | Y | O |
| ATOM | 7523 | N | ASN | 52 | 72.184 | 53.941 | 28.053 | 1.00 | 27.44 | Y | N |
| ATOM | 7524 | CA | ASN | 52 | 71.736 | 53.648 | 26.704 | 1.00 | 27.44 | Y | C |
| ATOM | 7525 | CB | ASN | 52 | 72.942 | 53.523 | 25.779 | 1.00 | 42.81 | Y | C |
| ATOM | 7526 | CG | ASN | 52 | 73.623 | 54.849 | 25.546 | 1.00 | 42.81 | Y | C |
| ATOM | 7527 | OD1 | ASN | 52 | 73.059 | 55.733 | 24.907 | 1.00 | 42.81 | Y | O |
| ATOM | 7528 | ND2 | ASN | 52 | 74.829 | 55.006 | 26.076 | 1.00 | 42.81 | Y | N |
| ATOM | 7529 | C | ASN | 52 | 70.896 | 52.390 | 26.623 | 1.00 | 27.44 | Y | C |
| ATOM | 7530 | O | ASN | 52 | 71.336 | 51.320 | 27.027 | 1.00 | 27.44 | Y | O |
| ATOM | 7531 | N | LEU | 53 | 69.682 | 52.519 | 26.100 | 1.00 | 46.42 | Y | N |
| ATOM | 7532 | CA | LEU | 53 | 68.805 | 51.367 | 25.954 | 1.00 | 46.42 | Y | C |
| ATOM | 7533 | CB | LEU | 53 | 67.349 | 51.803 | 25.887 | 1.00 | 19.90 | Y | C |
| ATOM | 7534 | CG | LEU | 53 | 66.763 | 52.595 | 27.051 | 1.00 | 19.90 | Y | C |
| ATOM | 7535 | CD1 | LEU | 53 | 65.255 | 52.685 | 26.846 | 1.00 | 19.90 | Y | C |
| ATOM | 7536 | CD2 | LEU | 53 | 67.071 | 51.918 | 28.382 | 1.00 | 19.90 | Y | C |
| ATOM | 7537 | C | LEU | 53 | 69.136 | 50.610 | 24.676 | 1.00 | 46.42 | Y | C |
| ATOM | 7538 | O | LEU | 53 | 69.414 | 51.220 | 23.644 | 1.00 | 46.42 | Y | O |
| ATOM | 7539 | N | ALA | 54 | 69.101 | 49.281 | 24.744 | 1.00 | 35.05 | Y | N |
| ATOM | 7540 | CA | ALA | 54 | 69.378 | 48.447 | 23.583 | 1.00 | 35.05 | Y | C |
| ATOM | 7541 | CB | ALA | 54 | 69.220 | 46.994 | 23.930 | 1.00 | 27.54 | Y | C |
| ATOM | 7542 | C | ALA | 54 | 68.373 | 48.829 | 22.530 | 1.00 | 35.05 | Y | C |
| ATOM | 7543 | O | ALA | 54 | 67.680 | 49.834 | 22.666 | 1.00 | 35.05 | Y | O |
| ATOM | 7544 | N | SER | 55 | 68.259 | 48.026 | 21.486 | 1.00 | 47.40 | Y | N |
| ATOM | 7545 | CA | SER | 55 | 67.319 | 48.376 | 20.443 | 1.00 | 47.40 | Y | C |
| ATOM | 7546 | CB | SER | 55 | 67.689 | 47.681 | 19.140 | 1.00 | 36.06 | Y | C |
| ATOM | 7547 | OG | SER | 55 | 67.083 | 48.359 | 18.051 | 1.00 | 36.06 | Y | O |
| ATOM | 7548 | C | SER | 55 | 65.866 | 48.073 | 20.801 | 1.00 | 47.40 | Y | C |
| ATOM | 7549 | O | SER | 55 | 64.993 | 48.921 | 20.631 | 1.00 | 47.40 | Y | O |
| ATOM | 7550 | N | GLY | 56 | 65.599 | 46.878 | 21.312 | 1.00 | 54.09 | Y | N |
| ATOM | 7551 | CA | GLY | 56 | 64.225 | 46.531 | 21.647 | 1.00 | 54.09 | Y | C |
| ATOM | 7552 | C | GLY | 56 | 63.650 | 47.071 | 22.948 | 1.00 | 54.09 | Y | C |
| ATOM | 7553 | O | GLY | 56 | 62.457 | 47.370 | 23.025 | 1.00 | 54.09 | Y | O |
| ATOM | 7554 | N | VAL | 57 | 64.497 | 47.197 | 23.965 | 1.00 | 63.10 | Y | N |
| ATOM | 7555 | CA | VAL | 57 | 64.082 | 47.667 | 25.282 | 1.00 | 63.10 | Y | C |
| ATOM | 7556 | CB | VAL | 57 | 65.311 | 48.113 | 26.120 | 1.00 | 46.15 | Y | C |
| ATOM | 7557 | CG1 | VAL | 57 | 64.923 | 48.248 | 27.588 | 1.00 | 46.15 | Y | C |
| ATOM | 7558 | CG2 | VAL | 57 | 66.446 | 47.118 | 25.961 | 1.00 | 46.15 | Y | C |
| ATOM | 7559 | C | VAL | 57 | 63.071 | 48.817 | 25.251 | 1.00 | 63.10 | Y | C |
| ATOM | 7560 | O | VAL | 57 | 63.363 | 49.898 | 24.747 | 1.00 | 63.10 | Y | O |
| ATOM | 7561 | N | PRO | 58 | 61.862 | 48.594 | 25.791 | 1.00 | 51.01 | Y | N |
| ATOM | 7562 | CD | PRO | 58 | 61.362 | 47.365 | 26.426 | 1.00 | 31.12 | Y | C |
| ATOM | 7563 | CA | PRO | 58 | 60.834 | 49.639 | 25.815 | 1.00 | 51.01 | Y | C |
| ATOM | 7564 | CB | PRO | 58 | 59.634 | 48.929 | 26.433 | 1.00 | 31.12 | Y | C |
| ATOM | 7565 | CG | PRO | 58 | 60.258 | 47.899 | 27.300 | 1.00 | 31.12 | Y | C |
| ATOM | 7566 | C | PRO | 58 | 61.305 | 50.829 | 26.643 | 1.00 | 51.01 | Y | C |
| ATOM | 7567 | O | PRO | 58 | 61.992 | 50.660 | 27.653 | 1.00 | 51.01 | Y | O |
| ATOM | 7568 | N | SER | 59 | 60.918 | 52.027 | 26.216 | 1.00 | 33.61 | Y | N |
| ATOM | 7569 | CA | SER | 59 | 61.330 | 53.267 | 26.874 | 1.00 | 33.61 | Y | C |
| ATOM | 7570 | CB | SER | 59 | 60.780 | 54.482 | 26.113 | 1.00 | 61.12 | Y | C |
| ATOM | 7571 | OG | SER | 59 | 59.368 | 54.481 | 26.096 | 1.00 | 61.12 | Y | O |
| ATOM | 7572 | C | SER | 59 | 61.023 | 53.411 | 28.359 | 1.00 | 33.61 | Y | C |
| ATOM | 7573 | O | SER | 59 | 61.495 | 54.353 | 28.990 | 1.00 | 33.61 | Y | O |
| ATOM | 7574 | N | ARG | 60 | 60.244 | 52.500 | 28.928 | 1.00 | 39.70 | Y | N |
| ATOM | 7575 | CA | ARG | 60 | 59.963 | 52.599 | 30.359 | 1.00 | 39.70 | Y | C |
| ATOM | 7576 | CB | ARG | 60 | 58.764 | 51.731 | 30.751 | 1.00 | 42.51 | Y | C |
| ATOM | 7577 | CG | ARG | 60 | 58.846 | 50.293 | 30.287 | 1.00 | 42.51 | Y | C |
| ATOM | 7578 | CD | ARG | 60 | 57.798 | 49.425 | 30.971 | 1.00 | 42.51 | Y | C |
| ATOM | 7579 | NE | ARG | 60 | 57.683 | 48.120 | 30.333 | 1.00 | 42.51 | Y | N |
| ATOM | 7580 | CZ | ARG | 60 | 57.277 | 47.939 | 29.079 | 1.00 | 42.51 | Y | C |
| ATOM | 7581 | NH1 | ARG | 60 | 56.943 | 48.979 | 28.324 | 1.00 | 42.51 | Y | N |
| ATOM | 7582 | NH2 | ARG | 60 | 57.210 | 46.718 | 28.569 | 1.00 | 42.51 | Y | N |
| ATOM | 7583 | C | ARG | 60 | 61.202 | 52.180 | 31.158 | 1.00 | 39.70 | Y | C |
| ATOM | 7584 | O | ARG | 60 | 61.311 | 52.451 | 32.357 | 1.00 | 39.70 | Y | O |
| ATOM | 7585 | N | PHE | 61 | 62.136 | 51.522 | 30.480 | 1.00 | 40.60 | Y | N |
| ATOM | 7586 | CA | PHE | 61 | 63.372 | 51.086 | 31.109 | 1.00 | 40.60 | Y | C |
| ATOM | 7587 | CB | PHE | 61 | 63.965 | 49.886 | 30.370 | 1.00 | 38.42 | Y | C |
| ATOM | 7588 | CG | PHE | 61 | 63.416 | 48.563 | 30.811 | 1.00 | 38.42 | Y | C |
| ATOM | 7589 | CD1 | PHE | 61 | 62.493 | 47.881 | 30.028 | 1.00 | 38.42 | Y | C |
| ATOM | 7590 | CD2 | PHE | 61 | 63.830 | 47.997 | 32.010 | 1.00 | 38.42 | Y | C |
| ATOM | 7591 | CE1 | PHE | 61 | 61.990 | 46.652 | 30.434 | 1.00 | 38.42 | Y | C |
| ATOM | 7592 | CE2 | PHE | 61 | 63.332 | 46.770 | 32.423 | 1.00 | 38.42 | Y | C |

FIG. 19A-105

| | | | | | | | | | | |
|---|---|---|---|---|---|---|---|---|---|---|
| ATOM | 7593 | CZ | PHE | 61 | 62.410 | 46.096 | 31.634 | 1.00 | 38.42 | Y C |
| ATOM | 7594 | C | PHE | 61 | 64.399 | 52.209 | 31.097 | 1.00 | 40.60 | Y C |
| ATOM | 7595 | O | PHE | 61 | 64.470 | 52.989 | 30.144 | 1.00 | 40.60 | Y O |
| ATOM | 7596 | N | SER | 62 | 65.202 | 52.284 | 32.152 | 1.00 | 26.58 | Y N |
| ATOM | 7597 | CA | SER | 62 | 66.238 | 53.306 | 32.247 | 1.00 | 26.58 | Y C |
| ATOM | 7598 | CB | SER | 62 | 65.658 | 54.604 | 32.802 | 1.00 | 47.08 | Y C |
| ATOM | 7599 | OG | SER | 62 | 65.071 | 54.395 | 34.076 | 1.00 | 47.08 | Y O |
| ATOM | 7600 | C | SER | 62 | 67.376 | 52.828 | 33.145 | 1.00 | 26.58 | Y C |
| ATOM | 7601 | O | SER | 62 | 67.160 | 52.123 | 34.125 | 1.00 | 26.58 | Y O |
| ATOM | 7602 | N | GLY | 63 | 68.595 | 53.208 | 32.797 | 1.00 | 30.78 | Y N |
| ATOM | 7603 | CA | GLY | 63 | 69.738 | 52.810 | 33.591 | 1.00 | 30.78 | Y C |
| ATOM | 7604 | C | GLY | 63 | 70.426 | 54.067 | 34.056 | 1.00 | 30.78 | Y C |
| ATOM | 7605 | O | GLY | 63 | 70.266 | 55.122 | 33.442 | 1.00 | 30.78 | Y O |
| ATOM | 7606 | N | SER | 64 | 71.195 | 53.964 | 35.130 | 1.00 | 54.48 | Y N |
| ATOM | 7607 | CA | SER | 64 | 71.884 | 55.130 | 35.652 | 1.00 | 54.48 | Y C |
| ATOM | 7608 | CB | SER | 64 | 70.869 | 56.075 | 36.290 | 1.00 | 25.06 | Y C |
| ATOM | 7609 | OG | SER | 64 | 71.519 | 57.204 | 36.839 | 1.00 | 25.06 | Y O |
| ATOM | 7610 | C | SER | 64 | 72.947 | 54.763 | 36.675 | 1.00 | 54.48 | Y C |
| ATOM | 7611 | O | SER | 64 | 73.000 | 53.632 | 37.154 | 1.00 | 54.48 | Y O |
| ATOM | 7612 | N | GLY | 65 | 73.793 | 55.732 | 37.007 | 1.00 | 43.76 | Y N |
| ATOM | 7613 | CA | GLY | 65 | 74.836 | 55.494 | 37.984 | 1.00 | 43.76 | Y C |
| ATOM | 7614 | C | GLY | 65 | 76.218 | 56.023 | 37.637 | 1.00 | 43.76 | Y C |
| ATOM | 7615 | O | GLY | 65 | 76.431 | 56.698 | 36.622 | 1.00 | 43.76 | Y O |
| ATOM | 7616 | N | SER | 66 | 77.167 | 55.703 | 38.508 | 1.00 | 27.01 | Y N |
| ATOM | 7617 | CA | SER | 66 | 78.546 | 56.110 | 38.339 | 1.00 | 27.01 | Y C |
| ATOM | 7618 | CB | SER | 66 | 78.641 | 57.635 | 38.286 | 1.00 | 58.01 | Y C |
| ATOM | 7619 | OG | SER | 66 | 77.927 | 58.229 | 39.355 | 1.00 | 58.01 | Y O |
| ATOM | 7620 | C | SER | 66 | 79.367 | 55.563 | 39.498 | 1.00 | 27.01 | Y C |
| ATOM | 7621 | O | SER | 66 | 78.817 | 55.039 | 40.464 | 1.00 | 27.01 | Y O |
| ATOM | 7622 | N | GLY | 67 | 80.685 | 55.668 | 39.385 | 1.00 | 73.15 | Y N |
| ATOM | 7623 | CA | GLY | 67 | 81.555 | 55.179 | 40.436 | 1.00 | 73.15 | Y C |
| ATOM | 7624 | C | GLY | 67 | 81.312 | 53.733 | 40.822 | 1.00 | 73.15 | Y C |
| ATOM | 7625 | O | GLY | 67 | 81.609 | 52.814 | 40.056 | 1.00 | 73.15 | Y O |
| ATOM | 7626 | N | THR | 68 | 80.758 | 53.530 | 42.011 | 1.00 | 44.05 | Y N |
| ATOM | 7627 | CA | THR | 68 | 80.506 | 52.186 | 42.506 | 1.00 | 44.05 | Y C |
| ATOM | 7628 | CB | THR | 68 | 81.118 | 52.003 | 43.894 | 1.00 | 42.61 | Y C |
| ATOM | 7629 | OG1 | THR | 68 | 80.524 | 52.945 | 44.793 | 1.00 | 42.61 | Y O |
| ATOM | 7630 | CG2 | THR | 68 | 82.627 | 52.225 | 43.845 | 1.00 | 42.61 | Y C |
| ATOM | 7631 | C | THR | 68 | 79.042 | 51.786 | 42.592 | 1.00 | 44.05 | Y C |
| ATOM | 7632 | O | THR | 68 | 78.743 | 50.632 | 42.879 | 1.00 | 44.05 | Y O |
| ATOM | 7633 | N | ASP | 69 | 78.128 | 52.720 | 42.352 | 1.00 | 35.15 | Y N |
| ATOM | 7634 | CA | ASP | 69 | 76.708 | 52.392 | 42.424 | 1.00 | 35.15 | Y C |
| ATOM | 7635 | CB | ASP | 69 | 76.066 | 53.103 | 43.617 | 1.00 | 108.02 | Y C |
| ATOM | 7636 | CG | ASP | 69 | 76.592 | 52.591 | 44.946 | 1.00 | 108.02 | Y C |
| ATOM | 7637 | OD1 | ASP | 69 | 76.357 | 51.406 | 45.268 | 1.00 | 108.02 | Y O |
| ATOM | 7638 | OD2 | ASP | 69 | 77.249 | 53.370 | 45.667 | 1.00 | 108.02 | Y O |
| ATOM | 7639 | C | ASP | 69 | 75.942 | 52.705 | 41.139 | 1.00 | 35.15 | Y C |
| ATOM | 7640 | O | ASP | 69 | 75.884 | 53.850 | 40.693 | 1.00 | 35.15 | Y O |
| ATOM | 7641 | N | TYR | 70 | 75.359 | 51.664 | 40.551 | 1.00 | 27.55 | Y N |
| ATOM | 7642 | CA | TYR | 70 | 74.599 | 51.787 | 39.317 | 1.00 | 27.55 | Y C |
| ATOM | 7643 | CB | TYR | 70 | 75.315 | 51.016 | 38.191 | 1.00 | 25.09 | Y C |
| ATOM | 7644 | CG | TYR | 70 | 76.543 | 51.737 | 37.662 | 1.00 | 25.09 | Y C |
| ATOM | 7645 | CD1 | TYR | 70 | 76.447 | 52.637 | 36.596 | 1.00 | 25.09 | Y C |
| ATOM | 7646 | CE1 | TYR | 70 | 77.562 | 53.365 | 36.158 | 1.00 | 25.09 | Y C |
| ATOM | 7647 | CD2 | TYR | 70 | 77.787 | 51.577 | 38.275 | 1.00 | 25.09 | Y C |
| ATOM | 7648 | CE2 | TYR | 70 | 78.906 | 52.299 | 37.848 | 1.00 | 25.09 | Y C |
| ATOM | 7649 | CZ | TYR | 70 | 78.785 | 53.194 | 36.790 | 1.00 | 25.09 | Y C |
| ATOM | 7650 | OH | TYR | 70 | 79.873 | 53.933 | 36.382 | 1.00 | 25.09 | Y O |
| ATOM | 7651 | C | TYR | 70 | 73.184 | 51.267 | 39.523 | 1.00 | 27.55 | Y C |
| ATOM | 7652 | O | TYR | 70 | 72.920 | 50.545 | 40.488 | 1.00 | 27.55 | Y O |
| ATOM | 7653 | N | THR | 71 | 72.270 | 51.635 | 38.627 | 1.00 | 38.36 | Y N |
| ATOM | 7654 | CA | THR | 71 | 70.893 | 51.184 | 38.767 | 1.00 | 38.36 | Y C |
| ATOM | 7655 | CB | THR | 71 | 70.074 | 52.152 | 39.657 | 1.00 | 44.65 | Y C |
| ATOM | 7656 | OG1 | THR | 71 | 69.921 | 53.403 | 38.978 | 1.00 | 44.65 | Y O |
| ATOM | 7657 | CG2 | THR | 71 | 70.770 | 52.394 | 40.989 | 1.00 | 44.65 | Y C |
| ATOM | 7658 | C | THR | 71 | 70.099 | 50.991 | 37.473 | 1.00 | 38.36 | Y C |
| ATOM | 7659 | O | THR | 71 | 70.281 | 51.707 | 36.485 | 1.00 | 38.36 | Y O |
| ATOM | 7660 | N | LEU | 72 | 69.216 | 50.001 | 37.499 | 1.00 | 32.67 | Y N |
| ATOM | 7661 | CA | LEU | 72 | 68.324 | 49.718 | 36.385 | 1.00 | 32.67 | Y C |
| ATOM | 7662 | CB | LEU | 72 | 68.392 | 48.238 | 35.985 | 1.00 | 53.11 | Y C |
| ATOM | 7663 | CG | LEU | 72 | 67.283 | 47.694 | 35.073 | 1.00 | 53.11 | Y C |
| ATOM | 7664 | CD1 | LEU | 72 | 66.871 | 48.731 | 34.059 | 1.00 | 53.11 | Y C |
| ATOM | 7665 | CD2 | LEU | 72 | 67.769 | 46.444 | 34.372 | 1.00 | 53.11 | Y C |

FIG. 19A-106

```
ATOM   7666  C    LEU  72   66.958  50.056  36.972  1.00   32.67  Y  C
ATOM   7667  O    LEU  72   66.688  49.738  38.129  1.00   32.67  Y  O
ATOM   7668  N    THR  73   66.106  50.715  36.195  1.00   42.60  Y  N
ATOM   7669  CA   THR  73   64.795  51.100  36.700  1.00   42.60  Y  C
ATOM   7670  CB   THR  73   64.780  52.597  37.094  1.00   57.15  Y  C
ATOM   7671  OG1  THR  73   66.018  52.943  37.730  1.00   57.15  Y  O
ATOM   7672  CG2  THR  73   63.639  52.879  38.058  1.00   57.15  Y  C
ATOM   7673  C    THR  73   63.665  50.854  35.708  1.00   42.60  Y  C
ATOM   7674  O    THR  73   63.791  51.132  34.516  1.00   42.60  Y  O
ATOM   7675  N    ILE  74   62.564  50.316  36.212  1.00   51.99  Y  N
ATOM   7676  CA   ILE  74   61.396  50.068  35.386  1.00   51.99  Y  C
ATOM   7677  CB   ILE  74   60.934  48.597  35.455  1.00   52.44  Y  C
ATOM   7678  CG2  ILE  74   60.081  48.271  34.231  1.00   52.44  Y  C
ATOM   7679  CG1  ILE  74   62.138  47.656  35.471  1.00   52.44  Y  C
ATOM   7680  CD1  ILE  74   61.757  46.182  35.513  1.00   52.44  Y  C
ATOM   7681  C    ILE  74   60.314  50.963  35.988  1.00   51.99  Y  C
ATOM   7682  O    ILE  74   59.739  50.639  37.030  1.00   51.99  Y  O
ATOM   7683  N    SER  75   60.058  52.094  35.335  1.00   41.67  Y  N
ATOM   7684  CA   SER  75   59.069  53.066  35.801  1.00   41.67  Y  C
ATOM   7685  CB   SER  75   59.090  54.291  34.889  1.00   51.63  Y  C
ATOM   7686  OG   SER  75   58.934  53.909  33.535  1.00   51.63  Y  O
ATOM   7687  C    SER  75   57.644  52.524  35.901  1.00   41.67  Y  C
ATOM   7688  O    SER  75   56.885  52.924  36.777  1.00   41.67  Y  O
ATOM   7689  N    SER  76   57.280  51.627  34.993  1.00   62.86  Y  N
ATOM   7690  CA   SER  76   55.950  51.032  34.996  1.00   62.86  Y  C
ATOM   7691  CB   SER  76   55.045  51.724  33.980  1.00   71.45  Y  C
ATOM   7692  OG   SER  76   53.779  51.086  33.932  1.00   71.45  Y  O
ATOM   7693  C    SER  76   56.056  49.558  34.649  1.00   62.86  Y  C
ATOM   7694  O    SER  76   55.970  49.176  33.480  1.00   62.86  Y  O
ATOM   7695  N    LEU  77   56.237  48.734  35.675  1.00   53.25  Y  N
ATOM   7696  CA   LEU  77   56.380  47.298  35.490  1.00   53.25  Y  C
ATOM   7697  CB   LEU  77   56.342  46.596  36.841  1.00   41.03  Y  C
ATOM   7698  CG   LEU  77   57.317  45.433  37.008  1.00   41.03  Y  C
ATOM   7699  CD1  LEU  77   56.911  44.632  38.239  1.00   41.03  Y  C
ATOM   7700  CD2  LEU  77   57.310  44.548  35.766  1.00   41.03  Y  C
ATOM   7701  C    LEU  77   55.303  46.703  34.590  1.00   53.25  Y  C
ATOM   7702  O    LEU  77   54.114  46.944  34.787  1.00   53.25  Y  O
ATOM   7703  N    GLN  78   55.723  45.921  33.602  1.00   82.27  Y  N
ATOM   7704  CA   GLN  78   54.781  45.285  32.691  1.00   82.27  Y  C
ATOM   7705  CB   GLN  78   55.094  45.667  31.243  1.00   41.92  Y  C
ATOM   7706  CG   GLN  78   54.907  47.148  30.956  1.00   41.92  Y  C
ATOM   7707  CD   GLN  78   53.508  47.627  31.288  1.00   41.92  Y  C
ATOM   7708  OE1  GLN  78   52.520  47.033  30.852  1.00   41.92  Y  O
ATOM   7709  NE2  GLN  78   53.416  48.711  32.056  1.00   41.92  Y  N
ATOM   7710  C    GLN  78   54.830  43.774  32.852  1.00   82.27  Y  C
ATOM   7711  O    GLN  78   55.851  43.213  33.244  1.00   82.27  Y  O
ATOM   7712  N    PRO  79   53.718  43.093  32.549  1.00   81.12  Y  N
ATOM   7713  CD   PRO  79   52.505  43.636  31.915  1.00   80.96  Y  C
ATOM   7714  CA   PRO  79   53.632  41.636  32.660  1.00   81.12  Y  C
ATOM   7715  CB   PRO  79   52.198  41.351  32.225  1.00   80.96  Y  C
ATOM   7716  CG   PRO  79   51.949  42.426  31.213  1.00   80.96  Y  C
ATOM   7717  C    PRO  79   54.663  40.914  31.792  1.00   81.12  Y  C
ATOM   7718  O    PRO  79   54.865  39.708  31.914  1.00   81.12  Y  O
ATOM   7719  N    GLU  80   55.316  41.670  30.921  1.00   44.20  Y  N
ATOM   7720  CA   GLU  80   56.316  41.120  30.021  1.00   44.20  Y  C
ATOM   7721  CB   GLU  80   56.117  41.729  28.636  1.00  102.65  Y  C
ATOM   7722  CG   GLU  80   55.853  43.217  28.678  1.00  102.65  Y  C
ATOM   7723  CD   GLU  80   55.814  43.833  27.301  1.00  102.65  Y  C
ATOM   7724  OE1  GLU  80   56.717  43.528  26.494  1.00  102.65  Y  O
ATOM   7725  OE2  GLU  80   54.891  44.629  27.026  1.00  102.65  Y  O
ATOM   7726  C    GLU  80   57.742  41.368  30.520  1.00   44.20  Y  C
ATOM   7727  O    GLU  80   58.672  40.652  30.145  1.00   44.20  Y  O
ATOM   7728  N    ASP  81   57.902  42.380  31.371  1.00   52.34  Y  N
ATOM   7729  CA   ASP  81   59.206  42.733  31.931  1.00   52.34  Y  C
ATOM   7730  CB   ASP  81   59.167  44.111  32.593  1.00   55.47  Y  C
ATOM   7731  CG   ASP  81   58.700  45.195  31.663  1.00   55.47  Y  C
ATOM   7732  OD1  ASP  81   58.950  45.085  30.446  1.00   55.47  Y  O
ATOM   7733  OD2  ASP  81   58.099  46.171  32.156  1.00   55.47  Y  O
ATOM   7734  C    ASP  81   59.641  41.740  32.991  1.00   52.34  Y  C
ATOM   7735  O    ASP  81   60.649  41.946  33.673  1.00   52.34  Y  O
ATOM   7736  N    PHE  82   58.884  40.664  33.138  1.00   63.15  Y  N
ATOM   7737  CA   PHE  82   59.207  39.685  34.158  1.00   63.15  Y  C
ATOM   7738  CB   PHE  82   57.917  39.041  34.647  1.00  168.46  Y  C
```

FIG. 19A-107

| | | | | | | | | | | | |
|---|---|---|---|---|---|---|---|---|---|---|---|
| ATOM | 7739 | CG | PHE | 82 | 57.024 | 40.004 | 35.381 | 1.00 | 168.46 | Y | C |
| ATOM | 7740 | CD1 | PHE | 82 | 57.371 | 40.454 | 36.650 | 1.00 | 168.46 | Y | C |
| ATOM | 7741 | CD2 | PHE | 82 | 55.866 | 40.498 | 34.791 | 1.00 | 168.46 | Y | C |
| ATOM | 7742 | CE1 | PHE | 82 | 56.579 | 41.384 | 37.321 | 1.00 | 168.46 | Y | C |
| ATOM | 7743 | CE2 | PHE | 82 | 55.067 | 41.430 | 35.458 | 1.00 | 168.46 | Y | C |
| ATOM | 7744 | CZ | PHE | 82 | 55.425 | 41.872 | 36.724 | 1.00 | 168.46 | Y | C |
| ATOM | 7745 | C | PHE | 82 | 60.238 | 38.657 | 33.742 | 1.00 | 63.15 | Y | C |
| ATOM | 7746 | O | PHE | 82 | 59.960 | 37.733 | 32.979 | 1.00 | 63.15 | Y | O |
| ATOM | 7747 | N | ALA | 83 | 61.447 | 38.867 | 34.256 | 1.00 | 34.42 | Y | N |
| ATOM | 7748 | CA | ALA | 83 | 62.601 | 38.015 | 34.000 | 1.00 | 34.42 | Y | C |
| ATOM | 7749 | CB | ALA | 83 | 63.138 | 38.260 | 32.595 | 1.00 | 53.93 | Y | C |
| ATOM | 7750 | C | ALA | 83 | 63.669 | 38.353 | 35.036 | 1.00 | 34.42 | Y | C |
| ATOM | 7751 | O | ALA | 83 | 63.389 | 39.033 | 36.025 | 1.00 | 34.42 | Y | O |
| ATOM | 7752 | N | THR | 84 | 64.890 | 37.877 | 34.821 | 1.00 | 50.51 | Y | N |
| ATOM | 7753 | CA | THR | 84 | 65.968 | 38.161 | 35.758 | 1.00 | 50.51 | Y | C |
| ATOM | 7754 | CB | THR | 84 | 66.566 | 36.849 | 36.323 | 1.00 | 63.35 | Y | C |
| ATOM | 7755 | OG1 | THR | 84 | 67.888 | 37.096 | 36.819 | 1.00 | 63.35 | Y | O |
| ATOM | 7756 | CG2 | THR | 84 | 66.584 | 35.766 | 35.260 | 1.00 | 63.35 | Y | C |
| ATOM | 7757 | C | THR | 84 | 67.028 | 39.021 | 35.065 | 1.00 | 50.51 | Y | C |
| ATOM | 7758 | O | THR | 84 | 67.474 | 38.708 | 33.959 | 1.00 | 50.51 | Y | O |
| ATOM | 7759 | N | TYR | 85 | 67.401 | 40.119 | 35.723 | 1.00 | 40.66 | Y | N |
| ATOM | 7760 | CA | TYR | 85 | 68.364 | 41.076 | 35.187 | 1.00 | 40.66 | Y | C |
| ATOM | 7761 | CB | TYR | 85 | 67.819 | 42.503 | 35.330 | 1.00 | 42.00 | Y | C |
| ATOM | 7762 | CG | TYR | 85 | 66.476 | 42.693 | 34.668 | 1.00 | 42.00 | Y | C |
| ATOM | 7763 | CD1 | TYR | 85 | 65.330 | 42.084 | 35.185 | 1.00 | 42.00 | Y | C |
| ATOM | 7764 | CE1 | TYR | 85 | 64.110 | 42.163 | 34.521 | 1.00 | 42.00 | Y | C |
| ATOM | 7765 | CD2 | TYR | 85 | 66.363 | 43.401 | 33.472 | 1.00 | 42.00 | Y | C |
| ATOM | 7766 | CE2 | TYR | 85 | 65.148 | 43.486 | 32.800 | 1.00 | 42.00 | Y | C |
| ATOM | 7767 | CZ | TYR | 85 | 64.028 | 42.860 | 33.327 | 1.00 | 42.00 | Y | C |
| ATOM | 7768 | OH | TYR | 85 | 62.841 | 42.889 | 32.633 | 1.00 | 42.00 | Y | O |
| ATOM | 7769 | C | TYR | 85 | 69.746 | 41.012 | 35.816 | 1.00 | 40.66 | Y | C |
| ATOM | 7770 | O | TYR | 85 | 69.891 | 40.982 | 37.042 | 1.00 | 40.66 | Y | O |
| ATOM | 7771 | N | TYR | 86 | 70.756 | 41.016 | 34.949 | 1.00 | 43.34 | Y | N |
| ATOM | 7772 | CA | TYR | 86 | 72.159 | 40.970 | 35.349 | 1.00 | 43.34 | Y | C |
| ATOM | 7773 | CB | TYR | 86 | 72.890 | 39.833 | 34.633 | 1.00 | 34.52 | Y | C |
| ATOM | 7774 | CG | TYR | 86 | 72.406 | 38.441 | 34.941 | 1.00 | 34.52 | Y | C |
| ATOM | 7775 | CD1 | TYR | 86 | 72.902 | 37.731 | 36.040 | 1.00 | 34.52 | Y | C |
| ATOM | 7776 | CE1 | TYR | 86 | 72.472 | 36.433 | 36.303 | 1.00 | 34.52 | Y | C |
| ATOM | 7777 | CD2 | TYR | 86 | 71.466 | 37.820 | 34.118 | 1.00 | 34.52 | Y | C |
| ATOM | 7778 | CE2 | TYR | 86 | 71.031 | 36.530 | 34.375 | 1.00 | 34.52 | Y | C |
| ATOM | 7779 | CZ | TYR | 86 | 71.538 | 35.841 | 35.462 | 1.00 | 34.52 | Y | C |
| ATOM | 7780 | OH | TYR | 86 | 71.124 | 34.549 | 35.683 | 1.00 | 34.52 | Y | O |
| ATOM | 7781 | C | TYR | 86 | 72.873 | 42.259 | 34.957 | 1.00 | 43.34 | Y | C |
| ATOM | 7782 | O | TYR | 86 | 72.662 | 42.780 | 33.851 | 1.00 | 43.34 | Y | O |
| ATOM | 7783 | N | CYS | 87 | 73.706 | 42.773 | 35.862 | 1.00 | 31.05 | Y | N |
| ATOM | 7784 | CA | CYS | 87 | 74.499 | 43.945 | 35.548 | 1.00 | 31.05 | Y | C |
| ATOM | 7785 | C | CYS | 87 | 75.857 | 43.346 | 35.237 | 1.00 | 31.05 | Y | C |
| ATOM | 7786 | O | CYS | 87 | 76.171 | 42.248 | 35.707 | 1.00 | 31.05 | Y | O |
| ATOM | 7787 | CB | CYS | 87 | 74.587 | 44.922 | 36.721 | 1.00 | 63.19 | Y | C |
| ATOM | 7788 | SG | CYS | 87 | 75.151 | 44.318 | 38.354 | 1.00 | 63.19 | Y | S |
| ATOM | 7789 | N | GLN | 88 | 76.653 | 44.040 | 34.431 | 1.00 | 35.54 | Y | N |
| ATOM | 7790 | CA | GLN | 88 | 77.964 | 43.536 | 34.058 | 1.00 | 35.54 | Y | C |
| ATOM | 7791 | CB | GLN | 88 | 77.834 | 42.732 | 32.769 | 1.00 | 42.46 | Y | C |
| ATOM | 7792 | CG | GLN | 88 | 79.114 | 42.125 | 32.259 | 1.00 | 42.46 | Y | C |
| ATOM | 7793 | CD | GLN | 88 | 79.594 | 42.783 | 30.983 | 1.00 | 42.46 | Y | C |
| ATOM | 7794 | OE1 | GLN | 88 | 78.834 | 42.928 | 30.019 | 1.00 | 42.46 | Y | O |
| ATOM | 7795 | NE2 | GLN | 88 | 80.863 | 43.183 | 30.965 | 1.00 | 42.46 | Y | N |
| ATOM | 7796 | C | GLN | 88 | 78.930 | 44.691 | 33.873 | 1.00 | 35.54 | Y | C |
| ATOM | 7797 | O | GLN | 88 | 78.530 | 45.774 | 33.436 | 1.00 | 35.54 | Y | O |
| ATOM | 7798 | N | GLN | 89 | 80.195 | 44.465 | 34.216 | 1.00 | 24.85 | Y | N |
| ATOM | 7799 | CA | GLN | 89 | 81.208 | 45.502 | 34.082 | 1.00 | 24.85 | Y | C |
| ATOM | 7800 | CB | GLN | 89 | 81.794 | 45.851 | 35.458 | 1.00 | 29.69 | Y | C |
| ATOM | 7801 | CG | GLN | 89 | 82.481 | 44.722 | 36.182 | 1.00 | 29.69 | Y | C |
| ATOM | 7802 | CD | GLN | 89 | 83.903 | 44.496 | 35.696 | 1.00 | 29.69 | Y | C |
| ATOM | 7803 | OE1 | GLN | 89 | 84.676 | 45.442 | 35.535 | 1.00 | 29.69 | Y | O |
| ATOM | 7804 | NE2 | GLN | 89 | 84.261 | 43.238 | 35.476 | 1.00 | 29.69 | Y | N |
| ATOM | 7805 | C | GLN | 89 | 82.294 | 45.043 | 33.128 | 1.00 | 24.85 | Y | C |
| ATOM | 7806 | O | GLN | 89 | 82.527 | 43.853 | 32.990 | 1.00 | 24.85 | Y | O |
| ATOM | 7807 | N | TRP | 90 | 82.943 | 45.993 | 32.460 | 1.00 | 39.13 | Y | N |
| ATOM | 7808 | CA | TRP | 90 | 84.008 | 45.672 | 31.510 | 1.00 | 39.13 | Y | C |
| ATOM | 7809 | CB | TRP | 90 | 83.529 | 45.955 | 30.069 | 1.00 | 30.35 | Y | C |
| ATOM | 7810 | CG | TRP | 90 | 83.422 | 47.437 | 29.678 | 1.00 | 30.35 | Y | C |
| ATOM | 7811 | CD2 | TRP | 90 | 83.088 | 47.967 | 28.385 | 1.00 | 30.35 | Y | C |

FIG. 19A-108

```
ATOM   7812  CE2 TRP  90   83.122  49.375  28.486  1.00  30.35  Y  C
ATOM   7813  CE3 TRP  90   82.762  47.389  27.152  1.00  30.35  Y  C
ATOM   7814  CD1 TRP  90   83.635  48.523  30.484  1.00  30.35  Y  C
ATOM   7815  NE1 TRP  90   83.460  49.686  29.776  1.00  30.35  Y  N
ATOM   7816  CZ2 TRP  90   82.840  50.217  27.398  1.00  30.35  Y  C
ATOM   7817  CZ3 TRP  90   82.480  48.232  26.063  1.00  30.35  Y  C
ATOM   7818  CH2 TRP  90   82.522  49.627  26.199  1.00  30.35  Y  C
ATOM   7819  C   TRP  90   85.290  46.457  31.816  1.00  39.13  Y  C
ATOM   7820  O   TRP  90   86.293  46.339  31.115  1.00  39.13  Y  O
ATOM   7821  N   SER  91   85.251  47.254  32.876  1.00  18.51  Y  N
ATOM   7822  CA  SER  91   86.395  48.067  33.257  1.00  18.51  Y  C
ATOM   7823  CB  SER  91   85.948  49.152  34.237  1.00  45.24  Y  C
ATOM   7824  OG  SER  91   84.909  49.937  33.686  1.00  45.24  Y  O
ATOM   7825  C   SER  91   87.555  47.267  33.866  1.00  18.51  Y  C
ATOM   7826  O   SER  91   88.717  47.649  33.739  1.00  18.51  Y  O
ATOM   7827  N   GLY  92   87.241  46.166  34.534  1.00  40.34  Y  N
ATOM   7828  CA  GLY  92   88.282  45.360  35.146  1.00  40.34  Y  C
ATOM   7829  C   GLY  92   88.273  43.910  34.687  1.00  40.34  Y  C
ATOM   7830  O   GLY  92   87.248  43.386  34.244  1.00  40.34  Y  O
ATOM   7831  N   ASN  93   89.420  43.249  34.801  1.00  37.36  Y  N
ATOM   7832  CA  ASN  93   89.544  41.863  34.380  1.00  37.36  Y  C
ATOM   7833  CB  ASN  93   90.765  41.702  33.492  1.00  14.59  Y  C
ATOM   7834  CG  ASN  93   90.634  42.451  32.208  1.00  14.59  Y  C
ATOM   7835  OD1 ASN  93   91.556  43.159  31.796  1.00  14.59  Y  O
ATOM   7836  ND2 ASN  93   89.482  42.305  31.552  1.00  14.59  Y  N
ATOM   7837  C   ASN  93   89.668  40.944  35.574  1.00  37.36  Y  C
ATOM   7838  O   ASN  93   90.346  41.265  36.539  1.00  37.36  Y  O
ATOM   7839  N   PRO  94   89.005  39.783  35.525  1.00  28.71  Y  N
ATOM   7840  CD  PRO  94   88.990  38.808  36.629  1.00   9.29  Y  C
ATOM   7841  CA  PRO  94   88.167  39.322  34.412  1.00  28.71  Y  C
ATOM   7842  CB  PRO  94   87.940  37.858  34.745  1.00   9.29  Y  C
ATOM   7843  CG  PRO  94   87.823  37.904  36.251  1.00   9.29  Y  C
ATOM   7844  C   PRO  94   86.845  40.076  34.372  1.00  28.71  Y  C
ATOM   7845  O   PRO  94   86.418  40.640  35.384  1.00  28.71  Y  O
ATOM   7846  N   TRP  95   86.200  40.084  33.206  1.00  37.86  Y  N
ATOM   7847  CA  TRP  95   84.910  40.743  33.082  1.00  37.86  Y  C
ATOM   7848  CB  TRP  95   84.428  40.762  31.629  1.00  24.14  Y  C
ATOM   7849  CG  TRP  95   85.220  41.665  30.744  1.00  24.14  Y  C
ATOM   7850  CD2 TRP  95   85.537  41.458  29.359  1.00  24.14  Y  C
ATOM   7851  CE2 TRP  95   86.285  42.575  28.929  1.00  24.14  Y  C
ATOM   7852  CE3 TRP  95   85.264  40.437  28.440  1.00  24.14  Y  C
ATOM   7853  CD1 TRP  95   85.770  42.867  31.085  1.00  24.14  Y  C
ATOM   7854  NE1 TRP  95   86.411  43.419  30.000  1.00  24.14  Y  N
ATOM   7855  CZ2 TRP  95   86.765  42.697  27.624  1.00  24.14  Y  C
ATOM   7856  CZ3 TRP  95   85.748  40.566  27.133  1.00  24.14  Y  C
ATOM   7857  CH2 TRP  95   86.487  41.685  26.744  1.00  24.14  Y  C
ATOM   7858  C   TRP  95   83.959  39.922  33.941  1.00  37.86  Y  C
ATOM   7859  O   TRP  95   83.997  38.688  33.920  1.00  37.86  Y  O
ATOM   7860  N   THR  96   83.105  40.605  34.695  1.00  19.88  Y  N
ATOM   7861  CA  THR  96   82.192  39.913  35.582  1.00  19.88  Y  C
ATOM   7862  CB  THR  96   82.692  40.028  37.038  1.00  22.31  Y  C
ATOM   7863  OG1 THR  96   82.747  41.408  37.404  1.00  22.31  Y  O
ATOM   7864  CG2 THR  96   84.091  39.443  37.186  1.00  22.31  Y  C
ATOM   7865  C   THR  96   80.759  40.413  35.508  1.00  19.88  Y  C
ATOM   7866  O   THR  96   80.500  41.491  34.998  1.00  19.88  Y  O
ATOM   7867  N   PHE  97   79.839  39.596  36.015  1.00  20.15  Y  N
ATOM   7868  CA  PHE  97   78.420  39.912  36.073  1.00  20.15  Y  C
ATOM   7869  CB  PHE  97   77.580  38.827  35.397  1.00  25.28  Y  C
ATOM   7870  CG  PHE  97   77.890  38.613  33.946  1.00  25.28  Y  C
ATOM   7871  CD1 PHE  97   79.062  37.994  33.554  1.00  25.28  Y  C
ATOM   7872  CD2 PHE  97   76.979  38.990  32.969  1.00  25.28  Y  C
ATOM   7873  CE1 PHE  97   79.322  37.750  32.204  1.00  25.28  Y  C
ATOM   7874  CE2 PHE  97   77.234  38.748  31.611  1.00  25.28  Y  C
ATOM   7875  CZ  PHE  97   78.404  38.128  31.233  1.00  25.28  Y  C
ATOM   7876  C   PHE  97   78.054  39.931  37.557  1.00  20.15  Y  C
ATOM   7877  O   PHE  97   78.841  39.487  38.394  1.00  20.15  Y  O
ATOM   7878  N   GLY  98   76.875  40.460  37.879  1.00  30.22  Y  N
ATOM   7879  CA  GLY  98   76.412  40.488  39.256  1.00  30.22  Y  C
ATOM   7880  C   GLY  98   75.676  39.178  39.406  1.00  30.22  Y  C
ATOM   7881  O   GLY  98   75.506  38.478  38.405  1.00  30.22  Y  O
ATOM   7882  N   GLN  99   75.235  38.819  40.608  1.00  24.51  Y  N
ATOM   7883  CA  GLN  99   74.537  37.541  40.755  1.00  24.51  Y  C
ATOM   7884  CB  GLN  99   74.350  37.163  42.231  1.00  60.71  Y  C
```

FIG. 19A-109

```
ATOM   7885  CG   GLN   99    74.599  38.274  43.209  1.00   60.71  Y  C
ATOM   7886  CD   GLN   99    73.728  39.464  42.945  1.00   60.71  Y  C
ATOM   7887  OE1  GLN   99    72.510  39.411  43.113  1.00   60.71  Y  O
ATOM   7888  NE2  GLN   99    74.346  40.551  42.515  1.00   60.71  Y  N
ATOM   7889  C    GLN   99    73.189  37.507  40.043  1.00   24.51  Y  C
ATOM   7890  O    GLN   99    72.587  36.443  39.894  1.00   24.51  Y  O
ATOM   7891  N    GLY   100   72.730  38.666  39.586  1.00   42.40  Y  N
ATOM   7892  CA   GLY   100   71.455  38.725  38.900  1.00   42.40  Y  C
ATOM   7893  C    GLY   100   70.355  39.043  39.886  1.00   42.40  Y  C
ATOM   7894  O    GLY   100   70.483  38.749  41.074  1.00   42.40  Y  O
ATOM   7895  N    THR   101   69.283  39.662  39.399  1.00   27.30  Y  N
ATOM   7896  CA   THR   101   68.144  40.021  40.236  1.00   27.30  Y  C
ATOM   7897  CB   THR   101   68.024  41.538  40.401  1.00   28.79  Y  C
ATOM   7898  OG1  THR   101   69.008  41.995  41.336  1.00   28.79  Y  O
ATOM   7899  CG2  THR   101   66.646  41.907  40.892  1.00   28.79  Y  C
ATOM   7900  C    THR   101   66.903  39.492  39.551  1.00   27.30  Y  C
ATOM   7901  O    THR   101   66.619  39.845  38.408  1.00   27.30  Y  O
ATOM   7902  N    LYS   102   66.166  38.635  40.240  1.00   67.88  Y  N
ATOM   7903  CA   LYS   102   64.978  38.064  39.642  1.00   67.88  Y  C
ATOM   7904  CB   LYS   102   64.806  36.618  40.106  1.00  117.75  Y  C
ATOM   7905  CG   LYS   102   63.920  35.785  39.198  1.00  117.75  Y  C
ATOM   7906  CD   LYS   102   63.925  34.321  39.608  1.00  117.75  Y  C
ATOM   7907  CE   LYS   102   63.094  33.485  38.651  1.00  117.75  Y  C
ATOM   7908  NZ   LYS   102   63.586  33.621  37.250  1.00  117.75  Y  N
ATOM   7909  C    LYS   102   63.749  38.885  39.996  1.00   67.88  Y  C
ATOM   7910  O    LYS   102   63.560  39.262  41.155  1.00   67.88  Y  O
ATOM   7911  N    VAL   103   62.926  39.176  38.989  1.00   55.50  Y  N
ATOM   7912  CA   VAL   103   61.706  39.941  39.208  1.00   55.50  Y  C
ATOM   7913  CB   VAL   103   61.779  41.349  38.510  1.00   68.46  Y  C
ATOM   7914  CG1  VAL   103   63.207  41.865  38.530  1.00   68.46  Y  C
ATOM   7915  CG2  VAL   103   61.258  41.290  37.084  1.00   68.46  Y  C
ATOM   7916  C    VAL   103   60.489  39.141  38.709  1.00   55.50  Y  C
ATOM   7917  O    VAL   103   60.378  38.828  37.517  1.00   55.50  Y  O
ATOM   7918  N    GLU   104   59.597  38.779  39.633  1.00   70.95  Y  N
ATOM   7919  CA   GLU   104   58.395  38.025  39.281  1.00   70.95  Y  C
ATOM   7920  CB   GLU   104   58.243  36.764  40.145  1.00  145.77  Y  C
ATOM   7921  CG   GLU   104   57.957  37.019  41.616  1.00  145.77  Y  C
ATOM   7922  CD   GLU   104   59.215  37.263  42.418  1.00  145.77  Y  C
ATOM   7923  OE1  GLU   104   59.106  37.542  43.631  1.00  145.77  Y  O
ATOM   7924  OE2  GLU   104   60.315  37.167  41.839  1.00  145.77  Y  O
ATOM   7925  C    GLU   104   57.157  38.897  39.443  1.00   70.95  Y  C
ATOM   7926  O    GLU   104   57.197  39.939  40.108  1.00   70.95  Y  O
ATOM   7927  N    ILE   105   56.058  38.459  38.834  1.00  139.77  Y  N
ATOM   7928  CA   ILE   105   54.791  39.184  38.876  1.00  139.77  Y  C
ATOM   7929  CB   ILE   105   53.838  38.730  37.757  1.00  105.35  Y  C
ATOM   7930  CG2  ILE   105   52.923  39.875  37.373  1.00  105.35  Y  C
ATOM   7931  CG1  ILE   105   54.633  38.232  36.553  1.00  105.35  Y  C
ATOM   7932  CD1  ILE   105   53.775  37.746  35.397  1.00  105.35  Y  C
ATOM   7933  C    ILE   105   54.047  38.952  40.180  1.00  139.77  Y  C
ATOM   7934  O    ILE   105   53.763  37.810  40.533  1.00  139.77  Y  O
ATOM   7935  N    LYS   106   53.706  40.031  40.880  1.00  101.75  Y  N
ATOM   7936  CA   LYS   106   52.969  39.916  42.135  1.00  101.75  Y  C
ATOM   7937  CB   LYS   106   53.545  40.870  43.189  1.00   95.13  Y  C
ATOM   7938  CG   LYS   106   52.954  40.690  44.584  1.00   95.13  Y  C
ATOM   7939  CD   LYS   106   53.556  41.665  45.586  1.00   95.13  Y  C
ATOM   7940  CE   LYS   106   52.939  41.482  46.965  1.00   95.13  Y  C
ATOM   7941  NZ   LYS   106   53.446  42.478  47.948  1.00   95.13  Y  N
ATOM   7942  C    LYS   106   51.492  40.235  41.897  1.00  101.75  Y  C
ATOM   7943  O    LYS   106   51.148  40.637  40.765  1.00  100.80  Y  O
ATOM   7944  OXT  LYS   106   50.694  40.080  42.844  1.00   94.18  Y  O
ATOM   7945  MN   MN    400   89.864  50.249  22.621  1.00   34.24  N

END
```

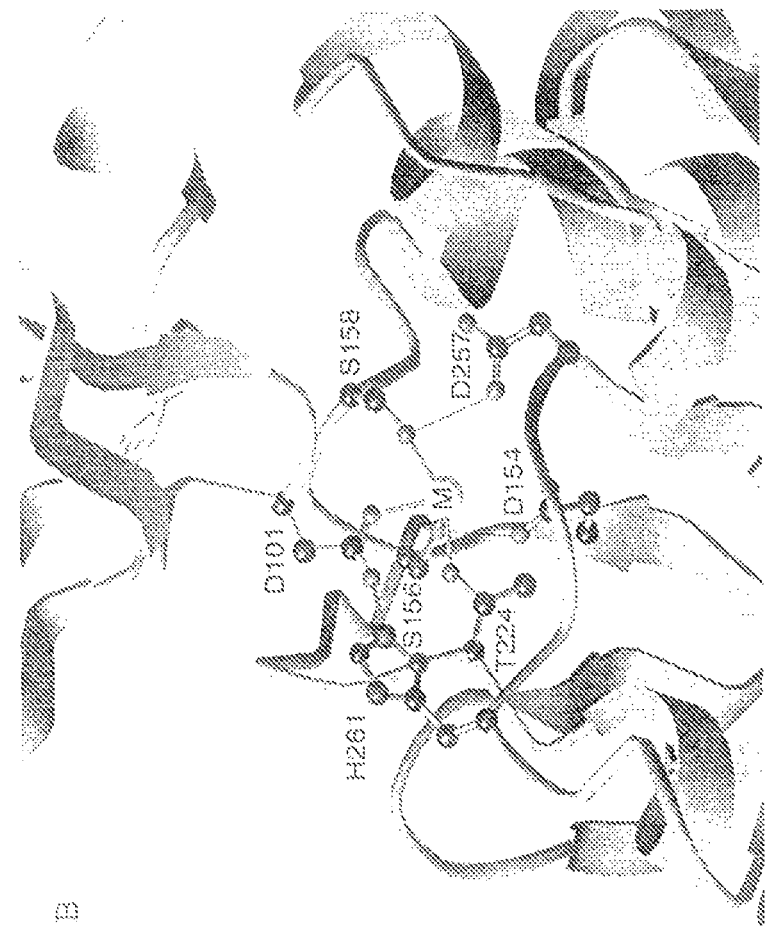
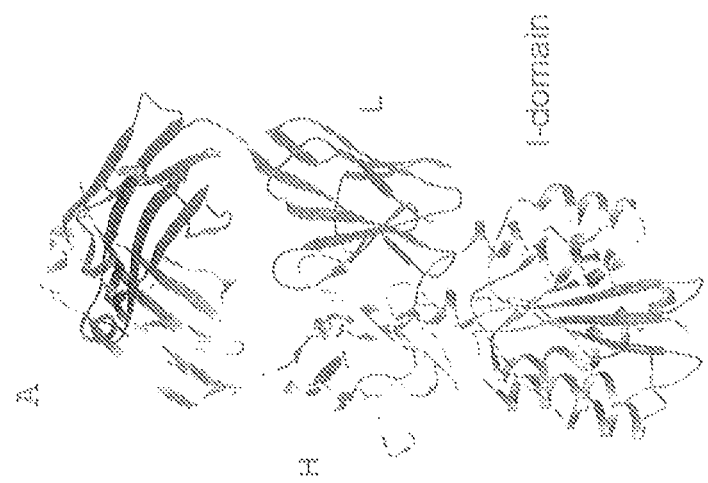
Fig. 20

SEQUENCE LISTING

```
<160> NUMBER OF SEQ ID NOS: 70

<210> SEQ ID NO 1
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 1

Gln Ile Val Leu Thr Gln Phe Pro Ala Leu Met Ser Ala Ser Pro Gly
1               5                   10                  15

Glu Lys Val Thr Met Thr Cys Ser Ala Ser Ser Val Asn His Met
            20                  25                  30

Phe Trp Tyr Gln Gln Lys Pro Lys Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Trp Thr
                85                  90                  95

Phe Gly Gly Gly Thr Lys Leu Glu Ile Lys
            100                 105

<210> SEQ ID NO 2
<211> LENGTH: 118
<212> TYPE: PRT
<213> ORGANISM: Artificial Sequence
```

```
<220> FEATURE:
<223> OTHER INFORMATION: Synthetically generated peptide

<400> SEQUENCE: 2

Asp Val Lys Val Val Glu Ser Gly Gly Gly Leu Val Lys Pro Gly Gly
 1               5                  10                  15

Ser Leu Lys Leu Ala Cys Ala Ala Ser Gly Phe Ser Phe Ser Arg Tyr
                20                  25                  30

Thr Met Ser Trp Val Arg Gln Ile Pro Glu Lys Arg Leu Glu Trp Val
            35                  40                  45

Ala Thr Ile Ser Gly Gly His Thr Tyr Tyr Leu Asp Ser Val Lys
        50                  55                  60

Gly Arg Phe Thr Ile Ser Arg Asp Asn Ala Lys Asn Thr Leu Tyr Leu
 65                  70                  75                  80

Gln Met Ser Ser Leu Arg Ser Glu Asp Thr Ala Met Tyr Tyr Cys Thr
                85                  90                  95

Arg Gly Phe Gly Asp Gly Gly Tyr Phe Asp Val Trp Gly Gln Gly Thr
                100                 105                 110

Thr Val Thr Val Ser Ser
            115

<210> SEQ ID NO 3
<211> LENGTH: 213
<212> TYPE: PRT
<213> ORGANISM: Artificial Sequence
<220> FEATURE:
<223> OTHER INFORMATION: Synthetically generated peptide

<400> SEQUENCE: 3

Gln Ile Gln Leu Thr Gln Ser Pro Ser Ser Leu Ser Ala Ser Val Gly
 1               5                  10                  15

Asp Arg Val Thr Ile Thr Cys Ser Ala Ser Ser Ser Val Asn His Met
                20                  25                  30

Phe Trp Tyr Gln Gln Lys Pro Gly Lys Ala Pro Lys Pro Trp Ile Tyr
            35                  40                  45

Leu Thr Ser Asn Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190
```

```
Cys Glu Val Thr His Gln Gly Leu Ser Ser Pro Val Thr Lys Ser Phe
            195                 200                 205

Asn Arg Gly Glu Cys
    210

<210> SEQ ID NO 4
<211> LENGTH: 447
<212> TYPE: PRT
<213> ORGANISM: Artificial Sequence
<220> FEATURE:
<223> OTHER INFORMATION: Synthetically generated peptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335
```

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 5
<211> LENGTH: 447
<212> TYPE: PRT
<213> ORGANISM: Artificial Sequence
<220> FEATURE:
<223> OTHER INFORMATION: Synthetically generated peptide

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
            35                  40                  45

Ala Thr Ile Ser Gly Gly Gly His Thr Tyr Tyr Leu Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

```
Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gln Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 6
<211> LENGTH: 447
<212> TYPE: PRT
<213> ORGANISM: Artificial Sequence
<220> FEATURE:
<223> OTHER INFORMATION: Synthetically generated peptide

<400> SEQUENCE: 6

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 7
<211> LENGTH: 26
<212> TYPE: DNA
<213> ORGANISM: Homo sapiens

<400> SEQUENCE: 7
caggatccgt cagccccaca tttcaa                                            26

<210> SEQ ID NO 8
<211> LENGTH: 26
<212> TYPE: DNA
<213> ORGANISM: Homo sapiens

<400> SEQUENCE: 8
tcctcgaggg cttgcagggc aaatat                                            26

<210> SEQ ID NO 9
<211> LENGTH: 26
<212> TYPE: DNA
<213> ORGANISM: Rattus sp.
```

```
<400> SEQUENCE: 9
caggatccgt cagtcctaca tttcaa                                    26

<210> SEQ ID NO 10
<211> LENGTH: 26
<212> TYPE: DNA
<213> ORGANISM: Rattus sp.

<400> SEQUENCE: 10
tcctcgagcg cttccaaagc gaatat                                    26

<210> SEQ ID NO 11
<211> LENGTH: 31
<212> TYPE: DNA
<213> ORGANISM: Artificial Sequence
<220> FEATURE:
<223> OTHER INFORMATION: Primer

<400> SEQUENCE: 11
tgaggagacg gtgaccgtgg cccttggccc c                              31

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
aggtsmarct gcagsagtcw gg                                        22

<210> SEQ ID NO 13
<211> LENGTH: 40
<212> TYPE: DNA
<213> ORGANISM: Artificial Sequence
<220> FEATURE:
<223> OTHER INFORMATION: Primer

<400> SEQUENCE: 13
actagtcgac atggatttwc aggtgcagat twtcagcttc                     40

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
actggatggt gggaagatgg a                                         21

<210> SEQ ID NO 15
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 15

Asp Val Lys Val Val Glu Ser Gly Gly
 1               5
```

```
<210> SEQ ID NO 16
<211> LENGTH: 6
<212> TYPE: PRT
<213> ORGANISM: Artificial Sequence
<220> FEATURE:
<223> OTHER INFORMATION: Synthetically generated peptide

<400> SEQUENCE: 16

Asp Val Lys Val Val Glu
 1               5

<210> SEQ ID NO 17
<211> LENGTH: 54
<212> TYPE: DNA
<213> ORGANISM: Artificial Sequence
<220> FEATURE:
<223> OTHER INFORMATION: Primer

<400> SEQUENCE: 17
gcaccaggtg cccactccga cgtcaaggtg gtggagtcag ggggaggctt agtg          54

<210> SEQ ID NO 18
<211> LENGTH: 38
<212> TYPE: DNA
<213> ORGANISM: Artificial Sequence
<220> FEATURE:
<223> OTHER INFORMATION: Primer

<400> SEQUENCE: 18
ggaggcacca agctggagat ctaacgggct gatgctgc                            38

<210> SEQ ID NO 19
<211> LENGTH: 34
<212> TYPE: DNA
<213> ORGANISM: Artificial Sequence
<220> FEATURE:
<223> OTHER INFORMATION: Primer

<400> SEQUENCE: 19
cataatgtcc agggagaaa ttgttctcac ccag                                 34

<210> SEQ ID NO 20
<211> LENGTH: 93
<212> TYPE: DNA
<213> ORGANISM: Artificial Sequence
<220> FEATURE:
<223> OTHER INFORMATION: Primer

<400> SEQUENCE: 20
ggtgcccact ccgacgtcca gctggtcgag tcaggggag gcttagtcca gcctggaggg     60
tccctgagac tctcctgtgc agcctctgga ttc                                 93

<210> SEQ ID NO 21
<211> LENGTH: 51
<212> TYPE: DNA
<213> ORGANISM: Artificial Sequence
<220> FEATURE:
<223> OTHER INFORMATION: Primer

<400> SEQUENCE: 21
atgtcttggg ttcgccaggc tccggggaag gggctggagt gggtcgcaac c             51

<210> SEQ ID NO 22
<211> LENGTH: 93
<212> TYPE: DNA
<213> ORGANISM: Artificial Sequence
```

```
<220> FEATURE:
<223> OTHER INFORMATION: Primer

<400> SEQUENCE: 22
ttcaccatct ccagagacaa ttccaagaac accctgtacc tgcagatgaa cagtctgagg        60
gccgaggaca cagccgtgta ttactgtaca aga                                    93

<210> SEQ ID NO 23
<211> LENGTH: 39
<212> TYPE: DNA
<213> ORGANISM: Artificial Sequence
<220> FEATURE:
<223> OTHER INFORMATION: Primer

<400> SEQUENCE: 23
tggggccaag gtaccctggt caccgtctcc tcaggtgag                               39

<210> SEQ ID NO 24
<211> LENGTH: 51
<212> TYPE: DNA
<213> ORGANISM: Artificial Sequence
<220> FEATURE:
<223> OTHER INFORMATION: Primer

<400> SEQUENCE: 24
tcctgtgcag cctctggatt caccttcagt aggtatacta tgtcttgggt t                 51

<210> SEQ ID NO 25
<211> LENGTH: 39
<212> TYPE: DNA
<213> ORGANISM: Artificial Sequence
<220> FEATURE:
<223> OTHER INFORMATION: Primer

<400> SEQUENCE: 25
gcaccaggtg cgcactccga ggtccagctg gtcgagtca                               39

<210> SEQ ID NO 26
<211> LENGTH: 39
<212> TYPE: DNA
<213> ORGANISM: Artificial Sequence
<220> FEATURE:
<223> OTHER INFORMATION: Primer

<400> SEQUENCE: 26
gagtcagggg gaggcttaat ccagcctgga gggtccctg                               39

<210> SEQ ID NO 27
<211> LENGTH: 81
<212> TYPE: DNA
<213> ORGANISM: Artificial Sequence
<220> FEATURE:
<223> OTHER INFORMATION: Primer

<400> SEQUENCE: 27
caaattgttc tcacccagtc tccatcctcc ctgtctgcgt ctgtagggga cagagtcacc        60
atcacatgca gtgccagctc a                                                 81

<210> SEQ ID NO 28
<211> LENGTH: 45
<212> TYPE: DNA
<213> ORGANISM: Artificial Sequence
<220> FEATURE:
<223> OTHER INFORMATION: Primer
```

<400> SEQUENCE: 28
ttctggtatc agcagaagcc cgggaaagcc cccaaaccct ggatt                            45

<210> SEQ ID NO 29
<211> LENGTH: 105
<212> TYPE: DNA
<213> ORGANISM: Artificial Sequence
<220> FEATURE:
<223> OTHER INFORMATION: Primer

<400> SEQUENCE: 29
gcttctggag tcccttcacg cttcagtggc agtgggtctg ggacagatta cactctcaca           60
atcagcagcc tgcaacctga agattttgcc acttattact gccag                          105

<210> SEQ ID NO 30
<211> LENGTH: 33
<212> TYPE: DNA
<213> ORGANISM: Artificial Sequence
<220> FEATURE:
<223> OTHER INFORMATION: Primer

<400> SEQUENCE: 30
ggtggaggca ctaaggtgga gatctaacgg gct                                        33

<210> SEQ ID NO 31
<211> LENGTH: 39
<212> TYPE: DNA
<213> ORGANISM: Artificial Sequence
<220> FEATURE:
<223> OTHER INFORMATION: Primer

<400> SEQUENCE: 31
cccgggaaag cgcccaaact cctgatttat ctcacatcc                                  39

<210> SEQ ID NO 32
<211> LENGTH: 51
<212> TYPE: DNA
<213> ORGANISM: Artificial Sequence
<220> FEATURE:
<223> OTHER INFORMATION: Primer

<400> SEQUENCE: 32
gcctcagtca taatgtcccg gggacaaatt cagctcaccc agtctccatc c                    51

<210> SEQ ID NO 33
<211> LENGTH: 51
<212> TYPE: DNA
<213> ORGANISM: Artificial Sequence
<220> FEATURE:
<223> OTHER INFORMATION: Primer

<400> SEQUENCE: 33
ggtaacccgt ggacgttcgg tcagggcact aaggtggaga tctaacgggc t                    51

<210> SEQ ID NO 34
<211> LENGTH: 51
<212> TYPE: DNA
<213> ORGANISM: Artificial Sequence
<220> FEATURE:
<223> OTHER INFORMATION: Primer

<400> SEQUENCE: 34
gcctcagtca taatgtcccg gggacaaatt cagctcaccc agtctccatc c                    51

<210> SEQ ID NO 35
<211> LENGTH: 51
<212> TYPE: DNA
<213> ORGANISM: Artificial Sequence
<220> FEATURE:
<223> OTHER INFORMATION: Primer

<400> SEQUENCE: 35
ggtaacccgt ggacgttcgg tcagggcact aaggtggaga tctaacgggc t        51

<210> SEQ ID NO 36
<211> LENGTH: 39
<212> TYPE: DNA
<213> ORGANISM: Artificial Sequence
<220> FEATURE:
<223> OTHER INFORMATION: Primer

<400> SEQUENCE: 36
gggaaagcac ccaaactctg gatctatctc acatccaac                       39

<210> SEQ ID NO 37
<211> LENGTH: 45
<212> TYPE: DNA
<213> ORGANISM: Artificial Sequence
<220> FEATURE:
<223> OTHER INFORMATION: Primer

<400> SEQUENCE: 37
aagcccggga aggcgcccaa acccctgatt tatctcacat ccaac                45

<210> SEQ ID NO 38
<211> LENGTH: 39
<212> TYPE: DNA
<213> ORGANISM: Artificial Sequence
<220> FEATURE:
<223> OTHER INFORMATION: Primer

<400> SEQUENCE: 38
gtcataatgt cccgggggaga tatccagctc acccagtct                      39

<210> SEQ ID NO 39
<211> LENGTH: 354
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

<400> SEQUENCE: 39

```
gac gtc aag gtg gtg gag tca ggg gga ggc tta gtg aag cct gga ggg    48
Asp Val Lys Val Val Glu Ser Gly Gly Gly Leu Val Lys Pro Gly Gly
  1               5                  10                  15 tcc ctg aaa ctc gcc tgt gca gcc tct gga ttc agt ttc agt aga tat    96
Ser Leu Lys Leu Ala Cys Ala Ala Ser Gly Phe Ser Phe Ser Arg Tyr
             20                  25                  30 act atg tct tgg gtt cgc cag att ccg gag aag agg ctg gag tgg gtc   144
Thr Met Ser Trp Val Arg Gln Ile Pro Glu Lys Arg Leu Glu Trp Val
         35                  40                  45 gca acc att agt ggt ggt ggt cac acc tac tat cta gac agt gtg aag   192
Ala Thr Ile Ser Gly Gly Gly His Thr Tyr Tyr Leu Asp Ser Val Lys
     50                  55                  60 ggc cga ttc acc atc tcc aga gac aat gcc aag aac acc ctg tac ctg   240
Gly Arg Phe Thr Ile Ser Arg Asp Asn Ala Lys Asn Thr Leu Tyr Leu
 65                  70                  75                  80
```

```
caa atg agc agt ctg agg tct gag gac aca gcc atg tat tac tgt aca        288
Gln Met Ser Ser Leu Arg Ser Glu Asp Thr Ala Met Tyr Tyr Cys Thr
            85                  90                  95 aga ggt ttt gga gac ggg ggg tac ttc gat gtc tgg ggc caa ggg acc        336
Arg Gly Phe Gly Asp Gly Gly Tyr Phe Asp Val Trp Gly Gln Gly Thr
            100                 105                 110 acg gtc acc gtc tcc tca                                                 354
Thr Val Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 40

Asp Val Lys Val Val Glu Ser Gly Gly Gly Leu Val Lys Pro Gly Gly
1               5                   10                  15

Ser Leu Lys Leu Ala Cys Ala Ala Ser Gly Phe Ser Phe Ser Arg Tyr
            20                  25                  30

Thr Met Ser Trp Val Arg Gln Ile Pro Glu Lys Arg Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ala Lys Asn Thr Leu Tyr Leu
65              70                  75                  80

Gln Met Ser Ser Leu Arg Ser Glu Asp Thr Ala Met Tyr Tyr Cys Thr
            85                  90                  95

Arg Gly Phe Gly Asp Gly Gly Tyr Phe Asp Val Trp Gly Gln Gly Thr
            100                 105                 110

Thr Val Thr Val Ser Ser
        115

<210> SEQ ID NO 41
<211> LENGTH: 354
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

<400> SEQUENCE: 41 gac gtc cag ctg gtc gag tca ggg gga ggc tta gtc cag cct gga ggg        48
Asp Val Gln Leu Val Glu Ser Gly Gly Gly Leu Val Gln Pro Gly Gly
1               5                   10                  15 tcc ctg aga ctc tcc tgt gca gcc tct gga ttc agt ttc agt aga tat        96
Ser Leu Arg Leu Ser Cys Ala Ala Ser Gly Phe Ser Phe Ser Arg Tyr
            20                  25                  30 act atg tct tgg gtt cgc cag gct ccg ggg aag ggg ctg gag tgg gtc        144
Thr Met Ser Trp Val Arg Gln Ala Pro Gly Lys Gly Leu Glu Trp Val
        35                  40                  45 gca acc att agt ggt ggt ggt cac acc tac tat cta gac agt gtg aag        192
Ala Thr Ile Ser Gly Gly Gly His Thr Tyr Tyr Leu Asp Ser Val Lys
    50                  55                  60 ggc cga ttc acc atc tcc aga gac aat tcc aag aac acc ctg tac ctg        240
Gly Arg Phe Thr Ile Ser Arg Asp Asn Ser Lys Asn Thr Leu Tyr Leu
65              70                  75                  80
```

```
cag atg aac agt ctg agg gcc gag gac aca gcc gtg tat tac tgt aca      288
Gln Met Asn Ser Leu Arg Ala Glu Asp Thr Ala Val Tyr Tyr Cys Thr
            85                  90                  95 aga ggt ttt gga gac ggg ggg tac ttc gat gtc tgg ggc caa ggt acc      336
Arg Gly Phe Gly Asp Gly Gly Tyr Phe Asp Val Trp Gly Gln Gly Thr
           100                 105                 110 ctg gtc acc gtc tcc tca                                              354
Leu Val Thr Val Ser Ser
        115
```

<210> SEQ ID NO 42
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 42

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
            85                  90                  95

Arg Gly Phe Gly Asp Gly Gly Tyr Phe Asp Val Trp Gly Gln Gly Thr
           100                 105                 110

Leu Val Thr Val Ser Ser
        115
```

<210> SEQ ID NO 43
<211> LENGTH: 356
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

<400> SEQUENCE: 43

```
gag gtc cag ctg gtc gag tca ggg gga ggc tta atc cag cct gga ggg       48
Glu Val Gln Leu Val Glu Ser Gly Gly Gly Leu Ile Gln Pro Gly Gly
1               5                   10                  15 tcc ctg aga ctc tcc tgt gca gcc tct gga ttc acc ttc agt agg tat       96
Ser Leu Arg Leu Ser Cys Ala Ala Ser Gly Phe Thr Phe Ser Arg Tyr
            20                  25                  30 act atg tct tgg gtt cgc cag gct ccg ggg aag ggg ctg gag tgg gtc      144
Thr Met Ser Trp Val Arg Gln Ala Pro Gly Lys Gly Leu Glu Trp Val
        35                  40                  45 gca acc att agt ggt ggt ggt cac acc tac tat cta gac agt gtg aag      192
Ala Thr Ile Ser Gly Gly Gly His Thr Tyr Tyr Leu Asp Ser Val Lys
    50                  55                  60 ggc cga ttc acc atc tcc aga gac aat tcc aag aac acc ctg tac ctg      240
Gly Arg Phe Thr Ile Ser Arg Asp Asn Ser Lys Asn Thr Leu Tyr Leu
65                  70                  75                  80
```

| | |
|---|---|
| cag atg aac agt ctg agg gcc gag gac aca gcc gtg tat tac tgt aca<br>Gln Met Asn Ser Leu Arg Ala Glu Asp Thr Ala Val Tyr Tyr Cys Thr<br>               85                    90                      95 | 288 |
| aga ggt ttt gga gac ggg ggg tac ttc gat gtc tgg ggc caa ggt acc<br>Arg Gly Phe Gly Asp Gly Gly Tyr Phe Asp Val Trp Gly Gln Gly Thr<br>            100                    105                   110 | 336 |
| ctg gtc acc gtc tcc tca gg<br>Leu Val Thr Val Ser Ser<br>        115 | 356 |

<210> SEQ ID NO 44
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 44

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
        115

<210> SEQ ID NO 45
<211> LENGTH: 356
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(354)

<400> SEQUENCE: 45

| | |
|---|---|
| gag gtc cag ctg gtc gag tca ggg gga ggc tta gtc cag cct gga ggg<br>Glu Val Gln Leu Val Glu Ser Gly Gly Gly Leu Val Gln Pro Gly Gly<br>1                5                   10                  15 | 48 |
| tcc ctg aga ctc tcc tgt gca gcc tct gga ttc acc ttc agt agg tat<br>Ser Leu Arg Leu Ser Cys Ala Ala Ser Gly Phe Thr Phe Ser Arg Tyr<br>           20                    25                    30 | 96 |
| act atg tct tgg gtt cgc cag gct ccg ggg aag ggg ctg gag tgg gtc<br>Thr Met Ser Trp Val Arg Gln Ala Pro Gly Lys Gly Leu Glu Trp Val<br>        35                    40                    45 | 144 |
| gca acc att agt ggt ggt ggt cac acc tac tat cta gac agt gtg aag<br>Ala Thr Ile Ser Gly Gly Gly His Thr Tyr Tyr Leu Asp Ser Val Lys<br>50                    55                    60 | 192 |
| ggc cga ttc acc atc tcc aga gac aat tcc aag aac acc ctg tac ctg<br>Gly Arg Phe Thr Ile Ser Arg Asp Asn Ser Lys Asn Thr Leu Tyr Leu<br>65                    70                    75                  80 | 240 |

```
cag atg aac agt ctg agg gcc gag gac aca gcc gtg tat tac tgt aca      288
Gln Met Asn Ser Leu Arg Ala Glu Asp Thr Ala Val Tyr Tyr Cys Thr
            85                  90                  95 aga ggt ttt gga gac ggg ggg tac ttc gat gtc tgg ggc caa ggt acc      336
Arg Gly Phe Gly Asp Gly Gly Tyr Phe Asp Val Trp Gly Gln Gly Thr
        100                 105                 110 ctg gtc acc gtc tcc tca gg                                           356
Leu Val Thr Val Ser Ser
        115

<210> SEQ ID NO 46
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 46 caa att gtt ctc acc cag ttt cca gca ctc atg tct gcg tct cca ggg       48
Gln Ile Val Leu Thr Gln Phe Pro Ala Leu Met Ser Ala Ser Pro Gly
1               5                   10                  15 gag aag gtc acc atg acc tgc agt gcc agc tca agt gta aat cac atg       96
Glu Lys Val Thr Met Thr Cys Ser Ala Ser Ser Ser Val Asn His Met
            20                  25                  30 ttc tgg tat cag cag aag cca aaa tcc tcc ccc aaa ccc tgg att tat      144
Phe Trp Tyr Gln Gln Lys Pro Lys Ser Ser Pro Lys Pro Trp Ile Tyr
        35                  40                  45 ctc aca tcc aac ctg gct tct gga gtc cct gct cgc ttc agt ggc agt      192
Leu Thr Ser Asn Leu Ala Ser Gly Val Pro Ala Arg Phe Ser Gly Ser
    50                  55                  60 ggg tct ggg acc tct tac tct ctc aca atc agc agc atg gag gct gaa      240
Gly Ser Gly Thr Ser Tyr Ser Leu Thr Ile Ser Ser Met Glu Ala Glu
65                  70                  75                  80 gat gct gcc act tat tac tgc cag cag tgg agt ggt aac ccg tgg acg      288
Asp Ala Ala Thr Tyr Tyr Cys Gln Gln Trp Ser Gly Asn Pro Trp Thr
                85                  90                  95 ttc ggt gga ggc acc aag ctg gag atc aaa                              318
Phe Gly Gly Gly Thr Lys Leu Glu Ile Lys
        100                 105

<210> SEQ ID NO 47
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 47

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Leu Trp Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80
```

```
Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
        100                 105

<210> SEQ ID NO 48
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 48 caa att gtt ctc acc cag tct cca tcc tcc ctg tct gcg tct gta ggg      48
Gln Ile Val Leu Thr Gln Ser Pro Ser Ser Leu Ser Ala Ser Val Gly
 1               5                  10                  15 gac aga gtc acc atc aca tgc agt gcc agc tca agt gta aat cac atg      96
Asp Arg Val Thr Ile Thr Cys Ser Ala Ser Ser Ser Val Asn His Met
            20                  25                  30 ttc tgg tat cag cag aag ccc ggg aaa gcc ccc aaa ccc tgg att tat     144
Phe Trp Tyr Gln Gln Lys Pro Gly Lys Ala Pro Lys Pro Trp Ile Tyr
        35                  40                  45 ctc aca tcc aac ctg gct tct gga gtc cct tca cgc ttc agt ggc agt     192
Leu Thr Ser Asn Leu Ala Ser Gly Val Pro Ser Arg Phe Ser Gly Ser
    50                  55                  60 ggg tct ggg aca gat tac act ctc aca atc agc agc ctg caa cct gaa     240
Gly Ser Gly Thr Asp Tyr Thr Leu Thr Ile Ser Ser Leu Gln Pro Glu
65                  70                  75                  80 gat ttt gcc act tat tac tgc cag cag tgg agt ggt aac ccg tgg acg     288
Asp Phe Ala Thr Tyr Tyr Cys Gln Gln Trp Ser Gly Asn Pro Trp Thr
                85                  90                  95 ttc ggt gga ggc act aag gtg gag atc aaa                             318
Phe Gly Gly Gly Thr Lys Val Glu Ile Lys
            100                 105

<210> SEQ ID NO 49
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 49

Gln Ile Val Leu Thr Gln Ser Pro Ser Ser Leu Ser Ala Ser Val Gly
 1               5                  10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Pro Trp Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gly Gly Thr Lys Val Glu Ile Lys
            100                 105
```

-continued

```
<210> SEQ ID NO 50
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 50 caa att gtt ctc acc cag tct cca tcc tcc ctg tct gcg tct gta ggg      48
Gln Ile Val Leu Thr Gln Ser Pro Ser Ser Leu Ser Ala Ser Val Gly
 1               5                  10                  15 gac aga gtc acc atc aca tgc agt gcc agc tca agt gta aat cac atg      96
Asp Arg Val Thr Ile Thr Cys Ser Ala Ser Ser Ser Val Asn His Met
             20                  25                  30 ttc tgg tat cag cag aag ccc ggg aaa gcg ccc aaa ctc ctg att tat     144
Phe Trp Tyr Gln Gln Lys Pro Gly Lys Ala Pro Lys Leu Leu Ile Tyr
         35                  40                  45 ctc aca tcc aac ctg gct tct gga gtc cct tca cgc ttc agt ggc agt     192
Leu Thr Ser Asn Leu Ala Ser Gly Val Pro Ser Arg Phe Ser Gly Ser
     50                  55                  60 ggg tct ggg aca gat tac act ctc aca atc agc agc ctg caa cct gaa     240
Gly Ser Gly Thr Asp Tyr Thr Leu Thr Ile Ser Ser Leu Gln Pro Glu
 65                  70                  75                  80 gat ttt gcc act tat tac tgc cag cag tgg agt ggt aac ccg tgg acg     288
Asp Phe Ala Thr Tyr Tyr Cys Gln Gln Trp Ser Gly Asn Pro Trp Thr
                 85                  90                  95 ttc ggt gga ggc act aag gtg gag atc aaa                             318
Phe Gly Gly Gly Thr Lys Val Glu Ile Lys
            100                 105

<210> SEQ ID NO 51
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 51

Gln Ile Val Leu Thr Gln Ser Pro Ser Ser Leu Ser Ala Ser Val Gly
 1               5                  10                  15

Asp Arg Val Thr Ile Thr Cys Ser Ala Ser Ser Ser Val Asn His Met
             20                  25                  30

Phe Trp Tyr Gln Gln Lys Pro Gly Lys Ala Pro Lys Leu Leu Ile Tyr
         35                  40                  45

Leu Thr Ser Asn Leu Ala Ser Gly Val Pro Ser Arg Phe Ser Gly Ser
     50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Gly Asn Pro Trp Thr
                 85                  90                  95

Phe Gly Gly Gly Thr Lys Val Glu Ile Lys
            100                 105

<210> SEQ ID NO 52
<211> LENGTH: 318
<212> TYPE: DNA
<213> ORGANISM: Artificial Sequence
<220> FEATURE:
<223> OTHER INFORMATION: Synthetically generated oligonucleotide
```

<220> FEATURE:
<221> NAME/KEY: CDS
<222> LOCATION: (1)...(318)

<400> SEQUENCE: 52

```
caa att cag ctc acc cag tct cca tcc tcc ctg tct gcg tct gta ggg      48
Gln Ile Gln Leu Thr Gln Ser Pro Ser Ser Leu Ser Ala Ser Val Gly
 1               5                  10                  15 gac aga gtc acc atc aca tgc agt gcc agc tca agt gta aat cac atg      96
Asp Arg Val Thr Ile Thr Cys Ser Ala Ser Ser Ser Val Asn His Met
            20                  25                  30 ttc tgg tat cag cag aag ccc ggg aaa gcc ccc aaa ccc tgg att tat     144
Phe Trp Tyr Gln Gln Lys Pro Gly Lys Ala Pro Lys Pro Trp Ile Tyr
        35                  40                  45 ctc aca tcc aac ctg gct tct gga gtc cct tca cgc ttc agt ggc agt     192
Leu Thr Ser Asn Leu Ala Ser Gly Val Pro Ser Arg Phe Ser Gly Ser
    50                  55                  60 ggg tct ggg aca gat tac act ctc aca atc agc agc ctg caa cct gaa     240
Gly Ser Gly Thr Asp Tyr Thr Leu Thr Ile Ser Ser Leu Gln Pro Glu
65                  70                  75                  80 gat ttt gcc act tat tac tgc cag cag tgg agt ggt aac ccg tgg acg     288
Asp Phe Ala Thr Tyr Tyr Cys Gln Gln Trp Ser Gly Asn Pro Trp Thr
                85                  90                  95 ttc ggt cag ggc act aag gtg gag atc aaa                             318
Phe Gly Gln Gly Thr Lys Val Glu Ile Lys
            100                 105
```

<210> SEQ ID NO 53
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 53

```
caa att cag ctc acc cag tct cca tcc tcc ctg tct gcg tct gta ggg      48
Gln Ile Gln Leu Thr Gln Ser Pro Ser Ser Leu Ser Ala Ser Val Gly
 1               5                  10                  15 gac aga gtc acc atc aca tgc agt gcc agc tca agt gta aat cac atg      96
Asp Arg Val Thr Ile Thr Cys Ser Ala Ser Ser Ser Val Asn His Met
            20                  25                  30 ttc tgg tat cag cag aag ccc ggg aaa gcc ccc aaa ctc ctg att tat     144
Phe Trp Tyr Gln Gln Lys Pro Gly Lys Ala Pro Lys Leu Leu Ile Tyr
        35                  40                  45 ctc aca tcc aac ctg gct tct gga gtc cct tca cgc ttc agt ggc agt     192
Leu Thr Ser Asn Leu Ala Ser Gly Val Pro Ser Arg Phe Ser Gly Ser
    50                  55                  60 ggg tct ggg aca gat tac act ctc aca atc agc agc ctg caa cct gaa     240
Gly Ser Gly Thr Asp Tyr Thr Leu Thr Ile Ser Ser Leu Gln Pro Glu
65                  70                  75                  80 gat ttt gcc act tat tac tgc cag cag tgg agt ggt aac ccg tgg acg     288
Asp Phe Ala Thr Tyr Tyr Cys Gln Gln Trp Ser Gly Asn Pro Trp Thr
                85                  90                  95 ttc ggt cag ggc act aag gtg gag atc aaa                             318
Phe Gly Gln Gly Thr Lys Val Glu Ile Lys
            100                 105
```

<210> SEQ ID NO 54
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 54

```
Gln Ile Gln Leu Thr Gln Ser Pro Ser Ser Leu Ser Ala Ser Val Gly
  1               5                  10                  15

Asp Arg Val Thr Ile Thr Cys Ser Ala Ser Ser Val Asn His Met
             20                  25                  30

Phe Trp Tyr Gln Gln Lys Pro Gly Lys Ala Pro Lys Leu Leu Ile Tyr
             35                  40                  45

Leu Thr Ser Asn Leu Ala Ser Gly Val Pro Ser Arg Phe Ser Gly Ser
         50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Gly Asn Pro Trp Thr
                 85                  90                  95

Phe Gly Gln Gly Thr Lys Val Glu Ile Lys
                100                 105
```

<210> SEQ ID NO 55
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 55

```
gaa att gtt ctc acc cag ttt cca gca ctc atg tct gcg tct cca ggg    48
Glu Ile Val Leu Thr Gln Phe Pro Ala Leu Met Ser Ala Ser Pro Gly
  1               5                  10                  15 gag aag gtc acc atg acc tgc agt gcc agc tca agt gta aat cac atg    96
Glu Lys Val Thr Met Thr Cys Ser Ala Ser Ser Ser Val Asn His Met
             20                  25                  30 ttc tgg tat cag cag aag cca aaa tcc tcc ccc aaa ccc tgg att tat   144
Phe Trp Tyr Gln Gln Lys Pro Lys Ser Ser Pro Lys Pro Trp Ile Tyr
             35                  40                  45 ctc aca tcc aac ctg gct tct gga gtc cct gct cgc ttc agt ggc agt   192
Leu Thr Ser Asn Leu Ala Ser Gly Val Pro Ala Arg Phe Ser Gly Ser
         50                  55                  60 ggg tct ggg acc tct tac tct ctc aca atc agc agc atg gag gct gaa   240
Gly Ser Gly Thr Ser Tyr Ser Leu Thr Ile Ser Ser Met Glu Ala Glu
 65                  70                  75                  80 gat gct gcc act tat tac tgc cag cag tgg agt ggt aac ccg tgg acg   288
Asp Ala Ala Thr Tyr Tyr Cys Gln Gln Trp Ser Gly Asn Pro Trp Thr
                 85                  90                  95 ttc ggt gga ggc acc aag ctg gag atc aaa                           318
Phe Gly Gly Gly Thr Lys Leu Glu Ile Lys
                100                 105
```

<210> SEQ ID NO 56
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 56

Glu Ile Val Leu Thr Gln Phe Pro Ala Leu Met Ser Ala Ser Pro Gly
1               5                   10                  15

Glu Lys Val Thr Met Thr Cys Ser Ala Ser Ser Ser Val Asn His Met
            20                  25                  30

Phe Trp Tyr Gln Gln Lys Pro Lys Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Gly Asn Pro Trp Thr
                85                  90                  95

Phe Gly Gly Gly Thr Lys Leu Glu Ile Lys
            100                 105

<210> SEQ ID NO 57
<211> LENGTH: 318
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (1)...(318)

<400> SEQUENCE: 57

```
gat atc cag ctc acc cag tct cca tcc tcc ctg tct gcg tct gta ggg      48
Asp Ile Gln Leu Thr Gln Ser Pro Ser Ser Leu Ser Ala Ser Val Gly
1               5                   10                  15 gac aga gtc acc atc aca tgc agt gcc agc tca agt gta aat cac atg      96
Asp Arg Val Thr Ile Thr Cys Ser Ala Ser Ser Ser Val Asn His Met
            20                  25                  30 ttc tgg tat cag cag aag ccc ggg aaa gcc ccc aaa ccc tgg att tat     144
Phe Trp Tyr Gln Gln Lys Pro Gly Lys Ala Pro Lys Pro Trp Ile Tyr
        35                  40                  45 ctc aca tcc aac ctg gct tct gga gtc cct tca cgc ttc agt ggc agt     192
Leu Thr Ser Asn Leu Ala Ser Gly Val Pro Ser Arg Phe Ser Gly Ser
    50                  55                  60 ggg tct ggg aca gat tac act ctc aca atc agc agc ctg caa cct gaa     240
Gly Ser Gly Thr Asp Tyr Thr Leu Thr Ile Ser Ser Leu Gln Pro Glu
65                  70                  75                  80 gat ttt gcc act tat tac tgc cag cag tgg agt ggt aac ccg tgg acg     288
Asp Phe Ala Thr Tyr Tyr Cys Gln Gln Trp Ser Gly Asn Pro Trp Thr
                85                  90                  95 ttc ggt cag ggc act aag gtg gag atc aaa                             318
Phe Gly Gln Gly Thr Lys Val Glu Ile Lys
            100                 105
```

<210> SEQ ID NO 58
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 58

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Pro Trp Ile Tyr
            35                  40                  45

Leu Thr Ser Asn Leu Ala Ser Gly Val Pro Ser Arg Phe Ser Gly Ser
 50                  55                  60

Gly Ser Gly Thr Asp Tyr Thr Leu Thr Ile Ser Ser Leu Gln Pro Glu
 65                  70                  75                  80

Asp Phe Ala Thr Tyr Tyr Cys Gln Gln Trp Ser Gly Asn Pro Trp Thr
                 85                  90                  95

Phe Gly Gln Gly Thr Lys Val Glu Ile Lys
            100                 105

<210> SEQ ID NO 59
<211> LENGTH: 192
<212> TYPE: PRT
<213> ORGANISM: Artificial Sequence
<220> FEATURE:
<223> OTHER INFORMATION: Rat and human chimeric I domain construct

<400> SEQUENCE: 59

Thr Gln Leu Asp Ile Val Ile Val Leu Asp Gly Ser Asn Ser Ile Tyr
 1               5                   10                  15

Pro Trp Glu Ser Val Ile Ala Phe Leu Asn Asp Leu Leu Lys Arg Asn
            20                  25                  30

Asp Ile Gly Pro Lys Gln Thr Gln Val Gly Ile Val Gln Tyr Gly Glu
        35                  40                  45

Asn Val Thr His Glu Phe Asn Leu Asn Lys Tyr Ser Ser Thr Glu Glu
 50                  55                  60

Val Leu Val Ala Ala Asn Lys Ile Val Gln Arg Gly Gly Arg Gln Thr
 65                  70                  75                  80

Met Thr Ala Leu Gly Ile Asp Thr Ala Arg Lys Glu Ala Phe Thr Glu
                 85                  90                  95

Ala Arg Gly Ala Arg Arg Gly Val Lys Lys Val Met Val Ile Val Thr
            100                 105                 110

Asp Gly Glu Ser His Asp Asn Tyr Arg Leu Lys Gln Val Ile Gln Asp
        115                 120                 125

Cys Glu Asp Glu Asn Ile Gln Arg Phe Ser Ile Ala Ile Leu Gly His
130                 135                 140

Tyr Asn Arg Gly Asn Leu Ser Thr Glu Lys Phe Val Glu Glu Ile Lys
145                 150                 155                 160

Ser Ile Ala Ser Glu Pro Thr Glu Lys His Phe Phe Asn Val Ser Asp
                165                 170                 175

Glu Leu Ala Leu Val Thr Thr Val Lys Ala Leu Gly Arg Ile Phe
            180                 185                 190

<210> SEQ ID NO 60
<211> LENGTH: 192
<212> TYPE: PRT
<213> ORGANISM: Rattus sp.

<400> SEQUENCE: 60

Thr Gln Leu Asp Ile Val Ile Val Leu Asp Gly Ser Asn Ser Ile Tyr
 1               5                   10                  15

Pro Trp Glu Ser Val Ile Ala Phe Leu Asn Asp Leu Leu Lys Arg Met
            20                  25                  30

Asp Ile Gly Pro Lys Gln Thr Gln Val Gly Ile Val Gln Tyr Gly Glu
        35                  40                  45

```
Asn Val Thr His Glu Phe Asn Leu Asn Lys Tyr Ser Ser Thr Glu Glu
 50                  55                  60

Val Leu Val Ala Ala Asn Lys Ile Gly Arg Gln Gly Gly Leu Gln Thr
 65                  70                  75                  80

Met Thr Ala Leu Gly Ile Asp Thr Ala Arg Lys Glu Ala Phe Thr Glu
                 85                  90                  95

Ala Arg Gly Ala Arg Arg Gly Val Lys Lys Val Met Val Ile Val Thr
                100                 105                 110

Asp Gly Glu Ser His Asp Asn Tyr Arg Leu Lys Gln Val Ile Gln Asp
                115                 120                 125

Cys Glu Asp Glu Asn Ile Gln Arg Phe Ser Ile Ala Ile Leu Gly His
130                 135                 140

Tyr Asn Arg Gly Asn Leu Ser Thr Glu Lys Phe Val Glu Glu Ile Lys
145                 150                 155                 160

Ser Ile Ala Ser Glu Pro Thr Glu Lys His Phe Phe Asn Val Ser Asp
                165                 170                 175

Glu Leu Ala Leu Val Thr Ile Val Lys Ala Leu Gly Glu Arg Ile Phe
                180                 185                 190

<210> SEQ ID NO 61
<211> LENGTH: 192
<212> TYPE: PRT
<213> ORGANISM: Homo sapiens

<400> SEQUENCE: 61

Thr Gln Leu Asp Ile Val Ile Val Leu Asp Gly Ser Asn Ser Ile Tyr
 1               5                   10                  15

Pro Trp Asp Ser Val Thr Ala Phe Leu Asn Asp Leu Leu Lys Arg Met
                 20                  25                  30

Asp Ile Gly Pro Lys Gln Thr Gln Val Gly Ile Val Gln Tyr Gly Glu
                 35                  40                  45

Asn Val Thr His Glu Phe Asn Leu Asn Lys Tyr Ser Ser Thr Glu Glu
 50                  55                  60

Val Leu Val Ala Ala Lys Lys Ile Val Gln Arg Gly Gly Arg Gln Thr
 65                  70                  75                  80

Met Thr Ala Leu Gly Ile Asp Thr Ala Arg Lys Glu Ala Phe Thr Glu
                 85                  90                  95

Ala Arg Gly Ala Arg Arg Gly Val Lys Lys Val Met Val Ile Val Thr
                100                 105                 110

Asp Gly Glu Ser His Asp Asn His Arg Leu Lys Lys Val Ile Gln Asp
                115                 120                 125

Cys Glu Asp Glu Asn Ile Gln Arg Phe Ser Ile Ala Ile Leu Gly Ser
130                 135                 140

Tyr Asn Arg Gly Asn Leu Ser Thr Glu Lys Phe Val Glu Glu Ile Lys
145                 150                 155                 160

Ser Ile Ala Ser Glu Pro Thr Glu Lys His Phe Phe Asn Val Ser Asp
                165                 170                 175

Glu Ile Ala Leu Val Thr Ile Val Lys Thr Leu Gly Glu Arg Ile Phe
                180                 185                 190

<210> SEQ ID NO 62
<211> LENGTH: 7
<212> TYPE: PRT
<213> ORGANISM: Artificial Sequence
<220> FEATURE:
<223> OTHER INFORMATION: Synthetically generated peptide
```

```
<400> SEQUENCE: 62

Gly Phe Gly Asp Gly Gly Tyr
 1               5

<210> SEQ ID NO 63
<211> LENGTH: 214
<212> TYPE: PRT
<213> ORGANISM: Rattus sp.

<400> SEQUENCE: 63

Val Ser Pro Thr Phe Gln Val Val Asn Ser Phe Ala Pro Val Gln Glu
 1               5                  10                  15

Cys Ser Thr Gln Leu Asp Ile Val Ile Val Leu Asp Gly Ser Asn Ser
                20                  25                  30

Ile Tyr Pro Trp Glu Ser Val Ile Ala Phe Leu Asn Asp Leu Leu Lys
            35                  40                  45

Arg Met Asp Ile Gly Pro Lys Gln Thr Gln Val Gly Ile Val Gln Tyr
        50                  55                  60

Gly Glu Asn Val Thr His Glu Phe Asn Leu Asn Lys Tyr Ser Ser Thr
 65                  70                  75                  80

Glu Glu Val Leu Val Ala Ala Lys Lys Ile Gly Arg Gln Gly Gly Leu
                85                  90                  95

Gln Thr Met Thr Ala Leu Gly Ile Asp Thr Ala Arg Lys Glu Ala Phe
            100                 105                 110

Thr Glu Ala Arg Gly Ala Arg Arg Gly Val Lys Lys Val Met Val Ile
        115                 120                 125

Val Thr Asp Gly Glu Ser His Asp Asn Tyr Arg Leu Lys Gln Val Ile
    130                 135                 140

Gln Asp Cys Glu Asp Glu Asn Ile Gln Arg Phe Ser Ile Ala Ile Leu
145                 150                 155                 160

Gly His Tyr Asn Arg Gly Asn Leu Ser Thr Glu Lys Phe Val Glu Glu
                165                 170                 175

Ile Lys Ser Ile Ala Ser Glu Pro Thr Glu Lys His Phe Phe Asn Val
            180                 185                 190

Ser Asp Glu Leu Ala Leu Val Thr Ile Val Lys Ala Leu Gly Glu Arg
        195                 200                 205

Ile Phe Ala Leu Glu Ala
    210

<210> SEQ ID NO 64
<211> LENGTH: 214
<212> TYPE: PRT
<213> ORGANISM: Homo sapiens

<400> SEQUENCE: 64

Val Ser Pro Thr Phe Gln Val Val Asn Ser Ile Ala Pro Val Gln Glu
 1               5                  10                  15

Cys Ser Thr Gln Leu Asp Ile Val Ile Val Leu Asp Gly Ser Asn Ser
                20                  25                  30

Ile Tyr Pro Trp Asp Ser Val Thr Ala Phe Leu Asn Asp Leu Leu Lys
            35                  40                  45

Arg Met Asp Ile Gly Pro Lys Gln Thr Gln Val Gly Ile Val Gln Tyr
        50                  55                  60

Gly Glu Asn Val Thr His Glu Phe Asn Leu Asn Lys Tyr Ser Ser Thr
 65                  70                  75                  80
```

Glu Glu Val Leu Val Ala Ala Lys Lys Ile Val Gln Arg Gly Gly Arg
            85                  90                  95

Gln Thr Met Thr Ala Leu Gly Thr Asp Thr Ala Arg Lys Glu Ala Phe
            100                 105                 110

Thr Glu Ala Arg Gly Ala Arg Arg Gly Val Lys Lys Val Met Val Ile
            115                 120                 125

Val Thr Asp Gly Glu Ser His Asp Asn His Arg Leu Lys Lys Val Ile
            130                 135                 140

Gln Asp Cys Glu Asp Glu Asn Ile Gln Arg Phe Ser Ile Ala Ile Leu
145                 150                 155                 160

Gly Ser Tyr Asn Arg Gly Asn Leu Ser Thr Glu Lys Phe Val Glu Glu
            165                 170                 175

Ile Lys Ser Ile Ala Ser Glu Pro Thr Glu Lys His Phe Phe Asn Val
            180                 185                 190

Ser Asp Glu Leu Ala Leu Val Thr Ile Val Lys Thr Leu Gly Glu Arg
            195                 200                 205

Ile Phe Ala Leu Glu Ala
        210

<210> SEQ ID NO 65
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 65

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Tyr Leu
            20                  25                  30

Asn Trp Tyr Gln Gln Lys Pro Gly Lys Ala Pro Lys Leu Leu Ile Tyr
        35                  40                  45

Ala Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser Tyr Ser Thr Pro Leu Thr
            85                  90                  95

Phe Gly Gly Gly Thr Lys Val Glu Ile Lys
            100                 105

<210> SEQ ID NO 66
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 66

Gln Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Pro Trp Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105

<210> SEQ ID NO 67
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 67

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ser Ile Arg Phe Leu Glu Trp Ser Phe Asp Tyr Trp Gly Gln Gly Thr
            100                 105                 110

Leu Val Thr Val Ser Ser
            115

<210> SEQ ID NO 68
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
            115

-continued

```
<210> SEQ ID NO 69
<211> LENGTH: 118
<212> TYPE: PRT
<213> ORGANISM: Artificial Sequence
<220> FEATURE:
<223> OTHER INFORMATION: Synthetically generated peptide

<400> SEQUENCE: 69

Glu Val Gln Leu Val Glu Ser Gly Gly Leu Val Gln Pro Gly Gly
 1               5                  10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Gly Gly Gly His Thr Tyr Tyr Leu Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Thr
                85                  90                  95

Arg Gly Phe Gly Asp Gly Gly Tyr Phe Asp Val Trp Gly Gln Gly Thr
            100                 105                 110

Leu Val Thr Val Ser Ser
        115

<210> SEQ ID NO 70
<211> LENGTH: 106
<212> TYPE: PRT
<213> ORGANISM: Artificial Sequence
<220> FEATURE:
<223> OTHER INFORMATION: Synthetically generated peptide

<400> SEQUENCE: 70

Gln Ile Gln Leu Thr Gln Ser Pro Ser Ser Leu Ser Ala Ser Val Gly
 1               5                  10                  15

Asp Arg Val Thr Ile Thr Cys Ser Ala Ser Ser Ser Val Asn His Met
            20                  25                  30

Phe Trp Tyr Gln Gln Lys Pro Gly Lys Ala Pro Lys Pro Leu Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Gly Asn Pro Trp Thr
                85                  90                  95

Phe Gly Gln Gly Thr Lys Val Glu Ile Lys
            100                 105
```

ANTIBODIES TO VLA-1

CROSS-REFERENCE TO RELATED APPLICATIONS

This application is a divisional application of U.S. application Ser. No. 13/297,124, filed Nov. 15, 2011, which is a continuation of U.S. application Ser. No. 13/017,919, filed Jan. 31, 2011 (which issued as U.S. Pat. No. 8,084,028 on Dec. 27, 2011), which is a continuation application of U.S. application Ser. No. 12/727,965, filed Mar. 19, 2010 (which issued as U.S. Pat. No. 7,910,099 on Mar. 22, 2011), which is a divisional application of U.S. application Ser. No. 12/015,213, filed Jan. 16, 2008 (which issued as U.S. Pat. No. 7,723,073 on May 25, 2010), which is a divisional application of U.S. application Ser. No. 10/474,832 (which issued as U.S. Pat. No. 7,358,054 on Apr. 15, 2008), which is the National Stage filing under 35 U.S.C. §371 of International Application No. PCT/US02/11521, filed Apr. 12, 2002, which claims benefit under 35 U.S.C. §119(e) of U.S. provisional application No. 60/283,794, filed Apr. 13, 2001, and 60/303,689, filed Jul. 6, 2001.

FIELD OF THE INVENTION

This invention relates to antibodies to VLA-1 integrin and the use of these antibodies in treating inflammatory diseases and other immunological disorders.

This invention also relates to the crystal structure of the complex between one such antibody and the α1-I domain of VLA-1, and to the use of this structural information for computational drug design.

BACKGROUND OF THE INVENTION

Integrins are a superfamily of cell surface receptors that mediate cell-cell and cell-matrix adhesion. These proteins are known to provide anchorage as well as signals for cellular growth, migration and differentiation during development and tissue repair. They have been implicated in immune and inflammatory processes.

Integrins are heterodimeric proteins composed of two noncovalently linked polypeptide chains, α and β. The amino terminus of each chain forms a globular head that contributes to interchain linking and to ligand binding. The globular heads are connected to the transmembrane segments by stalks. The cytoplasmic tails are usually less than 50 amino acid residues long. Integrin subfamilies were originally defined on the basis of which β subunit was used to form the heterodimers. The β1-containing integrins are also called VLA molecules, referring to "very late activation" antigens. VLA-1 to VLA-6 refer to β1 subfamily members containing α1 to α6 (i.e., CD49a to CD49f), respectively. For general review, see Cellular and Molecular Immunology, eds. Abul K. Abbas et al., W. B. Saunders Company, Philadelphia, Pa., 2000.

Collagen (both types I and IV) and laminin are known ligands of α1β1 integrin (i.e., VLA-1). VLA-1 has been implicated in cell adhesion and migration on collagen (Keely et al., 1995, J. Cell Sci. 108:595-607; and Gotwals et al., 1996, J. Clin. Invest. 97:2469-2477); in promoting contraction and reorganization of collagen matrices, a critical component of wound healing (Gotwals et al., supra; and Chiro, 1991, Cell 67:403-410); and in regulating the expression of genes involved in extracellular matrix remodeling (Riikonen et al., 1995, J. Biol. Chem. 270:1-5; and Langholz et al., 1995, J. Cell Biol. 131:1903-1915). Thus, improper regulation of VLA-1 may result in certain pathological conditions such as fibrosis.

Moreover, it has been suggested that VLA-1 may play a role in T cell/monocyte-driven diseases. Anti-VLA-1 antibodies block T-cell dependent cytokine expression (Miyake et al., 1993, J. Exp. Med. 177:863-868). Expression of VLA-1 is increased in persistently activated, 2 to 4 week old cultured T cells (Hemler et al., 1985, Eur. J. Immunol. 15:502-508). VLA-1 is also expressed on a high percentage of T cells isolated from the synovium of patients with rheumatoid arthritis (Hemler et al., 1986, J. Clin. Invest. 78:692-702).

Several crystal structures of integrin α subunits have been determined, including the structures of the α2-I domain of α2β1 (PDB accession code 1aox; Emsley et al., 1997, J. Biol. Chem. 272:28512-28517); the α1-I domain of rat α1β1 (PDB accession number 1ck4; Nolte et al., 1999, FEBS Lett. 452:379-85; WO 00/20459); the α1 subunit of human α1β1 (PDB accession code 1qc5; Rich et al., 1999, J. Biol. Chem. 274:24906-24913); the αL-I and αM-I domains; and vWF-A3 (Lee et al., 1995, Cell 80:631-635; Lee et al., 1995, Structure 3:1333-1340; Qu et al., 1995, Proc. Natl. Acad. Sci. USA 92:10277-10281; Qu et al., 1996, Structure 4:931-942). The α2β1 structure revealed a helix (i.e., the C-helix) that created a trench or groove on one face of the protein at the metal-ion binding site (Emsley et al., supra). The crystal structure of the α2-I domain complexed to a short collagen-based triple helical peptide revealed that the collagen-based peptide was bound to that trench, where the α2-I amino acids that made intermolecular or metal contacts included Asp151, Asn154, Tyr157, Gln215, Asp219, Leu220, Thr221, Asp254, Glu256, His258, Tyr285, Leu286, Asn289, Leu291, Asn295, and Lys298 (PDB accession code 1dzi; Emsley et al., 2000, Cell 101:47-56; WO 01/73444). The amino acid numbering immediately above is based on PDB accession code 1dzi and herein referred to as "crystal numbering." The crystal structures of the rat and human α1-I domains revealed a similar trench.

SUMMARY OF THE INVENTION

The present invention provides anti-VLA-1 antibodies and methods of using these antibodies to treat a variety of inflammatory and immunological disorders.

Specifically, the invention embraces an antibody that specifically binds to VLA-1 (e.g., human VLA-1). This antibody contains light chain complementarity determining regions ("CDR"s) defined by amino acid residues 24 to 33, 49 to 55, and 88 to 96 of SEQ ID NO:1, and/or heavy chain complementarity determining regions defined by amino acid residues 31 to 35, 50 to 65, and 98 to 107 of SEQ ID NO:2. These CDRs may contain mutations (e.g., deletions, insertions and/or substitutions) in the non-antigen-contacting portions, as determined from the crystal structure disclosed herein, without affecting the VLA-1-binding activity of the antibody. Exemplary mutations are S24N, G92S and D101A in the light chain CDRs, and G55S in the heavy chain CDR2. In one embodiment, the antibody of this invention contains a light chain variable domain sequence of SEQ ID NO:1 and/or a heavy chain variable domain sequence of SEQ ID NO:2.

In a related embodiment, the antibody of this invention contains the same heavy and light chain polypeptide sequences as an antibody produced by hybridoma mAQC2, deposited on Apr. 18, 2001 at the American Type Culture Collection ("ATCC"), 10801 University Boulevard, Manassas, Va. 20110-2209 and having ATCC accession number PTA3273. (All ATCC deposits recited herein were made under the Budapest Treaty). This antibody can be produced by, for example, hybridoma mAQC2, or cells containing nucleic acid sequences isolated from that hybridoma that encode the heavy and light chains of the mAQC2 monoclonal antibody.

In another embodiment, the antibody is a humanized antibody comprising at least one (e.g., 2, 3, 4, or 5) of the following residues in its light chain: Q1, L4, P46, W47 and Y71; or at least one (e.g., 2, 3, 4, 5, 6 or 7) of the following residues in its heavy chain: D1, V12, S28, F29, A49, T93, R94 (Kabat numbering convention). For instance, the antibody comprises Q1, L4 and Y71 in the light chain; and/or (i) F29, A49, T93 and R94, or (ii) A49 and T93, in the heavy chain.

The humanized antibody of this invention may contain a light chain variable domain sequence defined by amino acid residues 1 to 106 of SEQ ID NO:3, and/or a heavy chain variable domain sequence defined by amino acid residues 1 to 118 of SEQ ID NO:4. The humanized antibody may comprise the same heavy and/or light chain polypeptide sequences as an antibody produced by cell line hAQC2 (ATCC accession number PTA3275; deposited on Apr. 18, 2001).

In another embodiment, the humanized antibody of this invention may contain a mutation (e.g., deletion, substitution or addition) at one or more (e.g., 2, 3, 4, 5, 6, 7 or 8) of certain positions in the heavy chain such that an effector function of the antibody (e.g., the ability of the antibody to bind to a Fc receptor or a complement factor) is altered without affecting the antibody's ability to bind to VLA-1 (U.S. Pat. No. 5,648,260). These heavy chain positions include, without limitation, residues 234, 235, 236, 237, 297, 318, 320 and 322 (EU numbering system). The humanized antibody can, for instance, contain the mutations L234A (i.e., replacing leucine at position 234 of an unmodified antibody with alanine) and L235A (EU numbering system) in its heavy chain. In one related embodiment, the antibody comprises the same heavy chain polypeptide sequence as an antibody produced by cell line hsAQC2 (ATCC accession number PTA3356; deposited on May 4, 2001).

In yet another embodiment, the humanized antibody of this invention may contain a mutation (e.g., deletion or substitution) at an amino acid residue that is a site for glycosylation, such that the glycosylation site is eliminated. Such an antibody may be clinically beneficial for having reduced effector functions or other undesired functions while retaining its VLA-1 binding affinity. Mutations of glycosylation sites can also be beneficial for process development (e.g., protein expression and purification). For instance, the heavy chain of the antibody may contain the mutation N297Q (EU numbering system) such that the heavy chain can no longer be glycosylated at this site. In one related embodiment, the humanized antibody may comprise the same heavy chain polypeptide sequence as an antibody produced by cell line haAQC2 (ATCC accession number PTA3274; deposited on Apr. 18, 2001).

In still other embodiments, the heavy and/or light chains of the antibody of this invention contain mutations that increase affinity for binding to VLA-1 and thereby increase potency for treating VLA-1-mediated disorders.

Embraced in this invention are also a composition containing an antibody of the invention and a pharmaceutically acceptable carrier; an isolated nucleic acid containing a coding sequence for SEQ ID NO:1; an isolated nucleic acid containing a coding sequence for SEQ ID NO:2; an isolated nucleic acid containing a coding sequence for the light chain of an antibody produced by hybridoma mAQC2; an isolated nucleic acid containing a coding sequence for the heavy chain of an antibody produced by hybridoma mAQC2; an isolated nucleic acid containing a coding sequence for the light chain of an antibody produced by cell line hAQC2; an isolated nucleic acid containing a coding sequence for the heavy chain of an antibody produced by cell line hAQC2; an isolated nucleic acid containing a coding sequence for the heavy chain of an antibody produced by cell line haAQC2; an isolated nucleic acid containing a coding sequence for the heavy chain of an antibody produced by cell line hsAQC2; an isolated nucleic acid containing a coding sequence for residues 1 to 106 of SEQ ID NO:3; an isolated nucleic acid containing a coding sequence for residues 1 to 118 of SEQ ID NO:4; cells of hybridoma mAQC2; cells from cell line hAQC2; cells from cell line haAQC2; and cells from cell line hsAQC2.

The present invention also provides a method of treating a subject with an immunological disorder mediated by VLA-1, including administering to the subject an effective amount of an antibody of this invention. For instance, this method is used to treat a human subject to palliate, ameliorate, stabilize, reverse, prevent, slow or delay progression of the disorder. Alternatively, this method is used prophylactically to treat a human subject at risk for developing this immunological disorder so as to prevent or delay the onset of the disorder. An "effective amount" of the composition can be administered in one or more dosages.

VLA-1 mediated immunological disorders include, but are not limited to, disorders in which the VLA-1 activity level is elevated in one or more tissues as compared to a normal subject. Examples of such disorders are skin related conditions (e.g., psoriasis, eczema, burns, dermatitis, and abnormal proliferation of hair follicle cells), fibrosis (e.g., kidney or lung fibrosis), allergic rhinitis, respiratory distress syndrome, asthma, bronchitis, tendinitis, bursitis, fever, migraine headaches, gastrointestinal conditions (e.g., inflammatory bowel disease, Crohn's disease, gastritis, irritable bowel syndrome, colitis and colorectal cancer), vascular diseases (e.g., atherosclerosis), periarteritis nodosa, thyroiditis, aplastic anemia, Hodgkin's Disease, rheumatic fever, osteoarthritis, autoimmune diseases (e.g., type I diabetes, myasthenia gravis, rheumatoid arthritis, systemic lupus erythematosus, and multiple sclerosis), sarcoidosis, nephrotic syndrome, renal failure, Bechet's Syndrome, polymyositis, gingivitis, hypersensitivity (e.g., delayed type hypersensitivity or immediate hypersensitivity), graft and transplant rejections, graft versus host disease (GVHD), conjunctivitis, swelling occurring after injury, myocardial ischemia, and endotoxin shock syndrome.

The present invention also provides a method of determining the level of VLA-1 in a tissue (e.g., tissue specimen and body fluid) comprising contacting the tissue (e.g., in vivo or in vitro) with the antibody of the invention, and then detecting the binding of the antibody to the tissue, thereby determining the level of VLA-1 in the tissue.

As used herein, the antibody of this invention can be, for instance, a murine antibody, a humanized antibody, or a chimeric antibody. It can be a whole antibody (i.e., with two full length light chains and two full length heavy chains) of any isotype and subtypes (e.g., IgM, IgD, $IgG_1$, $IgG_2$, $IgG_3$, $IgG_4$, IgE, $IgA_1$, and $IgA_2$; with either kappa or lambda light chain). Alternatively, the antibody of this invention refers to an antigen-binding fragment (e.g., Fab, $F(ab')_2$, and single chain Fv) of a whole antibody.

The present invention further provides crystallizable compositions and crystals of complexes formed by a rat-human chimeric α1-I domain (mutant RΔH) and a hAQC2 Fab fragment, and methods for using such compositions and crystals. This invention also provides the structure coordinates and binding sites of the chimeric domain and the hAQC2 Fab fragment. The atomic coordinates derived from the crystal structure described herein provide a structural basis for the biological activities of hAQC2 as well as a basis for rational design of VLA-1 agonists or antagonists with predicted biological activities (e.g., small molecule compounds or antibodies such as hAQC2 variants).

The crystal structure disclosed herein is the first crystal structure of an α1-I domain of an α1β1 integrin/Fab complex. This structure shows the residues critical for Fab binding by α1-I domain. In addition, the Fab binds in the putative collagen-binding site and inhibits collagen binding. Amino acid residues found in the binding site on the α1-I domain include Asp154, Ser156, Asn157, Ser158, Tyr160, Glu192, Glu218, Arg219, Gly220, Gly221, Arg222, Gln223, Thr224, Asp257, His261, Asn263, Arg291, and Leu294 (crystal numbering). Residues on the Fab fragment found to bind to the α1-I domain include light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering).

This invention also provides a computer for producing a three-dimensional representation of a molecular complex, where the molecular complex is defined by the set of structure coordinates of a complex of a chimeric I domain of an α1β1 integrin RΔH and humanized antibody hAQC2, according to FIG. 19A-1 to A-109; or a homologue of the molecule or molecular complex, the homologue having a root mean square deviation from the backbone atoms of the amino acids of not more than 0.65 Å. The computer includes a machine-readable data storage medium including a data storage material encoded with machine-readable data, where the data contains at least a portion of the structure coordinates of the complex according to FIG. 19A-1 to A-109; a working memory for storing instructions for processing the machine-readable data; a central processing unit coupled to the working memory and to the machine-readable data storage medium for processing the machine readable data into the three-dimensional representations; and a display coupled to the central-processing unit for displaying the three-dimensional representation.

This invention further provides a computer for producing a three-dimensional representation of a molecule or molecular complex including a binding site defined by structure coordinates of hAQC2 amino acids including at least seven (e.g., 7, 8, 9, 10, 11, 12, 13, 14, 15, or 16) of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering), according to FIG. 19A-1 to A-109; or a homologue of the molecule or molecular complex, where the homologue includes a binding site that has a root mean square deviation from the backbone atoms of the hAQC2 amino acids of not more than 1.10 Å. This invention also provides a computer for producing a three-dimensional representation of: a binding site defined by structure coordinates of hAQC2 amino acids including at least seven (e.g., 7, 8, 9, 10, 11, 12, 13, 14, 15, or 16) of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering), according to FIG. 19A-1 to A-109; a binding site of a homologue that has a root mean square deviation from the backbone atoms of the hAQC2 amino acids of not more than 1.10 Å.

This invention also provides a method for identifying an inhibitor of an I domain of an integrin including the steps of using structure coordinates of hAQC2 amino acids including at least seven (e.g., 7, 8, 9, 10, 11, 12, 13, 14, 15, or 16) of light chain residues Asn30, Tyr48, Trp90, Ser91, Asn93 and Trp95, and heavy chain residues Ser30, Arg39, Trp47, Ser52, Gly53, His56, Tyr58, Phe99, Gly100 and Asp101 (crystal numbering), according to FIG. 19A-1 to A-109 or±a root mean square deviation from the backbone atoms of the hAQC2 amino acids not more than 1.10 Å, to generate a three-dimensional structure of a binding site; employing the three-dimensional structure to design or select a potential antagonist; synthesizing the potential antagonist; and contacting the potential antagonist with hAQC2 to determine the ability of the potential antagonist to interact with hAQC2, where the ability of the potential antagonist to interact with hAQC2 indicates that the potential antagonist is an inhibitor of the I domain. This invention further provides an inhibitor of I domain of integrin identified by this method.

This invention also provides a computer for producing a three-dimensional representation of a molecule or molecular complex including: a binding site defined by structure coordinates of I domain amino acid residues Asp 154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19A-1 to A-109; or a homologue of the molecule or molecular complex, where the homologue includes a second binding site that has a root mean square deviation from the backbone atoms of the I domain amino acids not more than 0.65 Å. This invention also provides a computer for producing a three-dimensional representation of: a first binding site defined by structure coordinates of I domain amino acids residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19A-1 to A-109; or a binding site of a homologue that has a root mean square deviation from the backbone atoms of the I domain amino acids not more than 0.65 Å.

This invention also provides a computer for producing a three-dimensional representation of a molecule or molecular complex including: a binding site defined by structure coordinates of I domain amino acids including at least three of residues Glu192, Gln218, Arg219, Gly220, and Gly221 (crystal numbering), according to FIG. 19A-1 to A-109; or a homologue of the molecule or molecular complex, where the homologue includes a second binding site that has a root mean square deviation from the backbone atoms of the I domain amino acids not more than 1.0 Å. The invention further provides a computer for producing a three-dimensional representation of a binding site defined by structure coordinates of I domain amino acids including at least three of residues Glu192, Gln218, Arg219, Gly220, and Gly221 (crystal numbering), according to FIG. 19A-1 to A-109; or a binding site of a homologue that has a root mean square deviation from the backbone atoms of the I domain amino acids not more than 1.0 Å.

This invention further provides methods for using these three-dimensional representations to design chemical entities that associate with the chimeric domain or the hAQC2 Fab fragment, or portions thereof; and act as potential inhibitors of the chimeric domain or the hAQC2 Fab fragment, or portions thereof. This invention also relates to compositions including chemical entities, such as inhibitors and variants of the chimeric domain or variants of the hAQC2 Fab fragment, where such chemical entities and variants are rationally designed by means of the structure coordinates of the chimeric domain or the hAQC2 Fab fragment, or binding sites. The invention further relates to use of the above-identified chemical entities to treat or prevent conditions associated with inappropriate or abnormal α1β1 activity in a subject.

This invention further provides a method for identifying an inhibitor of an I domain of an integrin including the steps of using the structure coordinates of I domain amino acids residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19A-1 to A-109, to generate a three-dimensional structure of a binding site; employing the three-dimensional structure to design or select a potential antagonist; synthesizing the potential antagonist; and contacting the potential antagonist with I domain to determine the ability of the potential antagonist to interact with I domain, where the ability of the potential antagonist to interact with the I domain indicates that the potential antagonist is an inhibitor of the I domain.

This invention also provides a method for identifying an inhibitor of an I domain of an integrin including the steps of using the structure coordinates of at least three of I domain amino acids including residues Glu192, Gln218, Arg219, Gly220, and Gly221 (crystal numbering), according to FIG. 19A-1 to A-109, or ±a root mean square deviation from the backbone atoms of the I domain amino acids not more than 0.65 Å, to generate a three-dimensional structure of a binding site; employing the three-dimensional structure to design or select a potential antagonist; synthesizing the potential antagonist; and contacting the potential antagonist with I domain to determine the ability of the potential antagonist to interact with I domain of integrin, where the ability of the potential antagonist to interact with the I domain indicates that the potential antagonist is an inhibitor of the I domain. This invention also provides an inhibitor of I domain of integrin identified by this method.

Other features and advantages of the invention will be apparent from the following detailed description, and from the claims.

BRIEF DESCRIPTION OF THE DRAWINGS

FIG. 1A. Flow cytometric analysis of α1 and α2β1 integrin expression on IL-2-activated splenocytes (d 11). Cells were labeled with either anti-α1 mAb, anti-α2 mAb, or non-binding control mAb (grey lines), and followed by FITC-anti-hamster immunoglobulin. FIG. 1B. Effect of anti-α1 and anti-α2 mAbs on leukocyte adhesion to collagen. $10^5$ IL-2 activated splenocytes were treated with indicated mAbs for 15 min before plating onto either type IV or type I collagen-coated wells for 1 h at 37° C. Adhesion was calculated as illustrated in Example 1, and expressed as % adhesion relative to control mAb-treated cells. Adhesion assays were done in triplicate, and at least three independent experiments were performed. One representative experiment is shown.

FIG. 11A. Amino acid sequence of the rat (top; SEQ ID NO:63) and human (below; residues of SEQ ID NO:64, which are different from rat, are shown) α1-I domain. The residues that comprise the MIDAS (metal ion dependent adhesion site) motif are shown in bold. The human amino acids that replaced the corresponding rat residues (RΔH) are shown below the rat sequence in the boxed region. For clarity, residue numbering in the text refers to this figure, unless otherwise designated, e.g., as crystal numbering. FIG. 11B. Increasing concentrations of mAb AJH10 (ATCC No. PTA-3580; deposited under the Budapest Treaty with the American Type Culture Collection, Manassas, Va., USA on Aug. 2, 2001) were bound to plates coated with 30 μg/ml human (circles), rat (triangles) or RΔH (squares) α1-I domain. Data shown is representative of three experiments.

FIG. 12. Amino acid sequence of the human α1-I domain (SEQ ID NO:64).

FIG. 13A. Increasing concentration of mAbs AEF3 (triangles) or AJH10 (circles) were bound to plates coated with 30 μg/ml α1-I domain. FIG. 13B. The α1-I domain was treated with increasing concentrations of mAb AJH10 (diamonds) or mAb BGCS (squares) and bound collagen IV (2 μg/ml) coated plates. FIG. 13C. K562-α1 cell were treated with increasing concentration of mAbs AEF3 (triangles) or AJH10 (circles) and bound to collagen IV (5 μg/ml) coated plates. 45-50% of cells added to each well adhered to collagen IV. Data shown is representative of three independent experiments.

FIG. 14. Species Cross-reactivity of the blocking mAbs analyzed by fluorescence activated cell sorter (FACS). Rabbit vascular smooth muscle cells were incubated with either mAb AJH10 (bottom) or murine IgG control (top) and analyzed by fluorescence activated cell sorter (FACS).

FIG. 15A. Increasing concentrations of the human α1-I domain were bound to plates previously coated with 1 μg/ml collagen I (squares) or collagen IV (circles). Values shown have been corrected for background binding to BSA. FIG. 15B. 2 μg/ml human α1-I domain was mixed with increasing concentration of an anti-human α1-I integrin antibody 5E8D9 (squares) or an anti-human α2-integrin antibody A2IIE10 (circles), and then bound to plates previously coated with 1 μg/ml collagen IV. FIG. 15C. Plates were coated with 1 μg/ml collagen TV or 3% BSA. α1-I domain (2 μg/ml) was subsequently bound to coated plates in the presence of 1 mM $Mn^{2+}$, 1 mM $Mg^{2+}$, or 5 mM EDTA. Data shown is representative of three independent experiments.

FIG. 16A. Inhibition of VLA-1 binding to type IV collagen.

FIG. 16B. Inhibition of α1-I domain binding to type IV collagen.

FIG. 16C. Binding to immobilized α1-I domain.

FIG. 16D. Competition with biotinylated mAQC2 for binding to immobilized α1-I domain.

FIG. 19A-1 to A-109. Atomic structure coordinates for the α1-I domain/Fab complex, as derived by X-ray crystallography from crystals of that complex in Protein Data Bank (PDB) format. The coordinates of the two complexes in the asymmetric unit are listed as follows.

Complex 1: molecule A=I domain of integrin
molecule H=heavy chain of hAQC2 Fab
molecule L=light chain of hAQC2 Fab
molecule M=$Mn^{+2}$
Complex 2: molecule B=I domain of integrin
molecule X=heavy chain of hAQC2 Fab
molecule Y=light chain of hAQC2 Fab
molecule M=$Mn^{+2}$ FIG. 20. I domain-Fab complex. A. Ribbon diagram of the I domain-Fab complex. The I domain and the antibody heavy and light chain are labeled. The $Mn^{+2}$ ion is shown as a sphere. B. Close-up of the MIDAS (Metal-Ion-Dependent-Adhesion-Site) site showing the coordination of the metal ion (sphere) by Asp101 (crystal numbering). The protein backbones are shown as ribbons and the side chains in the ball-and-stick representation. The cylinders represent interactions between the metal ion and protein atoms. The thin lines represent H-bonds. FIG. 20 was made with the software program RIBBONS (Carson, 1991, J. Appl. Cryst, 24:958-961).

DETAILED DESCRIPTION OF THE INVENTION

Figure 1A:
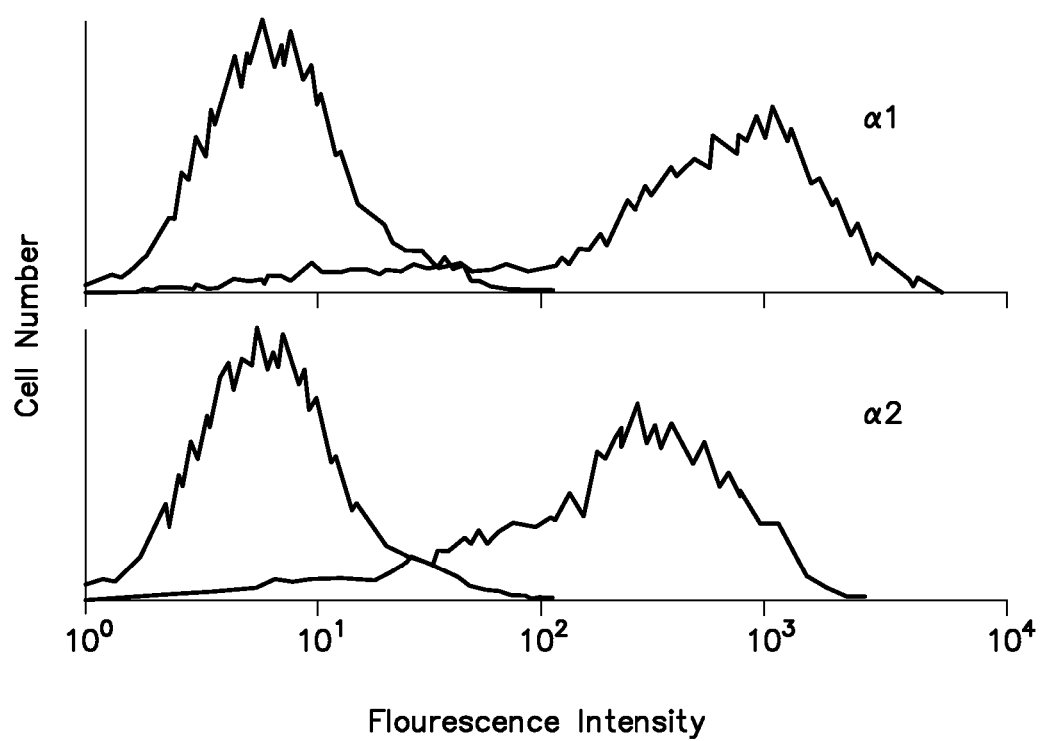
FIG. 1A-B. Collagen-binding integrins α1β1 and α2β1 on activated leukocytes.

It is a discovery of the present invention that an antibody to an integrin (e.g., VLA-1) and fragment thereof, particularly, an α1-integrin subunit, can block the interaction of pro-inflammatory leukocytes with components of the extracellular matrix including, but not limited to collagens, laminin and fibronectin. This discovery illustrates the importance of adhesion molecules of the integrin family, particularly α1 β1, in the peripheral tissue environment during conditions related to inflammation. It also extends the role of integrins family and fragments thereof in inflammation beyond leukocyte attachment and extravasation at the endothelial interface by highlighting the importance of the matrix-rich peripheral tissue environment to immune responses and it reveals peripheral tissues as a new point of intervention for adhesion based therapies.

I. Anti-Integrin Antibodies

The methods of the present invention contemplate the use of antibodies to integrins where the integrins contemplated include molecules which comprise a β chain, including but not limited to β1, β2, β3, β4, β5, β6, β7, β8, non-covalently bound to an α chain, including but not limited to α1, α2, α3, α4, α5, α6, α7, α8, α9, α10, αV, αL, αM, αX, αD, αE, αIIb. Examples of the various integrins contemplated for use in the invention include, but are not limited to:

α1β1, α2β1, α3β1, α4β1, α5β1, α6β1, α7β1, α8β1, α9β1, α10β1, αVβ1, αLβ1, αMβ1, αXβ1, αDβ1, αIIbβ1, αEβ1;

α1β2, α2β2, α3β2, α4β2, α5β2, α6β2, α7β2, α8β2, α9β2, α10β2, αVβ2, αLβ2, αMβ2, αXβ2, αDβ2, αIIbβ2, αEβ2;

α1β3, α2β3, α3β3, α4β3, α5β3, α6β3, α7β3, α8β3, α9β3, α10β3, αVβ3, αLβ3, αMβ3, αXβ3, αDβ3, αIIbβ3, αEβ3;

α1β4, α2β4, α3β4, α4β4, α5β4, α6β4, α7β4, α8β4, α9β4, α10β4, αVβ4, αLβ4, αMβ4, αXβ4, αDβ4, αIIbβ4, αEβ4;

α1β5, α2β5, α3β5, α4β5, α5β5, α6β5, α7β5, α8β5, α9β5, α10β5, αVβ5, αLβ5, αMβ5, αXβ5, αDβ5, αIIbβ5, αEβ5;

α1β6, α2β6, α3β6, α4β6, α5β6, α6β6, α7β6, α8β6, α9β6, α10β6, αVβ6, αLβ6, αMβ6, αXβ6, αDβ6, αIIbβ6, αEβ6;

α1β7, α2β7, α3β7, α4β7, α5β7, α6β7, α7β7, α8β7, α9β7, α10β7, αVβ7, αLβ7, αMβ7, αXβ7, αDβ7, αIIbβ7, αEβ7;

α1β8, α2β8, α3β8, α4β8, α5β8, α6β8, α7β8, α8β8, α9β8, α10β8, αVβ8, αLβ8, αMβ8, αXβ8, αDβ8, αIIbβ8, αEβ8;

The methods of the present invention also contemplate the use of antibodies to integrin fragments including for example antibodies to a β chain alone, including but not limited to β1, β2, β3, β4, β5, β6, β7, β8, as well as an α chain alone, including but not limited to α1, α2, α3, α4, α5, α6, α7, α8, α9, α10, αV, αL, αM, αX, αD, αE, αIIb. In addition, the methods of the present invention further contemplate the use of antibodies to integrin fragments including for example antibodies to the I domain of the α chain, including but not limited to the I domain from α1β1 (Briesewitz et al., 1993, J. Biol. Chem. 268:2989); α2β1 (Takada and Hemler, 1989, J Cell Biol 109:397), αLβ2 (Larson et al., 1989, J Cell Biol 108:703), αMβ2 (Corbi et al., 1988, J Biol Chem 263:12403), αXβ2 (Corbi et al., 1987, EMBO J 6:4023), αDβ2 (Grayson et al., 1988, J Exp Med 188:2187), αEβ7 (Shaw et al., 1994, J Biol Chem 269:6016). In one embodiment, the α1-I domain antigenic determinant includes an amino acid sequence of at least 6 contiguous amino acids, wherein the contiguous sequence is found within the sequence of FIG. 12. In a related embodiment, the contiguous sequence is Val-Gln-Arg-Gly-Gly-Arg (residues 91-96 of SEQ ID NO:64).

Methods for producing integrins for use in the present invention are known to those of skill in the art (see, e.g., Springer et al., 1990, Nature 346:425-434).

Embodiments of the present invention further include anti-integrin polyclonal and monoclonal antibodies. Embodiments of the present invention include a monoclonal antibody such an anti-α1 monoclonal antibody. Antibodies for treatment, in particular for human treatment, include human antibodies, humanized antibodies, chimeric antibodies, and antigen-binding fragments of whole antibodies such as Fab, Fab', F(ab')2 and F(v) antibody fragments. Some antibodies of this invention may also include proteins containing one or more immunoglobulin light chains and/or heavy chains, such as monomers and homo- or hetero-multimers (e.g., dimers or trimers) of these chains, where these chains are optionally disulfide-bonded or otherwise cross-linked. These antibodies may be capable of binding to one or more antigens (e.g., α1, α2, α6 or alpha-I domain containing integrin subunits).

An α1β1 function blocking antibody as used herein refers to an antibody that binds to the α1-I domain, for example, residues 91-97 of FIG. 12, and blocks α1β1 function as tested, for example, by their ability to inhibit K562-α1 dependent adhesion to Collagen IV (see Example 15).

The following describes the various methods of making the antibodies of this invention. Methods that are known in the art but not specifically described herein are also within the scope of this invention. For instance, antibodies of this invention can also be identified using phage-displayed antibody libraries, such as those described in Smith, 1985, Science 228:1315-7; U.S. Pat. Nos. 5,565,332, 5,733,743, 6,291,650, and 6,303,313. Additional antibodies of this invention can be made by coupling the heavy chains identified herein with a noncognate light chain, e.g., a light chain identified by phage display technology.

II. Non-Human Hybridoma Antibodies

The monoclonal antibodies of this invention can be generated by well known hybridoma technology. For instance, $\beta_1$-/- animals (e.g., mice, rats or rabbits) can be immunized with purified or crude $\alpha_1\beta_1$ preparations, cells transfected with cDNA constructs encoding $\alpha_1$, $\beta_1$ or both antigens, cells that constitutively express $\alpha_1\beta_1$, and the like. The antigen can be delivered as purified protein, protein expressed on cells, protein fragment or peptide thereof, or as naked DNA or viral vectors encoding the protein, protein fragment, or peptide. Sera of the immunized animals are then tested for the presence of anti-$\alpha_1\beta_1$ antibodies. B cells are isolated from animals that test positive, and hybridomas are made with these B cells.

Antibodies secreted by the hybridomas are screened for their ability to bind specifically to VLA-1 (e.g., binding to $\alpha_1$-transfected cells and not to untransfected parent cells) and for any other desired features, e.g., having the desired CDR consensus sequences, inhibiting (or not inhibiting in the case of nonblockers) the binding between collagen and VLA-1.

Hybridoma cells that test positive in the screening assays are cultured in a nutrient medium under conditions that allow the cells to secrete the monoclonal antibodies into the culture medium. The conditioned hybridoma culture supernatant is then collected and antibodies contained in the supernatant are purified. Alternatively, the desired antibody may be produced by injecting the hybridoma cells into the peritoneal cavity of an unimmunized animal (e.g., a mouse). The hybridoma cells proliferate in the peritoneal cavity, secreting the antibody which accumulates as ascites fluid. The antibody may then be harvested by withdrawing the ascites fluid from the peritoneal cavity with a syringe.

The monoclonal antibodies can also be generated by isolating the antibody-coding cDNAs from the desired hybridomas, transfecting mammalian host cells (e.g., CHO or NSO cells) with the cDNAs, culturing the transfected host cells, and recovering the antibody from the culture medium.

III. Chimeric Antibodies

The monoclonal antibodies of this invention can also be generated by engineering a cognate hybridoma (e.g., murine, rat or rabbit) antibody. For instance, a cognate antibody can be altered by recombinant DNA technology such that part or all of the hinge and/or constant regions of the heavy and/or light chains are replaced with the corresponding components of an antibody from another species (e.g., human). Generally, the variable domains of the engineered antibody remain identical or substantially so to the variable domains of the cognate antibody. Such an engineered antibody is called a chimeric antibody and is less antigenic than the cognate antibody when administered to an individual of the species from which the hinge and/or constant region is derived (e.g., a human). Methods of making chimeric antibodies are well known in the art. Human constant regions include those derived from IgG1 and IgG4.

IV. Fully Human Antibodies

The monoclonal antibodies of this invention also include fully human antibodies. They may be prepared using in vitro-primed human splenocytes, as described by Boerner et al., 1991, J. Immunol. 147:8695, or using phage-displayed antibody libraries, as described in, e.g., U.S. Pat. No. 6,300,064.

Alternatively, fully human antibodies may be prepared by repertoire cloning as described by Persson et al., 1991, Proc. Nat. Acad. Sci. USA 88: 2432-2436; and Huang and Stollar, 1991, J. Immunol, Methods 141: 227-236. In addition, U.S. Pat. No. 5,798,230 (Aug. 25, 1998) describes preparation of human monoclonal antibodies from human B cells, wherein human antibody-producing B cells are immortalized by infection with an Epstein-Barr virus, or a derivative thereof, that expresses Epstein Barr virus nuclear antigen 2 (EBNA2), a protein required for immortalization. The EBNA2 function is subsequently shut off, resulting in an increase in antibody production.

Some other methods for producing fully human antibodies involve the use of nonhuman animals that have inactivated endogenous Ig loci and are transgenic for un-rearranged human antibody heavy chain and light chain genes. Such transgenic animals can be immunized with $\alpha_1\beta_1$ and hybridomas are then made from B cells derived therefrom. These methods are described in, e.g., the various GenPharm/Medarex (Palo Alto, Calif.) publications/patents concerning transgenic mice containing human Ig miniloci (e.g., Lonberg U.S. Pat. No. 5,789,650); the various Abgenix (Fremont, Calif.) publications/patents with respect to XENOMICE (e.g., Kucherlapati U.S. Pat. Nos. 6,075,181, 6,150,584 and 6,162,963; Green et al., 1994, Nature Genetics 7:13-21; and Mendez et al., 1997, Nature Genetics 15(2):146-56); and the various Kirin (Japan) publications/patents concerning "transomic" mice (e.g., EP 843 961, and Tomizuka et al., 1997, Nature Genetics 16:133-1443).

V. Humanized Antibodies

The monoclonal antibodies of this invention also include humanized versions of cognate anti-$\alpha_1\beta_1$ antibodies derived from other species. A humanized antibody is an antibody produced by recombinant DNA technology, in which some or all of the amino acids of a human immunoglobulin light or heavy chain that are not required for antigen binding (e.g., the constant regions and the framework regions of the variable domains) are used to substitute for the corresponding amino acids from the light or heavy chain of the cognate, nonhuman antibody. By way of example, a humanized version of a murine antibody to a given antigen has on both of its heavy and light chains (1) constant regions of a human antibody; (2) framework regions from the variable domains of a human antibody; and (3) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Humanized antibodies generally are less likely to elicit an immune response in humans as compared to chimeric human antibodies because the former contain considerably fewer nonhuman components.

The methods for making humanized antibodies are described in, e.g., Winter EP 239 400; Jones et al., 1986, Nature 321:522-525; Riechmann et al., 1988, Nature 332:323-327 (1988); Verhoeyen et al., 1988, Science 239:1534-1536; Queen et al., 1989, Proc. Nat. Acad. Sci. USA 86:10029; U.S. Pat. No. 6,180,370; and Orlandi et al., 1989, Proc. Natl. Acad. Sci. USA 86:3833. Generally, the transplantation of murine (or other non-human) CDRs onto a human antibody is achieved as follows. The cDNAs encoding heavy and light chain variable domains are isolated from a hybridoma. The DNA sequences of the variable domains, including the CDRs, are determined by sequencing.

The DNAs encoding the CDRs are transferred to the corresponding regions of a human antibody heavy or light chain variable domain coding sequence by site directed mutagenesis. Then human constant region gene segments of a desired isotype (e.g, γ1 for CH and k for CL) are added. The humanized heavy and light chain genes are co-expressed in mammalian host cells (e.g., CHO or NSO cells) to produce soluble humanized antibody. To facilitate large scale production of antibodies, it is often desirable to produce such humanized antibodies in bioreactors containing the antibody-expressing cells, or to produce transgenic mammals (e.g., goats, cows, or sheep) that express the antibody in milk (see, e.g., U.S. Pat. No. 5,827,690).

At times, direct transfer of CDRs to a human framework leads to a loss of antigen-binding affinity of the resultant antibody. This is because in some cognate antibodies, certain amino acids within the framework regions interact with the CDRs and thus influence the overall antigen binding affinity of the antibody. In such cases, it would be critical to introduce "back mutations" (supra) in the framework regions of the acceptor antibody in order to retain the antigen-binding activity of the cognate antibody.

The general approach of making back mutations is known in the art. For instance, Queen et al. (supra), Co et al., 1991, Proc. Nat. Acad. Sci. USA 88:2869-2873, and WO 90/07861 (Protein Design Labs Inc.) describe an approach that involves two key steps. First, the human V framework regions are chosen by computer analysis for optimal protein sequence homology to the V region framework of the cognate murine antibody. Then, the tertiary structure of the murine V region is modeled by computer in order to visualize framework amino acid residues that are likely to interact with the murine CDRs, and these murine amino acid residues are then superimposed on the homologous human framework.

Under this two-step approach, there are several criteria for designing humanized antibodies. The first criterion is to use as the human acceptor the framework from a particular human immunoglobulin that is usually homologous to the nonhuman donor immunoglobulin, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRs.

One may also use a different approach as described in, e.g., Tempest, 1991, Biotechnology 9: 266-271. Under this approach, the V region frameworks derived from NEWM and REI heavy and light chains, respectively, are used for CDR-grafting without radical introduction of mouse residues. An advantage of using this approach is that the three-dimensional structures of NEWM and REI variable regions are known from X-ray crystallography and thus specific interactions between CDRs and V region framework residues can be readily modeled.

VI. Other Moieties

The monoclonal antibodies of this invention may further include other moieties to effect the desired functions. For instance, the antibodies may include a toxin moiety (e.g., tetanus toxoid or ricin) or a radionuclide (e.g., $^{111}$In or $^{90}$Y) for killing of cells targeted by the antibodies (see, e.g., U.S. Pat. No. 6,307,026). The antibodies may include a moiety (e.g., biotin, fluorescent moieties, radioactive moieties, histidine tag or other peptide tags) for easy isolation or detection. The antibodies may also include a moiety that can prolong their serum half life, for example, a polyethylene glycol (PEG) moiety, and a member of the immunoglobulin super family or fragment thereof (e.g., a portion of human IgG1 heavy chain constant region such as the hinge, CH2 and CH3 regions).

VII. Crystallizable Compositions and Crystals

This invention also provides a crystallizable composition containing a complex of: (1) a rat-human chimeric α1-I domain (e.g., mutant RΔH), or a portion thereof (e.g., a polypeptide including 135 to 336 amino acids of the rat-human chimeric α1-I domain); and (2) a Fab fragment of hAQC2, or a portion thereof (e.g., a polypeptide including 3 to 213 amino acids of the light chain and/or a polypeptide including 3 to 219 amino acids of the heavy chain). An exemplary complex is shown in FIG. 20. The RΔH α1-I domain can include, e.g., amino acid residues 145 to 336 (crystal numbering) (SEQ ID NO:59, infra) of the rat α1 subunit. The hAQC2 Fab fragments may include light chain amino acid residues 1 to 106 (e.g., 1-213) of SEQ ID NO:3 and heavy chain amino acid residues 1 to 118 (e.g., 1-219) of SEQ ID NO:4. The hAQC2 Fab fragments may be obtained by papain digestion of the whole antibody or made by recombinant methods. The Fab fragments include at least an antigen-binding portion of the variable domains of the light chain and/or the heavy chains of hAQC2.

```
                                              (SEQ ID NO: 59)
145 TQLDIV

151 IVLDGSNSIY PWESVIAFLN DLLKRMDIGP KQTQVGIVQY

191 GENVTHEFNL NKYSSTEEVL VAANKIVQRG GRQTMTALGI

231 DTARKEAFTE ARGARRGVKK VMVIVTDGES HDNYRLKQVI
```

```
                      -continued
271 QDCEDENIQR FSIAILGHYN RGNLSTEKFV EEIKSIASEP

311 TEKHPENVSD ELALVTIVKA LGERIF
```

Some crystallizable compositions and crystals of this invention may contain a molecule or molecular complex that is homologous to the α1-I domain and/or the hAQC2 Fab fragment by amino acid sequence or by three-dimensional structure. Examples of homologues include, but are not limited to: the α1-I domain and/or the hAQC2 Fab fragment with mutations, such as conservative substitutions, additions, deletions or a combination thereof. "Conservative substitutions" refer to replacement residues that are physically similar in size, shape, hydrophobicity, charge, and/or chemical properties to the corresponding reference residues. Methods for identifying a "corresponding" amino acid are known in the art and are based upon sequence, structural alignment, its functional position or a combination thereof as compared to the crystal structure solved in the present invention. For example, corresponding amino acids may be identified by superimposing the backbone atoms of the amino acids in the α1-I domain/hAQC2 complex and a α1-I domain and/or hAQC2 homologue using well known software applications, such as QUANTA (Molecular Simulations, Inc., San Diego, Calif. ©1998, 2000). The corresponding amino acids may also be identified using sequence alignment programs such as the "bestfit" program available from the Genetics Computer Group, which uses the local homology algorithm described by Smith and Waterman in Adv. Appl. Math. 2:482 (1981).

Crystallizable compositions of this invention may further include one or more components that promote crystallization and/or is compatible with crystallization conditions. Such components may include, but are not limited to, buffer, salts, precipitating agents and other reagents. One component can be 30% weight/volume Polyethylene Glycol 1500 (PEG1500).

The instant invention also provides methods of making crystals from crystallizable compositions including a complex of α1-I domain and an antigen-binding portion of hAQC2 (e.g., Fab, Fab' or other fragments, supra). Various techniques of crystallization can be used in the claimed invention, including, but not limited to, vapor-diffusion, dialysis, microbatch, batch, and liquid-liquid diffusion. Vapor diffusion methods include, but are not limited too, sitting-drop, hanging-drop and sandwich-drop techniques. Vapor-diffusion methods can use techniques to control the rate of crystallization, such as the addition of oils on the drops or reservoir solution. Crystallization methods can include mixing a reservoir solution containing precipitating agent with an aqueous solution of a complex of α1-I domain and an antigen-binding portion of hAQC2 to produce a crystallizable composition. The mixture or crystallizable composition may then be crystallized using the various above-listed techniques. The crystallizable composition of this invention may be an aqueous solution of a complex of α1-I domain and an antigen-binding portion of hAQC2 containing the complex at a concentration of about 1 to 50 mg per mL, such as a concentration of about 5 to 115 mg per mL (e.g., 11 mg per mL).

VIII. Crystal Structures and Structure Coordinates

This invention further provides the three-dimensional structure of a crystal including a complex of mutant RΔH, and a hAQC2 Fab fragment at 2.8 Å resolution (Example 24, infra). The three-dimensional structures of other related crystals may also be determined using techniques described herein and those known in the art. The three-dimensional structure of this complex is defined by a set of structure coordinates set forth in FIG. 19A-1 to A-109. These structure coordinates are Cartesian atomic coordinates derived from mathematical equations related to the patterns obtained from diffraction of a monochromatic beam of X-rays by the atoms or scattering centers of the crystalline complex of the α1-I domain and the hAQC2 Fab fragment. Diffraction data are first used to calculate an electron density map of the repeating unit of the crystal. The electron density map is then used to establish the positions of individual atoms of the complex.

This invention provides a molecule or a molecular complex defined by all or part of the structure coordinates of all amino acids set forth in FIG. 19A-1 to A-109, as well as a homologue of the molecule or molecular complex, where the homologue has a root mean square deviation from the backbone atoms of these amino acids between 0.00 Å and 0.65 Å, such as between 0.00 Å and 0.60 Å (e.g., between 0.00 Å and 0.50 Å). The term "root mean square deviation" or "r.m.s. deviation" means the square root of the arithmetic mean of the squares of the deviations from the mean. It is a way to express the deviation or variation from a trend or object. For purposes of this invention, the "root mean square deviation" or "r.m.s. positional deviation" defines the variation in the backbone of a protein from the relevant portion of the backbone of the polypeptide as defined by the structure coordinates described herein.

A molecule or a molecular complex of this invention may also include a binding site defined by structure coordinates of at least seven amino acids of the hAQC2 Fab fragment selected from the group including of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering) according to FIG. 19A-1 to A-109; or a homologue of the molecule or molecular complex, where the homologue includes a binding site that has a root mean square deviation from the backbone atoms of one or more of these amino acids between 0.00 Å and 1.10 Å, such as between 0.00 Å and 1.00 Å (e.g., between 0.00 Å and 0.50 Å.). The term "binding site" as used herein, refers to a region of a molecule or molecular complex that, as a result of its shape and charge, favorably associates with another chemical entity. The term "site" includes, but is not limited to, trench, cleft, channel or pocket. For instance, binding sites on the α1-I domain may include a collagen-binding site (Emsley et al., 1997, supra), an antibody-binding site, and an allosteric (or IDAS) binding site (Huth et al., 2000, Proc. Natl. Acad. Sci. U.S.A. 97:5231-5236). The term "chemical entity" includes, but is not limited to, any molecule, molecular complex, compound or fragment thereof. The term "associate with" refers to an association or binding in a condition of proximity between a chemical entity, or portions thereof, and a binding pocket or binding site on a protein. The association may be non-covalent—where the juxtaposition is energetically favored by hydrogen bonding or van der Waals or electrostatic interactions or it may be covalent. A molecule or molecular complex of this invention can include a binding site defined by structure coordinates of α1-I domain amino acids selected from the group consisting of residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19A-1 to A-109, or a homologue of the molecule or molecular complex, where the homologue includes a binding site that has a root mean square deviation from the backbone atoms of the α1-I domain amino acids between 0.00 Å and 0.92 Å.

A molecule or molecular complex of this invention also may include a binding site defined by structure coordinates of α1-I domain amino acids selected from the group consisting of residues Glu192, Gln218, Arg219, Gly220, and Gly221 (crystal numbering), according to FIG. 19A-1 to A-109; or a homologue of the molecule or molecular complex, where the homologue includes a binding site that has a root mean square deviation from the backbone atoms of the α1-I domain amino acids between 0.00 Å and 0.30 Å.

Those of skill in the art will understand that a set of structure coordinates for a polypeptide is a relative set of points that define a shape in three dimensions. Thus, it is possible that an entirely different set of coordinates that define a similar or identical shape could be generated using mathematical manipulations of the structure coordinates in FIG. 19A-1 to A-109. For example, the structure coordinates could be manipulated by crystallographic permutations of the structure coordinates, fractionalization of the structure coordinates, integer additions or subtractions to sets of the structure coordinates, inversion of the structure coordinates, or any combination thereof. Moreover, slight variations in the individual coordinates will have little effect on overall shape.

Alternatively, modification in the crystal structure due to mutations, such as additions, substitutions, and/or deletions of amino acids, or other changes in any of the polypeptide components (e.g., a hAQC2 Fab fragment or a α1-I domain) that make up the crystal can also account for variations in structure coordinates. If such variations are within an acceptable standard error as compared to the original coordinates, the resulting three-dimensional shape is considered to be the same as that of the unmodified crystal.

It is therefore necessary to determine whether an entity is sufficiently similar to all or parts of the structure described herein as to be considered the same. Such analyses may be carried out using current software applications, such as QUANTA (Accelrys, Inc. and Molecular Simulations, Inc., San Diego, Calif. ©1998, 2000) and O (Jones et al., 1991, Acta Cryst. A47:110-119), and accompanying User Guides. The Molecular Similarity application of QUANTA and the LSQ application of 0 permit comparisons between different structures, different conformations of the same structure, and different parts of the same structure. The general procedure used in both applications is to input the structures to be compared, define the equivalent atomic positions in these structures, perform a fitting operation, and analyze the results.

When each structure is input into the application, it is given a name. and identified as the fixed structure or a moving structures. Atom equivalency is usually defined by equivalent atoms such as protein backbone atoms (N, Cα, C and O) for all conserved residues between the two structures being compared. The moving structure is translated and rotated to obtain an optimum or least-squares fit with the fixed structure. The root mean square difference of the fit over the specified pairs of equivalent atom is reported by both programs in angstroms.

For the purpose of this invention, any molecular complex that has a root mean square deviation of conserved residue backbone atoms (N, Ca, C, O) between 0.00 Å and 1.50 Å, such as between 0.00 Å and 1.00 Å (e.g., between 0.00 Å and 0.50 Å), when superimposed on the relevant backbone atoms described by structure coordinates listed in FIG. 19A-1 to A-109 are considered identical.

IX. Determining Other Crystal Structures

The structure coordinates set forth in FIG. 19A-1 to A-109 can also be used to aid in obtaining structural information about another crystallized molecular entity, such as another hAQC2 containing amino acid substitutions in one of its CDRs. This may be achieved by any well-known techniques, including molecular replacement, an especially useful method for determining the structures of mutants and homologues of α1-I domain/Fab.

The structure coordinates set forth in FIG. 19A-1 to A-109 can also be used for determining at least a portion of the three-dimensional structure of molecular entities that contain at least some structural features similar to at least a portion of the α1-I domain or the hAQC2 Fab. Therefore, another embodiment of this invention provides a method of utilizing molecular replacement to obtain structural information about a crystallized molecule or molecular complex with unknown structure including the steps of: (a) generating an X-ray diffraction pattern from the crystallized molecule or molecular complex; and (b) applying at least a portion of the structure coordinates set forth in FIG. 19A-1 to A-109 to the X-ray diffraction pattern to generate a three-dimensional electron density map of the molecule or molecular complex with unknown structure.

By using molecular replacement, all or part of the structure coordinates set forth in FIG. 19A-1 to A-109 can be used to determine the unknown structure of a crystallized molecular entity more rapidly and efficiently than attempting to determine such information ab initio. Molecular replacement provides an accurate estimation of the phases for an unknown structure. Phases are a factor in equations used to solve crystal structures that cannot be determined directly. Obtaining accurate values for the phases, by methods other than molecular replacement, can often be a time-consuming process that involves iterative cycles of approximations and refinements and greatly hinders the solution of crystal structures. However, when the crystal structure of a protein containing at least a homologous portion has been solved, the phases from the known structure can often provide a satisfactory estimate of the phases for the unknown structure.

Thus, molecular replacement involves generating a preliminary model of a molecule or molecular complex whose structure coordinates are unknown, by orienting and positioning the relevant portion of the complex according to FIG. 19A-1 to A-109 within the unit cell of the crystal of the unknown molecule or molecular complex, so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (Lattman, 1985, Meth. Enzymol. 115:55-77; Rossmann, ed., "The Molecular Replacement Method", Int. Sci. Rev. Ser., No. 13, Gordon & Breach, New York, 1972). The structure of any portion of any crystallized molecule or molecular complex that is sufficiently homologous to any portion of the α1-I domain and/or the hAQC2 Fab fragment (according to FIG. 19A-1 to A-109) can be solved by this method.

X. Computer and Storage Medium

To use the structure coordinates of this invention, e.g., those set forth in FIG. 19A-1 to A-109, it is usually necessary to convert the coordinates into a three-dimensional representation or shape. Commercially available graphical software programs including, but not limited to, O (Jones et al., 1991, Acta Cryst. A47:110-119) and ISIGHTII (©Accelrys, Inc. and Molecular Simulations, Inc., San Diego, Calif.) are capable of generating three-dimensional representations of molecules or molecular complexes, or portions thereof, from a set of structure coordinates.

In accordance with the present invention, the structure coordinates of the molecular entities of this invention are stored in a storage medium readable by machine (e.g., a computer). Using a computer and appropriate software, such data may be used for a variety of purposes, such as drug discovery and X-ray crystallographic analysis of other protein crystals.

Accordingly, a machine-readable data storage medium may include a data storage material encoded with machine-readable data including at least a portion of the structure coordinates set forth in FIG. 19A-1 to A-109. The computer may further include instructions to produce three-dimensional representations of the molecular complexes of α1-I domain and the hAQC2 Fab fragment by processing the machine-readable data of this invention. The computer of this invention may also include a display, a graphical interface for displaying, or an input device for moving and manipulating the three-dimensional graphical representation of the structure coordinates.

This invention also provides a computer for determining at least a portion of the structure coordinates corresponding to X-ray diffraction data obtained from a molecular complex of α1β1 integrin and the Fab fragment of hAQC2 antibody, where the computer includes a machine-readable data storage medium including a data storage material encoded with machine-readable data, where the data includes at least a portion of the structure coordinates of the molecular complex of α1-I domain and the hAQC2 Fab fragment according to FIG. 19A-1 to A-109, or X-ray diffraction data obtained from the crystalline molecular complex. The computer further includes instructions for performing a Fourier transform of the machine readable coordinate data, and instructions for processing this machine readable diffraction data into structure coordinates. This computer may further include: a working memory for storing instructions for processing the machine-readable data; a central-processing unit coupled to the working memory and to the machine-readable data; and optionally a graphical interface or display coupled to the central-processing unit for displaying the three-dimensional graphical representation of the structure coordinates of the molecule or molecular complex.

This invention further provides a computer for producing a three-dimensional representation of: a molecule or a molecular complex defined by at least a portion or all of the structure coordinates of all the α1-I domain and the AQC2 Fab fragment amino acids set forth in FIG. 19A-1 to A-109, or a homologue of the molecule or molecular complex, where the homologue has a root mean square deviation from the backbone atoms of the amino acids of between 0.00 Å than 1.50 Å, such as between 0.00 Å and 1.00 Å, (e.g., between 0.00 Å and 0.50 Å). Further in this invention the computer includes: a machine-readable data storage medium including a data storage material encoded with machine-readable data, where the data includes at least a portion or all of the structure coordinates of all of the α1-I domain and the Fab hAQC2 fragment amino acids set forth in FIG. 19A-1 to A-109.

A computer of this invention may also produce a three-dimensional representation of a molecule or molecular complex including a binding site. The binding site may be defined by structure coordinates of at least seven amino acids of: the hAQC2 Fab fragment selected from the group including light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering) according to FIG. 19A-1 to A-109; or a homologue of the molecule or molecular complex, where the homologue includes a binding site that has a root mean square deviation from the backbone atoms of the at least one amino acid of the hAQC2 Fab fragment of between 0.00 Å and 1.10 Å, such as between 0.00 Å and 1.00 Å, (e.g., between 0.00 Å and 0.50 Å). Further, the computer of this invention includes: a machine-readable data storage medium including a data storage material encoded with machine-readable data, where the data includes the structure coordinates of at least seven amino acids of the hAQC2 Fab fragment selected from the group consisting of light chain residues Asn30, Tyr48, Trp90, Ser91, Asn93 and Trp95, and heavy chain residues Ser30, Arg31, Trp47, Ser52, Gly53, His56, Tyr58, Phe99, Gly100 and Asp101 (crystal numbering) according to FIG. 19A-1 to A-109.

This invention also provides a computer for producing a three-dimensional representation of: a molecule or molecular complex including a binding site defined by structure coordinates I domain amino acids selected from the group consisting of residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19A-1 to A-109; or a homologue of the molecule or molecular complex, where the homologue includes a binding site that has a root mean square deviation from the backbone atoms of the I domain amino acids between 0.00 Å and 0.92 Å. Further in this invention, the computer includes: a machine-readable data storage medium including a data storage material encoded with machine-readable data, where the data includes the structure coordinates of I domain amino acids selected from the group consisting of residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering), according to FIG. 19A-1 to A-109.

This invention also provides a computer for producing a three-dimensional representation of a molecule or molecular complex including a binding site defined by structure coordinates of I domain amino acids selected from the group consisting of residues Glu192, Gln218, Arg219, Gly220, and Gly221 (crystal numbering), according to FIG. 19A-1 to A-109; or a homologue of the molecule or molecular complex, where the homologue includes a binding site that has a root mean square deviation from the backbone atoms of I domain amino acids between 0.00 Å and 0.30 Å. Further in this invention the computer includes: a machine-readable data storage medium including a data storage material encoded with machine-readable data, where the data includes the structure coordinates I domain amino acids selected from the group consisting of residues Glu192, Gln218, Arg219, Gly220, and Gly221 (crystal numbering), according to FIG. 19A-1 to A-109.

Figure 21:
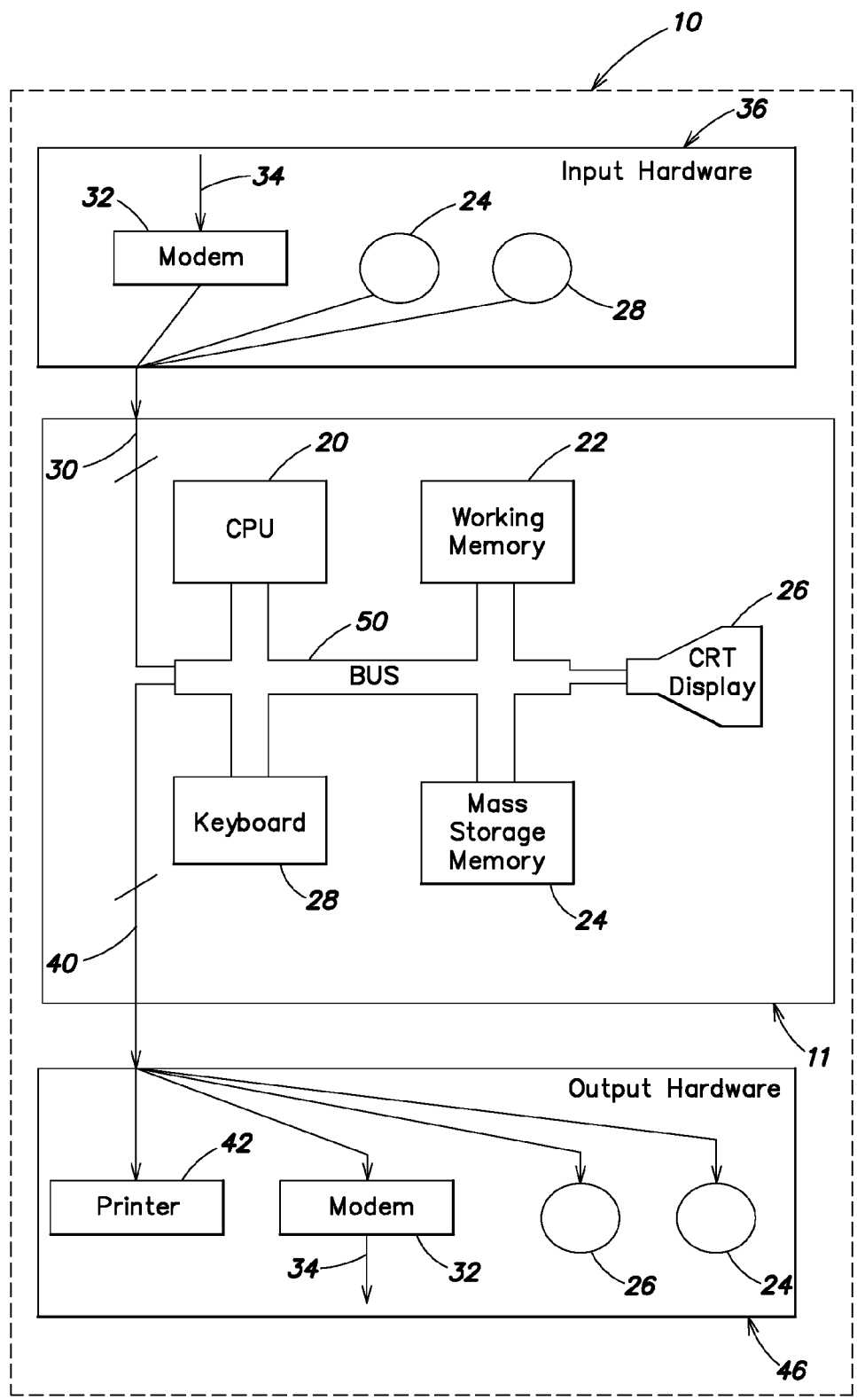
FIG. 21. A diagram of a system used to carry out the instructions encoded by the storage medium of FIGS. 22 and 23.

FIG. 21 demonstrates one such embodiment. System 10 includes a computer 11 including a central-processing unit ("CPU") 20, a working memory 22 which may be, e.g., Ram (random-access memory) or "core" memory, mass storage memory 24 (such as one or more disk or tape drives or CD-ROM or DVD-ROM drives), one or more cathode-ray tube ("CRT") display terminals 26, one or more keyboards 28, one or more input lines 30, and one or more output lines 40, all of which are interconnected by a conventional bidirectional system bus 50.

Input hardware 36, coupled to computer 11 by input lines 30, may be implemented in a variety of ways. Machine-readable data of this invention may be inputted via the use of a modem or modems 32 connected by a telephone line or dedicated data line 34. Alternatively or additionally, the input hardware 36 may include CD-ROM or DVD-ROM drives or tape or disk drives 24. In conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a graphical representation of a binding site of this invention using a program such as QUANTA as described herein. Output hardware might also include a printer 42, so that hard copy output may be produced, or a disk drive 24, to store system output for later use.

In operation, CPU 20 coordinates the use of the various input and output devices 36, 46, coordinates data accesses from mass storage 24 and accesses to and from working memory 22, and determines the sequence of data processing steps. A number of programs may be used to process the machine-readable data of this invention. Such programs are discussed in reference to the computational methods of drug discovery as described herein. Specific references to components of the hardware system 10 are included as appropriate throughout the following description of the data storage medium.

Figure 22:
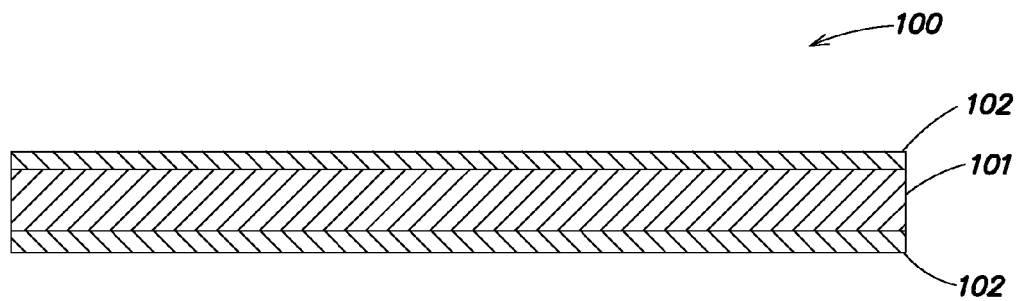
FIG. 22. A cross section of a magnetic storage medium.

FIG. 22 shows a cross-section of a magnetic data storage medium 100 which can be encoded with machine-readable data that can be carried out by a system such as system 10 of FIG. 21. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24.

The magnetic domains of coating 102 of medium 100 are polarized or oriented so as to encode in manner which may be conventional, machine readable data such as that described herein, for execution by a system such as system 11 of FIG. 21.

Figure 23:
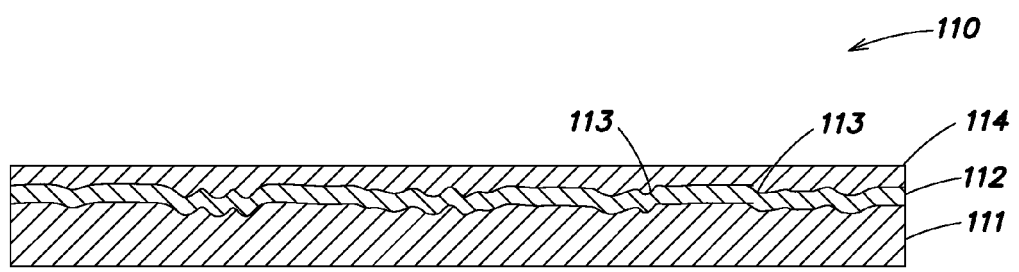
FIG. 23. A cross section of an optically-readable data storage medium.

FIG. 23 shows a cross-section of an optically-readable data storage medium 110 which also can be encoded with such machine-readable data, or a set of instructions, which can be carried out by a system such as system 10 of FIG. 21. Medium 110 can be a conventional compact disk or DVD disk read only memory (CD-ROM or DVD-ROM) or a rewritable medium, such as a magneto-optical disk which is optically readable and magneto-optically writable. Medium 100 has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

XI. Rational Drug Design

The present invention permits the use of structure-based and rational drug design techniques to design, select, and synthesize or isolate chemical entities, such as inhibitors of the α1-I domain and to improve known inhibitors of this domain. These inhibitors may be capable of blocking the collagen-binding site of VLA-1. This invention also permits the use of structure-based and rational drug design techniques to design variants that may act as inhibitors of collagen binding.

The three-dimensional representation of this invention can be used experimentally or computationally to design potential inhibitors, other chemical entities, variants of the Fab fragment or combinations of chemical entities that may bind to and effect the biological functions of the hAQC2 Fab fragment or the chimeric α1-I domain of the current invention.

One skilled in the art can use one of several methods to screen chemical entities for their ability to associate with the complex of the hAQC2 Fab fragment or the chimeric α1-I domain of the current invention and more particularly with a binding site of either the I domain or the Fab fragment. This process may begin by visual inspection of, for example, the binding site for either the I domain or the Fab fragment on the computer screen, based on the coordinates of the complex in FIG. 19A-1 to A-109. Selected chemical entities may then be positioned in a variety of orientations, or docked, within an individual binding site of either the I domain or the Fab fragment. Docking may be accomplished using software such as QUANTA, followed by energy minimization and molecular dynamics with standard molecular mechanics forcefields, such as CHARMM (Molecular Simulations, Inc., Burlington, Mass. ©1994) and AMBER (P. A. Kollman, University of California at San Francisco, ©1994).

Specialized computer programs may also assist in the process of selecting chemical entities. These include, inter alia:
1. GRID (Goodford, P. J., 1985, J. Med. Chem. 28:849-857). GRID is available from Oxford University, Oxford, UK.
2. MCSS (Miranker, A. and M. Karplus, 1991, Proteins: Structure, Function and Genetics 11:29-34). MCSS is available from Molecular Simulations, Burlington, Mass.
3. AUTODOCK (Goodsell, D. S, and A. J. Olsen, 1990, Proteins: Structure, Function, and Genetics 8:195-202). AUTODOCK is available from Scripps Research Institute, La Jolla, Calif.
4. DOCK (Kuntz, I. D. et al., 1982, J. Mol. Biol. 161:269-288). DOCK is available from University of California, San Francisco, Calif.

Once suitable chemical entities have been selected, they can be assembled into a single compound. Assembly may proceed by visual inspection of the relationship of the entities to each other on the three-dimensional image displayed on a computer screen in relation to the structure coordinates of the complex of hAQC2 Fab fragment and the chimeric α1-I domain. This is followed by manual model building using software such as Quanta or Sybyl.

The above-described evaluation process for chemical entities may be performed in a similar fashion for compounds or for variants that may bind the α1-I domain.

Useful programs to aid one of skill in the art in connecting the individual chemical entities include:
1. CAVEAT (Bartlett, P. A. et al, "CAVEAT: A Program to Facilitate the Structure-Derived Design of Biologically Active Molecules". In "Molecular Recognition in Chemical and Biological Problems", Special Pub., 1989, Royal Chem. Soc., 78:182-196). CAVEAT is available from the University of California, Berkeley, Calif.
2. 3D Database systems such as MACCS-3D (MDL Information Systems, San Leandro, Calif.). This area is reviewed in Martin, Y. C., 1992, J. Med. Chem. 35:2145-2154.
3. HOOK (available from Molecular Simulations, Burlington, Mass.).

Instead of proceeding to build an inhibitor or binding compound in a step-wise fashion one chemical entity at a time, as described above, binding compounds may be designed as a whole or "de novo" using either an empty binding site (such as a binding site of the α1-I domain or the hAQC2 Fab fragment) or optionally including some portion(s) of a known α1-I domain or the hAQC2 Fab fragment binding compound. These methods include:
1. LUDI (Bohm, H.-J., 1992, J. Comp. Aid. Molec. Design 6:61-78). LUDI is available from Biosym Technologies, San Diego, Calif.
2. LEGEND (Nishibata, Y. and A. Itai, 1991, Tetrahedron 47:8985). LEGEND is available from Molecular Simulations, Burlington, Mass.
3. LeapFrog (available from Tripos Associates, St. Louis, Mo.).

Other molecular modeling techniques may also be employed in accordance with this invention. See, e.g., Cohen, N. C. et al., 1990, J. Med. Chem. 33:883-894. See also Navia, M. A. and M. A. Murcko, 1992, Curr. Opin. Struct. Biol. 2:202-210.

Once an entity has been designed or selected by the above methods, the efficiency with which that entity may bind to the α1-I domain or the hAQC2 Fab fragment can be tested and optimized by computational evaluation. For example, a compound that has been designed or selected to function as α1-I domain binding compound can traverse a volume not overlapping that occupied by the binding site when it is bound to the chimeric α1-I domain. An effective α1-I domain binding compound can demonstrate a relatively small difference in energy between its bound and free states (i.e., a small deformation energy of binding). Thus, the most efficient α1-I domain binding compound should be designed with a deformation energy of binding of not greater than about 10 kcal/mole, e.g., not greater than 7 kcal/mole. α1-I domain binding compounds may interact with the α1-I domain in more than one conformation that is similar in overall binding energy. In those cases, the deformation energy of binding is taken to be the difference between the energy of the free compound and the average energy of the conformations observed when the compound binds to the protein.

A compound designed or selected as binding to α1-I domain may be further computationally optimized so that in its bound state it would lack repulsive electrostatic interaction with the target protein. Such non-complementary (e.g., electrostatic) interactions include repulsive charge-charge, dipole-dipole and charge-dipole interactions. Specifically, the sum of all electrostatic interactions between the compound and the protein when the compound is bound to α1-I domain, should make a neutral or favorable contribution to the enthalpy of binding.

Specific computer software is available in the art to evaluate compound deformation energy and electrostatic interaction. Examples of programs designed for such uses include: Gaussian 92, revision C (M. J. Frisch, Gaussian, Inc., Pittsburgh, Pa. ©1992); AMBER, version 4.0 (P. A. Kollman, University of California at San Francisco, ©1994); QUANTA/CHARMM (Molecular Simulations, Inc., Burlington, Mass. 1994); and Insight II/Discover (Biosysm Technologies Inc., San Diego, Calif. ©1994). These programs may be implemented, for instance, using a Silicon Graphics workstation. Other hardware systems and software packages will be known to those skilled in the alt.

One other useful drug design technique enabled by this invention is iterative drug design. Iterative drug design is a method for optimizing associations between a protein and a compound (that compound includes an antibody) by determining and evaluating the three-dimensional structures of successive sets of protein/compound complexes. In iterative drug design, a series of crystals of a protein complexed with entities that bind the protein are obtained and then the three-dimensional structure of each molecular complex is solved. Such an approach provides insight into the associations between the proteins and other entities of each complex. This is accomplished by selecting chemical entities with inhibitory activity, obtaining crystals of these new complexes, solving the three-dimensional structure of the complexes, and comparing the associations between the new complexes and the previously solved complex. Associations within a complex can be optimized by observing how changes in the components of the complex affect associations.

In some cases, iterative drug design is carried out by forming successive complexes and then crystallizing each new complex. Alternatively, a pre-formed protein crystal is soaked in the presence of another chemical entity, thereby forming a complex and obviating the need to crystallize each individual complex.

XII. Pharmaceutical Compositions

The pharmaceutical compositions of this invention contains one or more VLA-1 antagonists of the present invention (e.g., anti-VLA-1 antibodies and the small molecular VLA-1 antagonists identified by the above-described rational drug design methods), or pharmaceutically acceptable derivatives thereof. The compositions may further contain a pharmaceutically acceptable carrier, such as an adjuvant, a vehicle, a buffer, and a stabilizer.

The pharmaceutical compositions of this invention may be given orally, topically, intravenously, subcutaneously, intraperitoneally, intramuscularly, intramedullarily, intraarterially, intra-articularly, intra-synovially, intrasternally, intrathecally, intrahepatically, intraspinally, intracranially as desired, or just locally at sites of inflammation or tumor growth. The pharmaceutical compositions of this invention may also be administered by inhalation through the use of, e.g., a nebulizer, a dry powder inhaler or a metered dose inhaler, or by implantation of an infusion pump or a biocompatible sustained release implant into the subject.

The pharmaceutical compositions may be in the form of a sterile injectable preparation, for example a sterile injectable aqueous or oleaginous suspension. This suspension may be formulated according to techniques known in the art using suitable dispersing, wetting, and suspending agents. If given orally, the pharmaceutical compositions can be administered in form of capsules, tablets, aqueous suspensions or solutions. For topical applications, the pharmaceutical compositions may be formulated in a suitable ointment.

The dosage and dose rate of the VLA-1 antagonists of this invention effective to produce the desired effects will depend on a variety of factors, such as the nature of the disease to be treated, the size of the subject, the goal of the treatment, the specific pharmaceutical composition used, and the judgment of the treating physician. Dosage levels of between about 0.001 and about 100 mg/kg body weight per day, for example between about 0.1 and about 50 mg/kg body weight per day, of the active ingredient compound are useful. For instance, antibody of the invention will be administered at a dose ranging between about 0.01 mg/kg body weight/day and about 20 mg/kg body weight/day, e.g., ranging between about 0.1 mg/kg body weight/day and about 10 mg/kg body weight/day, and at intervals of every one to fourteen days. In another embodiment, the antibody is administered at a dose of about 0.3 to 1 mg/kg body weight when administered intraperitoneally. In yet another embodiment, the antibody is administered at a dose of about 5 to 12.5 mg/kg body weight when administered intravenously. In one embodiment, an antibody composition is administered in an amount effective to provide a plasma level of antibody of at least 1 mg/ml.

XIII. Diseased Conditions and Animal Models

The VLA-1 antagonists of the invention are useful in the treatment, including prevention, of $\alpha_1\beta_1$-mediated diseases such as those enumerated above. The treatments of this invention are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

The efficacy of the VLA-1 antagonists of the invention can be tested in various animal models. For instance, useful psoriasis and arthritis models include those described in WO 00/72881. Kidney fibrosis models include those described in WO 99/61040, the Alport's syndrome kidney model described in Cosgove et al., 2000, Am. J. Path. 157:1649-1659, and the SNF1 mouse model of lupus nephritis described in Kalled et al., 2001, Lupus 10:9-22. Vascular fibrosis models for restenosis include a rat carotid balloon injury model described in Smith et al., 1999, Circ. Res. 84:1212-1222. Lung fibrosis models for idiopathic pulmonary fibrosis and scleroderma-associated pulmonary fibrosis include a bleomycin-induced pulmonary fibrosis model described in Wang et al., 1999, Thorax 54:805-812. Liver cirrhosis models for hepatitis C- or alcohol-induced cirrhosis include the bile duct ligation model described in George et al., 1999, Proc. Natl. Acad. Sci. USA 96:12719-12724 and the CCL4-induced liver fibrosis model described in Shi et al., 1997, Proc. Natl. Acad. Sci. USA 94:10663-10668.

The efficacy of the treatments of this invention may be measured by a number of available diagnostic tools, including physical examination, blood tests, proteinuria measurements, creatinine levels and creatinine clearance, pulmonary function tests, chest X-rays, bronchoscopy, bronchioalveolar lavage, lung biopsy, plasma blood urea nitrogen (BUN) levels, observation and scoring of scarring or fibrotic lesions, deposition of extracellular matrix such as collagen, smooth muscle actin and fibronectin, kidney function tests, ultrasound, magnetic resonance imaging (MRI), and CT scan.

XIV. Diagnostic Methods

The antibodies of this invention can be used to diagnose diseased conditions associated with altered all expression levels. A tissue sample from a subject, such as a tissue biopsy, body fluid sample or lavage (e.g., alveolar lavage), can be tested in an antigen capture assay, ELISA, immunohistochemistry assay, and the like using the antibodies. A tissue sample from a normal individual is used as control.

Practice of the present invention will employ, unless indicated otherwise, conventional techniques of cell biology, cell culture, molecular biology, microbiology, recombinant DNA, protein chemistry, and immunology, which are within the skill of the art. Such techniques are described in the literature. See, for example, Molecular Cloning: A Laboratory Manual, 2nd edition (Sambrook et al., Eds.), 1989; Oligonucleotide Synthesis, (M. J. Gait, Ed.), 1984; U.S. Pat. No. 4,683,195 to Mullis et al.; Nucleic Acid Hybridization, (B. D. Hames and S. J. Higgins), 1984; Transcription and Translation, (B. D. Hames and S. J. Higgins), 1984; Culture of Animal Cells (R. I. Freshney, Ed.), 1987; Immobilized Cells and Enzymes, IRL Press, 1986; A Practical Guide to Molecular Cloning (B. Perbal), 1984; Methods in Enzymology, Volumes 154 and 155 (Wu et al., Eds.), Academic Press, New York; Gene Transfer Vectors for Mammalian Cells (J. H. Miller and M. P. Calos, Eds.), 1987; Immunochemical Methods in Cell and Molecular Biology (Mayer and Walker, Eds.), 1987; Handbook of Experiment Immunology, Volumes I-IV (D. M. Weir and C. C. Blackwell, Eds.), 1986; Manipulating the Mouse Embryo, 1986.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. The materials, methods, and examples are illustrative only and not intended to be limiting. Throughout this specification and claims, the word "comprise," or variations such as "comprises" or "comprising" will be understood to imply the inclusion of a stated integer or group of integers but not the exclusion of any other integer or group of integers.

The following Examples are provided to illustrate the present invention, and should not be construed as limiting thereof.

EXAMPLES

Chemical Reagents

Fluorescein isothiocyanate (FITC) was purchased from Sigma Chemical Co. (St. Louis, Mo.). Croton oil was purchased from ICN Biochemicals (Aurora, Ohio). Whole sheep blood in Alsevers solution was obtained from East Acres Biologicals (Southbridge, Mass.). Type I rat tail collagen and type IV mouse collagen were purchased from Collaborative Research Inc. (Bedford, Mass.) and Gibco (Gaithersburg, Md.), respectively.

Balb/c female mice of 6-8 weeks of age were purchased from Taconic (Germantown, N.Y.) and the $\alpha1\beta1$ integrin-deficient mice on a Balb/c background were as previously described (3).

Example 1

Monoclonal Antibodies. Function-blocking mAbs to murine antigens were prepared in an azide-free and low endotoxin format: Ha31/8 (hamster anti-CD49a; integrin oil) (Mendrick et al. 1995. Lab. Invest. 72:367-375), Ha1/29 (hamster anti-CD49b; integrin $\alpha2)(\beta1$) (Mendrick et al. 1995. Lab. Invest. 72:367-375; Mendrick, D. L. and D. M. Kelly 1993 Lab. Invest. 69:690-702), hamster group II control mAb Ha4/8 (hamster anti-KLH) (Mendrick, D. L. and D. M. Kelly 1993 Lab. Invest. 69:690-702), and PS/2 (rat anti-CD49d; integrin $\alpha4\beta1$ chain) (Miyake et al. 1991 J. Exp. Med. 173:599-607). In addition, the following function-blocking mAbs to murine antigens were purchased as no-azide/low endotoxin preparations from Pharmingen (San Diego, Calif.): HM$\beta$1-1 (hamster anti-CD29; integrin $\beta$1 chain) (Noto et al. 1995 Int. Immunol. 7:835-842), Ha2/5 (hamster anti-CD29; integrin $\beta$1 chain) (Mendrick, D. L. and D. M. Kelly 1993 Lab. Invest. 69:690-702), 3E2 (hamster anti-CD54, ICAM-1) (Scheynius et al. 1993 J. Immunol. 150:655-663), 5H10-27 (rat anti-CD49e; integrin $\alpha$5) (Kinashi, T., and T. A. Springer. 1994. Blood Cells. 20:25-44), GoH3 (rat anti-CD49f; integrin $\alpha$6) (Sonnenberg et al. 1987 J. Biol. Chem. 262:10376-10383), and the rat isotype control mAbs R35-95 (rat IgG2a) and R35-38 (rat IgG2b).

Adhesion Assay. Splenocytes from Balb/c mice were cultured with 20 ng/ml IL-2 for 7-12 d. Adhesion of cells to type I and type TV collagen was as previously described (Gotwals et al. 1996 J. Clin. Invest. 97:2469-2477). Briefly, 96-well Maxisorp plates (Nunc, Napierville, Ill.) were coated with either 10 μg/ml type IV or 5 μg/ml type I collagen and non-specific sites blocked with 1% BSA. IL-2 activated splenocytes were labeled with 2 μM BCECF [2',7'-bis(carboxyethyl)-5(6) carboxyl fluorescein penta acetoxymethylester] (Molecular Probes, Eugene, Oreg.) and incubated with 10 μg/ml of indicated mAbs for 15 min. $10^5$ cells in 0.25% BSA in RPMI were then added to coated wells and incubated for 60 min at 37° C. Unbound cells were removed by washing three times with 0.25% BSA in RPMI. Adhesion was quantified using a CytoFluor 2350 fluorescent plate reader (Millipore, Bedford, Mass.). The ratio of bound cells to input cells was measured and percent adhesion relative to control mAb-treated cells (normalized to 100%) calculated. Background values due to cell adhesion on wells coated with BSA alone were subtracted.

Figure 1B:
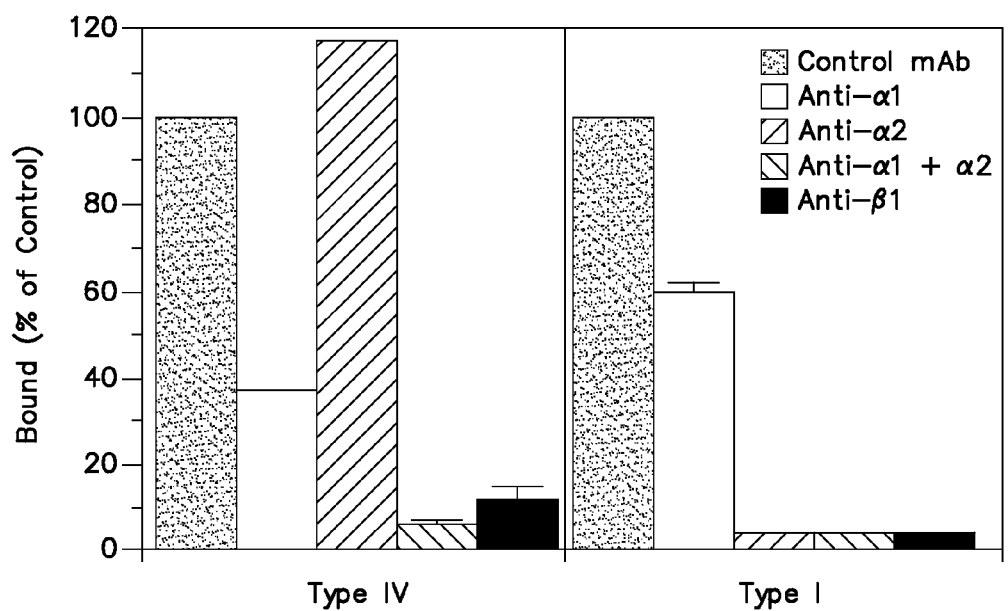

Expression and functional blockade of $\alpha1\beta1$ and $\alpha2\beta1$ on activated leukocytes. Given the key role leukocytes play in inflammation, we decided to test whether anti-$\alpha$1 and anti-$\alpha$2 mAbs were capable of blocking leukocyte adhesion to collagens. In order to obtain leukocytes expressing high levels of both $\alpha$1 and $\alpha$2, murine T cells were stimulated in vitro with IL-2 for 7-12 d. These cells expressed high levels of both $\alpha$1 and $\alpha$2 (FIG. 1A), and bound well to both collagen type IV and type I-coated surfaces (FIG. 1B). Adhesion to type IV collagen was partially inhibited by anti-$\alpha$1 mAb alone and was not inhibited by anti-$\alpha$2 mAb alone. In contrast, adhesion to type I collagen was completely inhibited by anti-$\alpha$2 mAb and anti-$\alpha$1 mAb alone showed only partial inhibition. Both anti-$\beta$1 mAb and the combination of anti-$\alpha$1 and anti-$\alpha$2 mAbs completely inhibited adhesion to types I and IV collagen. Having demonstrated that the $\alpha1\beta1$ and $\alpha2\beta1$ integrins are expressed on activated T cells and that anti-$\alpha$1 and $\alpha$2 mAbs are able to functionally block leukocyte adhesion to collagens, we used these mAbs to investigate the in vivo role of these integrins in animal models of inflammatory disorders.

Example 2

Inhibition of DTH responses by anti-integrin mAbs. SRBC-induced delayed type hypersensitivity (DTH) responses were adapted from a previously published protocol (Hurtrel et al., 1992, Cell. Immunol. 142:252-263). Briefly, mice were immunized s.c. in the back with $2 \times 10^7$ SRBC in 100 ul PBS on d 0. The mice were challenged on d 5 by injecting $1 \times 10^8$ SRBC in 25 ul PBS s.c into the right hind footpad. Footpad thickness was measured with an engineer's caliper (Mitutoyo/MTI, Paramus, N.J.) 20 h after antigen challenge, and the degree of footpad swelling calculated. Results are reported as the mean percent increase footpad thickness ±SEM and calculated as % increase=[1= (Right footpad thickness 20 h after antigen challenge/Uninjected left footpad thickness 20 h after antigen challenge)]×100. To block the effector phase of the SRBC-induced DTH response, therapeutic or control mAb (100 ug), which were prepared according to the methods described in Example 1, was given i.p. 1 h prior to antigen challenge on d 5.

Figure 2:
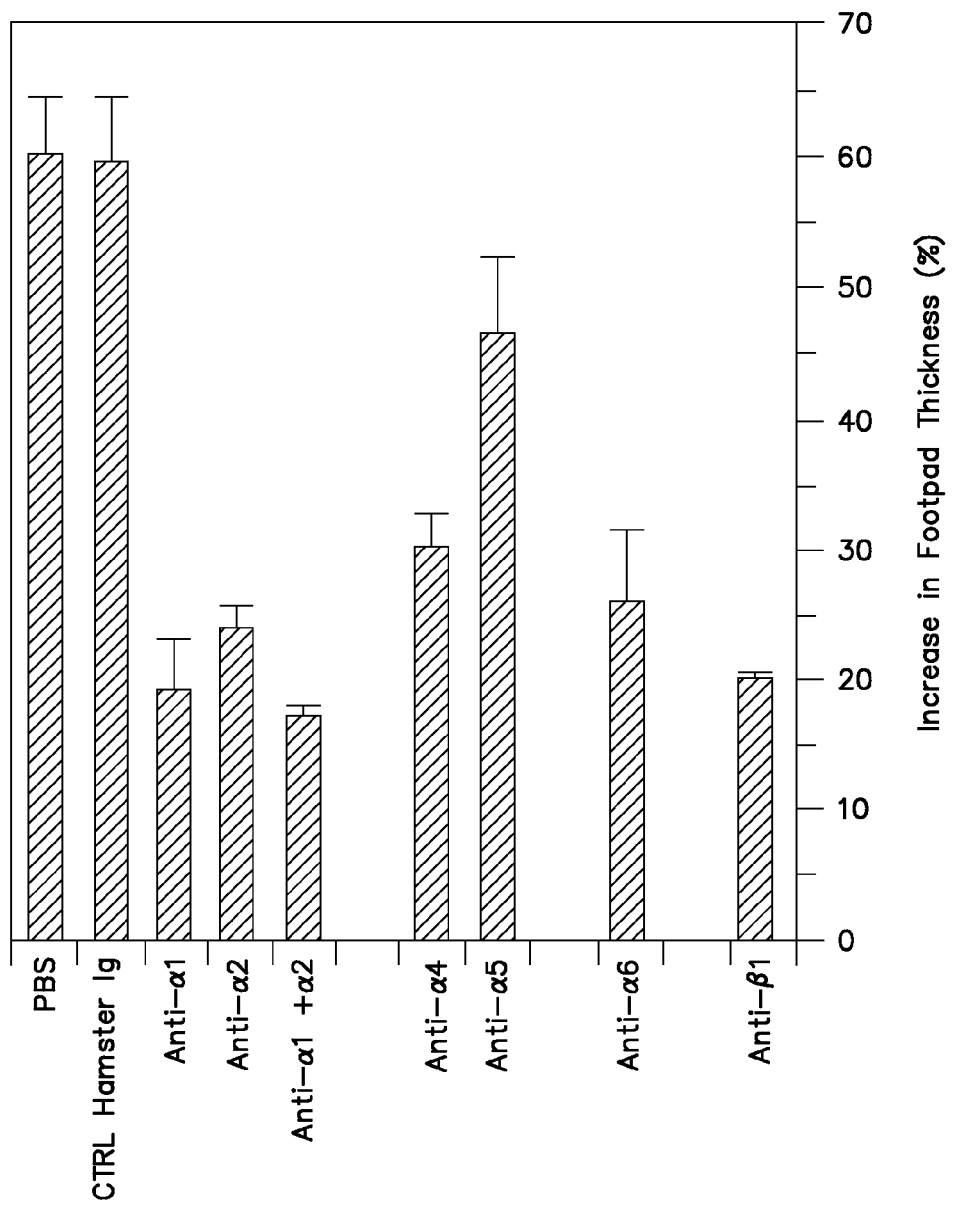
FIG. 2. Effect of anti-integrin mAbs on the effector phase of delayed-type hypersensitivity. SRBC-sensitized mice were injected i.p. with the indicated mAbs 1 h prior to SRBC challenge, Footpad thickness was measured 20 h after antigen challenge, and results shown as % increase in footpad thickness ±SEM as illustrated in Example 2. These data represent a summary of eight experiments with n=79 (PBS), 68 (control hamster Ig), 68 (anti-α1), 29 (anti-α2), 18 (anti-α1+anti-α2), 45 (anti-α4), 18 (anti-α5), 20 (anti-α6), and 10 (anti-β1). The mAbs used were: Ha4/8 (control hamster Ig group 2), Ha31/8 (anti-α1), Ha1/29 (anti-α2), PS/2 (anti-α4), 5H10-27 (anti-α5), GoH3 (anti-α6), and HM β1-1 (anti-β1).

SRBC-induced DTH is a well characterized in vivo model of inflammation, and in particular psoriasis, that has been used to demonstrate the importance of a variety of cytokines and adhesion molecules in inflammation (Tedder et al., 1995, J. Exp. Med. 181:2259-2264, Terashita et al., 1996, J Immunol 156:4638-4643). SRBC-sensitized mice received anti-integrin mAbs 1 h prior to footpad antigen challenge and inflammation was assessed 20 h later as measured by increased footpad thickness. PBS and control hamster Ig-treated mice showed a 60-70% increase in footpad thickness 20 h after antigen challenge (FIG. 2). Compared to control hamster Ig treatment, anti-α1 or anti-α2 mAbs resulted in a 68% and 60% inhibition in footpad thickness, respectively. The combination of anti-α1 and α2 mAbs resulted in 71% inhibition, demonstrating little additive effect over anti-α1 or anti-α2 mAbs alone. Treatment with other anti-integrin mAbs was also effective at inhibiting DTH effector response. The degree of inhibition seen with the various mAb treatments was 49% (anti-α4), 23% (anti-α5), and 57% (anti-α6). Lastly, mAb blockade of the common β1 integrin subunit (mAb HMBI-1) inhibited the effector DTH response by 67%.

Example 3

Inhibition of CHS effector responses by anti-integrin mAbs. Contact hypersensitivity (CHS) to FITC was assayed as previously described (Gaspari et al., 1991, In Current Protocols in Immunology. J. E. Coligan, A. M. Kruisbeek, D. H. Margulies, E. M. Shevach, and W. Strober, editors. John Wiley & Sons, New York. Section 4.2:1). Briefly, mice were sensitized by painting 100 ul 0.5% FITC in 1:1 acetone/dibutylphthalate onto the shaved back on d 0.10 d later, animals were challenged by applying 5 ul 0.5% FITC onto both sides of each ear. Ear swelling response was determined by ear thickness measured with an engineer's caliper (Mitutoyo/MTI, Paramus, N.J.) at the time of antigen challenge (d 10) and 24 h later, and the results reported as mean percent increase in baseline ear thickness ±SEM. Increase in ear thickness was calculated as % increase=[1= (Ear thickness 24 h after antigen challenge/Ear thickness at the time of antigen challenge)]×100. To block the effector phase of the CHS response, therapeutic or control in mAb (250 ug) was given i.p. 4 h prior to antigen challenge on d 10. Mice that were antigen-sensitized and ear challenged with vehicle only (vehicle control) or mice that were ear challenged without prior sensitization (irritant control) served as negative controls (never exceeded 2% increase in ear thickness).

Figure 3:
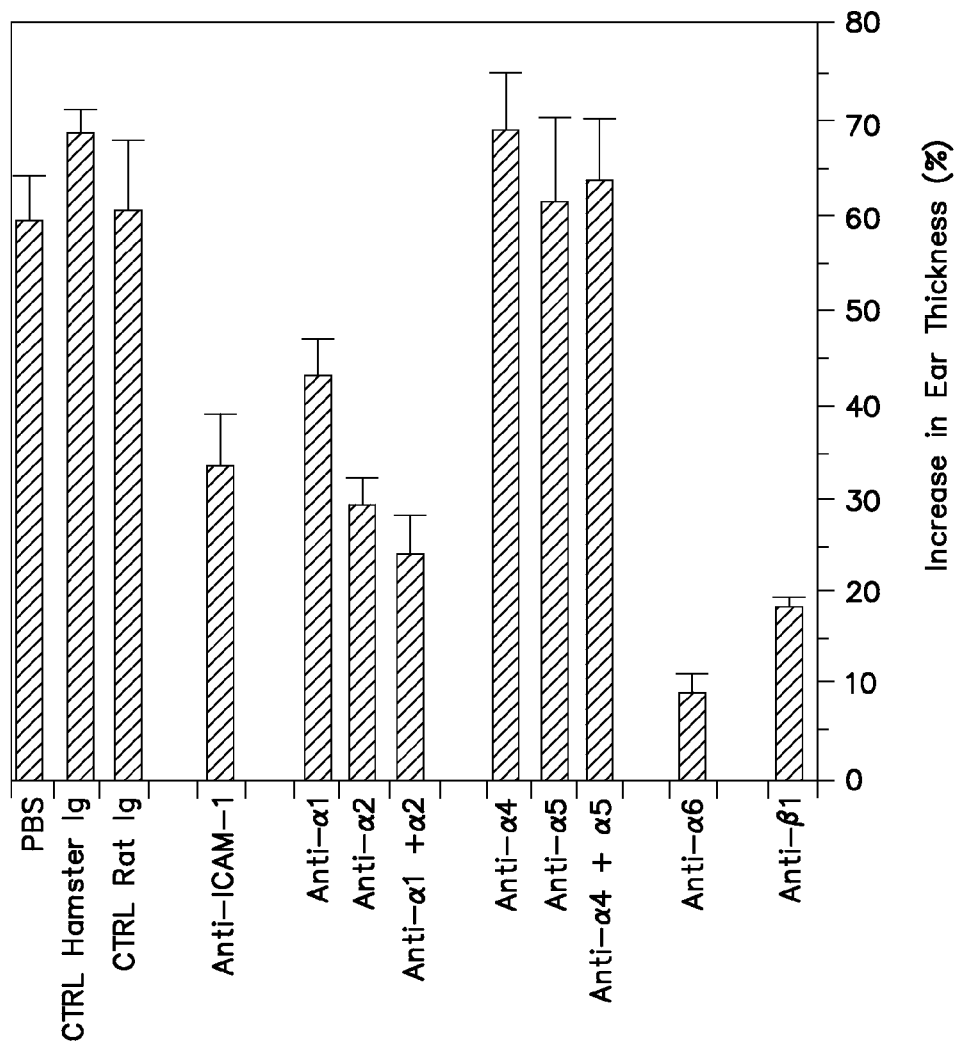
FIG. 3. Effect of anti-integrin mAbs on the effector phase of contact hypersensitivity. FITC-sensitized mice were injected i.p. with the indicated mAbs 4 h prior to FITC challenge. Ear thickness was measured at baseline and 24 h later, and results shown as % increase in ear thickness ±SEM as illustrated in Example 3. These data represent a summary of nine experiments with n=74 (PBS), 60 (control hamster Ig), 26 (anti-ICAM-1), 44 (anti-α1), 44 (anti-α2), 38 (anti-α1+anti-α2), 36 (anti-α4), 16 (anti-α5), 26 (anti-α4+anti-α5), 24 (anti-α6), and 22 (anti-β1). The hamster mAbs used were: Ha4/8 (control hamster Ig group 2), Ha31/8 (anti-α1), Ha1/29 (anti-α2), HMβ1-1 (anti-β1), 3E2 (anti-ICAM-1); the rat mAbs used were: R35-95 and R35-38 (control rat IgG2a and rat IgG2b, respectively), PS/2 (anti-α4), 5H10-27 (anti-α5), GoH3 (anti-α6).

Given that CHS is mechanistically distinct from DTH and involves different effector cells, we investigated what effect anti-integrin mAbs had on the effector phase of abacks, followed 10 d later with FITC challenge to the ear resulting in an inflammatory response the next day. FITC-sensitized mice demonstrated a 60-70% increase in thickness 24 h after antigen challenge (FIG. 3). Consistent with published results (Scheynius et al., J. Immunol. 150:655-663), anti-ICAM-1 mAb treatment resulted in 51% inhibition of ear swelling. Compared to control hamster mAb, treatment of mice with anti-α1 or anti-α2 mAb 4 h prior to antigen challenge resulted in 37% and 57% inhibition in ear swelling, respectively (FIG. 3). The combination of anti-α1 and anti-α2 mAbs resulted in slightly greater inhibition of ear swelling (65%). Treatment with other mAbs to β1 integrins revealed that while anti-α4 and anti-α5 mAbs resulted in no inhibition of FITC-induced CHS effector response when compared to control rat mAb, treatment with anti-α6 mAb resulted in an 86% inhibition of effector responses. Lastly, mAb blockade of the common β1 integrin subunit inhibited CHS effector responses by 74%. Similar CHS results were obtained using different strains of mice (C57/BL6, 129/Sv) and a different sensitizing agent (oxazolone) (data not shown). Similar to the results seen in the SRBC-induced DTH model, histologic analysis of inflamed ears revealed that both edema formation and leukocytic infiltration were inhibited by anti-α1 and anti-α2 mAb treatment.

Consistent with the finding that α1β1 and α2β1 can be expressed on IL-2-activated splenocytes, analysis of lymph nodes from antigen-sensitized mice (FITC or oxazolone) revealed of α1β1 and α2β1 to be expressed exclusively on $CD44^{hi}$ $LFA-1^{hi}$ activated CD4+ and CD8+ T cells (data not shown). Treatment of mice with anti-α1 and anti-α2 mAbs did not result in deletion of these cells, as the numbers of activated T cells in both spleen and lymph nodes seen in response to antigen sensitization in the CHS model was unaffected. In addition, effector cells were not functionally deleted as prolonged treatment of antigen-sensitized mice with anti-α1 and anti-α2 mAbs (d 10-16) did not affect the inflammatory response of mice challenged with antigen at d 20 (data not shown).

Example 4

Figure 4:
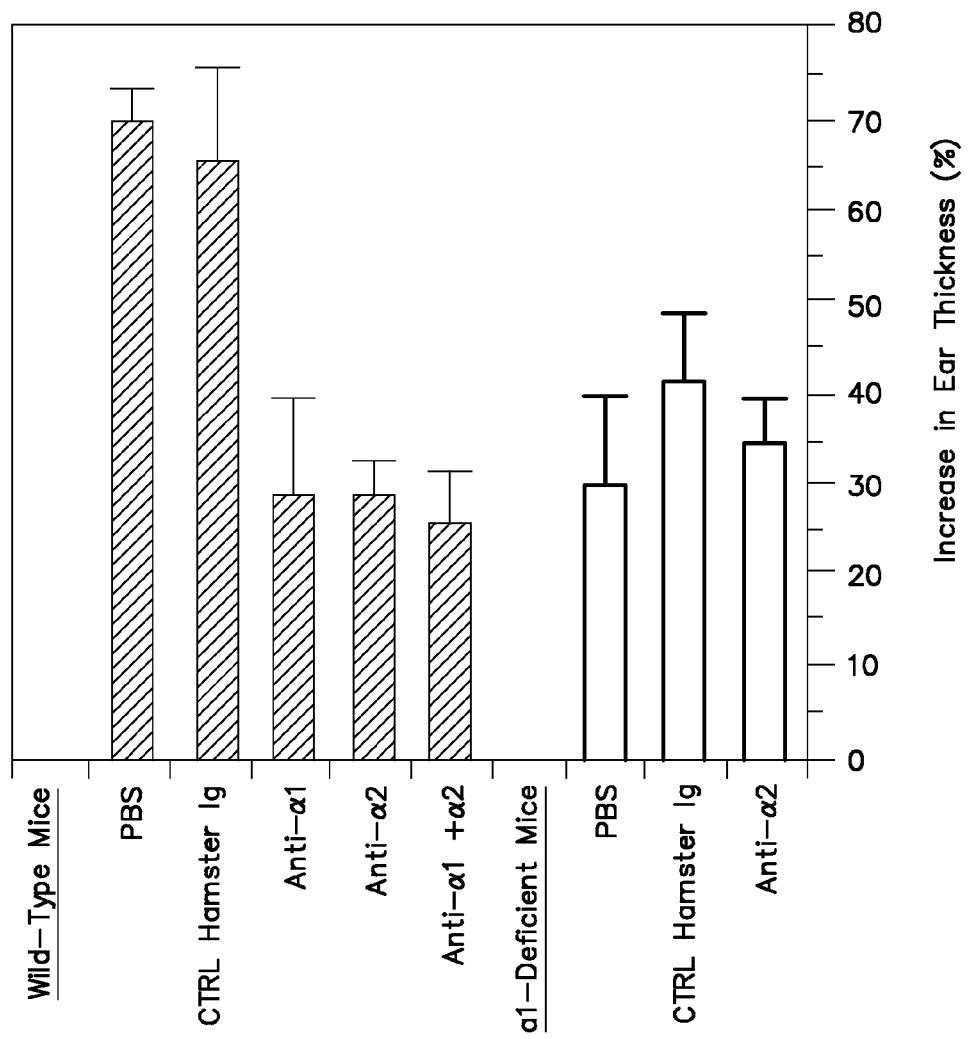
FIG. 4. Contact hypersensitivity responses in α1-deficient mice compared to wild-type mice. FITC-sensitized mice were injected i.p. with indicated mAbs 4 h prior to FITC challenge. Ear thickness was measured at baseline and 24 h later, and results shown as % increase in ear thickness ±SEM as illustrated in Example 4. Groups of four to five mice per condition were used, and all experiments were performed a minimum of three times. One representative experiment is shown.

CHS effector responses are decreased in α1β-deficient mice. To exclude the possibility that the inhibitory role of α1β1 in the effector response of FITC-mediated CHS was mAb-mediated, experiments were carried out in wild-type and α1β1 integrin deficient mice (FIG. 4). MAb inhibition of the effector phase in wild-type mice was consistent with previous results with 56% inhibition in ear thickness seen with anti-α1, 56% with anti-α2 and 62% with a combination of anti-α1 and anti-α2. The effector phase of CHS was significantly reduced in untreated α1β1-deficient mice as compared to untreated wild-type mice (30% vs 71% increase in ear thickness, respectively). As expected, the level of ear swelling in untreated α1β1-deficient mice was equivalent to the level of ear swelling seen in anti-α1 mAb-treated wild-type mice. Lastly, mAb blockade of α2β1 in the α1β1-deficient mice resulted in only slightly increased inhibition of ear swelling, consistent with the results seen in wild-type mice treated with a combination of anti-α1 and anti-α2 mAbs.

Example 5

To further exclude the possibility that the inhibitory effect of the anti-integrin mAbs seen in both the DTH and CHS models of inflammation is caused by a general anti-inflammatory effect mediated by the anti-α1 and anti-α2 mAbs, the effect of these mAbs on irritant dermatitis was studied.

To assess irritant dermatitis, mice were painted with 5 ul of 0.8% croton oil in acetone on both sides of each ear. Therapeutic or control antibodies were given 4 h prior to the application of the irritant. Ear swelling was measured 24 h later as described above and compared to ear thickness prior to croton oil application. Results are reported as mean percent increase in baseline ear thickness ±SEM as described above. Mice painted with acetone only (vehicle control) served as a negative control.

Figure 5:
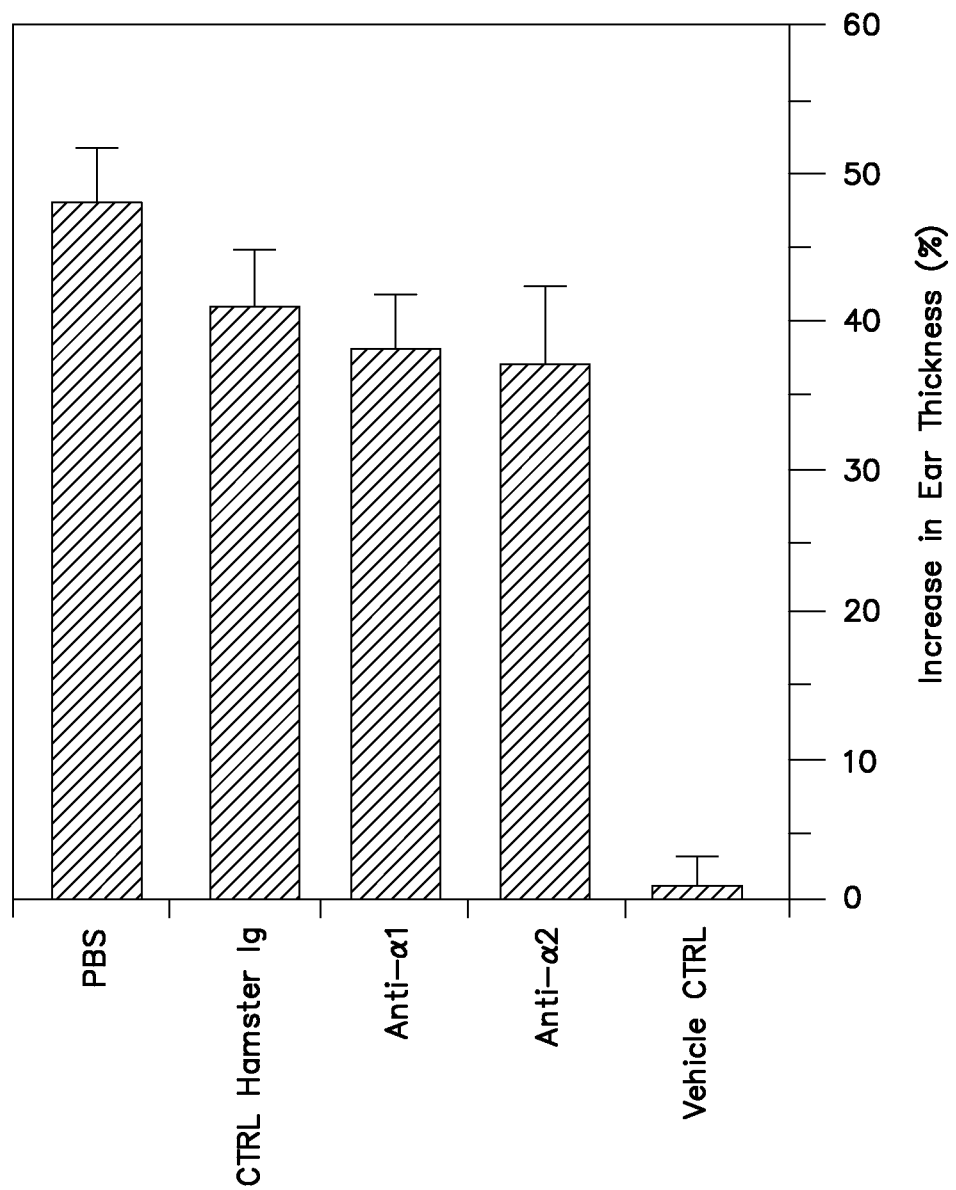
FIG. 5. Effect of anti-α1 and anti-α2 mAbs on croton oil-induced non-specific inflammation. Mice were injected i.p. with indicated mAbs 4 h prior to ear painting with croton oil. Ear thickness was measured at baseline and 24 h later, and results shown as % increase in ear thickness ±SEM as illustrated in Example 5. Groups of four to five mice per condition were used, and all experiments were performed a minimum of three times. One representative experiment is shown.

24 h later, ears of mice treated with croton oil showed a significant increase in ear thickness (48%), when compared to mice receiving vehicle only (acetone). Toxic ear swelling caused by croton oil was not significantly affected in mice pretreated with anti-α1 or anti-α2 mAbs when compared to either PBS or control mAb-treated animals (FIG. 5). Histologic examination of the croton oil-treated ears revealed no differences in numbers or types of infiltrating cells or edema formation in mice treated with anti-α1 or anti-α2 mAbs, as compared to control mAb-treated mice or PBS-treated mice (data not shown).

Example 6

Inhibition of arthritis bar α1β1 and α2β1. As α1β1 is well expressed on infiltrating cells in the synovium of arthritis patients, we decided to examine whether anti-α1 or anti-α2 mAbs would be inhibitory in an accelerated model of arthritis previously described (Terato et al., 1992, J. Immunol. 148:2103-2108; Terato et al., 1995, Autoimmunity 22:137-147).

Arthrogen-CIA Antibody kits were purchased from Stratagene (La Jolla, Calif.) and arthritis induced using a well established protocol (Terato et al., 1992, J. Immunol. 148:2103-2108; Terato et al., 1995, Autoimmunity 22:137-147). Briefly, arthritis was induced through i.p. injection of a cocktail of 4 anti-collagen type II mAbs (1 mg each) on d 0, followed by i.p. injection of 50 ug LPS on d 3. Over the course of the next 3-4 d, the mice developed swollen wrists, ankles and digits. Therapeutic or control mAb (250 ug) was administered i.p. 4 h prior to injection of the anti-collagen mAbs on d 0, and again 4 h prior to LPS administration on d 3, and then continuing every $3^{rd}$ day for the length of the experiment. Beginning on d 3, mice were evaluated for the development of arthritis. Severity of arthritis in each limb was scored using a four point system. 0=normal; 1=mild redness, slight swelling of ankle or wrist; 2=moderate swelling of ankle or wrist; 3=severe swelling including some digits, ankle, and foot; 4=maximally inflamed.

Figure 6:
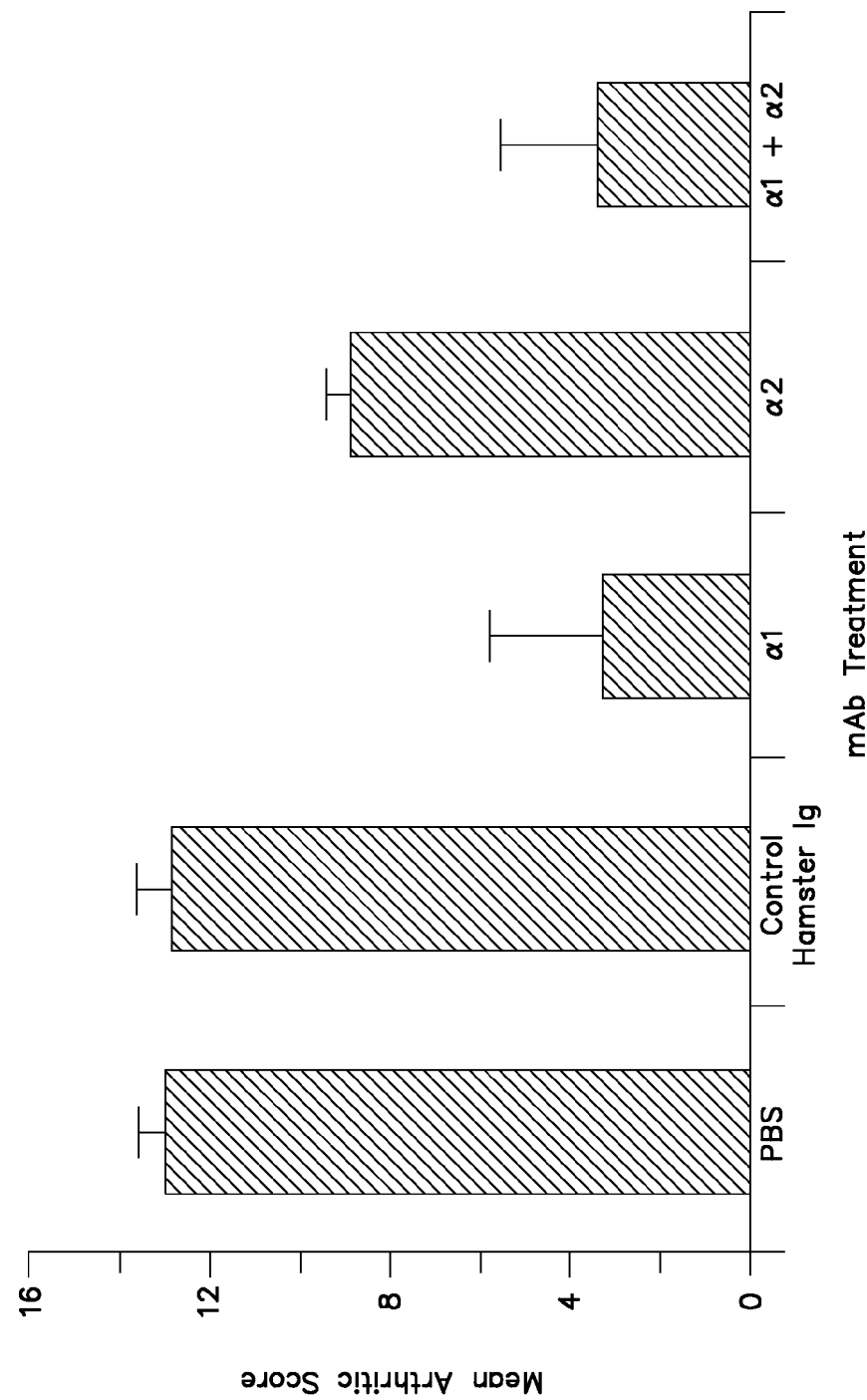
FIG. 6. Effect of anti-α1 and α2mAbs in collagen mAb-induced arthritis. Mice were injected i.p. with anti-collagen mAbs at d 0, followed by LPS on day 3. Mice were injected i.p. with indicated mAbs every $3^{rd}$ day starting on d 0. Clinical arthritis was apparent 2-3 d following LPS injection and continued for several weeks. Each limb was evaluated on a 0 to 4 scale every $3^{rd}$ day as illustrated in Example 6 and results are expressed as the mean arthritic score between d 9 and d 15 (±SEM) of all four limbs. These data represent a summary of four experiments with each experiment consisting of groups of three to four mice per condition.

Severe arthritis in Balb/c mice developed within 72 h after LPS injection and persisted for more than 3 weeks. Neither injection of anti-collagen mAbs alone nor LPS alone induced arthritis. Mice receiving control mAb treatment displayed equally severe arthritis as than seen in PBS-treated mice (FIG. 6). In contrast, treatment with anti-α1 mAb alone resulted in a marked reduction (78%) in arthritis, lasting the duration of the experiment. Treatment with anti-α2 mAb alone also had a beneficial effect, resulting in a 32% decrease in the arthritic score as compared to control b-treated mice. The combination of anti-α1 and anti-α2 mAbs resulted in a similar degree of inhibition as seen with anti-α1 mAb alone.

Example 7

Histological analysis of effect of anti-α1 and anti-α2 mAb treatment on the inflammatory cellular infiltrate. Further histological analysis of the SRBC-induced DTH response confirmed the ability of anti-α1 and anti-α2 mAb treatment to modulate the elicited inflammatory response. An unchallenged footpad from an SRBC-sensitized mouse showed virtually no inflammatory cellular infiltrate when compared to an SRBC-challenged footpad from the same mouse. Treatment of SRBC-sensitized mice with anti-α1 and anti-α2 mAbs either alone or combined greatly reduced the number of these infiltrating cells found in SRBC-challenged footpads when compared to control mAb-treated mice. Closer examination of the infiltrating cells revealed most cells to be composed of neutrophils, with some monocytes and lymphocytes present, and confirmed that anti-α1 and anti-α2 mAb treatment greatly decreased the numbers of these cells.

Example 8

Immunohistochemical demonstration of α1-expressing cells in the inflammatory cellular infiltrate. Immunohistochemistry was performed to more precisely determine the nature of the infiltrating cells and whether they express collagen-binding integrins. Infiltrating cells from an inflamed footpad of an untreated mouse were examined for expression of α1β1 integrin and cell lineage markers. α1β1 integrin was found to be expressed on many infiltrating leukocytes. Dual immunohistochemistry was utilized to identify the nature of the infiltrating cells and the distribution of α1β1 expression. Using cell lineage markers, the infiltrate was found to be composed largely of granulocyte/ monocytes (Mac-1+), with many of these cells being neutrophils (Gr1+), along with a smaller number of T lymphocytes (CD3+). Expression of α1β1 integrin was found among all three subsets of cells, with α1 expressed on a subset of Mac-1+ granulocyte/monocytes, a subset of Gr1+ neutrophils, and on the majority of infiltrating CD3+ T lymphocytes. Detailed immunohistochemical analysis revealed that although anti-α1 and anti-α2 mAb treatment reduced the numbers of infiltrating cells, no change in the cellular composition of the infiltrate was seen (data not shown). Immunohistochemistry staining with a FITC anti-hamster mAb confirmed the ability of the anti-α1 and antis α2 mAb to localize to the inflamed footpad (data not shown).

Example 9

Figure 7:
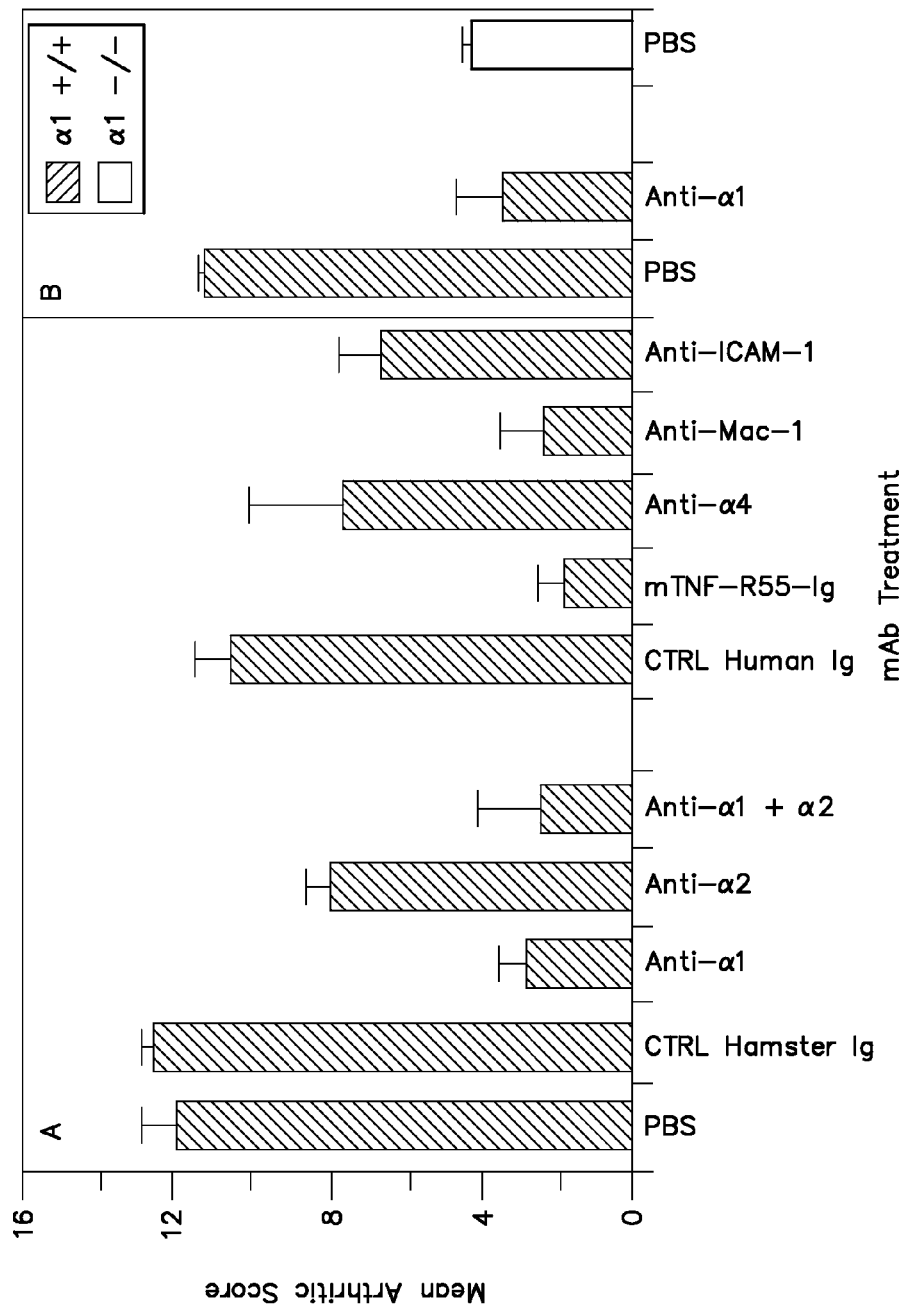
FIG. 7. Effect of anti-α1 and α2 mAbs in collagen mAb-induced arthritis. A. Preventative treatment of mice with either anti-α1 or anti-α2 mAb decreases arthritic score. Mice were treated with anti-collagen mAbs at d 0, followed by LPS on d 3. Arthritis was apparent by d 6 and continued for several weeks. Mice were treated with the indicated mAbs every $3^{rd}$ day starting on d 0. Each limb was evaluated and scored on a 0 to 4 scale every $3^{rd}$ day. Results are expressed as the mean arthritic score between d 9 and d 15 (±SEM) of all four limbs (maximum score of 16). Groups of 4 mice per condition were used; the average of 12 experiments is shown. B. α1-deficient mice have a reduced arthritic score comparable to anti-α1 mAb-treated wild-type mice. Experimental details and scoring are as outlined above. Groups of 4 mice per condition were used; the average of 2 experiments is shown.

Inhibition of arthritis by mAbs to α1β1 and α2β1 and in α1-deficient mice. As α1β1 is well expressed on infiltrating cells in the synovium of arthritis patients, we decided to examine whether anti-α1 or anti-α2 mAbs would be inhibitory in an accelerated model of arthritis previously described (Terato et al., 1992, J. Immunol 148:2103-2108; Terato et al., 1995, Autoimmunity 22:137-147). This model involves injection of a cocktail of anti-collagen type II mAbs into mice, followed later by LPS administration, resulting in the development of arthritis over the next 3-7 d. Mice were given mAb every $3^{rd}$ day starting at d 0, and scored for the development of arthritis every $3^{rd}$ day. Severe arthritis developed in all mice within 72 h after LPS injection and persisted for more than 3 weeks. Neither injection of anti-collagen mAbs alone nor LPS alone induced arthritis. Mice receiving control mAb treatment displayed equally severe arthritis as than seen in PBS-treated mice (FIG. 7). In contrast, treatment with anti-α1 mAb alone resulted in a marked reduction (79% and higher) in arthritis, lasting the duration of the experiment. Treatment with anti-α2 mAb alone also had a beneficial effect, resulting in a 37% decrease in the arthritic score as compared to control mAb-treated mice. The combination of anti-α1 and anti-α2 mAbs resulted in a similar degree of inhibition as seen with anti-α1 mAb alone. Reduction of arthritic score with anti-α1 mAb treatment was seen in all mice and compares favorably with several other mAb-based treatments for arthritis such as soluble TNF receptor Ig fusion protein (Mori et al., 1996, J. Immunol. 157:3178-3182), anti-Mac-1 (Taylor et al., 1996, Immunology. 88:315-321), anti-α4 (Seiffge, 1996, J. Rheumatol. 23:2086-2091), and anti-ICAM-1 (Kakimoto et al., 1992, Cell Immunol. 142:326-337). In agreement with mAb-based data showing an important role for α1β1 in arthritis, untreated α1-deficient mice showed significant reduction in arthritic score when compared to wild-type mice.

Example 10

Effect of anti-α1 mAb treatment on the immunopathology of arthritic joints. Joints from wild-type arthritic mice (day 8) receiving either control mAb or anti-α1 mAb treatment were compared visually and histologically to joints from a normal untreated mouse. Visually, joints from control mAb-treated mice demonstrated redness and swelling of the entire foot including digits, while anti-α1 mAb-treated mice showed little if any signs of inflammation in either joints or digits. Histologic examination showed severe changes in control mAb-treated arthritic joints, with extensive infiltration of the subsynovial tissue with inflammatory cells, adherence of cells to the joint surface, and marked cartilage destruction as evidenced by proteoglycan loss. Consistent with previous reports (Terato et al., 1992, J. Immunol 148:2103-2108; Terato et al., 1995, Autoimmunity 22:137-147), the majority of the infiltrating cells in this model are neutrophils. Anti-α1 mAb treatment of mice dramatically reduced the amount of inflammatory infiltrate and the degree of cartilage destruction.

Example 11

Figure 8:
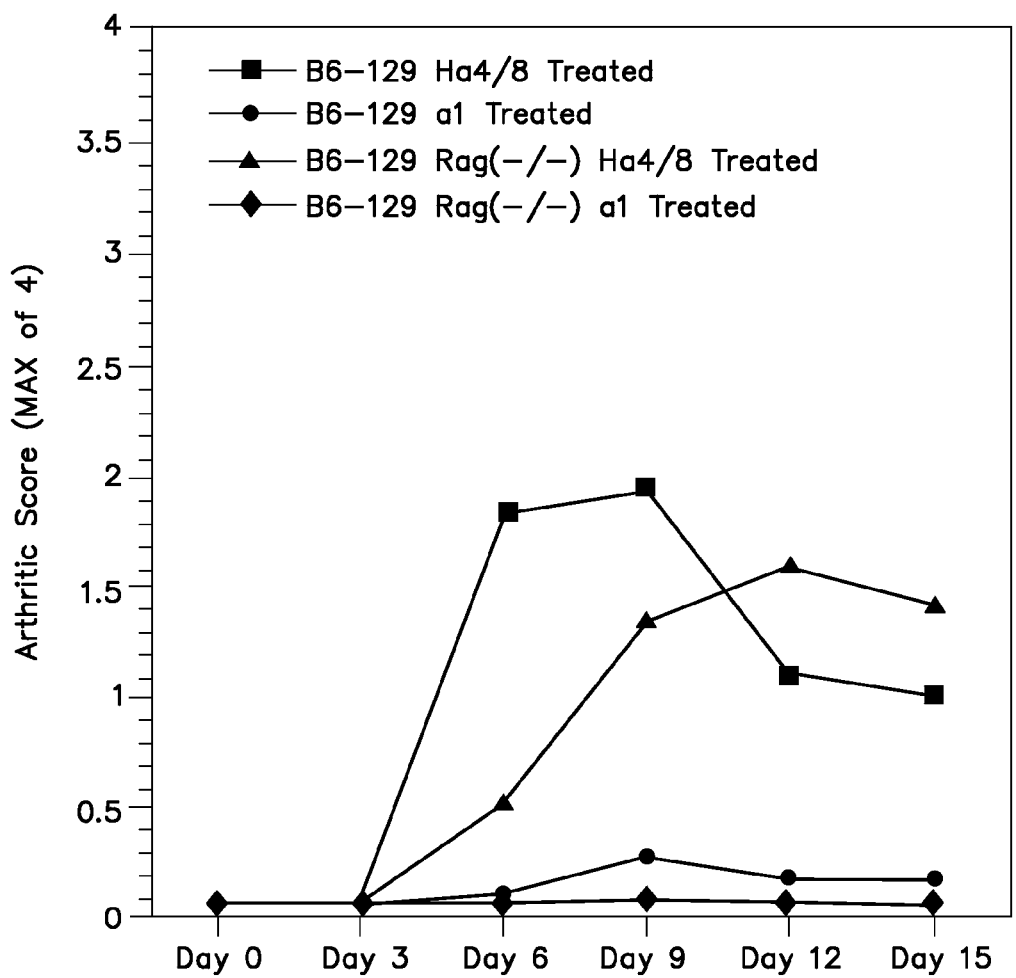
FIG. 8. Development of arthritis is delayed in the absence of lymphocytes and inhibition of arthritis by anti-α1 mAb occurs in the absence of lymphocytes. Wild-type B6,129 or RAG-1-deficient B6,129 mice were treated with anti-collagen mAbs at day 0, followed by LPS on day 3. Arthritis was apparent by day 6 and continued for several weeks. Mice were treated with the indicated mAbs every $3^{rd}$ day starting on day 0. Each limb was evaluated and scored on a 0 to 4 scale every $3^{rd}$ day. Results are expressed as the mean arthritic score per limb (maximum score of 4). Groups of 4 mice per condition were used.

Development of arthritis is delayed in the absence of lymphocytes and inhibition of arthritis by anti-α1 mAb occurs in the absence of lymphocytes. To determine what cell types might be important in the collagen mAb-induced arthritis model we compared the ability of wild-type B6-129 mice and RAG-1-deficient B6-129 mice to develop arthritis (FIG. 8). Genetic deletion of the RAG-1 (recombination activating gene-1) gene results in a complete loss of mature T and B lymphocytes (Mombaerts et al., 1992, Cell 68:869-877). Both the wild-type and RAG-1-deficient mice developed arthritis, though the kinetics of induction in the RAG-1-deficient mice is significantly slower (FIG. 8). These results suggest that while lymphocytes are involved in this model of arthritis, they are not required for the development and progression of the disease. Published reports examining the effect of the RAG-1-deficient mice in other models of arthritis also found that loss of T and B lymphocytes delayed the onset of arthritis (Plows et al., 1999, J. Immunol. 162:1018-1023). Treatment of either wild-type or RAG-1-deficient mice with anti-α1 mAb completely inhibited arthritis (FIG. 8). These results demonstrate that the effectiveness of anti-α1 mAb in this model is not dependent on the presence of lymphocytes, and that as suggested by previous experiments (FIG. 7), the efficacy of anti-α1 mAb in preventing disease may be through its action on other α1-expressing cells, such as macrophages and neutrophils.

Example 12

Figure 9:
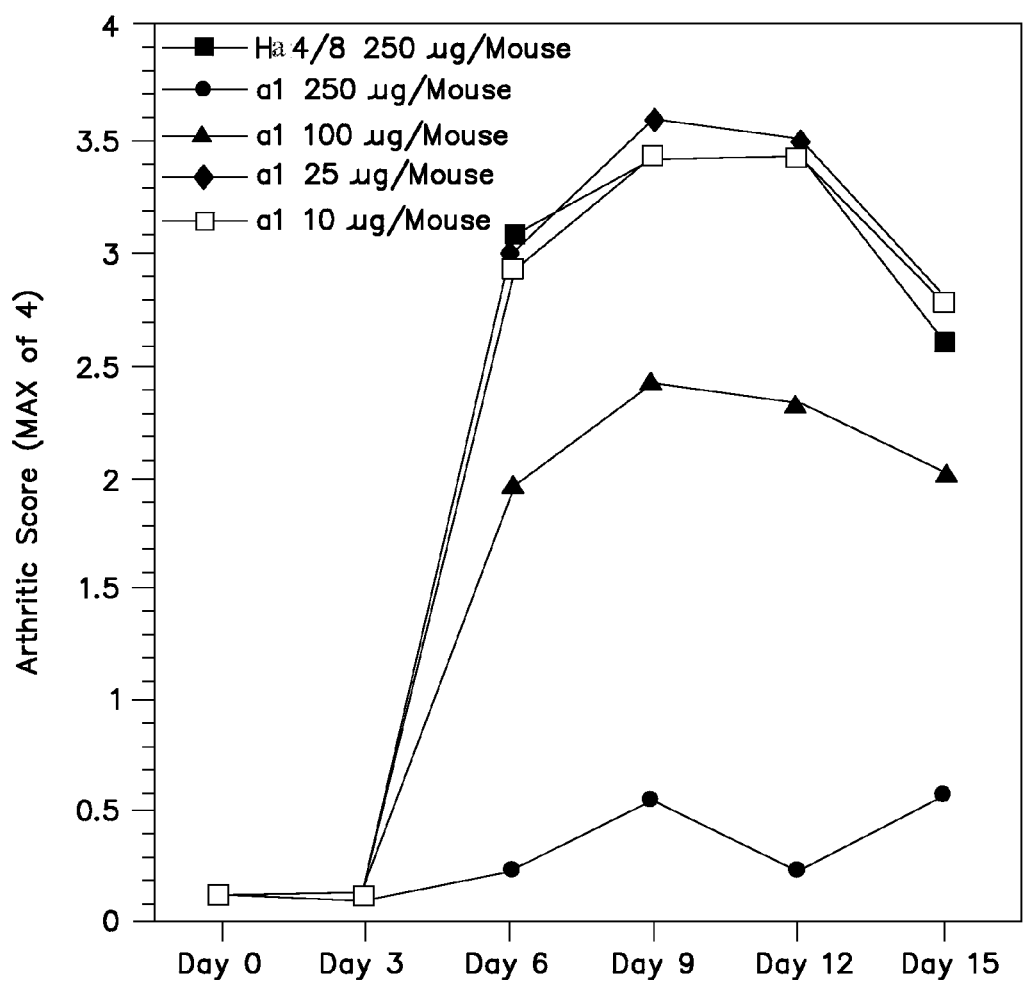
FIG. 9. Dose response of anti-α1 mAb inhibition of arthritis. Wild-type Balb/c mice were treated with anti-collagen mAbs at day 0, followed by LPS on day 3. Arthritis was apparent by day 6 and continued for several weeks. Mice were treated i.p. with the indicated dose of either Ha4/8 (isotype control) or Ha31/8 (anti-α1) mAbs every $3^{rd}$ day starting on day 0. Each limb was evaluated and scored on a 0 to 4 scale every $3^{rd}$ day. Results are expressed as the mean arthritic score per limb (maximum score of 4). Groups of 4 mice per condition were used.

Dose response of anti-α1 mAb inhibition of arthritis. Given the striking effects of anti-α1 mAb treatment on preventing arthritis, we extended these studies to include a dose response analysis (FIG. 9). Different doses of mAb were administered i.p. every $3^{rd}$ day starting at day 0. In agreement with earlier data, a 250 ug dose of anti-α1 mAb resulted in near complete prevention of arthritis. A lower dose of 100 ug of anti-α1 mAb was partially effective at preventing arthritis in this model, while lower doses did not have any discernable effect on arthritic score (FIG. 9).

Example 13

Figure 10:
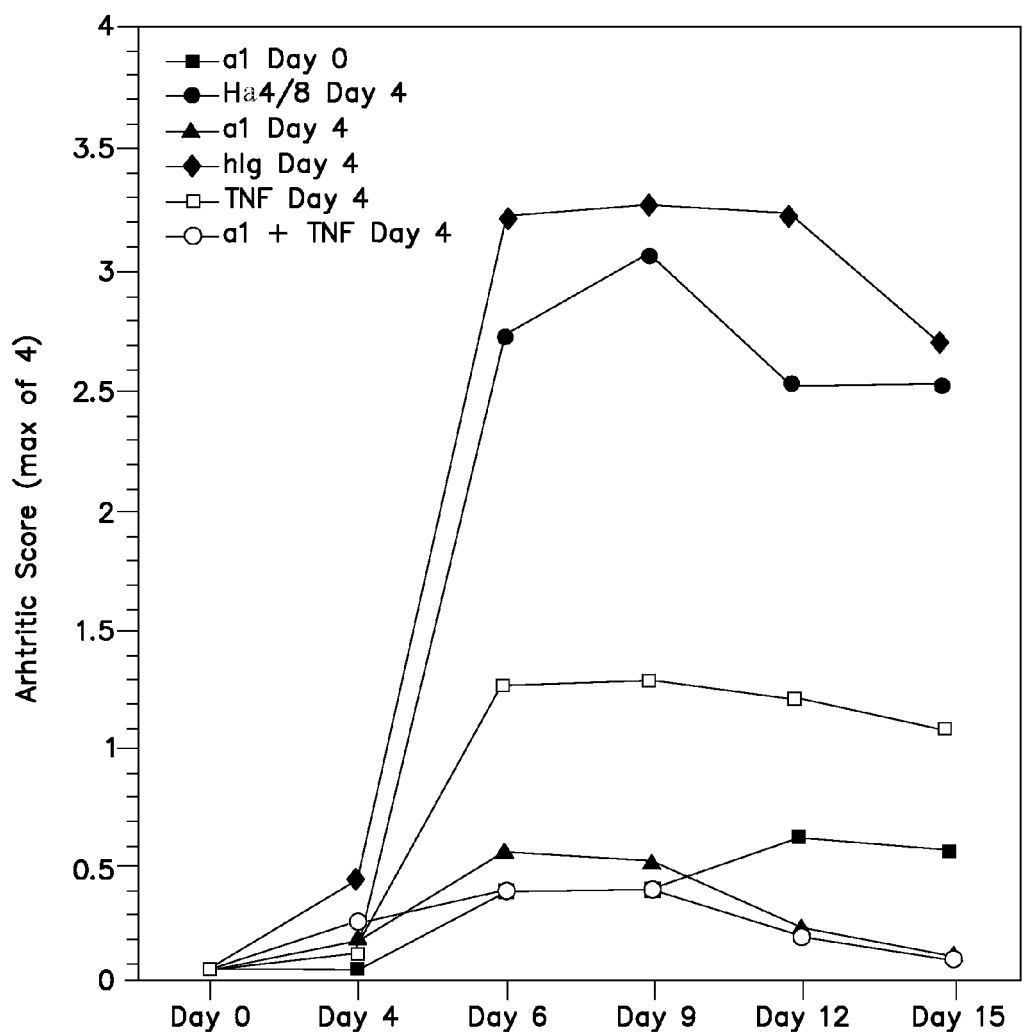
FIG. 10. Therapeutic treatment with anti-α1 mAb can decrease arthritic score. Wild-type Balb/c mice were treated with anti-collagen mAbs at day 0, followed by LPS on day 3. Arthritis was apparent by day 6 and continued for several weeks. Mice were treated i.p. with mAbs (250 μg) or Ig fusion protein (200 μg) every $3^{rd}$ day starting on day 4. Mice received either mAb (Ha4/8 isotype control or Ha31/8 anti-α1), Ig fusion protein (Isotype control Ig or TNF-R55-Ig) or a combination of both (250 ug Ha31/8 and 200 ug TNF-R55-Ig). Each limb was evaluated and scored on a 0 to 4 scale every $3^{rd}$ day. Results are expressed as the mean arthritic score per limb (maximum score of 4). Groups of 4 mice per condition were used.

Therapeutic treatment with anti-α1 mAb can decrease arthritic score. Given the effectiveness of anti-α1 mAb in preventing arthritis, we attempted to treat mice that are on their way to develop disease. Arthritis was induced in mice by injection of a cocktail of anti-collagen type II mAbs on day 0, followed by LPS administration on day 3. Mice were then treated with either anti-α1 mAb or a soluble TNF receptor Ig fusion protein starting on day 4. Progression of arthritis was completely blocked in mice receiving anti-α1 mAb starting at day 4, when compared to mice receiving control hamster mAb starting at day 4 (FIG. 10). The degree of inhibition seen with therapeutic administration of anti-α1 mAb was complete and was equal to that seen with preventative treatment of anti-α1 mAb (started at day 0) (FIG. 10). In comparison, treatment with TN receptor Ig fusion protein from day 4 onwards resulted in only a 60-70% inhibition in arthritic score when compared to control Ig fusion protein (FIG. 10). Combined treatment of anti-α1 mAb and TNF receptor Ig fusion together was effective at completely inhibiting arthritic score, which is not surprising given the complete effectiveness of anti-α1 mAb treatment alone in suppressing arthritis. In summary, these results indicate that therapeutic treatment with anti-α1 mAb is effective at inhibiting arthritic score, and compares favorably to therapeutic treatment with a TNF antagonist.

Example 14

Cloning and mutagenesis of the α1-I domain. Human and rat α1β1 integrin I domain sequences were amplified from full length cDNAs (Kem, et al., 1994, J. Biol. Chem. 269, 22811-22816; Ignatius et al., 1990, J. Cell Biol. 111, 709-720) by the polymerase chain reaction (PCR) (PCR CORE Kit; Boehringer Mannheim, GmbH Germany), using either human specific primers, 5'-CAGGATCCGTCAGCCCCA-CATTTCAA-3' [forward] (SEQ ED NO:7), and 5'-TCCTC-GAGGGCTTGCAGGGCAAATAT-3' [reverse] (SEQ ID NO:8), or rat specific primers, 5'-CAGGATCCGTCAGTC-CTACATTTCAA-3' [forward] (SEQ ID NO:9), and 5'-TC-CTCGAGCGCTTCCAAAGCGAATAT-3' [reverse] (SEQ ID NO:10).

The resulting PCR amplified products were purified, ligated into pGEX4t-i (Pharmacia), and transformed into competent DH5α cells (Life Technologies). Ampicillin resistant colonies were screened for the expression of the .about.45 kDa glutathione S-transferase-I domain fusion protein. The sequences from inserts of plasmid DNA of clones that were selected for further characterization were confirmed by DNA sequencing.

A rat/human chimeric α1-I domain (RΔH) was generated (MORPH Mutagenesis kit; 5 prime-3 prime), exchanging the rat residues G91, R92, Q93, and L96 (FIG. 11A) for the corresponding human residues, V, Q, R, and R, respectively. Clones harboring the RΔH I domain were identified by the loss of a diagnostic Stu 1 restriction enzyme site, and the inserts confirmed by DNA sequencing. The amino acid sequence of the human α1-I domain is shown in FIG. 12.

Example 15

Generation of mAbs specific to the α1-I domain. Monoclonal antibodies have proved to be very useful probes in studying the relationship between structure and function of integrin subunits. For example, mAbs were used extensively to study regions of the β1 subunit associated with an activated conformation (Qu, A., and Leahy, D. J. (1996) Structure 4, 931-942). Thus, to identify potential probes for conformational changes of the α1-I domain, we generated a panel of mAbs to the human α1-I domain.

Generation of anti-α1 I domain Monoclonal Antibodies. Female Robertsonian mice (Jackson Labs) were immunized intraperitoneally (i.p.) with 25 μg of purified human α1β1 (Edwards et al., 1995, J. Biol. Chem. 270, 12635-12640; Gotwals et al., 1999, Biochemistry 38:8280-8) emulsified with complete Freund's adjuvant (LifeTechnologies). They were boosted three times i.p. with 25 μg of α1β1 emulsified with incomplete Freund's adjuvant (LifeTechnologies). The mouse with the highest anti-α1-I domain titer was boosted i.p. with 100 μg of α1β1 three days prior to fusion, and intravenously with 50 μg of α1β1 one day prior to fusion. Spleen cells were fused with FL653 myeloma cells at a 1:6 ratio and were plated at 100,000 and 33,000 per well into 96 well tissue culture plates.

Supernatants were assessed for binding to the α1β1 integrin by single color FACS. Prior to FACS analysis, supernatants were incubated with untransfected K562 cells to eliminate IgG that bound solely to the D subunit. Subsequently, 3-5×10$^4$ K562 cells transfected with the α1 integrin subunit (K562-α1) suspended in FACS buffer (1% fetal calf serum (FCS) in PBS containing 0.5% NaN$_3$) were incubated with supernatant for 45 minutes at 4° C., washed and incubated with antis mouse IgG conjugated to phycoerythrin. After washing twice with FACS buffer, cells were analyzed in a Becton Dickinson Flow Cytometer.

Supernatants from the resulting hybridomas were screened for binding to the α1-I domain. Briefly, 50 μl of 30 μg/ml human α1-I-domain-(GST fusion in PBS was coated onto wells of a 96-well plate (Nunc) overnight at 4° C. The plates were washed with PBS, blocked with 1% BSA in PBS and the hybridoma supernatant was incubated with the I domain at room temperature for 1 hour. After extensive washing with PBS containing 0.03% Tween 20, alkaline phosphatase linked anti-mouse IgG (Jackson ImmunoResearch) was added for an additional hour. After a final wash, 1 mg/ml p-nitrophenylphosphate (pNPP) in 0.1 M glycine, 1 mM ZnCl$_2$, and 1 mM MgCl$_2$ was added for 30 minutes at room temperature, and the plates were read at O.D. 405.

Selected supernatants were tested for their ability to inhibit K562-α1 dependent adhesion to Collagen IV. K562-α1 cells were labeled with 2 mM 2',7' (bis-2-carboxyethyl-5 and 6) carboxyfluorescein penta acetoxymethylester (BCECF; Molecular Probes) in DMEM containing 0.25% BSA at 37° C. for 30 minutes. Labeled cells were washed with binding buffer (10 mM Hepes, pH 7.4; 0.9% NaCl; and 2% glucose) and resuspended in binding buffer plus 5 mM MgCl$_2$ at a final concentration of 1×10$^6$ cells/mL. 50 μl of supernatant was incubated with an equal volume of 2×10$^5$ K562-α1 cells in wells of a 96 well plate. The plate was then centrifuged and the supernatants removed. Cells were resuspended in binding buffer and transferred to wells of a collagen-coated plate and incubated for 1 hour at 37° C. Following incubation, the non-adherent cells were removed by washing three times with binding buffer. Attached cells were analyzed on a Cytofluor (Millipore).

Figure 13A:
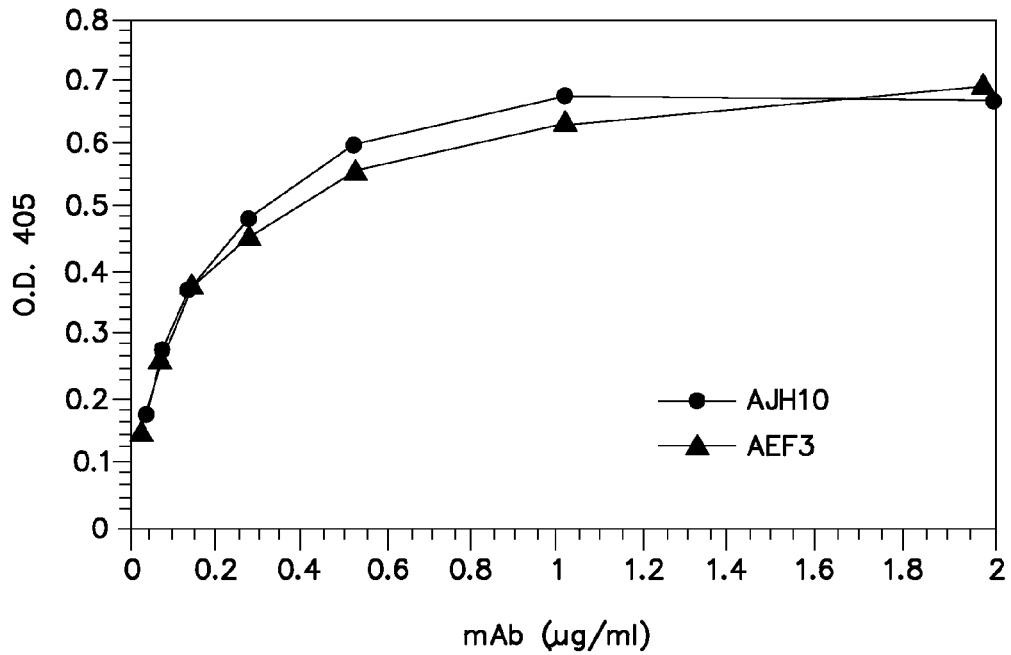
FIG. 13A-C. Identification of a blocking mAb to the α1-I domain.
Figure 13B:
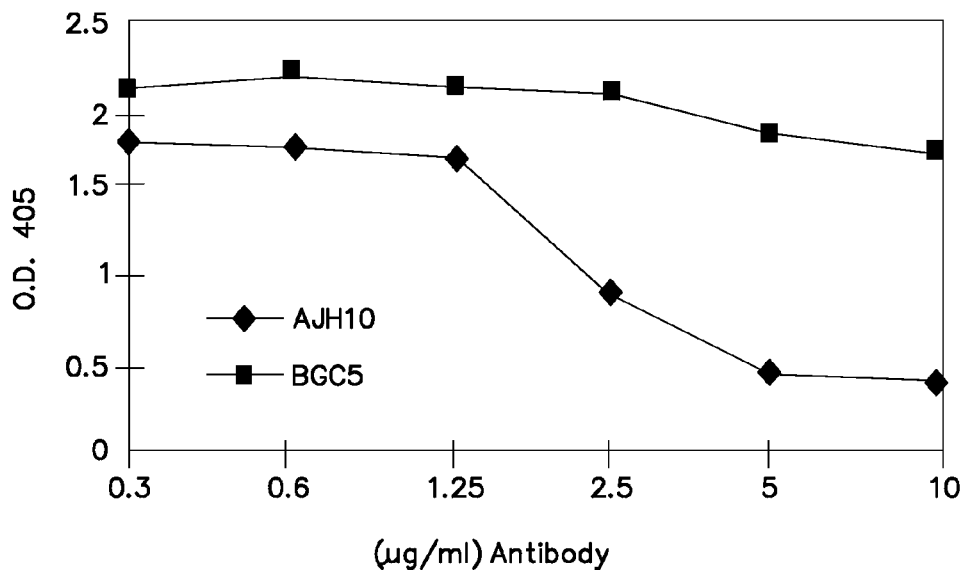
Figure 13C:
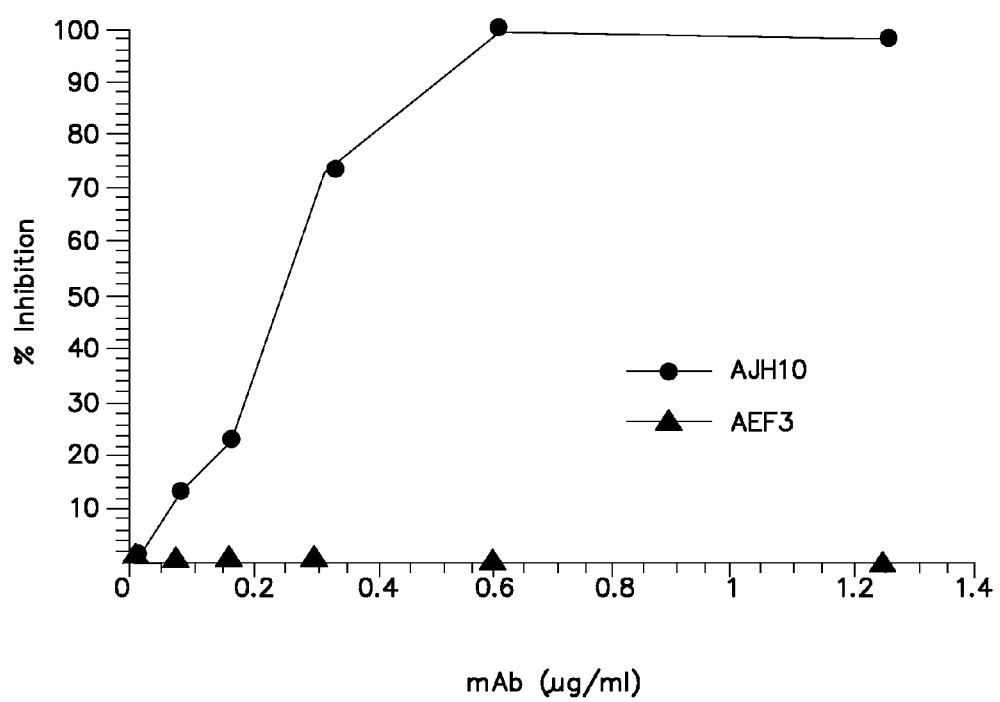
Figure 16A:
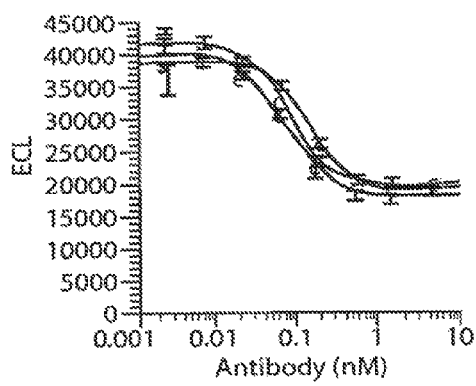
FIG. 16A-D. Characterization of Humanized AQC2 Forms. mAQC2 (triangles), chAQC2 (circles), hAQC2 (inverted triangles) and hAQC2' (squares) were evaluated.
Figure 16B:
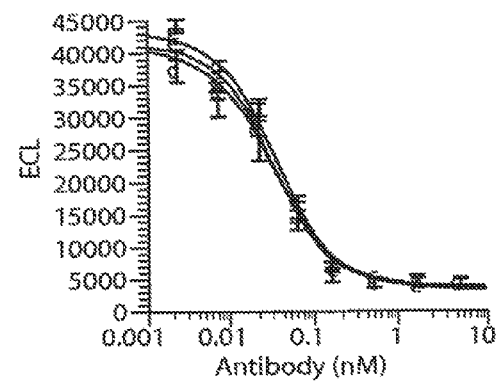
Figure 16C:
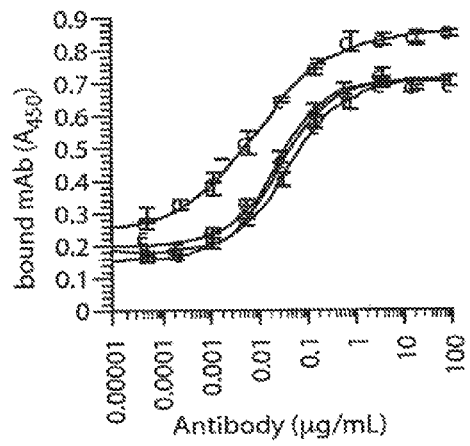
Figure 16D:
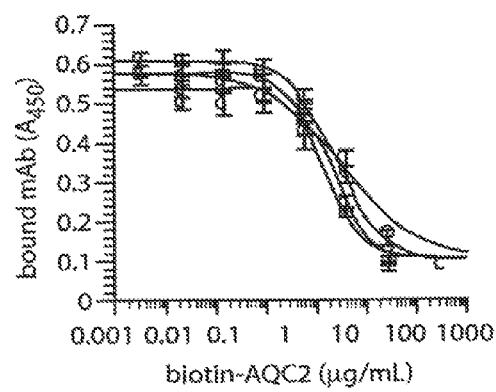

We initially identified 19 hybridomas, the supernatants of which bound to human leukemia K562 cells expressing the α1β1 integrin (K562-α1) and to the α1-I domain. The immunoglobulins were purified from each of these hybridomas and tested for the ability to block either K562-α1 or α1-I domain binding to collagen IV. The mAbs fall into two classes: those that block and those that do not block α1β1 function. For example, while the mAbs produced by clones AEF3, BGCS, AQC2 and AJH10 bind the α1-I domain (FIG. 13A, data not shown for BGCS), only mAbs AJH10 and AQC2 inhibit α1-I domain-dependent (FIG. 13B; FIG. 16B) or K562-α1 (FIG. 13C; FIG. 16C) adhesion to collagen IV.

Sequencing of the Complementarity Determining Regions.

To establish the clonal origin of this panel of mAbs, we amplified by PCR and sequenced the CDRs from 12 of the 19 antibodies (data not shown).

2 μg of mRNA, isolated from 10$^7$ hybridomas (FastTrack mRNA isolation kit, Invitrogen), was reverse transcribed (Ready-To-Go You Prime First Strand Kit, Pharmacia Biotech) using 25 pM each of the following primers: heavy chain VH1FOR-2 (Michishita et al., 1993, Cell 72:857-867); light chain, VK4FOR, which defines four separate oligos (Kern et al., 1994, J. Biol. Chem. 269:22811-22816). For each hybridoma, heavy and light chains were amplified in four separate PCR reactions using various combination of the following oligos: 1) Heavy chain: VH1FR1K (Kamata et al., 1995, J. of Biol. Chem. 270:12531-12535), VH1BACK, VH1BACK (Baldwin et al. (1998) Structure 6, 923-935), V$_H$fr1a, V$_H$fr1b, V$_H$fr1e, V$_H$fr1f, V$_H$fr1g (Ignatius et al. (1990) J. Cell Biol. 111, 709-720), or VH1FOR-2 (Michishita, M., Videm, V., and Arnaout, M. A. (1993) Cell 72, 857-867); 2) Light chain: VK1BACK (Baldwin et al. (1998) Structure 6, 923-935), VK4FOR, VK2BACK oligos (Kern et al. (1994) J. Biol. Chem. 269, 22811-22816), or V$_K$fr1a, V$_H$fr1c, V$_H$fr1e, V$_H$fr1f (Ignatius et al. (1990) J. Cell Biol. 111, 709-720). Products were amplified (5 min at 95° C., 50 cycles of 1 min at 94° C., 2 min at 55° C., 2 min at 72° C., and a final cycle of 10 min at 72° C.), gel purified (QIAquick, Qiagen), and sequenced directly using various of the listed oligos on an ABI 377 Sequencer.

Sequences from clones producing function-blocking mAbs were nearly identical across all the complementarity-determining regions (CDRs) and the intervening framework regions suggesting that these hybridomas are clonally related.

Example 16

Immunoblotting and FACS Analysis. Sequences of the variable regions of the non-blocking antibodies were markedly different from the clonally related family of sequences found for the blocking antibodies. As the blocking antibodies appear to originate from a single clone, we chose two (AJH10 and AQC2) to characterize further.

Immunoblotting. The smooth muscle cell layer dissected from sheep aorta, and K562-α1 cells were extracted with 1% Triton X-100 in 50 mM Hepes, pH 7.5, 150 mM NaCl, 10 mM phenylmethylsulfonyl fluoride (PMSF), 20 µg/ml aprotinin, 10 µg/ml leupeptin, 10 mM ethylenediaminetetraacetic acid (EDTA). Samples were subjected to 4-20% gradient SDS-PAGE, and electroblotted onto nitrocellulose membranes. The blots were blocked with 5% dry milk in TBS; washed in TBS containing 0.03% Tween-20, and incubated with antibodies in blocking buffer containing 0.05% NaN$_3$ for 2 hours. Blots were then washed as before, incubated with horseradish peroxidase conjugated anti-mouse IgG for one hour, washed again and then treated with ECL reagent (Amersham). Blots were then exposed to film (Kodak) for 30 to 60 seconds, and developed.

Immunoblotting and FACS analysis (FIG. 14) demonstrate that AJH10 reacts with human, rabbit, and sheep, but not rat α1β1 integrin suggesting that the blocking mAbs bind to an evolutionarily conserved, linear epitope. The non-blocking mAbs were neither efficient at immunoblotting nor did they react with species other than human.

Example 17

Binding of the α1-I Domain to Collagen is Divalent Cation-Dependent

A. Purification of the α1-I Domains.

The α1-I domains were expressed in *E. coli* as GST (glutathione-S-transferase) fusion proteins containing a thrombin cleavage site at the junction of the sequences. The clarified supernatant from cells lysed in PBS was loaded onto a glutathione Sepharose 4B column (Pharmacia) which was washed extensively with PBS. The α1-I domain-GST fusion protein was eluted with 50 mM Tris-HCl, pH 8.0, 5 mM glutathione (reduced). For denaturation studies, the I domain was cleaved with thrombin in 50 mM Tris, pH 7.5, and purified from the GST fusion partner. DTT was added to 2 mM and the sample was loaded on a glutathione Sepharose 4B column. The flow-through and wash fractions were pooled and loaded onto a Q Sepharose FF column (Pharmacia). The α1-I domain was eluted with 50 mM Tris HCl, pH 7.5, 10 mM 2-mercaptoethanol, 75 mM NaCl. The purified I domain displayed its predicted mass (Lee et al. (1995) Structure 3, 1333-1340, 871 Da) by electrospray ionization-mass spectrometry (ESI-MS), migrated as a single band by SDS-PAGE, and the protein eluted as a single peak of appropriate size by size exclusion chromotography on a Superose 6 FPLC column (Pharmacia).

B. Functional Analysis 96 well plates were coated overnight at 4° C. with 1 µg/ml collagen IV (Sigma) or collagen Type I (Collaborative Biomedical), washed with Triton buffer (0.1% Triton X-100; 1 mM MnCl$_2$; 25 mM Tris-HCl; 150 mM NaCl), and blocked with 3% bovine serum albumin (BSA) in 25 mM Tris-HCl; 150 mM NaCl (TBS). Serial dilutions of the α1-I domain-GST fusion protein in TBS containing 1 mM MnCl$_2$ and 3% BSA were incubated on the coated plates at room temperature for 1 hour, and washed in Triton buffer. Bound α1-I domain was detected with serial additions of 10 µg/ml biotinylated anti-GST polyclonal antibody (Pharmacia); ExtrAvidin-horseradish peroxidase (Sigma) diluted 1:3000 in TBS containing 1 mM MnCl$_2$ and 3% BSA, and 1-Step ABTS (2,2'-Azine-di[3-ethylbenzthiazoline sulfonate]; Pierce). Plates were read at O.D. 405 on a microplate reader (Molecular Devices).

Results.

Figure 15A:
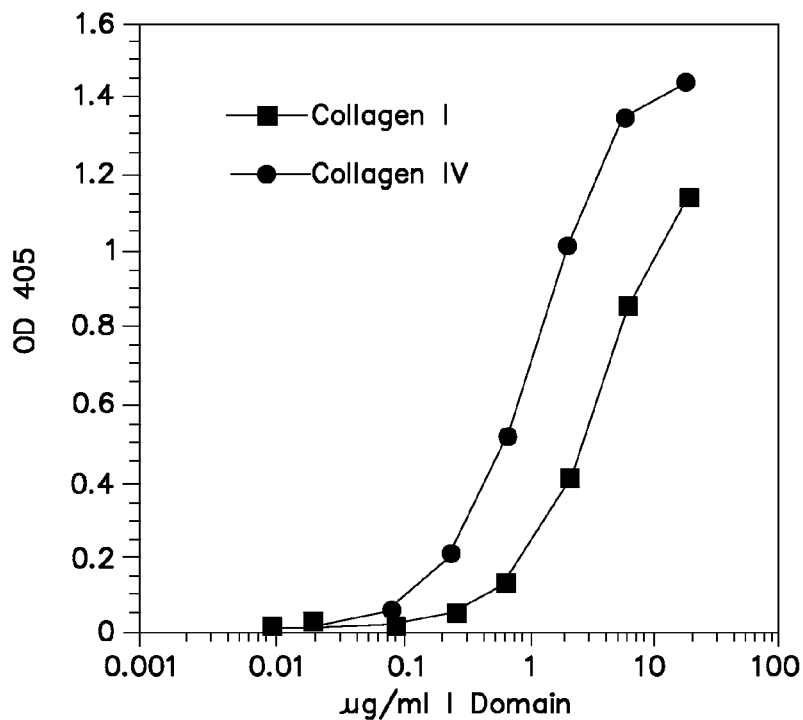
FIG. 15A-C. The α1-I domain binds collagen.
Figure 15B:
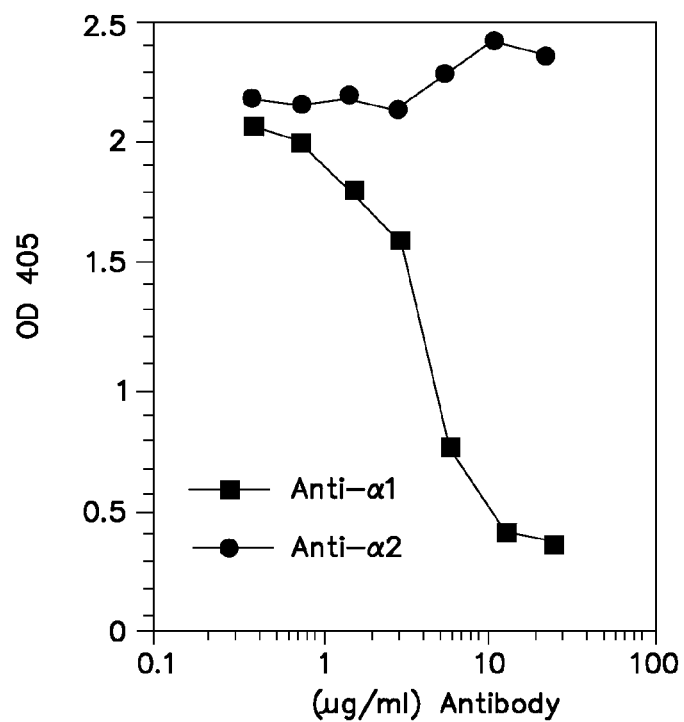
Figure 15C:
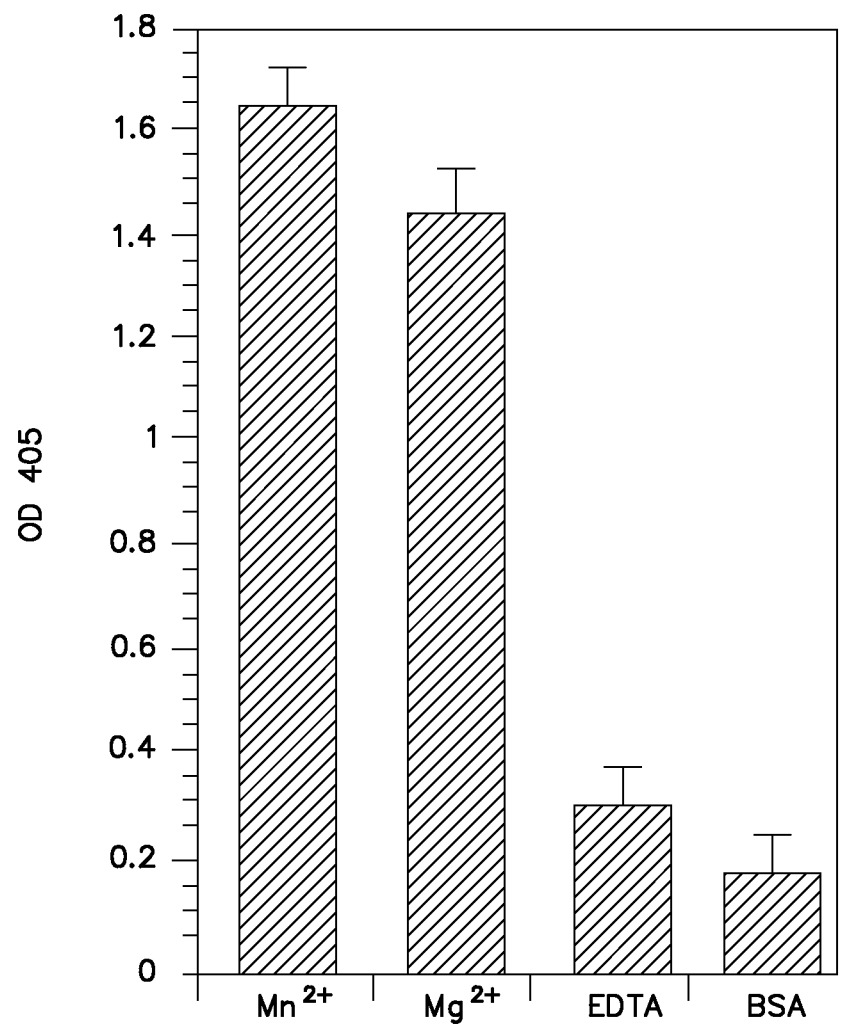

The human and rat (95% identity to human) α1-I domains were expressed in *E. coli* as GST-fusion proteins and purified over glutathione sepharose. Both proteins were examined for binding to collagen I and IV using a variation of an ELISA-based assay previously described (Qu, A., and Leahy, D. J. (1995) Proc. Natl. Acad. Sci. USA 92, 10277-10281). The human α1-I domain binds collagen IV with better efficiency than collagen I (FIG. 15A). An antibody specific to the α1-I domain, but not an antibody specific to the α2-I domain (FIG. 15B) abrogated binding to both ligands (data for collagen I is not shown). Both Mn$^{2+}$ and Mg$^{2+}$ stimulated binding, and EDTA reduced binding to background levels (FIG. 15C). No measurable differences in ligand binding were detected between the human and rat α1-I domains suggesting that the sequence differences between species are not functionally relevant (data not shown). Thus, the α1-I domain, specifically, require cation for efficient ligand binding.

Example 18

Figures 11A, 11B:
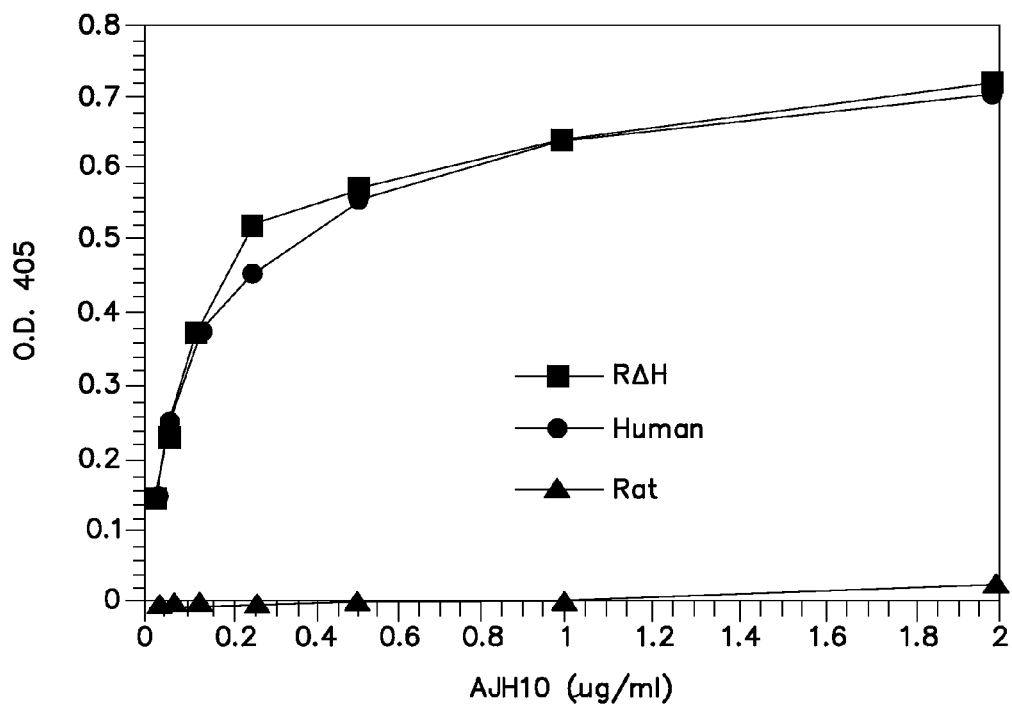
FIG. 11A-B. Location of the Epitope for the anti-α1 I domain Blocking mAbs.

A Cation-Dependent Epitope Resides near the MIDAS motif. We exploited the observation that AJH10 recognizes the human, but not the rat α1-I domain sequences to map the epitope for the α1β1 function-blocking mAbs. The human and rat sequences differ by only 12 amino acids, 4 of which lie in a stretch of 6 amino acids (aa 92-97, FIG. 11A) adjacent to the critical threonine (FIG. 11A, aa 98) within the MIDAS motif. To test the hypothesis that the 6 amino acid residues, Val-Gln-Arg-Gly-Gly-Arg (residues 91-96 of SEQ ID NO:64), comprise the epitope for the blocking mAbs, we constructed a chimeric I domain (RΔH), exchanging the rat residues G91, R92, Q93, and L96, for the corresponding human residues, V, Q, R, and R, respectively. AJH10, along with all the function-blocking mAbs, recognizes the chimeric I domain (RΔH; FIG. 11B).

To orient these residues with respect to the MIDAS domain in the tertiary structure of the α1-I domain, we modeled the α1-I domain using the coordinates of the crystal structure of the α2 I domain.

A homology model of the human α2 I-domain was built using the X ray crystal structure of the human α2 I-domain (Ward et al. (1989) Nature 341, 544-546). The model was built using the homology modeling module of Insight II (version 2.3.5; Biosym Technologies). The program CHARMM (Clackson et al. (1991) Nature 352, 624-628) was used with the all-hydrogen parameter set 22 with a distant dependent dielectric constant of two times the atom separation distance. We first did 1000 steps of steepest descent minimization with mass-weighted harmonic positional constraints of 1 kcal/(mol Å$^2$) on all atoms of the α1-I domain. This minimization was followed by another 1000 steps of steepest descent and 5000 steps of Adopted-Basis Newton Raphson with constraints of 0.1 kcal/(mol Å$^2$) on the C-α atoms of the α1-I domain to avoid significant deviations from the α2-I domain X-ray crystal structure.

The α1β1 and α2β1 integrin sequences exhibit 51% identity with no insertions or deletions, suggesting that the overall structure of the two I domains will be similar. The metal coordination site is predicted to be the same in the α1-I domain as in the α2-I domain, and the residues that comprise the epitope for the blocking mAbs lie on a loop between helix α3 and helix α4 which contains the threonine within the MIDAS motif critical for cation binding. The α1-I domain model predicts that the amide nitrogen of Q92 (FIG. 11A) hydrogen bonds with the carbonyl group of 133, the residue adjacent to S32. Thus, the loop that contains the epitope may play a functional role in stabilizing the MIDAS region.

Example 19

Monoclonal antibody AQC2 (i.e., mAQC2; "m" for murine) (Example 15, supra) is an IgG$_1$, kappa antibody. To identify the nucleotide sequences encoding the heavy and light chains of this antibody, total cellular RNA from AQC2 murine hybridoma cells was obtained by using a QIAGEN RNEASY midi kit in accordance with the manufacturer's instructions. Then cDNAs encoding the variable regions of the heavy and light chains were cloned by RT-PCR from total cellular RNA using a GIBCO BRL SUPERSCRIPT Preamplification System for First Strand cDNA Synthesis following the manufacturer's recommended protocol. Random hexamers were used for priming.

The heavy chain variable domain of mAQC2 was amplified by PCR from the first strand cDNA with the primers: 5' TGA GGA GAC GGT GAC CGT GGC CCT TGG CCC C 3' (SEQ ID NO:11) and 5' AGG TSM ARC TGC AGS AGT CWG G 3' (S=C/G, M=A/C, R=A/G, and W=A/T) (SEQ ID NO:12). The PCR was subjected to 30 cycles using Clontech's Advantage Taq polymerase: denature 30 sec at 94° C., anneal 1 min at 50° C., and elongate 1.5 min at 68° C. The mAQC2 light chain with its signal sequence was amplified by PCR using the primers: 5' ACT AGT CGA CAT GGA TTT WCA GGT GCA GAT TWT CAG CTT C 3' (W=A/T) (SEQ ID NO:13) and 5' ACT GGA TGG TGG GAA GAT GGA 3' (SEQ ID NO:14). The PCR was subjected to 30 cycles using Stratagene's cloned Pfu polymerase: denature 1 min at 94° C., anneal 1 min at 50° C., and elongate 2 min at 72° C. The PCR products for the heavy and light chains were gel-purified using a QIAGEN QIAQUICK gel extraction kit following the manufacturer's recommended protocol.

Purified heavy chain product was subcloned into Invitrogen's pCR2.1-TOPO TA vector using its TOPO TA cloning kit. Purified light chain was subcloned into Invitrogen's pCRbluntIITOPO vector using its Zero blunt TOPO cloning kit following the manufacturer's recommended protocol. Inserts from multiple independent subclones were sequenced. With the exception of degenerate positions within the PCR primers, the insert sequences of the independent subclones were identical.

The polypeptide sequences of mAQC2 were deduced from their coding sequences. The N-terminal amino acid sequence for the mature light chain predicted by the cDNA sequence from the PCR product amplified with a signal sequence exactly matched the N-terminal sequence of purified mAQC2 light chain derived from Edman degradation (DVKVVESGG; SEQ ID NO:15). BLAST analyses of the variable domain sequences confirmed their immunoglobulin identity.

The polypeptide sequence of the light chain variable domain of mAQC2 is shown below:

```
                                          (SEQ ID NO: 1)
  1  QIVLTQFPAL MSASPGEKVT MTCSASSSVN HMFWYQQKPK

41  SSPKPWIYLT SNLASGVPAR FSGSGSGTSY SLTISSMEAE

81  DAATYYCQQW SGNPWTFGGG TKLEIK 106
```

The CDRs are shown in boldface. The CDRs are defined according to Kabat et al., Sequences of Proteins of Immunological Interest, 5th Edition, The United States Department of Health and Human Services, The United States Government Printing Office, 1991. Using the Kabat numbering system, SEQ ID NO:1 is represented as follows, where a dash denotes the absence of an amino acid:

```
  1  QIVLTQFPAL MSASPGEKVT MTCSASS-SV NHMFWYQQKP

41  KSSPKPWIYL TSNLASGVPA RFSGSGSGTS YSLTISSMEA

81  EDAATYYCQQ WSGNPWTFGG GTKLEIK 107
```

The polypeptide sequence of the heavy chain variable domain of mAQC2 is:

```
                                          (SEQ ID NO: 2)
  1  DVKVVESGGG LVKPGGSLKL ACAASGFSFS RYTMSWVRQI

41  PEKRLEWVAT ISGGGHTYYL DSVKGRFTIS RDNAKNTLYL

81  QMSSLRSEDT AMYYCTRGFG DGGYFDVWGQ GTTVTVSS
```

The CDRs are shown in boldface. Using the Kabat numbering system, SEQ ID NO:2 is represented as follows, where positions numbers are consecutive numerals unless otherwise indicated:

```
  1     DVKVVESGGG LVKPGGSLKL ACAASGFSFS RYTMSWVRQI

41     PEKRLEWVAT ISGGGHTYYL DSVKGRFTIS RDNAKNTLYL

81     QM 82a-c  SSL

83     RSEDTAMY YCTRGFGDGG 100a-b  YF

101    DVWGQGTTVT VSS 113
```

As used herein, residue position numbers of variable domains are designated in accordance with the Kabat numbering system unless otherwise indicated.

Example 20

This example describes the generation of a murine-human chimeric antibody, chAQC2.

The cDNAs encoding the variable regions of the mAQC2 heavy and light chains were used to construct chAQC2 expression vectors, in which the mAQC2 variable regions were linked to human IgG$_1$ and kappa constant regions.

The heavy chain chimera was constructed as follows. A 0.33 kb PstI-BstEII fragment from the mAQC2 heavy chain plasmid pAND083 was subcloned into the phosphatased 2.82 kb PstI-BstEU vector fragment from the 5a8 heavy chain plasmid pLCB7, so as to add a murine heavy chain signal-encoding sequence and a murine splice donor site to the cDNA of the mAQC2 heavy chain variable region. 5a8 is a molecularly cloned CD4-specific mAb (see, e.g., Boon et al., 2002, Toxicology 172:191-203). In the mature heavy chain encoded by the resultant plasmid (pAND092), the N-terminus differed by five residues from the N-terminus (DVKVVE; SEQ ID NO:16) of the cognate mAQC2 heavy chain.

To correct the heavy chain N-terminus, pAND092 was subjected to unique site elimination (USE) mutagenesis using an USE mutagenesis kit (Amersham Pharmacia Biotech) following the manufacturer's recommended protocol. The Q1D, Q3K, L4V, QSV, Q6E substitutions were encoded by the mutagenic primer 5' GCA CCA GGT GCC CAC TCC GAC GTC AAG GTG GTG GAG TCA GGG GGA GGC TTA GTG 3' (SEQ ID NO:17). Mutated plasmid clones were identified by their new AatII and HinfI sites and eliminated PstI site. The heavy chain coding sequence was then confirmed by DNA sequencing. The correctly mutated plasmid was called pAND094. The 0.43 kb NotI-HindIII fragment from pAND094 and the 1.21 kb HindIII-NotI fragment from the plasmid pEAG964 (containing a coding sequence for a human IgG$_1$ constant region) were subcloned into the NotI site of pCH269, a plasmid derived from the pCEP4 EBV expression vector (Invitrogen). The resultant plasmid was named pAND099.

The light chain chimera was generated as follows. A 0.46 kb EcoRI fragment from the mAQC2 light chain variable domain plasmid pAND081 was subcloned into the phosphatased 2.7 kb vector fragment of the pUC-derived pNN09 cloning vector, to add a 5' NotI site. The resulting plasmid, pAND091, was subjected to mutagenesis using the Amersham USE kit (supra) to introduce a BglII site at the 3' end of the coding sequence.

The mutagenic primer had the sequence 5' GGA GGC ACC AAG CTG GAG ATC TAA CGG GCT GAT GCT GC 3' (SEQ TD NO: 18). The correctly mutated plasmid was identified by its BglII and BstYI site changes. The light chain coding sequence in the resultant plasmid pAND093 was confirmed by DNA sequencing. Then the 0.44 kb NotI-BglII light chain variable domain fragment from pAND093 and the 0.68 kb BclI-Nod fragment from the plasmid pEAG963 (containing a coding sequence for a human kappa light chain constant domain) were subcloned into the NotI site of pCH269 (supra), producing plasmid pAND102. To create an unblocked kappa light chain (Q1E), pAND093 was subjected to USE mutagenesis with the mutagenic primer 5' CAT MT GTC CAG GGG AGA AAT TGT TCT CAC CCA G 3' (SEQ ID NO:19), to introduce an XmnI site. The mutated plasmid was identified by screening for an XmnI site change. The light chain sequence in the resultant plasmid pAND097 was confirmed by DNA sequencing. The 0.44 kb NotI-BglII light chain variable domain fragment from pAND097 and the 0.68 kb BclI-NotI fragment from the plasmid pEAG963 (containing a human kappa light chain constant domain) were subcloned into the NotI site of pCH269, producing plasmid pAND098.

To generate chAQC2 antibodies, expression vectors (chAQC2 heavy chain vector pAND099-I chAQC2 light chain vector pAND102, and chAQC2 heavy chain vector pAND099+chAQC2 unblocked light chain vector pAND098) were co-transfected into 293-EBNA cells. The transfectants were tested for antibody secretion and specificity. The controls were cells transfected with the corresponding vectors without an insert or with DNA constructs encoding ch5c8 (a molecularly cloned CD154-specific mAb described in, e.g., Elster et al., 2001, Transplantation 72:1473-1478) or chCBE11 (a molecularly cloned LTβR-specific mAb described in, e.g., Browning et al., 1996, J. Biol. Chem. 271:24934-24938).

Then transfectants with the desired antibody secretion were lysed, and protein A immunoprecipitation was performed on the lysates and conditioned medium. Western blot analysis of the precipitates performed with anti-human heavy and light chain antibodies indicated that chAQC2-transfected cells synthesized and efficiently secreted heavy and light chains at levels similar to ch5c8-transfected and chCBE11-transfected cells. Further, huVLA-1-expressing K562α1 cells were stained with the conditioned medium from the transfected cells, and FACS analysis was performed on the stained cells. The results indicated that the chAQC2 antibody produced staining patterns similar to those of mAQC2, while conditioned media from mock-transfected and ch5c8-transfected cells failed to stain K562α1 cells. Chimeric AQC2 produced from scaled-up transient transfection was purified and shown to bind to VLA-1 by FACS titration. Chimeric AQC2 with either a wildtype or a genetically unblocked light chain bound to VLA-1. See also FIGS. 16A-D (discussed below).

Example 21

This example describes a method of humanizing the mAQC2 monoclonal antibody.

Analysis of the mAQC2 variable domains. The variable domains in the light and heavy chains of mAQC2 were compared with the consensus sequences for mouse and human subgroups (Kabat et al, supra) using the software program FASTA. The light chain variable domain was found to be a member of mouse subgroup VI with 89% identity in a 109 amino acid overlap. This domain also corresponded to human subgroup I with 72% identity in a 113 amino acid overlap. The heavy chain variable domain was found to be a member of mouse subgroup IIId with 86% identity in a 129 amino acid overlap. This heavy chain variable domain also corresponded to human subgroup III with 79% identity in a 130 amino acid overlap.

The CDRs were categorized into canonical classes according to Chothia et al., Nature 342, pp. 877-883 (1989). The key residues defining each canonical class determine to a large extent the structural conformation of the CDR loop, and thus should be retained in the reshaped antibody. The L1 loop of mAQC2 fell into canonical class 1 (10 residue loop), L2 into class 1 (7 residue loop) and L3 into class 1 (9 residue loop). The H1 loop fell into class 1 (5 residue loop) and the H2 loop into class 1 (16 residue loop) residues. The H3 loop did not seem to belong to any canonical class. The canonical residues important for these classes were all included in the humanized antibodies.

Unusual framework residues in mAQC2 were determined by analyzing all mouse and human variable chain sequences in the September 1999 version of the Kabat database. It was believed that mAQC2-specific differences might indicate somatic mutations that enhance binding affinity if these differences were close to the binding site. Unusual mAQC2 residues further away from the binding site and unusual human framework residues were removed in case they would create immunogenic epitopes in the humanized antibody. Unusual framework residues found in mAQC2 were 7(F), 10(L), and 41(K) in the light chain; and 4(V), 21(A), and 40(I) in the heavy chain. None of these unusual mouse framework residues were retained the humanized antibodies.

Modeling the structure of the variable regions. The light and heavy chains of mAQC2 were aligned against a nonredundant database to determine which structural frames to use to construct three-dimensional models of the mAQC2 light and heavy chains. Using FASTA, the light chain was found to have 82% sequence identity to monoclonal murine antibody ab57 (1CLOL), whereas the heavy chain was found to have 76% sequence identity to murine 6d9 Fab fragment (1HYY). Using the molecular modeling software package SYBYL (Tripos Inc.), the approximate three dimensional structures of the mAQC2 light and heavy chains were built using the light chain of ab57 and the heavy chain of 6d9, respectively. The structural integrity of the models was assessed at the console and was found to be reasonable.

Design of the reshaped variable regions. Two approaches were used to choose human acceptor frameworks to "accept" mAQC2's CDRs. The first approach was by homology matching and the other by using consensus human Ig sequences. Under the homology approach, the Kabat database, the nonredundant database from NCBI, ENTREZ (The National Institutes of Health), and the Incyte database were searched using the software programs FASTA and BLAST. The choice of human acceptor frameworks was made based on sequence identity between mAQC2 frameworks and human frameworks (excluding frameworks from previously humanized antibodies) and the source of the antibody.

The frameworks from an immunoglobulin variable region gene having a GENBANK accession number of gi:587330 (human kappa subgroup I Vκ-1c147) were eventually chosen for the light chain of the humanized antibody (Welschof et al., J. Immunol. Meth. 179:203-14 (1995)). The frameworks from Amu1c11 (Kabat ED 044469; human subgroup III) were chosen for the heavy chain of the humanized antibody (Huang et al., J. Immunol. 151:5290-300 (1993)).

Back mutations of the human frameworks. Strategies for determining which back mutations to make are available on the Humanization by Design web sites under mirrored urls on the worldwide web at mathbio.nimr.mrc.ac.uk/jsaldan and cryst.bbk.ac.uk/~ubcg07s. Previous experiments have shown that it is important to retain canonical residues, interface packing residues and unusual murine residues that are close to the binding site. In addition, residues in the "Vernier Zone," which forms a platform on which the CDRs rest (Foote et al., J. Mol. Biol. 224, p. 487 (1992)) and those close to CDR H3 should be considered.

Four reshaped versions were designed for each of the variable light and heavy chains, as shown in Table 1. Two of the four versions for each chain were designed by homology matching (designated huAQC2-h1 and -h2) and the other two versions by consensus matching (huAQC2-c1 and c2). It should be noted that the sequences for huAQC-h1 heavy chain and huAQC-c1 heavy chain are identical.

TABLE 1

Sequences of mAQC2, huAQC2, and human frameworks

LIGHT CHAIN

| | FR1 |
|---|---|
| Vk-1c147 | D--M---S-SSL---V-DR--I--* |
| huAQC2-h2 | ------S-SSL---V-DR--I-- |
| huAQC2-h1 | ------S-SSL---V-DR--I-- |
| mAQC2 | QIVLTQFPPALMSASPGEKVTMTC |
| huAQC2-c1 | --Q---S-SSL---V-DR--I-- |
| huAQC2-c2 | --Q---S-SSL---V-DR--I-- |

| | CDR1 | FR2 |
|---|---|---|
| Vk-1c147 | R---Q-ISYLN | ------GKA--LL-- |
| huAQC2-h2 | ---------------- | ------GKA--LL-- |
| huAQC2-h1 | ---------------- | ------GKA-------- |
| mAQC2 | SASSSVNHMF | WYQQKPKSSPKPWIY |
| huAQC2-c1 | ---------------- | ------GKA-------- |
| huAQC2-c2 | ---------------- | ------GKA --LL-- |

| | CDR2 | FR3 |
|---|---|---|
| Vk-1c147 | AA-S-Q- | ---S---------DFT-----LQP--F----- |
| huAQC2-h2 | ------- | ---S---------D -T------LQP--F----- |
| huAQC2-h1 | ------- | ---S---------D -T------LQP--F----- |
| mAQC2 | LTSNLAS | GVPARFSGSGSGTSYSLTISSMEAEDAATYYC |
| huAQC2-c1 | ------- | ---S---------D -T-----LQP--F----- |
| huAQC2-c2 | ------- | ---S---------D -T-----LQP--F----- |

| | CDR3 | FR4 | Framework Changes |
|---|---|---|---|
| Vk-1c147 | --SYST-L- | ------V--- | 25 |
| huAQC2-h2 | ------- | ------V--- | 21 |
| huAQC2-h1 | ------- | ------V--- | 19 |
| mAQC2 | QQWSGNPWT | FGGGTKLEIK** | 0 |
| huAQC2-c1 | ------- | --Q---V--- | 21 |
| huAQC2-c2 | ------- | --Q---V--- | 23 |

SEQ ID NOs: 65, 51, 49, 1, 66, and 54, respectively, in order of appearance.

HEAVY CHAIN:

| | FR1 | CDR1 |
|---|---|---|
| AMU1C11 | E-QL-------IQ-----R-S------TV- | SNY-- |
| huAQC2-h2 | E-QL-------IQ-----R-S------T-- | ----- |
| huAQC2-h1 | ---QL--------Q-----R-S--------- | ----- |
| mAQC2 | DVKVVESGGGLVKPGGSLKLACAASGFSFS | RYTMS |
| huAQC2-c1 | ---QL--------Q-----R-S--------- | ----- |
| huAQC2-c2 | E-QL--------Q-----R-S--------T-- | ----- |

| | FR2 | CDR2 |
|---|---|---|
| AMU1C11 | ----A-G-G----S | V-YS-S---A---------------- |
| huAQC2-h2 | ----A-G-G------ | -------------------------- |
| huAQC2-h1 | ----A-G-G------ | -------------------------- |

TABLE 1-continued

```
mAQC2       WVRQIPEKRLEWVA      TISGGGHTYYLDSVKG
huAQC2-c1   ----A-G-G------     --------------------------------
huAQC2-c2   ----A-G-G------     --------------------------------
```

```
            FR3                                          CDR3

AMU1C11     --------S---------N---A----V---AS            IRFLEWS--Y
huAQC2-h2   --------S---------N---A----V-------          ----------------
huAQC2-h1   --------S---------N---A----V-------          ----------------
mAQC2       RFTISRDNAKNTLYLQMSSLRSEDTAMYYCTR             GFGDGGYFDV
huAQC2-c1   --------S---------N---A----V-------          ----------------
huAQC2-c2   --------S---------N---A----V-------          ----------------
```

```
            FR4                 Framework changes

AMU1C11     -----L-----         20
huAQC2-h2   -----L-----         16
huAQC2-h1   -----L-----         13
mAQC2       WGQGTTVTVSS***      0
huAQC2-c1   -----L-----         13
huAQC2-c2   -----L-----         15
```

*Dashes indicate identity with the mAQC2 amino acid sequence.
*Part of SEQ ID NO: 1.
***Part of SEQ ID NO: 2.
SEQ ID NOs: 67, 44, 42, 2, 42 and 68, respectively, in order of appearance.

Some of the back mutations are discussed below.
(1) Light Chain:
  1 D->Q This mutation was made in all versions since previous reshaping experiments (e.g. Kolbinger et al, Protein Eng. 6, p. 971 (1993)) suggested its importance for antigen binding.
  4 M->L This is a vernier residue and was retained in all versions,
  46 L->P This residue is both an interfacial and vernier residue and was retained only in h1 and c1.
  47 L->W This is a vernier residue and was retained only in h1 and c1.
  71 F->Y This residue is in an important canonical position and was retained in all versions.
(2) Heavy Chain:
  1 E->D This back mutation was made in h1 (i.e., c1) only.
  12 I->V The residue I is unusual in human and was retained in the h2 only.
  28 T->S This is a vernier residue and was retained in h1 only.
  29 V->F This is a canonical residue and was retained in all versions.
  49 S->A This is a vernier residue and was retained in all versions.
  93 A->T This is a vernier residue and interfacial and was retained in all versions.
  94 S->R This is a canonical residue and was retained in both versions.

The huAQC2 variable regions were made by USE mutagenesis as described above, using the chAQC2 variable domain plasmids as starting templates. The human acceptor framework ("FR") cDNA sequences were Kabat #Z37334 for the light chain and Kabat #U00490 for the heavy chain. To facilitate identification of mutated plasmids, silent mutations were introduced to change restriction sites. Mutated plasmids were identified by the restriction site changes. The variable region cDNA sequences in the resultant plasmids were confirmed by DNA sequencing.

The h1 and c1 versions of heavy chain (which were identical) were made by using plasmid pAND094 as template. The mutagenic primers were: FR1 primer 5'GGT GCC CAC TCC GAC GTC CAG CTG GTC GAG TCA GGG GGA GGC TTA GTC CAC CCT GGA GGG TCC CTG AGA CTC TCC TGT GCA GCC TCT GGA TTC 3' (SEQ ID NO:20), which introduced TaqI and PvuII sites, and eliminated a DdeI site; FR2 primer 5' ATG TCT TGG GTT CGC CAG GCT CCG GGG AAG GGG CTG GAG TGG GTC GCA ACC 3' (SEQ ID NO:21), which introduced a NciI site, and eliminated BspEI and EarI sites; FR3 primer 5' TTC ACC ATC TCC AGA GAC AAT TCC AAG AAC ACC CTG TAC CTG CAG ATG AAC AGT CTG AGG GCC GAG GAC ACA GCC GTG TAT TAC TGT ACA AGA 3' (SEQ ID NO:22), which introduced PstI and DdeI sites; and FR4 primer 5' TGG GGC CAA GGT ACC CTG GTC ACC GTC TCC TCA GGT GAG 3' (SEQ ID NO:23), which introduced KpnI and Eco0109I sites. The resultant h1 (i.e., c1) heavy chain plasmid was designated pAND104.

The c2 version of heavy chain were made by using pAND104 as template with the following mutagenic primers: FR1 primer 5' TCC TGT GCA GCC TCT GGA TTC ACC TTC AGT AGG TAT ACT ATG TCT TGG GTT 3' (SEQ ID NO:24), which introduced an AccI site; and FR1 primer 5' GCA CCA GGT GCG CAC TCC GAG GTC CAG CTG GTC GAG TCA 3' (SEQ ID NO:25), which introduced an FspI site and eliminated an AatII site. The resultant c2 heavy chain plasmid was designated pAND115.

The h2 version of heavy chain were made by using pAND115 as template with the following primer: FR1 primer 5' GAG TCA GGG GGA GGC TTA ATC AGC CCT GGA GGG TCC CTG 3' (SEQ ID NO:26), which eliminated a DdeI site. The resultant h2 heavy chain plasmid was designated pAND113.

To generate expression vectors for the huAQC2 heavy chains, the 0.43 kb NotI-HindIII heavy chain variable domain fragment from pAND104, pAND115, or pAND113, and the 1.21 kb HindIII-NotI fragment from pEAG964 (supra) were subcloned into the NotI site of pCH269 (supra). The resultant heavy chain expression plasmids were designated pAND114 (h1), pAND121 (c2), and pAND124 (h2), respectively.

The h1 version of light chain were made by using plasmid pAND093 as template. The mutagenic primers were: FR1 primer 5' CAA ATT GTT CTC ACC CAG TCT CCA TCC TCC CTG TCT GCG TCT GTA GGG GAC AGA GTC ACC ATC ACA TGC AGT GCC AGC TCA 3' (SEQ ID NO:27), which removed BstEII and PstI sites; FW primer 5' TTC TGG TAT CAG CAG AAG CCC GGG AAA GCC CCC AAA CCC TGG ATT 3' (SEQ ID NO:28), which introduced an NciI site; FR3 primer 5 GCT TCT GGA GTC CCT TCA CGC TTC AGT GGC AGT GGG TCT GGG ACA GAT TAC ACT CTC ACA ATC AGC AGC CTG CAA CCT GAA GAT TTT GCC ACT TAT TAC TGC CAG 3' (SEQ ID NO:29), which introduced a DdeI site and eliminated Eco0109I and AvaII sites; and FR4 primer 5S GGT GGA GGC ACT AAG GTG GAG ATC TAA CGG GCT 3' (SEQ ID NO:30), which introduced DdeI and StyI sites. The resultant h1 light chain plasmid was designated pAND103.

The h2 version of light chain were made by using pAND103 as template with the following primer: FR2 primer 5' CCC GGG AAA GCG CCC AAA CTC CTG ATT TAT CTC ACA TCC 3' (SEQ ID NO:31), which introduced HhaI and HaeII sites. The resultant h2 light chain plasmid was designated pAND116.

The c1 version of light chain used plasmid pAND103 template with the following primers: FR1 primer 5' GCC TCA GTC ATA ATG TCC CGG GGA CAA ATT CAG CTC ACC CAG TCT CCA TCC 3' (SEQ ID NO:32), which introduced SmaI, NciI, and HpaII sites; FR4 primer 5' GGT AAC CCG TGG ACG TTC GGT CAG GGC ACT AAG GTG GAG ATC TAA CGG GCT 3' (SEQ ID NO:33), which introduced a Bsp1286I site. The resultant c1 light chain plasmid was designated pAND118.

The c2 version of light chain were made by using plasmid pAND116 template with the following primers: FR1 primer 5' GCC TCA GTC ATA ATG TCC CGG GGA CAA ATT CAG CTC ACC CAG TCT CCA TCC 3' (SEQ ID NO:34), which introduced SmaI, NciI, and HpaII sites; FR4 primer 5' GGT AAC CCG TGG ACG TTC GGT CAG GGC ACT AAG GTG GAG ATC TAA CGG GCT 3' (SEQ ID NO:35), which introduced a Bsp1286I site. The resultant c2 light chain plasmid was designated pAND119.

To generate expression vectors for the huAQC2 light chains, the 0.44 kb NotI-BglII light chain variable domain fragment from pAND103, pAND116, pAND118, or pAND119, and the 0.68 kb BclI-NotI fragment from pEAG963 (supra) were subcloned into the NotI site of pCH269 (supra). The resultant light chain expression vectors were designated pAND117 (h1), pAND120 (h2), pAND122 (c1), and pAND123 (c2), respectively.

The expression vectors were co-transfected into 293-EBNA cells, and transfected cells were tested for antibody secretion and specificity. Cells transfected with an empty vector served as negative control. The whole cell lysates and the conditioned medium were immuno-precipitated with protein A. Western blot analysis of the precipitates (developed with anti-human heavy and light chain antibodies) indicated that huAQC2-transfected cells synthesized and efficiently secreted heavy and light chains at levels similar to chAQC2-transfected cells.

FACS analysis of VLA-1 expressing K 562α1 cells stained with conditioned medium from the transfected cells was then performed. To do so, the K562α1 cells were incubated with the conditioned medium on ice for 120 min. The cells were then washed three times with a FACS buffer (PBS with 5% FBS and 0.05% sodium azide). The washed cells were resuspended in the buffer and incubated with PE-conjugated anti-human IgG (H+L) (Jackson ImmunoResearch Laboratories, Inc.) on ice for 30 min on ice. After the incubation, the cells were washed three times with the FACS buffer, and resuspended in the FACS buffer for analysis. The data are shown in Table 2, in which HuAQC2-h1 refers to an mAb consisting of the h1 version of the huAQC2 heavy chain (HC) and the h1 version of the huAQC2 light chain (LC) (see Table 1). Likewise, huAQC-h2 is an mAb consisting of the h2 versions of the heavy and light chains, huAQC2-c1 the c1 versions, and huAQC2-c2 the c2 versions. In the table, relative MFI refers to mean MFI normalized to that observed for chAQC2 blocked. Data shown represents the average from two independent transfections. These data indicated that the huAQC2-h2 and -c2 mAbs bound less well than huAQC2-h1 and -c1 relative to chAQC2.

TABLE 2

FACS staining of K562α1 cells by chAQC2 and huAQC2

|  | Light chain | Heavy chain | Relative MFI |
|---|---|---|---|
| chAQC2 | pAND102 | pAND099 | 1.00 |
| huAQC2-h1 | pAND117 | pAND114 | 1.50 |
| huAQC2-h2 | pAND120 | pAND124 | 0.64 |
| huAQC2-c1 | pAND122 | pAND114 | 1.50 |
| huAQC2-c2 | pAND123 | pAND121 | 0.68 |
| huAQC2 LC c1/HC c2 | pAND122 | pAND121 | 2.21 |
| huAQC2 LC c2/HC c1 | pAND123 | pAND114 | 0.76 |
| huAQC2 LC unblocked c1/HC c2 | pAND150* | pAND121 | 0.75 |
| huAQC2 LC L46P c2/HC c2 | pAND133** | pAND121 | 1.50 |
| huAQC2 LC L47W c2/HC c2 | pAND132*** | pAND121 | 1.00 |

*It encodes huAQC2 LC c1 with an unblocked N-terminus Q1D.
**It encodes huAQC2 LC c2 with L46P.
***It encodes huAQC2 LC c2 with L47W.

Co-transfections of 293-EBNA cells with chAQC2 and huAQC2h1, -h2, -c1 and -c2 were scaled up. Antibodies in the conditioned media were purified with Protein A-Sepharose. Purified mAbs were assayed by FACS for activity. The protocol as follows.

1. Count cells from flask that was split 1:4 on the day prior to the assay.
2. Pellet cells and resuspend at 2.5e5 cells/ml in FACS buffer (5% FBS in PBS with 0.02% NaAzide).
3. Pipette 100 µl of cells into the wells of a 96 well V bottom plate.
4. Prepare 1:3 serial dilutions of AQC2 starting at 3 µg/ml in FACS buffer.
5. Pellet the cells for 5 minutes at 800×g and flick plate to remove buffer.
6. Resuspend the cells in 100 µl of the diluted antibody series.
7. Incubate for 2 hours on ice.
8. Wash plate. Pellet the cells for 3 minutes at 800×g and flick plate to remove buffer.
9. Resuspend the cells in 100 µl of secondary antibody (diluted 1:100 in FACS buffer).
10. Incubate for 30 minutes on ice.
11. Wash plate (see above).
12. Resuspend cells in 25 µl of FACS buffer.
13. Centrifuge the FACS tubes briefly to ensure that the 50 µl is in the bottom of the tubes.
14. Vortex each tube vigorously and collect 5000 events.

Figure 17:
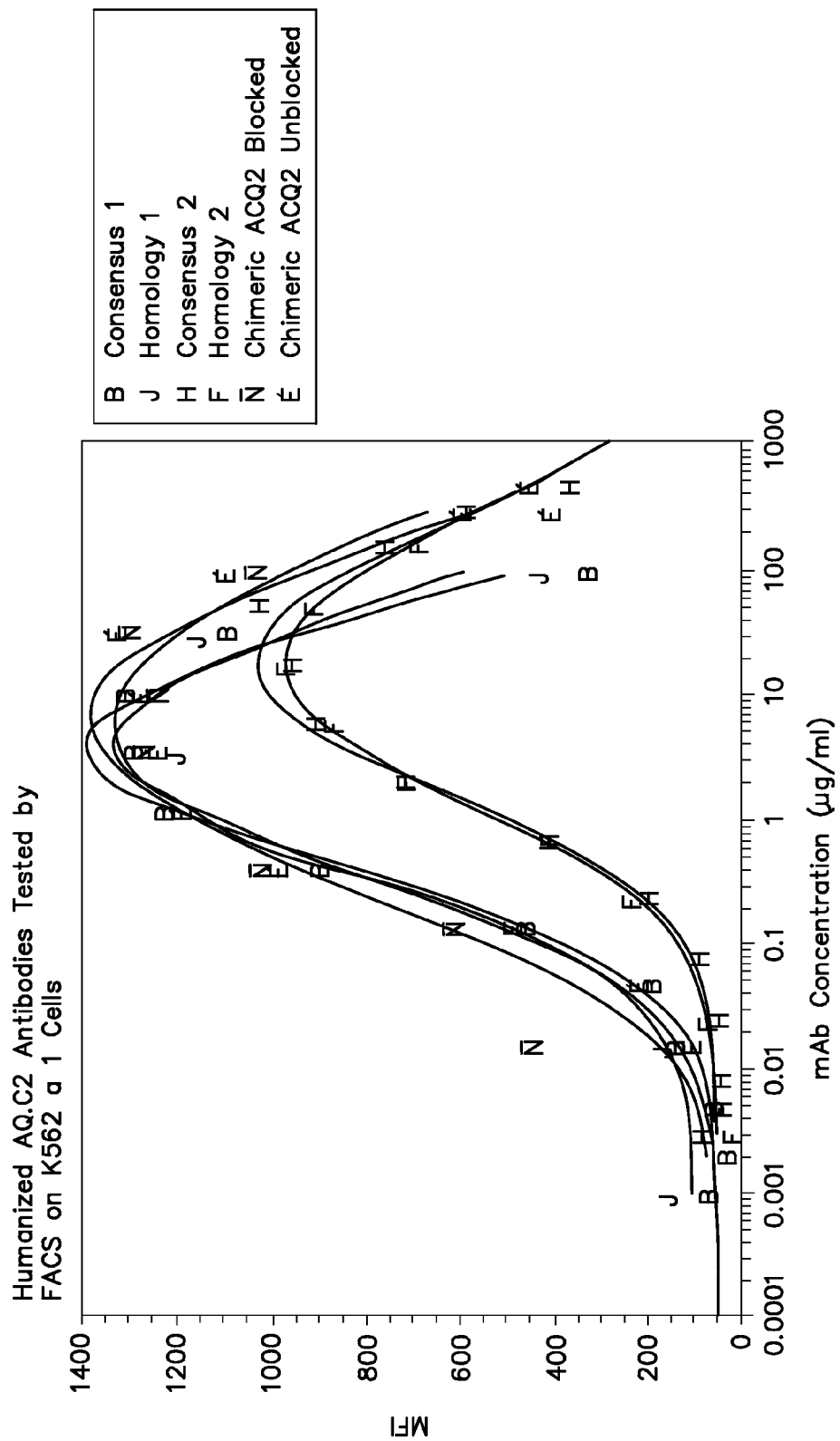
FIG. 17. Characterization of Humanized AQC2 Forms by FACS.

The data are shown in FIG. 17. These data confirmed that huAQC2-h2 and -c2 bound less well than huAQC2-h1 and c1 relative to chAQC2.

The consensus versions of huAQC2 were studied further because they would be less immunogenic when used to treat patients with chronic indications. Mix-and-match cotransfections were performed to identify whether a single chain was responsible for the apparent decrease in binding seen with huAQC2-c2. The co-transfections suggested that the reduction could be attributed to the c2 light chain (encoded by pAND123), which differed from the c1 light chain (encoded by pAND122) at only two residues in the FR region: P46L and W47L.

To examine the individual contributions of each of these two changes, new c2 light chain expression vectors were constructed. Plasmid pAND125, the L47W variant of the c2 light chain was made using pAND119 as a template with the following mutagenic primer: FR2 primer 5' GGG AAA GCA CCC AAA CTC TGG ATC TAT CTC ACA TCC AAC 3' (SEQ ID NO:36), which introduced HhaI and HaeII sites. Plasmid pAND126, the L46P variant of the c2 light chain, was made by using pAND119 as a template with the following mutagenic primer: FR2 primer 5' AAG CCC GGG AAG GCG CCC AAA CCC CTG ATT TAT CTC ACA TCC AAC 3' (SEQ ID NO:37), which introduced BsaHI, BanI, and NarI sites. Expression vectors for these new huAQC2 light chains were made by subcloning the 0.44 kb NotI-BglII light chain variable domain fragment from pAND125 or pAND126, and the 0.68 kb BclI-NodI fragment from pEAG963 (supra) into the NotI site of pCH269 (supra). The resultant plasmids were designated pAND132 (c2 with L47W) (SEQ ID NO:47), and pAND133 (c2 with L46P) (SEQ ID NO:70), respectively.

Co-transfections of the new light chain plasmids with each of the huAQC2 heavy chain plasmids were performed. VLA-1 binding was examined by FACS. The data demonstrate that the L47W back mutation failed to improve binding. The L46P mutation improved the peak of the binding curve, but the EC50 was still right-shifted relative to the behavior of huAQC2 version 1 (Table 2, supra). These results suggested that both back mutations were needed for full binding activity.

A genetically unblocked c1 light chain was also made, since the Q1D variant would be one residue more "humanized." The Q1D mutant, designated pAND148, was made with the template pAND118 with the following mutagenic primer: FR1 primer 5' GTC ATA ATG TCC CGG GGA GAT ATC CAG CTC ACC CAG TCT 3' (SEQ ID NO:38), which introduced a new EcoRI site and removed an ApoI site. An expression vector for this last variant of the huAQC2 light chain was made by subcloning the 0.44 kb NotI-BglII light chain variable domain fragment from pAND148 and the 0.68 kb BclI-NotI fragment from pEAG963 into the NotI site of pCH269, producing the light chain expression vector pAND150 (c1 with unblocked N-terminus Q1D). Co-expression of the genetically unblocked light chain with the c2 heavy chain (i.e., "huAQC2 LC c1 unblocked/HC c2"; designated huAQC2c4) was equivalent to that of "huAQC2 LC c1/HC c2" (designated as huAQC2-c3). VLA-1 binding was confirmed by FACS on VLA1-expressing K562α1 cells (Table 2).

Figure 18:
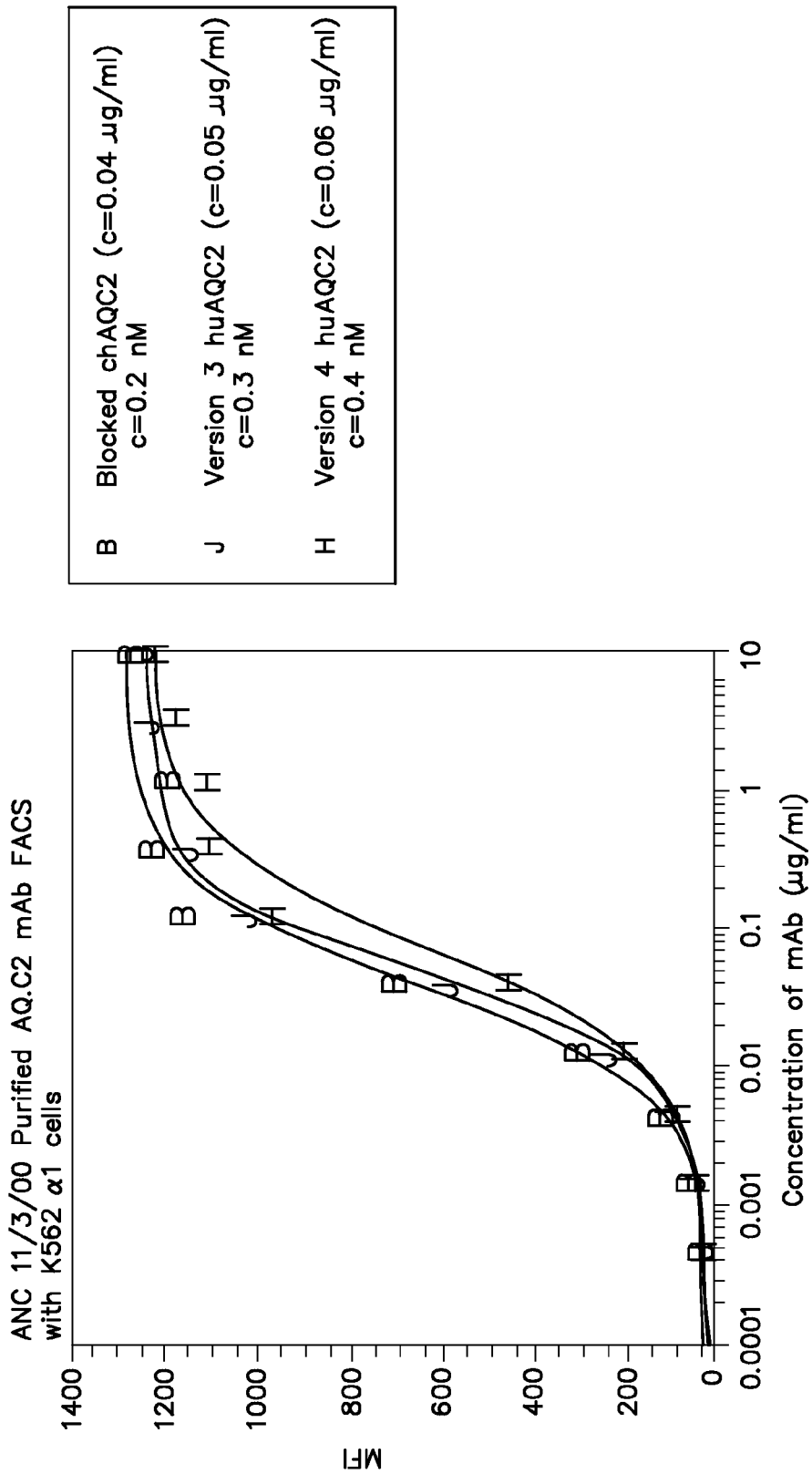
FIG. 18. Characterization of Humanized AQC2 Forms by FACS.

Co-transfections of 293EBNA cells with chAQC2 and huAQC2h1, -h2, -c1, -c2, -c3, and -c4 Antibodies in the conditioned media were purified on Protein A-Sepharose. The purified mAbs were assayed for activity (FIGS. 17 and 18). HuAQC2-c3 was chosen as the drug candidate, since its properties were more similar to chAQC2. Vectors were then designed for stable expression of huAQC2-c3 in CHO cells. The vectors contained a cDNA for the huAQC2 c1 LC or c2 HC, with the 5' and 3' UTRs eliminated and the heavy chain C-terminal lysine genetically deleted to ensure product homogeneity. The final vectors were pAND162 (light chain), pAND160 (heavy chain). As used herein, huAQC2-c3 is also called hAQC2.

The full polypeptide sequences of hAQC2 are as follows.
Light Chain (Plasmid: pAND162)

(SEQ ID NO: 3)
```
  1 QIQLTQSPSS LSASVGDRVT ITCSASSSVN HMFWYQQKPG
    KAPKPWIYLT
 51 SNLASGVPSR FSGSGSGTDY TLTISSLQPE DFATYYCQQW
    SGNPWTFGQG
101 TKVEIKRTVA APSVFIFPPS DEQLKSGTAS VVCLLNNFYP
    REAKVQWKVD
151 NALQSGNSQE SVTEQDSKDS TYSLSSTLTL SKADYEKHKV
    YACEVTHQGL
201 SSPVTKSNR GEC
```

Heavy Chain (Plasmid: pAND160) (SEQ ID NO:4)

(SEQ ID NO: 4)
```
  1 EVQLVFSGGG LVQPGGSLRL SCAASGFTFS RYTMSWVRQA
    PGKGLEWVAT
 51 ISGGGHTYYL DSVKGRFTIS RDNSKNTLYL QMNSLRAEDT
    AVYYCTRGFG
101 DGGYFDVNGQ GTLVTVSSAS TKGPSVFPLA PSSKSTSGGT
    AALGCLVKDY
151 FPEPVTVSWN SGALTSGVHT PPAVLQSSGL YSLSSVVTVP
    SSSLGTQTYI
201 CNVNHKPSNT KVDKKVEPKS CDKTHTCPPC PAPELLGGPS
    VFLFPPKPKD
251 TLMISRTPEV TCVVVDVSHE DPEVKFNWYV DGVEVHNAKT
    KPREEQYNST
301 YRVVSVLTVL HQDWLNGKEY KCKVSNKALP APIEKTISKA
    KGQPREPQVY
351 TLPPSRDELT KHQVSLTCLV KGFYPSDTAV EWESNGQPEN
    NYKTTPPVLD
401 SDGSFFLYSK LTVDKSRWQQ GNVFSCSVMH EALHNHYTQK
    SLSLSPG
```

Other heavy and light chain polypeptide and nucleotide sequences are shown below.

A. chAQC2 heavy chain (Pand099) (SEQ ID NOs:39 and 40. The former No refers to the nucleotide sequence and the latter to the polypeptide sequence. The same order is used in the following numbering.)

```
  1 GACGTCAAGGTGGTGGAGTCAGGGGGAGGCTTAGTGAAGCCTGGAGG
    GTCCCTGAAACTC  D V K V V E S G G G L V K P G G S
    L K L
```

```
 61 GCCTGTGCAGCCTCTGGATTCAGTTTCAGTAGATATACTATGTCTTG
    GGTTCGCCAGATT A C A A S G F S F S R Y T M S W
               V R Q I
121 CCGGAGAAGAGGCTGGAGTGGGTCGCAACCATTAGTGGTGGTGGTCA
    CACCTACTATCTA P E K R L E W V A T I S G G G H
               T Y Y L
181 GACAGTGTGAAGGGCCGATTCACCATCTCCAGAGACAATGCCAAGAA
    CACCCTGTACCTG D S V K G R F T I S R D N A K N
               T L Y L
241 CAAATGAGCAGTCTGAGGTCTGAGGACACAGCCATGTATTACTGTAC
    AAGAGGTTTTGGA Q M S S L R S E D T A M Y Y C T
               R G F G
301 GACGGGGGGTACTTCGATGTCTGGGGCCAAGGGACCACGGTCACCGT
    CTCCTCA D G G Y F D V W G Q G T T V T V S S
```

B. hAQC2 HC h1 and c1 (pAND114) (SEQ ID NOs:41 and 42)

```
  1 GACGTCCAGCTGGTCGACTCAGGGGGAGGCTTAGTCCAGCCTGGAGG
    GTCCCTGAGACTC D V Q L V E S G G G L V Q P G G
               S L R L
 61 TCCTGTGCACCCTCTGGATTCAGTTTCAGTAGATATACTATGTCTTG
    GGTTCGCCAGGCT S C A A S G F S F S R Y T M S W V
               R Q A
121 CCGGGGAAGGGGCTGGAGTGGGTCGCAACCATTAGTGGTGGTGGTCA
    CACCTACTATCTA P G K G L E W V A T I S G G G H T
               Y Y L
181 GACAGTGTGAAGGGCCGATTCACCATCTCCAGAGACAATTCCAAGAA
    CACCCTGTACCTG D S V K G R F T I S R D N S K N
               T L Y L
241 CAGATGAACAGTCTGAGGGCCGAGGACACAGCCGTGTATTACTGTA
    CAAGAGGTTTTGGA Q M N S L R A E D T A V Y Y C T
               R G F G
301 GACGGGGGGTACTTCGATGTCTGGGGCCAAGGTACCCTGGTCACCG
    TCTCCTCA D G G Y F D V W G Q G T L V T
               V S S
```

C. hAQC2 h2 heavy chain (pAND124) (SEQ ID NOs:43 and 44)

```
  1 GAGGTCCAGCTGGTCGAGTCAGGGGGAGGCTTAATCCAGCCTGGAGG
    GTCCCTGAGACTC E V Q L V E S G G G L I Q P G G
               S L R L
 61 TCCTGTGCAGCCTCTGGATTCACCTTCAGTAGGTATACTATGTCTTG
    GGTTCGCCAGGCT S C A A S G F T F S R Y T M S W
               V R Q A
121 CCGGGGAAGGGGCTGGAGTGGGTCGCAACCATTAGTGGTGGTGGTC
    ACACCTACTATCTA P G K G L E W V A T I S G G G H
               T Y Y L
181 GACAGTGTGAAGGGCCGATTCACCATCTCCAGAGACAATTCCAAGA
    ACACCCTGTACCTG D S V K G R F T I S R D N S K N
               T L Y L
241 CAGATGAACAGTCTGAGGGCCGAGGACACAGCCGTGTATTACTGTAC
    AAGAGGTTTTGGA Q M N S L R A E D T A V Y Y C T
               R G F G
301 GACGGGGGGTACTTCGATGTCTGGGGCCAAGGTACCCTGGTCACCG
    TCTCCTCAGG D G G Y F D V W G Q G T L V T V S S
```

D. hAQC2 c2 heavy chain (pAND121) (SEQ ID NOs:45 and 68)

```
  1 GAGGTCCAGCTGGTCGAGTCAGGGGGAGGCTTAGTCCAGCCTGGAG
    GGTCCCTGAGACTC E V Q L V E S G G G L V Q P G
               G S L R L
 61 TCCTGTGCAGCCTCTGGATTCACCTTCAGTAGGTATACTATGTCTT
    GGGTTCGCCAGGCT S C A A S G F T F S R Y T M S
               W V R Q A
121 CCGGGGAAGGGGCTGGAGTGGGTCGCAACCATTAGTGGTGGTGGT
    CACACCTACTATCTA P G K G L E W V A T I S G G G
               H T Y Y L
181 GACAGTGTGAAGGGCCGATTCACCATCTCCAGAGACAATTCCAAGA
    ACACCCTGTACCTG D S V K G R F T I S R D N S K N
               T L Y L
241 CAGATGAACAGTCTGAGGGCCGAGGACACAGCCGTGTATTACTGTA
    CAAGAGGTTTTGGA Q M N S L R A E D T A V Y Y C T
               R G F G
301 GACGGGGGGTACTTCGATGTCTGGGGCCAAGGTACCCTGGTCACC
    GTCTCCTCAGG D G G Y F D V W G Q G T L V T V S S
```

E. chAQC2 blocked light chain (Pand102) (SEQ ID NOs:46 and 1)

```
  1 CAAATTGTTCTCACCCAGTTTCCAGCACTCATGTCTGCGTCTCCAG
    GGGAGAAGCTCACC Q I V L T Q F P A L M S A S P
               G E K V T
```

```
 61 ATGACCTGCAGTGCCAGCTCAAGTGTAAATCACATGTTCTGGTAT
    CAGCAGAAGCCAAAA M T C S A S S S V N H M F W
                    Y Q Q K P K
121 TCCTCCCCCAAACCCTGGATTTATCTCACATCCAACCTGGCTTCTG
    GAGTCCCTGCTCGC S S P K P W I Y L T S N L A S G
                   V P A R
181 TTCAGTGGCAGTGGGTCTGGGACCTCTTACTCTCTCACAATCAGCA
    GCATGGAGGCTGAA F S G S G S G T S Y S L T I S S
                   M E A E
241 GATGCTGCCACTTATTACTGCCAGCAGTGGAGTGGTAACCCGTGG
    ACGTTCGGTGGAGGC D A A T Y Y C Q Q W S G N P W
                    T F G G G
301 ACCAAGCTGGAGATCAAA T K L E I K
```

F. hAQC2 h1 light chain (pAND117) (SEQ ID NOs:48 and 49)

```
  1 CAAATTGTTCTCACCCAGTCTCCATCCTCCCTGTCTGCGTCTGTAGG
    gGACAGAGTCACC Q I V L T Q S P S S L S A S V G
                  D R V T
 61 ATCACATGCAGTGCCAGCTCAAGTGTAAATCACATGTTCTGGTATC
    AGCAGAAGCCCGGG I T C S A S S S V N H M F W Y
                   Q Q K P G
121 AAAGCCCCCAAACCCTGGATTTATCTCACATCCAACCTGGCTTCTG
    GAGTCCCTTCACGC K A P K P W I Y L T S N L A S G
                   V P S R
181 TTCAGTGGCAGTGGGTCTGGGACAGATTACACTCTCACAATCAGCA
    GCCTGCAACCTGAA F S G S G S G T D Y T L T I S
                   S L Q P E
241 GATTTTGCCACTTATTACTGCCAGCAGTGGAGTGGTAACCCGTGGA
    CGTTCGGTGGAGGC D F A T Y Y C Q Q W S G N P W
                   T F G G G
301 ACTAAGGTGGAGATCAAA T K V E I K
```

G. hAQC2 h2 light chain (pAND120) (SEQ ID NOs:50 and 51)

```
  1 CAAATTGTTCTCACCCAGTCTCCATCCTCCCTGTCTGCGTCTGTAGG
    GGACAGAGTCACC Q I V L T Q S P S S L S A S V G
                  D R V T
 61 ATCACATGCAGTGCCAGCTCAAGTGTAAATCACATGTTCTGGTATC
    AGCAGAAGCCCGGG I T C S A S S S V N H M F W Y
                   Q Q K P G
121 AAAGCGCCCAAACTCCTGATTTATCTCACATCCAACCTGGCTTCTGG
    AGTCCCTTCACGC K A P K L L I Y L T S N L A S G
                  V P S R
181 TTCAGTGGCAGTGGGTCTGGGACAGATTACACTCTCACAATCAGCA
    GCCTGCAACCTGAA F S G S G S G T D Y T L T I S
                   S L Q P E
241 GATTTTGCCACTTATTACTGCCAGCAGTGGAGTGGTAACCCGTGGA
    CGTTCGGTGGAGGC D F A T Y Y C Q Q W S G N P W
                   T F G G G
301 ACTAAGGTGGAGATCAAA T K V E I K
```

H. hAQC2 c1 light chain (pAND122) (SEQ ID NOs:52 and 66)

```
  1 CAAATTCAGCTCACCCAGTCTCCATCCTCCCTGTCTGCGTCTGTAGG
    GGACAGAGTCACC Q I Q L T Q S P S S L S A S V
                  G D R V T
 61 ATCACATGCAGTGCCAGCTCAAGTGTAAATCACATGTTCTGGTAT
    CAGCAGAAGCCCGGG I T C S A S S S V N H M F W Y Q
                    Q K P G
121 AAAGCCCCCAAACCCTGGATTTATCTCACATCCAACCTGGCTTCTG
    GAGTCCCTTCACGC K A P K P W I Y L T S N L A S
                   G V P S R
181 TTCACTGGCAGTGGGTCTGGGACAGATTACACTCTCACAATCAGCA
    GCCTGCAACCTGAA F S G S G S G T D Y T L T I S S
                   L Q P E
241 GATTTTGCCACTTATTACTGCCAGCAGTGGAGTGGTAACCCGTGGA
    CGTTCGGTCAGGGC D F A T Y Y C Q Q W S G N P W T
                   F G Q G
301 ACTAAGGTGGAGATCAAA T K V E I K
```

I. hAQC2 c2 light chain (pAND123) (SEQ ID NOs:53 and 54)

```
  1 CAAATTCAGCTCACCCAGTCTCCATCCTCCCTGTCTGCGTCTGTAG
    GGGACAGAGTCACC Q I Q L T Q S P S S L S A S V
                   G D R V T
 61 ATCACATGCAGTGCCAGCTCAAGTGTAAATCACATGTTCTGGTAT
    CAGCAGAAGCCCGGG I T C S A S S S V N H M F W Y Q
                    Q K P G
121 AAAGCGCCCAAACTCCTGATTTATCTCACATCCAACCTGGCTTCT
    GGAGTCCCTTCACGC K A P K L L I Y L T S N L A S G
                    V P S R
```

-continued

```
181 TTCAGTGGCAGTGGGTCTGGGACAGATTACACTCTCACAATCAGC

AGCCTGCAACCTGAA F S G S G S G T D Y T L T I S S

L Q P E

241 GATTTTGCCACTTATTACTGCCAGCAGTGGAGTGGTAACCCGTGGA

CGTTCGGTCAGGGC D F A T Y Y C Q Q W S G N P W

T F G Q G

301 ACTAAGGTGGAGATCAAA T K V E I K
```

J. chAQC2 unblocked light chain (pAND098) (SEQ ID NOs:55 and 56)

```
  1 GAAATTGTTCTCACCCAGTTTCCAGCACTCATGTCTGCGTCTCCAG

GGGAGAAGGTCACC E I V L T Q F P A L M S A S P G

E K V T

61 ATGACCTGCAGTGCCAGCTCAAGTGTAAATCACATGTTCTGGTATC

AGCAGAAGCCAAAA M T C S A S S S V N H M F W Y

Q Q K P K

121 TCCTCCCCCAAACCCTGGATTTATCTCACATCCAACCTGGCTTCT

GGAGTCCCTGCTCGC S S P K P W I Y L T S N L A S

G V P A R

181 TTCAGTGGCAGTGGGTCTGGGACCTCTTACTCTCTCACAATCAGC

AGCATGGAGGCTGAA F S G S G S G T S Y S L T I S S

M E A E

241 GATGCTGCCACTTATTACTGCCAGCAGTGGAGTGGTAACCCGTG

GACGTTCGGTGGAGGC D A A T Y Y C Q Q W S G N P

W T F G G G

301 ACCAAGCTGGAGATCAAA T K L E I K
```

K. huAQC2 unblocked c1 light chain (pAND150) (SEQ ID NOs:57 and 58)

```
  1 GATATCCAGCTCACCCAGTCTCCATCCTCCCTGTCTGCGTCTGTAG

GGGACAGAGTCACC D I Q L T Q S P S S L S A S V

G D R V T

61 ATCACATGCAGTGCCAGCTCAAGTGTAAATCACATGTTCTGGTAT

CAGCAGAAGCCCGGG I T C S A S S S V N H M F W Y Q

Q K P G

121 AAAGCCCCCAAACCCTGGATTTATCTCACATCCAACCTGGCTTCTG

GAGTCCCTTCACGC K A P K P W I Y L T S N L A S G

V P S R

181 TTCAGTGGCAGTGGGTCTGGGACAGATTACACTCTCACAATCAGCA

GCCTGCAACCTGAA F S G S G S G T D Y T L T I S S

L Q P E

241 GATTTTGCCACTTATTACTGCCAGCAGTGGAGTGGTAACCCGTGGA

CGTTCGGTCAGGGC D F A T Y Y C Q Q W S G N P W

T F G Q G

301 ACTAAGGTGGAGATCAAA T K V E I K
```

Example 22

This example describes the characterization of various AQC2 antibodies of the invention.

Solid-phase assay for α1 I domain binding. Fifty μl of 10 mg/ml α1 I domain-GST fusion protein was added to a CORNING COSTAR EASY WASH polystyrene 96-well plate (Gotwals et al., Biochemistry, 38, 8280-8 (1999)). Following incubation at 4° C. for 16 hrs, the plate was washed four times with 350 μl of 0.1% Tween-20 in PBS in a plate washer. The plate was blocked by addition of 180 μl of 3% BSA in TBS at 25° C. for 60 min, and then washed as above. Dilutions of antibodies (50 μl/well) in TBS containing 1 mg/ml BSA (assay buffer) were prepared in a 96-well roundbottom plate, transferred to the α1 I domain-coated plate, and incubated for 60 min at 25° C. Following a final wash, 100 μl/well of TMB reagent (Pierce) was added. After 10 min, 100 μl of 1 M sulfuric acid was added, and the absorbance at 450 nm was read on a UV-Vis 96-well spectrophotometer.

Electrochemiluminescence assays for binding of α1 μl integrin or α1 I domain to collagen. Tosyl-activated DYNABEADS M-280 (Dynal, Inc.) were coated with 100 μg/ml type IV collagen (Sigma) according to the manufacturer's instructions. Cell lysates from α1-transfected K562 cells were prepared as follows. Cells were collected by centrifugation, resuspended at $10^8$ cells/ml in a lysis buffer containing 25 mM Tris, pH 7.4, 1% NP-40, 1 mM $CaCl_2$, 1 mM $MnCl_2$, 1 mM $MgCl_2$, 2% BSA, and 1 mM PMSF, and incubated at 4° C. for 60 ruin. Cell debris was removed by centrifugation at 12,000 rpm for 30 min and the resulting supernatant was used in subsequent experiments. Anti-β1 activating antibody TS2/16 and polyclonal anti-GST antibody (Pharmacia) were labeled with TAG-NHS ester (IGEN International, Inc., Gaithersburg, Md.) according to the manufacturer's instructions. Labeled antibodies were purified by gel filtration chromatography on SEPHADEX G25M (Pharmacia).

To carry out the binding assay, collagen-coated beads (1 mg/ml) were blocked for 5 min with 8% Lewis rat plasma in an assay buffer containing 50 mM HEPES, pH 7.5, 150 mM NaCl, and 0.1% Triton X-100. For the α1β1 binding assay, serial dilutions of antibodies were incubated with 10 μg of beads, cell lysate prepared from $10^5$ α1-transfected K562 cells (supra), and 0.1 μg/ml of TAG-TS2/16 in an assay buffer containing 1 mM $MnCl_2$. For the α1 I domain binding assay, the antibodies were incubated with 10 μg of beads, 0.1 μg/ml α1 I domain GST fusion protein, and 1 μg/ml of TAG-anti-GST in an assay buffer containing 1 mM $MnCl_2$. After one to two hours of agitation at room temperature, 200 μl of the assay buffer was added and the samples were read on an ORIGEN 1.5 electrochemiluminescence detector (IGEN). Plots are presented with arbitrary electrochemiluminescence units (ECL) on the ordinate axis.

Biotinylated mAQC2 competition assay. A 96-well plate was coated with 50 μl of 5 μg/ml α1 I domain GST fusion protein and blocked with 3% BSA in TBS as described above. Dilutions of antibodies (60 μl/well) in the assay buffer were prepared in a 96-well roundbottom plate, and 60 µl of 0.1 µg/ml biotinylated murine AQC2 in the assay buffer was added. Fifty microliters from each well was transferred to the coated plate and incubated for 3 hrs at 25° C. The plate was then washed as above, 50 µl of 1 µg/ml peroxidase-conjugated EXTRAVIDIN (Sigma) was added, and the plate was incubated another 2 hrs at 25° C. After a final wash, 100 µl/well of TMB reagent (Pierce) was added. After 10 min, 100 µl of 1 M sulfuric acid was added, and the absorbance at 450 nm was read on a UV-Vis 96-well spectrophotometer.

Experimental results. The experimental results are shown in FIGS. 16A-D and Table 3. The ability of mAQC2, chAQC2, hAQC2, and hAQC2' (i.e., huAQC2-c4; differing from hAQC2 only in that residue 1 of the hAQC2' light chain was D instead of Q) to (1) bind to human α1-transfected K562 cells (by FACS); (2) bind to immobilized α1-I domain (by ELISA); (3) compete with mAQC2 for binding to α1-I domain (ELISA); (4) block α1β1 domain binding to collagen (Electrochemiluminescence assay); or (5) block a α1β1 integrin binding to collagen (Electrochemiluminescence assay) was determined. The results are shown in FIGS. 16A-D, and calculated IC50 (for inhibition) or EC50 (for binding) values are given in Table 3. In each assay, each of the humanized AQC2 forms showed a similar ability to either bind VLA1 (or the α1 domain) or block binding to collagen (Note that in panel C, the observed difference in intensity between mAQC2 and the humanized forms derives from the use of an anti-murine-IgG secondary antibody, instead of an anti-human-IgG).

TABLE 3

Summary of assay results (all values in nM)

| Antibody | FACS (EC50) | VLA1 Inhibition (IC50) | α1I Inhibition (IC50) | ELISA (EC50) | Competition with biotin-AQC2 (IC50) |
|---|---|---|---|---|---|
| mAQC2 | n.d. | 0.0726 (±0.014) | 0.029 (±0.011) | 0.061 (±0.015) | 38 (±8.7) |
| Chimera | 0.25 | 0.071 (±0.002) | 0.027 (±0.007) | 0.176 (±0.058) | 30 (±6.9) |
| hAQC2 | 0.29 | 0.129 (±0.005) | 0.035 (±0.005) | 0.190 (±0.010) | 65 (±2.2) |
| hAQC2' | 0.43 | 0.125 (±0.018) | 0.037 (±0.001) | 0.313 (±0.072) | 69 (±25.7) |

We next tested whether changes at certain conservative residues in the CDRs could preserve the VLA-1 binding activity of hAQC2, DNA constructs encoding variants of hAQC2 with the following mutations were made by site-directed mutagenesis: (1) G55S in the heavy chain CDR2; (2) S24N in the light chain CDR1 (introducing an occupied N-linked glycosylation site); (3) G92S in the light chain CDR3; (4) a combination of (1) and (2); and (5) a combination of (1) and (3). The DNA constructs encoding both the heavy and light chains were then co-transfected into 293-EBNA cells, and the conditioned medium of the transfectants was assayed for antibody expression by Western blot and ELISA. The results indicated that the hAQC2 variants were expressed as efficiently as cognate h-AQC2. FACS analysis using VLA-1-expressing K562 cells further showed that the VLA-1 binding activities of these variants were similar to hAQC2 itself. In sum, the amino acid substitutions did not alter the VLA-1 binding activity of hAQC2. Indeed, X-ray crystal structure of the RΔH/hAQC2 Fab complex (infra) shows that S24 and G92 of the light chain and G55 of the heavy chain are not in the binding pocket that is in contact with the α1-I domain.

Example 23

The effector functions of an immunoglobulin couple the immunoglobulin's antigen-binding activity to the inflammatory, cytotoxic and stimulatory arms of the immune system. Effector functions may impair the safety and efficacy of an immunoglobulin therapeutic product. To reduce the potential effector functions of h-AQC2, mutations of L234A and L235A were made to its heavy chain to generate hsAQC2. For the same reason, a single mutation of N298Q (numbering according to SEQ ID NO:5) was made in the heavy chain of hAQC2 to generate an aglycosylated form of hAQC2, named haAQC2. Studies can be done to compare their efficacy, residual effector function, stability and immunogenicity to cognate hAQC2. Unless otherwise indicated, residue position numbers in constant regions as used herein are designated in accordance with the EU numbering convention.

The heavy chain polypeptide sequence of haAQC2 is as follows (Plasmid: pAND161):

```
                                            (SEQ ID NO: 5)
  1 EVQLVESGGG LVQPGGSLRL SCAASGFTFS RYTMSWVRQA

PGKGLEWVAT

51 ISGGGHTYYL DSVKGRFTIS RDNSKNTLYL QMNSLRAEDT

AVYYCTRGFG

101 DGGYFDVWGQ GTLVTVSSAS TKGPSVFPLA PSSKSTSGGT

AALGCLVKDY

151 FPEPVTVSWN SGALTSGVHT FPAVLQSSGL YSLSSVVTVP

SSSLGTQTYI

201 CNVNHKPSNT KVDKKVEPKS CDKTHTCPPC PAPELLGGPS

VFLFPPKPKD

251 TLMISRTPEV TCVVVDVSHE DPEVKFNWYV DGVEVHNAKT

KPREEQYQST

301 YRVVSVLTVL HQDWLNGKEY KCKVSNKALP APIEKTISKA

KGQPREPQVY

351 TLPPSRDELT KNQVSLTCLV KGFYPSDIAV EWESNGQPEN

NYKTTPPVLD

401 SDGSFFLYSK LTVDKSRWQQ GNVFSCSVMH EALHNHYTQK

SLSLSPG
```

The heavy chain polypeptide sequence of hsAQC2 is as follows (Plasmid: pAND171):

```
                                            (SEQ ID NO: 6)
  1 EVQLVESGGG LVQPGGSLRL SCAASGFTFS RYTMSWVRQA

PGKGLEWVAT

51 ISGGGHTYYL DSVKGRFTIS RDNSKNTLYL QMNSLRAEDT

AVYYCTRGFG
```

-continued

```
101 DGGYPDVWCQ GTLVTVSSAS TKGPSVFPLA PSSKSTSGGT

AALGCLVKDY

151 FPEPVTVSWN SGALTSGVHT FPAVLQSSGL YSLSSVVTVP

SSSLGTQTYI

201 CNVNHKPSNT KVDKKVEPKS CDKTHTCPPC PAPEAAGGPS

VFLFPPKPKD

251 TLMISRTPEV TCVVVDVSHE DPEVKFNWYV DGVEVHNAKT

KPREEQYNST

301 YRVVSVLTVL HQDWLNGKEY KCKVSNKALP APIEKTISKA

KGQPREPQVY

351 TLPPSRDELT KNQVSLTCLV KGFYPLDIAV EWESNGQPEN

NYKTTPPVLD

401 SDGSFFLYSK LTVDKSRWQQ GNVFSCSVMH EALHNHYTQK

SLSLSPG
```

Example 24

This example describes a method for determining the crystal structure of the complex of a rat/human chimeric α1-I domain of the α1β1 integrin and the hAQC2 Fab fragment.

Preparation of the Protein Complex

The hAQC2 Fab fragment was prepared from hAQC2 antibody using a variation of the procedure of the IMMUNOPURE® Fab preparation kit (Cat#44885, Pierce, Rockford, Ill.). The intact hAQC2 antibody was concentrated to 12 mg/ml in a buffer containing 20 mM phosphate, 10 mM EDTA and 25 mM cysteine (pH 7.0). Immobilized papain was added at an enzyme to substrate ratio of 1:50, and digestion was allowed to occur overnight at 37° C. The immobilized papain was removed and the crude digest was dialyzed against 20 mM sodium acetate buffer (pH 4.5). The Fab fragment was separated from residual intact antibody, dimeric Fab fragment, and Fc fragment by cation exchange chromatography using a S-column (Poros HS/M, PERSEPTIVE Biosystems #PO42M26) with a shallow salt gradient. The Fab fragment was then exchanged into 0.1 M Hepes buffer (pH 8.0).

The chimeric α1-I domain used in the present invention is a rat/human chimeric I domain construct (mutant RΔH) containing residues Thr145-Phe336 of the rat α1 integrin chain, where residues Gly217, Arg218, Gln219 and Leu222 (crystal numbering) have been substituted with equivalent human residues Val, Gln, Arg and Arg, respectively, in order to restore antibody binding. The amino acid sequences of chimeric RΔH, rat, and human α1-I domains are given below in SEQ ID NOs:59, 60 and 61, respectively. Recombinant α1-I domain was expressed in *E. coli* as a GST-fusion protein. The RΔH α1-I domain was cleaved with thrombin and purified from a *Pichia pastoris* clone as described previously (Gotwals et al., 1999, Biochemistry 38:8280-8288).

(SEQ ID NO: 59)

```
145 TQLDIV

151 IVLDGSNSIY PWESVIAFLN DLLKRMDIGP KQTQVGIVQY

191 GENVTHEFNL NKYSSTEEVL VAANKIVQRG GRQTMTALGI

231 DTARKEAFTE ARGARRGVKK VMVIVTDGES HDNYRLKQVI

271 QDCEDENIQR FSIAILGHYN RGNLSTEKFV EEIKSIASEP

311 TEKHFFNVSD ELALVTIVKA LGERIF
```

(SEQ ID NO: 60)

```
145 TQLDIV

151 IVLDGSNSIY PWESVIAFLN DLLKRMDIGP KQTQVGIVQY

191 GENVTHEFNL NKYSSTEEVL VAANKIGRQG GLQTMTALGI

231 DTARKEAFTE ARGARRGVKK VMVIVTDGES HDNYRLKQVI

271 QDCEDENIQR FSIAILGHYN RGNLSTEKFV EEIKSIASEP

311 TEKHFFNVSD ELALVTIVKA LGERIF
```

(SEQ ID NO: 61)

```
145 TQLDIV

151 IVLDGSNSIY PWDSVTAFLN DLLKRMDIGP KQTQVGIVQY

191 GENVTHEFNL NKYSSTEEVL VAAKKIVQRG GRQTMTALGI

231 DTARKEAFTE ARGARRGVKK VMVIVTDGES HDNHRLKKVI

271 QDCEDENIQR FSIAILGSYN RGNLSTEKFV EEIKSIASEP

311 TEKHFFNVSD EIALVTIVKT LGERIF
```

The hAQC2 Fab fragment was mixed with excess chimeric α1-I domain and incubated at 37° C. for 15 minutes. The saturated α1/Fab complexes were separated from uncomplexed α1-I domain by size exclusion chromatography using a S200 Sephacryl column (Pharmacia, Gibco). The complex was further concentrated to 11 mg/ml in a 20 mM Tris (pH 7.4) 150 mM NaCl 1 mM MnCl$_2$, 5 mM β-mercaptoethanol.

Preparation of Crystals

Crystallization conditions were found using the CRYSTAL SCREEN™ KITs from Hampton Research (Laguna Niguel, Calif.). Crystals of the complex described above were grown at 20° C. by vapor diffusion using an equal amount of protein complex solution and a 20-30% PEG 1500 reservoir solution. Typically, 2 μL of protein complex was added to 2 μL of well solution to yield drops of 4 μL. Crystals grew in two to seven days as hexagonal rods with dimensions 0.8×0.05×0.05 mm$^3$. The presence of the α1-I domain and hAQC2 Fab fragment was confirmed by SDS-PAGE analysis of dissolved crystals. In order to reduce the inherent radiation damage during data collection, X-ray diffraction data was collected at approximately 100 K. To prepare the crystals for data collection at this low temperature, crystals were gradually equilibrated into a cryoprotectant solution containing 25% PEG 400 and 30% PEG 1500, and flash cooled in liquid nitrogen.

Structure Determination

Native X-ray diffraction data to 2.8 Å resolution were collected from a single crystal at about 100 K using an ADSC Quantum 4 charged-coupled device detector at beamline X4A of the Brookhaven National Laboratory (BNL) National Synchrotron Light Source (NSLS). Data was processed using the software programs DENZO and SCALEPACK (Otwinowski & Minor, 1997, Methods in Enzymol. 276:307-326). Crystals belonged to the space group P6$_1$ or its enantiomorph P6$_5$, with unit cell dimensions a=b=255.09 Å, c=38.64 Å. The data set was 96.6% complete and had an R-merge of 8.3%. The Matthews coefficient (Matthews, 1968, J. Mol. Biol. 33:491-497) was 2.59 Å³ Da⁻¹ with a solvent content of 52.1%, which indicated that there were two complexes in the asymmetric unit. The two complexes in the asymmetric unit were related by non-crystallographic 2-fold symmetry. Data statistics are shown in Table 4.

Molecular replacement searches were done with the program AMoRe (Navaza, 1994, Acta Cryst. A50:157-163) from the CCP4 program package (Collaborative Computational Project No. 4. The CCP4 Suite: programs for protein crystallography. 1994, Acta Cryst. D50:760-763), and molecular graphics manipulations were done with the program QUANTA. A single α1-I domain from the structure of the rat α1-I domain of α1β1 integrin (Protein Data Bank (PDB) accession number 1ck4; Nolte et al., 1999, FEBS Lett. 452:379-385) was used as a model or probe for rotation and translation searches. The translation function search indicated that the 1$^{st}$ and 9$^{th}$ highest peaks of the rotation function corresponded to the correct solutions for the two α1-I domains in the asymmetric unit (correlation coefficient (cc)=21.1%, R=53.1%) and that the space group was P6$_5$. Subsequently, searches for the hAQC2 Fab fragments were done, keeping the I domain solutions fixed and using a model of the Fv domain of the hAQC2 Fab as a search probe. A clear solution was found for one of the two Fv domains (cc=22.1%, R=52.6%), but the second Fv could not be located. The position of the second Fv was derived using the non-crystallographic 2-fold symmetry. Rigid body refinement of the two I domains and two Fv domains reduced the R-factor to 43.6% (R-free=42.7%). An 2Fo-Fc electron density map showed clear electron density for the constant domain (Fconst) of the first Fab fragment, but no density for the Fconst domain of the second Fab fragment. A model of the Fconst domain of the first Fab was manually fit in the observed electron density. Subsequent rigid body refinement with the software program CNX (Accelrys Inc., San Diego, Calif. ©2000; Brunger, 1998, Acta Cryst. D54: 905-921), using data in the 500-2.8 Å resolution range, optimized the position of all domains, reducing the R-factor to 39.7% (R-free=38.9%).

All subsequent refinement steps were carried out with the CNX program. To reduce model bias, partial models were used for 2Fo-Fc map calculation and model refinement. The initial partial model, was subjected to simulated annealing and grouped B-factor refinement with non-crystallographic symmetry restraints. The R-working and R-free factors dropped to 28.3% and 32.9%, respectively. Several cycles consisting of iterative model building, maximum likelihood positional refinement and B-factor refinement followed. Only model adjustments that resulted in a drop in the K-free factor were accepted. A bulk-solvent correction was employed after the complete model was built. The R-working and K-free factors of the final model are 21.3% and 27.2%, respectively for the data (F>2σ) in the 500-2.8 Å resolution range.

The final 2Fo-Fc electron density map is of good quality for most of the complex with the exception of amino acid residues 288-295 of one I domain fragment (molecule A in FIG. 19A-1 to A-109) that are associated with weak electron density and have not been included in the model. In addition, the entire constant domain of one Fab fragment has no visible electron density, which indicates that it is disordered. This appears to be consequence of the absence of crystal contacts for the constant domain of the Fab fragment due to its position within a large solvent channel. This domain was also not included in the final model that consists of 1030 amino acid residues, constituting 6 polypeptide chains, and 2 manganese ions. The r.m.s. positional deviation between equivalent residues from the two complexes in the asymmetric unit is small (0.37 Å for 1660 equivalent main chain atoms). Stereochemistry statistics were calculated with the software programs PROCHECK (Laskowski et al., 1993, J. Appl. Cryst. 26:283-291; Morris et al., 1992, Proteins 12:345-364) and CNX. Hydrogen bonds (<3.6 Å) were found with the program CONTACT (Tadeusz Skarzvnski, Imperial College, London, Jan. 12, 1988; Collaborative Computational Project No. 4. The CCP4 Suite: programs for protein crystallography. 1994, Acta Cryst. D50, 760-763). All non-glycine residues (except residue Thr50 of the L chain that will be discussed below) are in the allowed regions of the Ramachandran diagram and 86% of the residues are in the most favored regions. The average B-factor of the main chain atoms is 38.5 Å². Crystallographic analysis data are in Table 4.

TABLE 4

Summary of Data Statistics and Crystallographic Analysis

| Data collection | |
|---|---|
| Cell dimensions a, b, c (Å) | 255.09, 255.09, 38.64 |
| Space group | P6$_5$ |
| Resolution (Å) | 500-2.8 (2.9-2.8)† |
| Unique reflections | 35275 |
| Completeness (%) | 96.6 (87.7)† |
| Average I/s | 11.92 (2.29)† |
| Rmerge* (%) | 8.3 (30.9)† |
| Model | |
| Number of non-H atoms | 7950 |
| Number of protein residues | 1030 |
| Contents of asymmetric unit | 2 I domains, 1 Fab fragment, 1 Fv domain |
| Average B-factor (Å²) | 38.5 |
| Refinement | |
| Resolution range used (F > 2σ) | 500-2.8 |
| R-factor (R-working) (%) | 21.3 |
| R-free†† (%) | 27.2 |
| Stereochemistry | |
| RMS deviations | |
| Bond lengths (Å) | 0.007 |
| Angles (°) | 1.43 |

*Rmerge = $\Sigma_h\Sigma_i |I_{hi} - I_h|/\Sigma_{hi}I_{hi}$
†Values for the highest resolution shell given in parenthesis.
††8% of the data were allocated for the calculation of R-free factor.

Example 25

This example describes the crystal structure of the complex of a rat/human chimeric α1-I domain of the α1β1 integrin and the hAQC2 Fab fragment.

Architecture of Crystal Structure

The crystal structure of the complex of the rat/human chimeric α1-I domain of the α1β1 integrin and the hAQC2 Fab fragment has an elongated shape (FIG. 20). The dimensions of the complex are 100 Å×50 Å×35 Å.

The Fab fragment exhibits the typical immunoglobulin fold. The light chain and heavy chains of the Fab fragment each form two broad sheets of anti-parallel β-strands which pack tightly together to form a scaffold for the complementarity determining region (CDR) loops which extend from the packed sheets. Both the light chain and the heavy chain contain three CDR loops. The light chain loops are called L1, L2 and L3, while the heavy chain loops are referred to as H1, H2 and H3. The complementarity determining region (CDR) loops correspond to canonical structure 1 for light chain L1, L2 and L3 loops and for heavy chain H1 and H2 loops (Chothia et al., 1989, Nature 342:877-883). The heavy chain H3 loop has a tight β-hairpin-like conformation that is stabilized by internal hydrogen bonds as well as two aromatic residues (Tyr104 and Phe105) that are packed against the light chain. Residue Thr50 of L2 adopts mainchain dihedral angles that fall in the disallowed regions of the Ramachandran diagram. The same observation for the corresponding residue has been made for other antibodies (Muller et al., 1998, Structure 6, pp. 1153-11567) which indicates that this is a natural characteristic of L2 loops.

The α1-I domain in the present invention has a structure very similar to the uncomplexed α1-I domain (PDB accession number 1ck4; Nolte et al., 1999, FEBS Lett. 452:379-385; PDB accession code 1qc5; Rich et al., 1999, J. Biol. Chem. 274:24906-24913). The I domain structure exhibits a "dinucleotide-binding" or "Rossman" fold (Rao & Rossman, 1973, J. Mol. Biol. 76:241-256) in which a central sheet of five parallel β-strands and one small antiparallel-strand is surrounded on both sides by a total of seven α-helices. The six β-strands of the structure in this invention will be referred to as βA, βB, βC, βD, βE, and βF and the seven α-helices are called α1, α2, α3, α4, α5, α6 and α7.

Three characteristic structural features exist for 1 domains. The first characteristic feature is the presence of an inserted small helix in the βE-α6 loop, termed as the C helix. Most of the C helix loop of molecule A (FIG. 19A-1 to A-109) in the present invention is associated with weak electron density, which suggests disorder. This appears to be a consequence of absence of crystal contacts or contacts with the Fab that would have stabilized the loop. However, the same loop in molecule B (FIG. 19A-1 to A-109) in the present invention has well-defined electron density and has been included in the model. The second characteristic feature of α1-I domains is the MIDAS or Metal-Ion-Dependent-Adhesion-Site where metal ions and ligands are implicated to bind to the I domain. Five key residues which form part of the MIDAS are referred to as the "DxSxS-T-D" motif. These residues, which are completely conserved among I domains, coordinate the metal ion (Gotwals et al., 1999, Biochemistry 38:8280-8288). The crystals in the present invention were grown in the presence of manganese and the MIDAS site of the I domain in this structure is observed to contain a $Mn^{+2}$ metal ion. The ion is directly coordinated by the side chains of residues Ser156, Ser158 and Thr224. The 2Fo-Fc electron density map shows no evidence that MIDAS residues Asp 154 and Asp257 make water-mediated indirect coordination of the metal ion (FIG. 20). However, the apparent absence of water molecules could be a consequence of the limited resolution (2.8 Å) of the electron density map. The third feature of X domains is that all determined structures of I domains belong to one of two conformations called "open" and "closed". The differences between the open and closed conformation include a different mode of metal ion coordination and a significant (about 10 Å) positional shift of the C-terminal helix of the I domain. The I domain in the complex in the present invention is in the closed conformation.

In the structure of the complex in the present invention, the Fab fragment binds to its epitope on the front upper surface of the I domain with a footprint 35 Å by 30 Å. The total buried surface area in the antibody-antigen interface is 1534 $Å^2$ which is typical of other antibody-antigen complexes (Davies et al., 1996, Proc. Natl. Acad. Sci. USA 93:7-12; Jones & Thornton, 1996, Proc. Natl. Acad. Sci. USA 93:13-20). The surface is 25% hydrophobic and 75% hydrophilic in character. The heavy chain contributes 65% of the buried surface area for the complex, while the remaining 35% is contributed by the light chain. The antibody epitope consists of residues located in four loops of the I domain (Emsley et al., 2000, Cell 101:47-56). Three of the loops form the MIDAS site: loop 1 (βA-α1) which contains the conserved DXSXS sequence, loop 2 (α3-α4) which contains the MIDAS Thr224 and loop 3 (βD-α5) that contains MIDAS residue Asp257. The fourth loop is the C-helix loop and is involved in only in minor contacts.

The central feature of the antigen-antibody interaction is the coordination of the MIDAS site metal ion by Asp101 from the CDR H3 of the antibody (FIG. 20). The distance between the ion and Oδ1 of Asp101 is 2.4 Å. In addition, the Oδ2 atom of Asp101 is interacting with His261 of the I domain. Interestingly, the CDR H3 contains several glycine residues adjacent to Asp101 (sequence GFGDGGY) (SEQ ID NO:62), presumably to allow enough flexibility to the CDR loop to permit proper coordination of the metal ion. The CDR H3 sequence is essentially invariant in monoclonal antibodies that were raised against the same antigen and found to belong in the same class. Most of the antibody residues that are involved in antibody-antigen contacts are located in L3, H1, H2 and H3CDR loops. A few residues from the L1 (Asn30) and L2 (Tyr48) loops appear to form minor Van Der Waals contacts. L3 primarily contributes to contacts through two large hydrophobic residues, Trp90 and Trp95. In addition, Asn93 from L3 forms hydrogen bonds with Gln223 of the I domain. The side chains of His56 and Tyr58 from the H2 loop form hydrogen bonds with main chain atoms of loop 2 of the I domain. Arg31 of H1 is in contact with Arg291 of loop 4 of the I domain. Arg222 from loop 2 of the I domain is sandwiched between several antibody residues including Tyr58, Trp95 and Asn93. This is the only residue out of the four mutated in the RΔH I domain, that is involved in contacts with the Fab. It is therefore likely to be the only residue responsible for restoring the binding of the antibody after the mutagenesis.

Comparison of the Crystal Structure of the Complex of a Rat/Human Chimeric α1-I Domain and the hAQC2 Fab Fragment with Other I Domain Structures The chimeric RΔH α1-I domain has four sequence differences with the rat α1-I domain (rat residues: 217G, 218R, 219Q and 222L), eight sequence differences with the human α1-I domain (human residues: 163D, 166T, 214K, 264H, 268K, 288S, 322I and 380T), and ten sequence differences with the clone used in the crystal structure studies of human α1-I domain (clone residues: 163D, 166T, 174E, 214K, 230I, 264H, 268K, 288S, 322I and 380T). In the unliganded rat α1β1 α1-I domain crystal structure (PDB accession code 1ck4; Nolte et al., 1999, FEBS Lett. 452:379-385), the α1-I domain contains no bound metal ions and adopts the "closed" conformation. In the unliganded human α1-I domain crystal structure (accession code 1qc5; Rich et al., 1999, J. Biol. Chem. 274:24906-24913), the α1-I domain contains bound $Mg^{+2}$ and similarly adopts the closed conformation. Superimposition of these two structures with the complexed chimeric α1-I domain indicates that there are only minor conformational changes upon hAQC2 antibody binding. The r.m.s. positional deviation between the rat and chimeric α1-I domain is 1.04 Å for all 768 main chain atoms. The r.m.s. positional deviation between the human and chimeric α1-I domain is 0.69 Å for all 764 main chain atoms. The biggest differences (human and chimeric α1-I domain pair) are observed in loop 1 (r.m.s. deviations 1.24 Å for main chain atoms of residues 154-161) and the loop 4 (C helix loop) of the α1-I domain (r.m.s. deviations 1.55 Å for main chain atoms of residues 288-296). However, these differences can be more accurately described as shifts of the whole secondary structure elements rather than complex conformational changes. These are likely to be within the normal range of conformational flexibility of proteins. The r.m.s. positional deviation between the human and chimeric α1-I domain for backbone atoms of amino acid residues Glu192, Gln218, Arg219, Gly220, and Gly221 (crystal numbering) is 0.33 Å. The r.m.s. positional deviation between the rat and chimeric α1-I domain for backbone atoms of amino acid residues Asp154, Ser156, Asn157, Ser158, Tyr160, Glu192, Gln218, Arg219, Gly220, Gly221, Arg222, Gln223, Thr224, Asp257, His261, Asn263, Arg291, and Leu294 (crystal numbering) is 0.97 Å.

The I domain maintains the "closed" I domain conformation that has been observed only for unliganded I domains crystallized in the absence of ligands or pseudo-ligands bound to the MIDAS site. The r.m.s. positional deviation of the C-terminal helices of the human and chimeric I domains (calculated for the main chain atoms of residues 321-335) is 0.64 Å. A simulated annealing omit map calculated for the final refined model unambiguously confirms that the position of the C-terminal helix and adjacent structural elements are consistent with the closed conformation.

In order to investigate the effects of ligand binding to the modes of metal ion coordination, the structure of the present invention was superimposed with the structures of the unliganded α2-I domain (PDB accession code 1aox; Emsley et al., 1997, J. Biol. Chem. 272:28512-28517) and the α2-I domain complexed with a collagen peptide (PDB accession code 1dzi; Emsley et al., 2000, Cell 101:47-56). The coordination of the metal ion by Asp101 from the antibody is remarkably similar to the coordination of the metal ion of the α2-I domain by a glutamic acid from the collagen peptide. Another feature that is conserved is the simultaneous interaction of the acidic group with His261 (His258 in the α2-I domain). All MIDAS residues of the I domain-Fab complex except Ser156 and Ser158 adopt conformations very similar to those observed in the unliganded I domain. In contrast, the side chains of Ser156 and Ser158, as well as the metal, adopt conformations similar with those of the liganded I domain. It is clear that the coordination of the metal ion by Asp101 does not allow the ion to maintain the position and coordination distances that are observed in the unliganded state. Thus, the metal ion is not directly coordinated by Asp257, a fact that permits the ion to maintain high electrophilicity.

Biological Implications

In the present invention, there is no direct coordination of the metal by Asp257, which may permit high affinity binding by lowering the energy barrier between a closed (no ligand bound) and open (ligand bound) conformation. However, the coordination of the metal by an aspartic acid from the antibody is not sufficient to induce the open conformation to the I domain in the present invention. The I domain-Fab complex structure indicates that it is possible to have strong binding to the I domain that adopts the closed conformation and that coordination of the metal ion by an acidic residue from the ligand may be necessary but not sufficient to induce a conformational change to the open state. Binding of the antibody is expected to stabilize the low affinity state of the integrin and prevent the outside-in signaling that would have accompanied integrin binding to collagen.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention.

What is claimed is:

1. A method of treating a subject having hypersensitivity, comprising administering to the subject a composition comprising an anti-VLA-1 antibody or antigen binding fragment thereof, and a pharmaceutically acceptable carrier, wherein the antibody or antigen binding fragment thereof comprises light chain complementarity determining regions defined by amino acid residues 24 to 33, 49 to 55 and 88 to 96 of SEQ ID NO:1, and heavy chain complementarity determining regions defined by amino acid residues 31 to 35, 50 to 65 and 98 to 107 of SEQ ID NO:2.

2. The method of claim 1, wherein the hypersensitivity is delayed type hypersensitivity.

3. The method of claim 1, wherein the hypersensitivity is contact hypersensitivity.

4. The method of claim 1, wherein the anti-VLA-1 antibody or antigen binding fragment thereof comprises a light chain variable domain sequence of SEQ ID NO:1 and a heavy chain variable domain sequence of SEQ ID NO:2.

5. The method of claim 1, wherein the anti-VLA-1 antibody or antigen binding fragment thereof comprises the same heavy and light chain polypeptide sequences as an antibody produced by hybridoma mAQC2 which is deposited under ATCC accession number PTA3273.

6. The method of claim 1, wherein the anti-VLA-1 antibody or antigen binding fragment thereof is humanized.

7. The method of claim 6, wherein the anti-VLA-1 antibody or antigen binding fragment thereof comprises at least one of the following residues in its light chain: Q1, L4, P45, W46 and Y70 according to SEQ ID NO:1; or at least one of the following residues in its heavy chain: D1, V12, S28, F29, A49, T96, and R97 according to SEQ ID NO:2.

8. The method of claim 6, wherein the anti-VLA-1 antibody or antigen binding fragment thereof comprises a light chain variable domain sequence defined by amino acid residues 1 to 106 of SEQ ID NO:3, and a heavy chain variable domain sequence defined by amino acid residues 1 to 118 of SEQ ID NO:4.

9. The method of claim 6, wherein the anti-VLA-1 antibody or antigen binding fragment thereof comprises the same heavy and light chain polypeptide sequences as an antibody produced by cell line hAQC2 which is deposited under ATCC accession number PTA3275.

10. The method of claim 6, wherein the anti-VLA-1 antibody or antigen binding fragment thereof comprises the same heavy and light chain polypeptide sequences as an antibody produced by cell line hsAQC2 which is deposited under ATCC accession number PTA3356.

11. The method of claim 6, wherein the anti-VLA-1 antibody or antigen binding fragment thereof comprises the same heavy and light chain polypeptide sequences as an antibody produced by cell line haAQC2 which is deposited under ATCC accession number PTA3274.

12. The method of claim 6, wherein the anti-VLA-1 antibody or antigen binding fragment thereof comprises a antibody or antigen-binding fragment thereof that has an alanine at amino acid position 235 and an alanine at amino acid position 236 as set forth in SEQ ID NO:6.

13. The method of claim 6, wherein the anti-VLA-1 antibody or antigen binding fragment thereof comprises an antibody or antigen-binding fragment thereof that has a glutamine at amino acid position 298 as set forth in SEQ ID NO:5.

14. The method of claim 1, wherein the subject is a human.

15. A method of treating a subject having delayed type hypersensitivity, the method comprising administering to the subject a composition comprising an anti-VLA-1 antibody or antigen binding fragment thereof, and a pharmaceutically acceptable carrier, wherein the antibody or antigen-binding fragment thereof comprises a light chain and a heavy chain selected from one of the following light chain and heavy chain pairs:

(i) a light chain of an anti-VLA-1 antibody, or antigen-binding fragment thereof, which has the sequence of SEQ ID NO:3,
and a heavy chain of an anti-VLA-1 antibody, or antigen-binding fragment thereof, which has the sequence of SEQ ID NO:4;

(ii) a light chain of an anti-VLA-1 antibody, or antigen-binding fragment thereof, whose light chain variable domain has the sequence of SEQ ID NO:49,
and a heavy chain of an anti-VLA-1 antibody, or antigen-binding fragment thereof, whose heavy chain variable domain has the sequence of SEQ ID NO:42;

(iii) a light chain of an anti-VLA-1 antibody, or antigen-binding fragment thereof, whose light chain variable domain has the sequence of SEQ ID NO:51,
and a heavy chain of an anti-VLA-1 antibody, or antigen-binding fragment thereof, whose heavy chain variable domain has the sequence of SEQ ID NO:44;

(iv) a light chain of an anti-VLA-1 antibody, or antigen-binding fragment thereof, whose light chain variable domain has the sequence of SEQ ID NO:54,
and a heavy chain of an anti-VLA-1 antibody, or antigen-binding fragment thereof, whose heavy chain variable domain has the sequence of SEQ ID NO:42;

(v) a light chain of an anti-VLA-1 antibody, or antigen-binding fragment thereof, whose light chain variable domain has the sequence of SEQ ID NO:58,
and a heavy chain of an anti-VLA-1 antibody, or antigen-binding fragment thereof, whose heavy chain variable domain has the sequence of SEQ ID NO:68;

(vi) a light chain of an anti-VLA-1 antibody, or antigen-binding fragment thereof, whose light chain variable domain has the sequence of SEQ ID NO:70,
and a heavy chain of an anti-VLA-1 antibody, or antigen-binding fragment thereof, whose heavy chain variable domain has the sequence of SEQ ID NO:68;

(vii) a light chain of an anti-VLA-1 antibody, or antigen-binding fragment thereof, whose light chain variable domain has the sequence of SEQ ID NO:66,
and a heavy chain of an anti-VLA-1 antibody, or antigen-binding fragment thereof, whose heavy chain variable domain has the sequence of SEQ ID NO:42;

(viii) a light chain of an anti-VLA-1 antibody, or antigen-binding fragment thereof, whose light chain variable domain has the sequence of SEQ ID NO:54,
and a heavy chain of an anti-VLA-1 antibody, or antigen-binding fragment thereof, whose heavy chain variable domain has the sequence of SEQ ID NO:68;

(ix) a light chain of an anti-VLA-1 antibody, or antigen-binding fragment thereof, whose light chain variable domain has the sequence of SEQ ID NO:47,
and a heavy chain of an anti-VLA-1 antibody, or antigen-binding fragment thereof, whose heavy chain variable domain has the sequence of SEQ ID NO:68;

(x) a light chain of an antibody produced by hybridoma mAQC2 (ATCC accession number PTA3273),
and a heavy chain of an antibody produced by hybridoma mAQC2 (ATCC accession number PTA3273);

(xi) a light chain of an antibody produced by cell line hAQC2 (ATCC accession number PTA3275),
and a heavy chain of an antibody produced by cell line hAQC2 (ATCC accession number PTA3275);

(xii) a light chain of an antibody produced by cell line haAQC2 (ATCC accession number PTA3274),
and a heavy chain of an antibody produced by cell line haAQC2 (ATCC accession number PTA3274);

(xiii) a light chain of an antibody produced by cell line hsAQC2 (ATCC accession number PTA3356),
and a heavy chain of an antibody produced by cell line hsAQC2 (ATCC accession number PTA3356); or (xiv) a light chain of an anti-VLA-1 antibody, or antigen-binding fragment thereof, whose light chain variable domain has the sequence of SEQ ID NO:66,
and a heavy chain of an anti-VLA-1 antibody, or antigen-binding fragment thereof, whose heavy chain variable domain has the sequence of SEQ ID NO:68.

16. The method of claim 15, wherein anti-VLA-1 antibody or antigen binding fragment thereof comprises a light chain having the sequence of SEQ ID NO:3 and a heavy chain having the sequence of SEQ ID NO:4.

17. The method of claim 15, wherein the subject is a human.

18. A method of treating a subject having contact hypersensitivity, the method comprising administering to the subject a composition comprising an anti-VLA-1 antibody or antigen binding fragment thereof, and a pharmaceutically acceptable carrier, wherein the antibody or antigen-binding fragment thereof comprises a light chain and a heavy chain selected from one of the following light chain and heavy chain pairs:

(i) a light chain of an anti-VLA-1 antibody, or antigen-binding fragment thereof, which has the sequence of SEQ ID NO:3,
and a heavy chain of an anti-VLA-1 antibody, or antigen-binding fragment thereof, which has the sequence of SEQ ID NO:4;

(ii) a light chain of an anti-VLA-1 antibody, or antigen-binding fragment thereof, whose light chain variable domain has the sequence of SEQ ID NO:49,
and a heavy chain of an anti-VLA-1 antibody, or antigen-binding fragment thereof, whose heavy chain variable domain has the sequence of SEQ ID NO:42;

(iii) a light chain of an anti-VLA-1 antibody, or antigen-binding fragment thereof, whose light chain variable domain has the sequence of SEQ ID NO:51,
and a heavy chain of an anti-VLA-1 antibody, or antigen-binding fragment thereof, whose heavy chain variable domain has the sequence of SEQ ID NO:44;

(iv) a light chain of an anti-VLA-1 antibody, or antigen-binding fragment thereof, whose light chain variable domain has the sequence of SEQ ID NO:54,
and a heavy chain of an anti-VLA-1 antibody, or antigen-binding fragment thereof, whose heavy chain variable domain has the sequence of SEQ ID NO:42;

(v) a light chain of an anti-VLA-1 antibody, or antigen-binding fragment thereof, whose light chain variable domain has the sequence of SEQ ID NO:58,
and a heavy chain of an anti-VLA-1 antibody, or antigen-binding fragment thereof, whose heavy chain variable domain has the sequence of SEQ ID NO:68;

(vi) a light chain of an anti-VLA-1 antibody, or antigen-binding fragment thereof, whose light chain variable domain has the sequence of SEQ ID NO:70,
and a heavy chain of an anti-VLA-1 antibody, or antigen-binding fragment thereof, whose heavy chain variable domain has the sequence of SEQ ID NO:68;

(vii) a light chain of an anti-VLA-1 antibody, or antigen-binding fragment thereof, whose light chain variable domain has the sequence of SEQ ID NO:66,
and a heavy chain of an anti-VLA-1 antibody, or antigen-binding fragment thereof, whose heavy chain variable domain has the sequence of SEQ ID NO:42;

(viii) a light chain of an anti-VLA-1 antibody, or antigen-binding fragment thereof, whose light chain variable domain has the sequence of SEQ ID NO:54,
and a heavy chain of an anti-VLA-1 antibody, or antigen-binding fragment thereof, whose heavy chain variable domain has the sequence of SEQ ID NO:68;

(ix) a light chain of an anti-VLA-1 antibody, or antigen-binding fragment thereof, whose light chain variable domain has the sequence of SEQ ID NO:47,
and a heavy chain of an anti-VLA-1 antibody, or antigen-binding fragment thereof, whose heavy chain variable domain has the sequence of SEQ ID NO:68;

(x) a light chain of an antibody produced by hybridoma mAQC2 (ATCC accession number PTA3273),
and a heavy chain of an antibody produced by hybridoma mAQC2 (ATCC accession number PTA3273);

(xi) a light chain of an antibody produced by cell line hAQC2 (ATCC accession number PTA275),
and a heavy chain of an antibody produced by cell line hAQC2 (ATCC accession number PTA3275);

(xii) a light chain of an antibody produced by cell line haAQC2 (ATCC accession number PTA3274),
and a heavy chain of an antibody produced by cell line haAQC2 (ATCC accession number PTA3274);

(xiii) a light chain of an antibody produced by cell line hsAQC2 (ATCC accession number PTA3356),
and a heavy chain of an antibody produced by cell line hsAQC2 (ATCC accession number PTA3356); or (xiv) a light chain of an anti-VLA-1 antibody, or antigen-binding fragment thereof, whose light chain variable domain has the sequence of SEQ ID NO:66,
and a heavy chain of an anti-VLA-1 antibody, or antigen-binding fragment thereof, whose heavy chain variable domain has the sequence of SEQ ID NO:68.

19. The method of claim 18, wherein anti-VLA-1 antibody or antigen binding fragment thereof comprises a light chain having the sequence of SEQ ID NO:3 and a heavy chain having the sequence of SEQ ID NO:4.

20. The method of claim 18, wherein the subject is a human.

21. A method of reducing edema in a subject having delayed type hypersensitivity or contact hypersensitivity, the method comprising administering to the subject a composition comprising an anti-VLA-1 antibody or antigen binding fragment thereof, and a pharmaceutically acceptable carrier, wherein the anti-VLA-1 antibody or antigen binding fragment thereof comprises a light chain having the sequence of SEQ ID NO:3 and a heavy chain having the sequence of SEQ ID NO:4.

* * * * *

UNITED STATES PATENT AND TRADEMARK OFFICE
CERTIFICATE OF CORRECTION

PATENT NO. : 9,644,030 B2
APPLICATION NO. : 14/597262
DATED : May 9, 2017
INVENTOR(S) : Michael Karpusas et al.

Page 1 of 1

It is certified that error appears in the above-identified patent and that said Letters Patent is hereby corrected as shown below:

In the Claims

At Column 120, Claim number 18 (xi), Line number 18, delete "(ATCC accession number PTA 275)," and replace it with --(ATCC accession number PTA 3275),--

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*